(12) United States Patent
Lin et al.

(10) Patent No.: US 11,702,423 B2
(45) Date of Patent: Jul. 18, 2023

(54) BRM TARGETING COMPOUNDS AND ASSOCIATED METHODS OF USE

(71) Applicant: Prelude Therapeutics, Incorporated, Wilmington, DE (US)

(72) Inventors: Hong Lin, Exton, PA (US); Philip Pitis, North Wales, PA (US); Liang Lu, Hockessin, DE (US); Andrew Paul Combs, Kennett Square, PA (US)

(73) Assignee: Prelude Therapeutics Incorporated, Wilmington, DE (US)

( * ) Notice: Subject to any disclaimer, the term of this patent is extended or adjusted under 35 U.S.C. 154(b) by 0 days.

(21) Appl. No.: 17/343,341

(22) Filed: Jun. 9, 2021

(65) Prior Publication Data
US 2022/0033409 A1 Feb. 3, 2022

Related U.S. Application Data

(60) Provisional application No. 63/036,811, filed on Jun. 9, 2020.

(51) Int. Cl.
| | | |
|---|---|---|
| *C07D 401/12* | (2006.01) | |
| *A61K 31/50* | (2006.01) | |
| *A61P 35/00* | (2006.01) | |
| *C07D 487/14* | (2006.01) | |
| *C07D 519/00* | (2006.01) | |

(52) U.S. Cl.
CPC ......... *C07D 487/14* (2013.01); *C07D 519/00* (2013.01)

(58) Field of Classification Search
CPC .... C07D 401/12; C07D 401/14; A61K 31/50; A61P 35/00
See application file for complete search history.

(56) References Cited

FOREIGN PATENT DOCUMENTS

| | | | |
|---|---|---|---|
| WO | 2016138114 | A1 | 9/2016 |
| WO | 2019195201 | A1 | 10/2019 |
| WO | 2018119448 | A1 | 12/2020 |
| WO | 2020251969 | A1 | 12/2020 |
| WO | 2020251971 | A1 | 12/2020 |
| WO | 2020251972 | A1 | 12/2020 |
| WO | 2020251974 | A1 | 12/2020 |
| WO | 2021133917 | A1 | 7/2021 |
| WO | 2021133920 | A1 | 7/2021 |

*Primary Examiner* — Bruck Kifle
(74) *Attorney, Agent, or Firm* — BakerHostetler

(57) ABSTRACT

The present disclosure provides bifunctional compounds comprising a target protein binding moiety and a E3 ubiquitin ligase binding moiety, and associated methods of use.

18 Claims, No Drawings
Specification includes a Sequence Listing.

SEQUENCE LISTING

```
<160> NUMBER OF SEQ ID NOS: 4

<210> SEQ ID NO 1
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Glu Ala Gly Arg Pro Arg Pro Val Leu Arg Ser Val Asn Ser Arg
1               5                   10                  15

Glu Pro Ser Gln Val Ile Phe Cys Asn Arg Ser Pro Arg Val Val Leu
            20                  25                  30

Pro Val Trp Leu Asn Phe Asp Gly Glu Pro Gln Pro Tyr Pro Thr Leu
        35                  40                  45

Pro Pro Gly Thr Gly Arg Arg Ile His Ser Tyr Arg Gly His Leu Trp
    50                  55                  60

Leu Phe Arg Asp Ala Gly Thr His Asp Gly Leu Leu Val Asn Gln Thr
65                  70                  75                  80

Glu Leu Phe Val Pro Ser Leu Asn Val Asp Gly Gln Pro Ile Phe Ala
                85                  90                  95

Asn Ile Thr Leu Pro Val Tyr Thr Leu Lys Glu Arg Cys Leu Gln Val
            100                 105                 110

Val Arg Ser Leu Val Lys Pro Glu Asn Tyr Arg Arg Leu Asp Ile Val
        115                 120                 125

Arg Ser Leu Tyr Glu Asp Leu Glu Asp His Pro Asn Val Gln Lys Asp
    130                 135                 140

Leu Glu Arg Leu Thr Gln Glu Arg Ile Ala His Gln Arg Met Gly Asp
145                 150                 155                 160

<210> SEQ ID NO 2
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 2

Met Asp Val Phe Leu Met Ile Arg Arg His Lys Thr Thr Ile Phe Thr
1               5                   10                  15

Asp Ala Lys Glu Ser Ser Thr Val Phe Glu Leu Lys Arg Ile Val Glu
                20                  25                  30

Gly Ile Leu Lys Arg Pro Pro Asp Glu Gln Arg Leu Tyr Lys Asp Asp
            35                  40                  45

Gln Leu Leu Asp Asp Gly Lys Thr Leu Gly Glu Cys Gly Phe Thr Ser
    50                  55                  60

Gln Thr Ala Arg Pro Gln Ala Pro Ala Thr Val Gly Leu Ala Phe Arg
65              70                  75                  80

Ala Asp Asp Thr Phe Glu Ala Leu Cys Ile Glu Pro Phe Ser Ser Pro
                85                  90                  95

Pro Glu Leu Pro Asp Val Met Lys
            100

<210> SEQ ID NO 3
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Tyr Val Lys Leu Ile Ser Ser Asp Gly His Glu Phe Ile Val Lys
1               5                   10                  15

Arg Glu His Ala Leu Thr Ser Gly Thr Ile Lys Ala Met Leu Ser Gly
                20                  25                  30

Pro Gly Gln Phe Ala Glu Asn Glu Thr Asn Glu Val Asn Phe Arg Glu
            35                  40                  45

Ile Pro Ser His Val Leu Ser Lys Val Cys Met Tyr Phe Thr Tyr Lys
    50                  55                  60

Val Arg Tyr Thr Asn Ser Ser Thr Glu Ile Pro Glu Phe Pro Ile Ala
65              70                  75                  80

Pro Glu Ile Ala Leu Glu Leu Leu Met Ala Ala Asn Phe Leu Asp Cys
                85                  90                  95

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
1               5
```

BRM TARGETING COMPOUNDS AND ASSOCIATED METHODS OF USE

CROSS-REFERENCE TO RELATED APPLICATION

This application claims the benefit of U.S. Provisional Application No. 63/036,811, filed on Jun. 9, 2020, the entirety of which is incorporated by reference herein.

SEQUENCE LISTING

The instant application contains a Sequence Listing which has been submitted electronically in ASCII format and is hereby incorporated by reference in its entirety. Said ASCII copy, created on Aug. 31, 2021, is named 105807_000171_SL.txt and is 4,020 bytes in size.

TECHNICAL FIELD

The description provides bifunctional compounds comprising a target protein binding moiety and a E3 ubiquitin ligase binding moiety, and associated methods of use. The bifunctional compounds are useful as modulators of targeted ubiquitination, especially with respect to Switch/Sucrose Non-Fermentable (SWI/SNF)-Related, Matrix-Associated, Actin-Dependent Regulator of Chromatin, Subfamily A, Member 2 (SMARCA2) (i.e. BRAHMA or BRM), which are degraded and/or otherwise inhibited by bifunctional compounds according to the present disclosure.

BACKGROUND

The human SWItch/Sucrose Non-Fermentable (SWI/SNF) complexes are ATP-dependent chromatin remodelers. These large complexes play important roles in essential cellular processes, such as transcription, DNA repair and replication by regulating DNA accessibility.

Mutations in the genes encoding up to 20 canonical SWI/SNF subunits are observed in nearly 20% of all human cancers with the highest frequency of mutations observed in rhabdoid tumors, female cancers (including ovarian, uterine, cervical and endometrial), lung adenocarcinoma, gastric adenocarcinoma, melanoma, esophageal, and renal clear cell carcinoma.

SMARCA2 (BRM) and SMARCA4 (BRG1) are the subunits containing catalytic ATPase domains and they are essential for the function of SWI/SNF in perturbation of histone-DNA contacts, thereby providing access points to transcription factors and cognate DNA elements that facilitate gene activation and repression.

SMARCA2 and SMARCA4 shares a high degree of homology (up to 75%). SMARCA4 is frequently mutated in primary tumors (i.e., deleted or inactivated), particularly in lung cancer (12%), melanoma, liver cancer and pancreatic cancer. SMARCA2 is one of the top essential genes in SMARCA4-mutant (deleted) cancer cell line. This is because SMARCA4 deleted cancer cells exclusively rely on SMARCA2 ATPase activity for their chromatin remodeling activity for cellular functions such as cell proliferation, survival and growth. Thus, targeting SMARCA2 may be promising therapeutic approach in SMARCA4-related or deficient cancers (genetic synthetic lethality).

Previous studies have demonstrated the strong synthetic lethality using gene expression manipulation such as RNAi; downregulating SMARCA2 gene expression in SMARCA4 mutated cancer cells results in suppression of cancer cell proliferation. However, SMARCA2/4 bromodomain inhibitors (e.g. PFI-3) exhibit none to minor effects on cell proliferation inhibition [Vangamudi et al. Cancer Res 2015]. This phenotypic discrepancy between gene expression downregulation and small molecule-based approach lead us to investigating protein degradation bispecific molecules in SMARCA4 deficient cancers.

SMARCA2 is also reported to play roles in multiple myeloma expressing t(4;14) chromosomal translocation [Chooi et al. Cancer Res abstract 2018]. SMARCA2 interacts with NSD2 and regulates gene expression such as PRL3 and CCND1. SMARCA2 gene expression downregulation with shRNA reduces cell cycle S phase and suppresses cell proliferation of t(4;14) MM cells.

Therapeutic compounds that inhibit SMARCA2 and/or SMARCA4 are needed.

SUMMARY

The present disclosure is directed to compounds of Formula (I):

$$\text{PTM-ULM} \qquad (I)$$

or a pharmaceutically acceptable salt or solvate thereof, wherein
PTM is a moiety of Formula IA:

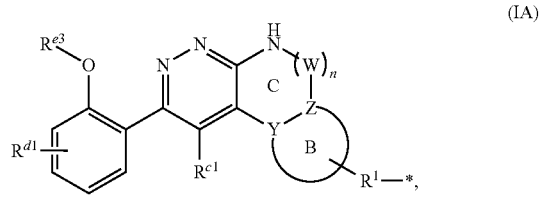

wherein
R$^1$ is a covalent bond, or chemical moiety that links PTM and ULM;
* is a point of attachment to ULM;
n=0-3;
W is optionally substituted —CH$_2$—, —C(O)—, —S(O)—, or —S(O)$_2$—, wherein when n=2 or 3, only one W may be —C(O)—, —S(O)—, or —S(O)$_2$—;
R$^{c1}$ and R$^{d1}$ are independently H, D, Halo, C$_{1-3}$ alkyl, C$_{1-3}$ haloalkyl, or C$_{1-4}$ alkoxyl;
R$^{e3}$ is H, —C(O)R$^f$, or —P(O)(OR$^g$)$_2$; wherein R$^f$ and R$^g$ are independently H, C$_{1-4}$ alkyl, C$_{1-4}$ substituted alkyl, C$_{3-8}$ cyclcoalkyl, C$_{3-8}$ substituted cyclcoalkyl, C$_{3-8}$ heterocyclcoalkyl, or C$_{3-8}$ substituted heterocyclcoalkyl;
Z and Y are each independently N, CR$^h$ wherein R$^h$=H or absent; or, if R$^1$ is attached to Z, then Z is C and Y is N or CR$^h$ wherein R$^h$ is H; or if R$^1$ is attached to Y, then Y is C and Z is N or CR$^h$ wherein R$^h$ is H;
B is an optionally substituted 5-7 membered cycloalkyl ring, an optionally substituted 5-7 membered heteroaryl ring, or an optionally substituted 5-7 membered heterocyclic ring, wherein ring B is fused to ring C through Y and Z; and
ULM is a small molecule E3 Ubiquitin Ligase binding moiety that binds a Von Hippel-Lindau E3 Ubiquitin Ligase.

DETAILED DESCRIPTION OF ILLUSTRATIVE EMBODIMENTS

Unless otherwise defined, all technical and scientific terms used herein have the same meaning as commonly understood by one of ordinary skill in the art to which this disclosure pertains. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (e.g., to at least one) of the grammatical object of the article unless the context clearly indicates otherwise. By way of example, "an element" means one element or more than one element.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are co-administered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder.

The term "ubiquitin ligase" refers to a family of proteins that facilitate the transfer of ubiquitin to a specific substrate protein, targeting the substrate protein for degradation. For example, an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

As used herein, the term "alkyl", by itself or as part of another substituent, means, unless otherwise stated, a straight or branched chain hydrocarbon radical having up to twelve carbon atoms. In some embodiments, the number of carbon atoms is designated (i.e., $C_1$-$C_8$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. Alkyl groups may be optionally substituted as provided herein. In some embodiments, the alkyl group is a $C_1$-$C_6$ alkyl; in some embodiments, it is a $C_1$-$C_4$ alkyl.

When a range of carbon atoms is used herein, for example, $C_1$-$C_6$, all ranges, as well as individual numbers of carbon atoms are encompassed. For example, "$C_1$-$C_3$" includes $C_1$-$C_3$, $C_1$-$C_2$, $C_2$-$C_3$, $C_1$, $C_2$, and $C_3$.

The term "optionally substituted", as used in combination with a substituent defined herein, means that the substituent may, but is not required to be, substituted with one or more suitable functional groups or other substituents as provided herein. For example, a substituent may be optionally substituted with one or more of: halo, cyano, $C_{1-6}$ alkyl, $C_{3-6}$ cycloalkyl, $C_{2-6}$ alkenyl, $C_{2-6}$ alkynyl, halo($C_{1-6}$)alkyl, $C_{1-6}$ alkoxy, halo($C_{1-6}$ alkoxy), $C_{1-6}$ alkylthio, $C_{1-6}$ alkylamino, $NH_2$, $NH(C_{1-6}$ alkyl), $N(C_{1-6}$ alkyl)$_2$, $NH(C_{1-6}$ alkoxy), $N(C_{1-6}$ alkoxy)$_2$, —C(O)NHC$_{1-6}$ alkyl, —C(O)N(C$_{1-6}$ alkyl)$_2$, —C(O)NH$_2$, —C(O)C$_{1-6}$ alkyl, —C(O)$_2$C$_{1-6}$ alkyl, —NHCO(C$_{1-6}$ alkyl), —N(C$_{1-6}$ alkyl)CO(C$_{1-6}$ alkyl), —S(O)C$_{1-6}$ alkyl, —S(O)$_2$C$_{1-6}$ alkyl, oxo, 6-12 membered aryl, benzyl, pyridinyl, pyrazolyl, thiazolyl, isothiazolyl, or other 5 to 12 membered heteroaryl groups. In some embodiments, each of the above optional substituents are themselves optionally substituted by one or two groups.

The term "cycloalkyl" as used herein refers to a 3-12 membered cyclic alkyl group, and includes bridged and spirocycles (e.g., adamantine). Cycloalkyl groups may be fully saturated or partially unsaturated. The term "cycloalkyl" also includes multiple condensed ring systems (e.g., ring systems comprising 2, 3 or 4 rings) wherein a single cycloalkyl ring (as defined above) can be condensed with one or more groups selected from heterocycles, carbocycles, aryls, or heteroaryls to form the multiple condensed ring system. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a cycloalkyl) can be at any position of the cycloalkylic ring. Examples of cycloalkyl groups include cyclopropyl, cyclobutyl, cyclopentyl, cycloheptyl, cyclohexyl, cycloheptyl, cyclooctyl, indenyl, bicyclo[2.2.1]heptanyl, bicyclo[3.1.1]heptanyl, bicyclo[4.1.0]heptanyl, spiro[3.3]heptanyl, and spiro[3.4]octanyl. In some embodiments, the cycloalkyl group is a 3-7 membered cycloalkyl.

The term "akenyl" as used herein refers to $C_2$-$C_{12}$ alkyl group that contains at least one carbon-carbon double bond. In some embodiments, the alkenyl group is optionally substituted. In some embodiments, the alkenyl group is a $C_2$-$C_6$ alkenyl.

The term "akynyl" as used herein refers to $C_2$-$C_{12}$ alkyl group that contains at least one carbon-carbon triple bond. In some embodiments, the alkenyl group is optionally substituted. In some embodiments, the alkynyl group is a $C_2$-$C_6$ alkynyl.

The terms "alkoxy," "alkylamino" and "alkylthio", are used in their conventional sense, and refer to those alkyl groups attached to the remainder of the molecule via an oxygen atom ("oxy"), an amino group ("amino") or thio group. The term "alkylamino" includes mono-di-alkylamino groups, the alkyl portions can be the same or different.

The terms "halo" or "halogen", by itself or as part of another substituent, means a fluorine, chlorine, bromine, or iodine atom.

The term "heteroalkyl" refers to an alkyl group in which one or more carbon atom has been replaced by a heteroatom selected from S, O, P and N. Exemplary heteroalkyls include alkyl ethers, secondary and tertiary alkyl amines, alkyl amides, alkyl sulfides, and the like. The group may be a terminal group or a bridging group. As used herein reference to the normal chain when used in the context of a bridging group refers to the direct chain of atoms linking the two terminal positions of the bridging group.

The term "aryl" as used herein refers to a single, all carbon aromatic ring or a multiple condensed all carbon ring system wherein at least one of the rings is aromatic. For example, in certain embodiments, an aryl group has 6 to 12 carbon atoms. Aryl includes a phenyl radical. Aryl also includes multiple condensed ring systems (e.g., ring systems comprising 2, 3 or 4 rings) having about 9 to 12 carbon atoms in which at least one ring is aromatic and wherein the other rings may be aromatic or not aromatic. Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the aromatic ring. Non-limiting examples of aryl groups include, but are not limited to, phenyl, indenyl, naphthyl, 1,2,3,4-tetrahydronaphthyl, and the like.

The term "heteroaryl" as used herein refers to a single aromatic ring that has at least one atom other than carbon in the ring, wherein the atoms are selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example a naphthyridinyl such as 1,8-naphthyridinyl), heterocycles, (to form for example a 1, 2, 3, 4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. A heteroaryl (a single aromatic ring or multiple condensed ring system) can also have about 5 to 12 or about 5 to 10 members within the heteroaryl ring. Multiple condensed ring systems may be optionally substituted with one or more (e.g., 1, 2, 3 or 4) oxo groups on the carbocycle or heterocycle portions of the condensed ring. The rings of a multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the heteroaryl ring. It is also to be understood that the point of attachment for a heteroaryl or heteroaryl multiple condensed ring system can be at any suitable atom of the heteroaryl ring including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclopenta[1,2-c]pyrazole. In one embodiment the term "heteroaryl" refers to a single aromatic ring containing at least one heteroatom. For example, the term includes 5-membered and 6-membered monocyclic aromatic rings that include one or more heteroatoms. Non-limiting examples of heteroaryl include but are not limited to pyridyl, furyl, thiazole, pyrimidine, oxazole, and thiadiazole.

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from heterocycles (to form for example a 1,8-decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. Accordingly, a heterocycle (a single saturated or single partially unsaturated ring or multiple condensed ring system) has about 3-20 atoms including about 1-6 heteroatoms within the heterocycle ring system. It is also to be understood that the point of attachment of a multiple condensed ring system (as defined above for a heterocylyl) can be at any position of the heterocyclic ring. It is also to be understood that the point of attachment for a heterocycle or heterocycle multiple condensed ring system can be at any suitable atom of the heterocyclic ring including a carbon atom and a heteroatom (e.g., a nitrogen). In one embodiment the term heterocycle includes a $C_{2-20}$ heterocycle. In one embodiment the term heterocycle includes a $C_{2-7}$ heterocycle. In one embodiment the term heterocycle includes a $C_{2-5}$ heterocycle. In one embodiment the term heterocycle includes a $C_{2-4}$ heterocycle. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one N-methylpiperidine, imidazolidine, pyrazolidine, butyrolactam, valerolactam, imidazolidinone, hydantoin, dioxolane, phthalimide, 1,4-dioxane, thiomorpholine, thiomorpholine-S-oxide, thiomorpholine-S,S-oxide, pyran, 3-pyrroline, thiopyran, pyrone, tetrhydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R, 4R)-2-oxa-5-azabicyclo[2.2.2]octane and pyrrolidin-2-one. In one embodiment the term "heterocycle" refers to a monocyclic, saturated or partially unsaturated, 3-8 membered ring having at least one heteroatom. For example, the term includes a monocyclic, saturated or partially unsaturated, 4, 5, 6, or 7 membered ring having at least one heteroatom. Non-limiting examples of heterocycle include aziridine, azetidine, pyrrolidine, piperidine, piperidine, piperazine, oxirane, morpholine, and thiomorpholine. The term "9- or 10-membered heterobicycle" as used herein refers to a partially unsaturated or aromatic fused bicyclic ring system having at least one heteroatom. For example, the term 9- or 10-membered heterobicycle includes a bicyclic ring system having a benzo ring fused to a 5-membered or 6-membered saturated, partially unsaturated, or aromatic ring that contains one or more heteroatoms.

As used herein, the term "heteroatom" is meant to include oxygen (O), nitrogen (N), sulfur (S) and silicon (Si). The nitrogen and sulfur can be in an oxidized form when feasible.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space, e.g., enantiomers, diastereomers, tautomers.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, e.g., in humans.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

A "solvate" refers to a physical association of a compound of Formula I with one or more solvent molecules.

"Treating" or "treatment" of any disease or disorder refers, in one embodiment, to ameliorating the disease or disorder (e.g., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

In one aspect, the disclosure is directed to a compound of Formula (I):

PTM-ULM            (I)

or a pharmaceutically acceptable salt or solvate thereof, wherein PTM is a moiety of Formula IA:

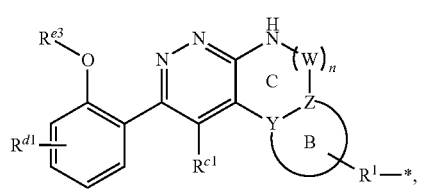

(IA)

wherein
$R^1$ is a covalent bond, or chemical moiety that links PTM and ULM;
* is a point of attachment to ULM;
n=0-3;
each W is independently optionally substituted —CH$_2$—, —C(O)—, —S(O)—, or —S(O)$_2$—, wherein when n=2 or 3, only one W may be —C(O)—, —S(O)—, or —S(O)$_2$—;
$R^{c1}$ and $R^{d1}$ are independently H, D, Halo, $C_{1-3}$ alkyl, $C_{1-3}$ haloalkyl, or $C_{1-4}$ alkoxyl;

$R^{e3}$ is H, —C(O)$R^f$, or —P(O)(O$R^g$)$_2$; wherein $R^f$ and $R^g$ are independently H, $C_{1-4}$ alkyl, $C_{1-4}$ substituted alkyl, $C_{3-8}$ cyclcoalkyl, $C_{3-8}$ substituted cyclcoalkyl, $C_{3-8}$ heterocyclcoalkyl, or $C_{3-8}$ substituted heterocyclcoalkyl;

Z and Y are each independently N, or CR$^h$ wherein R$^h$=H or absent or, if W is attached to Z, then Z is C and Y is N or CR$^h$ wherein R$^h$ is H; or if W is attached to Y, then Y is C and Z is N or CR$^h$ wherein R$^h$ is H;

B is an optionally substituted 5-7 membered cycloalkyl ring, an optionally substituted 5-7 membered heteroaryl ring, or an optionally substituted 5-7 membered heterocyclic ring, wherein ring B is fused to ring C through Y and Z; and ULM is a small molecule E3 Ubiquitin Ligase binding moiety that binds a Von Hippel-Lindau E3 Ubiquitin Ligase.

In some aspects, the compounds of Formula I include a protein targeting moiety (PTM). In some aspects, the PTM in the compounds of Formula I is a moiety of Formula IA

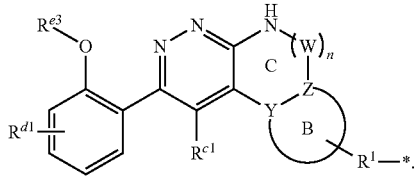

(IA)

According to the disclosure, B is a ring fused to ring "C" via Y and Z.

In some aspects, B in Formula IA is an optionally substituted 5-7 membered cycloalkyl ring. an optionally substituted 5-7 membered heteroaryl ring, or an optionally substituted 5-7 membered heterocyclic ring.

In some embodiments, B in Formula IA is an optionally substituted 5-7 membered cycloalkyl ring.

In some embodiments, B in Formula IA is an optionally substituted 5-7 membered cycloalkyl ring wherein the optional substituents are hydroxy, halogen, alkoxy, alkyl, haloalkyl, amino, alkylamino, or cyano.

In some embodiments, B in Formula IA is an optionally substituted 5-7 membered heteroaryl ring.

In some embodiments, B in Formula IA is an optionally substituted 5-7 membered heteroaryl ring wherein the optional substituents are hydroxy, halogen, alkoxy, alkyl, haloalkyl, amino, alkylamino, or cyano.

In other embodiments, B in Formula IA is an optionally substituted 5-7 membered heterocyclic ring.

In some embodiments, B in Formula IA is an optionally substituted 5-7 membered heterocyclic ring wherein the optional substituents are hydroxy, halogen, alkoxy, alkyl, haloalkyl, amino, alkylamino, cyano.

In some aspects, n in Formula IA is 0-3. In some embodiments, n=0. In other embodiments, n=1. In other embodiments, n=2. In other embodiments, n=3.

In some aspects, each W in Formula IA is independently optionally substituted —CH$_2$—, —C(O)—, —S(O)—, or —S(O)$_2$—, wherein when n=2 or 3, only one W may be —C(O)—, —S(O)—, or —S(O)$_2$—.

In some embodiments, W in Formula IA is optionally substituted —CH$_2$—. In other embodiments, W in Formula IA is —CH$_2$—.

In some embodiments, W in Formula IA is optionally substituted —CH$_2$— wherein the optional substituent is an alkyl group, such as, for example methyl (—CH$_3$), ethyl, propyl, and the like.

In other embodiments, W in Formula IA is —C(CH$_3$)H—.

In some embodiments, W in Formula IA is —C(O)—.

In some embodiments, W in Formula IA is —S(O)—.

In some embodiments, W in Formula IA is optionally substituted —S(O)$_2$—.

In embodiments of the disclosure wherein n is 2 or 3, then only one W may be —C(O)—, —S(O)—, or —S(O)$_2$—.

In some aspects, $R^{c1}$ and $R^{d1}$ in Formula IA are independently H, D, Halo, $C_{1-3}$ alkyl, $C_{1-3}$ haloalkyl, or $C_{1-4}$ alkoxyl.

In some embodiments, $R^{c1}$ is H.

In some embodiments, $R^{c1}$ is D.

In some embodiments, $R^{c1}$ is halo, e.g., —F, —Cl, —Br, or —I.

In some embodiments, $R^{c1}$ is $C_{1-3}$ alkyl, e.g., —$C_1$ alkyl, —$C_2$ alkyl, —$C_3$ alkyl, —CH$_3$, —CH$_2$CH$_3$, and the like.

In some embodiments, $R^{c1}$ is $C_{1-3}$ haloalkyl, e.g., —$C_1$ haloalkyl, —$C_2$ haloalkyl, —$C_3$ haloalkyl, —CF$_3$, —CH$_2$CF$_3$, and the like.

In some embodiments, $R^{c1}$ is $C_{1-4}$ alkoxyl, e.g., —$C_1$ alkoxyl, —$C_2$ alkoxyl, —$C_3$ alkoxyl, —$C_4$ alkoxyl, —OCH$_3$, —OCH$_2$CH$_3$, and the like.

In some embodiments, $R^{d1}$ is H.

In some embodiments, $R^{d1}$ is D.

In some embodiments, $R^{d1}$ is halo, e.g., —F, —Cl, —Br, or —I.

In some embodiments, $R^{d1}$ is $C_{1-3}$ alkyl, e.g., —$C_1$ alkyl, —$C_2$ alkyl, —$C_3$ alkyl, —CH$_3$, —CH$_2$CH$_3$, and the like.

In some embodiments, $R^{d1}$ is $C_{1-3}$ haloalkyl, e.g., —$C_1$ haloalkyl, —$C_2$ haloalkyl, —$C_3$ haloalkyl, —CF$_3$, —CH$_2$CF$_3$, and the like.

In some embodiments, $R^{d1}$ is $C_{1-4}$ alkoxyl, e.g., —$C_1$ alkoxyl, —$C_2$ alkoxyl, —$C_3$ alkoxyl, —$C_4$ alkoxyl, —OCH$_3$, —OCH$_2$CH$_3$, and the like.

In some aspects, $R^{e3}$ in Formula IA is H, —C(O)$R^f$, or —P(O)(O$R^g$)$_2$; wherein $R^f$ and $R^g$ are independently H, $C_{1-4}$ alkyl, $C_{1-4}$ substituted alkyl, $C_{3-8}$ cyclcoalkyl, $C_{3-8}$ substituted cyclcoalkyl, $C_{3-8}$ heterocyclcoalkyl, or $C_{3-8}$ substituted heterocyclcoalkyl.

In some embodiments, $R^{e3}$ is H.

In other embodiments, $R^{e3}$ is —C(O)$R^f$ wherein $R^f$ is H, $C_{1-4}$ alkyl, $C_{1-4}$ substituted alkyl, $C_{3-8}$ cyclcoalkyl, $C_{3-8}$ substituted cyclcoalkyl, $C_{3-8}$ heterocyclcoalkyl, or $C_{3-8}$ substituted heterocyclcoalkyl.

In other embodiments, $R^{e3}$ is —C(O)$R^f$ wherein $R^f$ is H.

In other embodiments, $R^{e3}$ is —C(O)$R^f$ wherein $R^f$ is $C_{1-4}$ alkyl, e.g., —$C_1$ alkyl, —$C_2$ alkyl, —$C_3$ alkyl, —$C_4$ alkyl, —CH$_3$, —CH$_2$CH$_3$, and the like.

In other embodiments, $R^{e3}$ is —C(O)$R^f$ wherein $R^f$ is $C_{1-4}$ substituted alkyl, e.g., —$C_1$ substituted alkyl, —$C_2$ substituted alkyl, —$C_3$ substituted alkyl, and —$C_4$ substituted alkyl.

In other embodiments, $R^{e3}$ is —C(O)$R^f$ wherein $R^f$ is $C_{3-8}$ cyclcoalkyl, e.g., $C_3$ cyclcoalkyl, $C_4$ cyclcoalkyl, $C_5$ cyclcoalkyl, $C_6$ cyclcoalkyl, $C_7$ cyclcoalkyl, and $C_8$ cyclcoalkyl.

In other embodiments, $R^{e3}$ is —C(O)$R^f$ wherein $R^f$ is $C_{3-8}$ substituted cyclcoalkyl, e.g., $C_3$ substituted cyclcoalkyl, $C_4$ substituted cyclcoalkyl, $C_5$ substituted cyclcoalkyl, $C_6$ substituted cyclcoalkyl, $C_7$ substituted cyclcoalkyl, and $C_8$ substituted cyclcoalkyl.

In other embodiments, $R^{e3}$ is —C(O)$R^f$ wherein $R^f$ is $C_{3-8}$ heterocyclcoalkyl, e.g., $C_3$ heterocyclcoalkyl, $C_4$ heterocyclcoalkyl, $C_5$ heterocyclcoalkyl, $C_6$ heterocyclcoalkyl, $C_7$ heterocyclcoalkyl, and $C_8$ heterocyclcoalkyl.

In other embodiments, $R^{e3}$ is —C(O)$R^f$ wherein $R^f$ is $C_{3-8}$ substituted heterocyclcoalkyl, e.g., $C_3$ substituted heterocyclcoalkyl, $C_4$ substituted heterocyclcoalkyl, $C_5$ substituted heterocyclcoalkyl, $C_6$ substituted heterocyclcoalkyl, $C_7$ substituted heterocyclcoalkyl, and $C_8$ substituted heterocyclcoalkyl.

In other embodiments, $R^{e3}$ is —P(O)(O$R^g$)$_2$; wherein each $R^g$ is independently H, $C_{1-4}$ alkyl, $C_{1-4}$ substituted alkyl, $C_{3-8}$ cyclcoalkyl, $C_{3-8}$ substituted cyclcoalkyl, $C_{3-8}$ heterocyclcoalkyl, or $C_{3-8}$ substituted heterocyclcoalkyl.

In other embodiments, $R^{e3}$ is —P(O)(O$R^g$)$_2$; wherein each $R^g$ is H.

In other embodiments, $R^{e3}$ is —P(O)(O$R^g$)$_2$; wherein each $R^g$ is $C_{1-4}$ alkyl, e.g., —$C_1$ alkyl, —$C_2$ alkyl, —$C_3$ alkyl, —$C_4$ alkyl, —CH$_3$, —CH$_2$CH$_3$, and the like.

In other embodiments, $R^{e3}$ is —P(O)(O$R^g$)$_2$; wherein one $R^g$ is H and the other $R^g$ is $C_{1-4}$ alkyl, e.g., —$C_1$ alkyl, —$C_2$ alkyl, —$C_3$ alkyl, —$C_4$ alkyl, —CH$_3$, —CH$_2$CH$_3$, and the like.

In other embodiments, $R^{e3}$ is —P(O)(O$R^g$)$_2$; wherein at least one $R^g$ is $C_{1-4}$ substituted alkyl, e.g., —$C_1$ substituted alkyl, —$C_2$ substituted alkyl, —$C_3$ substituted alkyl, and —$C_4$ substituted alkyl.

In other embodiments, $R^{e3}$ is —P(O)(O$R^g$)$_2$; wherein at least one W is $C_{3-8}$ cyclcoalkyl, e.g., $C_3$ cyclcoalkyl, $C_4$ cyclcoalkyl, $C_5$ cyclcoalkyl, $C_6$ cyclcoalkyl, $C_7$ cyclcoalkyl, and $C_8$ cyclcoalkyl.

In other embodiments, $R^{e3}$ is —P(O)(O$R^g$)$_2$; wherein at least one $R^g$ is $C_{3-8}$ substituted cyclcoalkyl, e.g., $C_3$ substituted cyclcoalkyl, $C_4$ substituted cyclcoalkyl, $C_5$ substituted cyclcoalkyl, $C_6$ substituted cyclcoalkyl, $C_7$ substituted cyclcoalkyl, and $C_8$ substituted cyclcoalkyl.

In other embodiments, $R^{e3}$ is —P(O)(O$R^g$)$_2$; wherein at least one $R^g$ is $C_{3-8}$ heterocyclcoalkyl, e.g., $C_3$ heterocyclcoalkyl, $C_4$ heterocyclcoalkyl, $C_5$ heterocyclcoalkyl, $C_6$ heterocyclcoalkyl, $C_7$ heterocyclcoalkyl, and $C_8$ heterocyclcoalkyl.

In other embodiments, $R^{e3}$ is —P(O)(O$R^g$)$_2$; wherein at least one $R^g$ is $C_{3-8}$ substituted heterocyclcoalkyl, e.g., $C_3$ substituted heterocyclcoalkyl, $C_4$ substituted heterocyclcoalkyl, $C_5$ substituted heterocyclcoalkyl, $C_6$ substituted heterocyclcoalkyl, $C_7$ substituted heterocyclcoalkyl, and $C_8$ substituted heterocyclcoalkyl.

In some aspects, Z and Y in Formula IA are each independently N, or C$R^h$ wherein $R^h$=H or may be absent when n=1-3 such that a double bond is formed between Z and Y, or, if $R^1$ is attached to Z, then Z is C and Y is N or C$R^h$ wherein $R^h$ is H; or if $R^1$ is attached to Y, then Y is C and Z is N or C$R^h$ wherein $R^h$ is H. Examples of these embodiments include:

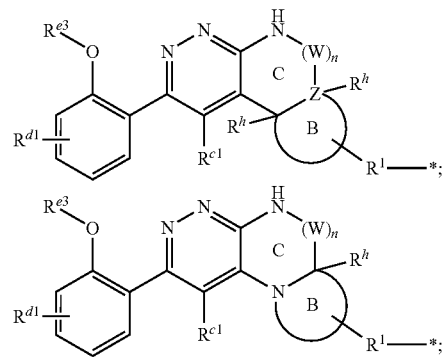

-continued

[Chemical structure diagrams showing pyridazine-containing compounds with substituents $R^{e3}$, $R^{d1}$, $R^{c1}$, $R^h$, ring B with $(W)_n$, and variations with $R^1$—* attachment points; one structure notes (n = 1-3); structures include variants with Z linker and stereochemistry markings]

and

[Final structure with $R^h$ group]

In some embodiments, Z is N.

In other embodiments, Z is $CR^h$ wherein $R^h$=H.

In other embodiments, Z is $CR^h$ wherein $R^h$=absent, and Z is bonded to Y by a double bond.

In some embodiments, Z is C and is attached to $R^1$.

In some embodiments, Y is N.

In other embodiments, Y is $CR^h$ wherein $R^h$=H.

In other embodiments, Y is $CR^h$ wherein $R^h$=absent, and Y is bonded to Z by a double bond.

In some embodiments, Y is C and is attached to $R^1$.

In some embodiments, the PTM is a moiety of Formula IA wherein * is a point of attachment to ULM.

In some aspects, $R^1$ in Formula IA is a covalent bond, or chemical moiety that links PTM and ULM.

In some embodiments, $R^1$ in Formula IA is a covalent bond.

In other embodiments, $R^1$ in Formula IA is a chemical moiety that links PTM and ULM.

Chemical moieties that are used to link PTM and ULM moieties are known in the art. These moieties are sometimes referred to as "linkers" in the art. In some embodiments, $R^1$ in Formula IA is a chemical moiety that is used to link a PTM and ULM that is known in the art.

In some embodiments, $R^1$ in Formula IA is a chemical moiety that is used to link a PTM and ULM as described in U.S. Patent Application Publication No. 2019/0300521, the entirety of which is incorporated by reference herein.

In other embodiments, $R^1$ in Formula IA is a chemical moiety that is used to link a PTM and ULM as described in U.S. Patent Application Publication No. 2019/0255066, the entirety of which is incorporated by reference herein.

In other embodiments, $R^1$ in Formula IA is a chemical moiety that is used to link a PTM and ULM as described in WO 2019/084030, the entirety of which is incorporated by reference herein.

In other embodiments, $R^1$ in Formula IA is a chemical moiety that is used to link a PTM and ULM as described in WO 2019/084026, the entirety of which is incorporated by reference herein.

In some embodiments, $R^1$ in Formula IA is a chemical structural unit represented by the formula:

$$-(A)_q-,$$

wherein:

q is an integer from 1 to 14;

each A is independently selected from the group consisting of $CR^{1a}R^{1b}$, O, S, SO, $SO_2$, $NR^{1c}$, $SO_2NR^{1c}$, $SONR^{1c}$, $SO(=NR^{1c})$, $SO(=NR^{1c})NR^{1d}$, $CONR^{1c}$, $NR^{1c}CONR^{1d}$, $NR^{1c}C(O)O$, $NR^{1c}SO_2NR^{1d}$, CO, $CR^{1a}=CR^{1b}$, $SiR^{1a}R^{1b}$, $P(O)R^{1a}$, $P(O)OR^{1a}$, $(CR^{1a}R^{1b})_{1-4}$, $—(CR^{1a}R^{1b})_{1-4}O(CR^{1a}R^{1b})_{1-4}$, $—(CR^{1a}R^{1b})_{1-4}S(CR^{1a}R^{1b})_{1-4}$, $—(CR^{1a}R^{1b})_{1-4}NR(CR^{1a}R^{1b})_{1-4}$, $NR^{1c}C(=NCN)NR^{1d}$, $NR^{1c}C(=NCN)$, $NR^{1c}C(=CNO_2)NR^{1d}$, 3-11 membered cycloalkyl, optionally substituted with 0-6 $R^{1a}$ and/or $R^{1b}$ groups, 3-11 membered heterocyclyl optionally substituted with 0-6 $R^{1a}$ and/or $R^{1b}$ groups, aryl optionally substituted with 0-6 $R^{1a}$ and/or $R^{1b}$ groups, heteroaryl optionally substituted with 0-6 $R^{1a}$ and/or $R^{1b}$ groups, and $R^{1a}$, $R^{1b}$, $R^{1c}$, $R^{1d}$ and $R^{1e}$ are each independently, —H, D, -halo, —$C_1$-$C_8$alkyl, —$C_1$-$C_6$haloalkyl, —O—$C_1$-$C_8$alkyl, —S—$C_1$-$C_8$alkyl, —NH$C_1$-$C_8$alkyl, —N($C_1$-$C_8$alkyl)$_2$, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)($C_1$-$C_8$alkyl), —OH, —NH$_2$, —SH, —SO$_2C_1$-$C_8$alkyl, SO(NH)$C_1$-$C_8$alkyl, P(O)(O$C_1$-$C_8$alkyl)($C_1$-$C_8$alkyl), —P(O)(O$C_1$-$C_8$alkyl)$_2$, —C≡C—$C_1$-$C_8$alkyl, —C≡CH, —CH=CH($C_1$-$C_8$alkyl), —C($C_1$-$C_8$alkyl)=CH($C_1$-$C_8$alkyl), —C(($C_1$-$C_8$alkyl))=C($C_1$-$C_8$alkyl)$_2$, —Si(OH)$_3$, —Si($C_1$-$C_8$alkyl)$_3$, —Si(OH)($C_1$-$C_8$alkyl)$_2$, —C(O)$C_1$-$C_8$alkyl, —CO$_2$H, —CN, —CF$_3$, —CHF$_2$, —CH$_2$F, —NO$_2$, —SF$_5$, —SO$_2$NH$C_1$-$C_8$alkyl, —SO$_2$N($C_1$-$C_8$alkyl)$_2$, —SO(NH)NH$C_1$-$C_8$alkyl, —SO(NH)N($C_1$-$C_8$alkyl)$_2$, —SONH$C_1$-$C_8$alkyl, —SON($C_1$-$C_8$alkyl)$_2$, —CONH$C_1$-$C_8$alkyl, —CON($C_1$-$C_8$alkyl)$_2$, —N($C_1$-$C_8$alkyl)CONH($C_1$-$C_8$alkyl), —N($C_1$-$C_8$alkyl)CON($C_1$-$C_8$alkyl)$_2$, —NHCONH($C_1$-$C_8$alkyl), —NHCON($C_1$-$C_8$alkyl)$_2$, —NHCONH$_2$, —N($C_1$-$C_8$alkyl)SO$_2$NH($C_1$-$C_8$alkyl), —N($C_1$-$C_8$alkyl)SO$_2$N($C_1$-$C_8$alkyl)$_2$, —NHSO$_2$NH($C_1$-$C_8$alkyl), —NHSO$_2$N($C_1$-$C_8$alkyl)$_2$, or —NHSO$_2$NH$_2$, or where the context permits, $R^{1a}$ or $R^{1b}$, are linked to other groups, or to each other, to form a cycloalkyl and/or a heterocyclyl moiety, optionally substituted with 0-4 $R^{1e}$ groups.

In these embodiments, q represents the number of connected A groups. For example, when q=1, -(A)$_q$- is -A$_1$-; when q=2, -(A)$_q$- is -A$_1$-A$_2$-; when q=3, -(A)$_q$- is -A$_1$-A$_2$-A$_3$-; when q=4, -(A)$_q$- is -A$_1$-A$_2$-A$_3$-A$_4$-; when q=5, -(A)$_q$- is -A$_1$-A$_2$-A$_3$-A$_4$-A$_5$-; when q=6, -(A)$_q$- is -A$_1$-A$_2$-A$_3$-A$_4$-A$_5$-A$_6$-; when q=7, -(A)$_q$- is -A$_1$-A$_2$-A$_3$-A$_4$-A$_5$-A$_6$-A$_7$-; when q=8, -(A)$_q$- is -A$_1$-A$_2$-A$_3$-A$_4$-A$_5$-A$_6$-A$_7$-A$_8$-; when q=9, $-(A)_q-$ is $-A_1-A_2-A_3-A_4-A_5-A_6-A_7-A_8-A_9-$; when q=10, $-(A)_q-$ is $-A_1-A_2-A_3-A_4-A_5-A_6-A_7-A_8-A_9-A_{10}-$; when q=11, $-(A)_q-$ is $-A_1-A_2-A_3-A_4-A_5-A_6-A_7-A_8-A_9-A_{10}-A_{11}-$; when q=12, $-(A)_q-$ is $-A_1-A_2-A_3-A_4-A_5-A_6-A_7-A_8-A_9-A_{10}-A_{11}-A_{12}-$; when q=13, $-(A)_q-$ is $-A_1-A_2-A_3-A_4-A_5-A_6-A_7-A_8-A_9-A_{10}-A_{11}-A_{12}-A_{13}-$; and when q=14, $-(A)_q-$ is $-A_1-A_2-A_3-A_4-A_5-A_6-A_7-A_8-A_9-A_{10}-A_{11}-A_{12}-A_{13}-A_{14}-$.

In some embodiments, q=4 and $R^t$ is a chemical moiety represented by the formula: $-A_1-A_2-A_3-A_4-$, wherein each of $A_{1-4}$ is independently selected from the group consisting of O, S, SO, $SO_2$, $NR^{1c}$, $SO_2NR^{1c}$, $SONR^{1c}$, $SO(=NR^{1c})$, $SO(=NR^{1c})NR^{1d}$, $CONR^{1c}$, $NR^{1c}CONR^{1d}$, $NR^{1c}C(O)O$, $NR^{1c}SO_2NR^{1d}$, CO, $CR^{1a}=CR^{1b}$, C≡C, $SiR^{1a}R^{1b}$, $P(O)R^{1a}$, $P(O)OR^{1a}$, $(CR^{1a}R^{1b})_{1-4}$, $-(CR^{1a}R^{1b})_{1-4}O(CR^{1a}R^{1b})_{1-4}$, $-(CR^{1a}R^{1b})_{1-4}S(CR^{1a}R^{1b})_{1-4}$, $-(CR^{1a}R^{1b})_{1-4}NR(CR^{1a}R^{1b})_{1-4}$, optionally substituted 3-11 membered cycloalkyl, 3-11 membered heterocyclyl, aryl, and heteroaryl;

wherein $R^{1a}$ and $R^{1b}$ are each independently selected from the group consisting of —H, D, -halo, —$C_1$-$C_8$alkyl, —O—$C_1$-$C_8$alkyl, —$C_1$-$C_6$haloalkyl, —S—$C_1$-$C_8$alkyl, —NH$C_1$-$C_8$alkyl, —N($C_1$-$C_8$alkyl)$_2$, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)($C_1$-$C_8$alkyl), —OH, —NH$_2$, —SH, —SO$_2C_1$-$C_8$alkyl, SO(NH)$C_1$-$C_8$alkyl, P(O)(O$C_1$-$C_8$alkyl)($C_1$-$C_8$alkyl), —P(O)(O$C_1$-$C_8$alkyl)$_2$, —C≡C—$C_1$-$C_8$alkyl, —C≡CH, —CH=CH($C_1$-$C_8$alkyl), —C($C_1$-$C_8$alkyl)=CH($C_1$-$C_8$alkyl), —C($C_1$-$C_8$alkyl)=C($C_1$-$C_8$alkyl)$_2$, —Si(OH)$_3$, —Si($C_1$-$C_8$alkyl)$_3$, —Si(OH)($C_1$-$C_8$alkyl)$_2$, —C(O)$C_1$-$C_8$alkyl, —CO$_2$H, —CN, —NO$_2$, —SF$_5$, —SO$_2$NH$C_1$-$C_8$alkyl, —SO$_2$N($C_1$-$C_8$alkyl)$_2$, —SO(NH)NH$C_1$-$C_8$alkyl, —SO(NH)N($C_1$-$C_8$alkyl)$_2$, —SONH$C_1$-$C_8$alkyl, —SON($C_1$-$C_8$alkyl)$_2$, —CONH$C_1$-$C_8$alkyl, —CON($C_1$-$C_8$alkyl)$_2$, —N($C_1$-$C_8$alkyl)CONH($C_1$-$C_8$alkyl), —N($C_1$-$C_8$alkyl)CON($C_1$-$C_8$alkyl)$_2$, —NHCONH($C_1$-$C_8$alkyl), —NHCON($C_1$-$C_8$alkyl)$_2$, —NHCONH$_2$, —N($C_1$-$C_8$alkyl)SO$_2$NH($C_1$-$C_8$alkyl), —N($C_1$-$C_8$alkyl)SO$_2$N($C_1$-$C_8$alkyl)$_2$, —NHSO$_2$NH($C_1$-$C_8$alkyl), —NHSO$_2$N($C_1$-$C_8$alkyl)$_2$, or —NHSO$_2$NH$_2$; and $R^{1c}$ and $R^{1d}$ are each independently selected from the group consisting of H, D, optionally substituted $C_{1-4}$ alkyl, $C_{3-8}$ cyclcoalkyl, $C_{3-8}$ heterocyclcoalkyl, aryl, or heteroaryl.

In other embodiments, q=3 and $R^t$ is a chemical moiety represented by the formula: $-A_1-A_2-A_3-$, wherein each of $A_{1-3}$ is independently selected from the group consisting of O, S, SO, $SO_2$, $NR^{1c}$, $SO_2NR^{1c}$, $SONR^{1c}$, $SO(=NR^{1c})$, $SO(=NR^{1c})NR^{1d}$, $CONR^{1c}$, $NR^{1c}CONR^{1d}$, $NR^{1c}C(O)O$, $NR^{1c}SO_2NR^{1d}$, CO, $CR^{1a}=CR^{1b}$, C≡C, $SiR^{1a}R^{1b}$, $P(O)R^{1a}$, $P(O)OR^{1a}$, $(CR^{1a}R^{1b})_{1-4}$, $-(CR^{1a}R^{1b})_{1-4}O(CR^{1a}R^{1b})_{1-4}$, $-(CR^{1a}R^{1b})_{1-4}S(CR^{1a}R^{1b})_{1-4}$, $-(CR^{1a}R^{1b})_{1-4}NR(CR^{1a}R^{1b})_{1-4}$, optionally substituted 3-11 membered cycloalkyl, 3-11 membered heterocyclyl, aryl, and heteroaryl;

wherein $R^{1a}$ and $R^{1b}$ are each independently selected from the group consisting of —H, D, -halo, —$C_1$-$C_8$alkyl, —O—$C_1$-$C_8$alkyl, —$C_1$-$C_6$haloalkyl, —S—$C_1$-$C_8$alkyl, —NH$C_1$-$C_8$alkyl, —N($C_1$-$C_8$alkyl)$_2$, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)($C_1$-$C_8$alkyl), —OH, —NH$_2$, —SH, —SO$_2C_1$-$C_8$alkyl, SO(NH)$C_1$-$C_8$alkyl, P(O)(O$C_1$-$C_8$alkyl)($C_1$-$C_8$alkyl), —P(O)(O$C_1$-$C_8$alkyl)$_2$, —C≡C—$C_1$-$C_8$alkyl, —C≡CH, —CH=CH($C_1$-$C_8$alkyl), —C($C_1$-$C_8$alkyl)=CH($C_1$-$C_8$alkyl), —C($C_1$-$C_8$alkyl)=C($C_1$-$C_8$alkyl)$_2$, —Si(OH)$_3$, —Si($C_1$-$C_8$alkyl)$_3$, —Si(OH)($C_1$-$C_8$alkyl)$_2$, —C(O)$C_1$-$C_8$alkyl, —CO$_2$H, —CN, —NO$_2$, —SF$_5$, —SO$_2$NH$C_1$-$C_8$alkyl, —SO$_2$N($C_1$-$C_8$alkyl)$_2$, —SO(NH)NH$C_1$-$C_8$alkyl, —SO(NH)N($C_1$-$C_8$alkyl)$_2$, —SONH$C_1$-$C_8$alkyl, —SON($C_1$-$C_8$alkyl)$_2$, —CONH$C_1$-$C_8$alkyl, —CON($C_1$-$C_8$alkyl)$_2$, —N($C_1$-$C_8$alkyl)CONH($C_1$-$C_8$alkyl), —N($C_1$-$C_8$alkyl)CON($C_1$-$C_8$alkyl)$_2$, —NHCONH($C_1$-$C_8$alkyl), —NHCON($C_1$-$C_8$alkyl)$_2$, —NHCONH$_2$, —N($C_1$-$C_8$alkyl)SO$_2$NH($C_1$-$C_8$alkyl), —N($C_1$-$C_8$alkyl)SO$_2$N($C_1$-$C_8$alkyl)$_2$, —NHSO$_2$NH($C_1$-$C_8$alkyl), —NHSO$_2$N($C_1$-$C_8$alkyl)$_2$, or —NHSO$_2$NH$_2$; and $R^{1c}$ and $R^{1d}$ are each independently selected from the group consisting of H, D, optionally substituted $C_{1-4}$ alkyl, $C_{3-8}$ cyclcoalkyl, $C_{3-8}$ heterocyclcoalkyl, aryl, or heteroaryl.

In other embodiments, q=2 and $R^1$ is a chemical moiety represented by the formula: $-A_1-A_2-$, wherein each of $A_{1-2}$ is independently selected from the group consisting of O, S, SO, $SO_2$, $NR^{1c}$, $SO_2NR^{1c}$, $SONR^{1c}$, $SO(=NR^{1c})$, $SO(=NR^{1c})NR^{1d}$, $CONR^{1c}$, $NR^{1c}CONR^{1d}$, $NR^{1c}C(O)O$, $NR^{1c}SO_2NR^{1d}$, CO, $CR^{1a}=CR^{1b}$, C≡C, $SiR^{1a}R^{1b}$, $P(O)R^{1a}$, $P(O)OR^{1a}$, $(CR^{1a}R^{1b})_{1-4}$, $-(CR^{1a}R^{1b})_{1-4}O(CR^{1a}R^{1b})_{1-4}$, $-(CR^{1a}R^{1b})_{1-4}S(CR^{1a}R^{1b})_{1-4}$, $-(CR^{1a}R^{1b})_{1-4}NR(CR^{1a}R^{1b})_{1-4}$, optionally substituted 3-11 membered cycloalkyl, 3-11 membered heterocyclyl, aryl, and heteroaryl;

wherein $R^{1a}$ and $R^{1b}$ are each independently selected from the group consisting of —H, D, -halo, —$C_1$-$C_8$alkyl, —O—$C_1$-$C_8$alkyl, —$C_1$-$C_6$haloalkyl, —S—$C_1$-$C_8$alkyl, —NH$C_1$-$C_8$alkyl, —N($C_1$-$C_8$alkyl)$_2$, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)($C_1$-$C_8$alkyl), —OH, —NH$_2$, —SH, —SO$_2C_1$-$C_8$alkyl, SO(NH)$C_1$-$C_8$alkyl, P(O)(O$C_1$-$C_8$alkyl)($C_1$-$C_8$alkyl), —P(O)(O$C_1$-$C_8$alkyl)$_2$, —C≡C—$C_1$-$C_8$alkyl, —C≡CH, —CH=CH($C_1$-$C_8$alkyl), —C($C_1$-$C_8$alkyl)=CH($C_1$-$C_8$alkyl), —C($C_1$-$C_8$alkyl)=C($C_1$-$C_8$alkyl)$_2$, —Si(OH)$_3$, —Si($C_1$-$C_8$alkyl)$_3$, —Si(OH)($C_1$-$C_8$alkyl)$_2$, —C(O)$C_1$-$C_8$alkyl, —CO$_2$H, —CN, —NO$_2$, —SF$_5$, —SO$_2$NH$C_1$-$C_8$alkyl, —SO$_2$N($C_1$-$C_8$alkyl)$_2$, —SO(NH)NH$C_1$-$C_8$alkyl, —SO(NH)N($C_1$-$C_8$alkyl)$_2$, —SONH$C_1$-$C_8$alkyl, —SON($C_1$-$C_8$alkyl)$_2$, —CONH$C_1$-$C_8$alkyl, —CON($C_1$-$C_8$alkyl)$_2$, —N($C_1$-$C_8$alkyl)CONH($C_1$-$C_8$alkyl), —N($C_1$-$C_8$alkyl)CON($C_1$-$C_8$alkyl)$_2$, —NHCONH($C_1$-$C_8$alkyl), —NHCON($C_1$-$C_8$alkyl)$_2$, —NHCONH$_2$, —N($C_1$-$C_8$alkyl)SO$_2$NH($C_1$-$C_8$alkyl), —N($C_1$-$C_8$alkyl)SO$_2$N($C_1$-$C_8$alkyl)$_2$, —NHSO$_2$NH($C_1$-$C_8$alkyl), —NHSO$_2$N($C_1$-$C_8$alkyl)$_2$, or —NHSO$_2$NH$_2$; and $R^{1c}$ and $R^{1d}$ are each independently selected from the group consisting of H, D, optionally substituted $C_{1-4}$ alkyl, $C_{3-8}$ cyclcoalkyl, $C_{3-8}$ heterocyclcoalkyl, aryl, or heteroaryl.

In other embodiments, q=1 and $R^1$ is a chemical moiety represented by the formula: $-A_1-$, wherein $A_1$ is selected from the group consisting of O, S, SO, $SO_2$, $NR^{1c}$, $SO_2NR^{1c}$, $SONR^{1c}$, $SO(=NR^{1c})$, $SO(=NR^{1c})NR^{1d}$, $CONR^{1c}$, $NR^{1c}CONR^{1d}$, $NR^{1c}C(O)O$, $NR^{1c}SO_2NR^{1d}$, CO, $CR^{1a}=CR^{1b}$, C≡C, $SiR^{1a}R^{1b}$, $P(O)R^{1a}$, $P(O)OR^{1a}$, $(CR^{1a}R^{1b})_{1-4}$, $-(CR^{1a}R^{1b})_{1-4}O(CR^{1a}R^{1b})_{1-4}$, $-(CR^{1a}R^{1b})_{1-4}S(CR^{1a}R^{1b})_{1-4}$, $-(CR^{1a}R^{1b})_{1-4}NR(CR^{1a}R^{1b})_{1-4}$, optionally substituted 3-11 membered cycloalkyl, 3-11 membered heterocyclyl, aryl, and heteroaryl;

wherein $R^{1a}$ and $R^{1b}$ are each independently selected from the group consisting of —H, D, -halo, —$C_1$-$C_8$alkyl, —O—$C_1$-$C_8$alkyl, —$C_1$-$C_6$haloalkyl, —N($C_1$-$C_8$alkyl)$_2$, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)(C$_1$-C$_8$alkyl), —OH, —NH$_2$, —SH, —SO$_2$C$_1$-C$_8$alkyl, SO(NH)C$_1$-C$_8$alkyl, P(O)(OC$_1$-C$_8$alkyl)(C$_1$-C$_8$alkyl), —P(O)(OC$_1$-C$_8$alkyl)$_2$, C≡C—C$_1$-C$_8$alkyl, —C≡CH, —CH═CH(C$_1$-C$_8$alkyl), —C(C$_1$-C$_8$alkyl)═CH(C$_1$-C$_8$alkyl), —C(C$_1$-C$_8$alkyl)═C(C$_1$-C$_8$alkyl)$_2$, —Si(OH)$_3$, —Si(C$_1$-C$_8$alkyl)$_3$, —Si(OH)(C$_1$-C$_8$alkyl)$_2$, —C(O)C$_1$-C$_8$alkyl, —CO$_2$H, —CN, —NO$_2$, —SF$_5$, —SO$_2$NHC$_1$-C$_8$alkyl, —SO$_2$N(C$_1$-C$_8$alkyl)$_2$, —SO(NH)NHC$_1$-C$_8$alkyl, —SO(NH)N(C$_1$-C$_8$alkyl)$_2$, —SONHC$_1$-C$_8$alkyl, —SON(C$_1$-C$_8$alkyl)$_2$, —CONHC$_1$-C$_8$alkyl, —CON(C$_1$-C$_8$alkyl)$_2$, —N(C$_1$-C$_8$alkyl)CONH(C$_1$-C$_8$alkyl), —N(C$_1$-C$_8$alkyl)CON(C$_1$-C$_8$alkyl)$_2$, —NHCONH(C$_1$-C$_8$alkyl), —NHCON(C$_1$-C$_8$alkyl)$_2$, —NHCONH$_2$, —N(C$_1$-C$_8$alkyl)SO$_2$NH(C$_1$-C$_8$alkyl), —N(C$_1$-C$_8$alkyl)SO$_2$N(C$_1$-C$_8$alkyl)$_2$, —NHSO$_2$NH(C$_1$-C$_8$alkyl), —NHSO$_2$N(C$_1$-C$_8$alkyl)$_2$, or —NHSO$_2$NH$_2$; and $R^{1c}$ and $R^{1d}$ are each independently selected from the group consisting of H, D, optionally substituted C$_{1-4}$ alkyl, C$_{3-8}$ cycloalkyl, C$_{3-8}$ heterocylcoalkyl, aryl, or heteroaryl.

In some embodiments, $R^1$ is a covalent bond, 3-11 membered cycloalkyl optionally substituted with 0-6 $R^{1a}$ and/or $R^{1b}$ groups, 3-11 membered heterocyclyl optionally substituted with 0-6 $R^{1a}$ and/or $R^{1b}$ groups, —(CR$^{1a}$R$^{1b}$)$_{1-5}$, —(CR$^{1a}$═CR$^{1b}$)—, —(CR$^{1a}$R$^{1b}$)$_{1-5}$-A- wherein A is O, S, or NR$^{1c}$, —(CR$^{1a}$R$^{1b}$)$_{1-5}$-A-(CR$^{1a}$R$^{1b}$)$_{1-5}$— wherein A is O, S, or NR$^{1c}$, —(CR$^{1a}$R$^{1b}$)$_{1-5}$-A-(CR$^{1a}$R$^{1b}$)$_{1-5}$-A- wherein A is O, S, or NR$^{1c}$, —(CR$^{1a}$R$^{1b}$)$_{1-5}$—(CR$^{1a}$═CR$^{1b}$)—(CR$^{1a}$R$^{1b}$)$_{1-5}$—, —(CR$^{1a}$R$^{1b}$)$_{1-5}$—(CR$^{1a}$═CR$^{1b}$)—(CR$^{1a}$R$^{1b}$)$_{1-5}$-A- wherein A is O, S, or NR$^{1c}$, —(CR$^{1a}$R$^{1b}$)$_{1-5}$—(C≡C)—(CR$^{1a}$R$^{1b}$)$_{1-5}$—, —(CR$^{1a}$R$^{1b}$)$_{1-5}$—(C≡C)—(CR$^{1a}$R$^{1b}$)$_{1-5}$-A- wherein A is O, S, or NR$^{1c}$, —(C≡C)—(CR$^{1a}$R$^{1b}$)$_{1-5}$-A-(CR$^{1a}$R$^{1b}$)$_{1-5}$— wherein A is O, S, or NR$^{1c}$, —(C≡C)—(CR$^{1a}$R$^{1b}$)$_{1-5}$, —(CR$^{1a}$R$^{1b}$)$_{1-5}$-(3-11 membered cycloalkyl optionally substituted with 0-6 $R^{1a}$ and/or $R^{1b}$ groups)-, —(CR$^{1a}$R$^{1b}$)$_{1-5}$-(3-11 membered heterocyclyl optionally substituted with 0-6 $R^{1a}$ and/or $R^{1b}$ groups)-, -(3-11 membered cycloalkyl optionally substituted with 0-6 $R^{1a}$ and/or $R^{1b}$ groups)-(CR$^{1a}$R$^{1b}$)$_{1-5}$—, -(3-11 membered heterocyclyl optionally substituted with 0-6 $R^{1a}$ and/or $R^{1b}$ groups) —(CR$^{1a}$R$^{1b}$)$_{1-5}$— (3-11 membered cycloalkyl optionally substituted with 0-6 $R^{1a}$ and/or $R^{1b}$ groups)-A-, —(CR$^{1a}$R$^{1b}$)$_{1-5}$-(3-11 membered heterocyclyl optionally substituted with 0-6 $R^{1a}$ and/or $R^{1b}$ groups)-A-, —(CR$^{1a}$R$^{1b}$)$_{1-5}$ (3-11 membered cycloalkyl optionally substituted with 0-6 $R^{1a}$ and/or $R^{1b}$ groups)-(CR$^{1a}$R$^{1b}$)$_{1-5}$, (CR$^{1a}$R$^{1b}$)$_{1-5}$-(3-11 membered cycloalkyl optionally substituted with 0-6 $R^{1a}$ and/or $R^{1b}$ groups)-A- wherein A is O, S, or NR$^{1c}$, —(CR$^{1a}$R$^{1b}$)$_{1-5}$ (3-11 membered cycloalkyl optionally substituted with 0-6 $R^{1a}$ and/or $R^{1b}$ groups)-(CR$^{1a}$R$^{1b}$)$_{1-5}$-A- wherein A is O, S, or NR$^{1c}$, —(CR$^{1a}$R$^{1b}$)$_{1-5}$-A-(3-11 membered cycloalkyl optionally substituted with 0-6 $R^{1a}$ and/or $R^{1b}$ groups)- wherein A is O, S, or NR$^{1c}$, —(CR$^{1a}$R$^{1b}$)$_{1-5}$ (3-11 membered heterocyclyl optionally substituted with 0-6 $R^{1a}$ and/or $R^{1b}$ groups)-(CR$^{1a}$R$^{1b}$) (CR$^{1a}$R$^{1b}$)$_{1-5}$-(3-11 membered heterocyclyl optionally substituted with 0-6 $R^{1a}$ and/or $R^{1b}$ groups)-(CR$^{1a}$R$^{1b}$)$_{1-5}$-A- wherein A is O, S, or NR$^{1c}$, —(CR$^{1a}$R$^{1b}$)$_{1-5}$-(3-11 membered heterocyclyl optionally substituted with 0-6 $R^{1a}$ and/or $R^{1b}$ groups)-A- wherein A is O, S, or NR$^{1c}$, —(CR$^{1a}$R$^{1b}$)$_{1-5}$-A-(3-11 membered heterocyclyl optionally substituted with 0-6 $R^{1a}$ and/or $R^{1b}$ groups)- wherein A is O, S, or NR$^{1c}$, —(CR$^{1a}$R$^{1b}$)$_{1-5}$-A-(CR$^{1a}$R$^{1b}$)$_{1-5}$-A- wherein A is O, S, or NR$^{1c}$, —(CR$^{1a}$R$^{1b}$)$_{1-5}$-A- wherein A is O, S, or NR$^{1c}$, —(CR$^{1a}$R$^{1b}$)$_{1-5}$-A-(3-11 membered cycloalkyl optionally substituted with 0-6 $R^{1a}$ and/or $R^{1b}$ groups)- wherein A is O, S, or NR$^{1c}$, —(CR$^{1a}$R$^{1b}$)$_{1-5}$-A-(3-11 membered cycloalkyl optionally substituted with 0-6 $R^{1a}$ and/or $R^{1b}$ groups)-(CR$^{1a}$R$^{1b}$)$_{1-5}$-A- wherein each A is independently O, S, or NR$^{1c}$, —(CR$^{1a}$R$^{1b}$)$_{1-5}$-A-(3-11 membered heterocyclyl optionally substituted with 0-6 $R^{1a}$ and/or $R^{1b}$ groups)-(CR$^{1a}$R$^{1b}$)$_{1-5}$-A- wherein each A is independently O, S, or NR$^{1c}$, —(CR$^{1a}$R$^{1b}$)$_{1-5}$-A-(CR$^{1a}$R$^{1b}$)$_{1-5}$-A- wherein A is O, S, or NR$^{1c}$, —(CR$^{1a}$R$^{1b}$)$_{1-5}$-A-(CR$^{1a}$R$^{1b}$)$_{1-5}$-A-(CR$^{1a}$R$^{1b}$)$_{1-5}$-A-(CR$^{1a}$R$^{1b}$)$_{1-5}$-A- wherein A is O, S, or NR$^{1c}$, —(CR$^{1a}$R$^{1b}$)$_{1-5}$-A-(CO) wherein A is O, S, or NR$^{1c}$, —(CR$^{1a}$R$^{1b}$)$_{1-5}$—(CR$^{1a}$═CR$^{1b}$)—(CR$^{1a}$CR$^{1b}$)$_{1-5}$-A-(CO)— wherein A is O, S, or NR$^{1c}$, —(CR$^{1a}$R$^{1b}$)$_{1-5}$—(C≡C)—(CR$^{1a}$R$^{1b}$)$_{1-5}$-A-(CO)— wherein A is O, S, or NR$^{1c}$, —(CR$^1$R$^{1b}$)$_{1-5}$-(3-11 membered cycloalkyl optionally substituted with 0-6 $R^{1a}$ and/or $R^{1b}$ groups)-(CR$^{1a}$R$^{1b}$)$_{1-5}$-A-(CO)— wherein A is O, S, or NR$^{1c}$, —(CR$^{1a}$R$^{1b}$)$_{1-5}$-A-(CO)-(3-11 membered cycloalkyl optionally substituted with 0-6 $R^{1a}$ and/or $R^{1b}$ groups)- wherein A is O, S, or NR$^{1c}$, —(CR$^{1a}$R$^{1b}$)$_{1-5}$ (3-11 membered heterocyclyl optionally substituted with 0-6 $R^{1a}$ and/or $R^{1b}$ groups)-(CR$^{1a}$R$^{1b}$)$_{1-5}$-A-(CO)— wherein A is O, S, or NR$^{1c}$, —(CR$^{1a}$R$^{1b}$)$_{1-5}$-A-(CO)-(3-11 membered heterocyclyl optionally substituted with 0-6 $R^{1a}$ and/or $R^{1b}$ groups)- wherein A is O, S, or NR$^{1c}$, —(CR$^{1a}$R$^{1b}$)$_{1-5}$-A-(3-11 membered cycloalkyl optionally substituted with 0-6 $R^{1a}$ and/or $R^{1b}$ groups)-A-(CO)— wherein each A is independently O, S, or NR$^{1c}$, -(3-11 membered cycloalkyl optionally substituted with 0-6 $R^{1a}$ and/or $R^{1b}$ groups)-CO—(CR$^{1a}$R$^{1b}$)$_{1-5}$-A- wherein A is O, S, or NR$^{1c}$, —(CR$^{1a}$R$^{1b}$)$_{1-5}$ (3-11 membered cycloalkyl optionally substituted with 0-6 $R^{1a}$ and/or $R^{1b}$ groups)-(CR$^{1a}$R$^{1b}$)$_{1-5}$-A-(CO)— wherein A is O, S, or NR$^{1c}$, —(CR$^{1a}$R$^{1b}$)$_{1-5}$-(3-11 membered heterocyclyl optionally substituted with 0-6 $R^{1a}$ and/or $R^{1b}$ groups)-(CR$^{1a}$R$^{1b}$)$_{1-5}$-A-(CO)— wherein A is O, S, or NR$^{1c}$, -(3-11 membered cycloalkyl optionally substituted with 0-6 $R^{1a}$ and/or $R^{1b}$ groups)-(CR$^{1a}$R$^{1b}$)$_{1-5}$—, or -(3-11 membered heterocyclyl optionally substituted with 0-6 $R^{1a}$ and/or $R^{1b}$ groups)-(CR$^{1a}$R$^{1b}$)$_{1-5}$-. In some embodiments, $R^1$ is -(3-11 membered heterocyclyl optionally substituted with 0-6 $R^{1a}$ and/or $R^{1b}$ groups)-(CO)—(CR$^{1a}$R$^{1b}$)$_{1-5}$-A- wherein A is O, S, or NR$^{1c}$; -(3-11 membered heterocyclyl optionally substituted with 0-6 $R^{1a}$ and/or $R^{1b}$ groups)-(CO)-A-(CR$^{1a}$R$^{1b}$)$_{1-5}$— wherein A is O, S, or NR$^{1c}$; -A-(3-11 membered heterocyclyl optionally substituted with 0-6 $R^{1a}$ and/or $R^{1b}$ groups)-(CR$^{1a}$R$^{1b}$)$_{1-5}$-A- wherein each A is independently O, S, or NR$^{1c}$; -(3-11 membered heterocyclyl optionally substituted with 0-6 $R^{1a}$ and/or $R^{1b}$ groups)-(CR$^{1a}$R$^{1b}$)$_{1-5}$-(3-11 membered heterocyclyl optionally substituted with 0-6 $R^{1a}$ and/or $R^{1b}$ groups)-(CR$^{1a}$R$^{1b}$)$_{1-5}$-A- wherein A is O, S, or NR$^{1c}$; -(3-11 membered heterocyclyl optionally substituted with 0-6 $R^{1a}$ and/or $R^{1b}$ groups)-(3-11 membered heterocyclyl optionally substituted with 0-6 $R^{1a}$ and/or $R^{1b}$ groups)-(CR$^{1a}$R$^{1b}$)$_{1-5}$-A- wherein A is O, S, or NR$^{1c}$; -(3-11 membered heterocyclyl optionally substituted with 0-6 $R^{1a}$ and/or $R^{1b}$ groups)-A-(CR$^{1a}$R$^{1b}$)$_{1-5}$-A- wherein each A is independently O, S, or NR$^{1c}$; -(heteroaryl optionally substituted with 0-4 $R^{1a}$ and/or $R^{1b}$ groups)-A-(CR$^{1a}$R$^{1b}$)$_{1-5}$— wherein A is O, S, or NR$^{1c}$; -(3-11 membered cycloalkyl optionally substituted with 0-6 $R^{1a}$ and/or $R^{1b}$ groups)-(CO)—(CR$^{1a}$R$^{1b}$)$_{1-5}$-A- wherein A is O, S, or NR$^{1c}$; -(3-11 membered heterocyclyl optionally substituted with 0-6 $R^{1a}$ and/or $R^{1b}$ groups)-(CR$^{1a}$R$^{1b}$ wherein A is O, S, or NR$^{1c}$; -(3-11 membered heterocyclyl optionally substituted with 0-6 $R^{1a}$ and/or $R^{1b}$ groups)-A-(CR$^{1a}$R$^{1b}$)$_{1-5}$— wherein A is O, S, or $NR^{1c}$; —(CO)-(3-11 membered cycloalkyl optionally substituted with 0-6 $R^{1a}$ and/or $R^{1b}$ groups)-$(CR^{1a}R^{1b})_{1-5}$-A- wherein A is O, S, or $NR^{1c}$.

In some embodiments, $R^1$ is $-CR^{1a}=CR^{1b}-$, such as, for example, —CH=CH—.

In some embodiments, $R^1$ is $-(CR^{1a}R^{1b})_{1-5}$, for example $-(CH_2)_{1-5}-$, —CH$_2$—, —CH$_2$CH$_2$CH$_2$— and the like.

In some embodiments, $R^1$ is $-(CR^{1a}R^{1b})_{1-5}$-A- wherein A is O, S, or $NR^{1c}$, such as for example, $-(CH_2)_{1-5}-O-$, $-(CH_2)_{1-5}-S-$, $-(CH_2)_{1-5}-NH-$, or $-(CH_2)_{0-2}-C(CH_3)_2-(CH_2)_{0-2}-O-$.

In other embodiments, $R^1$ is $-(CR^{1a}R^{1b})_{1-5}$-A-$(CR^{1a}R^{1b})_{1-5}-$ wherein A is O, S, or $NR^{1c}$, such as, for example, $-(CH_2)_{1-5}-O-(CH_2)_{1-5}-$, $-(CH_2)_{1-5}-S-(CH_2)_{1-5}-$, $-(CH_2)_{1-5}-NH-(CH_2)_{1-5}-$.

In some embodiments, $R^1$ is $-(C\equiv C)-(CR^{1a}R^{1b})_{1-5}$, such as, for example, $-(C\equiv C)-(CH_2)_2-$, and the like.

In some embodiments, $R^{1b}$ is $-(CR^{1a}R^{1b})_{1-5}$ (3-11 membered cycloalkyl optionally substituted with 0-6 $R^{1a}$ and/or $R^{1b}$ groups)-, such as, for example, —CH$_2$-cyclobutyl-.

In some embodiments, $R^1$ is $-(CR^{1a}R^{1b})_{1-5}$ (3-11 membered cycloalkyl optionally substituted with 0-6 $R^{1a}$ and/or $R^{1b}$ groups)-$(CR^{1a}R^{1b})_{1-5}$, such as, for example, —CH$_2$-cyclobutyl-CH$_2$— and the like.

In some embodiments, $R^1$ is $-(CR^{1a}R^{1b})_{1-5}$ (3-11 membered heterocyclyl optionally substituted with 0-6 $R^{1a}$ and/or $R^{1b}$ groups)-$(CR^{1a}R^{1b})_{1-5}$, such as, for example, —CH$_2$-azetidinyl-CH$_2$—.

In some embodiments, $R^1$ is $-(CR^{1a}R^{1b})_{1-5}$ (3-11 membered heterocyclyl optionally substituted with 0-6 $R^{1a}$ and/or $R^{1b}$ groups)-, such as, for example, —CH$_2$-azetidinyl-.

In some embodiments, $R^1$ is -(3-11 membered heterocyclyl optionally substituted with 0-6 $R^{1a}$ and/or $R^{1b}$ groups)-$(CR^{1a}R^{1b})_{1-5}$—, such as, for example, -azetidinyl-CH$_2$—, -pyrrolidinyl-CH$_2$—, -piperidinyl-CH$_2$—, and the like.

In some embodiments, $R^1$ is $-(CR^{1a}R^{1b})_{1-5}$ (3-11 membered cycloalkyl optionally substituted with 0-6 $R^{1a}$ and/or $R^{1b}$ groups)-$(CR^{1a}R^{1b})_{1-5}$-A- wherein A is O, S, or $NR^{1c}$, such as, for example, —CH$_2$-cyclopropyl-CH$_2$—O—, and the like.

In some embodiments, $R^1$ is $-(CR^{1a}R^{1b})_{1-5}$ (3-11 membered heterocyclyl optionally substituted with 0-6 $R^{1a}$ and/or $R^{1b}$ groups)-$(CR^{1a}R^{1b})_{1-5}$-A- wherein A is O, S, or $NR^{1c}$, such as, for example, —CH$_2$-piperidinyl-CH$_2$CH$_2$—O—, and the like.

In some embodiments, $R^1$ is $-(CR^{1a}R^{1b})_{1-5}$ (3-11 membered heterocyclyl optionally substituted with 0-6 $R^{1a}$ and/or $R^{1b}$ groups)-A- wherein A is O, S, or $NR^{1c}$, such as, for example, —CH$_2$-azetidinyl-O—, and the like.

In some embodiments, $R^1$ is $-(CR^{1a}R^{1b})_{1-5}$-A-(3-11 membered heterocyclyl optionally substituted with 0-6 $R^{1a}$ and/or $R^{1b}$ groups)- wherein A is O, S, or $NR^{1c}$, such as, for example, —CH$_2$—O-azetidinyl-, —CH$_2$—NH-azetidinyl-, and the like.

In other embodiments, $R^1$ is $-(CR^{1a}R^{1b})_{1-5}$-A-A (3-11 membered cycloalkyl optionally substituted with 0-6 $R^{1a}$ and/or $R^{1b}$ groups)- wherein A is O, S, or $NR^{1c}$, such as —CH$_2$—O— cyclobutylene-, —CH$_2$—NH-cyclobutylene-, and the like.

In some embodiments, $R^1$ is $-(CR^{1a}R^{1b})_{1-5}$-A-$(CR^{1a}R^{1b})_{1-5}$-A- wherein A is O, S, or $NR^{1c}$, such as, for example, —CH$_2$—O—CH$_2$CH$_2$—O—.

In some aspects, the Y in the compound of Formula IA is $CR^h$ wherein $R^h$ is H, and the compound of Formula IA has Formula IA-1:

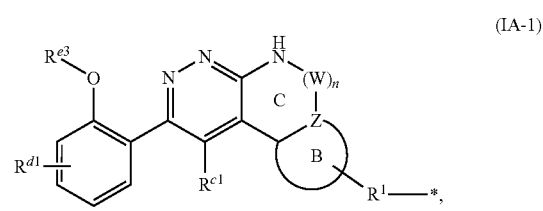

(IA-1)

wherein $R^{c1}$, $R^{d1}$, $R^{e1}$, W, Z, B, n, and $R^1$ are as described above for Formula IA.

In some embodiments, n in Formula IA-1 is 1.

In some embodiments of the compound of Formula IA-1, at least one W is optionally substituted —CH$_2$—.

In some embodiments of the compound of Formula IA-1, at least one W is optionally substituted —CH$_2$— wherein the optional substituents are alkyl, alkoxy, alkylamino.

In some embodiments of the compound of Formula IA-1, at least one W is —CH$_2$—.

In some embodiments, W in Formula IA-1 is optionally substituted —CH$_2$— wherein the optional substituent is an alkyl group, such as, for example methyl (—CH$_3$), ethyl, propyl, and the like.

In other embodiments, W in Formula IA-1 is —CH(CH$_3$)—.

In some embodiments of the compound of Formula IA-1, one W is —C(O)—.

In some embodiments of the compound of Formula IA-1, one W is —S(O)—.

In some embodiments of the compound of Formula IA-1, one W is —S(O)$_2$—.

In some embodiments, B in Formula IA-1 is an optionally substituted 5-7 membered cycloalkyl ring.

In some embodiments, B in Formula IA-1 is an optionally substituted 5-7 membered cycloalkyl ring wherein the optional substituents are hydroxy, halogen, alkoxy, alkyl, haloalkyl, amino, alkylamino, or cyano.

In other embodiments, B in Formula IA-1 is an optionally substituted 5-7 membered heterocyclic ring.

In some embodiments, B in Formula IA-1 is an optionally substituted 5-7 membered heterocyclic ring wherein the optional substituents are hydroxy, halogen, alkoxy, alkyl, haloalkyl, amino, alkylamino, cyano.

In other aspects, the Y in the compound of Formula IA is N, and Z is $CR^h$ wherein $R^h$ is H, and the compound of Formula IA has Formula IA-2.

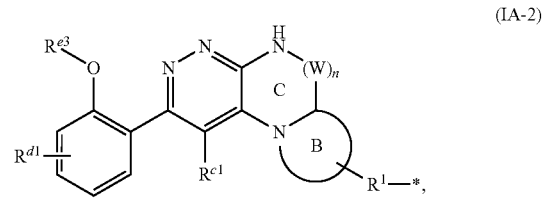

(IA-2)

wherein $R^{c1}$, $R^{d1}$, $R^{e1}$, W, B, n, and $R^1$ are as described above for Formula IA.

In some embodiments, n in Formula IA-2 is 1.

In some embodiments of the compound of Formula IA-2, at least one W is optionally substituted —CH$_2$—.

In some embodiments of the compound of Formula IA-2, at least one W is optionally substituted —CH$_2$— wherein the optional substituents are alkyl, alkoxy, or alkylamino.

In some embodiments of the compound of Formula IA-2, at least one W is —CH$_2$—.

In some embodiments, W in Formula IA-2 is optionally substituted —CH$_2$— wherein the optional substituent is an alkyl group, such as, for example methyl (—CH$_3$), ethyl, propyl, and the like.

In other embodiments, W in Formula IA-2 is —CH(CH$_3$)—.

In some embodiments of the compound of Formula IA-2, one W is —C(O)—.

In some embodiments of the compound of Formula IA-2, one W is —S(O)—.

In some embodiments of the compound of Formula IA-2, one W is —S(O)$_2$—.

In some embodiments, B in Formula IA-2 is an optionally substituted 5-7 membered heterocyclic ring.

In some embodiments, B in Formula IA-2 is an optionally substituted 5-7 membered heterocyclic ring wherein the optional substituents are hydroxy, halogen, alkoxy, alkyl, haloalkyl, amino, alkylamino, cyano.

In other embodiments, B in Formula IA-2 is an optionally substituted 5-7 membered heterocyclic ring.

In some embodiments, B in Formula IA-2 is an optionally substituted 5-7 membered heterocyclic ring wherein the optional substituents are hydroxy, halogen, alkoxy, alkyl, haloalkyl, amino, alkylamino, or cyano.

In some aspects, the compound of Formula IA is a compound of Formula IA-3:

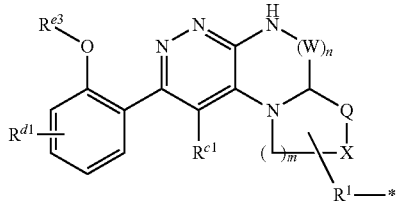

(IA-3)

wherein m=1 to 3;

X is optionally substituted —CH$_2$—, or NH; or, if IV is attached to X, then X is —CH— or N; Q is optionally substituted —CH$_2$—, optionally substituted —(CH$_2$)$_2$—, —C(O)—, optionally substituted —CH$_2$C(O)—, —S(O)—, —S(O)$_2$—, optionally substituted —CH$_2$S(O)$_2$—, or optionally substituted —CH$_2$S(O)—; and wherein R$^{c1}$, R$^{d1}$, R$^{e3}$, W, Z, B, n, and R$^1$ are as described above for Formula IA.

In some embodiments of the compound of Formula IA-3, n=1. In other embodiments of the compound of Formula IA-3, n=2. In other embodiments of the compound of Formula IA-3, n=3.

In some embodiments of the compound of Formula IA-3, X is —CH—.

In other embodiments of the compound of Formula IA-3, X is NH.

In some of those embodiments of the compound of Formula IA-3 wherein IV is attached to X, then X is CH.

In other of those embodiments of the compound of Formula IA-3 wherein IV is attached to X, then X is N.

In some embodiments of the compound of Formula IA-3, Q is optionally substituted —CH$_2$—.

In some embodiments of the compound of Formula IA-3, Q is optionally substituted —CH$_2$— wherein the optional substituents are alkyl, alkoxy, or alkylamino.

In some embodiments of the compound of Formula IA-3, Q is optionally substituted —(CH$_2$)$_2$—.

In some embodiments of the compound of Formula IA-3, Q is optionally substituted —(CH$_2$)$_2$— wherein the optional substituents are alkyl, alkoxy, or alkylamino.

In some embodiments of the compound of Formula IA-3, Q is —C(O)—.

In some embodiments of the compound of Formula IA-3, Q is optionally substituted —CH$_2$C(O)—.

In some embodiments of the compound of Formula IA-3, Q is —S(O)—.

In some embodiments of the compound of Formula IA-3, Q is —S(O)$_2$—.

In some embodiments of the compound of Formula IA-3, Q is optionally substituted —CH$_2$S(O)$_2$—.

In some embodiments of the compound of Formula IA-3, Q is optionally substituted —CH$_2$S(O)—.

In some aspects, the compound of Formula IA is a compound of Formula IA-4

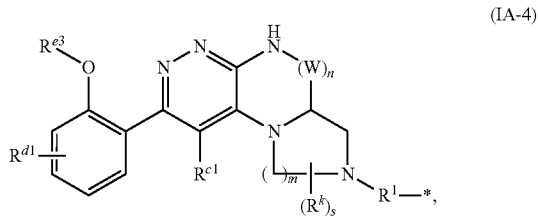

(IA-4)

wherein R$^k$=H, D, F, C$_{1-3}$ alkyl, C$_{1-3}$ haloalkyl, C$_{1-4}$ alkoxyl, substituted C$_{1-3}$ alkyl, substituted C$_{1-3}$ haloalkyl, or substituted C$_{1-4}$ alkoxyl; s=0-7; and m=1-3; and wherein R$^{c1}$, R$^{d1}$, R$^{e3}$, W, n, and R$^1$ are as described above for Formula IA.

In some embodiments of the compound of Formula IA-4, n=1. In other embodiments of the compound of Formula IA-4, n=2. In other embodiments of the compound of Formula IA-4, n=3.

In some embodiments of the compound of Formula IA-4, m=1. In other embodiments of the compound of Formula IA-4, m=2. In other embodiments of the compound of Formula IA-4, m=3.

In some embodiments of the compound of Formula IA-4, s=0. In some embodiments of the compound of Formula IA-4, s=1. In other embodiments of the compound of Formula IA-4, s=2. In other embodiments of the compound of Formula IA-4, s=3.

In some embodiments of the compound of Formula IA-4, R$^k$=H.

In some embodiments of the compound of Formula IA-4, R$^k$=D.

In some embodiments of the compound of Formula IA-4, R$^k$=F.

In some embodiments of the compound of Formula IA-4, R$^k$=C$_{1-3}$ alkyl, for example, C$_1$ alkyl, C$_2$ alkyl, C$_3$ alkyl, —CH$_3$, —CH$_2$CH$_3$, and the like.

In some embodiments of the compound of Formula IA-4, R$^k$=C$_{1-3}$ haloalkyl, for example, C$_1$ haloalkyl, C$_2$ haloalkyl, C$_3$ haloalkyl, —CF$_3$, —CH$_2$CF$_3$, and the like.

In some embodiments of the compound of Formula IA-4, R$^k$=C$_{1-4}$ alkoxyl, for example, C$_1$ alkoxyl, C$_2$ alkoxyl, C$_3$ alkoxyl, —OCH$_3$, —OCH$_2$CH$_3$, and the like.

In some embodiments of the compound of Formula IA-4, R$^k$=substituted C$_{1-3}$ alkyl, for example, substituted C$_1$ alkyl, substituted C$_2$ alkyl, substituted C$_3$ alkyl, and the like.

In some embodiments of the compound of Formula IA-4, $R^k$=substituted $C_{1-3}$ haloalkyl, for example, substituted $C_1$ haloalkyl, substituted $C_2$ haloalkyl, substituted $C_3$ haloalkyl, and the like.

In some embodiments of the compound of Formula IA-4, $R^k$=substituted $C_{1-4}$ alkoxyl, for example, substituted $C_1$ alkoxyl, substituted $C_2$ alkoxyl, substituted $C_3$ alkoxyl, and the like.

In some aspects, the compound of Formula IA is a compound of Formula IA-5:

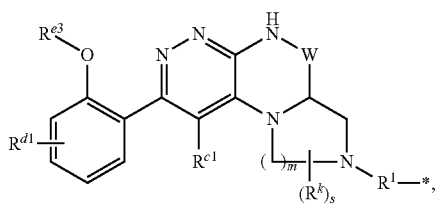

(IA-5)

wherein $R^k$=H, D, F, $C_{1-3}$ alkyl, $C_{1-3}$ haloalkyl, or $C_{1-4}$ alkoxyl; m=1-3; and s=0-3, and wherein $R^{c1}$, $R^{d1}$, $R^{e3}$, W and $R^1$ are as described above for Formula IA.

In some embodiments of the compound of Formula IA-5, m=1. In other embodiments of the compound of Formula IA-5, m=2. In other embodiments of the compound of Formula IA-5, m=3.

In some embodiments of the compound of Formula IA-5, s=0. In some embodiments of the compound of Formula IA-5, s=1. In other embodiments of the compound of Formula IA-5, s=2. In other embodiments of the compound of Formula IA-5, s=3.

In some embodiments of the compound of Formula IA-5, $R^k$=H.

In some embodiments of the compound of Formula IA-5, $R^k$=D.

In some embodiments of the compound of Formula IA-5, $R^k$=F.

In some embodiments of the compound of Formula IA-5, $R^k$=$C_{1-3}$ alkyl, for example, $C_1$ alkyl, $C_2$ alkyl, $C_3$ alkyl, —$CH_3$, —$CH_2CH_3$, and the like.

In some embodiments of the compound of Formula IA-5, $R^k$=$C_{1-3}$ haloalkyl, for example, $C_1$ haloalkyl, $C_2$ haloalkyl, $C_3$ haloalkyl, —$CF_3$, —$CH_2CF_3$, and the like.

In some embodiments of the compound of Formula IA-5, $R^k$=H. or $C_{1-4}$ alkoxyl, for example, $C_1$ alkoxyl, $C_2$ alkoxyl, $C_3$ alkoxyl, —$OCH_3$, —$OCH_2CH_3$, and the like.

In some aspects, the compound of Formula IA is a compound of Formula IA-6:

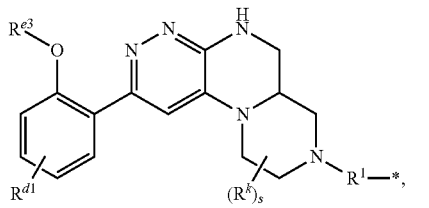

(IA-6)

wherein $R^k$=H, D, F, $C_{1-3}$ alkyl, $C_{1-3}$ haloalkyl, or $C_{1-4}$ alkoxyl; and s=0-3, and wherein $R^{c1}$, $R^{d1}$, $R^{e3}$, and $R^1$ are as described above for Formula IA.

In some embodiments of the compound of Formula IA-6, s=0. In some embodiments of the compound of Formula IA-6, s=1. In other embodiments of the compound of Formula IA-6, s=2. In other embodiments of the compound of Formula IA-6, s=3.

In some embodiments of the compound of Formula IA-6, $R^k$=H.

In some embodiments of the compound of Formula IA-6, $R^k$=D.

In some embodiments of the compound of Formula IA-6, $R^k$=F.

In some embodiments of the compound of Formula IA-6, $R^k$=$C_{1-3}$ alkyl, for example, $C_1$ alkyl, $C_2$ alkyl, $C_3$ alkyl, —$CH_3$, —$CH_2CH_3$, and the like.

In some embodiments of the compound of Formula IA-6, $R^k$=$C_{1-3}$ haloalkyl, for example, $C_1$ haloalkyl, $C_2$ haloalkyl, $C_3$ haloalkyl, —$CF_3$, —$CH_2CF_3$, and the like.

In some embodiments of the compound of Formula IA-6, $R^k$=H. or $C_{1-4}$ alkoxyl, for example, $C_1$ alkoxyl, $C_2$ alkoxyl, $C_3$ alkoxyl, —$OCH_3$, —$OCH_2CH_3$, and the like.

In some aspects, the ULM moiety in the compounds of the disclosure is a small molecule E3 Ubiquitin Ligase binding moiety that binds a Von Hippel-Lindau E3 Ubiquitin Ligase (VHL). Such ULM moieties that bind to VHL are known to those of skill in the art. Methods of determining whether a small molecule binds a Von Hippel-Lindau E3 Ubiquitin Ligase are known in the art.

In some embodiments, the ULM is a previously described ULM.

In some embodiments, the ULM is a ULM moiety described in U.S. Patent Application Publication No. 2019/0300521, the entirety of which is incorporated by reference herein.

In other embodiments, the ULM is a ULM moiety described in U.S. Patent Application Publication No. 2019/0255066, the entirety of which is incorporated by reference herein.

In other embodiments, the ULM is a ULM moiety described in WO 2019/084030, the entirety of which is incorporated by reference herein.

In other embodiments, the ULM is a ULM moiety described in WO 2019/084026, the entirety of which is incorporated by reference herein.

In some embodiments, the ULM is a moiety having the Formula ULM-I

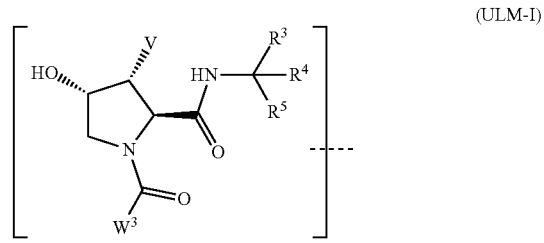

(ULM-I)

wherein

------ indicates the position of attachment of the ULM to $R^1$;

V is H or F;

$R^3$ is optionally substituted phenyl, optionally substituted napthyl, or an optionally substituted 5-10 membered heteroaryl;

one of $R^4$ or $R^5$ is H, D, haloalkyl, optionally substituted alkyl, optionally substituted cycloalkyl, optionally substituted heterocycloalkyl, —$COR^d$, $CONR^{e1}R^{e2}$;

the other of R⁴ or R⁵ is H or D;

or R⁴ and R⁵, together with the carbon atom to which they are both attached, form an optionally substituted 3-5 membered cycloalkyl, or heterocyclyl;

W³ is an optionally substituted aryl, optionally substituted heteroaryl, or

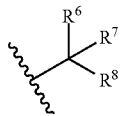

R⁶ and R⁷ are independently H, D, optionally substituted alkyl, optionally substituted cycloalkyl, or optionally substituted haloalkyl, or R⁶, R⁷, and the carbon atom to which they are attached form an optionally substituted cycloalkyl or optionally substituted heterocyclyl;

R⁸ is an optionally substituted heterocyclyl, optionally substituted heteroaryl, optionally substituted aryl, —C(O)NRᵃRᵇ, —NRᵃRᵇ,

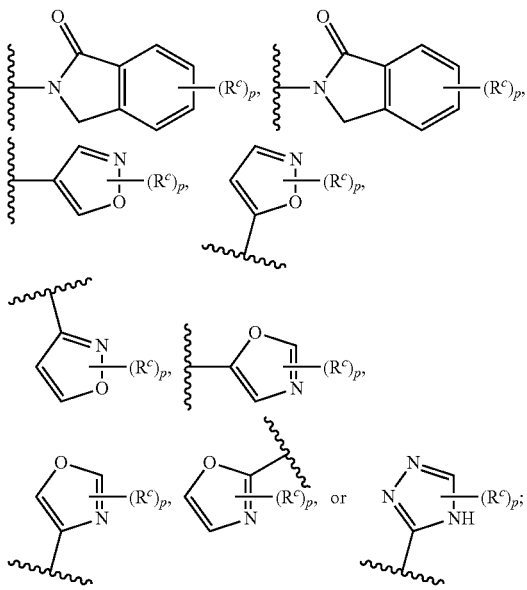

Rᵃ is selected from H or optionally substituted alkyl;

Rᵇ is selected from H, —C(O)—* wherein * is a point of attachment to R¹, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (cycloalkyl)carbonyl, optionally substituted (heterocyclyl)carbonyl, or optionally substituted aralkyl;

each Rᶜ is independently H, halo, optionally substituted alkoxy, cyano, optionally substituted alkyl, haloalkyl, or haloalkoxy;

each Rᵈ is independently selected from H, optionally substituted alkyl or NRᵉ¹Rᵉ², each Rᵉ¹ and Rᵉ² is independently H, D, optionally substituted alkyl, or Rᵉ¹ and Rᵉ² together with the nitrogen atom to which they are attached form a 4-7 membered heterocyclyl; and p is 0, 1, 2, 3, or 4.

In some embodiments of ULM-I, V is H.

In other embodiments of ULM-I, V is F.

In some embodiments of ULM-I, R³ is optionally substituted phenyl having the formula:

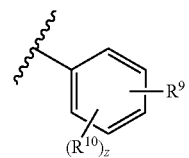

wherein

R⁹ is H, D, halo, —CN, —OH, —NO₂, —NRᵉ¹Rᵉ², —ORᵉ¹, —CONRᵉ¹Rᵉ², —NRᵉ¹CORᵉ², —SO₂NRᵉ¹Rᵉ², —NRᵉ¹SO₂Rᵉ², optionally substituted alkyl, optionally substituted alkoxyl, optionally substituted haloalkyl, optionally substituted haloalkoxy; optionally substituted aryl; optionally substituted heteroaryl; optionally substituted cycloalkyl; or optionally substituted heterocyclyl;

R¹⁰ is H, D, halo, CN, optionally substituted alkyl, optionally substituted haloalkyl, hydroxy, optionally substituted alkoxy, or optionally substituted haloalkoxy; and z is 0, 1, 2, 3, or 4.

In some embodiments wherein R³ is optionally substituted phenyl, R¹⁰ is —F or —OCH₃.

In some embodiments wherein R³ is optionally substituted phenyl, R⁹ is —CN.

In some embodiments wherein R³ is optionally substituted phenyl, R⁹ is an optionally substituted heteroaryl.

In some embodiments wherein R³ is optionally substituted phenyl, R⁹ is

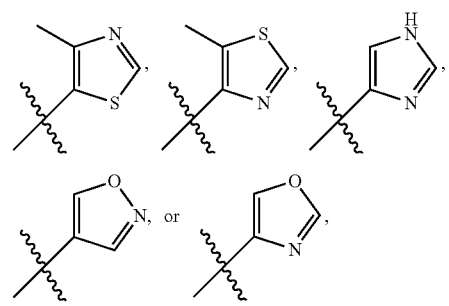

each optionally substituted.

In other embodiments wherein R³ is optionally substituted phenyl, R⁹ is

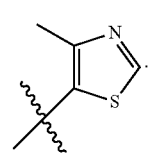 [SMILES: *c1scnc1C]

In other embodiments wherein $R^3$ is optionally substituted phenyl, $R^9$ is

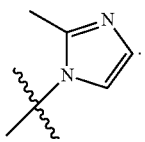

In other embodiments, $R^3$ is

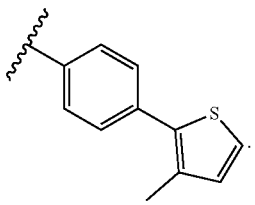 [SMILES: *c1ccc(-c2sccc2C)cc1]

In some embodiments wherein $R^3$ is optionally substituted phenyl, $R^{10}$ is hydroxy, halogen, —NH($C_1$-$C_4$alkyl), or $C_1$-$C_6$alkoxy, and z is 0, 1, 2, 3, or 4.

In some embodiments of ULM-I, one of $R^4$ or $R^5$ is H, and the other of $R^4$ or $R^5$ is H or optionally substituted alkyl.

In other embodiments of ULM-I, one of $R^4$ or $R^5$ is H, and the other of $R^4$ or $R^5$ is optionally substituted $C_1$-$C_6$alkyl.

In other embodiments of ULM-I, one of $R^4$ or $R^5$ is H, and the other of $R^4$ or $R^5$ is $C_1$-$C_6$alkyl.

In other embodiments of ULM-I, one of $R^4$ or $R^5$ is H, and the other of $R^4$ or $R^5$ is —$CH_3$.

In other embodiments of ULM-I, one of $R^4$ or $R^5$ is H, and the other of $R^4$ or $R^5$ is —$CH_2OH$.

In other embodiments of ULM-I, both $R^4$ and $R^5$ are H.

In some embodiments of ULM-I, $W^3$ is

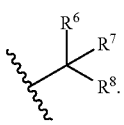

In some embodiments of ULM-I, $R^6$ is H.

In some embodiments of ULM-I, $R^7$ is H, or optionally substituted alkyl.

In some embodiments of ULM-I, $R^7$ is H.

In some embodiments of ULM-I, $R^7$ is optionally substituted alkyl.

In some embodiments of ULM-I, $R^7$ is optionally substituted $C_1$-$C_6$alkyl.

In some embodiments of ULM-I, $R^7$ is $C_1$-$C_6$alkyl.

In some embodiments of ULM-I, $R^7$ is $C_1$-$C_6$alk-OH, $C_1$-$C_6$alk-$NH_2$, —$C_1$-$C_6$alk-CONH—*, or —$C_1$-$C_6$alk-NHCO—* wherein * is a point of attachment to $R^1$.

In some embodiments of ULM-I, $R^7$ is -t-butyl or -isopropyl.

In some embodiments of ULM-I, $R^7$ is -t-butyl.

In some embodiments of ULM-I, $R^7$ is -isopropyl.

In some embodiments of ULM-I, $R^8$ is $NR^aR^b$.

In some embodiments, $R^a$ is H or optionally substituted alkyl.

In some embodiments, $R^a$ is H.

In some embodiments, $R^b$ is H, optionally substituted alkyl, —C(O)—* wherein * is a point of attachment to $R^1$, optionally substituted (cycloalkyl)carbonyl, or optionally substituted alkylcarbonyl.

In some embodiments, $R^b$ is optionally substituted alkylcarbonyl.

In some embodiments, $R^b$ is —C(O)—* wherein * is a point of attachment to $R^1$.

In some embodiments of ULM-I, $R^8$ is $CONR^aR^b$.

In some embodiments of ULM-I, $R^8$ is

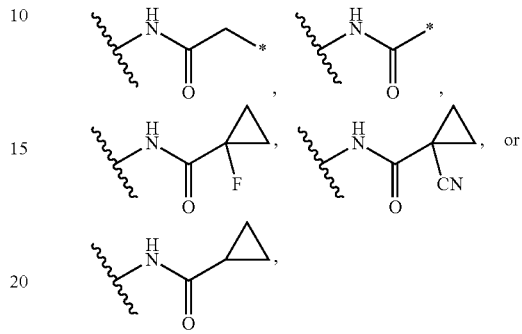

wherein * is a point of attachment to $R^1$.

In some embodiments of ULM-I, $R^8$ is

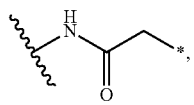

wherein * is a point of attachment to $R^1$.

In some embodiments of ULM-I, $R^8$ is

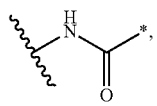

wherein * is a point of attachment to $R^1$.

In some embodiments of ULM-I, $R^8$ is

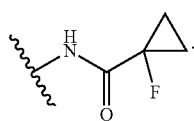

In some embodiments, $R^8$ is —NH—* wherein * is a point of attachment to $R^1$.

In some embodiments of ULM-I, $R^8$ is optionally substituted heteroaryl.

In some embodiments of ULM-I, $R^8$ is

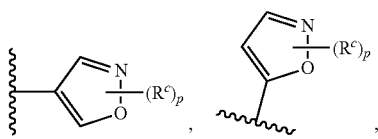

-continued

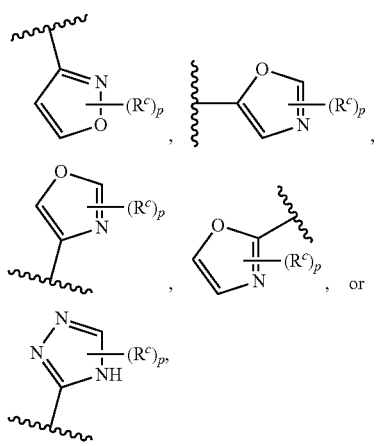

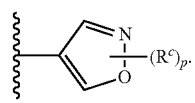, or wherein each $R^c$ is independently halo, optionally substituted alkoxy, cyano, optionally substituted alkyl, haloalkyl, or haloalkoxy, and p is 0, 1, or 2.

In some embodiments, $R^8$ is

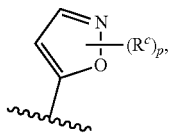

wherein each $R^c$ is independently halo, optionally substituted alkoxy, cyano, optionally substituted alkyl, haloalkyl, or haloalkoxy, and p is 0, 1, or 2.

In some embodiments, $R^8$ is

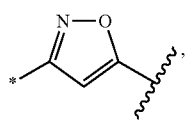

wherein * is a point of attachment to $R^1$.

In some embodiments, $R^8$ is

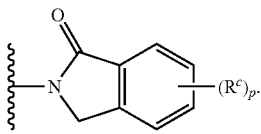

In some embodiments, $R^8$ is

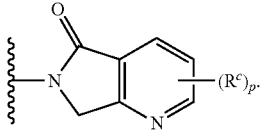

In some embodiments, $R^8$ is

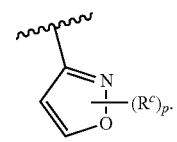

In some embodiments, $R^8$ is

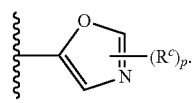

In some embodiments, $R^8$ is

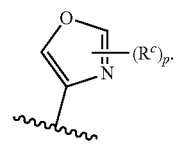

In some embodiments, $R^8$ is

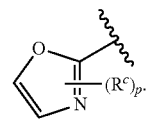

In some embodiments, $R^8$ is

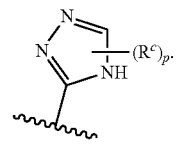

In some embodiments, $R^8$ is

In some embodiments, ULM-I is a compound of formula:

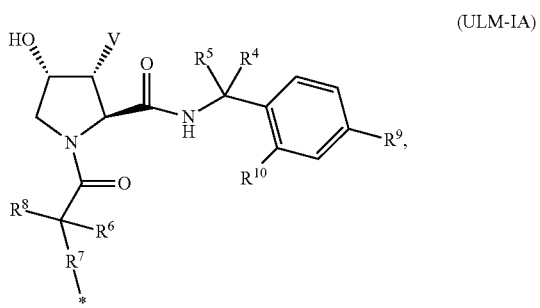
(ULM-IA)

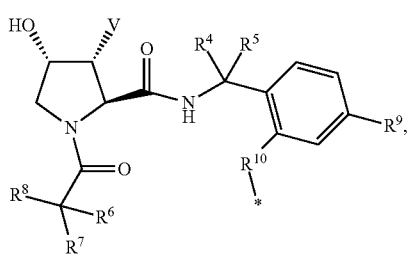
(ULM-IB)

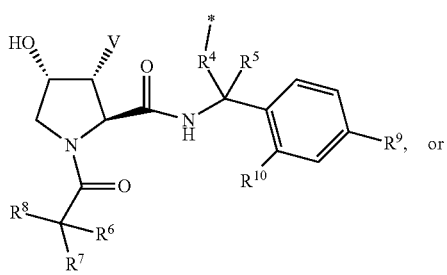
(ULM-IC), or

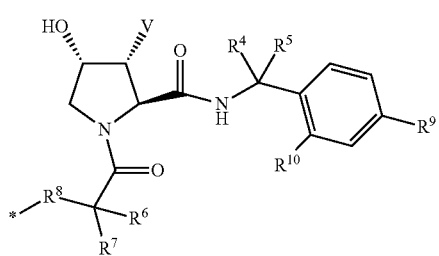
(ULM-ID)

* is a point of attachment of the ULM to $R^1$.

In some embodiments of ULM-IA, ULM-IB, ULM-IC, or ULM-ID, $R^9$ is optionally substituted

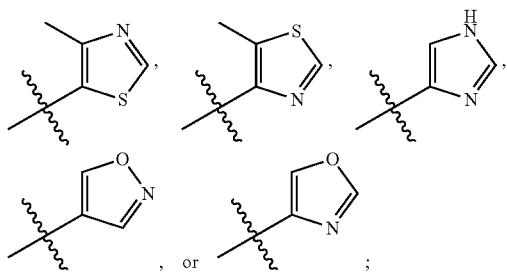

, or

;

and and $R^{19}$ is H, D, hydroxy, halogen, amino$C_{1-4}$alkyl, or $C_{1-4}$alkyloxy.

In some embodiments, the ULM is a moiety having the Formula ULM-II

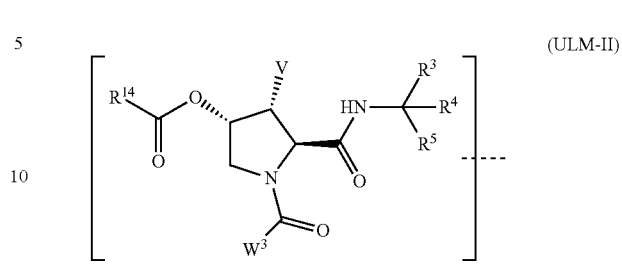
(ULM-II)

wherein

------ indicates the position of attachment of the ULM to $R^1$;
$R^{14}$ is $C_1$-$C_6$alkyl, such as, for example, —$CH_3$, —$CH_2CH_3$, —$CH(CH_3)_2$, and the like; and all of the other variables have the same scope as set forth above with respect to ULM-I.

In some embodiments, $R^{14}$ in ULM-II is —$CH_3$. In other embodiments, $R^{14}$ in ULM-II is —$CH(CH_3)_2$.

In some aspects, the compounds of Formula I are those having the formula IA-7 or IA-8:

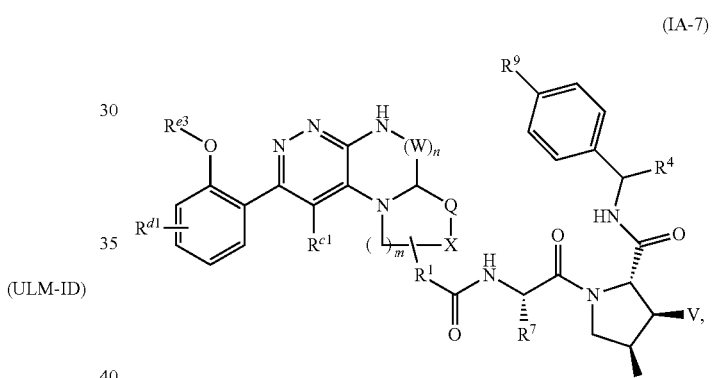
(IA-7)

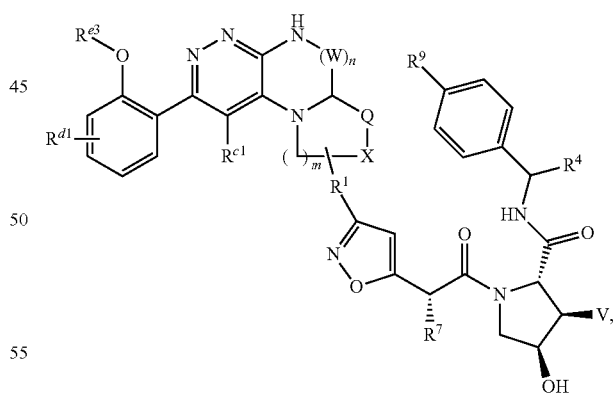
(IA-8)

wherein V is H or F;
W is optionally substituted —$CH_2$—, —C(O)—, —S(O)—, or —$S(O)_2$—; wherein when n=2 or 3, only one W may be —C(O)—, —S(O)—, or —$S(O)_2$—;
n=0-3;
m=1-3;
$R^k$=H, D, F, $C_{1-3}$ alkyl, $C_{1-3}$ haloalkyl, or $C_{1-4}$ alkoxyl;
$R^{c1}$ and $R^{d1}$ are independently H, D, Halo, $C_{1-3}$ alkyl, $C_{1-3}$ haloalkyl, or $C_{1-4}$ alkoxyl;

$R^{e3}$ is H, —C(O)$R^f$, or —P(O)(O$R^g$)$_2$; wherein $R^f$ and $R^g$ are independently H, $C_{1-4}$ alkyl, $C_{1-4}$ substituted alkyl, $C_{3-8}$ cyclcoalkyl, $C_{3-8}$ substituted cyclcoalkyl, $C_{3-8}$ heterocyclcoalkyl, or $C_{3-8}$ substituted heterocyclcoalkyl;

$R^1$ is a covalent bond, 3-11 membered cycloalkyl optionally substituted with 0-6 $R^{1a}$ and/or $R^{1b}$ groups, 3-11 membered heterocyclyl optionally substituted with 0-6 $R^{1a}$ and/or $R^{1b}$ groups, —(C$R^{1a}R^{1b}$)$_{1-5}$(C$R^{1a}$=C$R^{1b}$)—, —(C$R^{1a}R^{1b}$)$_{1-5}$-A- wherein A is O, S, or N$R^{1c}$, —(C$R^{1a}R^{1b}$)$_{1-5}$-A-(C$R^{1a}R^{1b}$)$_{1-5}$— wherein A is O, S, or N$R^{1c}$, —(C$R^{1a}R^{1b}$)$_{1-5}$-A-(C$R^{1a}R^{1b}$)$_{1-5}$-A- wherein A is O, S, or N$R^{1c}$, —(C$R^{1a}R^{1b}$)$_{1-5}$—(C$R^{1a}$=C$R^{1b}$)—(C$R^{1a}R^{1b}$)$_{1-5}$— (C$R^{1a}R^{1b}$)$_{1-5}$—(C$R^{1a}$=C$R^{1b}$)—(C$R^{1a}R^{1b}$)$_{1-5}$-A- wherein A is O, S, or N$R^{1c}$, —(C$R^{1a}R^{1b}$)$_{1-5}$—(C≡C)—(C$R^{1a}R^{1b}$)$_{1-5}$—, —(C$R^{1a}R^{1b}$)$_{1-5}$—(C≡C)—(C$R^{1a}R^{1b}$)$_{1-5}$-A- wherein A is O, S, or N$R^{1c}$, —(C≡C)—(C$R^{1a}R^{1b}$)$_{1-5}$-A-(C$R^{1a}R^{1b}$)$_{1-5}$— wherein A is O, S, or N$R^{1c}$, —(C≡C)—(C$R^{1a}R^{1b}$)$_{1-5}$, (C$R^{1a}R^{1b}$)$_{1-5}$ (3-11 membered cycloalkyl optionally substituted with 0-6 $R^{1a}$ and/or $R^{1b}$ groups)-, —(C$R^{1a}R^{1b}$)$_{1-5}$ (3-11 membered heterocyclyl optionally substituted with 0-6 $R^{1a}$ and/or $R^{1b}$ groups)-, -(3-11 membered cycloalkyl optionally substituted with 0-6 $R^{1a}$ and/or $R^{1b}$ groups)-(C$R^{1a}R^{1b}$)$_{1-5}$—, -(3-11 membered heterocyclyl optionally substituted with 0-6 $R^{1a}$ and/or $R^{1b}$ groups)—(C$R^{1a}R^{1b}$)$_{1-5}$—, —(C$R^{1a}R^{1b}$)$_{1-5}$ (3-11 membered cycloalkyl optionally substituted with 0-6 $R^{1a}$ and/or $R^{1b}$ groups)-A-, —(C$R^{1a}R^{1b}$)$_{1-5}$ (3-11 membered heterocyclyl optionally substituted with 0-6 $R^{1a}$ and/or $R^{1b}$ groups)-A-, —(C$R^{1a}R^{1b}$)$_{1-5}$ (3-11 membered cycloalkyl optionally substituted with 0-6 $R^{1a}$ and/or $R^{1b}$ groups)-(C$R^{1a}R^{1b}$)$_{1-5}$, —(C$R^{1a}R^{1b}$)$_{1-5}$-(3-11 membered cycloalkyl optionally substituted with 0-6 $R^{1a}$ and/or $R^{1b}$ groups)-A- wherein A is O, S, or N$R^{1c}$, —(C$R^{1a}R^{1b}$)$_{1-5}$ (3-11 membered cycloalkyl optionally substituted with 0-6 $R^{1a}$ and/or $R^{1b}$ groups)-(C$R^{1a}R^{1b}$)$_{1-5}$-A- wherein A is O, S, or N$R^{1c}$, —(C$R^{1a}R^{1b}$)$_{1-5}$-A-(3-11 membered cycloalkyl optionally substituted with 0-6 $R^{1a}$ and/or $R^{1b}$ groups)- wherein A is O, S, or N$R^{1c}$, —(C$R^{1a}R^{1b}$)$_{1-5}$-(3-11 membered heterocyclyl optionally substituted with 0-6 $R^{1a}$ and/or $R^{1b}$ groups)-(C$R^{1a}R^{1b}$)$_{1-5}$, (C$R^{1a}R^{1b}$)$_{1-5}$ (3-11 membered heterocyclyl optionally substituted with 0-6 $R^{1a}$ and/or $R^{1b}$ groups)-(C$R^{1a}R^{1b}$)$_{1-5}$-A- wherein A is O, S, or N$R^{1c}$, —(C$R^{1a}R^{1b}$)$_{1-5}$ (3-11 membered heterocyclyl optionally substituted with 0-6 $R^{1a}$ and/or $R^{1b}$ groups)-A- wherein A is O, S, or N$R^{1c}$, —(C$R^{1a}R^{1b}$)$_{1-5}$-A-(3-11 membered cycloalkyl optionally substituted with 0-6 $R^{1a}$ and/or $R^{1b}$ groups)- wherein A is O, S, or N$R^{1c}$, —(C$R^{1a}R^{1b}$)$_{1-5}$-A-(3-11 membered cycloalkyl optionally substituted with 0-6 $R^{1a}$ and/or $R^{1b}$ groups)-(C$R^{1a}R^{1b}$)$_{1-5}$-A- wherein each A is independently O, S, or N$R^{1c}$), —(C$R^{1a}R^{1b}$)$_{1-5}$-A-(3-11 membered heterocyclyl optionally substituted with 0-6 $R^{1a}$ and/or $R^{1b}$ groups)-(C$R^{1a}R^{1b}$)$_{1-5}$-A- wherein each A is independently O, S, or N$R^{1c}$, —(C$R^{1a}R^{1b}$)$_{1-5}$-A-(C$R^{1a}R^{1b}$)$_{1-5}$-A- wherein A is O, S, or N$R^{1c}$, —(C$R^{1a}R^{1b}$)$_{1-5}$-A-(C$R^{1a}R^{1b}$)$_{1-5}$-A-(C$R^{1a}R^{1b}$)$_{1-5}$-A- wherein A is O, S, or N$R^{1c}$, —(C$R^{1a}R^{1b}$)$_{1-5}$-A-(CO) wherein A is O, S, or N$R^{1c}$, —(C$R^{1a}R^{1b}$)$_{1-5}$—(C$R^{1a}$=C$R^{1b}$)—(C$R^{1a}R^{1b}$)$_{1-5}$-A-(CO)— wherein A is O, S, or N$R^{1c}$, —(C$R^{1a}R^{1b}$)$_{1-5}$—(C≡C)—(C$R^{1a}R^{1b}$)$_{1-5}$-A-(CO)— wherein A is O, S, or N$R^{1c}$), —(C$R^{1a}R^{1b}$)$_{1-5}$-(3-11 membered cycloalkyl optionally substituted with 0-6 $R^{1a}$ and/or $R^{1b}$ groups)-(C$R^{1a}R^{1b}$)$_{1-5}$-A-(CO)— wherein A is O, S, or N$R^{1c}$, —(C$R^{1a}R^{1b}$)$_{1-5}$-A-(CO)-(3-11 membered cycloalkyl optionally substituted with 0-6 $R^{1a}$ and/or $R^{1b}$ groups)- wherein A is O, S, or N$R^{1c}$), —(C$R^{1a}R^{1b}$)$_{1-5}$-(3-11 membered heterocyclyl optionally substituted with 0-6 $R^{1a}$ and/or $R^{1b}$ groups)-(C$R^{1a}R^{1b}$)$_{1-5}$-A-(CO)— wherein A is O, S, or N$R^{1c}$, —(C$R^{1a}R^{1b}$)$_{1-5}$-A-(CO)-(3-11 membered heterocyclyl optionally substituted with 0-6 $R^{1a}$ and/or $R^{1b}$ groups)- wherein A is O, S, or N$R^{1c}$, —(C$R^{1a}R^{1b}$)$_{1-5}$-A-(3-11 membered cycloalkyl optionally substituted with 0-6 $R^{1a}$ and/or $R^{1b}$ groups)-A-(CO)— wherein each A is independently O, S, or N$R^{1c}$, -(3-11 membered cycloalkyl optionally substituted with 0-6 $R^{1a}$ and/or $R^{1b}$ groups)-CO—(C$R^{1a}R^{1b}$)$_{1-5}$-A- wherein A is O, S, or N$R^{1c}$, —(C$R^{1a}R^{1b}$)$_{1-5}$-(3-11 membered cycloalkyl optionally substituted with 0-6 $R^{1a}$ and/or $R^{1b}$ groups)-(C$R^{1a}R^{1b}$)$_{1-5}$-A-(CO)— wherein A is O, S, or N$R^{1c}$, -(3-11 membered heterocyclyl optionally substituted with 0-6 $R^{1a}$ and/or $R^{1b}$ groups)-(C$R^{1a}R^{1b}$)$_{1-5}$-A- wherein A is O, S, or N$R^{1c}$; —(C$R^{1a}R^{1b}$)$_{1-5}$-(3-11 membered heterocyclyl optionally substituted with 0-6 $R^{1a}$ and/or $R^{1b}$ groups)-(C$R^{1a}R^{1b}$)$_{1-5}$-A-(CO)— wherein A is O, S, or N$R^{1c}$, -(3-11 membered cycloalkyl optionally substituted with 0-6 $R^{1a}$ and/or $R^{1b}$ groups)-(C$R^{1a}R^{1b}$)$_{1-5}$—, or -(3-11 membered heterocyclyl optionally substituted with 0-6 $R^{1a}$ and/or $R^{1b}$ groups)-(C$R^{1a}R^{1b}$)$_{1-5}$—, $R^4$ is H, optionally substituted alkyl, optionally substituted $C_1$-$C_6$alkyl, or —CH$_3$;

$R^7$ is optionally substituted alkyl, preferably optionally substituted $C_1$-$C_6$alkyl, and more preferably $C_1$-$C_6$alkyl; and $R^9$ is H, D, halo, —CN, —OH, —NO$_2$, —N$R^{e1}R^{e2}$, —O$R^{e1}$, —CON$R^{e1}R^{e2}$, —N$R^{e1}$CO$R^{e2}$, —SO$_2$N$R^{e1}R^{e2}$, —N$R^{e1}$SO$_2R^{e2}$, optionally substituted alkyl, optionally substituted alkoxyl, optionally substituted haloalkyl, optionally substituted haloalkoxy; optionally substituted aryl; optionally substituted heteroaryl; optionally substituted cycloalkyl; or optionally substituted heterocyclyl;

$R^{1a}$, $R^{1b}$, $R^{1c}$, and $R^{1e}$ are each independently, —H, D, -halo, —$C_1$-$C_8$alkyl, —$C_1$-$C_6$haloalkyl, —O—$C_1$-$C_8$alkyl, —S—$C_1$-$C_8$alkyl, —NH$C_1$-$C_8$alkyl, —N($C_1$-$C_8$alkyl)$_2$, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)($C_1$-$C_8$alkyl), —OH, —NH$_2$, —SH, —SO$_2C_1$-$C_8$alkyl, SO(NH)$C_1$-$C_8$alkyl, P(O)(O$C_1$-$C_8$alkyl)($C_1$-$C_8$alkyl), —P(O)(O$C_1$-$C_8$alkyl)$_2$, —C≡C—$C_1$-$C_8$alkyl, —C≡CH—, —CH=CH($C_1$-$C_8$alkyl), —C($C_1$-$C_8$alkyl)=CH($C_1$-$C_8$alkyl), —C($C_1$-$C_8$alkyl)=C($C_1$-$C_8$alkyl)$_2$, —Si(OH)$_3$, —Si($C_1$-$C_8$alkyl)$_3$, —Si(OH)($C_1$-$C_8$alkyl)$_2$, —C(O)$C_1$-$C_8$alkyl, —CO$_2$H, —CN, —CF$_3$, —CHF$_2$, —CH$_2$F, —NO$_2$, —SF$_5$, —SO$_2$NH$C_1$-$C_8$alkyl, —SO$_2$N($C_1$-$C_8$alkyl)$_2$, —SO(NH)NH$C_1$-$C_8$alkyl, —SO(NH)N($C_1$-$C_8$alkyl)$_2$, —SONH$C_1$-$C_8$alkyl, —SON($C_1$-$C_8$alkyl)$_2$, —CONH$C_1$-$C_8$alkyl, —CON($C_1$-$C_8$alkyl)$_2$, —N($C_1$-$C_8$alkyl)CONH($C_1$-$C_8$alkyl), —N($C_1$-$C_8$alkyl)CON($C_1$-$C_8$alkyl)$_2$, —NHCONH($C_1$-$C_8$alkyl), —NHCON($C_1$-$C_8$alkyl)$_2$, —NHCONH$_2$, —N($C_1$-$C_8$alkyl)SO$_2$NH($C_1$-$C_8$alkyl), —N($C_1$-$C_8$alkyl)SO$_2$N($C_1$-$C_8$alkyl)$_2$, —NHSO$_2$NH($C_1$-$C_8$alkyl), —NHSO$_2$N($C_1$-$C_8$alkyl)$_2$, or —NHSO$_2$NH$_2$, or where the context permits, $R^{1a}$ or $R^{1b}$, are linked to other groups, or to each other, to form a cycloalkyl and/or a heterocyclyl moiety, optionally substituted with 0-4 $R^{1e}$ groups; and each $R^{e1}$ and $R^{e2}$ is independently H, D, optionally substituted alkyl, or $R^{e1}$ and $R^{e2}$ together with the nitrogen atom to which they are attached form a 4-7 membered heterocyclyl.

In some aspects, the compounds of Formula I are those having the formula IA-9 or IA-10:

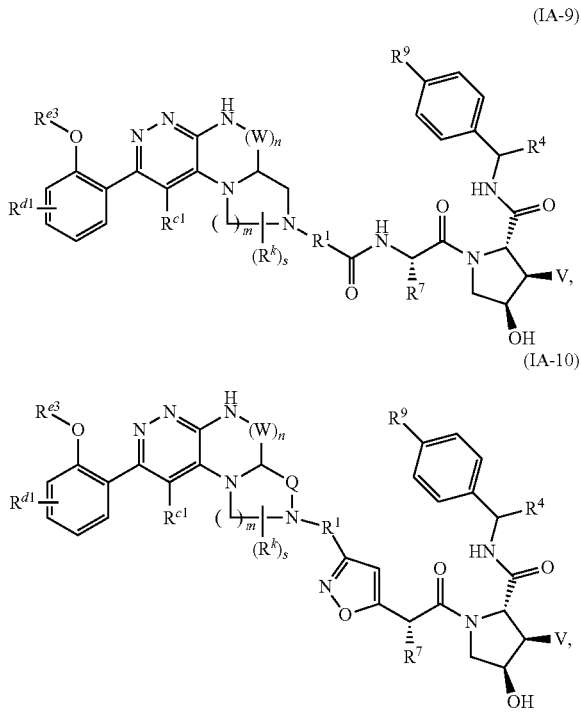

(IA-9)

(IA-10)

wherein V is H or F;

W is optionally substituted —CH$_2$—, —C(O)—, —S(O)—, or —S(O)$_2$—; wherein when n=2 or 3, only one W may be —C(O)—, —S(O)—, or —S(O)$_2$—;

n=0-3;

m=1-3;

R$^k$=H, D, F, C$_{1-3}$ alkyl, C$_{1-3}$ haloalkyl, or C$_{1-4}$ alkoxyl;

s=0-3;

R$^{c1}$ and R$^{d1}$ are independently H, D, Halo, C$_{1-3}$ alkyl, C$_{1-3}$ haloalkyl, or C$_{1-4}$ alkoxyl;

R$^{e3}$ is H, —C(O)R$^f$, or —P(O)(OR$^g$)$_2$; wherein R$^f$ and R$^g$ are independently H, C$_{1-4}$ alkyl, C$_{1-4}$ substituted alkyl, C$_{3-8}$ cyclcoalkyl, C$_{3-8}$ substituted cyclcoalkyl, C$_{3-8}$ heterocyclcoalkyl, or C$_{3-8}$ substituted heterocyclcoalkyl;

R$^1$ is a covalent bond, 3-11 membered cycloalkyl optionally substituted with 0-6 R$^{1a}$ and/or R$^{1b}$ groups, 3-11 membered heterocyclyl optionally substituted with 0-6 R$^{1a}$ and/or R$^{1b}$ groups, —(CR$^{1a}$R$^{1b}$)$_{1-5}$, —(CR$^{1a}$=CR$^{1b}$)—, —(CR$^{1a}$R$^{1b}$)$_{1-5}$-A- wherein A is O, S, or NR$^{1c}$, —(CR$^{1a}$R$^{1b}$)$^{1-5}$-A-(CR$^{1a}$R$^{1b}$)$_{1-5}$— wherein A is O, S, or NR$^{1c}$, —(CR$^{1a}$R$^{1b}$)$_{1-5}$-A-(CR$^{1a}$R$^{1b}$)$_{1-5}$-A- wherein A is O, S, or NR$^{1c}$), —(CR$^{1a}$R$^{1b}$)$_{1-5}$—(CR$^{1a}$=CR$^{1b}$)—(CR$^{1a}$R$^{1b}$)$_{1-5}$—, —(CR$^{1a}$R$^{1b}$)$_{1-5}$—(CR$^{1a}$=CR$^{1b}$)—(CR$^{1a}$R$^{1b}$)$_{1-5}$-A- wherein A is O, S, or NR$^{1c}$), —(CR$^{1a}$R$^{1b}$)$_{1-5}$—(C≡C)—(CR$^{1a}$R$^{1b}$)$_{1-5}$—, —(CR$^{1a}$R$^{1b}$)$_{1-5}$—(C≡C)—(CR$^{1a}$R$^{1b}$)$_{1-6}$-A- wherein A is O, S, or NR$^{1c}$, —(C≡C)—(CR$^{1a}$R$^{1b}$)$_{1-5}$-A-(CR$^{1a}$R$^{1b}$)$_{1-5}$— wherein A is O, S, or NR$^{1c}$, —(C≡C)—(CR$^{1a}$R$^{1b}$)$_{1-5}$, —(CR$^{1a}$R$^{1b}$)$_{1-5}$-(3-11 membered cycloalkyl optionally substituted with 0-6 R$^{1a}$ and/or R$^{1b}$ groups)-, —(CR$^{1a}$R$^{1b}$)$_{1-5}$ (3-11 membered heterocyclyl substituted with 0-6 R$^{1a}$ and/or R$^{1b}$ groups)-, -(3-11 membered cycloalkyl optionally substituted with 0-6 R$^{1a}$ and/or R$^{1b}$ groups)-(CR$^{1a}$R$^{1b}$)$_{1-5}$—, -(3-11 membered heterocyclyl optionally substituted with 0-6 R$^{1a}$ and/or R$^{1b}$ groups)—(CR$^{1a}$R$^{1b}$)$_{1-5}$—, —(CR$^{1a}$R$^{1b}$)$_{1-5}$ (3-11 membered cycloalkyl optionally substituted with 0-6 R$^{1a}$ and/or R$^{1b}$ groups)-A-, —(CR$^{1a}$R$^{1b}$)$_{1-5}$-(3-11 membered heterocyclyl optionally substituted with 0-6 R$^{1a}$ and/or R$^{1b}$ groups)-A-, —(CR$^{1a}$R$^{1b}$)$_{1-5}$ (3-11 membered cycloalkyl optionally substituted with 0-6 R$^{1a}$ and/or R$^{1b}$ groups)-(CR$^{1a}$R$^{1b}$)$_{1-5}$, —(CR$^{1a}$R$^{1b}$)$_{1-5}$-(3-11 membered cycloalkyl optionally substituted with 0-6 R$^{1a}$ and/or R$^{1b}$ groups)-A- wherein A is O, S, or NR$^{1c}$, —(CR$^{1a}$R$^{1b}$)$_{1-5}$-(3-11 membered cycloalkyl optionally substituted with 0-6 R$^{1a}$ and/or R$^{1b}$ groups)-(CR$^{1a}$R$^{1b}$)$_{1-5}$-A- wherein A is O, S, or NR$^{1c}$, —(CR$^{1a}$R$^{1b}$)$_{1-5}$-A-(3-11 membered cycloalkyl optionally substituted with 0-6 R$^{1a}$ and/or R$^{1b}$ groups)- wherein A is O, S, or NR$^{1c}$, —(CR$^{1a}$R$^{1b}$)$_{1-5}$-(3-11 membered heterocyclyl optionally substituted with 0-6 R$^{1a}$ and/or R$^{1b}$ groups)-(CR$^{1a}$R$^{1b}$)$_{1-5}$, —(CR$^{1a}$R$^{1b}$)$_{1-5}$ (3-11 membered heterocyclyl optionally substituted with 0-6 R$^{1a}$ and/or R$^{1b}$ groups)-(CR$^{1a}$R$^{1b}$)$_{1-5}$-A- wherein A is O, S, or NR$^{1c}$, —(CR$^{1a}$R$^{1b}$)$_{1-5}$ (3-11 membered heterocyclyl optionally substituted with 0-6 R$^{1a}$ and/or R$^{1b}$ groups)-A- wherein A is O, S, or NR$^{1c}$, —(CR$^{1a}$R$^{1b}$)$_{1-5}$-A-(3-11 membered heterocyclyl optionally substituted with 0-6 R$^{1a}$ and/or R$^{1b}$ groups)- wherein A is O, S, or NR$^{1c}$, —(CR$^{1a}$R$^{1b}$)$_{1-5}$-(3-11 membered cycloalkyl optionally substituted with 0-6 R$^{1a}$ and/or R$^{1b}$ groups)-(CR$^{1a}$R$^{1b}$)$_{1-5}$-A- wherein A is O, S, or NR$^{1c}$, —(CR$^{1a}$R$^{1b}$)$_{1-5}$-A-(3-11 membered cycloalkyl optionally substituted with 0-6 R$^{1a}$ and/or R$^{1b}$ groups)-(CR$^{1a}$R$^{1b}$)$_{1-5}$-A- wherein each A is independently O, S, or NR$^{1c}$, —(CR$^{1a}$R$^{1b}$)$_{1-5}$-A-(3-11 membered heterocyclyl optionally substituted with 0-6 R$^{1a}$ and/or R$^{1b}$ groups)-(CR$^{1a}$R$^{1b}$)$_{1-5}$-A- wherein each A is independently O, S, or NR$^{1c}$, —(CR$^{1a}$R$^{1b}$)$_{1-5}$-A-(CR$^{1a}$R$^{1b}$)$_{1-5}$-A- wherein A is O, S, or NR$^{1c}$, —(CR$^{1a}$R$^{1b}$)$_{1-5}$-A-(CR$^{1a}$R$^{1b}$)$_{1-5}$-A-(CR$^{1a}$R$^{1b}$)$_{1-5}$-A-(CR$^{1a}$R$^{1b}$)$_{1-5}$-A- wherein A is O, S, or NR$^{1c}$, —(CR$^{1a}$R$^{1b}$)$_{1-5}$-A-(CO) wherein A is O, S, or NR$^{1c}$, —(CR$^{1a}$R$^{1b}$)$_{1-5}$—(CR$^{1a}$=CR$^{1b}$)—(CR$^{1a}$R$^{1b}$)$_{1-5}$-A-(CO)— wherein A is O, S, or NR$^{1c}$, —(CR$^{1a}$R$^{1b}$)$_{1-5}$—(C≡C)—(CR$^{1a}$R$^{1b}$)$_{1-5}$-A-(CO)— wherein A is O, S, or NR$^{1c}$, —(CR$^{1a}$R$^{1b}$)$_{1-5}$-(3-11 membered cycloalkyl optionally substituted with 0-6 R$^{1a}$ and/or R$^{1b}$ groups)-(CR$^{1a}$R$^{1b}$)$_{1-5}$-A-(CO)— wherein A is O, S, or NR$^{1c}$, —(CR$^{1a}$R$^{1b}$)$_{1-5}$-A-(CO)-(3-11 membered cycloalkyl optionally substituted with 0-6 R$^{1a}$ and/or R$^{1b}$ groups)- wherein A is O, S, or NR$^{1c}$, —(CR$^{1a}$R$^{1b}$)$_{1-5}$-(3-11 membered heterocyclyl optionally substituted with 0-6 R$^{1a}$ and/or R$^{1b}$ groups)-(CR$^{1a}$R$^{1b}$)$_{1-5}$-A-(CO)— wherein A is O, S, or NR$^{1c}$, —(CR$^{1a}$R$^{1b}$)$_{1-5}$-A-(CO)-(3-11 membered heterocyclyl optionally substituted with 0-6 R$^{1a}$ and/or R$^{1b}$ groups)- wherein A is O, S, or NR$^{1c}$, —(CR$^{1a}$R$^{1b}$)$_{1-5}$-A-(3-11 membered cycloalkyl optionally substituted with 0-6 R$^{1a}$ and/or R$^{1b}$ groups)-A-(CO)— wherein each A is independently O, S, or NR$^{1c}$, -(3-11 membered cycloalkyl optionally substituted with 0-6 R$^{1a}$ and/or R$^{1b}$ groups)-CO—(CR$^{1a}$R$^{1b}$)$_{1-5}$-A- wherein A is O, S, or NR$^{1c}$, —(CR$^{1a}$R$^{1b}$)$_{1-5}$ (3-11 membered cycloalkyl optionally substituted with 0-6 R$^{1a}$ and/or R$^{1b}$ groups)-(CR$^{1a}$R$^{1b}$)$_{1-5}$-A-(CO)— wherein A is O, S, or NR$^{1c}$, —(CR$^{1a}$R$^{1b}$)$_{1-5}$-(3-11 membered heterocyclyl optionally substituted with 0-6 R$^{1a}$ and/or R$^{1b}$ groups)-(CR$^{1a}$R$^{1b}$)$_{1-5}$-A-(CO)— wherein A is O, S, or NR$^{1c}$, -(3-11 membered cycloalkyl optionally substituted with 0-6 R$^{1a}$ and/or R$^{1b}$ groups)-(CR$^{1a}$R$^{1b}$)$_{1-5}$—, or -(3-11 membered heterocyclyl optionally substituted with 0-6 R$^{1a}$ and/or R$^{1b}$ groups)-(CR$^{1a}$R$^{1b}$)$_{1-5}$—; or R$^1$ is -(3-11 membered heterocyclyl optionally substituted with 0-6 R$^{1a}$ and/or R$^{1b}$ groups)-(CO)—(CR$^{1a}$R$^{1b}$)$_{1-5}$-A- wherein A is O, S, or NR$^{1c}$; -(3-11 membered heterocyclyl optionally substituted with 0-6 R$^{1a}$ and/or R$^{1b}$ groups)-(CO)-A-(CR$^{1a}$R$^{1b}$)$_{1-5}$— wherein A is O, S, or NR$^{1c}$; -A-(3-11 membered heterocyclyl optionally substituted with 0-6 $R^{1a}$ and/or $R^{1b}$ groups)-$(CR^{1a}R^{1b})_{1-5}$-A- wherein each A is independently O, S, or $NR^{1c}$; -(3-11 membered heterocyclyl optionally substituted with 0-6 $R^{1a}$ and/or $R^{1b}$ groups)-$(CR^{1a}R^{1b})_{1-5}$ (3-11 membered heterocyclyl optionally substituted with 0-6 $R^{1a}$ and/or $R^{1b}$ groups)-$(CR^{1a}R^{1b})_{1-5}$-A- wherein A is O, S, or $NR^{1c}$; -(3-11 membered heterocyclyl optionally substituted with 0-6 $R^{1a}$ and/or $R^{1b}$ groups)-(3-11 membered heterocyclyl optionally substituted with 0-6 $R^{1a}$ and/or $R^{1b}$ groups)-$(CR^{1a}R^{1b})_{1-5}$-A- wherein A is O, S, or $NR^{1c}$; -(3-11 membered heterocyclyl optionally substituted with 0-6 $R^{1a}$ and/or $R^{1b}$ groups)-A-$(CR^{1a}R^{1b})_{1-5}$-A- wherein each A is independently O, S, or $NR^{1c}$; -(heteroaryl optionally substituted with 0-4 $R^{1a}$ and/or $R^{1b}$ groups)-A-$(CR^{1a}R^{1b})_{1-5}$— wherein A is O, S, or $NR^{1c}$; -(3-11 membered heterocyclyl optionally substituted with 0-6 $R^{1a}$ and/or $R^{1b}$ groups)-$(CR^{1a}R^{1b})_{1-5}$-A- wherein A is O, S, or $NR^{1c}$; -(3-11 membered cycloalkyl optionally substituted with 0-6 $R^{1a}$ and/or $R^{1b}$ groups)-(CO)—$(CR^{1a}R^{1b})_{1-5}$-A- wherein A is O, S, or $NR^{1c}$; -(3-11 membered cycloalkyl optionally substituted with 0-6 $R^{1a}$ and/or $R^{1b}$ groups)-(CO)-A-$(CR^{1a}R^{1b})_{1-5}$— wherein A is O, S, or $NR^{1c}$; —(CO)-(3-11 membered cycloalkyl optionally substituted with 0-6 $R^{1a}$ and/or $R^{1b}$ groups)-$(CR^{1a}R^{1b})_{1-5}$-A- wherein A is O, S, or $NR^{1c}$;

$R^4$ is H, optionally substituted alkyl, optionally substituted $C_1$-$C_6$alkyl, or —$CH_3$;

$R^7$ is optionally substituted alkyl, preferably optionally substituted $C_1$-$C_6$alkyl, and more preferably $C_1$-$C_6$alkyl; and $R^9$ is H, D, halo, —CN, —OH, —$NO_2$, —$NR^{e1}R^{e2}$, —$OR^{e1}$, —$CONR^{e1}R^{e2}$, —$NR^{e1}COR^{e2}$, —$SO_2NR^{e1}R^{e2}$, —$NR^{e1}SO_2R^{e2}$, optionally substituted alkyl, optionally substituted alkoxyl, optionally substituted haloalkyl, optionally substituted haloalkoxy; optionally substituted aryl; optionally substituted heteroaryl; optionally substituted cycloalkyl; or optionally substituted heterocyclyl;

$R^{1a}$, $R^{1b}$, $R^{1c}$, and $R^{1e}$ are each independently, —H, D, -halo, —$C_1$-$C_8$alkyl, —$C_1$-$C_6$haloalkyl, —O—$C_1$-$C_8$alkyl, —S—$C_1$-$C_8$alkyl, —N($C_1$-$C_8$alkyl)$_2$, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)($C_1$-$C_8$alkyl), —OH, —$NH_2$, —SH, —$SO_2C_1$-$C_8$alkyl, SO(NH)$C_1$-$C_8$alkyl, P(O)(O$C_1$-$C_8$alkyl)($C_1$-$C_8$alkyl), —P(O)(O$C_1$-$C_8$alkyl)$_2$, —CH=CH($C_1$-$C_8$alkyl), —C($C_1$-$C_8$alkyl)=CH($C_1$-$C_8$alkyl), —C($C_1$-$C_8$alkyl)=C($C_1$-$C_8$alkyl)$_2$, —Si(OH)$_3$, —Si($C_1$-$C_8$alkyl)$_3$, —Si(OH)($C_1$-$C_8$alkyl)$_2$, —C(O)$C_1$-$C_8$alkyl, —$CO_2H$, —CN, —$CF_3$, —$CHF_2$, —$CH_2F$, —$NO_2$, —$SF_5$, —$SO_2NHC_1$-$C_8$alkyl, —$SO_2N(C_1$-$C_8$alkyl)$_2$, —SO(NH)NH$C_1$-$C_8$alkyl, —SO(NH)N($C_1$-$C_8$alkyl)$_2$, —SONH$C_1$-$C_8$alkyl, —SON($C_1$-$C_8$alkyl)$_2$, —CONH$C_1$-$C_8$alkyl, —CON($C_1$-$C_8$alkyl)$_2$, —N($C_1$-$C_8$alkyl)CONH($C_1$-$C_8$alkyl), —N($C_1$-$C_8$alkyl)CON($C_1$-$C_8$alkyl)$_2$, —NHCONH($C_1$-$C_8$alkyl), —NHCON($C_1$-$C_8$alkyl)$_2$, —$NHCONH_2$, —N($C_1$-$C_8$alkyl)$SO_2NH$($C_1$-$C_8$alkyl), —N($C_1$-$C_8$alkyl)$SO_2N$($C_1$-$C_8$alkyl)$_2$, —NH$SO_2NH$($C_1$-$C_8$alkyl), —NH$SO_2N$($C_1$-$C_8$alkyl)$_2$, or —NH$SO_2NH_2$, or where the context permits, $R^{1a}$ or $R^{1b}$, are linked to other groups, or to each other, to form a cycloalkyl and/or a heterocyclyl moiety, optionally substituted with 0-4 $R^{1e}$ groups; and each $R^{e1}$ and $R^{e2}$ is independently H, D, optionally substituted alkyl, or $R^{e1}$ and $R^{e2}$ together with the nitrogen atom to which they are attached form a 4-7 membered heterocyclyl.

In some embodiments of the compound of Formula IA-9 or IA-10, n=1. In other embodiments of the compound of Formula IA-9 or IA-10, n=2. In other embodiments of the compound of Formula IA-9 or IA-10, n=3.

In some embodiments of the compound of Formula IA-7 or IA-8, m=1. In other embodiments of the compound of Formula IA-7 or IA-8, m=2. In other embodiments of the compound of Formula IA-7 or IA-8, m=3.

In some embodiments of the compound of Formula IA-9 or IA-10, s=0. In some embodiments of the compound of Formula IA-9 or IA-10, s=1. In other embodiments of the compound of Formula IA-9 or IA-10, s=2. In other embodiments of the compound of Formula IA-9 or IA-10, p=3.

In some embodiments of the compound of Formula IA-9 or IA-10, $R^k$=H.

In some embodiments of the compound of Formula IA-9 or IA-10, $R^k$=D.

In some embodiments of the compound of Formula IA-9 or IA-10, $R^k$=F.

In some embodiments of the compound of Formula IA-9 or IA-10, $R^k$=$C_{1-3}$ alkyl, for example, $C_1$ alkyl, $C_2$ alkyl, $C_3$ alkyl, —$CH_3$, —$CH_2CH_3$, and the like.

In some embodiments of the compound of Formula IA-9 or IA-10, $R^k$=$C_{1-3}$ haloalkyl, for example, $C_1$ haloalkyl, $C_2$ haloalkyl, $C_3$ haloalkyl, —$CF_3$, —$CH_2CF_3$, and the like.

In some embodiments of the compound of Formula IA-9 or IA-10, $R^k$=H. or $C_{1-4}$ alkoxyl, for example, $C_1$ alkoxyl, $C_2$ alkoxyl, $C_3$ alkoxyl, —$OCH_3$, —$OCH_2CH_3$, and the like.

In some embodiments of the compound of Formula IA-9 or IA-10, $R^{c1}$ and $R^{d1}$ are each H.

In some embodiments of the compound of Formula IA-9 or IA-10, $R^{e3}$ is H.

In some embodiments of the compound of Formula IA-9 or IA-10, $R^{c1}$, $R^{d1}$, and $R^{e3}$ and K are each H.

In some aspects, the compounds of Formula I are compounds of Formula IA-9a or IA-10a:

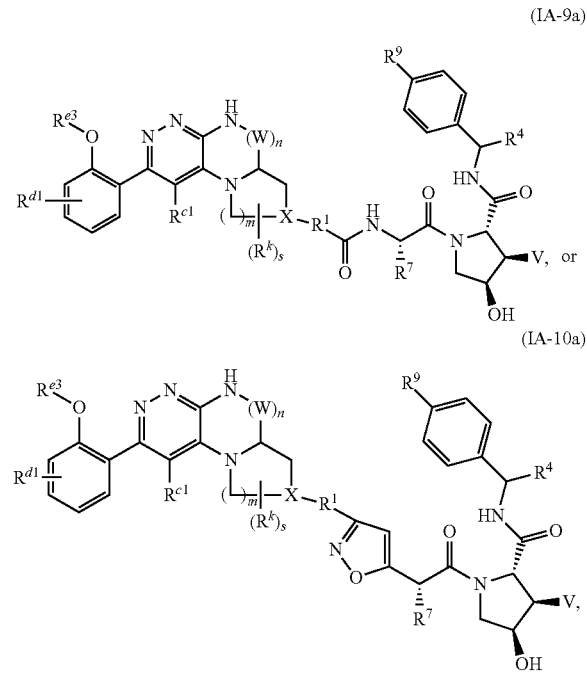

wherein X is N or CH, and the other variables are as set forth above with respect to Formula IA-9 and IA-10.

In some aspects, the compounds of Formula I are those having the formula IA-11 or IA-12:

(IA-11)

[Chemical structure of formula IA-11]

(IA-12)

[Chemical structure of formula IA-12]

wherein
W is —CH$_2$— or —CH(CH$_3$)—
X is N or CH;
R$^1$ is a covalent bond;
  3-11 membered cycloalkyl optionally substituted with 0-6 R$^{1a}$ and/or R$^{1b}$ groups;
  3-11 membered heterocyclyl optionally substituted with 0-6 R$^{1a}$ and/or R$^{1b}$ groups;
  —(CR$^{1a}$R$^{1b}$)$_{1-5}$—;
  —(CR$^{1a}$=CR$^{1b}$)—;
  —(CR$^{1a}$R$^{1b}$)$_{1-5}$-A- wherein A is O, S, or NR$^{1c}$;
  —(CR$^{1a}$R$^{1b}$)$_{1-5}$-A-(CR$^{1a}$R$^{1b}$)$_{1-5}$— wherein A is O, S, or NR$^{1c}$;
  —(CR$^{1a}$R$^{1b}$)$_{1-5}$-A-(CR$^{1a}$R$^{1b}$)$_{1-5}$-A- wherein A is O, S, or NR$^{1c}$;
  —(CR$^{1a}$R$^{1b}$)$_{1-5}$—(CR$^{1a}$=CR$^{1b}$)—(CR$^{1a}$R$^{1b}$)$_{1-5}$—;
  —(CR$^{1a}$R$^{1b}$)$_{1-5}$—(CR$^{1a}$=CR$^{1b}$)—(CR$^{1a}$R$^{1b}$)$_{1-5}$-A- wherein A is O, S, or NR$^{1c}$;
  —(CR$^{1a}$R$^{1b}$)$_{1-5}$—(C≡C)—(CR$^{1a}$R$^{1b}$)$_{1-5}$—;
  —(CR$^{1a}$R$^{1b}$)$_{1-5}$—(C≡C)—(CR$^{1a}$R$^{1b}$)$_{1-5}$-A- wherein A is O, S, or NR$^{1c}$;
  —(C≡C)—(CR$^{1a}$R$^{1b}$)$_{1-5}$-A-(CR$^{1a}$R$^{1b}$)$_{1-5}$— wherein A is O, S, or NR$^{1c}$;
  —(C≡C)—(CR$^{1a}$R$^{1b}$)$_{1-5}$;
  —(CR$^{1a}$R$^{1b}$)$_{1-5}$-(3-11 membered cycloalkyl optionally substituted with 0-6 R$^{1a}$ and/or R$^{1b}$ groups)-;
  —(CR$^{1a}$R$^{1b}$)$_{1-5}$-(3-11 membered heterocyclyl optionally substituted with 0-6 R$^{1a}$ and/or R$^{1b}$ groups)-;
  -(3-11 membered cycloalkyl optionally substituted with 0-6 R$^{1a}$ and/or R$^{1b}$ groups)-(CR$^{1a}$R$^{1b}$)$_{1-5}$;
  -(3-11 membered cycloalkyl optionally substituted with 0-6 R$^{1a}$ and/or R$^{1b}$ groups)-(CR$^{1a}$R$^{1b}$)$_{1-5}$-A- wherein A is O, S, or NR$^{1c}$;
  -(3-11 membered heterocyclyl optionally substituted with 0-6 R$^{1a}$ and/or R$^{1b}$ groups)-(CR$^{1a}$R$^{1b}$)$_{1-5}$-A- wherein A is O, S, or NR$^{1c}$;
  -(3-11 membered heterocyclyl optionally substituted with 0-6 R$^{1a}$ and/or R$^{1b}$ groups) —(CR$^{1a}$R$^{1b}$)$_{1-5}$—;
  —(CR$^{1a}$R$^{1b}$)$_{1-5}$ (3-11 membered cycloalkyl optionally substituted with 0-6 R$^{1a}$ and/or R$^{1b}$ groups)-A- wherein A is O, S, or NR$^{1c}$;
  —(CR$^{1a}$R$^{1b}$)$_{1-5}$ (3-11 membered heterocyclyl optionally substituted with 0-6 R$^{1a}$ and/or R$^{1b}$ groups)-A- wherein A is O, S, or NR$^{1c}$;
  —(CR$^{1a}$R$^{1b}$)$_{1-5}$ (3-11 membered cycloalkyl optionally substituted with 0-6 R$^{1a}$ and/or R$^{1b}$ groups)-(CR$^{1a}$R$^{1b}$)$_{1-5}$;
  —(CR$^{1a}$R$^{1b}$)$_{1-5}$-(3-11 membered cycloalkyl optionally substituted with 0-6 R$^{1a}$ and/or R$^{1b}$ groups)-A- wherein A is O, S, or NR$^{1c}$;
  —(CR$^{1a}$R$^{1b}$)$_{1-5}$ (3-11 membered cycloalkyl optionally substituted with 0-6 R$^{1a}$ and/or R$^{1b}$ groups)-(CR$^{1a}$R$^{1b}$)$_{1-5}$-A- wherein A is O, S, or NR$^{1c}$;
  —(CR$^{1a}$R$^{1b}$)$_{1-5}$-A-(3-11 membered cycloalkyl optionally substituted with 0-6 R$^{1a}$ and/or R$^{1b}$ groups)- wherein A is O, S, or NR$^{1c}$;
  —(CR$^{1a}$R$^{1b}$)$_{1-5}$ (3-11 membered heterocyclyl optionally substituted with 0-6 R$^{1a}$ and/or R$^{1b}$ groups)-(CR$^{1a}$R$^{1b}$)$_{1-5}$;
  —(CR$^{1a}$R$^{1b}$)$_{1-5}$ (3-11 membered heterocyclyl optionally substituted with 0-6 R$^{1a}$ and/or R$^{1b}$ groups)-(CR$^{1a}$R$^{1b}$)$_{1-5}$-A- wherein A is O, S, or NR$^{1c}$;
  —(CR$^{1a}$R$^{1b}$)$_{1-5}$ (3-11 membered heterocyclyl optionally substituted with 0-6 R$^{1a}$ and/or R$^{1b}$ groups)-A- wherein A is O, S, or NR$^{1c}$;
  —(CR$^{1a}$R$^{1b}$)$_{1-5}$-A-(3-11 membered heterocyclyl optionally substituted with 0-6 R$^{1a}$ and/or R$^{1b}$ groups)- wherein A is O, S, or NR$^{1c}$;
  —(CR$^{1a}$R$^{1b}$)$_{1-5}$ (3-11 membered cycloalkyl optionally substituted with 0-6 R$^{1a}$ and/or R$^{1b}$ groups)-(CR$^{1a}$R$^{1b}$)$_{1-5}$-A- wherein A is O, S, or NR$^{1c}$;
  —(CR$^{1a}$R$^{1b}$)$_{1-5}$-A-(3-11 membered cycloalkyl optionally substituted with 0-6 R$^{1a}$ and/or R$^{1b}$ groups)- wherein A is O, S, or NR$^{1c}$;
  —(CR$^{1a}$R$^{1b}$)$_{1-5}$-A-(3-11 membered cycloalkyl optionally substituted with 0-6 R$^{1a}$ and/or R$^{1b}$ groups)-(CR$^{1a}$R$^{1b}$)$_{1-5}$-A- wherein each A is independently O, S, or NR$^{1c}$;
  —(CR$^{1a}$R$^{1b}$)$_{1-5}$-A-(3-11 membered heterocyclyl optionally substituted with 0-6 R$^{1a}$ and/or R$^{1b}$ groups)-(CR$^{1a}$R$^{1b}$)$_{1-5}$-A- wherein each A is independently O, S, or NR$^{1c}$;
  —(CR$^{1a}$R$^{1b}$)$_{1-5}$-A-(CR$^{1a}$R$^{1b}$)$_{1-5}$-A- wherein A is O, S, or NR$^{1c}$;
  —(CR$^{1a}$R$^{1b}$)$_{1-5}$-A-(CR$^{1a}$R$^{1b}$)$_{1-5}$-A-(CR$^{1a}$R$^{1b}$)$_{1-5}$-A-(CR$^{1a}$R$^{1b}$)$_{1-5}$-A- wherein each A is independently O, S, or NR$^{1c}$;
  —(CR$^{1a}$R$^{1b}$)$_{1-5}$-A-(CO) wherein A is O, S, or NR$^{1c}$;
  —(CR$^{1a}$R$^{1b}$)$_{1-5}$—(CR$^{1a}$=CR$^{1b}$)—(CR$^{1a}$R$^{1b}$)$_{1-5}$-A-(CO)— wherein A is O, S, or NR$^{1c}$;
  —(CR$^{1a}$R$^{1b}$)$_{1-5}$—(C≡C)—(CR$^{1a}$R$^{1b}$)$_{1-5}$-A-(CO)— wherein A is O, S, or NR$^{1c}$;
  —(CR$^{1a}$R$^{1b}$)$_{1-5}$-(3-11 membered cycloalkyl optionally substituted with 0-6 R$^{1a}$ and/or R$^{1b}$ groups)-(CR$^{1a}$R$^{1b}$)$_{1-5}$-A-(CO)— wherein A is O, S, or NR$^{1c}$;
  —(CR$^{1a}$R$^{1b}$)$_{1-5}$-A-(CO)-(3-11 membered cycloalkyl optionally substituted with 0-6 R$^{1a}$ and/or R$^{1b}$ groups)- wherein A is O, S, or NR$^{1c}$;
  —(CR$^{1a}$R$^{1b}$)$_{1-5}$-(3-11 membered heterocyclyl optionally substituted with 0-6 R$^{1a}$ and/or R$^{1b}$ groups)-(CR$^{1a}$R$^{1b}$)$_{1-5}$-A-(CO)— wherein A is O, S, or NR$^{1c}$;

—(CR$^{1a}$R$^{1b}$)$_{1-5}$-A-(CO)-(3-11 membered heterocyclyl optionally substituted with 0-6 R$^{1a}$ and/or R$^{1b}$ groups)- wherein A is O, S, or NR$^{1c}$;

—(CR$^{1a}$R$^{1b}$)$_{1-5}$-A-(3-11 membered cycloalkyl optionally substituted with 0-6 R$^{1a}$ and/or R$^{1b}$ groups)-A-(CO)— wherein each A is independently O, S, or NR$^{1c}$;

-(3-11 membered cycloalkyl optionally substituted with 0-6 R$^{1a}$ and/or R$^{1b}$ groups)-CO—(CR$^{1a}$R$^{1b}$)$_{1-5}$-A- wherein A is O, S, or NR$^{1c}$;

—(CR$^{1a}$R$^{1b}$)$_{1-5}$-(3-11 membered cycloalkyl optionally substituted with 0-6 R$^{1a}$ and/or R$^{1b}$ groups)-(CR$^{1a}$R$^{1b}$)$_{1-5}$-A-(CO)— wherein A is O, S, or NR$^{1c}$;

—(CR$^{1a}$R$^{1b}$)$_{1-5}$-(3-11 membered heterocyclyl optionally substituted with 0-6 R$^{1a}$ and/or R$^{1b}$ groups)-(CR$^{1a}$R$^{1b}$)$_{1-5}$-A-(CO)— wherein A is O, S, or NR$^{1c}$;

-(3-11 membered cycloalkyl optionally substituted with 0-6 R$^{1a}$ and/or R$^{1b}$ groups)-(CR$^{1a}$R$^{1b}$)$_{1-5}$—;

-(3-11 membered heterocyclyl optionally substituted with 0-6 R$^{1a}$ and/or R$^{1b}$ groups)-(CR$^{1a}$R$^{1b}$)$_{1-5}$—;

-A-(3-11 membered heterocyclyl optionally substituted with 0-6 R$^{1a}$ and/or R$^{1b}$ groups)-(CR$^{1a}$R$^{1b}$)$_{1-5}$-A- wherein each A is independently O, S, or NR$^{1c}$;

-(3-11 membered heterocyclyl optionally substituted with 0-6 R$^{1a}$ and/or R$^{1b}$ groups)-(CR$^{1a}$R$^{1b}$)$_{1-5}$-(3-11 membered heterocyclyl optionally substituted with 0-6 R$^{1a}$ and/or R$^{1b}$ groups)-(CR$^{1a}$R$^{1b}$)$_{1-5}$-A- wherein A is O, S, or NR$^{1c}$;

-(3-11 membered heterocyclyl optionally substituted with 0-6 R$^{1a}$ and/or R$^{1b}$ groups)-(3-11 membered heterocyclyl optionally substituted with 0-6 R$^{1a}$ and/or R$^{1b}$ groups)-(CR$^{1a}$R$^{1b}$)$_{1-5}$-A- wherein A is O, S, or NR$^{1c}$;

-(3-11 membered heterocyclyl optionally substituted with 0-6 R$^{1a}$ and/or R$^{1b}$ groups)-A-(CR$^{1a}$R$^{1b}$)$_{1-5}$-A- wherein each A is independently O, S, or NR$^{1c}$;

-(3-11 membered heterocyclyl optionally substituted with 0-6 R$^{1a}$ and/or R$^{1b}$ groups)-(CO)-A-(CR$^{1a}$R$^{1b}$)$_{1-5}$— wherein A is O, S, or NR$^{1c}$;

-(heteroaryl optionally substituted with 0-4 R$^{1a}$ and/or R$^{1b}$ groups)-A-(CR$^{1a}$R$^{1b}$)$_{1-5}$— wherein A is O, S, or NR$^{1c}$;

-(3-11 membered cycloalkyl optionally substituted with 0-6 R$^{1a}$ and/or R$^{1b}$ groups)-(CO)—(CR$^{1a}$R$^{1b}$)$_{1-5}$-A- wherein A is O, S, or NR$^{1c}$;

-(3-11 membered cycloalkyl optionally substituted with 0-6 R$^{1a}$ and/or R$^{1b}$ groups)-(CO)-A-(CR$^{1a}$R$^{1b}$)$_{1-5}$— wherein A is O, S, or NR$^{1c}$; or —(CO)-(3-11 membered cycloalkyl optionally substituted with 0-6 R$^{1a}$ and/or R$^{1b}$ groups)-(CR$^{1a}$R$^{1b}$)$_{1-5}$-A- wherein A is O, S, or NR$^{1c}$;

R$^4$ is H, —CH$_3$, or —CH$_2$OH;

R$^7$ is C$_1$-C$_6$alkyl, preferably —C(CH$_3$)$_3$ or —CH(CH$_3$)$_2$; and

R$^9$ is —CN or optionally substituted heteroaryl, preferably,

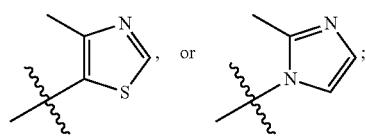

R$^{1a}$, R$^{1b}$, R$^{1c}$, and R$^{1e}$ are each independently, —H, D, -halo, —C$_1$-C$_8$alkyl, —C$_1$-C$_6$haloalkyl, —O—C$_1$-C$_8$alkyl, —S—C$_1$-C$_8$alkyl, —NHC$_1$-C$_8$alkyl, —N(C$_1$-C$_8$alkyl)$_2$, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)(C$_1$-C$_8$alkyl), —OH, —NH$_2$, —SH, —SO$_2$C$_1$-C$_8$alkyl, SO(NH)C$_1$-C$_8$alkyl, P(O)(OC$_1$-C$_8$alkyl)(C$_1$-C$_8$alkyl), —P(O)(OC$_1$-C$_8$alkyl)$_2$, —CH═CH(C$_1$-C$_8$alkyl), —C(C$_1$-C$_8$alkyl)═CH(C$_1$-C$_8$alkyl), —C(C$_1$-C$_8$alkyl)═C(C$_1$-C$_8$alkyl)$_2$, —Si(OH)$_3$, —Si(C$_1$-C$_8$alkyl)$_3$, —Si(OH)(C$_1$-C$_8$alkyl)$_2$, —C(O)C$_1$-C$_8$alkyl, —CO$_2$H, —CN, —CF$_3$, —CHF$_2$, —CH$_2$F, —NO$_2$, —SF$_5$, —SO$_2$NHC$_1$-C$_8$alkyl, —SO$_2$N(C$_1$-C$_8$alkyl)$_2$, —SO(NH)NHC$_1$-C$_8$alkyl, —SO(NH)N(C$_1$-C$_8$alkyl)$_2$, —SONHC$_1$-C$_8$alkyl, —SON(C$_1$-C$_8$alkyl)$_2$, —CONHC$_1$-C$_8$alkyl, —CON(C$_1$-C$_8$alkyl)$_2$, —N(C$_1$-C$_8$alkyl)CONH(C$_1$-C$_8$alkyl), —N(C$_1$-C$_8$alkyl)CON(C$_1$-C$_8$alkyl)$_2$, —NHCONH(C$_1$-C$_8$alkyl), —NHCON(C$_1$-C$_8$alkyl)$_2$, —NHCONH$_2$, —N(C$_1$-C$_8$alkyl)SO$_2$NH(C$_1$-C$_8$alkyl), —N(C$_1$-C$_8$alkyl)SO$_2$N(C$_1$-C$_8$alkyl)$_2$, —NHSO$_2$NH(C$_1$-C$_8$alkyl), —NHSO$_2$N(C$_1$-C$_8$alkyl)$_2$, or —NHSO$_2$NH$_2$, or where the context permits, R$^{1a}$ or R$^{1b}$, are linked to other groups, or to each other, to form a cycloalkyl and/or a heterocyclyl moiety, optionally substituted with 0-4 R$^{1e}$ groups.

In some embodiments, W is —CH$_2$—.
In some embodiments, X is —N.
In other embodiments, X is —CH.
In some embodiments, R$^4$ is —CH$_3$.
In some embodiments, R$^7$ is ably —C(CH$_3$)$_3$ or —CH(CH$_3$)$_2$.
In some embodiments, R$^k$ is —CH$_3$ and s=1.
In some embodiments, s=0.
In some embodiments, R$^9$ is

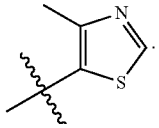

In some embodiments of the compound of formula I, such as formula IA-11 or formula IA-12, R$^1$ is:

—(CR$^{1a}$R$^{1b}$)$_{1-5}$;

—(CR$^{1a}$R$^{1b}$)$_{1-5}$-A- wherein A is O, S, or NR$^{1c}$;

—(CR$^{1a}$R$^{1b}$)$_{1-5}$-A-(CR$^{1a}$R$^{1b}$)$_{1-5}$— wherein A is O, S, or NR$^{1c}$;

-(3-11 membered heterocyclyl optionally substituted with 0-6 R$^{1a}$ and/or R$^{1b}$ groups)-(CO)—(CR$^{1a}$R$^{1b}$)$_{1-5}$-A- wherein A is O, S, or NR$^{1c}$;

-(3-11 membered heterocyclyl optionally substituted with 0-6 R$^{1a}$ and/or R$^{1b}$ groups)-(CO)-A-(CR$^{1a}$R$^{1b}$)$_{1-5}$— wherein A is O, S, or NR$^{1c}$;

—(CR$^{1a}$R$^{1b}$)$_{1-5}$-(3-11 membered cycloalkyl optionally substituted with 0-6 R$^{1a}$ and/or R$^{1b}$ groups)-A- wherein A is O, S, or NR$^{1c}$;

—(CR$^{1a}$R$^{1b}$)$_{1-5}$-(3-11 membered heterocyclyl optionally substituted with 0-6 R$^{1a}$ and/or R$^{1b}$ groups)-(CR$^{1a}$R$^{1b}$)$_{1-5}$;

—(CR$^{1a}$R$^{1b}$)$_{1-5}$ (3-11 membered heterocyclyl optionally substituted with 0-6 R$^{1a}$ and/or R$^{1b}$ groups)-(CR$^{1a}$R$^{1b}$)$_{1-5}$-A- wherein A is O, S, or NR$^{1c}$;

-(3-11 membered heterocyclyl optionally substituted with 0-6 R$^{1a}$ and/or R$^{1b}$ groups)-(CR$^{1a}$R$^{1b}$)$_{1-5}$-A- wherein A is O, S, or NR$^{1c}$; -A-(3-11 membered heterocyclyl optionally substituted with 0-6 R$^{1a}$ and/or R$^{1b}$ groups)-(CR$^{1a}$R$^{1b}$)$_{1-5}$-A- wherein each A is independently O, S, or NR$^{1c}$;

- -(3-11 membered heterocyclyl optionally substituted with 0-6 $R^{1a}$ and/or $R^{1b}$ groups)-$(CR^{1a}R^{1b})_{1-5}$ (3-11 membered heterocyclyl optionally substituted with 0-6 $R^{1a}$ and/or $R^{1b}$ groups)-$(CR^{1a}R^{1b})_{1-5}$-A- wherein A is O, S, or $NR^{1c}$;
- -(3-11 membered heterocyclyl optionally substituted with 0-6 $R^{1a}$ and/or $R^{1b}$ groups)-(3-11 membered heterocyclyl optionally substituted with 0-6 $R^{1a}$ and/or $R^{1b}$ groups)-$(CR^{1a}R^{1b})_{1-5}$-A- wherein A is O, S, or $NR^{1c}$;
- -(3-11 membered heterocyclyl optionally substituted with 0-6 $R^{1a}$ and/or $R^{1b}$ groups)-A-$(CR^{1a}R^{1b})_{1-5}$-A- wherein each A is independently O, S, or $NR^{1c}$;
- -(3-11 membered heterocyclyl optionally substituted with 0-6 $R^{1a}$ and/or $R^{1b}$ groups)-(CO)-A-$(CR^{1a}R^{1b})_{1-5}$— wherein A is O, S, or $NR^{1c}$;
- (heteroaryl optionally substituted with 0-4 $R^{1a}$ and/or $R^{1b}$ groups)-A-$(CR^{1a}R^{1b})_{1-5}$— wherein A is O, S, or $NR^{1c}$;
- -(3-11 membered cycloalkyl optionally substituted with 0-6 $R^{1a}$ and/or $R^{1b}$ groups)-(CO)—$(CR^{1a}R^{1b})_{1-5}$-A- wherein A is O, S, or $NR^{1c}$;
- -(3-11 membered cycloalkyl optionally substituted with 0-6 $R^{1a}$ and/or $R^{1b}$ groups)-(CO)-A-$(CR^{1a}R^{1b})_{1-5}$— wherein A is O, S, or $NR^{1c}$; or
- —(CO)-(3-11 membered cycloalkyl optionally substituted with 0-6 $R^{1a}$ and/or $R^{1b}$ groups)-$(CR^{1a}R^{1b})_{1-5}$-A- wherein A is O, S, or $NR^{1c}$.

In some embodiments of the compounds of formula IA-11 or formula IA-12, each $R^{1a}$ each $R^{1b}$, and each $R^{1c}$ is independently H or $C_1$-$C_6$alkyl.

In some embodiments of the compound of formula IA-11 or formula IA-12, $R^1$ is —$(CR^{1a}R^{1b})_{1-5}$, such as, for example, —$CH_2$—, —$CH_2CH_2$—, —$CH_2CH_2CH_2$—, —$CH_2CH_2CH_2CH_2$—, —$CH_2CH_2CH_2CH_2CH_2$—, and the like.

In some embodiments of the compound of formula IA-11 or formula IA-12, $R^1$ is —$(CR^{1a}R^{1b})_{1-5}$-A- wherein A is O, S, or $NR^{1c}$, such as, for example, —$CH_2$—O—, —$CH_2CH_2$—O—, —$CH_2CH_2CH_2$—O—, and the like.

In some embodiments of the compounds of formula I, $R^1$ is —$(CR^{1a}R^{1b})_{1-5}$-A-$(CR^{1a}R^{1b})_{1-5}$— wherein A is O, S, or $NR^{1c}$, such as, for example, —$CH_2CH_2CH_2$—$N(CH_3)$—$CH_2CH_2$—, —$CH_2CH_2$—$N(CH_3)$—$CH_2CH_2$—, —$CH_2CH_2$—O—$CH_2$—, and the like.

In some embodiments of the compounds of formula I, $R^1$ is -(3-11 membered heterocyclyl optionally substituted with 0-6 $R^{1a}$ and/or $R^{1b}$ groups)-(CO)—$(CR^{1a}R^{1b})_{1-5}$-A- wherein A is O, S, or $NR^{1c}$, such as, for example, -piperidinyl-(CO)—$CH(CH_3)$—O—, -pyrrolidinyl-(CO)—$CH(CH_3)$—O—, -piperidinyl-(CO)—$CH_2$—O—, -methylpiperidinyl-(CO)—$CH_2$—O—, and the like.

In some embodiments of the compounds of formula I, $R^1$ is -(3-11 membered heterocyclyl optionally substituted with 0-6 $R^{1a}$ and/or $R^{1b}$ groups)-(CO)-A-$(CR^{1a}R^{1b})_{1-5}$— wherein A is O, S, or $NR^{1c}$, such as, for example, -piperidinyl-(CO)—O—$CH_2$—, and the like.

In some embodiments of the compounds of formula I, $R^1$ is -(3-11 membered heterocyclyl optionally substituted with 0-6 $R^{1a}$ and/or $R^{1b}$ groups)-$(CR^{1a}R^{1b})_{1-5}$-A- wherein A is O, S, or $NR^{1c}$, such as, for example, -azabicyclo[3.1.1]heptanyl-$CH_2CH_2$—O—, -azaspiro[3.3]heptanyl-$CH_2CH_2$—O—, -piperidinyl-$CH_2CH_2$—O—, -fluoropiperidinyl-$CH_2CH_2$—O—, -azepanyl-$CH_2CH_2$—O—, -pyrrolidinyl-$CH_2CH_2$—O—, -piperidinyl-$CH_2CH(CH_3)$—O—, -octahydrocyclopenta[c]pyrrolyl-$CH_2CH_2$—O—, -pyrrolidinyl-$CH_2CH(CH_3)$—O—, -methylpiperidinyl-$CH_2CH_2$—O—, -piperidinyl-$CH_2CH(CH_2CH_3)$—O—, -pyrrolidinyl-$CH_2CH(CH_2CH_3)$—O—, -pyrrolidinyl-$CH_2CH(CH_3)$—O—, -hydroxypyrrolidinyl-$CH_2CH_2$—O—, -hydroxypiperidinyl-$CH_2CH_2$—O—, and the like.

In some embodiments of the compounds of formula I, $R^1$ is -(3-11 membered heterocyclyl optionally substituted with 0-6 $R^{1a}$ and/or $R^{1b}$ groups)-$(CR^{1a}R^{1b})_{1-5}$—, such as, for example, -piperidinyl-$CH_2$—, -piperidinyl-$CH_2CH_2$—, -piperidinyl-$CH_2CH_2CH_2$—, azetidinyl-$CH_2CH_2CH_2$—, -aziridinyl-$CH_2$—, -pyrrolidinyl-$CH_2CH_2$—, and the like.

In some embodiments of the compounds of formula I, $R^1$ is -(3-11 membered heterocyclyl optionally substituted with 0-6 $R^{1a}$ and/or $R^{1b}$ groups)-(3-11 membered heterocyclyl optionally substituted with 0-6 $R^{1a}$ and/or $R^{1b}$ groups)-$(CR^{1a}R^{1b})_{1-5}$-A- wherein A is O, S, or $NR^{1c}$, such as, for example, -piperidinyl-pyrrolidinyl-$CH_2CH_2$—O—, -piperidinyl-piperidinyl-$CH_2CH_2$—O—, -pyrrolidinyl-piperidinyl-$CH_2CH_2$—O—, and the like.

In some embodiments of the compounds of formula I, $R^1$ is -(3-11 membered heterocyclyl optionally substituted with 0-6 $R^{1a}$ and/or $R^{1b}$ groups)-$(CR^{1a}R^{1b})_{1-5}$ (3-11 membered heterocyclyl optionally substituted with 0-6 $R^{1a}$ and/or $R^{1b}$ groups)-$(CR^{1a}R^{1b})_{1-5}$-A- wherein A is O, S, or $NR^{1c}$, such as, for example, -piperidinyl-$CH_2$-piperidinyl-$CH_2CH_2$—O—, -piperidinyl-$CH_2CH_2$-piperidinyl-$CH_2CH_2$—O—, and the like.

In some embodiments of the compounds of formula I, $R^1$ is -(3-11 membered cycloalkyl optionally substituted with 0-6 $R^{1a}$ and/or $R^{1b}$ groups)-A-$(CR^{1a}R^{1b})_{1-5}$— wherein each A is independently O, S, or $NR^{1c}$, such as, for example, -cyclohexyl-$N(CH_3)$—$CH_2CH_2$—O—, and the like.

In some embodiments of the compounds of formula I, $R^1$ is —(CO)-(3-11 membered heterocyclyl optionally substituted with 0-6 $R^{1a}$ and/or $R^{1b}$ groups)-$(CR^{1a}R^{1b})_{1-5}$-A- wherein A is O, S, or $NR^{1c}$, such as, for example, —(CO)-piperidinyl-$CH_2CH_2$—O—, and the like.

In some embodiments of the compounds of formula I, $R^1$ is —$(CR^{1a}R^{1b})_{1-5}$ (3-11 membered heterocyclyl optionally substituted with 0-6 $R^{1a}$ and/or $R^{1b}$ groups)-$(CR^{1a}R^{1b})_{1-5}$, such as, for example, —$CH_2$-piperidinyl-$CH_2$—, —$CH_2$-piperidinyl-$CH_2CH_2$—, —$CH_2$-piperidinyl-$CH_2CH_2CH_2$—, and the like.

In some embodiments of the compounds of formula I, $R^1$ is —$(CR^{1a}R^{1b})_{1-5}$ (3-11 membered heterocyclyl optionally substituted with 0-6 $R^{1a}$ and/or $R^{1b}$ groups)-$(CR^{1a}R^{1b})_{1-5}$-A-, wherein each A is independently O, S, or $NR^{1c}$, such as, for example, —$CH_2$-pyrrolidinyl-$CH_2CH_2$—O—, —$CH_2$-pyridinyl-$CH_2CH(CH_3)$—O—, —$CH_2$-pyridinyl-$CH_2CH_2$—O—, —$CH(CH_3)$-pyridinyl-$CH_2CH_2$—O—, —$CH_2$-azepanyl-$CH_2CH(CH_3)$—O—, —$CH_2$-azabicyclo[3.2.1]octanyl-$CH_2CH_2$—O—, —$CH_2$-(dimethyl)piperidinyl-$CH_2CH_2$—O—, —$CH_2$dihydropiperidinyl-$CH_2CH_2$—O—, and the like.

In some embodiments of the compounds of formula I, $R^1$ is —$(CR^{1a}R^{1b})_{1-5}$ (3-11 membered heterocyclyl optionally substituted with 0-6 $R^{1a}$ and/or $R^{1b}$ groups)-A- wherein A is O, S, or $NR^{1c}$, such as, for example, —$CH_2CH_2CH_2$-pyrrolidinyl-O—, and the like.

In some embodiments of the compounds of formula I, $R^1$ is -(heteroaryl optionally substituted with 0-4 $R^{1a}$ and/or $R^{1b}$ groups)-A-$(CR^{1a}R^{1b})_{1-5}$— wherein A is O, S, or $NR^{1c}$, such as, for example, -pyridinyl-O—$CH_2$—, and the like.

In some embodiments of the compounds of formula I, $R^1$ is -A-(3-11 membered heterocyclyl optionally substituted with 0-6 $R^{1a}$ and/or $R^{1b}$ groups)-$(CR^{1a}R^{1b})_{1-5}$-A- wherein each A is independently O, S, or $NR^{1c}$, such as, for example, —$N(CH_3)$-piperidinyl-$CH_2CH_2$—O—, and the like.

In some aspects, the compounds of Formula I are those having the formula IA-13a, IA-13b, IA-14a or IA-14b:

(IA-13a)

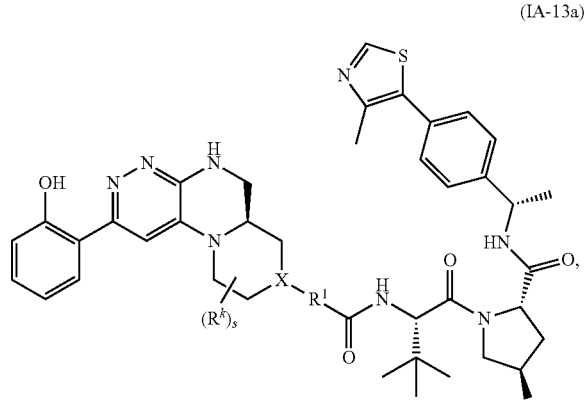

(IA-13b)

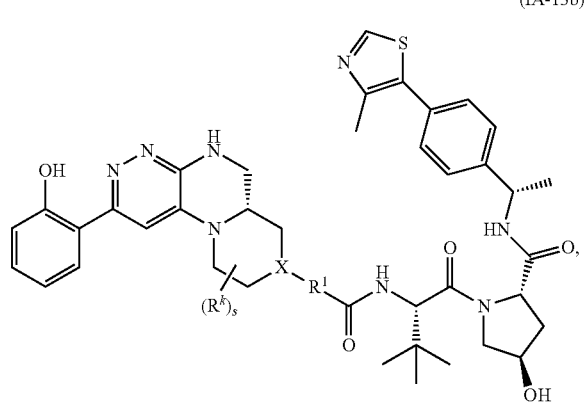

(IA-14a)

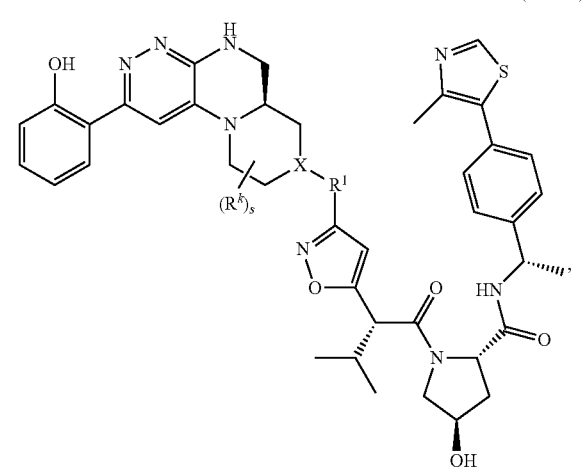

(IA-14b)

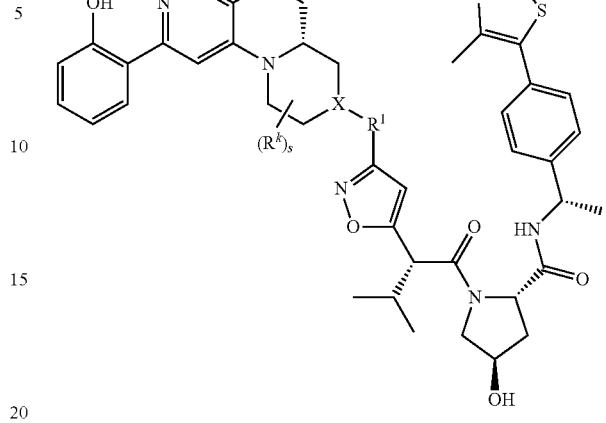

wherein X is N or CH.

In some embodiments of the compounds of formula IA-13a, IA-13b, IA-14a or IA-14b, $R^1$ is -(3-11 membered heterocyclyl optionally substituted with 0-6 $R^{1a}$ and/or $R^{1b}$ groups)-(CO)—$(CR^{1a}R^{1b})_{1-5}$-A- wherein A is O, S, or $NR^{1c}$, or -(3-11 membered heterocyclyl optionally substituted with 0-6 $R^{1a}$ and/or $R^{1b}$ groups)-$(CR^{1a}R^{1b})_{1-5}$-A- wherein A is O, S, or $NR^{1c}$, $R^{1a}$, $R^{1b}$, $R^{1c}$, and $R^{1e}$ are each independently, —H, D, -halo, —$C_1$-$C_8$alkyl, —$C_1$-$C_6$haloalkyl, —O—$C_1$-$C_8$alkyl, —S—$C_1$-$C_8$alkyl, —NH$C_1$-$C_8$alkyl, —N($C_1$-$C_8$alkyl)$_2$, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)($C_1$-$C_8$alkyl), —OH, —NH$_2$, —SH, —SO$_2C_1$-$C_8$alkyl, SO(NH)$C_1$-$C_8$alkyl, P(O)(O$C_1$-$C_8$alkyl)($C_1$-$C_8$alkyl), —P(O)(O$C_1$-$C_8$alkyl)$_2$, —C≡C—$C_1$-$C_8$alkyl, —CH═CH($C_1$-$C_8$alkyl), —C($C_1$-$C_8$alkyl)═CH($C_1$-$C_8$alkyl), —C($C_1$-$C_8$alkyl)═C($C_1$-$C_8$alkyl)$_2$, —Si(OH)$_3$, —Si($C_1$-$C_8$alkyl)$_3$, —Si(OH)($C_1$-$C_8$alkyl)$_2$, —C(O)$C_1$-$C_8$alkyl, —CO$_2$H, —CN, —CF$_3$, —CHF$_2$, —CH$_2$F, —NO$_2$, —SF$_5$, —SO$_2$NH$C_1$-$C_8$alkyl, —SO$_2$N($C_1$-$C_8$alkyl)$_2$, —SO(NH)NH$C_1$-$C_8$alkyl, —SO(NH)N($C_1$-$C_8$alkyl)$_2$, —SONH$C_1$-$C_8$alkyl, —SON($C_1$-$C_8$alkyl)$_2$, —CONH$C_1$-$C_8$alkyl, —CON($C_1$-$C_8$alkyl)$_2$, —N($C_1$-$C_8$alkyl)CONH($C_1$-$C_8$alkyl), —N($C_1$-$C_8$alkyl)CON($C_1$-$C_8$alkyl)$_2$, —NHCONH($C_1$-$C_8$alkyl), —NHCON($C_1$-$C_8$alkyl)$_2$, —NHCONH$_2$, —N($C_1$-$C_8$alkyl)SO$_2$NH($C_1$-$C_8$alkyl), —N($C_1$-$C_8$alkyl)SO$_2$N($C_1$-$C_8$alkyl)$_2$, —NHSO$_2$NH($C_1$-$C_8$alkyl), —NHSO$_2$N($C_1$-$C_8$alkyl)$_2$, or —NHSO$_2$NH$_2$, or where the context permits, $R^{1a}$ or $R^{1b}$, are linked to other groups, or to each other, to form a cycloalkyl and/or a heterocyclyl moiety, optionally substituted with 0-4 $R^{1e}$ groups.

In some embodiments of the compounds of formula IA-13a, IA-13b, IA-14a or IA-14b, $R^1$ is -(3-11 membered heterocyclyl)-(CO)—$(CR^{1a}R^{1b})_{1-3}$—O— wherein each $R^{1a}$ is H and each $R^{1b}$ is independently H or —$C_1$-$C_8$alkyl, preferably —CH$_3$.

In other embodiments of the compounds of formula IA-13a, IA-13b, IA-14a or IA-14b, $R^1$ is -(3-11 membered heterocyclyl)-$(CR^{1a}R^{1b})_{1-3}$—O—, wherein each $R^{1a}$ is H and each $R^{1b}$ is independently H or —$C_1$-$C_8$alkyl, preferably —CH$_3$.

In other embodiments of the compounds of formula IA-13a, IA-13b, IA-14a or IA-14b, $R^1$ is -azabicyclo[3.1.1]heptanyl-CH$_2$CH$_2$—O—, -azaspiro[3.3]heptanyl-CH$_2$CH$_2$—O—, -piperidinyl-CH$_2$CH$_2$—O—, -fluoropiperidinyl-CH$_2$CH$_2$—O—, -azepanyl-CH$_2$CH$_2$—O—, -pyrrolidinyl-CH$_2$CH$_2$—O—, -piperidinyl-CH$_2$CH(CH$_3$)—O—, -octahydrocyclopenta[c]pyrrolyl-CH$_2$CH$_2$—O—, -pyrrolidinyl-CH$_2$CH(CH$_3$)—O—, -methylpiperidinyl-CH$_2$CH$_2$—O—, -piperidinyl-CH$_2$CH(CH$_2$CH$_3$)—O—, -pyrrolidinyl-CH$_2$CH(CH$_2$CH$_3$)—O—, -pyrrolidinyl-CH$_2$CH(CH$_3$)—O—, -hydroxypyrrolidinyl-CH$_2$CH$_2$—O—, -hydroxypiperidinyl-CH$_2$CH$_2$—O—, and the like.

In some aspects, the compounds of Formula I are those having the formula IA-15a, IA-15b, IA-16a, or IA-16b:

(IA-15a)

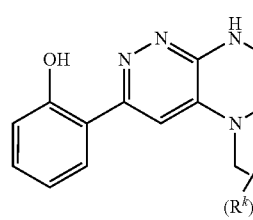
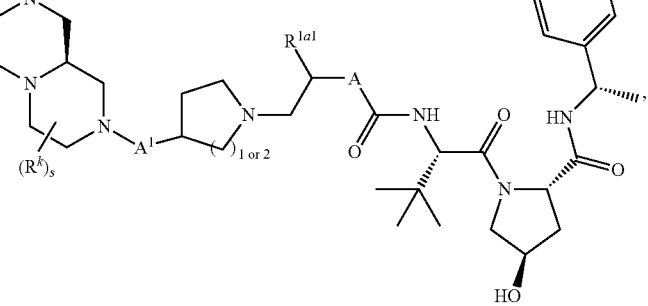

(IA-15b)

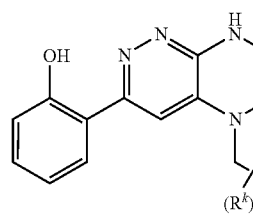
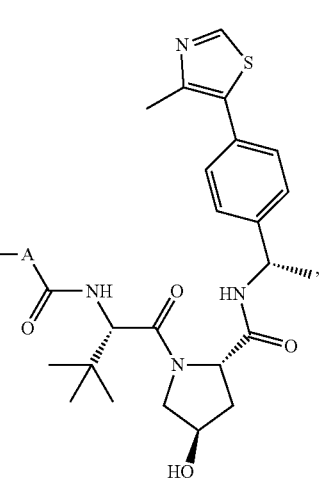

(IA-16a)

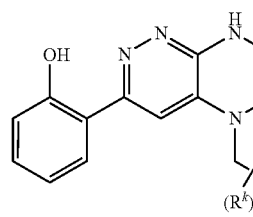
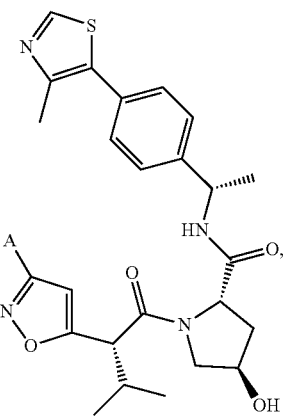

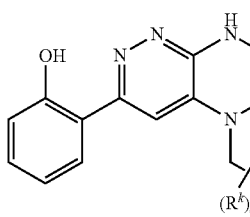 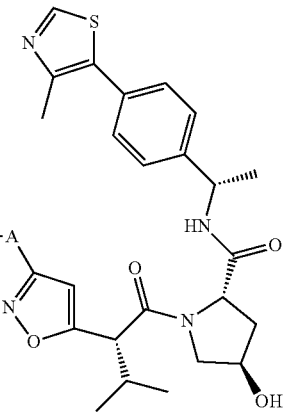

(IA-16b)

wherein A is O, S, or NR$^{1c}$,
R$^{1a1}$ is H or —C$_1$-C$_8$alkyl, preferably —CH$_2$CH$_3$, or —CH$_3$;
R$^{1c}$ is —H, or —C$_1$-C$_8$alkyl, preferably —CH$_3$;
A$^1$ is a covalent bond or —(CR$^{1a}$R$^{1b}$)$_{1-3}$; and
each R$^k$ is independently H, D, F, C$_{1-3}$ alkyl, C$_{1-3}$ haloalkyl, C$_{1-4}$ alkoxyl, substituted C$_{1-3}$ alkyl, substituted C$_{1-3}$ haloalkyl, or substituted C$_{1-4}$ alkoxyl; and s=0-7.

In some embodiments of the compound of formula IA-15a, IA-15b, IA-16a, or IA-16b, A is O and R$^{1a1}$ is —C$_1$-C$_8$alkyl, preferably —CH$_2$CH$_3$, or —CH$_3$.

In some embodiments of the compound of formula IA-15a, IA-15b, IA-16a, or IA-16b, A$^1$ is a covalent bond.

In some embodiments of the compound of formula IA-15a, IA-15b, IA-16a, or IA-16b, A$^1$ is —(CR$^{1a}$R$^{1b}$)$_{1-3}$.

In some embodiments of the compound of formula IA-15a, IA-15b, IA-16a, or IA-16b, A is O and R$^{1a1}$ is —CH$_3$.

In some embodiments of the compound of formula IA-15a, IA-15b, IA-16a, or IA-16b, s=0.

In some embodiments of the compound of formula IA-15a, IA-15b, IA-16a, or IA-16b, s=1 and R$^k$ is —CH$_3$.

In some embodiments, the compounds of the disclosure include:
(2S,4R)-4-hydroxy-1-((S)-2-(2-((R)-2-(2-hydroxyphenyl)-5,6,6a,7,9,10-hexahydro-8H-pyrazino[1',2':4,5]pyrazino[2,3-c]pyridazin-8-yl)acetamido)-3,3-dimethylbutanoyl)-N—((S)-1-(4-(4-methylthiazol-5-yl)phenyl)ethyl)pyrrolidine-2-carboxamide;
(2S,4R)-4-hydroxy-1-((S)-2-(2-((S)-2-(2-hydroxyphenyl)-5,6,6a,7,9,10-hexahydro-8H-pyrazino[1',2':4,5]pyrazino[2,3-c]pyridazin-8-yl)acetamido)-3,3-dimethylbutanoyl)-N—((S)-1-(4-(4-methylthiazol-5-yl)phenyl)ethyl)pyrrolidine-2-carboxamide;
(2S,4R)-4-hydroxy-1-((S)-2-(2-((S)-2-(2-hydroxyphenyl)-5,6,6a,7,9,10-hexahydro-8H-pyrazino[1',2':4,5]pyrazino[2,3-c]pyridazin-8-yl)acetamido)-3,3-dimethylbutanoyl)-N-(4-(5-methylthiazol-4-yl)benzyl)pyrrolidine-2-carboxamide;
(2S,4R)-4-hydroxy-1-((S)-2-(2-((R)-2-(2-hydroxyphenyl)-5,6,6a,7,9,10-hexahydro-8H-pyrazino[1',2':4,5]pyrazino[2,3-c]pyridazin-8-yl)acetamido)-3,3-dimethylbutanoyl)-N-(4-(5-methylthiazol-4-yl)benzyl)pyrrolidine-2-carboxamide;
(2S,4R)-4-hydroxy-1-((S)-2-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)-4-methylpiperidin-1-yl)acetamido)-3,3-dimethylbutanoyl)-N—((S)-1-(4-(4-methylthiazol-5-yl)phenyl)ethyl)pyrrolidine-2-carboxamide;
(2S,4R)-4-hydroxy-1-((S)-2-(2-(4-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)acetamido)-3,3-dimethylbutanoyl)-N—((S)-1-(4-(4-methylthiazol-5-yl)phenyl)ethyl)pyrrolidine-2-carboxamide;
(2S,4R)-4-hydroxy-1-((R)-2-(3-(2-((S)-2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-N—((S)-1-(4-(4-methylthiazol-5-yl)phenyl)ethyl)pyrrolidine-2-carboxamide;
(2S,4R)-4-hydroxy-1-((R)-2-(3-(2-((R)-2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-N—((S)-1-(4-(4-methylthiazol-5-yl)phenyl)ethyl)pyrrolidine-2-carboxamide;
(2S,4R)-4-hydroxy-1-((S)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;
(2S,4R)-4-hydroxy-1-((S)-2-(3-(2-(4-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;
(2S,4R)-4-hydroxy-1-((S)-2-(4-((R)-2-(2-hydroxyphenyl)-5,6,6a,7,9,10-hexahydro-8H-pyrazino[1',2':4,5]pyrazino[2,3-c]pyridazin-8-yl)butanamido)-3,3-dimethylbutanoyl)-N—((S)-1-(4-(4-methylthiazol-5-yl)phenyl)ethyl)pyrrolidine-2-carboxamide;
(2S,4R)-4-hydroxy-1-((S)-2-(4-((S)-2-(2-hydroxyphenyl)-5,6,6a,7,9,10-hexahydro-8H-pyrazino[1',2':4,5]pyrazino[2,3-c]pyridazin-8-yl)butanamido)-3,3-dimethylbutanoyl)-N—((S)-1-(4-(4-methylthiazol-5-yl)phenyl)ethyl)pyrrolidine-2-carboxamide;
2-((S)-2-(2-hydroxyphenyl)-5,6,6a,7,9,10-hexahydro-8H-pyrazino[1',2':4,5]pyrazino[2,3-c]pyridazin-8-yl)ethyl ((R)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamate;

2-((R)-2-(2-hydroxyphenyl)-5,6,6a,7,9,10-hexahydro-8H-pyrazino[1',2':4,5]pyrazino[2,3-c]pyridazin-8-yl)ethyl ((R)-1-((2S,4R)-4-hydroxy-2-(((S)-1-(4-(4-methylthiazol-5-yl)phenyl)carbamoyl)pyrrolidin-1-yl)-3,3-dimethyl-1-oxobutan-2-yl)carbamate;

(2S,4R)-4-hydroxy-1-((S)-2-(3-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propanamido)-3,3-dimethylbutanoyl)-N—((S)-1-(4-(4-methylthiazol-5-yl)phenyl)ethyl)pyrrolidine-2-carboxamide;

(2S,4R)-4-hydroxy-1-((S)-2-(3-(4-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propanamido)-3,3-dimethylbutanoyl)-N—((S)-1-(4-(4-methylthiazol-5-yl)phenyl)ethyl)pyrrolidine-2-carboxamide;

(3R,5S)-1-((R)-2-(3-(2-((S)-2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-5-(((S)-1-(4-(4-methylthiazol-5-yl)phenyl)ethyl)carbamoyl)pyrrolidin-3-yl acetate;

(3R,5S)-1-((R)-2-(3-(2-((R)-2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-5-(((S)-1-(4-(4-methylthiazol-5-yl)phenyl)ethyl)carbamoyl)pyrrolidin-3-yl acetate; (3R,5S)-1-((R)-2-(3-(2-((S)-2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-5-(((S)-1-(4-(4-methylthiazol-5-yl)phenyl)ethyl)carbamoyl)pyrrolidin-3-yl isobutyrate;

(3R,5 S)-1-((R)-2-(3-(2-((R)-2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-5-(((S)-1-(4-(4-methylthiazol-5-yl)phenyl)ethyl)carbamoyl)pyrrolidin-3-yl isobutyrate;

(2S,4R)-4-hydroxy-1-((S)-2-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)acetamido)-3,3-dimethylbutanoyl)-N—(S)-1-(4-(4-methylthiazol-5-yl)phenyl)ethyl)pyrrolidine-2-carboxamide;

(2S,4R)-4-hydroxy-1-((S)-2-(2-(4-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)acetamido)-3,3-dimethylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(6-((S)-2-(2-hydroxyphenyl)-5,6,6a,7,9,10-hexahydro-8H-pyrazino[1',2':4,5]pyrazino[2,3-c]pyridazin-8-yl)-3-azabicyclo[3.1.1]heptan-3-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(6-((R)-2-(2-hydroxyphenyl)-5,6,6a,7,9,10-hexahydro-8H-pyrazino[1',2':4,5]pyrazino[2,3-c]pyridazin-8-yl)-3-azabicyclo[3.1.1]heptan-3-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(6-((S)-2-(2-hydroxyphenyl)-5,6,6a,7,9,10-hexahydro-8H-pyrazino[1',2':4,5]pyrazino[2,3-c]pyridazin-8-yl)-2-azaspiro[3.3]heptan-2-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(6-((R)-2-(2-hydroxyphenyl)-5,6,6a,7,9,10-hexahydro-8H-pyrazino[1',2':4,5]pyrazino[2,3-c]pyridazin-8-yl)-2-azaspiro[3.3]heptan-2-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((R)-1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((R)-1-(4-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-(4-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((S)-3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((R)-3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((S)-3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((R)-3-((R)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-((S)-3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-((S)-3-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-((R)-3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-((R)-3-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((R)-1-((S)-3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((R)-1-((S)-3-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((R)-1-((R)-3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((R)-1-((R)-3-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((S)-3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl) ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((R)-3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl) ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((R)-3-(4-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl) ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((S)-3-(4-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl) ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((S)-3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl) ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((S)-3-(4-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl) ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((R)-3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl) ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((R)-3-(4-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl) ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3 S,4R)-4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)-2-oxoethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3 S,4 S)-4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)-2-oxoethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3R,4R)-4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)-2-oxoethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3R,4S)-4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)-2-oxoethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3 S,4R)-4-((R)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)-2-oxoethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3R,4R)-4-((R)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)-2-oxoethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3R,4S)-4-((R)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)-2-oxoethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3 S,4S)-4-((R)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)-2-oxoethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((S)-3-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)

ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((R)-3-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((R)-3-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((S)-3-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide; (2S,4R)-4-hydroxy-1-((R)-2-(3-(((S)-1-((R)-3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-((S)-3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-((S)-3-((R)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-((R)-3-((R)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((R)-1-((R)-3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((R)-1-((S)-3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((R)-1-((S)-3-((R)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((R)-1-((R)-3-((R)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((2R,4R)-4-((S)-2-(2-hydroxyphenyl)-5,6,6a,7,9,10-hexahydro-8H-pyrazino[1',2':4,5]pyrazino[2,3-c]pyridazin-8-yl)-2-methylpiperidin-1-yl)ethoxy)isoxazol-5-yl)-3-methylbutanoyl)-N—(S)-1-(4-(4-methylthiazol-5-yl)phenyl)ethyl)pyrrolidine-2-carboxamide;

(2S,4R)-4-hydroxy-1-((R)-2-(3-(2-((2S,4R)-4-((S)-2-(2-hydroxyphenyl)-5,6,6a,7,9,10-hexahydro-8H-pyrazino[1',2':4,5]pyrazino[2,3-c]pyridazin-8-yl)-2-methylpiperidin-1-yl)ethoxy)isoxazol-5-yl)-3-methylbutanoyl)-N—(S)-1-(4-(4-methylthiazol-5-yl)phenyl)ethyl)pyrrolidine-2-carboxamide;

(2S,4R)-4-hydroxy-1-((R)-2-(3-(2-((2R,4S)-4-((S)-2-(2-hydroxyphenyl)-5,6,6a,7,9,10-hexahydro-8H-pyrazino[1',2':4,5]pyrazino[2,3-c]pyridazin-8-yl)-2-methylpiperidin-1-yl)ethoxy)isoxazol-5-yl)-3-methylbutanoyl)-N—(S)-1-(4-(4-methylthiazol-5-yl)phenyl)ethyl)pyrrolidine-2-carboxamide;

(2S,4R)-4-hydroxy-1-((R)-2-(3-(2-((2S,4S)-4-((S)-2-(2-hydroxyphenyl)-5,6,6a,7,9,10-hexahydro-8H-pyrazino[1',2':4,5]pyrazino[2,3-c]pyridazin-8-yl)-2-methylpiperidin-1-yl)ethoxy)isoxazol-5-yl)-3-methylbutanoyl)-N—(S)-1-(4-(4-methylthiazol-5-yl)phenyl)ethyl)pyrrolidine-2-carboxamide;

(2S,4R)-4-hydroxy-1-((R)-2-(3-(2-((2R,4R)-4-((R)-2-(2-hydroxyphenyl)-5,6,6a,7,9,10-hexahydro-8H-pyrazino[1',2':4,5]pyrazino[2,3-c]pyridazin-8-yl)-2-methylpiperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((2S,4R)-4-((R)-2-(2-hydroxyphenyl)-5,6,6a,7,9,10-hexahydro-8H-pyrazino[1',2':4,5]pyrazino[2,3-c]pyridazin-8-yl)-2-methylpiperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((2R,4S)-4-((R)-2-(2-hydroxyphenyl)-5,6,6a,7,9,10-hexahydro-8H-pyrazino[1',2':4,5]pyrazino[2,3-c]pyridazin-8-yl)-2-methylpiperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((2S,4S)-4-((R)-2-(2-hydroxyphenyl)-5,6,6a,7,9,10-hexahydro-8H-pyrazino[1',2':4,5]pyrazino[2,3-c]pyridazin-8-yl)-2-methylpiperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide; (2S,4R)-4-hydroxy-1-((R)-2-(3-(2-((3R,4S)-4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3S,4R)-4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3R,4R)-4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin- 1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3S,4S)-4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3R,4S)-4-((R)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3S,4R)-4-((R)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3R,4R)-4-((R)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3S,4S)-4-((R)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-((S)-1-((S)-2-(2-hydroxyphenyl)-5,6,6a,7,9,10-hexahydro-8H-pyrazino[1',2':4,5]pyrazino[2,3-c]pyridazin-8-yl)ethyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-((R)-1-((S)-2-(2-hydroxyphenyl)-5,6,6a,7,9,10-hexahydro-8H-pyrazino[1',2':4,5]pyrazino[2,3-c]pyridazin-8-yl)ethyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-((S)-1-((R)-2-(2-hydroxyphenyl)-5,6,6a,7,9,10-hexahydro-8H-pyrazino[1',2':4,5]pyrazino[2,3-c]pyridazin-8-yl)ethyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-((R)-1-((R)-2-(2-hydroxyphenyl)-5,6,6a,7,9,10-hexahydro-8H-pyrazino[1',2':4,5]pyrazino[2,3-c]pyridazin-8-yl)ethyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-((R)-3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-((S)-3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-((S)-3-((R)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-((R)-3-((R)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((S)-3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((R)-3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((R)-3-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((S)-3-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(3-((S)-3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propyl)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(3-((R)-3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propyl)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(3-((R)-3-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propyl)isoxazol-5-yl)-3-methylbutanoyl)-N—((S)-1-(4-(4-methylthiazol-5-yl)phenyl)ethyl)pyrrolidine-2-carboxamide; or (2S,4R)-4-hydroxy-1-((R)-2-(3-(3-((S)-3-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propyl)isoxazol-5-yl)-3-methylbutanoyl)-N—((S)-1-(4-(4-methylthiazol-5-yl)phenyl)ethyl)pyrrolidine-2-carboxamide.

It will be apparent that the compounds of the invention, including all subgenera described herein, may have multiple stereogenic centers. As a result, there exist multiple stereoisomers (enantiomers and diastereomers) of the compounds (and subgenera described herein). The present disclosure contemplates and encompasses each stereoisomer of any compound encompassed by the disclosure as well as mixtures of said stereoisomers.

Pharmaceutically acceptable salts and solvates of the compounds of the disclosure (including all subgenera described herein) are also within the scope of the disclosure.

Isotopic variants of the compounds of the disclosure (including all subgenera described herein) are also contemplated by the present disclosure.

References to formula I or subgenera thereof (e.g., formula IA, IA-1, IA-2, IA-3, IA-4, IA-5, IA-6, IA-7, IA-8, IA-9, IA-9a, IA-10, IA-10a, IA-11, IA-12, IA-13a, IA-13b, IA-14a, IA-14b, IA-15a, IA-15b, IA-16a, IA-16b) are meant to encompass the identified formula and all applicable subgenera.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. While an embodiment may be described as part of a series of steps or part of a more general structure, each said step may also be considered an independent embodiment in itself, combinable with others.

Pharmaceutical Compositions and Methods of Administration

The subject pharmaceutical compositions are typically formulated to provide a therapeutically effective amount of a compound of the present disclosure as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds of the invention and other agent(s) may be mixed into a preparation or both components may be formulated into separate preparations to use them in combination separately or at the same time. In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v or v/v.

In some embodiments, the concentration of one or more compounds of the invention is greater than 90%, 80%, 70%, 60%, 50%, 40%, 30%, 20%, 19.75%, 19.50%, 19.25%, 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25%, 12%, 11.75%, 11.50%, 11.25% 11%, 10.75%, 10.50%, 10.25% 10%, 9.75%, 9.50%, 9.25%, 9%, 8.75%, 8.50%, 8.25% 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g (or a number in the range defined by and including any two numbers above).

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g 0.15 g, 0.2 g 0.25 g, 0.3 g 0.35 g, 0.4 g 0.45 g, 0.5 g, 0.55 g, 0.6 g 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g (or a number in the range defined by and including any two numbers above).

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the invention typically contains an active ingredient (e.g., a compound of the disclosure) of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration.

In some embodiments, the invention provides a pharmaceutical composition for oral administration containing a compound of the invention, and a pharmaceutical excipient suitable for oral administration.

In some embodiments, the invention provides a solid pharmaceutical composition for oral administration containing: (i) an effective amount of a compound of the invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or nonaqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (e.g., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof, polyoxyethylated vitamins and derivatives thereof, polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%), 100%, or up to about 200%>by weight, based on the combined weight of the drug, and other excipients. If desired, very small amounts of solubilizer may also be used, such as 5%>, 2%>, 1%) or even less. Typically, the solubilizer may be present in an amount of about 1%>to about 100%, more typically about 5%>to about 25%>by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g. Transdermal) Delivery.

In some embodiments, the invention provides a pharmaceutical composition for transdermal delivery containing a compound of the present invention and a pharmaceutical excipient suitable for transdermal delivery.

Compositions of the present invention can be formulated into preparations in solid, semisolid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation.

Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins, 2000; Martindale, The Extra Pharmacopoeia, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

In some embodiments, the compounds or pharmaceutical composition of the present invention are administered by intravenous injection.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (etherester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention is administered in a composition that comprises one or more agents, and the agent has a shorter half-life than the compound of the invention unit dose forms of the agent and the compound of the invention may be adjusted accordingly. The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc. Exemplary parenteral administration forms include solutions or suspensions of active compound in sterile aqueous solutions, for example, aqueous propylene glycol or dextrose solutions. Such dosage forms can be suitably buffered, if desired.

Methods of Use

The method typically comprises administering to a subject a therapeutically effective amount of a compound of the invention. The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

In certain embodiment, the present invention provides a pharmaceutical composition comprising a compound of bispecific formula, or pharmaceutically acceptable salt thereof.

In certain embodiment, the present invention provides a pharmaceutical composition comprising a compound of bispecific formula for use in degrading a target protein in a cell.

In certain embodiment, a method of degrading a target protein comprising administering to a cell therapeutically effective amount of a bispecific compound, or pharmaceutically acceptable salt, wherein the compound is effective for degrading the target protein.

In certain embodiment, the present invention provides a pharmaceutical composition comprising a compound of bispecific formula, for use in treating or preventing of a disease or disorder in which SMARCA2 and/or SMARCA4 plays a role.

In certain embodiment, the present invention provides a pharmaceutical composition comprising a compound of bispecific formula, for use in treating or preventing of a disease or disorder in which SWI/SNF mutations plays a role.

In certain embodiment, target proteins are SMARCA2, SMARCA4 and/or PB1.

In certain embodiment, target protein complex is SWI/SNF in a cell.

In certain embodiment, diseases or disorders dependent on SMARCA2 or SMARCA4 include cancers.

In certain embodiment, diseases or disorders dependent on SWI/SNF complex include cancers.

Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

In certain further embodiment, the cancer is a SMARCA2 and/or SMARAC4-dependent cancer.

In some embodiments, the cancer harbors a SMARCA4 mutation.

In certain embodiment, the present invention provides a pharmaceutical composition comprising a compound of bispecific formula for use in the diseases or disorders dependent upon SMARCA2 and/or SMARCA4 is cancer.

Compounds of the disclosure, as well as pharmaceutical compositions comprising them, can be administered to treat any of the described diseases, alone or in combination with a medical therapy. Medical therapies include, for example, surgery and radiotherapy (e.g., gamma-radiation, neutron beam radiotherapy, electron beam radiotherapy, proton therapy, brachytherapy, systemic radioactive isotopes).

In other aspects, compounds of the disclosure, as well as pharmaceutical compositions comprising them, can be administered to treat any of the described diseases, alone or in combination with one or more other agents.

In other methods, the compounds of the disclosure, as well as pharmaceutical compositions comprising them, can be administered in combination with agonists of nuclear receptors agents.

In other methods, the compounds of the disclosure, as well as pharmaceutical compositions comprising them, can be administered in combination with antagonists of nuclear receptors agents.

In other methods, the compounds of the disclosure, as well as pharmaceutical compositions comprising them, can be administered in combination with an anti-proliferative agent.

Combination Therapies

For treating cancer and other proliferative diseases, the compounds of the invention can be used in combination with chemotherapeutic agents, agonists or antagonists of nuclear receptors, or other anti-proliferative agents. The compounds of the invention can also be used in combination with a medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, all-trans retinoic acid, altretamine, anastrozole, arsenic trioxide, asparaginase, azacitidine, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinstat and zoledronate.

In some embodiments, the compounds of the invention can be used in combination with a therapeutic agent that targets an epigenetic regulator. Examples of epigenetic regulators include bromodomain inhibitors, the histone lysine methyltransferase inhibitors, histone arginine methyl transferase inhibitors, histone demethylase inhibitors, histone deacetylase inhibitors, histone acetylase inhibitors, and DNA methyltransferase inhibitors. Histone deacetylase inhibitors include, e.g., vorinostat. Histone arginine methyl transferase inhibitors include inhibitors of protein arginine methyltransferases (PRMTs) such as PRMT5, PRMT1 and PRMT4. DNA methyltransferase inhibitors include inhibitors of DNMT1 and DNMT3.

For treating cancer and other proliferative diseases, the compounds of the invention can be used in combination with targeted therapies, including JAK kinase inhibitors (e.g. Ruxolitinib), PI3 kinase inhibitors including PI3K-delta selective and broad spectrum PI3K inhibitors, MEK inhibitors, Cyclin Dependent kinase inhibitors, including CDK4/6 inhibitors and CDK9 inhibitors, BRAF inhibitors, mTOR inhibitors, proteasome inhibitors (e.g. Bortezomib, Carfilzomib), HDAC inhibitors (e.g. panobinostat, vorinostat), DNA methyl transferase inhibitors, dexamethasone, bromo and extra terminal family member (BET) inhibitors, BTK inhibitors (e.g. ibrutinib, acalabrutinib), BCL2 inhibitors (e.g. venetoclax), dual BCL2 family inhibitors (e.g. BCL2/BCLxL), PARP inhibitors, FLT3 inhibitors, or LSD1 inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), or PDR001. In some embodiments, the anti-PD-1 monoclonal antibody is nivolumab or pembrolizumab. In some embodiments, the anti-PD1 antibody is pembrolizumab. In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, durvalumab, or BMS-935559. In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Compounds of the present invention include, but are not limited to, those shown in Table 1.

TABLE 1

| Ex | Structure | Name |
|---|---|---|
| 1a | 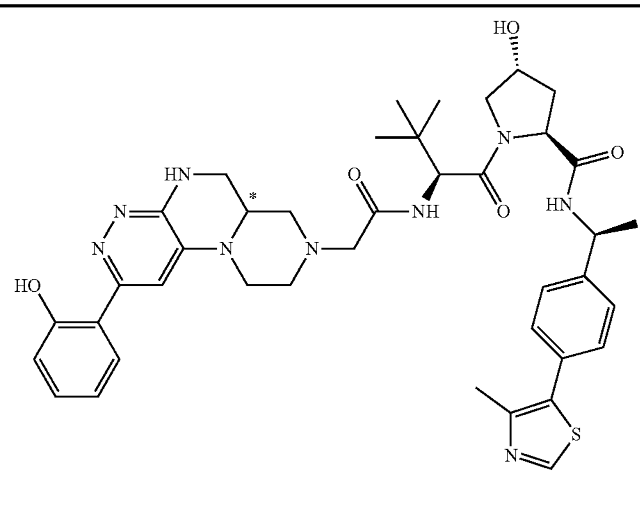 | (2S,4R)-4-hydroxy-1-((2S)-2-(2-(2-(2-hydroxyphenyl)-5,6,6a,7,9,10-hexahydro-8H-pyrazino[1',2':4,5]pyrazino[2,3-c]pyridazin-8-yl)acetamido)-3,3-dimethylbutanoyl)-N-((S)-1-(4-(4-methylthiazol-5-yl)phenyl)ethyl)pyrrolidine-2-carboxamide (Diastereomer 1 - *) |

TABLE 1-continued

| Ex | Structure | Name |
|---|---|---|
| 1b | 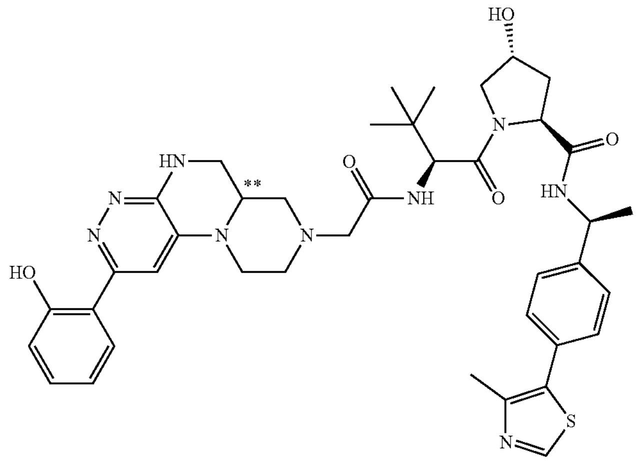 [SMILES: Cc1ncsc1-c1ccc([C@H](C)NC(=O)[C@@H]2C[C@@H](O)CN2C(=O)[C@@H](NC(=O)CN2CCN3c4cc(-c5ccccc5O)nnc4NCC3C2)C(C)(C)C)cc1] | (2S,4R)-4-hydroxy-1-((2S)-2-(2-(2-(2-hydroxyphenyl)-5,6,6a,7,9,10-hexahydro-8H-pyrazino[1',2':4,5]pyrazino[2,3-c]pyridazin-8-yl)acetamido)-3,3-dimethylbutanoyl)-N-((S)-1-(4-(4-methylthiazol-5-yl)phenyl)ethyl)pyrrolidine-2-carboxamide (Diastereomer 2 - **) |
| 2a | 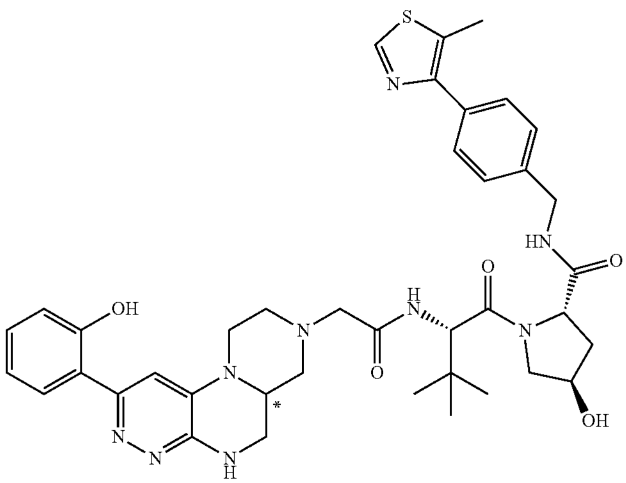 [SMILES: Cc1scnc1-c1ccc(CNC(=O)[C@@H]2C[C@@H](O)CN2C(=O)[C@@H](NC(=O)CN2CCN3c4cc(-c5ccccc5O)nnc4NCC3C2)C(C)(C)C)cc1] | (2S,4R)-4-hydroxy-N-[[4-(5-methyl-1,3-thiazol-4-yl)phenyl]methyl]-1-[(2S)-2-[[2-[4-(2-hydroxyphenyl)-1,5,6,8,12-pentazatricyclo[8.4.0.02,7]tetradeca-2,4,6-trien-12-yl]acetyl]amino]-3,3-dimethylbutanoyl]pyrrolidine-2-carboxamide (Diastereomer 1 - *) |
| 2b | 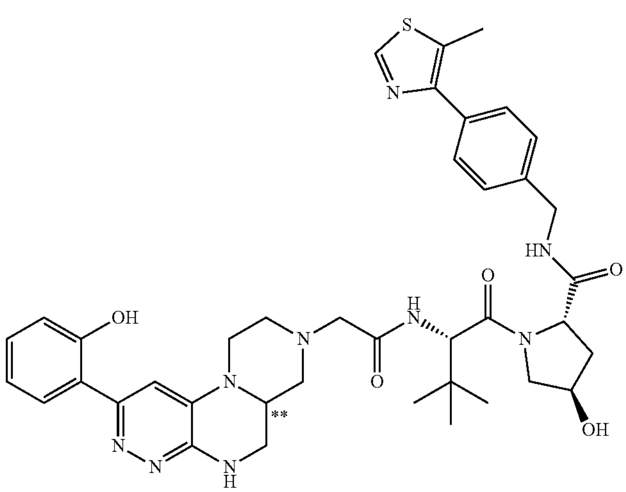 [SMILES: Cc1scnc1-c1ccc(CNC(=O)[C@@H]2C[C@@H](O)CN2C(=O)[C@@H](NC(=O)CN2CCN3c4cc(-c5ccccc5O)nnc4NCC3C2)C(C)(C)C)cc1] | (2S,4R)-4-hydroxy-N-[[4-(5-methyl-1,3-thiazol-4-yl)phenyl]methyl]-1-[(2S)-2-[[2-[4-(2-hydroxyphenyl)-1,5,6,8,12-pentazatricyclo[8.4.0.02,7]tetradeca-2,4,6-trien-12-yl]acetyl]amino]-3,3-dimethylbutanoyl]pyrrolidine-2-carboxamide (Diastereomer 2 - **) |

TABLE 1-continued

| Ex | Structure | Name |
|---|---|---|
| 3 | 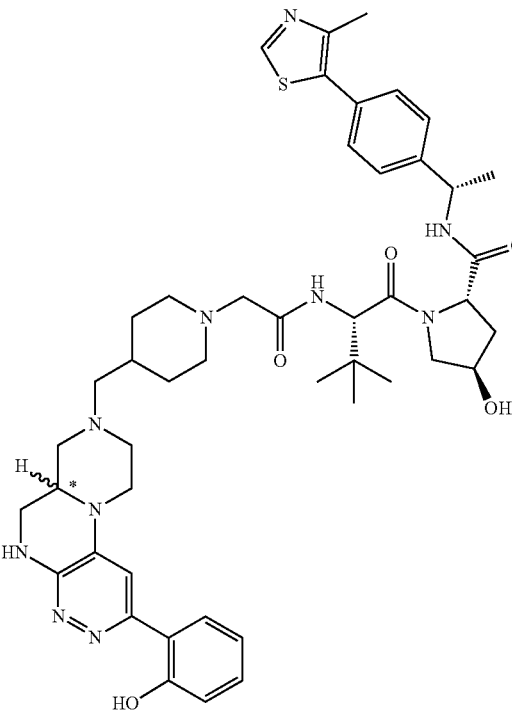 | (2S,4R)-4-hydroxy-1-((2S)-2-(2-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)acetamido)-3,3-dimethylbutanoyl)-N-((S)-1-(4-(4-methylthiazol-5-yl)phenyl)ethyl)pyrrolidine-2-carboxamide (Mixture of Diastereomers at *) |
| 4 | 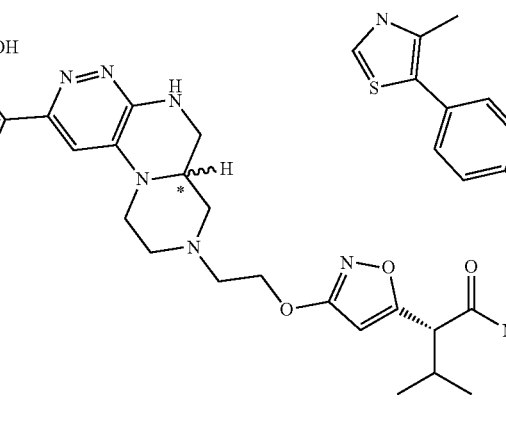 | (2S,4R)-4-hydroxy-1-((2R)-2-(3-(2-(2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-N-((S)-1-(4-(4-methyl-1λ³,3λ²-thiazol-5-yl)phenyl)ethyl)pyrrolidine-2-carboxamide (Mixture of Diastereomers at *) |
| 5 | 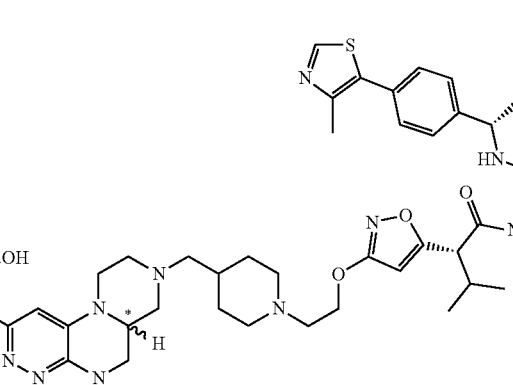 | (2S,4R)-4-hydroxy-1-((2S)-2-(3-(2-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide (Mixture of Diastereomers at *) |

TABLE 1-continued

| Ex | Structure | Name |
|----|-----------|------|
| 6 | 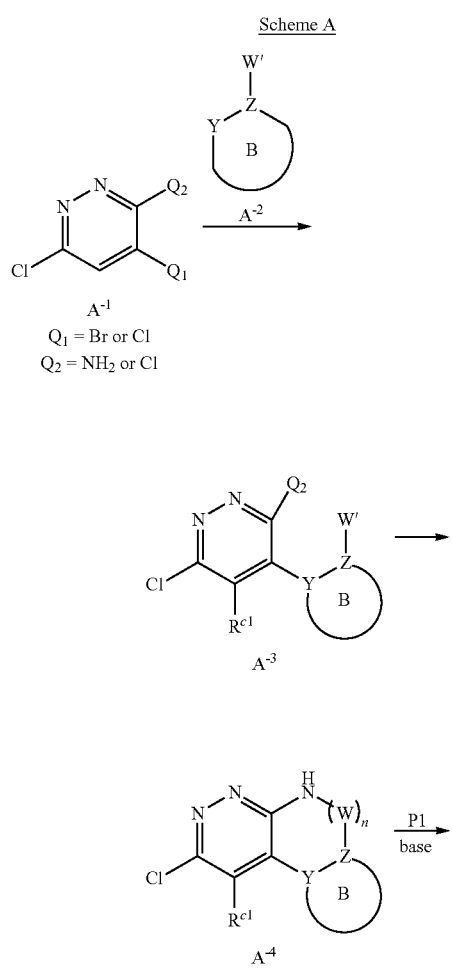 | (2S,4R)-4-hydroxy-1-((2S)-2-(4-(2-(2-hydroxyphenyl)-5,6,6a,7,9,10-hexahydro-8H-pyrazino[1',2':4,5]pyrazino[2,3-c]pyridazin-8-yl)butanamido)-3,3-dimethylbutanoyl)-N-((S)-1-(4-(4-methylthiazol-5-yl)phenyl)ethyl)pyrrolidine-2-carboxamide (Mixture of Diastereomers at *) |

EXAMPLES

The compounds of the Invention may be prepared using the general procedures described below.

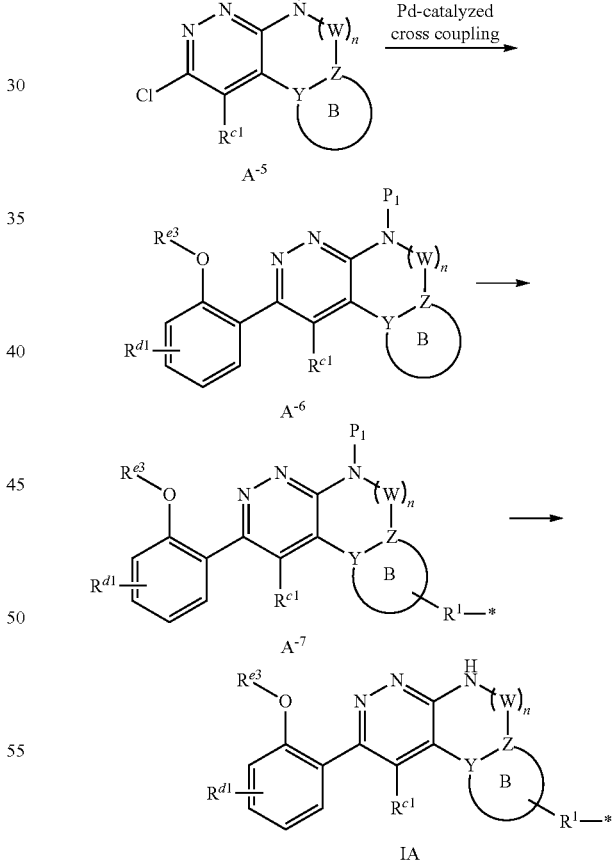

Compounds of Formula (IA) can be synthesized using, for example, the sequences shown in Scheme A. The coupling between compounds A-1 and A-2 via a $S_NAr$ reaction or Pd-catalyzed cross coupling gives compound A-3. The following intramolecular $S_NAr$ reaction or amide formation can afford cyclized product A-4. Introduction of a protecting group to facilitate organometallic addition of Ar via, e.g., Suzuki conditions (e.g., in the presence of a palladium catalyst, such as but not limited to tetrakis(triphenylphosphine)palladium(0) or [1,1'-bis(diphenylphosphino)ferrocene]dichloropalladium (II), complex with dichloromethane and a base (e.g., a carbonate base)) using the appropriate boronic acid or ester or other Pd catalyzed reactions gives A-6. Introduction of $R^1$ using appropriate synthetic methods (such as, but not limited to, $S_N2$ reaction, $S_NAr$ reaction, reductive amination, Buchwald reaction, amide formation, Mitsunobu reaction, olefin metathesis, etc.) can give compounds A-7. The protecting groups on A-7 can be removed using standard conditions to give compounds IA.

1-3 to a leaving group (LG) under appropriate conditions (such as, but not limited to, treatment with $SOCl_2$, or $CBr_4/PPh_3$, or $MsCl/Et_3N$) can afford compounds I-4. Treatment of 1-4 with $NaN_3$ gives compounds I-5. Reduction of the azido group of compounds I-5 using $PPh_3$ or $Pd/H_2$ to the corresponding amines, followed by intramolecular cyclization results in compounds I-6. Alternately compounds I-4 may be treated with ammonium hydroxide at elevated temperatures to give compounds I-6. Protection of the —NH group with an appropriate group (e.g., Boc, SEM, Bn, etc.) can afford compounds I-7, which can be converted to compounds I-8 under standard Suzuki conditions (e.g., in the presence of a palladium catalyst, such as but not limited

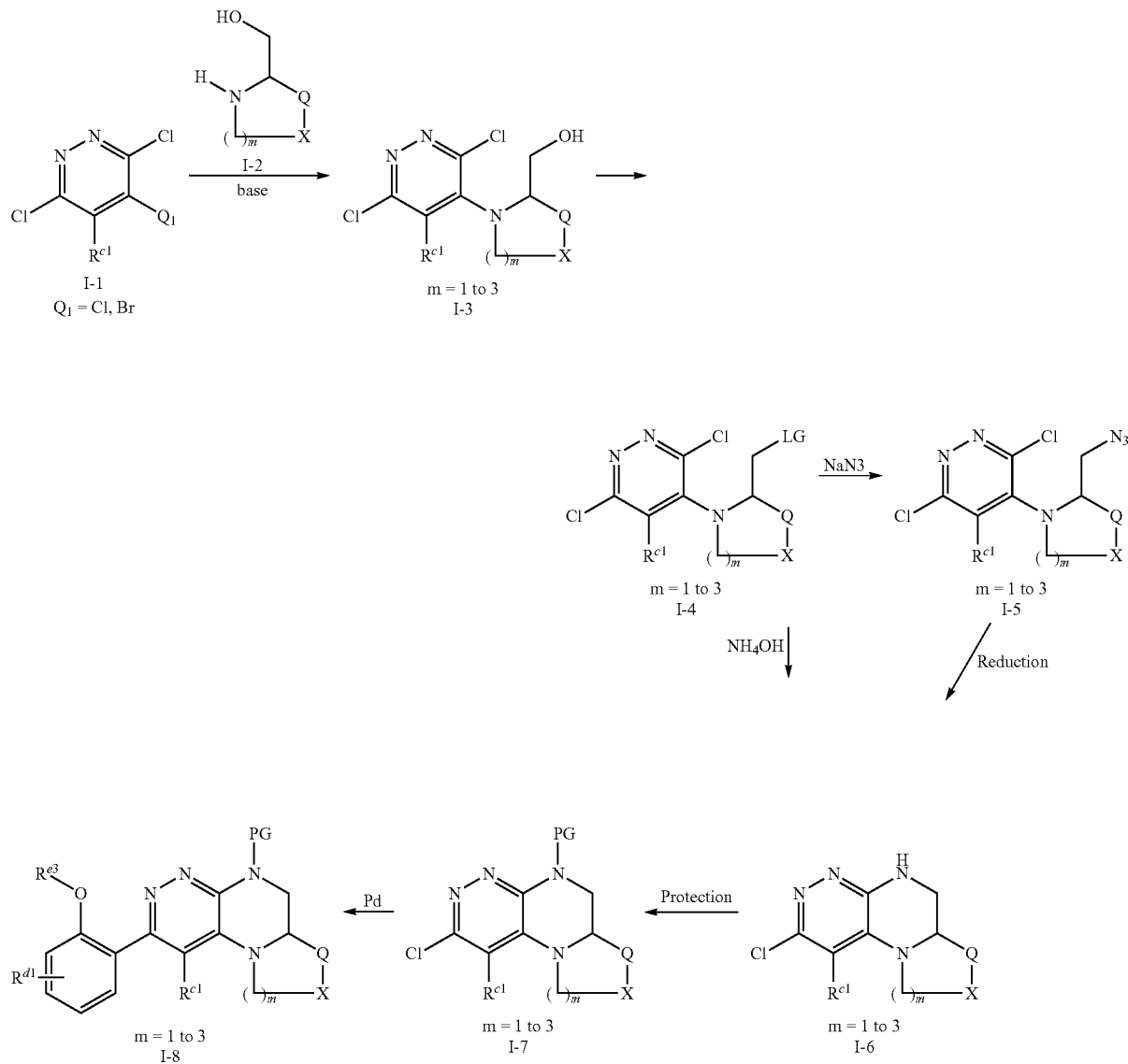

Scheme I

Compounds of formula I-8 can be synthesized using, for example, the sequences shown in Scheme I. $S_NAr$ reaction between I-1 and compound I-2 in the presence of a base (e.g., $Cs_2CO_3$, $NaHCO_3$, DIPEA) at elevated temperatures can give alcohol 1-3. Conversion of the hydroxyl group of to tetrakis(triphenylphosphine)palladium(0) or [1,1'-bis(diphenylphosphino)ferrocene]dichloropalladium (II), complex with dichloromethane and a base (e.g., a carbonate base)) using the appropriate boronic acid or ester (e.g., 2-hydroxyphenylboronic acid).

Scheme II

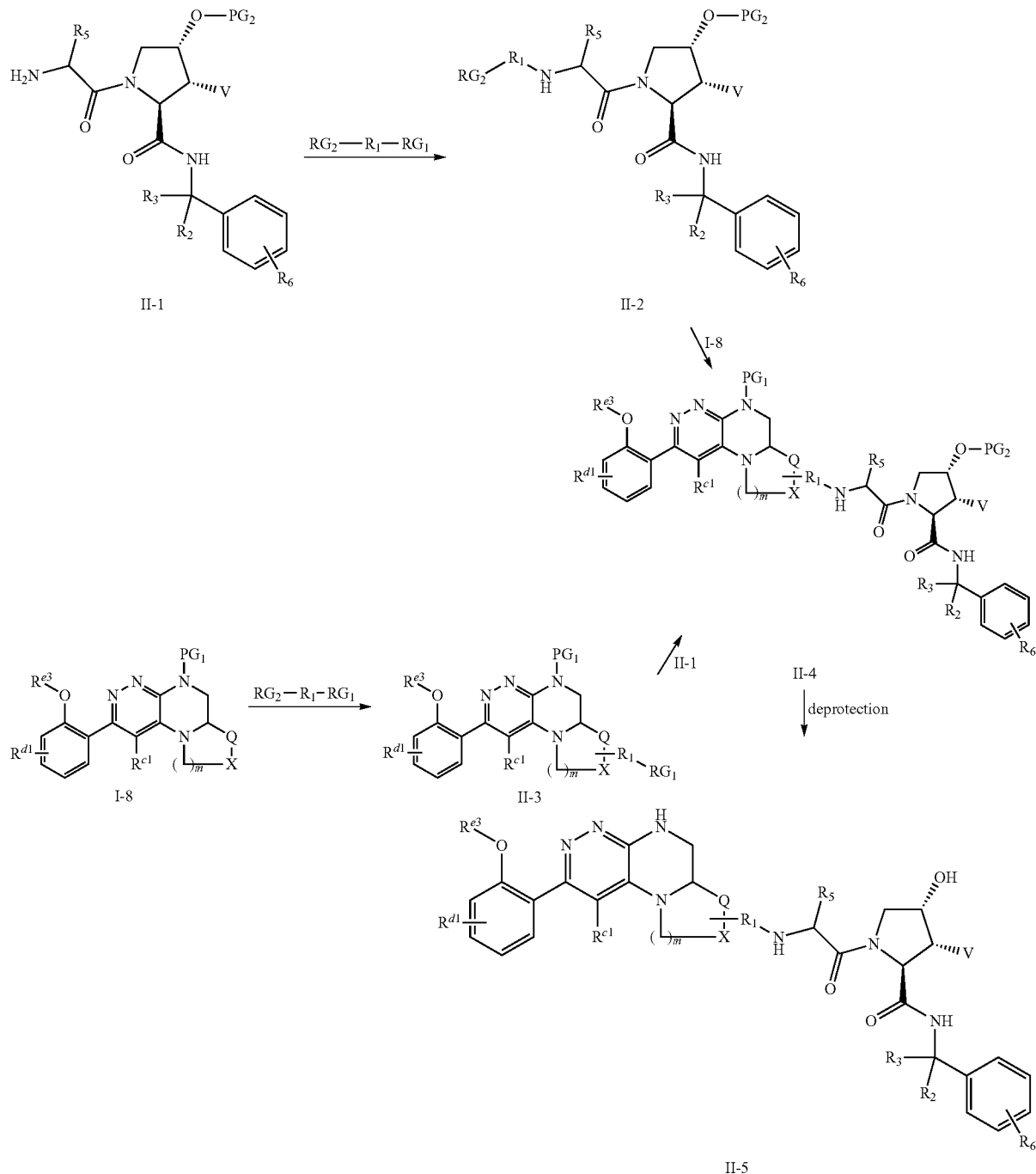

V = H, F
m = 1 to 3
RG$_1$ and RG$_2$ = reacting groups
PG$_1$ and PG$_2$ = protecting groups Compounds of formula II-5 can be synthesized using, for example, the sequences shown in Scheme II. Coupling of compounds II-1 with R$_1$ using appropriate synthetic methods (such as but not limited to amide formation, S$_N$2 reaction, reductive amination, etc.; e.g., RG$_1$ is a leaving group, such as a bromide and is displaced the amine of II-1) can afford compounds II-2. Compounds I-8 can be introduced using appropriate synthetic methods (such as, but not limited to, S$_N$2 reaction, S$_N$Ar reaction, reductive amination, Buchwald reaction, amide formation, Mitsunobu reaction, olefin metathesis, etc.) to give compounds II-4. Alternatively, the synthesis of II-4 can be achieved by the coupling of I-8 with R$_1$, followed by the introduction of II-1 using appropriate synthetic methods mentioned above. Removal of the protecting groups can afford compounds of formula II-5.

Scheme III
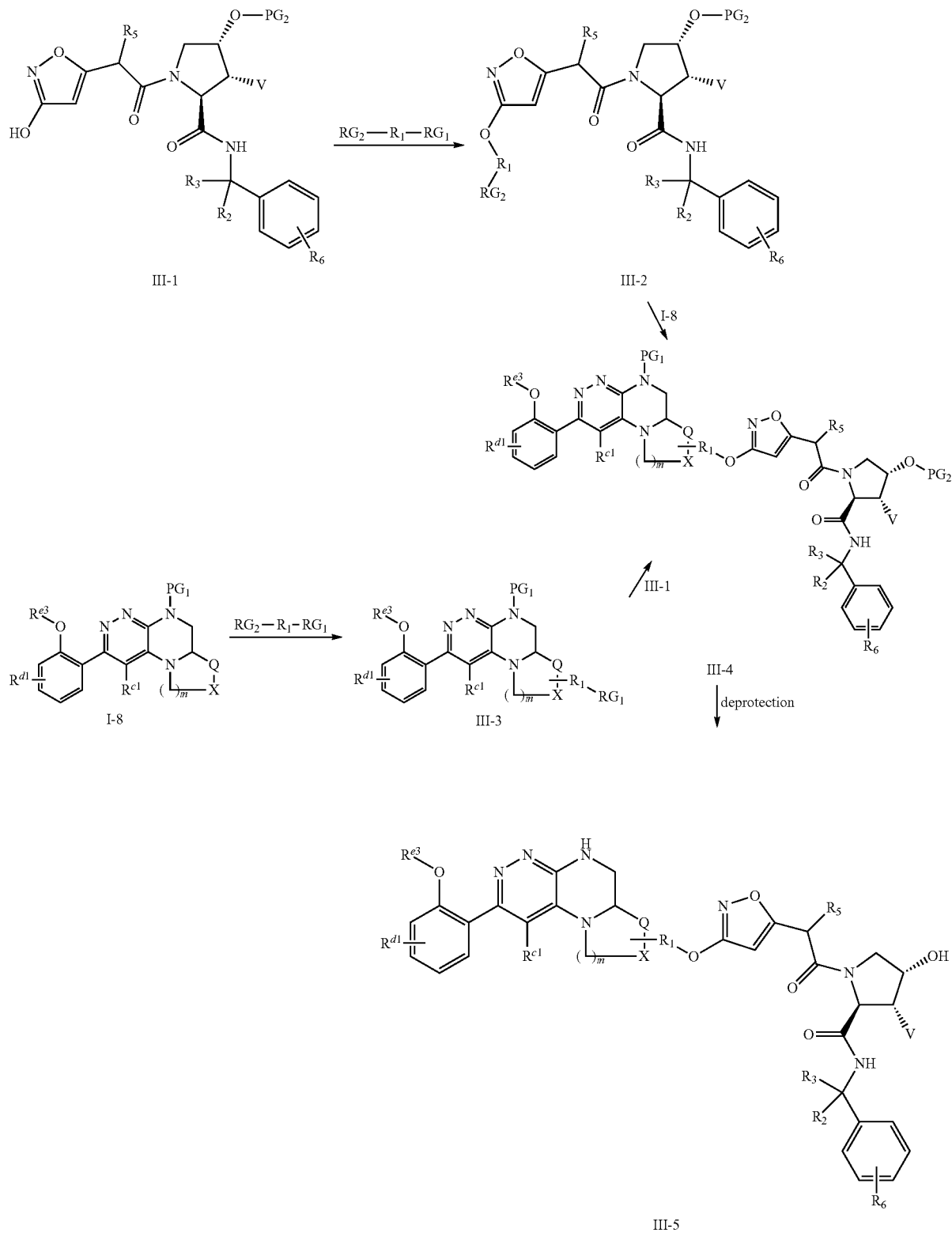
V = H, F
m = 1 to 3
RG$_1$ and RG$_2$ = reacting groups
PG$_1$ and PG$_2$ = protecting groups The compounds of formula III-5 can be synthesized using, for example, the sequences shown in Scheme III. Coupling of compounds III-1 with $R_1$ using appropriate synthetic methods (such as but not limited to $S_N2$ reaction, $S_NAr$ reaction, Mitsunobu reaction, etc.) can afford compounds III-2. Compounds I-8 can be introduced using appropriate synthetic methods (such as, but not limited to, $S_N2$ reaction, $S_NAr$ reaction, reductive amination, Buchwald reaction, amide formation, Mitsunobu reaction, olefin metathesis, etc.) to give compounds III-4. Alternatively, the synthesis of III-4 can be achieved by the coupling of 1-8 with $R_1$, followed by the introduction of intermediates III-1 using appropriate synthetic methods mentioned above. Removal of the protecting groups can result in compounds of formula III-5.

Scheme IV

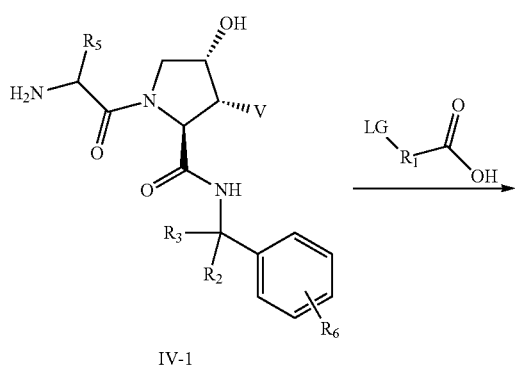

IV-1

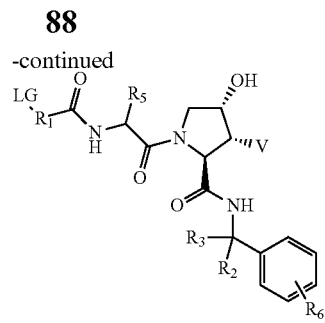

IV-2

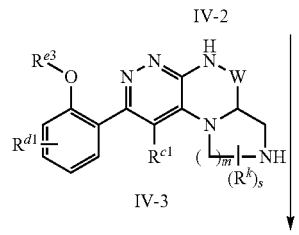

IV-3

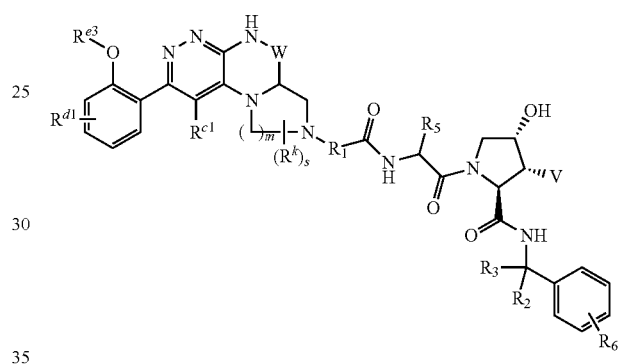

IV-4

V = H, F
LG = Cl, Br, I, OMs, OTs, etc.
m = 2 to 3

The compounds of formula IV-4 can be synthesized using, for example, the sequences shown in Scheme IV. Coupling of compounds IV-1 with acids under standard amide coupling conditions (e.g., treatment with an appropriate base such as DIPEA or $Et_3N$ and in the presence of coupling agents such as HATU, HOBt, or PyBOP) gives amides IV-2. Nucleophilic addition of compounds IV-3 under basic conditions (e.g., in the presence of a carbonate base, DIPEA, $Et_3N$, etc.) can afford compounds of formula IV-4.

Scheme V

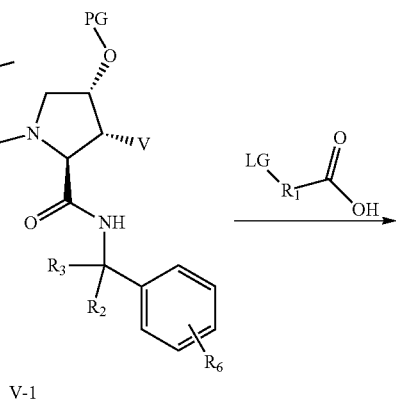

V-1

-continued

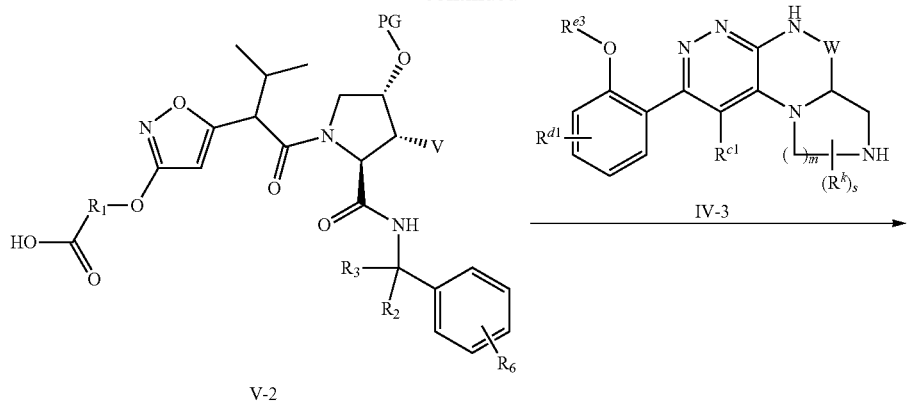

V-2

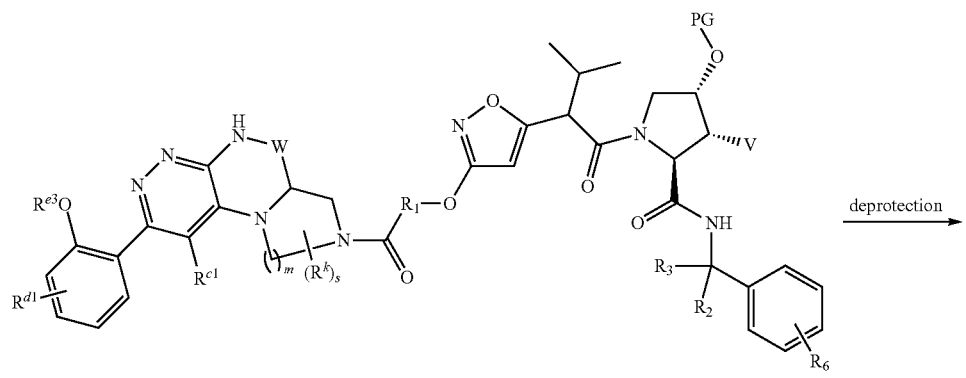

V-2 deprotection

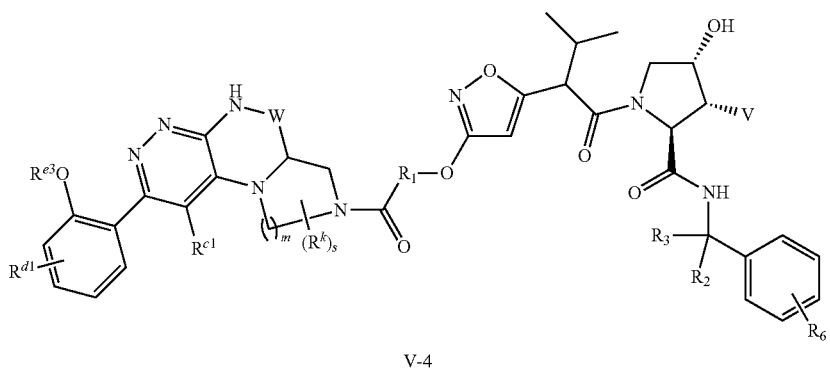

V-4

V = H, F
m = 2, 3
LG = Cl, Br, I, OMs, OTs, etc.

An exemplary synthesis for preparing compound of V-4 is depicted in Scheme V. Nucleophilic substitution of haloalkylacids with compounds V-1 under basic conditions (e.g., in the presence of a carbonate base, DIPEA, $Et_3N$, etc.) can give ethers V-2. Coupling of amines IV-3 with carboxylic acids V-2 under standard amide coupling conditions (e.g., treatment with an appropriate base such as DIPEA or trimethylamine and in the presence of coupling agents such as HATU, HOBt, or PyBOP) can give amides V-3. Removal of the protecting group using appropriate conditions can afford compounds of formula V-4.

Scheme VI
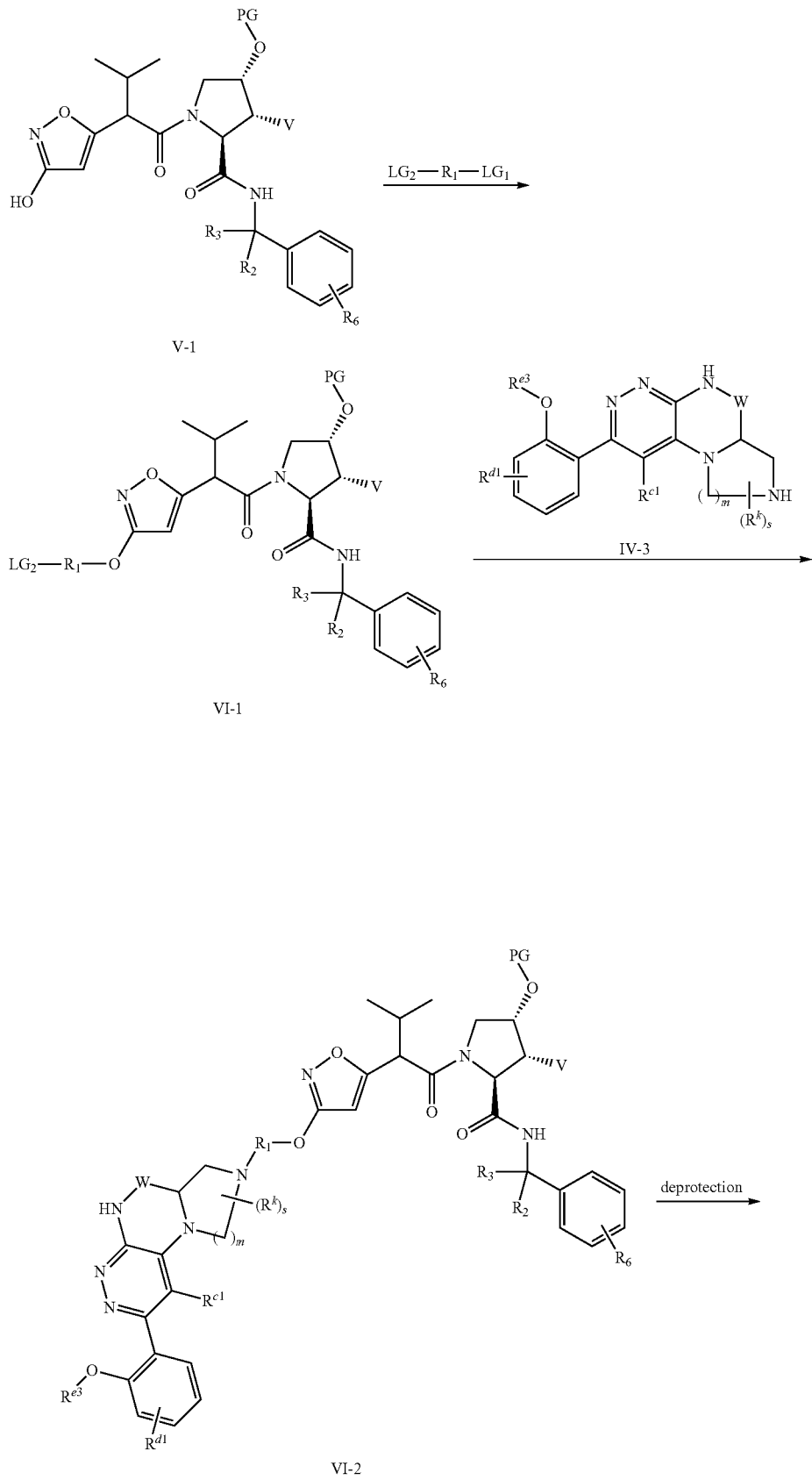

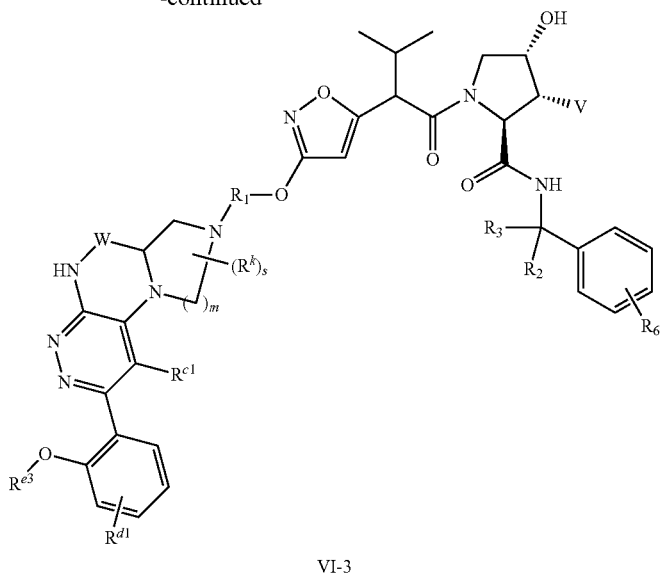

VI-3

V = H, F
m = 2, 3
LG₁ and LG₂ = Cl, Br, I, OMs, OTs, etc.

An exemplary synthesis for preparing compound of VI-3 is depicted in Scheme VI. Nucleophilic substitution of alkyldihalide with alcohol V-1 under basic conditions (e.g., in the presence of a carbonate base, DIPEA, Et₃N, etc.) can give ethers VI-1. Nucleophilic substitution of VI-1 where LG₂ is a leaving group, such as halo, with an amine IV-3 under basic conditions (e.g., in the presence of a carbonate base, DIPEA, Et₃N, etc.) can give compounds VI-2. Removal of the protecting group appropriate conditions can afford compounds of formula VI-3.

Scheme VII

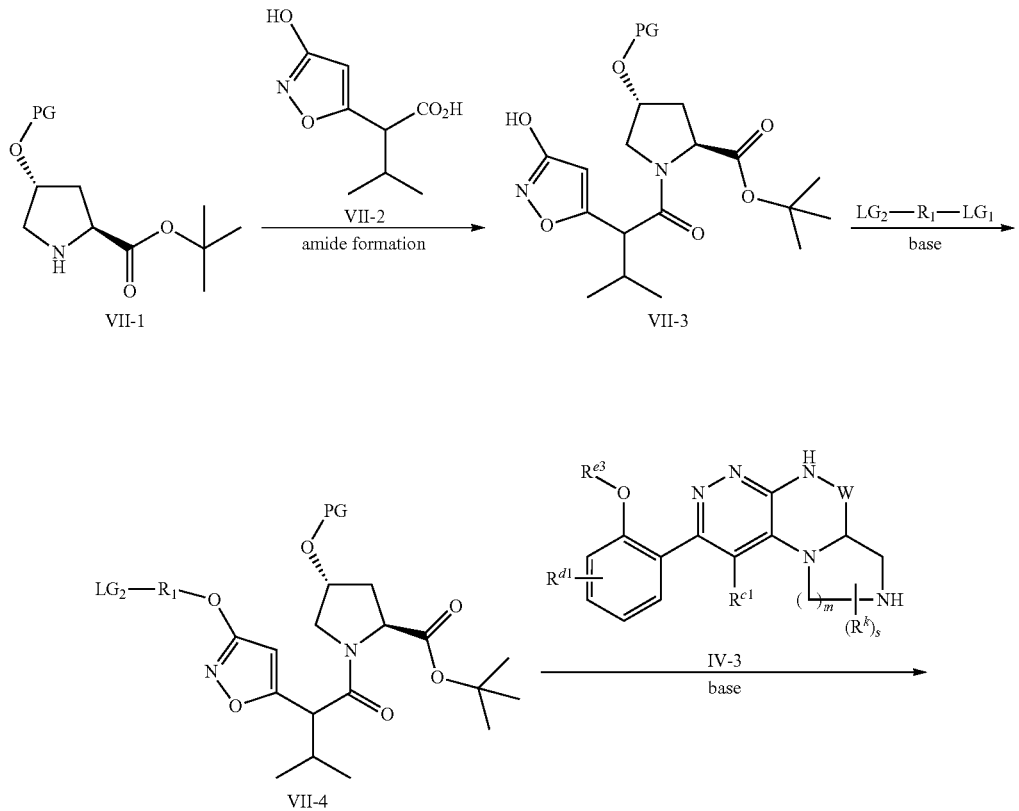

-continued
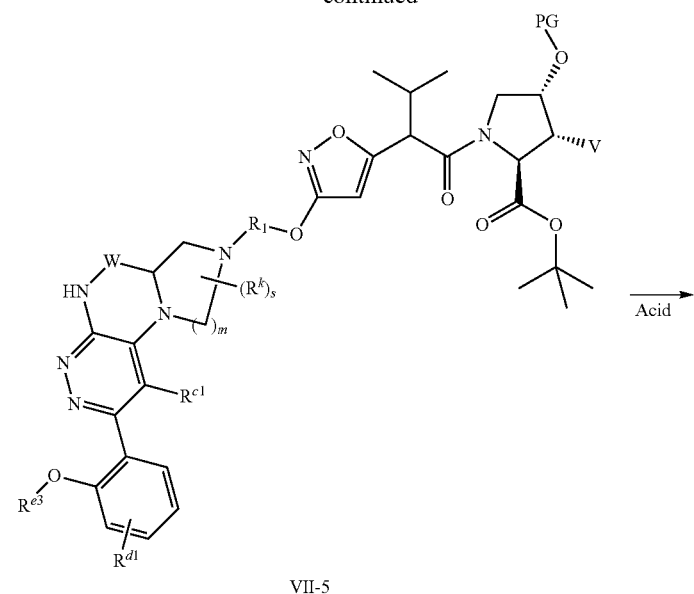
VII-5
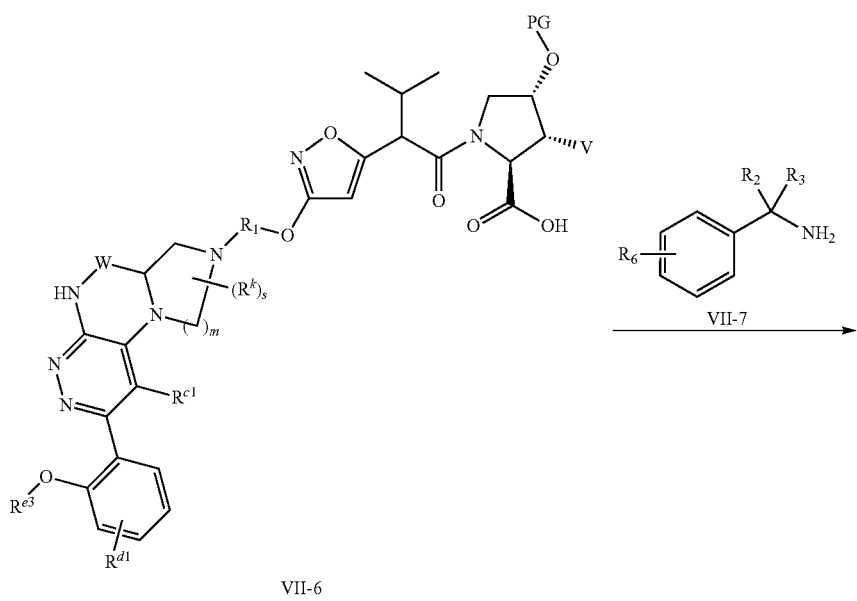
VII-6

-continued

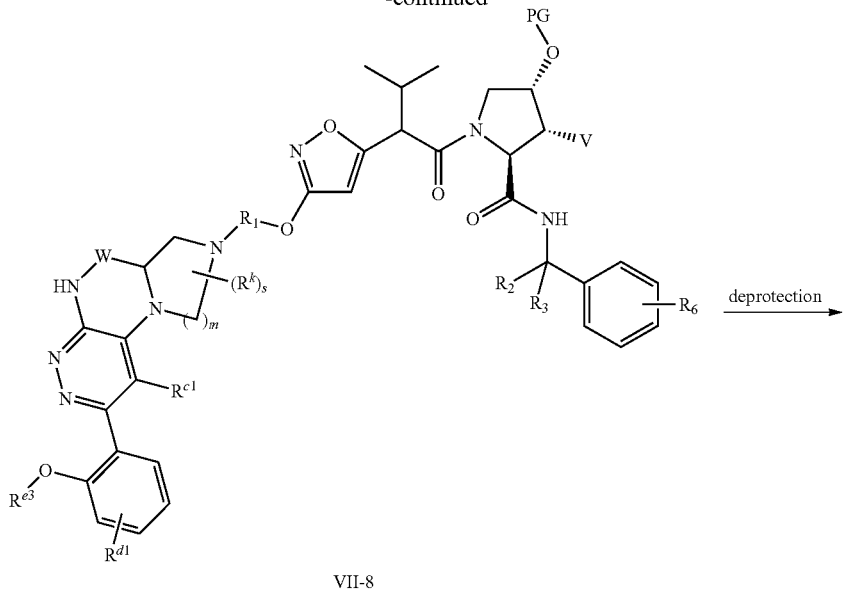

VII-8

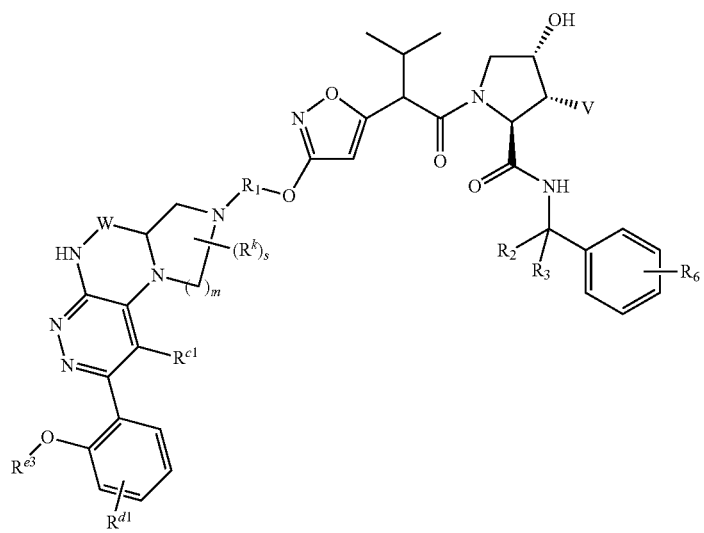

VII-9

PG = protecting group
LG₁ and LG₂ = Cl, Br, I, OMs, OTs, etc.
m = 2, 3
V = H, F

Compounds of formula VII-9 can be synthesized using, for example, the sequences shown in Scheme VII. Coupling of amine VII-1 with carboxylic acid VII-2 under standard amide coupling conditions (treatment with an appropriate base such as, but not limited to, DIPEA or trimethylamine and in the presence of coupling agents such as HATU, HOBt, or PyBOP) gives amides VII-3. Nucleophilic substitution of VII-3 with an alkyl-dihalide under basic conditions (e.g., in the presence of a carbonate base, DIPEA, Et₃N, etc.) can give compounds VII-4. A second nucleophilic substitution of VII-4 where LG₂ is halo with IV-3 under basic conditions (e.g., in the presence of a carbonate base, DIPEA, Et₃N, etc.) can give compounds VII-5. Hydrolysis of t-butyl-ester using appropriate conditions can give compounds VII-6. Coupling of compounds VII-6 with compounds VII-7 under standard amide coupling conditions such as a base, (e.g., DIPEA or trimethylamino) and in the presence of coupling (e. HATU, HOBt or PyBOP) can afford amides VII-8. Deprotection of VII-8 can afford compounds of formula VII-9.

Scheme VIII

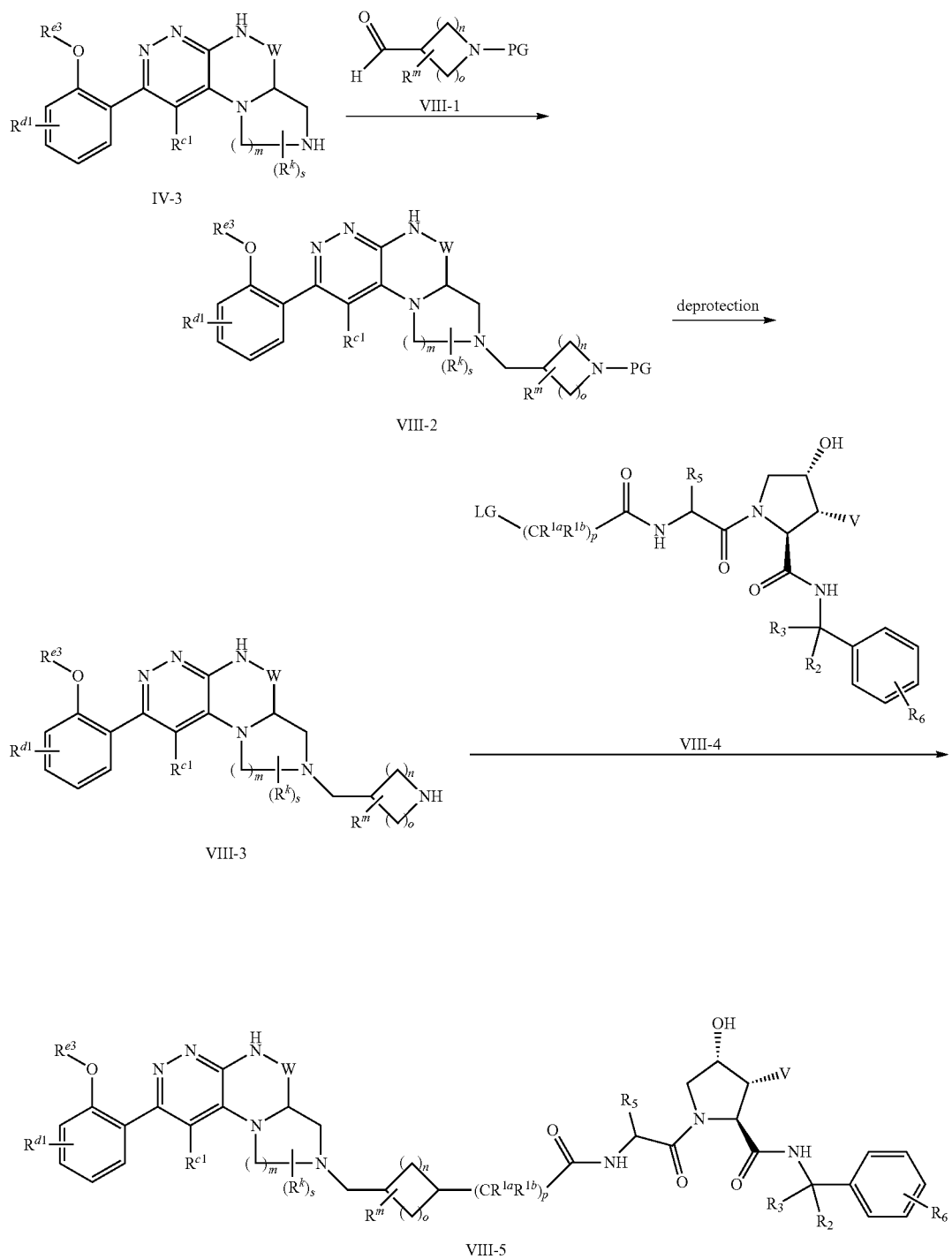

PG = protecting group
LG = Cl, Br, I, OMs, OTs, etc.
m = 2, 3
n, o = 0-3
p = 1 to 4
V = H, F The compounds of formula VIII-5 can be synthesized using, for example, the sequences shown in Scheme VIII. The reductive amination between compounds IV-3 and VIII-1 can provide compounds VIII-2. Removal of the protecting groups, followed by a nucleophilic substitution of VIII-4 where LG is halo with VIII-3 under basic conditions (e.g., in the presence of a carbonate base, DIPEA, Et$_3$N, etc.) can give compounds of formula VIII-5.

Scheme IX

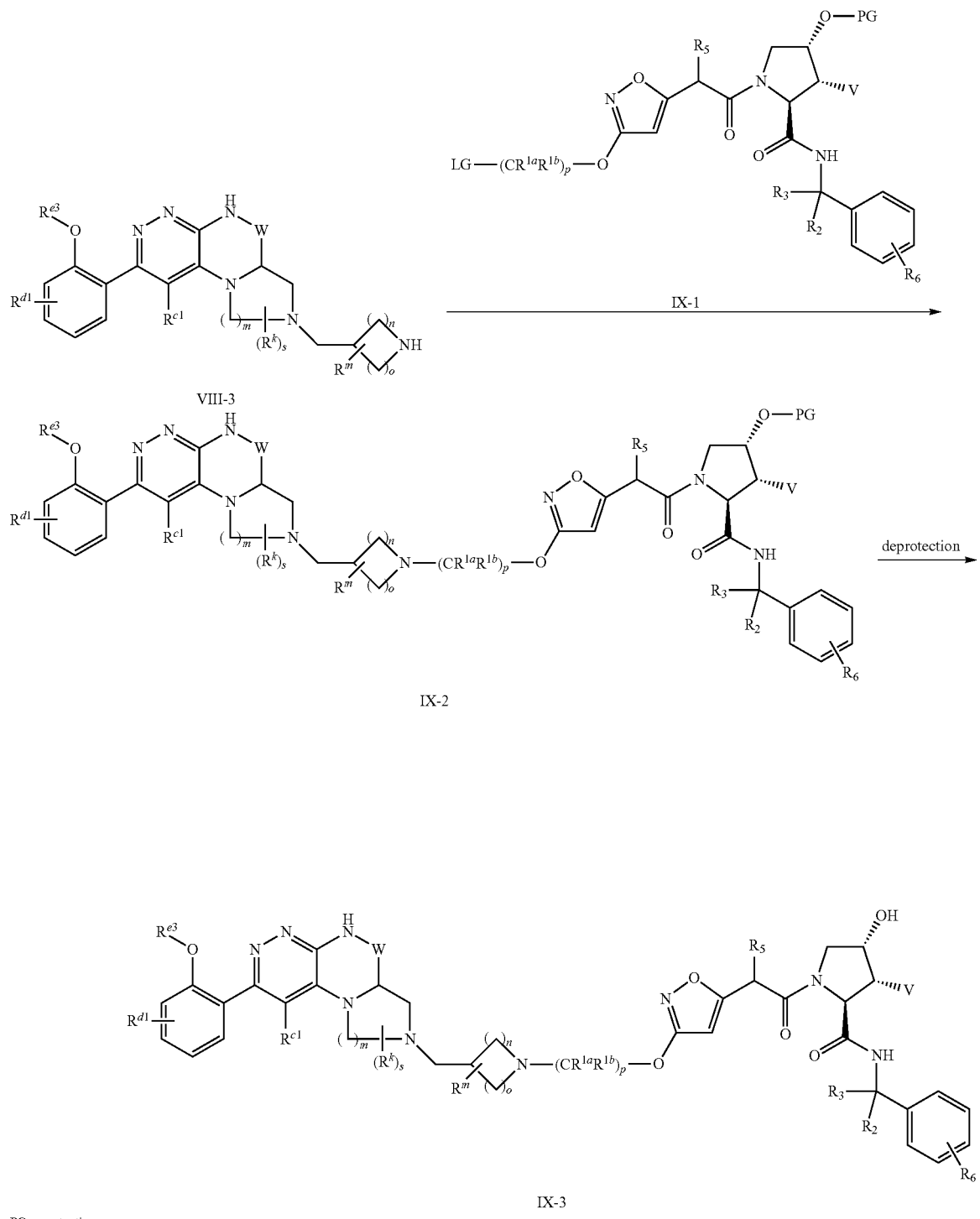

PG = protecting group
LG = Cl, Br, I, OMs, OTs, etc.
m = 2, 3
n, o = 0-3
p = 1 to 4
V = H, F The compounds of formula IX-3 can be synthesized as shown in Scheme IX. A nucleophilic substitution of IX-1 where LG is halo with VIII-3 under basic conditions (e.g., in the presence of a carbonate base, DIPEA, Et$_3$N, etc.) can give compounds IX-2. Removal of the protecting groups can afford compounds of formula IX-3.

Synthesis of Intermediates

Intermediate 1: 2-(6,6a,7,8,9,10-hexahydro-5H-pyrazino[1',2':4,5]pyrazino[2,3-c]pyridazine-2-yl)phenol (Int-1)

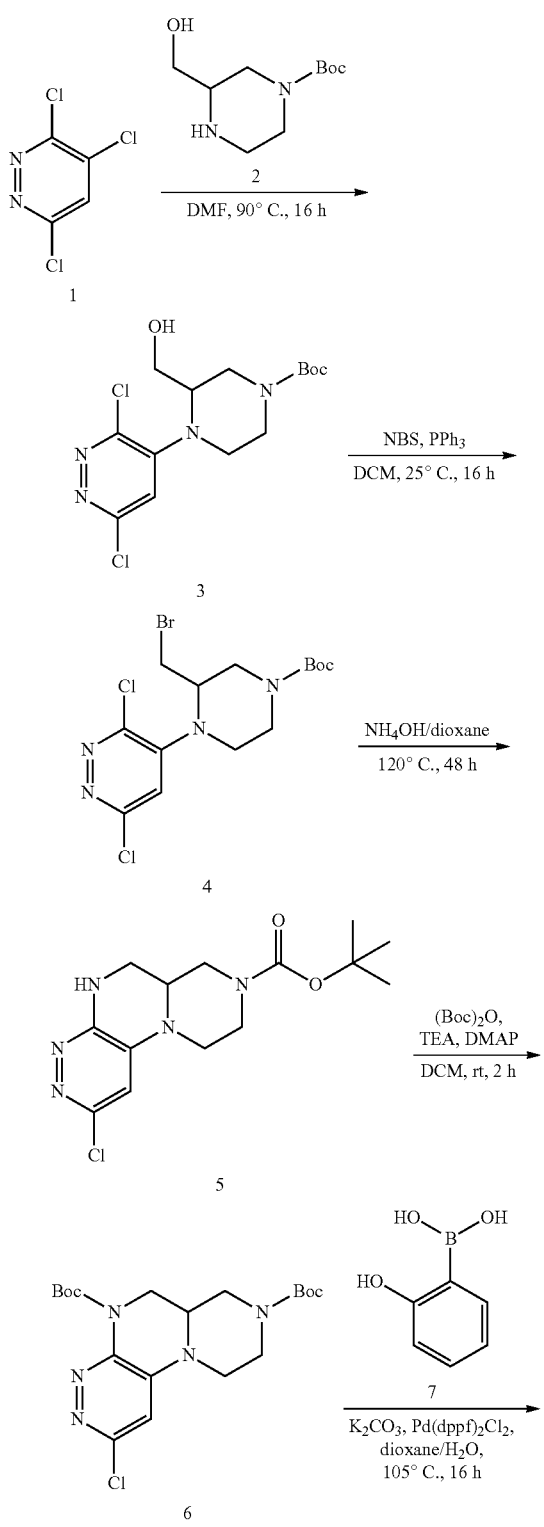

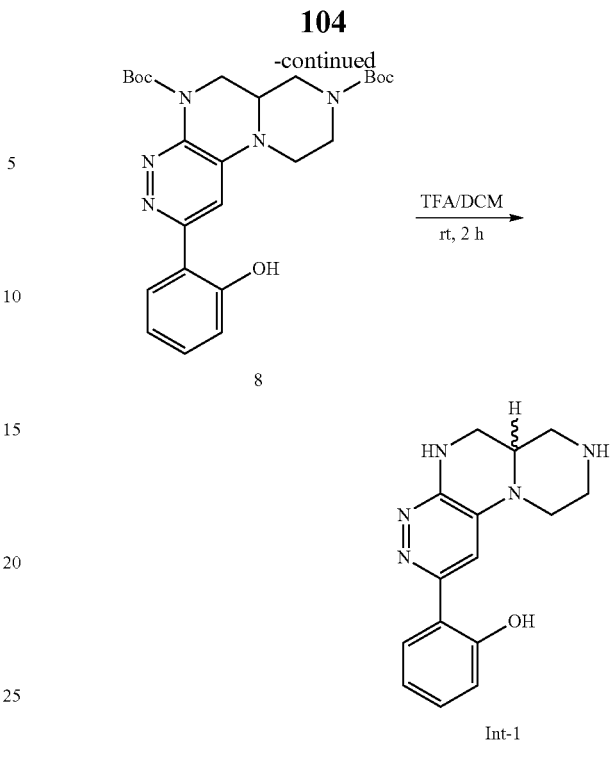

Step a. Synthesis of tert-butyl 4-(3,6-dichloropyridazin-4-yl)-3-(hydroxymethyl)piperazine-1-carboxylate (3)

To a solution of pent-4-yn-1-ol (5.0 g, 59.4 mmol) and 3,4-dihydro-2H-pyran (10 g, 118 mmol) in DCM (10 mL) was added pyridine (9.6 mL, 118 mmol) and TsOH (22.6 g, 118 mmol) at 0° C., the mixture was stirred at 25° C. for 16 h. The residue was washed with water (20 mL×2) then saturated brine solution (20 mL). The organics were then separated and dried (MgSO$_4$) before concentration to dryness. The crude was then purified by silica gel column chromatography (100-200 mesh size, eluted with PE:EtOAc=20:1) to give tert-butyl 4-(3,6-dichloropyridazin-4-yl)-3-(hydroxymethyl)piperazine-1-carboxylate (3) (2.0 g, 11.8 mmol, 20% yield) as white oil. $^1$H NMR (DMSO, 400 MHz): δ 4.54-4.52 (t, 1H), 3.75-3.71 (m, 2H), 3.43-3.35 (m, 2H), 2.72-2.71 (t, 1H), 2.23-2.22 (m, 2H), 1.70-1.59 (m, 4H), 1.47-1.39 (m, 4H).

Step b. Synthesis of tert-butyl 3-(bromomethyl)-4-(3,6-dichloropyridazin-4-yl)piperazine-1-carboxylate (4)

To a solution of N-bromosuccinimide (2.0 g, 11.3 mmol) and tert-butyl 4-(3,6-dichloropyridazin-4-yl)-3-(hydroxymethyl)piperazine-1-carboxylate (3) (4.1 g, 11.3 mmol) in DCM (50 mL) was added triphenylphosphine (5.9 mg, 22.6 mmol). The mixture was stirred at 25° C. for 16 h. The mixture was washed with water (50 mL), concentrated in vacuum, and the residue was purified by silica gel chromatography (PE:EtOAc=2:1) to give tert-butyl 3-(bromomethyl)-4-(3,6-dichloropyridazin-4-yl)piperazine-1-carboxylate (4) (3.2 g, 7.5 mmol, 66.5% yield) as a white solid. LCMS calc'd for C$_{14}$H$_{19}$BrCl$_2$N$_4$O$_2$: 426.1; Found: LCMS [M+H]: 427.1.

Step c. Synthesis of tert-butyl 2-chloro-5,6,6a,7,9,10-hexahydro-8H-pyrazino[1',2':4,5]pyrazino[2,3-c]

pyridazine-8-carboxylate (5). A mixture solution of tert-butyl 3-(bromomethyl)-4-(3,6-dichloropyridazin-4-yl)piperazine-1-carboxylate (4) (1.1 g, 2.6 mmol) in a solution of ammonium hydroxide (20 mL, 240 mmol) and 1,4-dioxane (20 mL) was stirred at 80° C. for 48 h in an autoclave. The reaction was concentrated in vacuum and the residue was purified by silica gel chromatography (SiO$_2$, 200-300 mesh, PE:EtOAc=1:2) to give tert-butyl 2-chloro-5,6,6a,7,9,10-hexahydro-8H-pyrazino[1',2':4,5]pyrazino[2,3-c]pyridazine-8-carboxylate (5) (330 mg, 1.0 mmol, 39% yield) as a white solid. LCMS calc'd for C$_{14}$H$_{20}$ClN$_5$O$_2$: 325.8; Found: LCMS [M+H]: 326.2.

Step d. Synthesis of di-tert-butyl 2-chloro-6a,7,9,10-tetrahydro-5H-pyrazino[1',2':4,5]pyrazino[2,3-c]pyridazine-5,8(6H)-dicarboxylate (6). To a solution of di-tert-butyl dicarbonate (401 mg, 1.8 mmol) and tert-butyl 2-chloro-5,6,6a,7,9,10-hexahydro-8H-pyrazino[1',2':4,5]pyrazino[2,3-c]pyridazine-8-carboxylate (5) (200 mg, 0.61 mmol) in DCM (5 mL) was added DMAP (62 mg, 0.61 mmol) and triethylamine (0.4 mL, 2.5 mmol) at rt. The mixture was stirred at rt for 2 h. The reaction was concentrated in vacuum and the residue was purified by silica gel chromatography (PE:EtOAc=20:1 to 5:1) to give di-tert-butyl 2-chloro-6a,7,9,10-tetrahydro-5H-pyrazino[1',2':4,5]pyrazino[2,3-c]pyridazine-5,8(6H)-dicarboxylate (6) (130 mg, 0.31 mmol, 50% yield) as a white solid. LCMS calc'd for C$_{19}$H$_{28}$ClN$_5$O$_4$: 425.9; Found LCMS [M+H]: 426.3.

Step e. Synthesis of di-tert-butyl 2-(2-hydroxyphenyl)-6a,7,9,10-tetrahydro-5H-pyrazino[1',2':4,5]pyrazino[2,3-c]pyridazine-5,8(6H)-dicarboxylate (8). To a solution of di-tert-butyl 2-chloro-6a,7,9,10-tetrahydro-5H-pyrazino[1',2':4,5]pyrazino[2,3-c]pyridazine-5,8(6H)-dicarboxylate (6) (130 mg, 0.31 mmol) and 2-hydroxyphenylboronic acid (42 mg, 0.31 mmol) in 1,4-dioxane (5 mL) was added potassium carbonate (84.4 mg, 0.61 mmol) and Pd(dppf)$_2$Cl$_2$ (24.9 mg, 0.03 mmol) at rt. The mixture was stirred at 105° C. for 18 h. The reaction was concentrated and the residue was purified by gel chromatography (SiO$_2$, 200-300 mesh, PE:EtOAc=1:2) to give di-tert-butyl 2-(2-hydroxyphenyl)-6a,7,9,10-tetrahydro-5H-pyrazino[1',2':4,5]pyrazino[2,3-c]pyridazine-5,8(6H)-dicarboxylate (8) (180 mg, 0.41 mmol, 99.9% yield) as a white solid. LCMS calc'd for C$_{25}$H$_{33}$N$_5$O$_5$: 483.5; Found: LCMS [M+H]: 484.3.

Step f. Synthesis of 2-(6,6a,7,8,9,10-hexahydro-5H-pyrazino[1',2':4,5]pyrazino[2,3-c]pyridazin-2-yl)phenol (Int-1)

A solution of di-tert-butyl 2-(2-hydroxyphenyl)-6a,7,9,10-tetrahydro-5H-pyrazino[1',2':4,5]pyrazino[2,3-c]pyridazine-5,8(6H)-dicarboxylate (8) (180 mg, 0.37 mmol) in DCM (1.5 mL) and TFA (1.5 mL, 19.6 mmol) was stirred at 25° C. for 2 h. The mixture solution was concentrated in vacuum, the residue was added to 5 mL water, adjust pH >7 with NaHCO$_3$(aq), extracted with EtOAc, and filtered to give 2-(6,6a,7,8,9,10-hexahydro-5H-pyrazino[1',2':4,5]pyrazino[2,3-c]pyridazin-2-yl)phenol (Int-1) (70 mg, 0.24 mmol, 64% yield) as a white solid. LCMS calc'd for C$_{15}$H$_{17}$N$_5$O: 283.3; Found: LCMS [M+H]: 284.1. $^1$H NMR (400 MHz, DMSO-d$_6$) δ 14.8 (s, 1H), 7.91 (s, 1H), 7.30 (s, 1H), 7.19 (s, 2H), 6.83-6.86 (m, 2H), 3.92-3.94 (m, 1H), 3.40-3.44 (m, 1H), 3.13-3.15 (m, 2H), 3.00-3.11 (m, 2H), 2.66-2.76 (m, 2H), 2.45-2.50 (m, 1H), 2.28-2.33 (m, 1H).

Alternate Synthesis of tert-butyl 2-chloro-5,6,6a,7,9,10-hexahydro-8H-pyrazino[1',2':4,5]pyrazino[2,3-c]pyridazine-8-carboxylate (5)

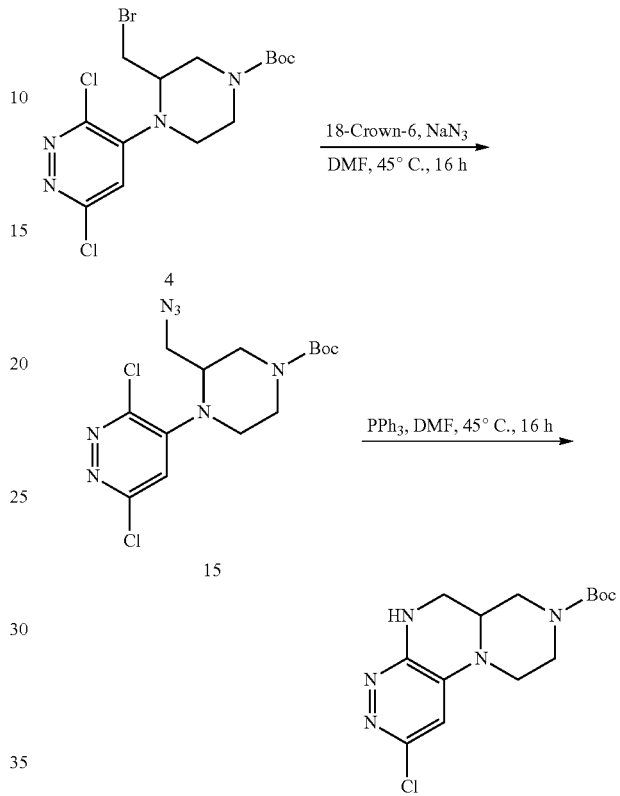

Step a. Synthesis of tert-butyl 3-(azidomethyl)-4-(3,6-dichloropyridazin-4-yl)piperazine-1-carboxylate (15)

To a solution of tert-butyl 3-(bromomethyl)-4-(3,6-dichloropyridazin-4-yl)piperazine-1-carboxylate (4) (2.7 g, 6.3 mmol) in DMF (15 mL) was added sodium azide (535 mg, 8.2 mmol) and 18-crown-6 (1.6 g, 6.3 mmol), the mixture solution was stirred at 45° C. for 18 h. water (50 mL) and EtOAc (60 mL) was added to the mixture. Extracted with EtOAc (60 mL×2). The EtOAc layer was concentrated in vacuum to give tert-butyl 3-(azidomethyl)-4-(3,6-dichloropyridazin-4-yl)piperazine-1-carboxylate (15) (2.0 g, 5.2 mmol, 81% yield) as a yellow oil. LCMS calc'd for C$_{14}$H$_{19}$O$_2$N$_7$O$_2$: 387.1; Found: LCMS [M+H]: 388.1.

Step b. Synthesis of tert-butyl 2-chloro-5,6,6a,7,9,10-hexahydro-8H-pyrazino[1',2':4,5]pyrazino[2,3-c]pyridazine-8-carboxylate (5)

To a solution of tert-butyl 3-(azidomethyl)-4-(3,6-dichloropyridazin-4-yl)piperazine-1-carboxylate (15) (2.0 g, 5.2 mmol) in DMF (10 mL) was added and triphenylphosphine (1.4 g, 5.2 mmol), the mixture was stirred at 45° C. for 18 h. The solution was added to a mixture of water (60 mL) and EtOAc (50 mL), extracted with EtOAc (60 mL×2), concentrated in vacuum and the residue was purified by gel silica chromatography (SiO2, 200-300 mesh, PE:EtOAc from 10:1 to 1:2) to give tert-butyl 2-chloro-5,6,6a,7,9,10-hexahydro-8H-pyrazino[1',2':4,5]pyrazino[2,3-c]pyridazine-8-carboxylate (5) (1500 mg, 4.6 mmol, 89% yield) as a yellow solid. LCMS calc'd for $C_{14}H_{20}ClN_5O_2$: 325.1; Found: LCMS [M+H]: 326.2.

Intermediate 2. 2-((5-(1-(((2S,4R)-4-((tert-butyldimethylsilyl)oxy)-2-(((S)-1-(4-(4-methyl-1λ$^3$,3λ$^2$-thiazol-5-yl)phenyl)ethyl)carbamoyl)pyrrolidin-1-yl)-3-methyl-1-oxobutan-2-yl)isoxazol-3-yl)oxy)acetic acid (Int-2)

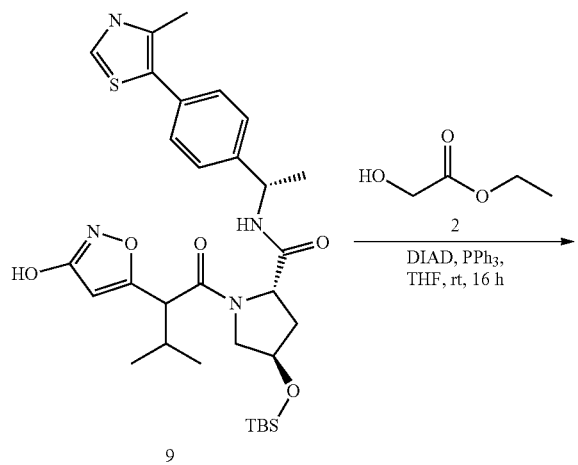

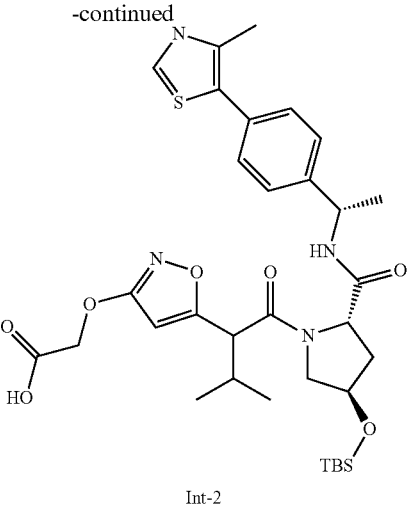

Int-2

Step a. Synthesis of ethyl 2-((5-(1-((2S,4R)-4-((tert-butyldimethylsilyl)oxy)-2-(((S)-1-(4-(4-methyl-1λ$^3$, 3λ$^2$-thiazol-5-yl)phenyl)ethyl)carbamoyl)pyrrolidin-1-yl)-3-methyl-1-oxo butan-2-yl)isoxazol-3-yl)oxy) acetate (10)

To a solution of (2S,4R)-4-((tert-butyldimethylsilyl)oxy)-1-(2-(3-hydroxyisoxazol-5-yl)-3-methylbutanoyl)-N—((S)-1-(4-(4-methyl-1λ$^3$,3λ$^2$-thiazol-5-yl)phenyl)ethyl)pyrrolidine-2-carboxamide (9) (prepared using the procedure described in US2020/0038378, 150 mg, 0.24 mmol) and ethyl 2-hydroxyacetate (51 mg, 0.48 mmol) in THF (15 mL) was added PPh$_3$ (128 mg, 0.48 mmol) and DIAD (0.15 mL, 0.48 mmol) at 25° C., the mixture was stirred at 25° C. for 2 h. The mixture was concentrated, the residue was purified by prep-TLC (PE:EtOAc=1:1) to give ethyl 2-((5-(1-((2S, 4R)-4-((tert-butyldimethylsilyl)oxy)-2-(((S)-1-(4-(4-methyl-1λ$^3$,3λ$^2$-thiazol-5-yl)phenyl)ethyl)carbamoyl)pyrrolidin-1-yl)-3-methyl-1-oxobutan-2-yl)isoxazol-3-yl)oxy)acetate (10) (90 mg, 0.13 mmol, 53% yield) as a yellow oil. LCMS calc'd for $C_{35}H_{50}N_4O_7SSi$: 698.32; Found: LCMS [M+H]: 699.4.

Step b. Synthesis of 2-((5-(1-((2S,4R)-4-((tert-butyldimethylsilyl)oxy)-2-(((S)-1-(4-(4-methyl-1λ$^3$, 3λ$^2$-thiazol-5-yl)phenyl)ethyl)carbamoyl)pyrrolidin-1-yl)-3-methyl-1-oxobutan-2-yl)isoxazol-3-yl)oxy) acetic acid (Int-2)

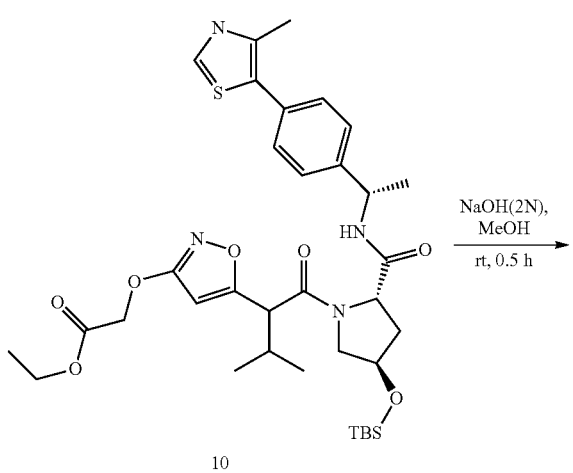

A solution of ethyl 2-((5-(1-(((2S,4R)-4-((tert-butyldimethylsilyl)oxy)-2-(((S)-1-(4-(4-methyl-1λ$^3$,3λ$^2$-thiazol-5-yl)phenyl)ethyl)carbamoyl)pyrrolidin-1-yl)-3-methyl-1-oxobutan-2-yl)isoxazol-3-yl)oxy)acetate (10) (90 mg, 0.13 mmol) in a mixture of NaOH (10.2 mg, 0.3 mmol), water (6.0 mL) and methanol (12.0 mL) was stirred at 25° C. for 2 h. The mixture was adjust pH 4-5 by HCl (1 N), extracted with EtOAc (40 mL×2), concentrated, and the residue was purified by prep-TLC (PE:EtOAc=1:1) to give 2-((5-(1-((2S, 4R)-4-((tert-butyldimethylsilyl)oxy)-2-(((S)-1-(4-(4-methyl-1λ$^3$,3λ$^2$-thiazol-5-yl)phenyl)ethyl)carbamoyl)pyrrolidin-1-yl)-3-methyl-1-oxobutan-2-yl)isoxazol-3-yl)oxy) acetic acid (Int-2) (45 mg, 0.06 mmol, 52% yield) as a yellow oil. LCMS calc'd for $C_{33}H_{46}N_4O_7SSi$: 670.29; Found: LCMS [M+H]: 671.4.

Intermediate 3. (2S,4R)-1-(2-(3-(2-bromoethoxy)isoxazol-5-yl)-3-methylbutanoyl)-4-((tert-butyldimethylsilyl)oxy)-N—((S)-1-(4-(4-methyl-1λ³,3λ²-thiazol-5-yl)phenyl)ethyl)pyrrolidine-2-carboxamide (Int-3)

Intermediate 4. (2S,4R)-1-((R)-2-(3-(2-bromoethoxy)isoxazol-5-yl)-3-methylbutanoyl)-4-((tert-butyldimethylsilyl)oxy)-N—((S)-1-(4-(4-methylthiazol-5-yl)phenyl)ethyl)pyrrolidine-2-carboxamide (Int-4)

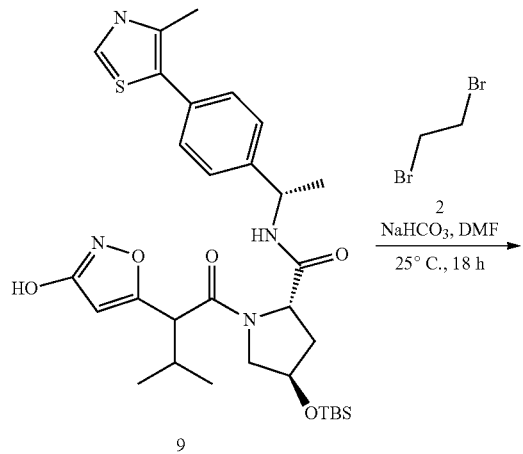

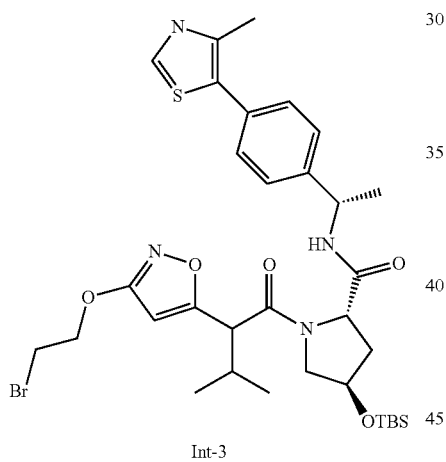

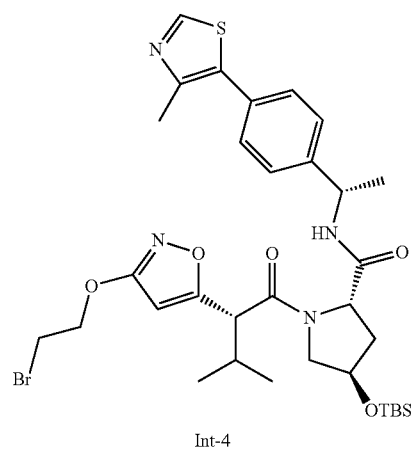

To a solution of (2S,4R)-4-((tert-butyldimethylsilyl)oxy)-1-(2-(3-hydroxyisoxazol-5-yl)-3-methylbutanoyl)-N—((S)-1-(4-(4-methyl-1λ³,3λ²-thiazol-5-yl)phenyl)ethyl)pyrrolidine-2-carboxamide (9) (prepared using the procedure described in US2020/0038378, 100 mg, 0.16 mmol) and 1,2-dibromoethane (45 mg, 0.24 mmol) in DMF (3 mL) was added and NaHCO$_3$ (60 mg, 0.67 mmol) at 25° C., the mixture was stirred at 30° C. for 16 h. The reaction was taken up in EtOAc (20 mL) and the organics were washed with water (20 mL×3) and brine (20 mL). The organics were then separated and dried (MgSO$_4$) before concentration to dryness. The crude product was then purified by prep-TLC (EtOAc:PE=2:1) to give (2S,4R)-1-(2-(3-(2-bromoethoxy)isoxazol-5-yl)-3-methylbutanoyl)-4-((tert-butyldimethylsilyl)oxy)-N—((S)-1-(4-(4-methyl-1λ³,3λ²-thiazol-5-yl)phenyl)ethyl)pyrrolidine-2-carboxamide (Int-3) (50 mg, 0.07 mmol, 51% yield) as a sticky colorless solid. LCMS calc'd for C$_{33}$H$_{47}$BrN$_4$O$_5$SSi: 718.2; Found: LCMS [M+H]: 719.3.

(2S,4R)-4-((tert-butyl dimethylsilyl)oxy)-1-(2-(3-hydroxy isoxazol-5-yl)-3-methylbutanoyl)-N—((S)-1-(4-(4-methyl-1λ³,3λ²-thiazol-5-yl)phenyl)ethyl)pyrrolidine-2-carboxamide (Int-3) was separated by prep-HPLC (eluting with H₂O:CH₃CN (0.1% of FA) from 50% to 90%) to give (2S,4R)-1-(2-(3-(2-bromoethoxy)isoxazol-5-yl)-3-methylbutanoyl)-4-((tert-butyldimethylsilyl)oxy)-N—((S)-1-(4-(4-methyl-1λ³,3λ²-thiazol-5-yl)phenyl)ethyl)pyrrolidine-2-carboxamide (30 mg, 0.04 mmol, 25% yield) as a white solid. LCMS calc'd for $C_{33}H_{47}BrN_4O_5SSi$: 718.2; Found: LCMS [M+H]: 719.2.

Intermediate 5. (2S,4R)-1-((S)-2-(2-chloroacetamido)-3,3-dimethylbutanoyl)-4-hydroxy-N-(4-(4-methyl-1λ³,3λ²-thiazol-5-yl)benzyl)pyrrolidine-2-carboxamide (Int-5)

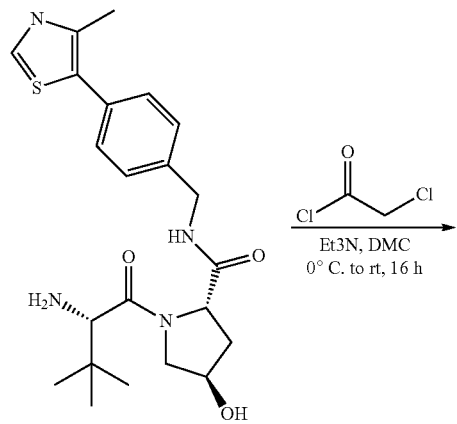

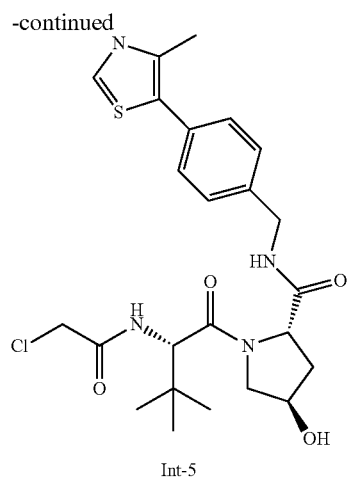

Int-5

To a solution of (2S,4R)-1-((S)-2-amino-3,3-dimethylbutanoyl)-4-hydroxy-N-(4-(4-methyl-1λ³,3λ²-thiazol-5-yl)benzyl)pyrrolidine-2-carboxamide (prepared using the procedure described in WO2018/0140809, 500 mg, 1.2 mmol) in DCM (15 mL) and was added TEA (0.81 mL, 5.8 mmol), the reaction was cooled to 0° C., a solution of chloroacetyl chloride (262 mg, 2.3 mmol) in DCM (2 mL) was added, the reaction was stirred at 25° C. for 16 h under N₂. The reaction was washed with water (10 mL×2), dried over Na₂SO₄, filtered and concentrated in vacuum, the residue was purified by silica gel column chromatography (100-200 mesh size, eluted with DCM:MeOH=25:1) to afford (2S,4R)-1-((S)-2-(2-chloroacetamido)-3,3-dimethylbutanoyl)-4-hydroxy-N-(4-(4-methyl-1λ³,3λ²-thiazol-5-yl)benzyl)pyrrolidine-2-carboxamide (Int-5). (520 mg, 0.98 mmol, 84% yield) as a yellow solid. LCMS calc'd for $C_{24}H_{31}ClN_4O_4S$: 507.0; Found: LCMS [m/z]: 507.2.

The intermediates in the table below were prepared by the method used in preparing Int-5:

| Int. | Structure | Name | MF | LCMS (M + H) |
|---|---|---|---|---|
| Int-6 | 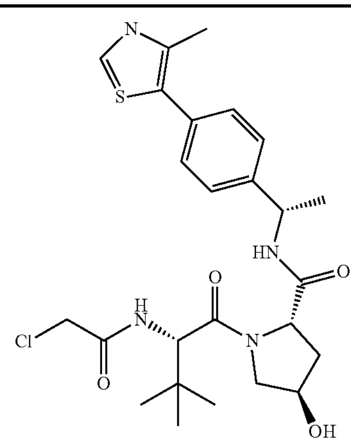 | (2S,4R)-1-((S)-2-(2-chloroacetamido)-3,3-dimethylbutanoyl)-4-hydroxy-N-((S)-1-(4-(4-methyl-1λ³,3λ²-thiazol-5-yl)phenyl)ethyl)pyrrolidine-2-carboxamide | $C_{25}H_{33}ClN_4O_4S$ | 521.1 |

| Int. | Structure | Name | MF | LCMS (M + H) |
|---|---|---|---|---|
| Int-7 | 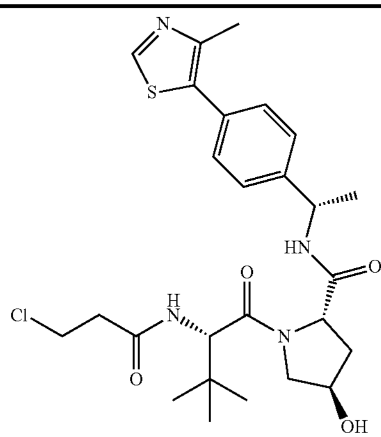 | (2S,4R)-1-((S)-2-(3-chloropropanamido)-3,3-dimethylbutanoyl)-4-hydroxy-N-((S)-1-(4-(4-methylthiazol-5-yl)phenyl)ethyl)pyrrolidine-2-carboxamide | $C_{26}H_{35}ClN_4O_4S$ | 535.13 |
| Int-10 | 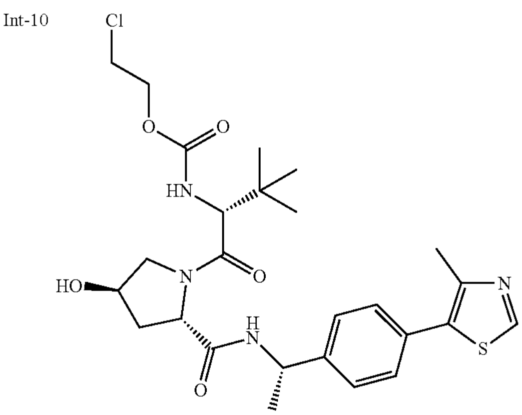 | 2-chloroethyl ((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamate | $C_{26}H_{35}ClN_4O_5S$ | 551.1 |

Intermediate 8. 2-(8-(piperidin-4-ylmethyl)-6,6a,7,8,9,10-hexahydro-5H-pyrazino[1',2':4,5]pyrazino[2,3-c]pyridazin-2-yl)phenol (Int-8)

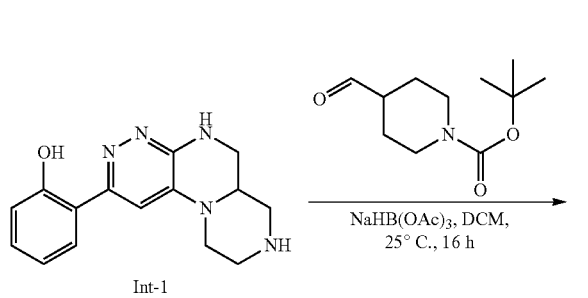

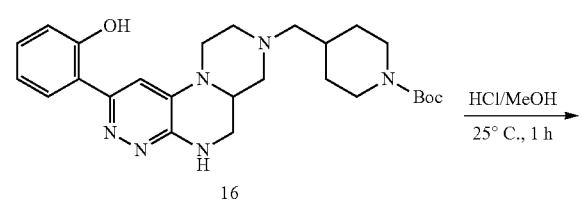

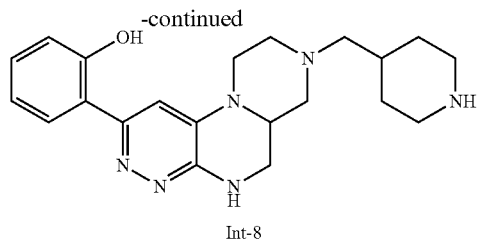

Step a. Synthesis of tert-butyl 4-((2-(2-hydroxyphenyl)-5,6,6a,7,9,10-hexahydro-8H-pyrazino[1',2':4,5]pyrazino[2,3-c]pyridazin-8-yl)methyl)piperidine-1-carboxylate (16)

To a solution of 1-Boc-piperidine-4-carboxaldehyde (63.2 mg, 0.30 mmol) and 2-(6,6a,7,8,9,10-hexahydro-5H-pyrazino[1',2':4,5]pyrazino[2,3-c]pyridazin-2-yl)phenol (Int-1) (56 mg, 0.20 mmol) in DCM (10 ml) was added NaBH(OAc)₃ (0.12 ml, 0.59 mmol) at rt. The mixture was stirred at rt for 16 h. The mixture was concentrated in vacuum and purified by prep-TLC (MeOH:DCM=1:10) to give tert-butyl 4-((2-(2-hydroxyphenyl)-5,6,6a,7,9,10-hexahydro-8H-pyrazino[1',2':4,5]pyrazino[2,3-c]pyridazin-8-yl)methyl)piperidine-1-carboxylate (16) (60 mg, 0.12 mmol, 63% yield) as a yellow solid. LCMS calc'd for $C_{26}H_{36}N_6O_3$: 480.3; Found: LCMS [m/z]=481.3.

Step b. Synthesis of 2-(8-(piperidin-4-ylmethyl)-6,6a,7,8,9,10-hexahydro-5H-pyrazino[1',2':4,5]pyrazino[2,3-c]pyridazin-2-yl)phenol (Int-8)

To a solution of tert-butyl 4-((2-(2-hydroxyphenyl)-5,6,6a,7,9,10-hexahydro-8H-pyrazino[1',2':4,5]pyrazino[2,3-c]pyridazin-8-yl)methyl)piperidine-1-carboxylate (16) (60 mg, 0.12 mmol) in methanol (3 ml) was added HCl (0.07 ml, 0.37 mmol) at rt. The mixture was stirred at rt for 1 h. The mixture was concentrated in vacuum to give 2-(8-(piperidin-4-ylmethyl)-6,6a,7,8,9,10-hexahydro-5H-pyrazino[1',2':4,5]pyrazino[2,3-c]pyridazin-2-yl)phenol (Int-8) (60 mg, 0.11 mmol, 91% yield) as a solid. LCMS calc'd for $C_{21}H_{28}N_6O$, 380.2; Found: LCMS [m/z]=381.2.

The intermediates in the table below were prepared by the method used in preparing Int-8 using appropriate starting materials:

| Int. | Structure | Name | Calcd. $(M + H)^+$ m/z | Found $(M + H)^+$ m/z |
|---|---|---|---|---|
| Int-8a | 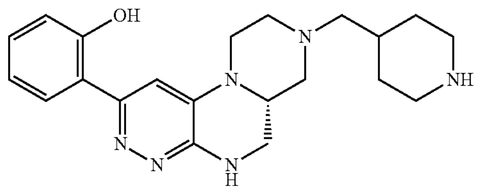 [SMILES: Oc1ccccc1-c1cc2c(nn1)NC[C@H]1CN(CC3CCNCC3)CCN21] | (S)-2-(8-(piperidin-4-ylmethyl)-6,6a,7,8,9,10-hexahydro-5H-pyrazino[1',2':4,5]pyrazino[2,3-c]pyridazin-2-yl)phenol | 381.2 | 381.2 |
| Int-11 | 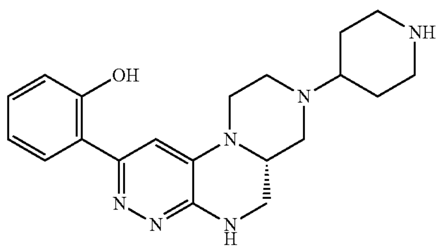 [SMILES: Oc1ccccc1-c1cc2c(nn1)NC[C@H]1CN(C3CCNCC3)CCN21] | (S)-2-(8-(piperidin-4-yl)-6,6a,7,8,9,10-hexahydro-5H-pyrazino[1',2':4,5]pyrazino[2,3-c]pyridazin-2-yl)phenol | 367.2 | 367.3 |
| Int-14 | 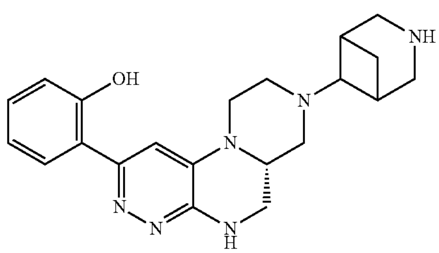 [SMILES: Oc1ccccc1-c1cc2c(nn1)NC[C@H]1CN(C3C4CNCC3C4)CCN21] | 2-(8-(3-azabicyclo[3.1.1]heptan-6-yl)-6,6a,7,8,9,10-hexahydro-5H-pyrazino[1',2':4,5]pyrazino[2,3-c]pyridazin-2-yl)phenol | 379.2 | 379.3 |
| Int-15 | 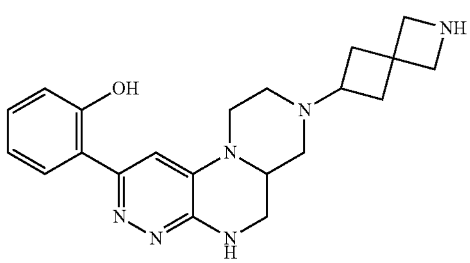 [SMILES: Oc1ccccc1-c1cc2c(nn1)NCC1CN(C3CC4(CNC4)C3)CCN21] | 2-(8-(2-azaspiro[3.3]heptan-6-yl)-6,6a,7,8,9,10-hexahydro-5H-pyrazino[1',2':4,5]pyrazino[2,3-c]pyridazin-2-yl)phenol | 379.2 | 379.2 |
| Int-16 | 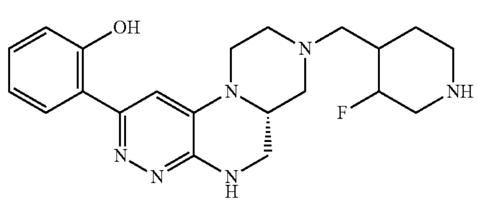 [SMILES: Oc1ccccc1-c1cc2c(nn1)NC[C@H]1CN(CC3CCNCC3F)CCN21] | 2-((6aS)-8-((3-fluoropiperidin-4-yl)methyl)-6,6a,7,8,9,10-hexahydro-5H-pyrazino[1',2':4,5]pyrazino[2,3-c]pyridazin-2-yl)phenol | 399.2 | 399.3 |

-continued

| Int. | Structure | Name | Calcd. (M + H)+ m/z | Found (M + H)+ m/z |
|---|---|---|---|---|
| Int-17 | 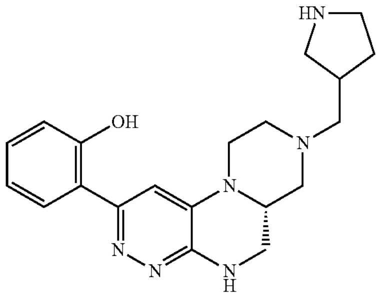 [SMILES: Oc1ccccc1-c1cc2c(nn1)NC[C@H]1CN(CC3CCNC3)CCN21] | 2-((6aS)-8-(pyrrolidin-3-ylmethyl)-6,6a,7,8,9,10-hexahydro-5H-pyrazino[1',2':4,5]pyrazino[2,3-c]pyridazin-2-yl)phenol | 367.2 | 367.2 |
| Int-18 | 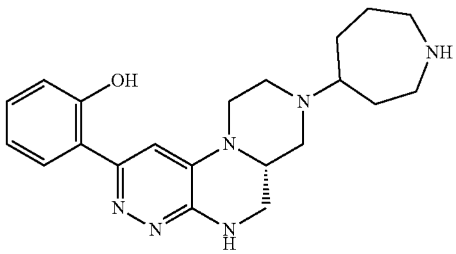 [SMILES: Oc1ccccc1-c1cc2c(nn1)NC[C@H]1CN(C3CCCNCC3)CCN21] | 2-((6aS)-8-(azepan-4-yl)-6,6a,7,8,9,10-hexahydro-5H-pyrazino[1',2':4,5]pyrazino[2,3-c]pyridazin-2-yl)phenol | 381.2 | 381.2 |
| Int-21 | 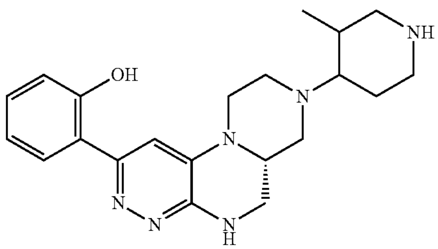 [SMILES: CC1CNCCC1N1CCN2c3cc(-c4ccccc4O)nnc3NC[C@H]2C1] | 2-((6aS)-8-(3-methylpiperidin-4-yl)-6,6a,7,8,9,10-hexahydro-5H-pyrazino[1',2':4,5]pyrazino[2,3-c]pyridazin-2-yl)phenol | 381.2 | 381.2 |
| Int-22 | 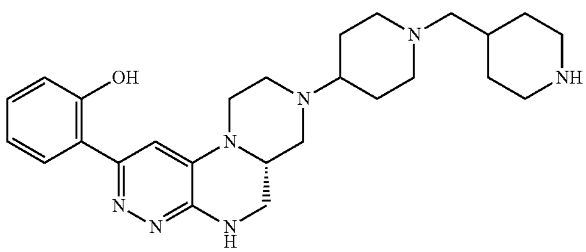 [SMILES: Oc1ccccc1-c1cc2c(nn1)NC[C@H]1CN(C3CCN(CC4CCNCC4)CC3)CCN21] | (S)-2-(8-(1-(piperidin-4-ylmethyl)piperidin-4-yl)-6,6a,7,8,9,10-hexahydro-5H-pyrazino[1',2':4,5]pyrazino[2,3-c]pyridazin-2-yl)phenol | 464.3 | 464.2 |
| Int-25 | Diastereomer 1 | 2-((6aS)-8-(piperidin-3-ylmethyl)-6,6a,7,8,9,10-hexahydro-5H-pyrazino[1',2':4,5]pyrazino[2,3-c]pyridazin-2-yl)phenol | 381.2 | 381.3 |
| Int-26 | Diastereomer 2 | 2-((6aS)-8-(piperidin-3-ylmethyl)-6,6a,7,8,9,10-hexahydro-5H-pyrazino[1',2':4,5]pyrazino[2,3-c]pyridazin-2-yl)phenol | 381.2 | 381.2 |

-continued

| Int. | Structure | Name | Calcd. (M + H)+ m/z | Found (M + H)+ m/z |
|---|---|---|---|---|
| Int-29 | Diastereomer 1 | 2-((6aS)-8-(1-(pyrrolidin-3-yl)piperidin-4-yl)-6,6a,7,8,9,10-hexahydro-5H-pyrazino[1',2':4,5]pyrazino[2,3-c]pyridazin-2-yl)phenol | 436.3 | 436.2 |
| Int-30 | Diastereomer 2 | 2-((6aS)-8-(1-(pyrrolidin-3-yl)piperidin-4-yl)-6,6a,7,8,9,10-hexahydro-5H-pyrazino[1',2':4,5]pyrazino[2,3-c]pyridazin-2-yl)phenol | 436.3 | 436.2 |
| Int-42 | 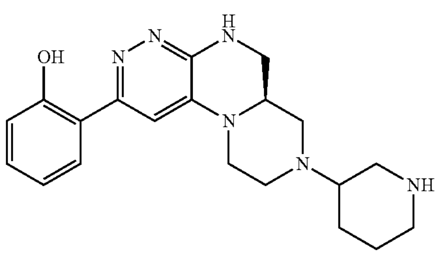 [SMILES: Oc1ccccc1-c1cc2c(nn1)NC[C@H]1CN(C3CCCNC3)CCN21] | 2-((6aS)-8-(piperidin-3-yl)-6,6a,7,8,9,10-hexahydro-5H-pyrazino[1',2':4,5]pyrazino[2,3-c]pyridazin-2-yl)phenol | 367.2 | 367.4 |
| Int-43 | 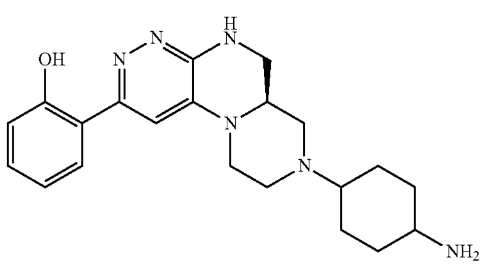 [SMILES: NC1CCC(N2CCN3c4cc(-c5ccccc5O)nnc4NC[C@H]3C2)CC1] | (S)-2-(8-(4-aminocyclohexyl)-6,6a,7,8,9,10-hexahydro-5H-pyrazino[1',2':4,5]pyrazino[2,3-c]pyridazin-2-yl)phenol | 381.2 | 381.4 |
| Int-44 | 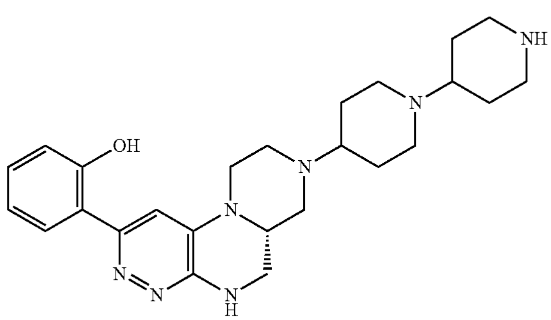 [SMILES: Oc1ccccc1-c1cc2c(nn1)NC[C@H]1CN(C3CCN(C4CCNCC4)CC3)CCN21] | (S)-2-(8-([1,4'-bipiperidin]-4-yl)-6,6a,7,8,9,10-hexahydro-5H-pyrazino[1',2':4,5]pyrazino[2,3-c]pyridazin-2-yl)phenol | 450.3 | 450.3 |

-continued

| Int. | Structure | Name | Calcd. (M + H)+ m/z | Found (M + H)+ m/z |
|---|---|---|---|---|
| Int-46 | (mixture of 2 diastereomers) | 2-((6aS)-8-(pyrrolidin-3-yl)-6,6a,7,8,9,10-hexahydro-5H-pyrazino[1',2':4,5]pyrazino[2,3-c]pyridazin-2-yl)phenol | 353.2 | 353.2 |
| Int-47 | 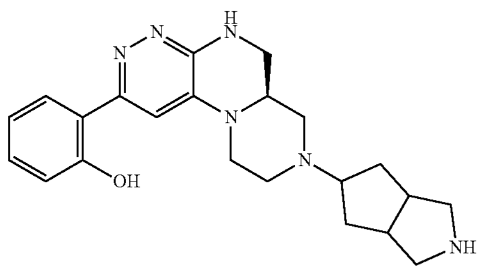 [SMILES: Oc1ccccc1-c1cc2c(nn1)NC[C@H]1CN(C3CC4CNCC4C3)CCN21] | 2-((6aS)-8-(octahydrocyclopenta[c]pyrrol-5-yl)-6,6a,7,8,9,10-hexahydro-5H-pyrazino[1',2':4,5]pyrazino[2,3-c]pyridazin-2-yl)phenol | 393.2 | 393.2 |
| Int-48 | 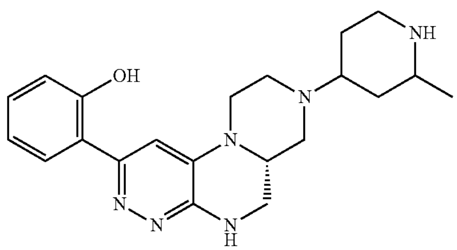 [SMILES: CC1CC(N2CCN3c4cc(-c5ccccc5O)nnc4NC[C@H]3C2)CCN1] | 2-((6aS)-8-(2-methylpiperidin-4-yl)-6,6a,7,8,9,10-hexahydro-5H-pyrazino[1',2':4,5]pyrazino[2,3-c]pyridazin-2-yl)phenol | 381.2 | 381.4 |
| Int-49 | 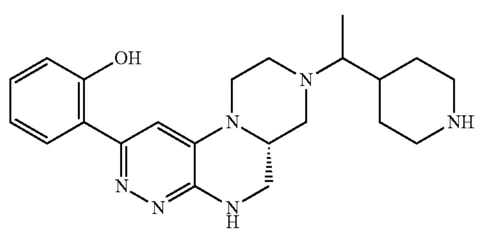 [SMILES: CC(C1CCNCC1)N1CCN2c3cc(-c4ccccc4O)nnc3NC[C@H]2C1] | 2-((6aS)-8-(1-(piperidin-4-yl)ethyl)-6,6a,7,8,9,10-hexahydro-5H-pyrazino[1',2':4,5]pyrazino[2,3-c]pyridazin-2-yl)phenol | 395.3 | 395.3 |
| Int-51 | 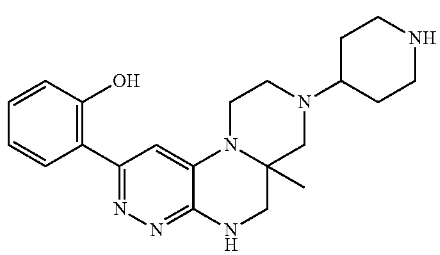 [SMILES: CC12CNc3nnc(-c4ccccc4O)cc3N1CCN(C1CCNCC1)C2] | 2-(6a-methyl-8-(piperidin-4-yl)-6,6a,7,8,9,10-hexahydro-5H-pyrazino[1',2':4,5]pyrazino[2,3-c]pyridazin-2-yl)phenol | 381.2 | 381.3 |
| Int-53 | 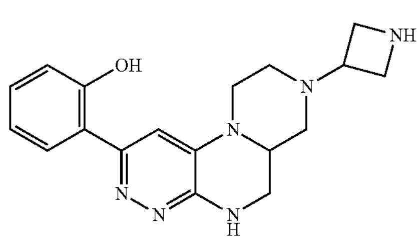 [SMILES: Oc1ccccc1-c1cc2c(nn1)NCC1CN(C3CNC3)CCN21] | 2-(8-(azetidin-3-yl)-6,6a,7,8,9,10-hexahydro-5H-pyrazino[1',2':4,5]pyrazino[2,3-c]pyridazin-2-yl)phenol | 339.2 | 339.2 |

-continued

| Int. | Structure | Name | Calcd. (M + H)+ m/z | Found (M + H)+ m/z |
|---|---|---|---|---|
| Int-54 | 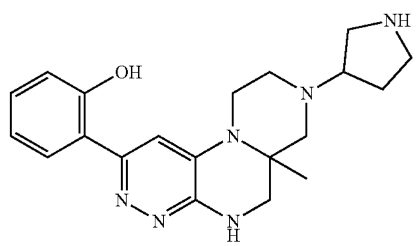 [SMILES: CC12CNc3nnc(-c4ccccc4O)cc3N1CCN(C1CCNC1)C2] | 2-(6a-methyl-8-(pyrrolidin-3-yl)-6,6a,7,8,9,10-hexahydro-5H-pyrazino[1',2':4,5]pyrazino[2,3-c]pyridazin-2-yl)phenol | 367.2 | 367.1 |
| Int-55 | 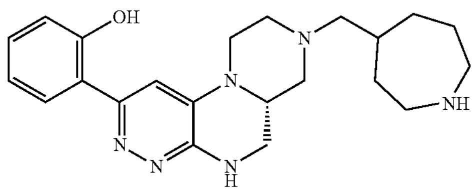 [SMILES: Oc1ccccc1-c1cc2c(nn1)NC[C@H]1CN(CC3CCCNCC3)CCN21] | 2-((6aS)-8-(azepan-4-ylmethyl)-6,6a,7,8,9,10-hexahydro-5H-pyrazino[1',2':4,5]pyrazino[2,3-c]pyridazin-2-yl)phenol | 395.3 | 395.2 |
| Int-56 | 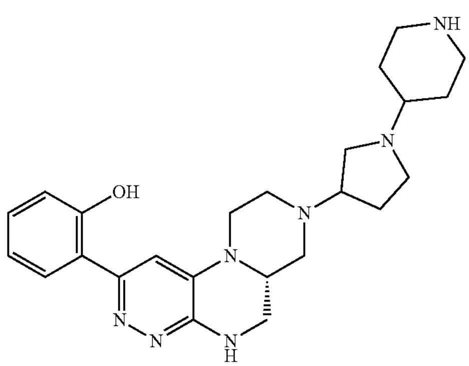 [SMILES: Oc1ccccc1-c1cc2c(nn1)NC[C@H]1CN(C3CCN(C4CCNCC4)C3)CCN21] | 2-((6aS)-8-(1-(piperidin-4-yl)pyrrolidin-3-yl)-6,6a,7,8,9,10-hexahydro-5H-pyrazino[1',2':4,5]pyrazino[2,3-c]pyridazin-2-yl)phenol | 436.3 | 436.3 |
| Int-57 | 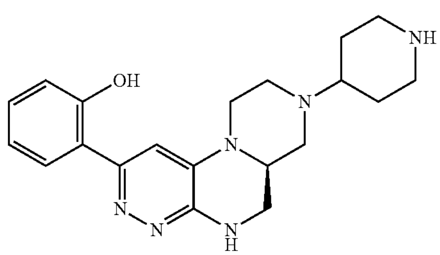 [SMILES: Oc1ccccc1-c1cc2c(nn1)NC[C@@H]1CN(C3CCNCC3)CCN21] | (R)-2-(8-(piperidin-4-yl)-6,6a,7,8,9,10-hexahydro-5H-pyrazino[1',2':4,5]pyrazino[2,3-c]pyridazin-2-yl)phenol | 367.2 | 367.4 |
| Int-58 | 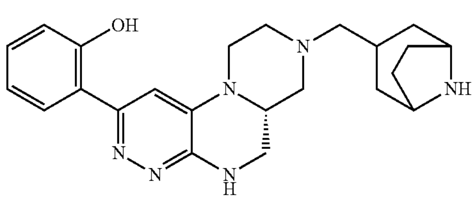 [SMILES: Oc1ccccc1-c1cc2c(nn1)NC[C@H]1CN(CC3CC4CCC(C3)N4)CCN21] | 2-((6aS)-8-((8-azabicyclo[3.2.1]octan-3-yl)methyl)-6,6a,7,8,9,10-hexahydro-5H-pyrazino[1',2':4,5]pyrazino[2,3-c]pyridazin-2-yl)phenol | 407.3 | 407.3 |
| Int-61 | 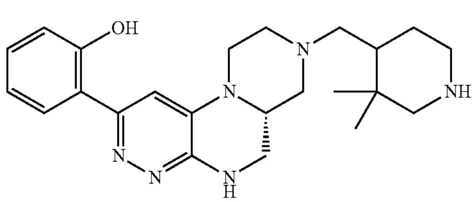 [SMILES: CC1(C)CNCCC1CN1CCN2c3cc(-c4ccccc4O)nnc3NC[C@H]2C1] | 2-((6aS)-8-((3,3-dimethylpiperidin-4-yl)methyl)-6,6a,7,8,9,10-hexahydro-5H-pyrazino[1',2':4,5]pyrazino[2,3-c]pyridazin-2-yl)phenol | 409.3 | 409.3 |

-continued

| Int. | Structure | Name | Calcd. (M + H)+ m/z | Found (M + H)+ m/z |
|---|---|---|---|---|
| Int-63 | 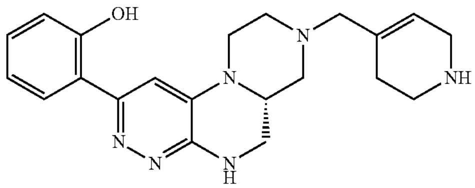 [SMILES: Oc1ccccc1-c1cc2c(nn1)NC[C@H]1CN(CC3=CCNCC3)CCN21] | (S)-2-(8-((1,2,3,6-tetrahydropyridin-4-yl)methyl)-6,6a,7,8,9,10-hexahydro-5H-pyrazino[1',2':4,5]pyrazino[2,3-c]pyridazin-2-yl)phenol | 379.2 | 379.3 |
| Int-66 | 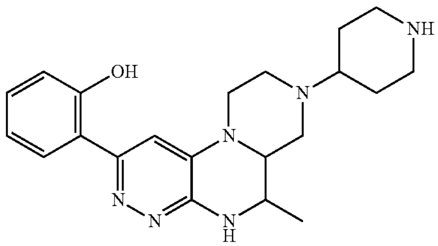 [SMILES: CC1Nc2nnc(-c3ccccc3O)cc2N2CCN(C3CCNCC3)CC12] | 2-(6-methyl-8-(piperidin-4-yl)-6,6a,7,8,9,10-hexahydro-5H-pyrazino[1',2':4,5]pyrazino[2,3-c]pyridazin-2-yl)phenol | 381.2 | 381.2 |
| Int-70 | 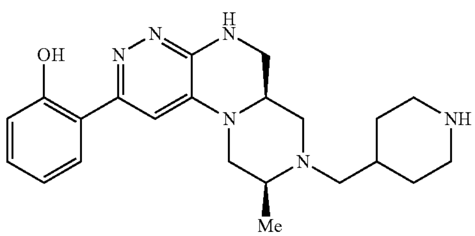 [SMILES: C[C@H]1CN2c3cc(-c4ccccc4O)nnc3NC[C@H]2CN1CC1CCNCC1] | 2-((6aS,9S)-9-methyl-8-(piperidin-4-ylmethyl)-6,6a,7,8,9,10-hexahydro-5H-pyrazino[1',2':4,5]pyrazino[2,3-c]pyridazin-2-yl)phenol | 395.3 | 395.2 |
| Int-71 | 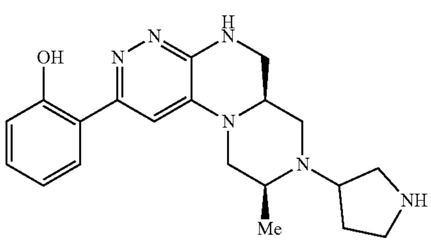 [SMILES: C[C@H]1CN2c3cc(-c4ccccc4O)nnc3NC[C@H]2CN1C1CCNC1] | 2-((6aS,9S)-9-methyl-8-(pyrrolidin-3-yl)-6,6a,7,8,9,10-hexahydro-5H-pyrazino[1',2':4,5]pyrazino[2,3-c]pyridazin-2-yl)phenol | 367.2 | 367.2 |

Intermediate 9: (R)-2-(6,6a,7,8,9,10-hexahydro-5H-pyrazino[1',2':4,5]pyrazino[2,3-c]pyridazin-2-yl)phenol (Int-9)

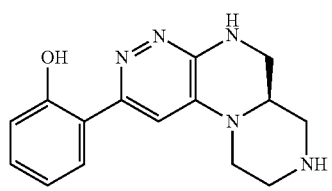

Int-9

Step 1: Synthesis of tert-butyl (R)-4-(3,6-dichloropyridazin-4-yl)-3-(hydroxymethyl)piperazine-1-carboxylate

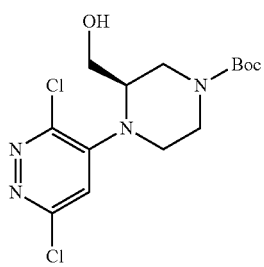 [SMILES: CC(C)(C)OC(=O)N1CCN(c2cc(Cl)nnc2Cl)[C@@H](CO)C1]

To a solution of 3,4,6-trichloropyridazine (5.7 g, 31.1 mmol) in DMF (24 mL) was added N,N-diisopropylethylamine (5.9 mL, 34.2 mmol) and tert-butyl (R)-3-(hydroxymethyl) piperazine-1-carboxylate (7.1 g, 32.8 mmol). The reaction was stirred at 80° C. overnight. The reaction was cooled to 45° C. and water (17 mL) was added slowly. The resulted clear solution was stirred at 35° C. for 30 min until precipitate formed. Another portion of water (23 mL) was charged slowly and the mixture was stirred at 0° C. for an additional 1 h. The mixture was filtered and the resulting solid was washed with water and dried under vacuum to give tert-butyl (R)-4-(3,6-dichloropyridazin-4-yl)-3-(hydroxymethyl)piperazine-1-carboxylate (8.5 g, 75% yield) as an off-white solid. LCMS m/z calcd for $C_{14}H_{21}Cl_2N_4O_3$ [M+H]$^+$: 363.1; found: 363.1.

Step 2: Synthesis of tert-butyl (R)-3-(azidomethyl)-4-(3,6-dichloropyridazin-4-yl)piperazine-1-carboxylate

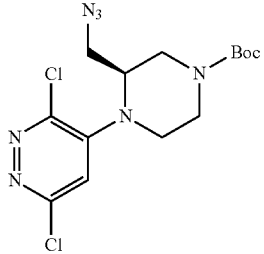 [SMILES: CC(C)(C)OC(=O)N1CCN(c2cc(Cl)nnc2Cl)[C@@H](CN=[N+]=[N-])C1]

To a solution of tert-butyl (R)-4-(3,6-dichloropyridazin-4-yl)-3-(hydroxymethyl) piperazine-1-carboxylate (5.45 g, 15 mmol) and triphenylphosphine (4.7 g, 18 mmol) in THF (150 mL) was added diisopropyl azodicarboxylate (3.5 mL, 18 mmol) and DPPA (3.9 mL, 18 mmol) at 0° C. The reaction was then stirred at RT overnight. The reaction mixture was cooled to 0° C., quenched with water and extracted with EtOAc. The combined organic layers were washed with brine and water, dried over $Na_2SO_4$ and filtered. The filtrate was concentrated under reduced pressure to give crude tert-butyl (R)-3-(azidomethyl)-4-(3,6-dichloropyridazin-4-yl)piperazine-1-carboxylate (19.4 g, 100% yield), which was used without further purification. Assumed 100% yield, 30% purity. LCMS m/z calcd for $C_{14}H_{20}Cl_2N_7O_2$ [M+H]$^+$: 388.1; found: 388.0.

Step 3: Synthesis of tert-butyl (S)-2-chloro-5,6,6a,7,9,10-hexahydro-8H-pyrazino[1',2':4,5]pyrazino[2,3-c]pyridazine-8-carboxylate

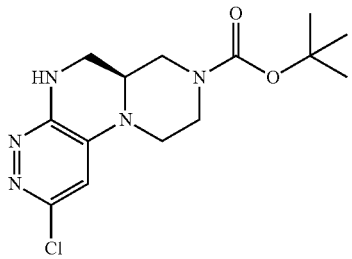 [SMILES: CC(C)(C)OC(=O)N1CCN2c3cc(Cl)nnc3NC[C@H]2C1]

To a stirred solution of crude tert-butyl (R)-3-(azidomethyl)-4-(3,6-dichloropyridazin-4-yl) piperazine-1-carboxylate (30% purity, 20.3 g, 15.7 mmol) in THF (200 mL), triphenylphosphine (4.9 g, 18.8 mmol) was added. The resulted solution was stirred at 60° C. for 3 h. Water (20 mL) and N,N-diisopropylethylamine (8.2 mL, 47.1 mmol) were added sequentially. After 20 h, the reaction mixture was diluted with EtOAc (100 mL) and water (100 mL). The aqueous layer was separated and extracted with EtOAc. The combined organic layers were washed with brine, dried over $Na_2SO_4$ and filtered. The filtrate was concentrated under reduced pressure. The residue was purified by silica gel chromatography, eluting with 0-100% EtOAc/hexanes to give tert-butyl (S)-2-chloro-5,6,6a,7,9,10-hexahydro-8H-pyrazino[1',2':4,5]pyrazino[2,3-c]pyridazine-8-carboxylate (3.1 g, 60% yield) as an off-white solid. LCMS m/z calcd for $C_{14}H_{21}ClN_5O_2$ [M+H]$^+$: 326.1; found: 326.2.

Step 4: Synthesis of di-tert-butyl (R)-2-chloro-6a,7,9,10-tetrahydro-5H-pyrazino[1',2':4,5]pyrazino[2,3-c]pyridazine-5,8(6H)-dicarboxylate

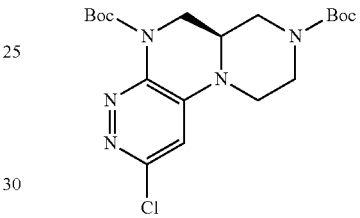

To a stirred solution of tert-butyl (S)-2-chloro-5,6,6a,7,9,10-hexahydro-8H-pyrazino[1',2':4,5]pyrazino[2,3-c]pyridazine-8-carboxylate (3.1 g, 9.5 mmol) in DCM (120 mL), di-tert butyl dicarbonate (6.2 g, 28.6 mmol) and 4-(dimethylamino)pyridine (1.2 g, 9.5 mmol) were added at RT. After 1 h, the reaction was diluted with DCM (120 mL) and sat. aq. NH$_4$Cl (50 mL). After another 1 h, the aqueous layer was separated and extracted with DCM. The organic layers were combined, washed with brine, dried over $Na_2SO_4$ and filtered. The filtrate was concentrated under reduced pressure. The residue was purified by silica gel chromatography, eluting with 50% EtOAc/hexanes to give di-tert-butyl (R)-2-chloro-6a,7,9,10-tetrahydro-5H-pyrazino[1',2':4,5]pyrazino[2,3-c]pyridazine-5,8(6H)-dicarboxylate (3.9 g, 96% yield). LCMS m/z calcd for $C_{19}H_{29}ClN_5O_4$ [M+H]$^+$: 426.2; found: 426.3.

Step 5: Synthesis of di-tert-butyl (R)-2-(2-hydroxyphenyl)-6a,7,9,10-tetrahydro-5H-pyrazino[1',2':4,5]pyrazino[2,3-c]pyridazine-5,8(6H)-dicarboxylate

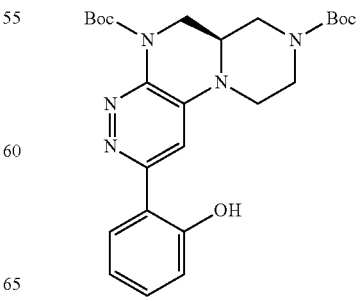

To a solution of di-tert-butyl (R)-2-chloro-6a,7,9,10-tetrahydro-5H-pyrazino[1',2':4,5]pyrazino[2,3-c]pyridazine-5,8(6H)-dicarboxylate and 2-hydroxyphenyl boronic acid (1.9 g, 14.1 mmol) in 1,4-dioxane (110 mL) was added potassium carbonate (3.89 g, 28.2 mmol) and [1,1'-bis(diphenylphosphino)ferrocene]dichloropalladium(II), complex with dichloromethane (0.58 g, 0.70 mmol) at RT. The mixture was stirred at 105° C. for 18 h. The reaction was concentrated and the residue was purified by flash chromatography (SiO₂, 200-300 mesh, EtOAc/hexanes=2/1) to give di-tert-butyl (R)-2-(2-hydroxyphenyl)-6a,7,9,10-tetrahydro-5H-pyrazino[1',2':4,5]pyrazino [2,3-c]pyridazine-5,8(6H)-dicarboxylate (2.6 g, 5.4 mmol, 76.% yield) as a white solid. LCMS m/z calcd for $C_{25}H_{34}N_5O_5$ [M+H]⁺: 484.3; found: 484.3.

Step 6: Synthesis of (R)-2-(6,6a,7,8,9,10-hexahydro-5H-pyrazino[1',2':4,5]pyrazino[2,3-c]pyridazin-2-yl)phenol To a stirred solution of di-tert-butyl (R)-2-(2-hydroxyphenyl)-6a,7,9,10-tetrahydro-5H-pyrazino[1',2':4,5]pyrazino[2,3-c]pyridazine-5,8(6H)-dicarboxylate (1.3 g, 2.7 mmol) in DCM (10 mL), 2,2,2-trifluoroacetic acid (4.1 mL) was added at RT. After 1 h, the reaction mixture was concentrated to dryness under reduced pressure. The residue was dissolved in MeOH/DCM (1/6, 400 mL) and saturated aqueous NaHCO₃ (80 mL) was added. The resulted mixture was stirred at 30° C. for 30 min. The aqueous layer was separated and extracted with MeOH/DCM (1/6, 80 mL×4). The combined organic layers were washed with brine, dried over Na₂SO₄ and filtered. The filtrate was concentrated under reduced pressure to give crude (R)-2-(6,6a,7,8,9,10-hexahydro-5H-pyrazino[1',2':4,5]pyrazino[2,3-c]pyridazin-2-yl)phenol (700 mg, 92% yield) as a beige solid. LCMS m/z calcd for $C_{15}H_{18}N_5O$ [M+H]⁺: 284.2; found: 284.1. ¹H NMR (400 MHz, DMSO-d₆) δ 4.8 (s, 1H), 7.91 (s, 1H), 7.30 (s, 1H), 7.19 (s, 2H), 6.83-6.86 (m, 2H), 3.92-3.94 (m, 1H), 3.40-3.44 (m, 1H), 3.13-3.15 (m, 2H), 3.00-3.11 (m, 2H), 2.66-2.76 (m, 2H), 2.45-2.50 (m, 1H), 2.28-2.33 (m, 1H).

Intermediate 9a. (S)-2-(6,6a,7,8,9,10-hexahydro-5H-pyrazino[1',2':4,5]pyrazino[2,3-c]pyridazin-2-yl)phenol

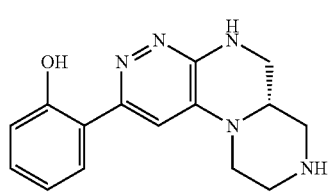

Int-9a

The title compound was prepared using procedure analogous to those described for Int-9, using appropriate starting materials. LCMS m/z calcd for $C_{15}H_{18}N_5O$ [M+H]⁺: 284.2; found: 284.2.

Intermediate 12. (3R,5S)-1-((R)-2-(3-(2-bromoethoxy)isoxazol-5-yl)-3-methylbutanoyl)-5-(((S)-1-(4-(4-methylthiazol-5-yl)phenyl)ethyl)carbamoyl)pyrrolidin-3-yl acetate

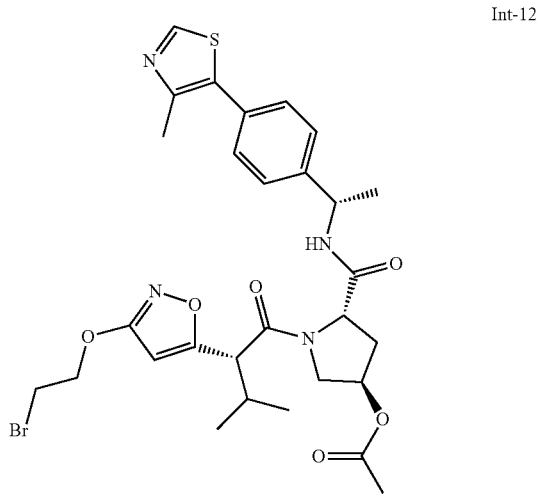 [SMILES: CC(=O)O[C@@H]1C[C@@H](C(=O)N[C@@H](C)c2ccc(-c3scnc3C)cc2)N(C(=O)[C@@H](c2cc(OCCBr)no2)C(C)C)C1]

Int-12

Step 1: (2S,4R)-1-((R)-2-(3-(2-bromoethoxy)isoxazol-5-yl)-3-methylbutanoyl)-4-hydroxy-N—((S)-1-(4-(4-methylthiazol-5-yl)phenyl)ethyl)pyrrolidine-2-carboxamide

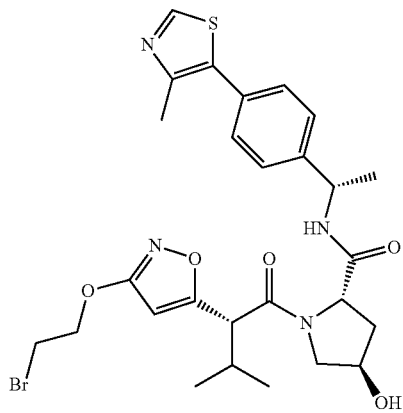 [SMILES: Cc1ncsc1-c1ccc([C@H](C)NC(=O)[C@@H]2C[C@@H](O)CN2C(=O)[C@@H](c2cc(OCCBr)no2)C(C)C)cc1]

To a solution of (2S,4R)-1-((R)-2-(3-(2-bromoethoxy)isoxazol-5-yl)-3-methylbutanoyl)-4-((tert-butyldimethylsilyl)oxy)-N—((S)-1-(4-(4-methylthiazol-5-yl)phenyl)ethyl)pyrrolidine-2-carboxamide (Int-4)(100 mg, 0.14 mmol) in THF (5 mL) were added TBAF in THF (0.1 mL, 7.3 mmol) the mixture solution was stirred at rt for 2 h. The reaction was diluted with EA (20 ml) and washed with brine (30 mL×2), the organic layer was concentrated to give the crude product, which was used in the next step without further purification. LCMS m/z calcd for $C_{27}H_{34}BrN_4O_5S$ [M+H]⁺: 605.1; Found: 605.1.

Step 2: (3R,5S)-1-((R)-2-(3-(2-bromoethoxy)isoxazol-5-yl)-3-methylbutanoyl)-5-(S)-1-(4-(4-methylthiazol-5-yl)phenyl)ethyl)carbamoyl)pyrrolidin-3-yl acetate To a solution of (2S,4R)-1-((R)-2-(3-(2-bromoethoxy)isoxazol-5-yl)-3-methylbutanoyl)-4-hydroxy-N—((S)-1-(4-(4-methylthiazol-5-yl)phenyl)ethyl)pyrrolidine-2-carboxamide (45 mg, 0.07 mmol) in DCM (5 mL) were added DMAP (48.0 mg, 0.37 mmol) and acetic anhydride (37.9 mg, 0.37 mmol), the mixture solution was stirred at rt for 16 h.

The reaction mixture was diluted with EtOAc (20 mL) and the organic layer washed with water (2×10 mL) then saturated brine (1×10 mL). The organic layer was separated, dried over MgSO₄, and filtered. The filtration was concentrated to dryness under reduced pressure. The residue was purified by prep-TLC (PE:EA=1:1) to get (3R,5S)-1-((R)-2-(3-(2-bromoethoxy)isoxazol-5-yl)-3-methylbutanoyl)-5-(((S)-1-(4-(4-methylthiazol-5-yl)phenyl)ethyl)carbamoyl)pyrrolidin-3-yl acetate (40 mg, 0.06 mmol, 83% yield). LCMS m/z calcd for $C_{29}H_{36}BrN_4O_6S$ [M+H]⁺: 647.1; Found: 647.1.

Intermediate 13. (3R,5S)-1-((R)-2-(3-(2-bromoethoxy)isoxazol-5-yl)-3-methylbutanoyl)-5-(((S)-1-(4-(4-methylthiazol-5-yl)phenyl)ethyl)carbamoyl)pyrrolidin-3-yl isobutyrate

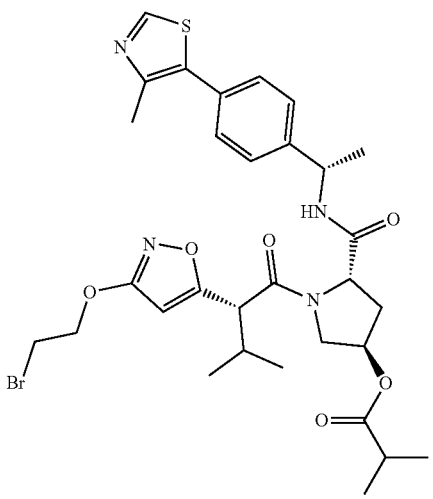

Int-13

The title compound was prepared using procedure analogous to those described for Int-12, with isobutyric anhydride replacing acetic anhydride in step 2. LCMS m/z calcd for $C_{31}H_{40}BrN_4O_6S$ [M+H]⁺: 675.2; Found: 675.2.

Intermediate 19. 2-((6aS)-8-(pyrrolidin-3-yl)-6,6a,7,8,9,10-hexahydro-5H-pyrazino[1',2':4,5]pyrazino[2,3-c]pyridazin-2-yl)phenol (diastereomer 1)

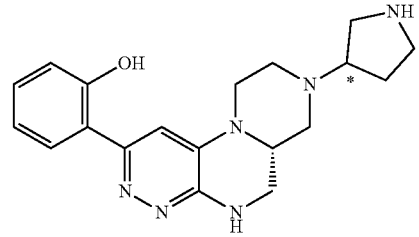

Int-19

Step 1: tert-butyl 3-((S)-2-(2-hydroxyphenyl)-5,6,6a,7,9,10-hexahydro-8H-pyrazino[1',2':4,5]pyrazino[2,3-c]pyridazin-8-yl)pyrrolidine-1-carboxylate (mixture of 2 diastereomers)

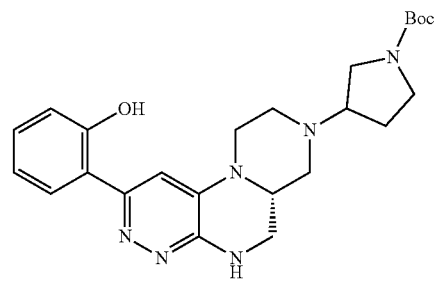 [SMILES: CC(C)(C)OC(=O)N1CCC(N2CCN3c4cc(-c5ccccc5O)nnc4NC[C@H]3C2)C1]

The title compound was prepared using procedure analogous to those described for Int-8, step a with appropriate starting materials. LCMS m/z calcd for $C_{24}H_{33}N_6O_3$ [M+H]⁺: 453.3; Found: 453.3.

Step 2: tert-butyl 3-((S)-2-(2-hydroxyphenyl)-5,6,6a,7,9,10-hexahydro-8H-pyrazino[1',2':4,5]pyrazino[2,3-c]pyridazin-8-yl)pyrrolidine-1-carboxylate (diastereomer 1)

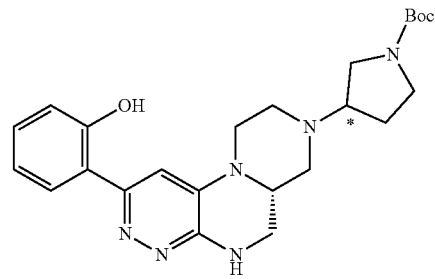 [SMILES: CC(C)(C)OC(=O)N1CCC(N2CCN3c4cc(-c5ccccc5O)nnc4NC[C@H]3C2)C1]

46.8 g of tert-butyl 3-((S)-2-(2-hydroxyphenyl)-5,6,6a,7,9,10-hexahydro-8H-pyrazino[1',2':4,5]pyrazino[2,3-c]pyridazin-8-yl)pyrrolidine-1-carboxylate (mixture of 2 diastereomers) was purified on chiral supercritical fluid chromatography using the following conditions: column: DAICELCHIRALPAK®OJ (250*25 mm 10 µm); mobile phase: 50% EtOH/CO$_2$; pressure: 100 bar; flow rate: 70 g/min; UV: 214 nM; injection: 3.0 mL, 58.5 mg/mL MeOH. 22 g tert-butyl 3-((S)-2-(2-hydroxyphenyl)-5,6,6a,7,9,10-hexahydro-8H-pyrazino[1',2':4,5]pyrazino[2,3-c]pyridazin-8-yl)pyrrolidine-1-carboxylate (diastereomer 1, t$_r$=3.0 min) was afforded. LCMS m/z calcd for C$_{24}$H$_{33}$N$_6$O$_3$[M+H]$^+$: 453.3; Found: 453.2. 18 g tert-butyl 3-((S)-2-(2-hydroxyphenyl)-5,6,6a,7,9,10-hexahydro-8H-pyrazino[1',2':4,5]pyrazino[2,3-c]pyridazin-8-yl)pyrrolidine-1-carboxylate (diastereomer 2, t$_r$=4.5 min) was afforded. LCMS m/z calcd for C$_{24}$H$_{33}$N$_6$O$_3$ [M+H]$^+$: 453.3; Found: 453.3.

Step 3: 2-((6aS)-8-(pyrrolidin-3-yl)-6,6a,7,8,9,10-hexahydro-5H-pyrazino[1',2':4,5]pyrazino[2,3-c]pyridazin-2-yl)phenol (diastereomer 1)

To a stirred solution of tert-butyl 3-((S)-2-(2-hydroxyphenyl)-5,6,6a,7,9,10-hexahydro-8H-pyrazino[1',2':4,5]pyrazino[2,3-c]pyridazin-8-yl)pyrrolidine-1-carboxylate (diastereomer 1, 2.0 g, 4.4 mmol) in DCM (10 mL) was added TFA (1.0 mL) at rt. After 16 h, the volatiles were removed under reduced pressure and the residue was used for next step without further purification. LCMS m/z calcd for C$_{19}$H$_{25}$N$_6$O [M+H]$^+$: 353.2; Found: 353.0.

Intermediate 20. 2-((6aS)-8-(pyrrolidin-3-yl)-6,6a,7,8,9,10-hexahydro-5H-pyrazino[1',2':4,5]pyrazino[2,3-c]pyridazin-2-yl)phenol (diastereomer 2)

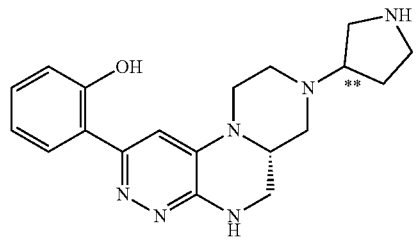
Int-20

To a stirred solution of tert-butyl 3-((S)-2-(2-hydroxyphenyl)-5,6,6a,7,9,10-hexahydro-8H-pyrazino[1',2':4,5]pyrazino[2,3-c]pyridazin-8-yl)pyrrolidine-1-carboxylate (diastereomer 2 from the synthesis of Int-19, step 2, 2.0 g, 4.42 mmol) in DCM (10 mL) was added TFA (1 mL) at rt. After 16 h, the volatiles were removed under reduced pressure and the residue was used for next step without further purification. LCMS m/z calcd for C$_{19}$H$_{25}$N$_6$O [M+H]$^+$: 353.2; Found: 353.1.

Intermediate 23. (S)-2-(8-(1-(2-(piperazin-1-yl)ethyl)piperidin-4-yl)-6,6a,7,8,9,10-hexahydro-5H-pyrazino[1',2':4,5]pyrazino[2,3-c]pyridazin-2-yl)phenol

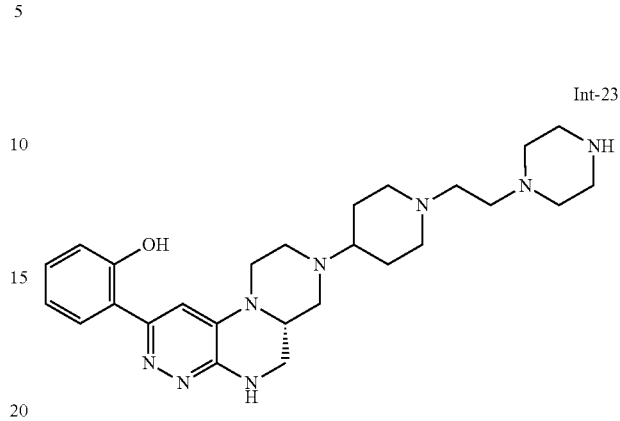
Int-23

Step 1: tert-butyl (S)-4-(2-(4-(2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)piperazine-1-carboxylate

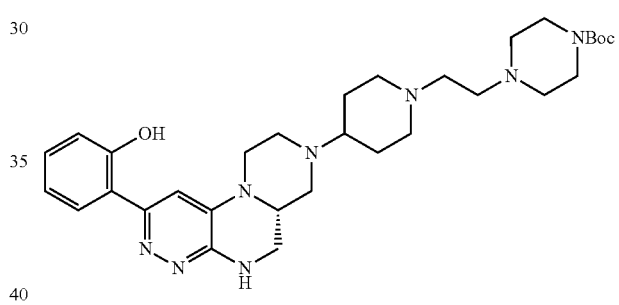

To a solution of Int-11 (30 mg, 0.08 mmol) and tert-butyl 4-(2-bromoethyl)piperazine-1-carboxylate (40 mg, 0.14 mmol) in DMF (30 mL) was added NaHCO$_3$ (13.8 mg, 0.40 mmol) at rt. The mixture was stirred at 65° C. for 48 h. The reaction mixture was concentrated and purified by prep-TLC (MeOH:DCM=1:10) to give tert-butyl (S)-4-(2-(4-(2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)piperazine-1-carboxylate (40 mg, 0.069 mmol, 84% yield) as a yellow solid. LCMS m/z calcd for C$_{31}$H$_{47}$N$_8$O$_3$[M+H]$^+$: 579.4; Found: 579.2.

Step 2: (S)-2-(8-(1-(2-(piperazin-1-yl)ethyl)piperidin-4-yl)-6,6a,7,8,9,10-hexahydro-5H-pyrazino[1',2':4,5]pyrazino[2,3-c]pyridazin-2-yl)phenol To a solution of tert-butyl (S)-4-(2-(4-(2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)piperazine-1-carboxylate (40 mg, 0.07 mmol) in DCM (1 mL) was added TFA (0.03 mL, 0.16 mmol) at rt. The mixture was stirred at rt for 16 h. The volatiles were removed in vacuum and the residue was used for next step without further purification. LCMS m/z calcd for C$_{26}$H$_{39}$N$_8$O [M+H]$^+$: 479.3; Found: 479.2.

Intermediate 24. (S)-2-(8-(1-(2-(piperidin-4-yl)ethyl)piperidin-4-yl)-6,6a,7,8,9,10-hexahydro-5H-pyrazino[1',2':4,5]pyrazino[2,3-c]pyridazin-2-yl)phenol

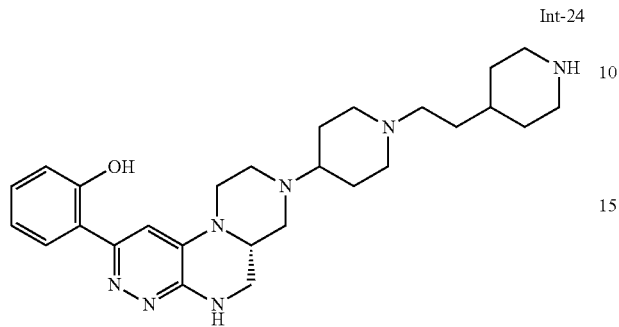

Int-24

Step 1: tert-butyl (S)-4-(2-(4-(2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)piperidine-1-carboxylate

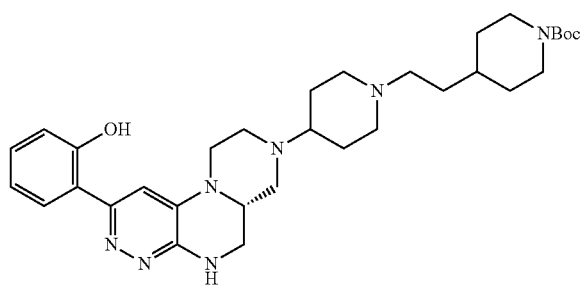 [SMILES: CC(C)(C)OC(=O)N1CCC(CCN2CCC(N3CCN4c5cc(-c6ccccc6O)nnc5NC[C@H]4C3)CC2)CC1]

To a solution of Int-11 (30.0 mg, 0.08 mmol) and tert-butyl 4-(2-oxoethyl)piperidine-1-carboxylate (27.91 mg, 0.12 mmol) in DCM (30 mL) was added NaBH(OAc)$_3$ (34 mg, 0.16 mmol) at rt. The mixture was stirred at rt for 16 h. The volatiles were removed in vacuum and the residue was purified by prep-TLC (MeOH:DCM=1:10) to give tert-butyl (S)-4-(2-(4-(2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)piperidine-1-carboxylate (30.0 mg, 0.051 mmol, 63.4% yield) as a yellow solid. LCMS m/z calcd for $C_{32}H_{48}N_7O_3[M+H]^+$: 578.4; Found: 578.1.

Step 2: (S)-2-(8-(1-(2-(piperidin-4-yl)ethyl)piperidin-4-yl)-6,6a,7,8,9,10-hexahydro-5H-pyrazino[1',2':4,5]pyrazino[2,3-c]pyridazin-2-yl)phenol To a solution of tert-butyl (S)-4-(2-(4-(2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)piperidine-1-carboxylate (40.0 mg, 0.07 mmol) in DCM (30 mL) was added TFA (0.3 mL) at rt. The mixture was stirred at rt for 16 h. LCMS showed the reaction was completed. The volatiles were removed in vacuum and the residue was used for next step without further purification. LCMS m/z calcd for $C_{27}H_{40}N_7O$ [M+H]$^+$: 478.3; Found: 478.2.

Intermediate 27. (2S,4R)-4-((tert-butyldimethylsilyl)oxy)-1-((R)-2-(3-hydroxyisoxazol-5-yl)-3-methylbutanoyl)-N—((S)-1-(4-(4-methylthiazol-5-yl)phenyl)ethyl)pyrrolidine-2-carboxamide

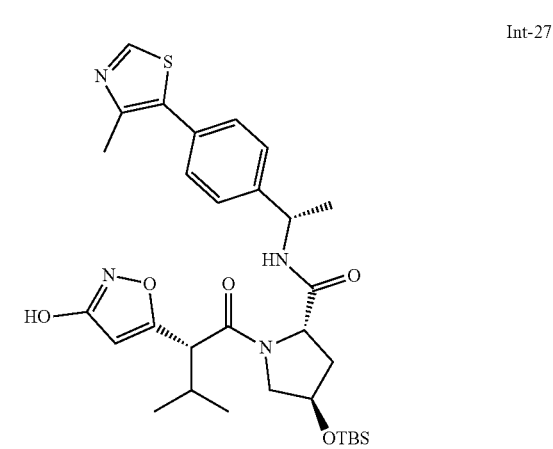 [SMILES: Cc1ncsc1-c1ccc([C@H](C)NC(=O)[C@@H]2C[C@@H](O[Si](C)(C)C(C)(C)C)CN2C(=O)[C@@H](c2cc(O)no2)C(C)C)cc1]

Int-27

23 g of (2S,4R)-4-((tert-butyldimethylsilyl)oxy)-1-(2-(3-hydroxyisoxazol-5-yl)-3-methylbutanoyl)-N—((S)-1-(4-(4-methylthiazol-5-yl)phenyl)ethyl)pyrrolidine-2-carboxamide was purified on chiral supercritical fluid chromatography using the following conditions: column: DAICEL CHIRALPAK® Whelk (250*25 mm 10 μm); mobile phase: 50% IPA/CO$_2$; pressure: 100 bar; flow rate: 70 g/min; UV: 214 nM; injection: 2.5 mL, 76.7 mg/mL in MeOH, 10.7 g (peak 1, t$_r$=5.0 min) (2S,4R)-4-((tert-butyldimethylsilyl)oxy)-1-((R)-2-(3-hydroxyisoxazol-5-yl)-3-methylbutanoyl)-N—((S)-1-(4-(4-methylthiazol-5-yl)phenyl)ethyl)pyrrolidine-2-carboxamide was afforded. LCMS m/z calcd for $C_{31}H_{45}N_4O_5SSi$ [M+H]$^+$: 613.3; Found: 613.3.

Intermediate 28. (S)-2-((5-((R)-1-((2S,4R)-4-((tert-butyldimethylsilyl)oxy)-2-(((S)-1-(4-(4-methylthiazol-5-yl)phenyl)ethyl)carbamoyl)pyrrolidin-1-yl)-3-methyl-1-oxobutan-2-yl)isoxazol-3-yl)oxy)propanoic acid

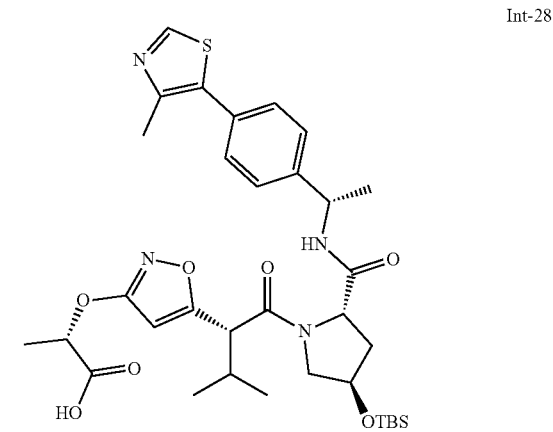 [SMILES: Cc1ncsc1-c1ccc([C@H](C)NC(=O)[C@@H]2C[C@@H](O[Si](C)(C)C(C)(C)C)CN2C(=O)[C@@H](c2cc(O[C@@H](C)C(=O)O)no2)C(C)C)cc1]

Int-28

137

Step 1: methyl (S)-2-((5-((R)-1-((2S,4R)-4-((tert-butyldimethylsilyl)oxy)-2-(((S)-1-(4-(4-methylthiazol-5-yl)phenyl)ethyl)carbamoyl)pyrrolidin-1-yl)-3-methyl-1-oxobutan-2-yl)isoxazol-3-yl)oxy)propanoate

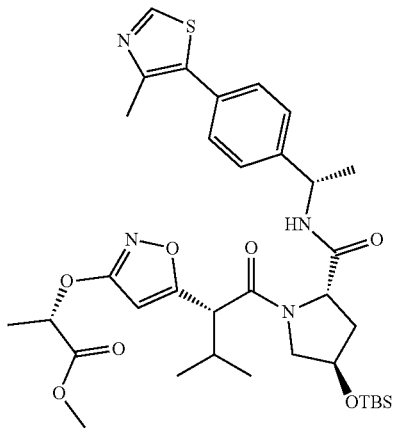 [SMILES: COC(=O)[C@H](C)Oc1cc([C@H](C(=O)N2C[C@H](O[Si](C)(C)C(C)(C)C)C[C@H]2C(=O)N[C@@H](C)c2ccc(-c3scnc3C)cc2)C(C)C)on1]

To a stirred mixture of methyl (2R)-2-hydroxypropanoate (67.9 mg, 0.65 mmol), (2S,4R)-4-((tert-butyldimethylsilyl)oxy)-1-4R)-2-(3-hydroxyisoxazol-5-yl)-3-methylbutanoyl)-N—((S)-1-(4-(4-methylthiazol-5-yl)phenyl)ethyl)pyrrolidine-2-carboxamide (200 mg, 0.33 mmol) and PPh$_3$ (171 mg, 0.65 mmol) in THF (10 mL), DIAD (0.12 mL, 0.65 mmol) was added at 0° C. After 1 h, the reaction mixture was warmed up to rt. After another 16 h, the volatiles were removed under reduced pressure and the residue was purified by prep-HPLC (eluting with CH$_3$CN in H$_2$O: (0.1% NH$_4$HCO$_3$) from 10% to 95%) to give methyl (S)-2-((5-((R)-1-((2S,4R)-4-((tert-butyldimethylsilyl)oxy)-2-(((S)-1-(4-(4-methylthiazol-5-yl)phenyl)ethyl)carbamoyl)pyrrolidin-1-yl)-3-methyl-1-oxobutan-2-yl)isoxazol-3-yl)oxy)propanoate (180 mg, 0.25 mmol, 77.3% yield) as a white solid. LCMS m/z calcd for C$_{35}$H$_{51}$N$_4$O$_7$SSi [M+H]$^+$: 699.3; Found: 699.3.

Step 2: (S)-2-((5-((R)-1-((2S,4R)-4-((tert-butyldimethylsilyl)oxy)-2-(((S)-1-(4-(4-methylthiazol-5-yl)phenyl)ethyl)carbamoyl)pyrrolidin-1-yl)-3-methyl-1-oxobutan-2-yl)isoxazol-3-yl)oxy)propanoic Acid A mixture of LiOH (31 mg, 1.29 mmol) and (S)-2-((5-((R)-1-((2S,4R)-4-((tert-butyldimethylsilyl)oxy)-2-(((S)-1-(4-(4-methylthiazol-5-yl)phenyl)ethyl)carbamoyl)pyrrolidin-1-yl)-3-methyl-1-oxobutan-2-yl)isoxazol-3-yl)oxy)propanoate (180 mg, 0.26 mmol) in THF (5 mL) and water (5 mL) was stirred at 0° C. for 2 h. The volatiles were removed under reduced pressure and the residue was purified by prep-HPLC (eluting with CH$_3$CN in H$_2$O: (0.1% NH$_4$HCO$_3$) from 10% to 95%) to give (S)-2-((5-((R)-1-((2S, 4R)-4-((tert-butyldimethylsilyl)oxy)-2-(((S)-1-(4-(4-methylthiazol-5-yl)phenyl)ethyl)carbamoyl)pyrrolidin-1-yl)-3-methyl-1-oxobutan-2-yl)isoxazol-3-yl)oxy)propanoic acid (150 mg, 0.21 mmol, 83.4% yield) as a white solid. LCMS m/z calcd for C$_{34}$H$_{49}$N$_4$O$_7$SSi [M+H]$^+$: 685.3; Found: 685.3.

138

Intermediate 31. 2-(6a-methyl-6,6a,7,8,9,10-hexahydro-5H-pyrazino[1',2':4,5]pyrazino[2,3-c]pyridazin-2-yl)phenol

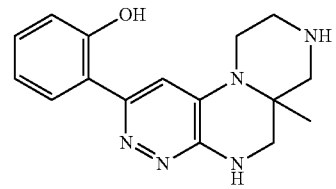

Int-31

Step 1: 1,4-di-tert-butyl 2-methyl piperazine-1,2,4-tricarboxylate

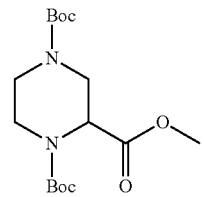 [SMILES: COC(=O)C1CN(C(=O)OC(C)(C)C)CCN1C(=O)OC(C)(C)C]

To a solution of 1,4-bis(tert-butoxycarbonyl)piperazine-2-carboxylic acid (5.0 g, 15.1 mmol) and potassium carbonate (4.18 g, 30.3 mmol) in acetone (50 mL) was added iodomethane (2.17 g, 15.3 mmol) at rt. The mixture was stirred at rt for 16 h. The reaction mixture was filtered and the filtrate was concentrated in vacuum. The residue was dissolved in EA (100 ml) and washed with brine (100 mL×2). The organic layer was concentrated in vacuum to give 1,4-di-tert-butyl 2-methyl piperazine-1,2,4-tricarboxylate (5.2 g, 15.1 mmol, 99.7% yield) as a white solid. LCMS calc'd for C$_{16}$H$_{29}$N$_2$O$_6$[M+H]$^+$: 345.2; Found: 345.2.

Step 2: 1,4-di-tert-butyl 2-methyl 2-methylpiperazine-1,2,4-tricarboxylate

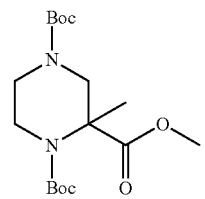 [SMILES: COC(=O)C1(C)CN(C(=O)OC(C)(C)C)CCN1C(=O)OC(C)(C)C]

To a solution of 1,4-di-tert-butyl 2-methyl piperazine-1, 2,4-tricarboxylate (5.2 g, 15.1 mmol) in THF (100 mL) was added LiHMDS (2.8 g, 16.6 mmol) at −78° C. The mixture was stirred at −78° C. for 2 h then iodomethane (6.4 g, 45.3 mmol) was added at −78° C. The resulted mixture was stirred at rt. for 16 h. The reaction was quenched with saturated aqueous NH$_4$Cl (100 ml) at 0° C., diluted with EA (200 ml), and washed with water (2×100 mL) then brine (50 ml). The organic layer was dried (MgSO$_4$), filtered, and the filtrate was concentrated to dryness. The crude was purified by silica gel column chromatography (100-200 mesh size), eluted with PE:EA=3:1 to 1:1 to give 1,4-di-tert-butyl 2-methyl 2-methylpiperazine-1,2,4-tricarboxylate (5.0 g, 13.9 mmol, 91.4% yield) as a yellow oil. LCMS calc'd for $C_{17}H_{31}N_2O_6$ [M+H]$^+$: 359.2; Found: 359.3.

Step 3: 1,4-bis(tert-butoxycarbonyl)-2-methylpiperazine-2-carboxylic Acid

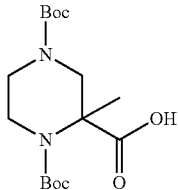 [SMILES: CC(C)(C)OC(=O)N1CCN(C(=O)OC(C)(C)C)C(C)(C(=O)O)C1]

To a solution of 1,4-di-tert-butyl 2-methyl 2-methylpiperazine-1,2,4-tricarboxylate (5.0 g, 13.9 mmol) in THF (12 mL)/methanol (2 mL)/water (2 mL) was added LiOH (713 mg, 17.0 mmol). The mixture was stirred at 50° C. for 16 h. TLC showed the reaction was complete. The reaction mixture was washed with PE (100 mL×2). The pH of the aqueous layer was adjusted to 3-4 with 1 N HCl, then extracted with EA (100 mL×3). The organic layers were combined, washed with brine (50 ml), and concentrated under reduced pressure to give the product 1,4-bis(tert-butoxycarbonyl)-2-methylpiperazine-2-carboxylic acid (4.5 g, 13.1 mmol, 93.7% yield) as a white solid. LCMS calc'd for $C_{16}H_{29}N_2O_6$ [M+H]$^+$: 345.2; Found: 345.2.

Step 4: tert-butyl 2-chloro-6a-methyl-6-oxo-5,6,6a,7,9,10-hexahydro-8H-pyrazino[1',2':4,5]pyrazino[2,3-c]pyridazine-8-carboxylate

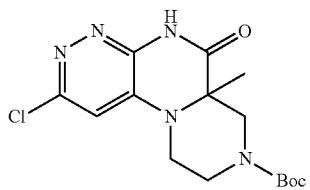 [SMILES: CC(C)(C)OC(=O)N1CCN2c3cc(Cl)nnc3NC(=O)C2(C)C1]

To a solution of 1,4-bis(tert-butoxycarbonyl)-2-methylpiperazine-2-carboxylic acid (4.2 g, 12.2 mmol) in DCM (25 mL) was added DMF (1 mL) and oxalyl chloride (4.6 g, 36.6 mmol). The mixture was stirred at rt for 30 min. The volatiles were removed under reduced pressure and DMF (25 mL), DIEA (10.1 mL, 61.0 mmol) and 5-bromo-6-chloropyridazin-3-amine (5.1 g, 24.4 mmol) were added sequentially. The resulted mixture was stirred at 120° C. for 16 h. The reaction mixture was diluted with EA (100 ml) and washed with brine (30 mL×2). The organic layer was concentrated in vacuum and purified by prep-TLC, eluting with PE:EA=1:1 to give tert-butyl 2-chloro-6a-methyl-6-oxo-5,6,6a,7,9,10-hexahydro-8H-pyrazino[1',2':4,5]pyrazino[2,3-c]pyridazine-8-carboxylate (1.5 g, 4.2 mmol, 34.7% yield) as a yellow solid. LCMS calc'd for $C_{15}H_{21}ClN_5O_3$[M+H]$^+$: 354.1; Found: 354.1.

Step 5: tert-butyl 2-chloro-6a-methyl-5,6,6a,7,9,10-hexahydro-8H-pyrazino[1',2':4,5]pyrazino[2,3-c]pyridazine-8-carboxylate

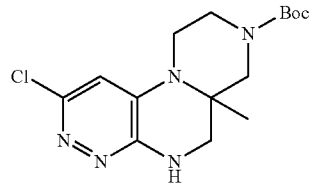 [SMILES: CC(C)(C)OC(=O)N1CCN2c3cc(Cl)nnc3NCC2(C)C1]

To a solution of tert-butyl 2-chloro-6a-methyl-6-oxo-5,6,6a,7,9,10-hexahydro-8H-pyrazino[1',2':4,5]pyrazino[2,3-c]pyridazine-8-carboxylate (87.3 mg, 0.25 mmol) in THF (8 mL) was added BH$_3$ in THF (1 M, 0.74 mL, 0.74 mmol). The resulted mixture was stirred at 80° C. for 16 h. The reaction was diluted with MeOH (20 ml) and was stirred at 80° C. for additional 16 h. The volatiles were removed under reduce pressure and the residue was purified by prep-TLC (DCM:MeOH=10:1) to give tert-butyl 2-chloro-6a-methyl-5,6,6a,7,9,10-hexahydro-8H-pyrazino[1',2':4,5]pyrazino[2,3-c]pyridazine-8-carboxylate (40.0 mg, 0.12 mmol, 47.7% yield) as a yellow solid. LCMS calc'd for $C_{15}H_{23}ClN_5O_2$ [M+H]$^+$: 340.2; Found: 340.1.

Step 6: tert-butyl 2-(2-hydroxyphenyl)-6a-methyl-5,6,6a,7,9,10-hexahydro-8H-pyrazino[1',2':4,5]pyrazino[2,3-c]pyridazine-8-carboxylate

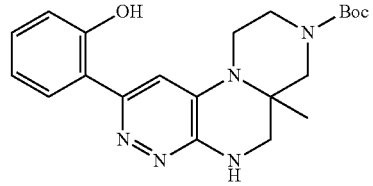 [SMILES: CC(C)(C)OC(=O)N1CCN2c3cc(-c4ccccc4O)nnc3NCC2(C)C1]

To a solution of 2-hydroxyphenylboronic acid (731 mg, 5.3 mmol), potassium carbonate (1.1 g, 7.95 mmol) and tert-butyl 2-chloro-6a-methyl-5,6,6a,7,9,10-hexahydro-8H-pyrazino[1',2':4,5]pyrazino[2,3-c]pyridazine-8-carboxylate (900 mg, 2.65 mmol) in 1,4-dioxane (10 mL) and water (1 mL) was added Pd(dppf)$_2$Cl$_2$ (216 mg, 0.26 mmol). The mixture was stirred at 105° C. for 16 h under N$_2$. The reaction was diluted with EA (200 ml) and washed with brine (100 mL×2). The organic layer was concentrated and the residue was purified by silica gel column chromatography (100-200 mesh size), eluting with PE:EA=3:1 to 1:1 to give tert-butyl 2-(2-hydroxyphenyl)-6a-methyl-5,6,6a,7,9,10-hexahydro-8H-pyrazino[1',2':4,5]pyrazino[2,3-c]pyridazine-8-carboxylate (1.0 g, 2.51 mmol, 95.0% yield) as a yellow solid. LCMS calc'd for $C_{21}H_{28}N_5O_3$[M+H]$^+$: 398.2; Found: 398.2.

Step 7: 2-(6a-methyl-6,6a,7,8,9,10-hexahydro-5H-pyrazino[1',2':4,5]pyrazino[2,3-c]pyridazin-2-yl)phenol To a solution of tert-butyl 2-(2-hydroxyphenyl)-6a-methyl-5,6,6a,7,9,10-hexahydro-8H-pyrazino[1',2':4,5]pyrazino[2,3-c]pyridazine-8-carboxylate (60.0 mg, 0.15 mmol) in DCM (1 mL) was added TFA (1.2 mL). The mixture was stirred at 25° C. for 2 h. The volatiles were removed under reduced pressure and the residue was purified by prep-HPLC, eluting with CH₃CN in H₂O (0.1% HCl) from 5.0% to 95% to get 2-(6a-methyl-6,6a,7,8,9,10-hexahydro-5H-pyrazino[1',2':4,5]pyrazino[2,3-c]pyridazin-2-yl)phenol as its HCl salt (45.0 mg, 0.13 mmol, 87.9% yield). $^1$H NMR (400 MHz, CD3OD) δ 7.54-7.52 (m, 1H), 7.45-7.41 (m, 1H), 7.26 (s, 1H), 7.06-7.01 (m, 2H), 4.26-4.22 (m, 1H), 3.65-3.44 (m, 5H), 3.24-3.12 (m, 2H), 1.55 (m, 3H). LCMS calc'd for $C_{16}H_{20}N_5O$ [M+H]$^+$: 298.2; Found: 298.2.

Intermediate 32: (2S,4R)-4-((tert-butyldimethylsilyl)oxy)-1-(2-(3-formylisoxazol-5-yl)-3-methylbutanoyl)-N—((S)-1-(4-(4-methylthiazol-5-yl)phenyl)ethyl)pyrrolidine-2-carboxamide

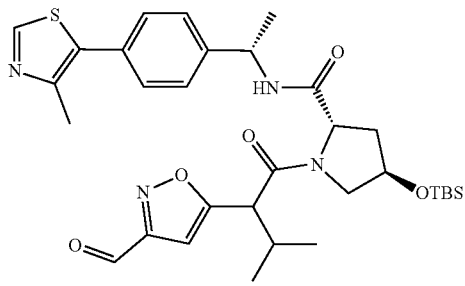

Int-32

Step 1: 2-(benzyloxy)acetaldehyde

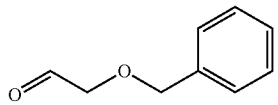 [SMILES: O=CCOCc1ccccc1]

To a solution of 2-(benzyloxy)ethan-1-ol (1.0 g, 6.6 mmol) in MeCN (30 mL) was added IBX (8.4 g, 19.7 mmol). The mixture was stirred at 90° C. for 10 min. The reaction was diluted with EtOAc (30 mL) and was washed with water (2×10 mL) then saturated brine (1×10 mL). The organic layer was dried over MgSO₄, filtered and concentrated to dryness. The crude was then purified by silica gel chromatography (EA:PE=1:5) to give 2-(benzyloxy)acetaldehyde (150 mg, 1.00 mmol). LCMS calc'd for $C_9H_{11}O_2$ [M+H]$^+$: 151.1; Found: 151.1.

Step 2: (E)-2-(benzyloxy)acetaldehyde oxime

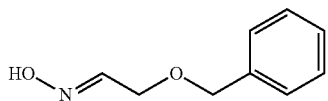 [SMILES: O/N=C/COCc1ccccc1]

To a solution of 2-(benzyloxy)acetaldehyde (1.0 g, 6.7 mmol) and hydroxylamine hydrochloride (508 mg, 7.33 mmol) in ethanol (10 mL) and water (30 mL) was added NaOH (666 mg, 16.6 mmol) at 0° C. The reaction was stirred at 0° C. for 2 h. The resulting mixture was acidified with HCl (5 N) to pH 2. The mixture was extracted with EA (30 mL×2). The combined organic layers were washed with brine (8.0 mL), dried over MgSO₄, and concentrated to give (E)-2-(benzyloxy)acetaldehyde oxime (500 mg, 3.0 mmol, 44.5% yield) as a colorless oil. LCMS calc'd for $C_9H_{12}NO_2$ [M+H]$^+$: 166.1; Found: 166.1.

Step 3: (Z)-2-(benzyloxy)-N-hydroxyacetimidoyl chloride

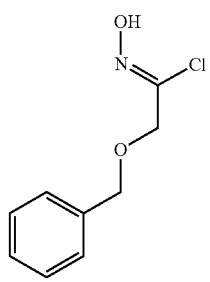 [SMILES: O/N=C(\Cl)COCc1ccccc1]

To a solution of (E)-2-(benzyloxy)acetaldehyde oxime (500 mg, 3.0 mmol) in DMF (10 mL) was added NCS (808 mg, 6.0 mmol). The reaction was stirred at 90° C. for 2 h. The resulted mixture was diluted with EA (50 mL) and was washed with water (2×30 mL) and saturated brine (1×10 mL). The organic layer was dried over MgSO₄ and concentrated to dryness. The residue was purified by silica gel chromatography (PE:EA=8:1) to get (Z)-2-(benzyloxy)-N-hydroxyacetimidoyl chloride (603 mg, 2.96 mmol, 97.8% yield) as a colorless oil. $^1$H-NMR (CD₃OD-d₄, 400 MHz): δ 12.080 (s, 1H), 7.324-7.369 (m, 5H), 4.492 (s, 2H), 4.262 (s, 2H).

Step 4: 2-(3-((benzyloxy)methyl)isoxazol-5-yl)ethan-1-ol

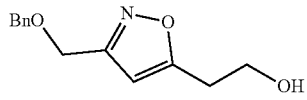 [SMILES: OCCc1cc(COCc2ccccc2)no1]

To a solution of (Z)-2-(benzyloxy)-N-hydroxyacetimidoyl chloride (6.4 g, 32.1 mmol) and NaHCO₃ (3.4 g, 40.1 mmol) in EA (20 mL) and water (20 mL) was added 3-butyn-1-ol (2.76 g, 39.4 mmol). The reaction was stirred at 25° C. for 2 h. The resulted mixture was diluted with EA (50 mL) then washed with water (2×30 mL) and brine (1×10 mL). The organic layer was dried over MgSO₄ and concentrated to dryness. The residue was purified by silica gel chromatography (PE:EA=1:1) to afford 2-(3-((benzyloxy)methyl)isoxazol-5-yl)ethan-1-ol (2.7 g, 11.6 mmol, 36.1% yield) as an oil. LCMS calc'd for $C_{13}H_{16}NO_3$[M+H]$^+$: 234.1; Found: 234.0.

Step 5: 2-(3-((benzyloxy)methyl)isoxazol-5-yl)acetic acid

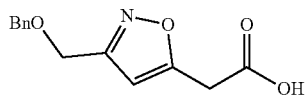 [SMILES: O=C(O)Cc1cc(COCc2ccccc2)no1]

To a solution of 2-(3-((benzyloxy)methyl)isoxazol-5-yl)ethan-1-ol (100 mg, 0.43 mmol) in water (0.20 mL) and acetone (2 mL) was added chromium (III) oxide (65.2 mg, 0.43 mmol) and sulfuric acid (0.04 mL, 0.43 mmol). The reaction was stirred at 25° C. for 2 h. The reaction mixture was diluted with water (20 mL) and extracted with EA (2×30 mL). The combined organic layers were concentrated to give 2-(3-((benzyloxy)methyl)isoxazol-5-yl)acetic acid (100 mg, 0.40 mmol, 92.5% yield) as a colorless oil. $^1$H-NMR (CD$_3$OD-d$_4$, 400 MHz): δ 12.858 (s, 1H), 7.284-7.387 (m, 5H), 6.334-6.445 (s, 1H), 4.483-4.647 (m, 4H), 3.884-4.031 (m, 2H).

Step 6: ethyl 2-(3-((benzyloxy)methyl)isoxazol-5-yl)acetate

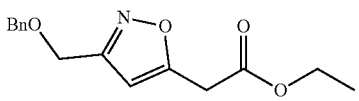 [SMILES: CCOC(=O)Cc1cc(COCc2ccccc2)no1]

To a solution of 2-(3-((benzyloxy)methyl)isoxazol-5-yl) acetic acid (80.0 mg, 0.32 mmol) in ethanol (5 mL) was added sulfuric acid (0.1 mL, 0.32 mmol). The reaction was stirred at 70° C. for 2 h. The reaction mixture was diluted with water (20 mL) and extracted with EA (2×30 mL). The combined organic layers were concentrated to afford ethyl 2-(3-((benzyloxy)methyl)isoxazol-5-yl)acetate (60 mg, 0.21 mmol, 66.0% yield) as a colorless oil. LCMS calc'd for C$_{15}$H$_{18}$NO$_4$ [M+H]$^+$: 276.1; Found: 276.1.

Step 7: ethyl 2-(3-((benzyloxy)methyl)isoxazol-5-yl)-3-methylbutanoate

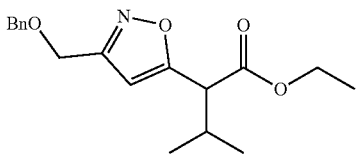 [SMILES: CCOC(=O)C(c1cc(COCc2ccccc2)no1)C(C)C]

To a solution of ethyl 2-[3-(phenylmethoxymethyl)-1,2-oxazol-5-yl]acetate (1.0 g, 3.63 mmol) and potassium tert-butoxide (815 mg, 7.26 mmol) in THF (15 mL) was added 2-iodopropane (926 mg, 5.45 mmol) at 0° C. The resulted solution was stirred at rt for 3 h. The mixture was diluted with EA (20 mL) and was washed with water (2×10 mL) and brine (1×10 mL). The organic layer was separated, dried over MgSO$_4$, and concentrated to dryness to give ethyl 2-(3-((benzyloxy)methyl)isoxazol-5-yl)-3-methylbutanoate (800 mg, 2.52 mmol, 69.4% yield) as an oil.

Step 8: ethyl 2-(3-(hydroxymethyl)isoxazol-5-yl)-3-methylbutanoate

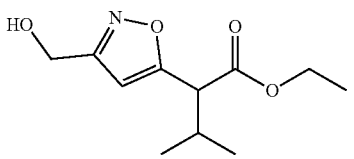 [SMILES: CCOC(=O)C(c1cc(CO)no1)C(C)C]

To a solution of ethyl 2-(3-((benzyloxy)methyl)isoxazol-5-yl)-3-methylbutanoate (100 mg, 0.32 mmol) in DCM (5 mL) was added phosphorus tribromide (0.05 mL, 0.52 mmol) at −78° C. The reaction was stirred at rt for 2 h. The mixture was diluted with EA (30 mL) and washed with water (2×10 mL) and saturated brine (1×10 mL). The organic layer was separated, dried over MgSO$_4$, and concentrated to dryness. The residue was purified by silica gel chromatography (PE:EA=5:1) to get ethyl 2-(3-(hydroxymethyl)isoxazol-5-yl)-3-methylbutanoate (50 mg, 0.22 mmol, 69.8% yield) as a colorless oil. $^1$H-NMR (CD$_3$OD-d$_4$, 400 MHz): δ 6.397 (s, 1H), 4.446-4.516 (m, 2H), 4.097-4.414 (m, 2H), 3.662-3.784 (m, 1H), 2.286-2.373 (m, 1H), 1.166-1.286 (m, 3H), 0.892-0.964 (m, 3H), 0.779-0.843 (m, 3H).

Step 9: 2-(3-(hydroxymethyl)isoxazol-5-yl)-3-methylbutanoic Acid

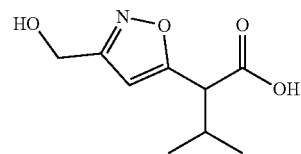

To a solution of ethyl 2-(3-(hydroxymethyl)isoxazol-5-yl)-3-methylbutanoate (370 mg, 1.63 mmol) in ethanol (5 mL) was added NaOH (651 mg, 16.3 mmol) at 25° C. The resulted solution was stirred at rt for 2 h. The mixture was diluted with EA (50 mL) and was washed with water (2×20 mL) and saturated brine (1×10 mL). The organic layer was separated, dried over MgSO$_4$, and concentrated to dryness. The residue was purified by silica gel chromatography (PE:EA=5:1) to afford 2-(3-(hydroxymethyl)isoxazol-5-yl)-3-methylbutanoic acid (320 mg, 1.6 mmol, 98.7% yield) as a colorless oil. $^1$H-NMR (DMSO-d$_6$, 400 MHz): δ 12.90 (s, 1H), 6.364 (s, 1H), 5.453 (m, 1H), 4.469-4.582 (m, 2H), 3.624-3.645 (m, 1H), 0.954-0.971 (m, 3H), 0.821-0.837 (m, 3H).

Step 10: (2S,4R)-4-((tert-butyldimethylsilyl)oxy)-1-(2-(3-(hydroxymethyl)isoxazol-5-yl)-3-methylbutanoyl)-N—((S)-1-(4-(4-methylthiazol-5-yl)phenyl)ethyl)pyrrolidine-2-carboxamide

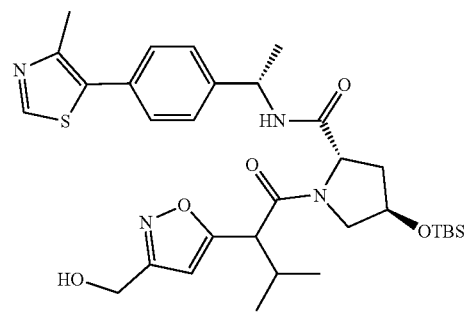 [SMILES: Cc1ncsc1-c1ccc([C@H](C)NC(=O)[C@@H]2C[C@@H](O[Si](C)(C)C(C)(C)C)CN2C(=O)C(c2cc(CO)no2)C(C)C)cc1]

To a solution of 2-(3-(hydroxymethyl)isoxazol-5-yl)-3-methylbutanoic acid (300.0 mg, 1.51 mmol) in DMF (2 mL) was added (2S,4R)-4-((tert-butyldimethylsilyl)oxy)-N—((S)-1-(4-(4-methylthiazol-5-yl)phenyl)ethyl)pyrrolidine-2-carboxamide (1.01 g, 2.26 mmol), HATU (859 mg, 2.26 mmol), DIEA (0.75 mL, 4.52 mmol). The mixture was stirred at 25° C. for 16 h. The reaction mixture was diluted with H₂O and extracted with EA (20 mL×3). The organic layers were combined and the volatiles were removed under reduced pressure. The residue was purified by silica gel chromatography to give (2S,4R)-4-((tert-butyldimethylsilyl)oxy)-1-(2-(3-(hydroxymethyl)isoxazol-5-yl)-3-methylbutanoyl)-N—((S)-1-(4-(4-methylthiazol-5-yl)phenyl)ethyl)pyrrolidine-2-carboxamide (550 mg, 0.88 mmol, 58.3% yield) as a yellow oil. LCMS calc'd for $C_{32}H_{47}N_4O_5SSi$ [M+H]⁺: 627.3; Found: 627.4.

Step 11: (2S,4R)-4-((tert-butyldimethylsilyl)oxy)-1-(2-(3-formylisoxazol-5-yl)-3-methylbutanoyl)-N—((S)-1-(4-(4-methylthiazol-5-yl)phenyl)ethyl)pyrrolidine-2-carboxamide To a solution of (2S,4R)-4-((tert-butyldimethylsilyl)oxy)-1-(2-(3-(hydroxymethyl)isoxazol-5-yl)-3-methylbutanoyl)-N—((S)-1-(4-(4-methylthiazol-5-yl)phenyl)ethyl)pyrrolidine-2-carboxamide (60 mg, 0.10 mmol) in DCM (2 mL) was added MnO₂ (167 mg, 1.91 mmol). The mixture was stirred at 45° C. for 1 h. The reaction mixture was diluted with H₂O and extracted with EA (10 mL×3). The organic layers were combined and the volatiles were removed under reduced pressure. The residue was purified by silica gel chromatography to give (2S,4R)-4-((tert-butyldimethylsilyl)oxy)-1-(2-(3-formylisoxazol-5-yl)-3-methylbutanoyl)-N—((S)-1-(4-(4-methylthiazol-5-yl)phenyl)ethyl)pyrrolidine-2-carboxamide (40 mg, 0.06 mmol, 66.9% yield) as a yellow oil. LCMS calc'd for $C_{32}H_{45}N_4O_5SSi$ [M+H]⁺: 625.3; Found: 625.2.

Intermediate 33: (2S,4R)-4-((tert-butyldimethylsilyl)oxy)-1-(3-methyl-2-(3-(3-oxopropyl)isoxazol-5-yl)butanoyl)-N—((S)-1-(4-(4-methylthiazol-5-yl)phenyl)ethyl)pyrrolidine-2-carboxamide Int-33

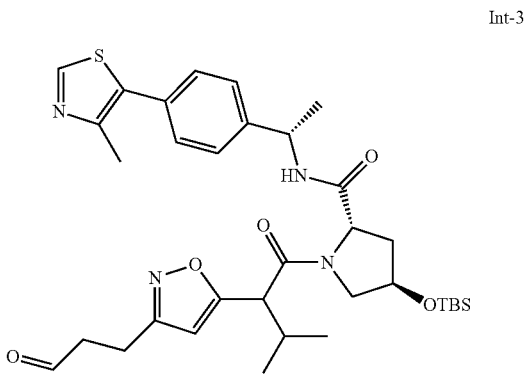

Step 1-10: (2S,4R)-4-((tert-butyldimethylsilyl)oxy)-1-(2-(3-(3-hydroxypropyl)isoxazol-5-yl)-3-methylbutanoyl)-N—((S)-1-(4-(4-methylthiazol-5-yl)phenyl)ethyl)pyrrolidine-2-carboxamide

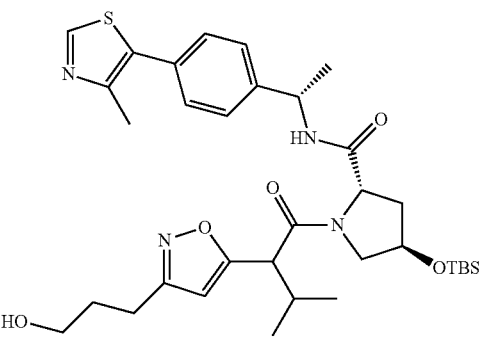 [SMILES: Cc1ncsc1-c1ccc([C@H](C)NC(=O)[C@@H]2C[C@@H](O[Si](C)(C)C(C)(C)C)CN2C(=O)C(c2cc(CCCO)no2)C(C)C)cc1]

The title compound was prepared using procedures analogous to those described for Int-32, from step 1 to step 10, with appropriate starting materials. LCMS m/z calcd for $C_{34}H_{51}N_4O_5SSi$ [M+H]⁺: 655.3; Found: 655.3.

Step 11: (2S,4R)-4-((tert-butyldimethylsilyl)oxy)-1-(3-methyl-2-(3-(3-oxopropyl)isoxazol-5-yl)butanoyl)-N—((S)-1-(4-(4-methylthiazol-5-yl)phenyl)ethyl)pyrrolidine-2-carboxamide To a solution of (2S,4R)-4-((tert-butyldimethylsilyl)oxy)-1-(2-(3-(3-hydroxypropyl)isoxazol-5-yl)-3-methylbutanoyl)-N—((S)-1-(4-(4-methylthiazol-5-yl)phenyl)ethyl)pyrrolidine-2-carboxamide (80 mg, 0.12 mmol) in MeCN (5 mL) was added IBX (104 mg, 0.24 mmol). The mixture was stirred at 80° C. for 2 h. The reaction was filtered and concentrated in vacuum to give (2S,4R)-4-((tert-butyldimethylsilyl)oxy)-1-(3-methyl-2-(3-(3-oxopropyl)isoxazol-5-yl)butanoyl)-N—((S)-1-(4-(4-methylthiazol-5-yl)phenyl)ethyl)pyrrolidine-2-carboxamide (80 mg, 0.12 mmol, 100% yield) as a yellow oil. LCMS m/z calcd for $C_{34}H_{49}N_4O_5SSi$ [M+H]⁺: 653.3; Found: 653.3.

Intermediate 34: (2S,4R)-4-((tert-butyldimethylsilyl)oxy)-1-(3-methyl-2-(3-(2-oxoethyl)isoxazol-5-yl)butanoyl)-N—((S)-1-(4-(4-methylthiazol-5-yl)phenyl)ethyl)pyrrolidine-2-carboxamide Int-34

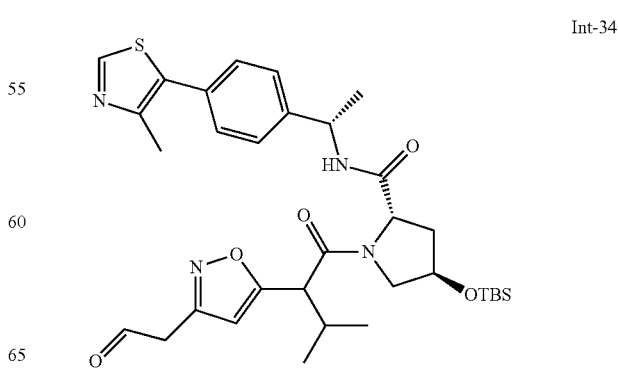

The title compound was prepared using procedures analogous to those described for Int-33 with appropriate starting materials. LCMS m/z calcd for $C_{33}H_{47}N_4O_5SSi$ [M+H]$^+$: 639.3; Found: 639.3.

Intermediate 35: (2S,4R)-4-hydroxy-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)pyrrolidine-2-carboxylic acid

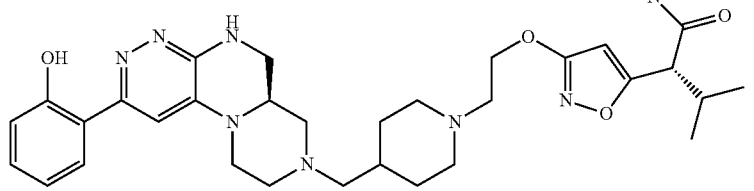

Int-35

Step 1: methyl (2S,4R)-1-((R)-2-(3-(2-bromoethoxy)isoxazol-5-yl)-3-methylbutanoyl)-4-((tert-butyldimethylsilyl)oxy)pyrrolidine-2-carboxylate

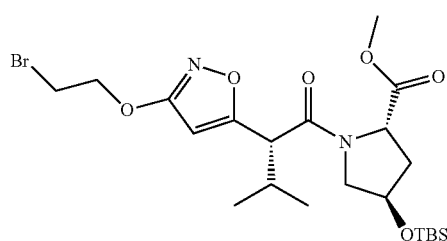 [SMILES: COC(=O)[C@@H]1C[C@@H](O[Si](C)(C)C(C)(C)C)CN1C(=O)[C@@H](c1cc(OCCBr)no1)C(C)C]

To a solution of 1,2-dibromoethane (15.3 g, 81.6 mmol) and methyl (2S,4R)-4-((tert-butyldimethylsilyl)oxy)-1-((R)-2-(3-hydroxyisoxazol-5-yl)-3-methylbutanoyl)pyrrolidine-2-carboxylate (3.5 g, 8.16 mmol) in DMF (5 mL) was added potassium carbonate (3.4 g, 24.5 mmol) at rt. The mixture was stirred at rt for 16 h. The reaction mixture was diluted with EA (50 mL) and washed with water (2×20 mL) and saturated brine (1×10 mL). The organic layer was separated, dried over MgSO$_4$, and concentrated to dryness. The residue was purified by prep-HPLC, eluted with CH$_3$CN in H$_2$O (0.1% NH$_3$·H$_2$O) from 5.0% to 95% to give methyl (2S, 4R)-1-((R)-2-(3-(2-bromoethoxy)isoxazol-5-yl)-3-methylbutanoyl)-4-((tert-butyldimethylsilyl)oxy)pyrrolidine-2-carboxylate (1.0 g, 1.87 mmol, 22.9% yield). LCMS m/z calcd for $C_{22}H_{38}BrN_2O_6Si$ [M+H]$^+$: 533.2; Found: 533.3.

Step 2: methyl (2S,4R)-4-((tert-butyldimethylsilyl)oxy)-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)pyrrolidine-2-carboxylate

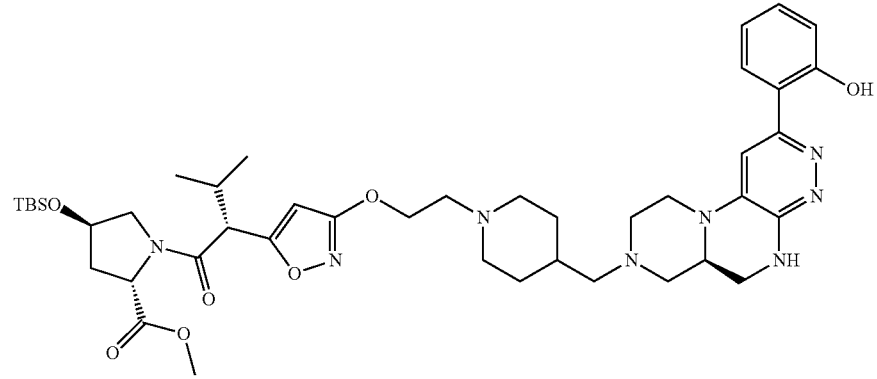 [SMILES: COC(=O)[C@@H]1C[C@@H](O[Si](C)(C)C(C)(C)C)CN1C(=O)[C@@H](c1cc(OCCN2CCC(CN3CCN4c5cc(-c6ccccc6O)nnc5NC[C@H]4C3)CC2)no1)C(C)C]

To a solution of (S)-2-(8-(piperidin-4-ylmethyl)-6,6a,7,8,9,10-hexahydro-5H-pyrazino[1',2':4,5]pyrazino[2,3-c]pyridazin-2-yl)phenol (60 mg, 0.16 mmol) and methyl (2S,4R)-1-((R)-2-(3-(2-bromoethoxy)isoxazol-5-yl)-3-methylbutanoyl)-4-((tert-butyldimethylsilyl)oxy)pyrrolidine-2-carboxylate (92.5 mg, 0.17 mmol) in DMF (5 mL) was added NaHCO$_3$ (132 mg, 1.58 mmol) at rt. The mixture was stirred at rt for 16 h. The mixture was diluted with EA (50 mL) and washed with water (2×20 mL) and brine (1×10 mL). The organic layer was dried over MgSO$_4$, and concentrated to dryness. The residue was purified by silica gel chromatography to afford methyl (2S,4R)-4-((tert-butyldimethylsilyl)oxy)-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)pyrrolidine-2-carboxylate (18.0 mg, 0.021 mmol, 13.7% yield). LCMS m/z calcd for C$_{43}$H$_{65}$N$_8$O$_7$Si [M+H]$^+$: 833.5; Found: 833.3.

Step 3: (2S,4R)-4-hydroxy-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)pyrrolidine-2-carboxylic Acid Intermediate 36: 2-(6-methyl-6,6a,7,8,9,10-hexahydro-5H-pyrazino[1',2':4,5]pyrazino[2,3-c]pyridazin-2-yl)phenol

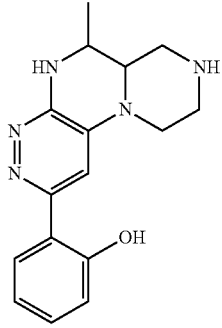

Int-36

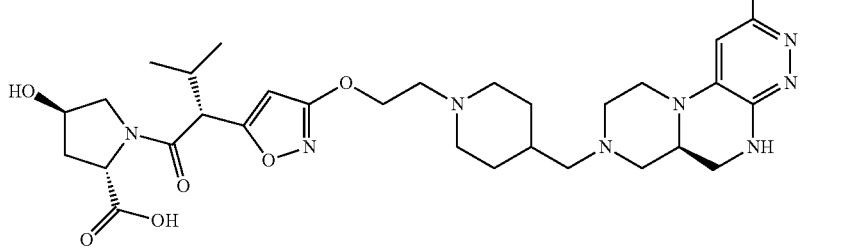

To a solution of methyl (2S,4R)-4-((tert-butyldimethylsilyl)oxy)-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)pyrrolidine-2-carboxylate (30.0 mg, 0.04 mmol) in THF (2 mL) and water (2 mL) was added LiOH (15.1 mg, 0.36 mmol) at rt. The reaction was stirred at rt for 16 h. The mixture was diluted with EA (30 mL) and washed with water (2×10 mL) and brine (1×10 mL). The organic layer was dried over MgSO$_4$, and concentrated to dryness. The residue was purified by prep-HPLC (eluting with MeCN in H$_2$O, 0.1% HCl) to get the des-TBS product (2S,4R)-4-hydroxy-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)pyrrolidine-2-carboxylic acid (18.0 mg, 0.025 mmol, 70.9% yield). LCMS m/z calcd for C$_{36}$H$_{49}$H$_8$O$_7$ [M+H]$^+$: 705.4; Found: 705.5.

Step 1: tert-butyl 4-(3,6-dichloropyridazin-4-yl)-3-formylpiperazine-1-carboxylate

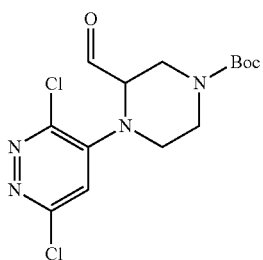 [SMILES: CC(C)(C)OC(=O)N1CCN(c2cc(Cl)nnc2Cl)C(C=O)C1]

To a solution of tert-butyl 4-(3,6-dichloropyridazin-4-yl)-3-(hydroxymethyl)piperazine-1-carboxylate (3.96 g, 10.9 mmol) in DCM (70 mL) was added Dess-Martin periodinane (9.25 g, 21.8 mmol) at 0° C. The mixture was stirred at 0° C. for 1 h. The reaction was quenched with saturated aqueous Na$_2$S$_2$O$_3$ (80 mL) and extracted with DCM (80.0 mL×3). The organic layers were combined, dried over Na$_2$SO$_4$, filtered, and concentrated reduced pressure to give crude tert-butyl 4-(3,6-dichloropyridazin-4-yl)-3-formylpiperazine-1-carboxylate (3.6 g, 9.97 mmol, 91.4% yield). LCMS m/z calcd for $C_{14}H_{19}Cl_2N_4O_3$ [M+H]$^+$: 361.1; Found: 361.1.

Step 2: tert-butyl 4-(3,6-dichloropyridazin-4-yl)-3-(1-hydroxyethyl)piperazine-1-carboxylate

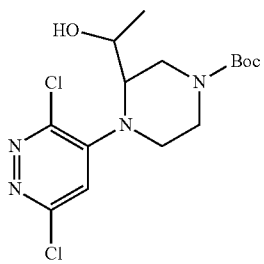 [SMILES: CC(O)C1CN(C(=O)OC(C)(C)C)CCN1c1cc(Cl)nnc1Cl]

To a solution of tert-butyl 4-(3,6-dichloropyridazin-4-yl)-3-formylpiperazine-1-carboxylate (3.6 g, 9.97 mmol) in THF (70 mL) was added $CH_3MgBr$ (1 M in $Et_2O$, 19.9 mL, 19.9 mmol) at 0° C. The mixture was stirred at 0° C. for 2 h. The reaction was quenched with saturated aqueous $NH_4Cl$ (80 mL) and extracted with EA (80 mL×3). The organic layers were combined, dried over $Na_2SO_4$, filtered, and concentrated reduced pressure. The residue was purified by silica gel chromatography (PE:EA=3:1) to give tert-butyl 4-(3,6-dichloropyridazin-4-yl)-3-(1-hydroxyethyl)piperazine-1-carboxylate (2.1 g, 5.6 mmol, 56.9% yield) as a yellow solid. LCMS m/z calcd for $C_{15}H_{23}Cl_2N_4O_3$ [M+H]$^+$: 377.1; Found: 377.0.

Step 3 to step 7: 2-(6-methyl-6,6a,7,8,9,10-hexahydro-5H-pyrazino[1',2':4,5]pyrazino[2,3-c]pyridazin-2-yl)phenol The title compound was prepared using procedures analogous to those described for Int-9, from step 2 to step 6, with appropriate starting materials. LCMS m/z calcd for $C_{16}H_{20}N_5O$ [M+H]$^+$: 298.2; Found: 298.2. $^1$H NMR (400 MHz, $CD_3OD$): δ 7.75-7.78 (m, 1H), 7.16-7.24 (m, 2H), 6.87-6.90 (m, 2H), 3.91-4.07 (m, 1H), 3.35-3.48 (m, 1H), 3.11-3.30 (m, 2H), 2.99-3.09 (m, 1H), 2.83-2.92 (m, 2H), 2.46-2.65 (m, 1H), 1.22-1.29 (m, 3H).

Intermediate 37. (2S,4R)-1-((2R)-2-(3-((1-bromopropan-2-yl)oxy)isoxazol-5-yl)-3-methylbutanoyl)-4-((tert-butyldimethylsilyl)oxy)-N—((S)-1-(4-(4-methylthiazol-5-yl)phenyl)ethyl)pyrrolidine-2-carboxamide

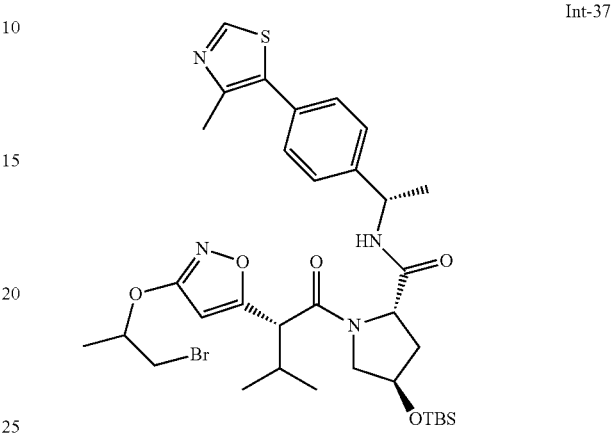

To a solution of (2S,4R)-4-((tert-butyldimethylsilyl)oxy)-1-((R)-2-(3-hydroxyisoxazol-5-yl)-3-methylbutanoyl)-N—((S)-1-(4-(4-methylthiazol-5-yl)phenyl)ethyl)pyrrolidine-2-carboxamide (300 mg, 0.49 mmol), 1-bromopropan-2-ol (292 mg, 1.47 mmol) and triphenylphosphine (385 mg, 1.47 mmol) in THF (10 mL) was added diisopropyl azodicarboxylate (297 mg, 1.47 mmol) dropwise at 0° C. The resulting mixture was stirred at rt for 16 h. The volatiles were removed under reduced pressure and the residue was purified by silica gel chromatography (PE:EA=2:1) to give (2S,4R)-1-((2R)-2-(3-((1-bromopropan-2-yl)oxy)isoxazol-5-yl)-3-methylbutanoyl)-4-((tert-butyldimethylsilyl)oxy)-N—((S)-1-(4-(4-methylthiazol-5-yl)phenyl)ethyl)pyrrolidine-2-carboxamide (300 mg, 0.41 mmol, 83.5% yield). LCMS m/z calcd for $C_{34}H_{50}BrN_4O_5SSi$ [M+H]$^+$: 733.2; Found: 733.4.

Intermediate 38. (S)-2-(8-(2-aminoethyl)-6,6a,7,8,9,10-hexahydro-5H-pyrazino[1',2':4,5]pyrazino[2,3-c]pyridazin-2-yl)phenol

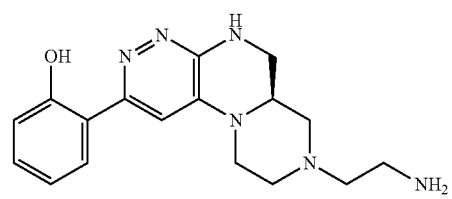

Step 1: tert-butyl (S)-(2-(2-(2-hydroxyphenyl)-5,6,6a,7,9,10-hexahydro-8H-pyrazino[1',2':4,5]pyrazino[2,3-c]pyridazin-8-yl)ethyl)carbamate

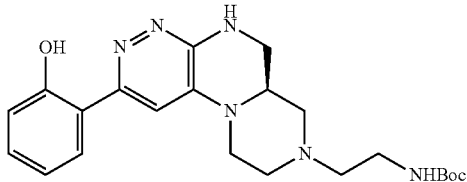 [SMILES: CC(C)(C)OC(=O)NCCN1CCN2c3cc(-c4ccccc4O)nnc3NC[C@H]2C1]

A mixture of (R)-2-(6,6a,7,8,9,10-hexahydro-5H-pyrazino[1',2':4,5]pyrazino[2,3-c]pyridazin-2-yl)phenol (29 mg, 0.10 mmol), tert-butyl (2-bromoethyl)carbamate (24.1 mg, 0.11 mmol) and NaHCO$_3$ (82.1 mg, 0.98 mmol) in DMF (3 mL) was stirred at 65° C. for 16 h. The reaction mixture was diluted with EA (40 mL), washed with H$_2$O (15 mL×3) and brine (30 mL). The organic layer was separated, dried over Na$_2$SO$_4$, filtered then concentrated under reduced pressure. The residue was purified by prep-TLC (DCM:MeOH=10:1) to tert-butyl (S)-(2-(2-(2-hydroxyphenyl)-5,6,6a,7,9,10-hexahydro-8H-pyrazino[1',2':4,5]pyrazino[2,3-c]pyridazin-8-yl)ethyl)carbamate (40 mg, 0.094 mmol, 95.9% yield) as a light yellow solid. LCMS m/z calcd for C$_{22}$H$_{31}$N$_6$O$_3$ [M+H]$^+$: 427.2; Found: 427.1.

Step 2: (S)-2-(8-(2-aminoethyl)-6,6a,7,8,9,10-hexahydro-5H-pyrazino[1',2':4,5]pyrazino[2,3-c]pyridazin-2-yl)phenol To a solution of tert-butyl (S)-(2-(2-(2-hydroxyphenyl)-5,6,6a,7,9,10-hexahydro-8H-pyrazino[1',2':4,5]pyrazino[2,3-c]pyridazin-8-yl)ethyl)carbamate (40 mg, 0.094 mmol) in DCM (10 mL) was added TFA (1.0 mL). The mixture was stirred at 25° C. for 10 h. The volatiles were removed under reduced pressure to afford crude (S)-2-(8-(2-aminoethyl)-6,6a,7,8,9,10-hexahydro-5H-pyrazino[1',2':4,5]pyrazino[2,3-c]pyridazin-2-yl)phenol as its TFA salt (40 mg). LCMS m/z calcd for C$_{17}$H$_{23}$N$_6$O [M+H]$^+$: 327.2; Found: 327.2.

Intermediate 39. (S)-1-(2-fluoro-4-(4-methylthiazol-5-yl)phenyl)ethan-1-amine

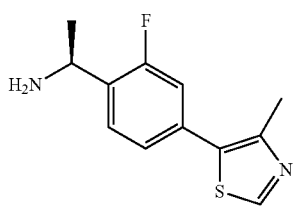

Int-39

Step 1: tert-butyl (S)-(1-(4-bromo-2-fluorophenyl)ethyl)carbamate

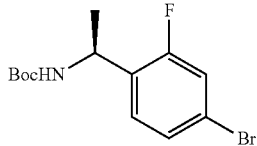 [SMILES: C[C@H](NC(=O)OC(C)(C)C)c1ccc(Br)cc1F]

TEA (2.1 mL, 15.0 mmol) was added to a solution of (S)-1-(4-bromo-2-fluorophenyl)ethan-1-amine (1.0 g, 5 mmol) and Di-tert-butyl dicarbonate (1.6 g, 7.5 mmol) in DCM (10 mL). The resulting mixture was stirred at 25° C. for 1.5 h. The reaction mixture was washed with water (3×10 mL). The organic layer was dried over sodium sulfate, filtered, and the filtrate was concentrated under reduced pressure to afford tert-butyl (S)-(1-(4-bromo-2-fluorophenyl)ethyl)carbamate (1.2 g, 3.8 mmol, 76.0% yield) as colorless solid. LCMS m/z calcd for C$_{13}$H$_{18}$BrFNO$_2$ [M+H]$^+$: 318.0; Found: 318.0.

Step 2: tert-butyl (S)-(1-(2-fluoro-4-(4-methylthiazol-5-yl)phenyl)ethyl)carbamate

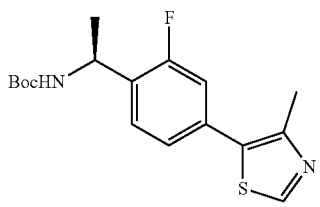 [SMILES: Cc1ncsc1-c1ccc([C@H](C)NC(=O)OC(C)(C)C)c(F)c1]

Palladium acetate (5.71 mg, 0.03 mmol) was added to the solution of tert-butyl (S)-(1-(4-bromo-2-fluorophenyl)ethyl)carbamate (90.0 mg, 0.25 mmol), potassium acetate (50 mg, 0.51 mmol) and 4-methyl-1,3-thiazole (50.5 mg, 0.51 mmol) in DMF (2 mL). The resulting mixture was purged with nitrogen for 3 times. The reaction mixture was heated to 90° C. and stirred for 16 h. The combined reaction mixture was diluted with EtOAc (25 mL) and washed with water (4×10 mL). The organic layer was dried over sodium sulfate, filtered, and the filtrate was concentrated under reduced pressure. The residue was purified by prep-TLC with PE/EA (6/1) to afford tert-butyl (S)-(1-(2-fluoro-4-(4-methylthiazol-5-yl)phenyl)ethyl)carbamate (36 mg, 0.093 mmol, 36.5% yield). LCMS m/z calcd for C$_{17}$H$_{22}$FN$_2$O$_2$S [M+H]$^+$: 337.1; Found: 337.3.

Step 3: (S)-1-(2-fluoro-4-(4-methylthiazol-5-yl)phenyl)ethan-1-amine

TFA (1.0 mL) was added to the solution of tert-butyl (S)-(1-(2-fluoro-4-(4-methylthiazol-5-yl)phenyl)ethyl)carbamate (15 mg, 0.04 mmol) in DCM (5 mL). The resulting mixture was stirred at 25° C. for 3 h. The volatiles were removed under reduced pressure to afford (S)-1-(2-fluoro-4-(4-methylthiazol-5-yl)phenyl)ethan-1-amine (10 mg, 0.04 mmol, 94.9% yield) as an oil. LCMS m/z calcd for C$_{12}$H$_{14}$FN$_2$S [M+1-1]$^+$: 237.1; Found: 237.1.

Intermediate 40. (S)-1-(4-(2-methyl-1H-imidazol-1-yl)phenyl)ethan-1-amine

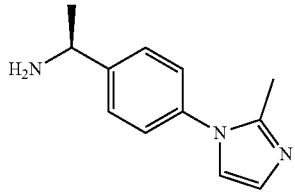

Int-40

Step 1: tert-butyl (S)-(1-(4-bromophenyl)ethyl)carbamate

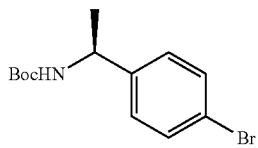 [SMILES: C[C@H](NC(=O)OC(C)(C)C)c1ccc(Br)cc1]

The title compound was prepared using procedure analogous to those described for Int-39, step 1 with appropriate starting materials. LCMS m/z calcd for $C_9H_{11}BrNO_2$ [M+H-tBu]$^+$: 244.0; Found: 244.2.

Step 2: tert-butyl (S)-(1-(4-(2-methyl-1H-imidazol-1-yl)phenyl)ethyl)carbamate

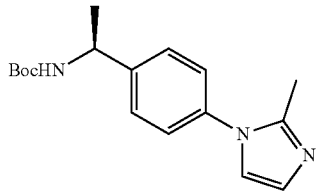 [SMILES: Cc1nccn1-c1ccc([C@H](C)NC(=O)OC(C)(C)C)cc1]

CuI (74 mg, 0.39 mmol) was added to the solution of tert-butyl (S)-(1-(4-bromophenyl)ethyl)carbamate (1.2 g, 3.9 mmol), 2-methyl-1H-imidazole (640 mg, 7.8 mmol), cesium carbonate (2.5 g, 7.8 mmol) and proline (899 mg, 7.8 mmol) in DMSO (3 mL). The resulting mixture was purged with nitrogen for 3 times. The reaction mixture was heated to 130° C. and stirred for 2 h. The reaction mixture was diluted with water (50 mL) and extracted with EA (3×20 mL). The organic layers were combined, dried over sodium sulfate, filtered and concentrated to dryness. The residue was purified by prep-TLC with EA/PE (2/1) to afford tert-butyl (S)-(1-(4-(2-methyl-1H-imidazol-1-yl)phenyl)ethyl)carbamate (120 mg, 0.38 mmol, 9.7% yield) as yellow oil. LCMS m/z calcd for $C_{17}H_{24}N_3O_2$ [M+1-1]$^+$: 302.2; Found: 302.1.

Step 3: (S)-1-(4-(2-methyl-1H-imidazol-1-yl)phenyl)ethan-1-amine

TFA (1.0 mL) was added to the solution of tert-butyl (S)-(1-(4-(2-methyl-1H-imidazol-1-yl)phenyl)ethyl)carbamate (15 mg, 0.05 mmol) in DCM (5 mL). The resulting mixture was stirred at 25° C. for 3 h. The volatiles were removed under reduced pressure to afford (S)-1-(2-fluoro-4-(4-methylthiazol-5-yl)phenyl)ethan-1-amine (10 mg, 0.05 mmol, 99.8% yield) as an oil. LCMS m/z calcd for $C_{12}H_{16}N_3$ [M+1-1]$^+$: 202.1; Found: 202.1.

Intermediate 41. (S)-1-(2-methoxy-4-(4-methylthiazol-5-yl)phenyl)ethan-1-amine

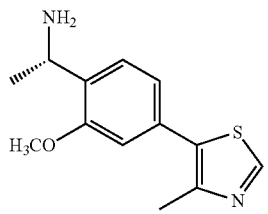

Int-41

Step 1: (SE)-N-(1-(4-bromo-2-methoxyphenyl)ethylidene)-2-methylpropane-2-sulfinamide

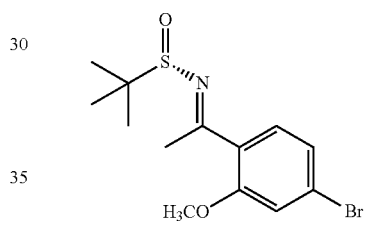

To a solution of 1-(4-bromo-2-methoxyphenyl)ethanone (1.0 g, 4.4 mmol) in THF (10 mL) was added titanium ethoxide (2.0 g, 8.7 mmol) and (R)-tert-butanesulfinamide (635 mg, 5.24 mmol). After being purged with $N_2$ 3 times, the mixture was stirred at 70° C. for 12 h. The reaction mixture was diluted with water (20 mL) and extracted with EA (3×30 mL). The organic layers were combined, washed with brine, concentrated in vacuo and the residue was purified by silica gel chromatography (PE:EA=20:1 to 3:1) to give (S,E)-N-(1-(4-bromo-2-methoxyphenyl)ethylidene)-2-methylpropane-2-sulfinamide (400 mg, 1.2 mmol, 27% yield) as a yellow oil. LCMS m/z calcd for $C_{13}H_{19}BrNO_2S$ [M+1-1]$^+$: 332.0; Found: 332.0.

Step 2: N—((S)-1-(4-bromo-2-methoxyphenyl)ethyl)-2-methylpropane-2-sulfinamide

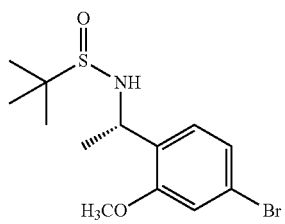 [SMILES: COc1cc(Br)ccc1[C@H](C)NS(=O)C(C)(C)C]

To a solution of (SE)-N-(1-(4-bromo-2-methoxyphenyl)ethylidene)-2-methylpropane-2-sulfinamide (400 mg, 1.2 mmol) in THF (20 mL) was added and L-selectride (1 M, 8.73 mL, 8.73 mmol) at 0° C. After being purged with $N_2$ 3 times, the mixture was stirred at 70° C. for 12 h. The reaction mixture was diluted with water (20 mL) and extracted with EA (3×30 mL). The organic layers were combined, washed with brine, concentrated in vacuo and the residue was purified by silica gel chromatography (PE:EA=20:1 to 1:1) to give N—((S)-1-(4-bromo-2-methoxyphenyl)ethyl)-2-methylpropane-2-sulfinamide (206 mg, 0.59 mmol, 51.2% yield) as a yellow oil. LCMS m/z calcd for $C_{13}H_{21}BrNO_2S$ [M+1-1]$^+$: 334.0; Found: 334.1.

Step 3: N—((S)-1-(2-methoxy-4-(4,4,5,5-tetramethyl-1,3,2-dioxaborolan-2-yl)phenyl)ethyl)-2-methylpropane-2-sulfinamide

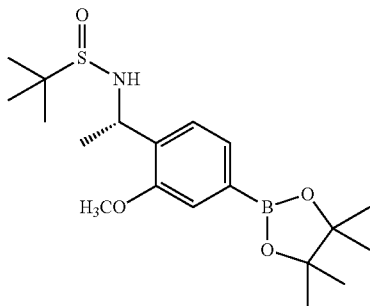 [SMILES: COc1cc(B2OC(C)(C)C(C)(C)O2)ccc1[C@H](C)NS(=O)C(C)(C)C]

To a solution of N—((S)-1-(4-bromo-2-methoxyphenyl)ethyl)-2-methylpropane-2-sulfinamide (175 mg, 0.52 mmol) and bis(pinacolato)diboron (200 mg, 0.79 mmol) in 1,4-dioxane (5 mL) was added Pd(dppf)Cl$_2$ (38 mg, 0.05 mmol) and potassium acetate (154 mg, 1.57 mmol). The resulted solution was stirred at 90° C. under the atmosphere of $N_2$ for 16 h. The volatiles were removed under reduced pressure and the residue was purified by silica gel chromatography (PE:EA=10:1 to 1:1) to give N—((S)-1-(2-methoxy-4-(4,4,5,5-tetramethyl-1,3,2-dioxaborolan-2-yl)phenyl)ethyl)-2-methylpropane-2-sulfinamide (160 mg, 0.4 mmol, 76.8% yield) as a solid. LCMS m/z calcd for $C_{19}H_{33}BNO_4S$ [M+1-1]$^+$: 382.2; Found: 382.3.

Step 4: N—((S)-1-(2-methoxy-4-(4-methylthiazol-5-yl)phenyl)ethyl)-2-methylpropane-2-sulfinamide

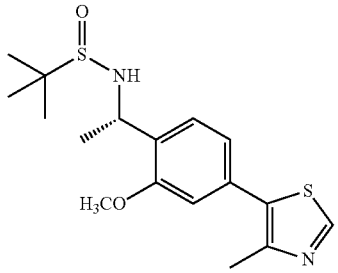 [SMILES: COc1cc(-c2scnc2C)ccc1[C@H](C)NS(=O)C(C)(C)C]

To a solution of N—((S)-1-(2-methoxy-4-(4,4,5,5-tetramethyl-1,3,2-dioxaborolan-2-yl)phenyl)ethyl)-2-methylpropane-2-sulfinamide (100 mg, 0.26 mmol) and 5-bromo-4-methyl-1,3-thiazole (70 mg, 0.39 mmol) in 1,4-dioxane (5 mL) was added Pd(dppf)Cl$_2$ (19 mg, 0.03 mmol) and potassium acetate (77 mg, 0.79 mmol). The resulted solution was stirred at 90° C. under the atmosphere of $N_2$ for 16 h. The volatiles were removed under reduced pressure and the residue was purified by prep-TLC (DCM:MeOH=20:1) to give N—((S)-1-(2-methoxy-4-(4-methylthiazol-5-yl)phenyl)ethyl)-2-methylpropane-2-sulfinamide (50 mg, 0.14 mmol, 52% yield) as a solid. LCMS m/z calcd for $C_{17}H_{25}N_2O_2S_2$[M+H]$^+$: 353.1; Found: 353.3.

Step 5: (S)-1-(2-methoxy-4-(4-methylthiazol-5-yl)phenyl)ethan-1-amine

A solution of N—((S)-1-(2-methoxy-4-(4-methylthiazol-5-yl)phenyl)ethyl)-2-methylpropane-2-sulfinamide (100 mg, 0.28 mmol) in HCl in dioxane (1 M, 1.42 mL, 1.42 mmol) was stirred at rt for 2 h. The volatiles were removed under reduced pressure to give (S)-1-(2-methoxy-4-(4-methylthiazol-5-yl)phenyl)ethan-1-amine (60 mg, 0.24 mmol, 85% yield) as a yellow solid which was used for the next step directly. LCMS m/z calcd for $C_{13}H_{17}N_2OS$ [M+H]$^+$: 249.1; Found: 249.2.

Intermediate 45. (2S,4R)-1-(2-(3-(2-bromoethoxy)isoxazol-5-yl)-3-methylbutanoyl)-4-((tert-butyldimethylsilyl)oxy)-N—((R)-2-((tert-butyldimethylsilyl)oxy)-1-(4-(4-methylthiazol-5-yl)phenyl)ethyl)pyrrolidine-2-carboxamide Int-45

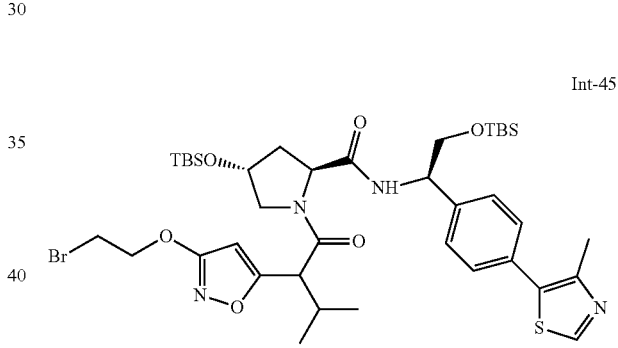

Step 1: tert-butyl (R)-(1-(4-bromophenyl)-2-((tert-butoxycarbonyl)oxy)ethyl)carbamate

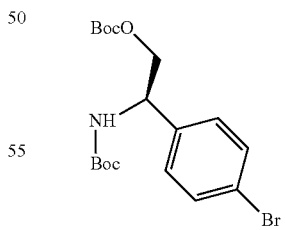

To a solution of (2S)-2-amino-2-(4-bromophenyl)ethanol (1.0 g, 4.6 mmol) in DCM (100 mL) was added di-tert butyl dicarbonate (3.0 g, 13.9 mmol) and triethylamine (3.2 mL, 23.1 mmol). The mixture was stirred at rt for 16 h. The volatiles were removed under reduced pressure and the residue was purified by silica gel chromatography (PE:EA=100:1 to 5:1) to give tert-butyl (R)-(1-(4-bromophenyl)-2-((tert-butoxycarbonyl)oxy)ethyl)carbamate (1.4 g, 3.4 mmol, 72.6% yield) as colorless oil. LCMS m/z calcd for $C_{18}H_{27}BrNO_5$ [M+H]$^+$: 416.1; Found: 416.1.

Step 2: tert-butyl (R)-(2-((tert-butoxycarbonyl)oxy)-1-(4-(4-methylthiazol-5-yl)phenyl)ethyl)carbamate

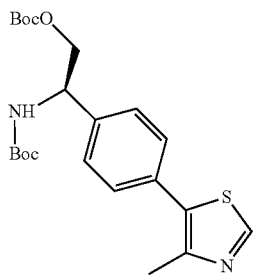

The title compound was prepared using procedure analogous to those described for Int-39, step 2 with appropriate starting materials. LCMS m/z calcd for $C_{22}H_{31}N_2O_5S$ [M+H]$^+$: 435.2; Found: 435.1.

Step 3: (R)-2-amino-2-(4-(4-methylthiazol-5-yl)phenyl)ethan-1-ol

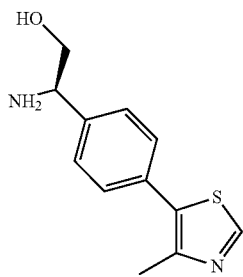 [SMILES: Cc1ncsc1-c1ccc([C@@H](N)CO)cc1]

To a solution of tert-butyl (R)-(2-((tert-butoxycarbonyl)oxy)-1-(4-(4-methylthiazol-5-yl)phenyl)ethyl)carbamate (1.0 g, 2.3 mmol) in DCM (10 mL) was added TFA (10 mL). The mixture was stirred at rt for 2 h. The volatiles were removed under reduced pressure to give (R)-2-amino-2-(4-(4-methylthiazol-5-yl)phenyl)ethan-1-ol (741 mg, 2.2 mmol, 99% yield) as a brown oil. LCMS m/z calcd for $C_{12}H_{15}N_2OS$ [M+H]$^+$: 235.1; Found: 235.2.

Step 4: (R)-2-((tert-butyldimethylsilyl)oxy)-1-(4-(4-methylthiazol-5-yl)phenyl)ethan-1-amine

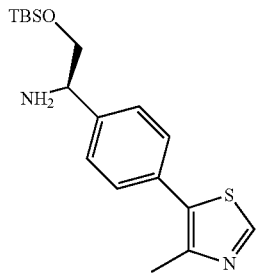 [SMILES: Cc1ncsc1-c1ccc([C@@H](N)CO[Si](C)(C)C(C)(C)C)cc1]

To a solution of (R)-2-amino-2-(4-(4-methylthiazol-5-yl)phenyl)ethan-1-ol (850 mg, 3.63 mmol) in DCM (10 mL) was added imidazole (741 mg, 10.9 mmol) and tert-butyl dimethylchlorosilane (820 mg, 5.44 mmol). The mixture was stirred at rt for 16 h. The reaction mixture was diluted with water and extracted with DCM. The organic layers were combined, dried over MgSO$_4$, filtered and concentrated to dryness. The residue was purified by silica gel chromatography (DCM:MeOH=20:1) to get (R)-2-((tert-butyldimethylsilyl)oxy)-1-(4-(4-methylthiazol-5-yl)phenyl)ethan-1-amine (500 mg, 1.24 mmol, 34.3% yield) as a yellow oil. LCMS m/z calcd for $C_{18}H_{29}N_2OSSi$ [M+H]$^+$: 349.2; Found: 349.2.

Step 5: (2S,4R)-4-((tert-butyldimethylsilyl)oxy)-N—((R)-2-((tert-butyldimethylsilyl)oxy)-1-(4-(4-methylthiazol-5-yl)phenyl)ethyl)-1-(2-(3-hydroxy-isoxazol-5-yl)-3-methylbutanoyl)pyrrolidine-2-carboxamide

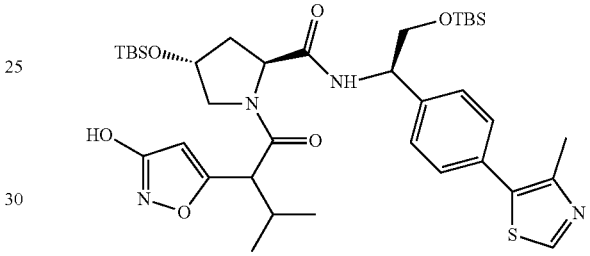

To a stirred solution of (R)-2-((tert-butyldimethylsilyl)oxy)-1-(4-(4-methylthiazol-5-yl)phenyl)ethan-1-amine (360 mg, 1.03 mmol) and (2S,4R)-4-((tert-butyldimethylsilyl)oxy)-1-(2-(3-hydroxyisoxazol-5-yl)-3-methylbutanoyl)pyrrolidine-2-carboxylic acid (639 mg, 1.55 mmol) in DMF (10 mL) was added HATU (141 mg, 2.07 mmol) and DIPEA (0.54 mL, 3.1 mmol) at rt. After 16 h, water (20 ml) was added and the resulted mixture was extracted with EA (20 ml×3). The organic layers were combined, dried over MgSO$_4$, filtered, and concentrated to dryness. The residue was purified by gel chromatography (DCM:MeOH=20:1) to give (2S,4R)-4-((tert-butyldimethylsilyl)oxy)-N—((R)-2-((tert-butyldimethylsilyl)oxy)-1-(4-(4-methylthiazol-5-yl)phenyl)ethyl)-1-(2-(3-hydroxyisoxazol-5-yl)-3-methylbutanoyl)pyrrolidine-2-carboxamide (200 mg, 0.23 mmol, 22.6% yield) as a yellow solid. LCMS m/z calcd for $C_{37}H_{59}N_4O_6SSi_2$ [M+H]$^+$: 743.4; Found: 743.5.

Step 6: (2S,4R)-1-(2-(3-(2-bromoethoxy)isoxazol-5-yl)-3-methylbutanoyl)-4-((tert-butyldimethylsilyl)oxy)-N—((R)-2-((tert-butyldimethylsilyl)oxy)-1-(4-(4-methylthiazol-5-yl)phenyl)ethyl)pyrrolidine-2-carboxamide To a stirred solution of (2S,4R)-4-((tert-butyldimethylsilyl)oxy)-N—((R)-2-((tert-butyldimethylsilyl)oxy)-1-(4-(4-methylthiazol-5-yl)phenyl)ethyl)-1-(2-(3-hydroxyisoxazol-5-yl)-3-methylbutanoyl)pyrrolidine-2-carboxamide (40.0 mg, 0.05 mmol) and 1,2-dibromoethane (15.2 mg, 0.08 mmol) in DMF (10 mL) was added potassium carbonate (0.06 mL, 0.11 mmol) at rt. After 16 h, water (20 ml) was added and the resulted mixture was extracted with EA (20 ml×3). The organic layers were combined, dried over MgSO$_4$, filtered, and concentrated to dryness. The residue was purified by silica gel chromatography column (DCM:MeOH=20:1) to give (2S,4R)-1-(2-(3-(2-bromoethoxy)isoxazol-5-yl)-3-methylbutanoyl)-4-((tert-butyldimethylsilyl)oxy)-N—((R)-2-((tert-butyldimethylsilyl)oxy)-1-(4-(4-methylthiazol-5-yl)phenyl)ethyl)pyrrolidine-2-carboxamide (40.6 mg, 0.048 mmol, 89.2% yield) as a yellow solid. LCMS m/z calcd for $C_{39}H_{62}BrN_4O_6SSi_2[M+H]^+$: 849.3; Found: 849.5.

Intermediate 50. (2S,4R)-1-(2-(3-((1-bromobutan-2-yl)oxy)isoxazol-5-yl)-3-methylbutanoyl)-4-((tert-butyldimethylsilyl)oxy)-N—((S)-1-(4-(4-methylthiazol-5-yl)phenyl)ethyl)pyrrolidine-2-carboxamide

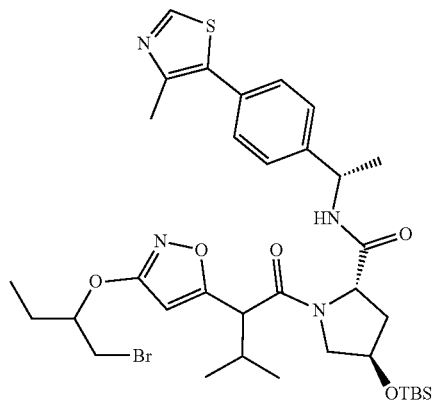

Int-50

The title compound was prepared using procedure analogous to those described for Int-37 with appropriate starting materials. LCMS m/z calcd for $C_{35}H_{52}BrN_4O_5SSi$ $[M+H]^+$: 747.3; Found: 747.3.

Intermediate 52. (2S,4R)-1-((S)-2-(2-(2-chloroethoxy)acetamido)-3,3-dimethylbutanoyl)-4-hydroxy-N—((S)-1-(4-(4-methylthiazol-5-yl)phenyl)ethyl)pyrrolidine-2-carboxamide

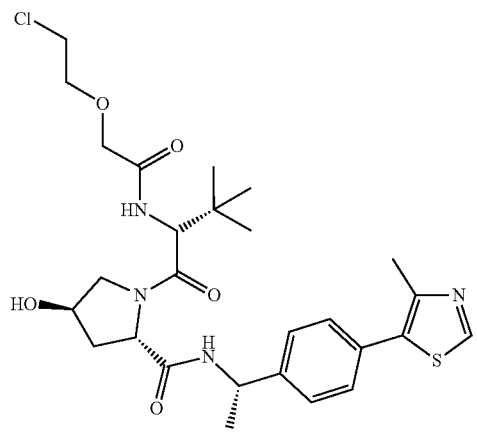

Int-52

To a solution of (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (50 mg, 0.11 mmol) in DMF (2 mL) was added (2-chloroethoxy)acetic acid (18.7 mg, 0.13 mmol), 2-(7-Azabenzotriazol-1-yl)-N,N,N',N'-tetramethyluronium hexafluorophosphate (64 mg, 0.17 mmol) and TEA (0.08 mL, 0.45 mmol). The mixture was stirred at 110° C. for 4 h under the atmosphere of $N_2$. The reaction was quenched with $H_2O$ and extracted with EA (10.0 mL×3). The organic layers were combined, dried over $Na_2SO_4$, filtered and concentrated in vacuo. The residue was purified by prep-TLC (DCM:MeOH=10:1) to give (2S,4R)-1-((S)-2-(2-(2-chloroethoxy)acetamido)-3,3-dimethylbutanoyl)-4-hydroxy-N—((S)-1-(4-(4-methylthiazol-5-yl)phenyl)ethyl)pyrrolidine-2-carboxamide (57 mg, 0.10 mmol, 89.7% yield) as a white solid. LCMS m/z calcd for $C_{27}H_{38}ClN_4O_5S$ $[M+H]^+$: 565.2; Found: 565.0.

Intermediate 59. 3-(2-(2-hydroxyphenyl)-5,6,6a,7,9,10-hexahydro-8H-pyrazino[1',2':4,5]pyrazino[2,3-c]pyridazin-8-yl)propanal

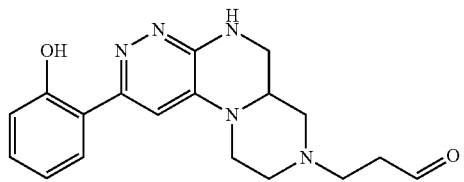

Int-59

Step 1: 2-(8-(2-(1,3-dioxolan-2-yl)ethyl)-6,6a,7,8,9,10-hexahydro-5H-pyrazino[1',2':4,5]pyrazino[2,3-c]pyridazin-2-yl)phenol

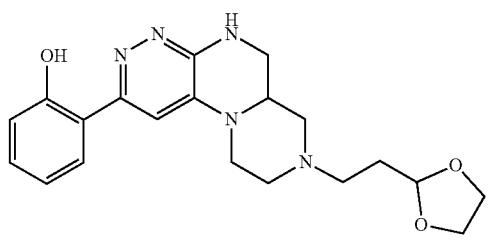 [SMILES: Oc1ccccc1-c1cc2c(nn1)NCC1CN(CCC3OCCO3)CCN21]

To a stirred solution of 2-(6,6a,7,8,9,10-hexahydro-5H-pyrazino[1',2':4,5]pyrazino[2,3-c]pyridazin-2-yl)phenol (60 mg, 0.21 mmol) in DMF (2 mL) was added 2-(2-bromoethyl)-1,3-dioxolane (96 mg, 0.53 mmol) and potassium carbonate (218 mg, 1.58 mmol) at rt. After 2 h, the volatiles were removed and the residue then purified by prep-TLC (EA) to give the desired product (40 mg, 0.10 mmol, 48% yield) as a white solid. LCMS m/z calc'd for $C_{20}H_{26}N_5O_3$ $[M+H]^+$; 384.4; Found: 384.2.

Step 2: 3-(2-(2-hydroxyphenyl)-5,6,6a,7,9,10-hexahydro-8H-pyrazino[1',2':4,5]pyrazino[2,3-c]pyridazin-8-yl)propanal To a stirred solution of 2-(8-(2-(1,3-dioxolan-2-yl)ethyl)-6,6a,7,8,9,10-hexahydro-5H-pyrazino[1',2':4,5]pyrazino[2,3-c]pyridazin-2-yl)phenol (60 mg, 0.16 mmol) in MeCN (2 mL) was added aqueous HCl (1 N, 1 mL) at rt. After 16 h, the reaction mixture was quenched with aqueous $NaHCO_3$ and extracted with EA (30 mL). The organic layer was concentrated to get 3-[4-(2-hydroxyphenyl)-1,5,6,8,12-pentazatricyclo[8.4.0.02,7]tetradeca-2,4,6-trien-12-yl]propanal (35 mg, 0.10 mmol, 65.9% yield). LCMS m/z calcd for C₁₈H₂₂N₅O₂[M+H]⁺: 340.2; Found: 340.1.

Intermediate 60. (2S,4R)-4-hydroxy-1-((2R)-3-methyl-2-(3-(pyrrolidin-3-yloxy)isoxazol-5-yl)butanoyl)-N—((S)-1-(4-(4-methylthiazol-5-yl)phenyl)ethyl)pyrrolidine-2-carboxamide

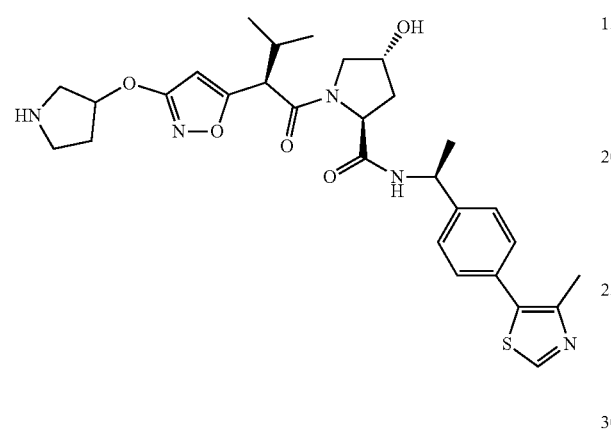

Int-60

Step 1: tert-butyl 34(5-((R)-1-((2S,4R)-4-((tert-butyldimethylsilyl)oxy)-2-(((S)-1-(4-(4-methylthiazol-5-yl)phenyl)ethyl)carbamoyl)pyrrolidin-1-yl)-3-methyl-1-oxobutan-2-yl)isoxazol-3-yl)oxy)pyrrolidine-1-carboxylate

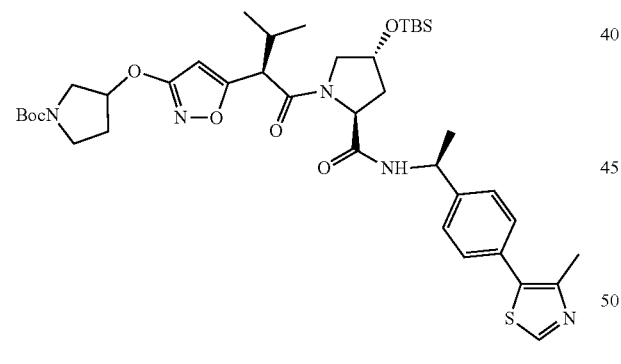

A mixture of (2S,4R)-4-((tert-butyldimethylsilyl)oxy)-1-((R)-2-(3-hydroxyisoxazol-5-yl)-3-methylbutanoyl)-N—((S)-1-(4-(4-methylthiazol-5-yl)phenyl)ethyl)pyrrolidine-2-carboxamide (500 mg, 0.82 mmol) and triphenylphosphine (428 mg, 1.6 mmol) was azeotroped in PhMe. THF (30 mL) was added, followed by the addition of tert-butyl 3-hydroxypyrrolidine-1-carboxylate (306 mg, 1.6 mmol) and DIAD (0.45 mL, 1.63 mmol) at 0° C. The resulted mixture was stirred at 25° C. for 16 h. The volatiles were removed and the residue was purified by silica gel chromatography column (eluting with DCM:MeOH=100:1 to 25:1) to afford the desired product (480 mg, 0.45 mmol, 56.3% yield) as a yellow oil. LCMS m/z calcd for C₄₀H₆₀N₅O₇SSi [M+H]⁺: 782.4; Found: 782.4.

Step 2: (2S,4R)-4-hydroxy-1-((2R)-3-methyl-2-(3-(pyrrolidin-3-yloxy)isoxazol-5-yl)butanoyl)-N—((S)-1-(4-(4-methylthiazol-5-yl)phenyl)ethyl)pyrrolidine-2-carboxamide To a stirred solution of tert-butyl 3-((5-((R)-1-((2S,4R)-4-((tert-butyldimethylsilyl)oxy)-2-(((S)-1-(4-(4-methylthiazol-5-yl)phenyl)ethyl)carbamoyl)pyrrolidin-1-yl)-3-methyl-1-oxobutan-2-yl)isoxazol-3-yl)oxy)pyrrolidine-1-carboxylate (300 mg, 0.29 mmol) in DCM (5 mL) was added TFA (1.9 mL) at 25° C. After 2 h, the volatiles were removed to afford the crude product (400 mg, 0.68 mmol, 100% yield) as a yellow solid. LCMS m/z calcd for C₂₉H₃₈N₅O₅S [M+H]⁺: 568.3; Found: 568.4.

Intermediate 62. tert-butyl 4-formyl-3,6-dihydropyridine-1(2H)-carboxylate

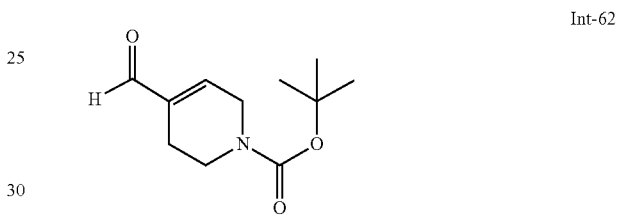

Int-62

To a stirred solution of (methoxymethyl)triphenylphosphonium chloride (1.58 g, 4.6 mmol) in THF (3.0 mL) was added LiHMDS (1 M in THF, 4.6 mL, 4.6 mmol) at 0° C. After 30 mins, tert-butyl 3-fluoro-4-oxopiperidine-1-carboxylate (500 mg, 2.3 mmol) was added. After another 2 h, the reaction was quenched with H₂O (20 mL) and extracted with EA (20 mL×3). The organic layers were combined, dried over Na₂SO₄, filtered and concentrated in vacuo. The residue was purified by silica gel chromatography column (PE:EA=5:1) to give tert-butyl 4-formyl-3,6-dihydro-2H-pyridine-1-carboxylate (370 mg, 1.75 mmol, 76.0% yield) as a colorless oil. LCMS m/z calcd for C₇H₁₀NO₃ [M+H−56]⁺: 156.0; Found: 156.1.

Intermediate 64. 4-((8)-2-(2-hydroxyphenyl)-5,6,6a,7,9,10-hexahydro-8H-pyrazino[1',2':4,5]pyrazino[2,3-c]pyridazin-8-yl)pyrrolidin-3-ol

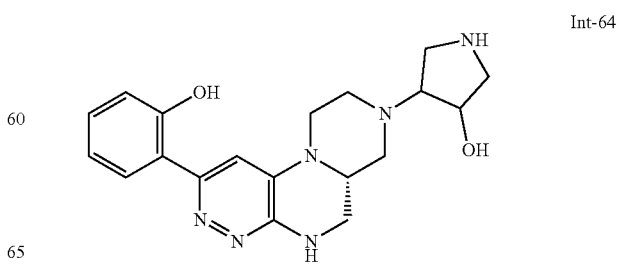

Int-64

Step 1: tert-butyl 3-hydroxy-4-((S)-2-(2-hydroxy-phenyl)-5,6,6a,7,9,10-hexahydro-8H-pyrazino[1',2':4,5]pyrazino[2,3-c]pyridazin-8-yl)pyrrolidine-1-carboxylate

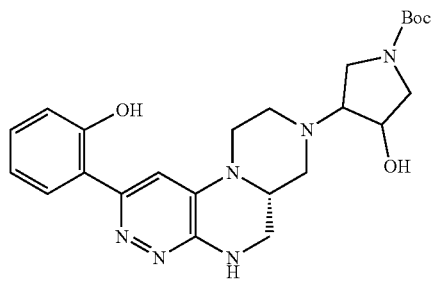 [SMILES: CC(C)(C)OC(=O)N1CC(O)C(N2CCN3c4cc(-c5ccccc5O)nnc4NC[C@H]3C2)C1]

To a solution of (R)-2-(6,6a,7,8,9,10-hexahydro-5H-pyrazino[1',2':4,5]pyrazino[2,3-c]pyridazin-2-yl)phenol (50 mg, 0.18 mmol) in ethanol (5 mL) was added tert-butyl 6-oxa-3-azabicyclo[3.1.0]hexane-3-carboxylate (327 mg, 1.76 mmol) and the solution was stirred at 80° C. for 6 h. The volatiles were removed and the residue was purified by prep-TLC to get the desired product (60 mg, 0.12 mmol, 72.5% yield). LCMS m/z calcd for $C_{24}H_{33}N_6O_4$ $[M+H]^+$: 469.2; Found: 469.2.

Step 2: 4-((S)-2-(2-hydroxyphenyl)-5,6,6a,7,9,10-hexahydro-8H-pyrazino[1',2':4,5]pyrazino[2,3-c]pyridazin-8-yl)pyrrolidin-3-ol To a stirred solution of tert-butyl 3-hydroxy-4-((S)-2-(2-hydroxyphenyl)-5,6,6a,7,9,10-hexahydro-8H-pyrazino[1',2':4,5]pyrazino[2,3-c]pyridazin-8-yl)pyrrolidine-1-carboxylate (60 mg, 0.13 mmol) in DCM (1.5 mL) was added TFA (1 mL) at rt. After 2 h, the volatiles were removed under reduced pressure to give 4-((S)-2-(2-hydroxyphenyl)-5,6,6a,7,9,10-hexahydro-8H-pyrazino[1',2':4,5]pyrazino[2,3-c]pyridazin-8-yl)pyrrolidin-3-ol as its TFA salt (60 mg, 0.16 mmol, 100% yield). LCMS m/z calc'd for $C_{19}H_{25}N_6O_2$ $[M+H]^+$: 369.2; Found: 369.2.

Intermediate 65. 4-((S)-2-(2-hydroxyphenyl)-5,6,6a,7,9,10-hexahydro-8H-pyrazino[1',2':4,5]pyrazino[2,3-c]pyridazin-8-yl)piperidin-3-ol

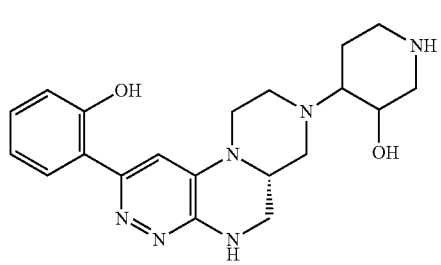

Int-65

The title compound was prepared using a procedure analogous to those described for Int-64 with appropriate starting materials. LCMS m/z calcd for $C_{20}H_{27.6}N_6O_2$ $[M+H]^+$: 383.2; Found: 383.2.

Intermediate 67. (S)-(2-(2-hydroxyphenyl)-5,6,6a,7,9,10-hexahydro-8H-pyrazino[1',2':4,5]pyrazino[2,3-c]pyridazin-8-yl)(piperidin-4-yl)methanone

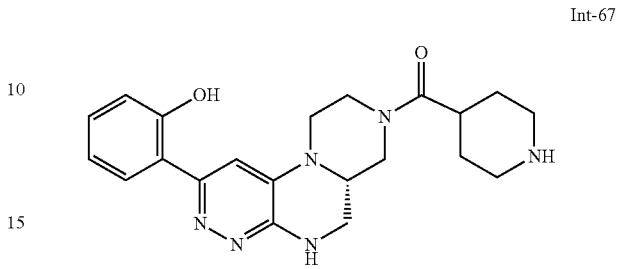

Int-67

Step 1: ter t-butyl (S)-4-(2-(2-hydroxyphenyl)-6,6a,7,8,9,10-hexahydro-5H-pyrazino[1',2':4,5]pyrazino[2,3-c]pyridazine-8-carbonyl)piperidine-1-carboxylate

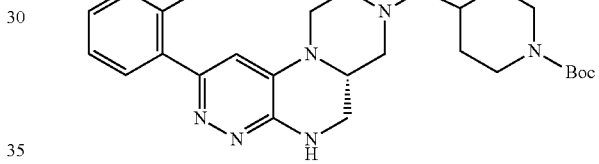

To a stirred solution of (R)-2-(6,6a,7,8,9,10-hexahydro-5H-pyrazino[1',2':4,5]pyrazino[2,3-c]pyridazin-2-yl)phenol (200 mg, 0.71 mmol), 1-(tert-butoxycarbonyl)piperidine-4-carboxylic acid (135 mg, 0.59 mmol) and DIEA (0.29 mL, 1.76 mmol) in DMF (10 mL) was added HATU (671 mg, 1.76 mmol) at 30° C. After 16 h, the volatiles were removed under reduced pressure and the residue was purified by prep-HPLC (eluting with $CH_3CN$ in $H_2O$: (0.1% $NH_3 \cdot H_2O$) from 10% to 95%) to give the desired product (170 mg, 0.33 mmol, 46.4% yield) as a yellow solid. LCMS m/z calcd for $C_{26}H_{35}N_6O_4$ $[M+H]^+$: 495.3; Found: 495.3.

Step 2: (S)-(2-(2-hydroxyphenyl)-5,6,6a,7,9,10-hexahydro-8H-pyrazino[1',2': 4,5]pyrazino[2,3-c]pyridazin-8-yl)(piperidin-4-yl)methanone To a stirred solution of tert-butyl (S)-4-(2-(2-hydroxyphenyl)-6,6a,7,8,9,10-hexahydro-5H-pyrazino[1',2':4,5]pyrazino[2,3-c]pyridazine-8-carbonyl)piperidine-1-carboxylate (170 mg, 0.34 mmol) in DCM (2 mL) was added trifluoroacetic acid (0.5 mL) at rt. After 16 h, the volatiles were removed under reduced pressure and the residue was purified by prep-HPLC (eluting with $CH_3CN$ in $H_2O$: (0.1% $NH_3 \cdot H_2O$) from 10% to 95%) to give the desired product (150 mg, 0.38 mmol, 99% yield) as a white solid. LCMS m/z calcd for $C_{21}H_{27}N_6O_2$ $[M+H]^+$: 395.2; Found: 395.2.

Intermediate 68. 2-(8-(methyl(piperidin-4-yl)amino)-6,6a,7,8,9,10-hexahydro-5H-pyrido[1',2':4,5]pyrazino[2,3-c]pyridazin-2-yl)phenol

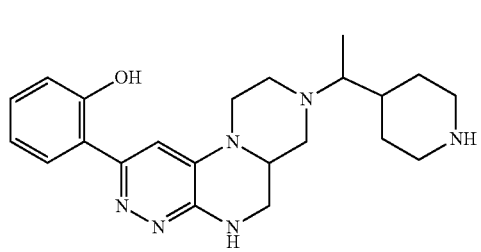

Int-68

Step 1: 1-(tert-butyl) 2-methyl 4-hydroxypiperidine-1,2-dicarboxylate

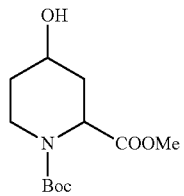

To a stirred solution of 1-(tert-butyl) 2-methyl 4-oxopiperidine-1,2-dicarboxylate (4.9 g, 19.0 mmol) in THF (80 mL) was added L-selectride (1 M, 28.6 mL, 28.6 mmol) at −78° C. After 1 h, the reaction was quenched with aq. NH₄Cl (70 mL) and extracted with EA (100 mL×3). The organic layers were combined, dried over Na₂SO₄, filtered, and concentrated to dryness. The residue was purified by silica gel chromatography column (PE:EA=2:1) to give 1-(tert-butyl) 2-methyl 4-hydroxypiperidine-1,2-dicarboxylate (4.90 g, 18.9 mmol, 99% yield) as a white solid.

Step 2: 1-(tert-butyl) 2-methyl 4-((tert-butyldimethylsilyl)oxy)piperidine-1,2-dicarboxylate

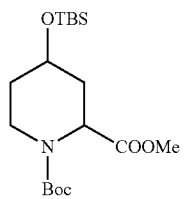 [SMILES: COC(=O)C1CC(O[Si](C)(C)C(C)(C)C)CCN1C(=O)OC(C)(C)C]

To a stirred solution of 1-(tert-butyl) 2-methyl 4-hydroxypiperidine-1,2-dicarboxylate (4.4 g, 17.0 mmol) in DMF (60 mL) was added imidazole (5.8 g, 84.8 mmol) and TBSCl (7.7 g, 50.9 mmol) at 25° C. After 16 h, the reaction was quenched with H₂O (400 mL) and extracted with EA (150 mL×3). The organic layers were combined, dried over Na₂SO₄, filtered, and concentrated to dryness. The residue was purified by silica gel chromatography column (PE:EA=10:1) to give 1-(tert-butyl) 2-methyl 4-((tert-butyldimethylsilyl)oxy)piperidine-1,2-dicarboxylate (5.6 g, 14.9 mmol, 87.5% yield) as a colorless oil. LCMS m/z calcd for $C_{18}H_{35}NNaO_5Si$ [M+Na]⁺: 396.2; Found: 396.5.

Step 3: tert-butyl 4-((tert-butyldimethylsilyl)oxy)-2-(hydroxymethyl)piperidine-1-carboxylate

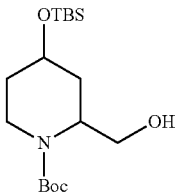 [SMILES: CC(C)(C)OC(=O)N1CCC(O[Si](C)(C)C(C)(C)C)CC1CO]

To a stirred solution of 1-(tert-butyl) 2-methyl 4-((tert-butyldimethylsilyl)oxy)piperidine-1,2-dicarboxylate (5.6 g, 14.9 mmol) in THF (70 mL) was added LiAlH₄ (0.85 g, 22.3 mmol) at 0° C. After 2 h, the reaction was quenched with H₂O (0.90 mL), aqueous NaOH (15%, 0.90 mL), and H₂O (2.70 mL). The resulted mixture was filtered and concentrated under reduced pressure. The residue was purified by silica gel chromatography column (PE:EA=10:1 PE:EA=5:1) to give the desired product (4.0 g, 11.6 mmol, 77.9% yield) as a colorless oil. LCMS m/z calcd for $C_{17}H_{36}NO_4Si$ [M+H]⁺: 346.2; Found [M+H−100]: 246.2.

Step 4: (4-((tert-butyldimethylsilyl)oxy)piperidin-2-yl)methanol

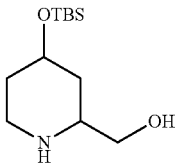 [SMILES: CC(C)(C)[Si](C)(C)OC1CCNC(CO)C1]

To a stirred solution of tert-butyl 4-((tert-butyldimethylsilyl)oxy)-2-(hydroxymethyl)piperidine-1-carboxylate (3.3 g, 9.6 mmol) in DCM (50 mL) was added TFA (15 mL) at 0° C. After 2 h, the volatiles were removed under reduced pressure. The residue was treated with NaOH aqueous (2 N, 30 mL) and extracted with DCM:MeOH=20:1 (30 mL×3). The organic layers were combined, dried over Na₂SO₄, filtered, and concentrated to give the crude product (2.6 g, 8.5 mmol, 89% yield). LCMS m/z calcd for $C_{12}H_{28}NO_2Si$ [M+H]⁺: 246.2; Found: 246.2.

Step 5-8: tert-butyl 8-((tert-butyldimethylsilyl)oxy)-2-chloro-6,6a,7,8,9,10-hexahydro-5H-pyrido[1',2':4,5]pyrazino[2,3-c]pyridazine-5-carboxylate

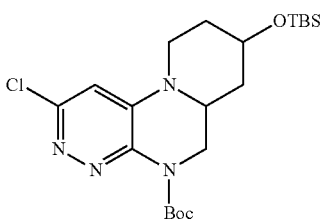 [SMILES: CC(C)(C)OC(=O)N1CC2CC(O[Si](C)(C)C(C)(C)C)CCN2c2cc(Cl)nnc21]

The title compound was prepared using procedure analogous to those described for Int-9, step 1 to step 4 with appropriate starting materials. LCMS m/z calcd for CIII-136ClN$_4$O$_3$Si [M+H]$^+$: 455.2; Found: 455.3.

Step 9: tert-butyl 2-chloro-8-hydroxy-6,6a,7,8,9,10-hexahydro-5H-pyrido[1',2':4,5]pyrazino[2,3-c]pyridazine-5-carboxylate

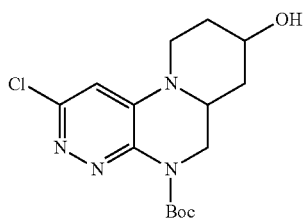 [SMILES: CC(C)(C)OC(=O)N1CC2CC(O)CCN2c2cc(Cl)nnc21]

To a stirred solution of tert-butyl 8-((tert-butyldimethylsilyl)oxy)-2-chloro-6,6a,7,8,9,10-hexahydro-5H-pyrido[1',2':4,5]pyrazino[2,3-c]pyridazine-5-carboxylate (170 mg, 0.37 mmol) in THF (5 mL) was added TBAF (0.75 mL, 0.75 mmol) at 0° C. After 1 h, the reaction was diluted with EA (30 mL) and washed with H$_2$O (20 mL×3) and brine (20 mL). The organic layer was separated, dried over Na$_2$SO$_4$, filtered, and concentrated to dryness. The residue was purified by prep-TLC (DCM:MeOH=20:1) to give the desired product (120 mg, 0.35 mmol, 94.2% yield) as a white solid. LCMS m/z calcd for C$_{15}$H$_{22}$ClN$_4$O$_3$[M+H]$^+$: 341.1; Found: 341.1.

Step 10: tert-butyl 2-chloro-8-oxo-6,6a,7,8,9,10-hexahydro-5H-pyrido[1',2':4,5]pyrazino[2,3-c]pyridazine-5-carboxylate

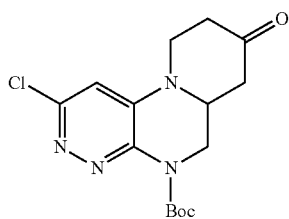 [SMILES: CC(C)(C)OC(=O)N1CC2CC(=O)CCN2c2cc(Cl)nnc21]

To a stirred solution of tert-butyl 2-chloro-8-hydroxy-6,6a,7,8,9,10-hexahydro-5H-pyrido[1',2':4,5]pyrazino[2,3-c]pyridazine-5-carboxylate (110 mg, 0.32 mmol) in DCM (5 mL) was added Dess-Martin periodinane (274 mg, 0.65 mmol) at 0° C. The resulted mixture was stirred at 25° C. for 2 h. The reaction was diluted with DCM (30 mL), washed with aqueous NaHCO$_3$ (20 mL) and brine (20 mL). The organic layer was separated, dried over Na$_2$SO$_4$, filtered, and concentrated to dryness. The residue was purified by prep-TLC (DCM:MeOH=20:1) to give the desired product (100 mg, 0.29 mmol, 91.4% yield) as a white solid. LCMS m/z calcd for C$_{15}$H$_{20}$ClN$_4$O$_3$[M+H]$^+$: 339.1; Found: 339.2.

Step 11: tert-butyl 8-((1-(tert-butoxycarbonyl)piperidin-4-yl)amino)-2-chloro-6,6a,7,8,9,10-hexahydro-5H-pyrido[1',2':4,5]pyrazino[2,3-c]pyridazine-5-carboxylate

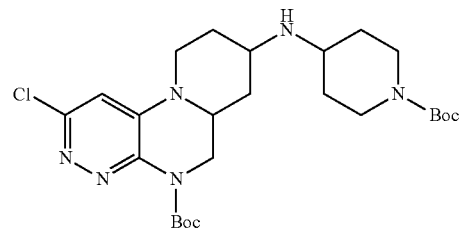 [SMILES: CC(C)(C)OC(=O)N1CCC(NC2CCN3c4cc(Cl)nnc4N(C(=O)OC(C)(C)C)CC3C2)CC1]

To a stirred solution of tert-butyl 2-chloro-8-oxo-6,6a,7,8,9,10-hexahydro-5H-pyrido[1',2':4,5]pyrazino[2,3-c]pyridazine-5-carboxylate (80 mg, 0.24 mmol) in methanol (5.00 mL) was added 4-amino-1-boc-piperidine (47.3 mg, 0.24 mmol), one drop AcOH, and NaBH$_3$CN (29.7 mg, 0.47 mmol) at 25° C. After 3 h, the reaction was diluted with DCM (40 mL) and washed with aqueous NaHCO$_3$ (20 mL) and brine (20 mL). The organic layer was separated, dried over Na$_2$SO$_4$, filtered, and concentrated to dryness. The residue was purified by prep-TLC (DCM:MeOH=20:1) to give the desired product (80 mg, 0.15 mmol, 64.7% yield) as a white solid. LCMS m/z calcd for C$_{25}$H$_{40}$ClN$_6$O$_4$ [M+H]$^+$: 523.3; Found: 523.3.

Step 12: tert-butyl 8-((1-(tert-butoxycarbonyl)piperidin-4-yl)(methyl)amino)-2-chloro-6,6a,7,8,9,10-hexahydro-5H-pyrido[1',2':4,5]pyrazino[2,3-c]pyridazine-5-carboxylate

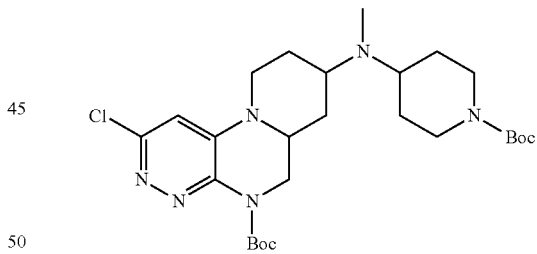

To a stirred solution of tert-butyl 8-((1-(tert-butoxycarbonyl)piperidin-4-yl)amino)-2-chloro-6,6a,7,8,9,10-hexahydro-5H-pyrido[1',2':4,5]pyrazino[2,3-c]pyridazine-5-carboxylate (60 mg, 0.11 mmol) in methanol (3 mL) was added 37 wt % formaldehyde solution in H$_2$O/MeOH (0.02 mL, 0.57 mmol), one drop AcOH, and NaBH$_3$CN (21.6 mg, 0.34 mmol) sequentially at 25° C. After 16 h, the reaction was diluted with DCM (40 mL) and washed with aqueous NaHCO$_3$ (20 mL) and brine (20 mL). The organic layer was separated, dried over Na$_2$SO$_4$, filtered, and concentrated to dryness. The residue was purified by prep-TLC (DCM:MeOH=20:1) to give the desired product (60 mg, 0.11 mmol, 97.3% yield) as a white solid. LCMS m/z calcd for C$_{26}$H$_{41}$ClNaN$_6$O$_4$[M+Na]$^+$: 559.3; Found: 559.3.

Step 13: tert-butyl 84(1-(tert-butoxycarbonyl)piperidin-4-yl)(methyl)amino)-2-(2-hydroxyphenyl)-6,6a,7,8,9,10-hexahydro-5H-pyrido[1',2':4,5]pyrazino[2,3-c]pyridazine-5-carboxylate

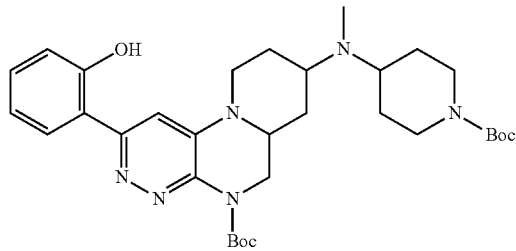 [SMILES: CN(C1CCN(C(=O)OC(C)(C)C)CC1)C1CCN2c3cc(-c4ccccc4O)nnc3N(C(=O)OC(C)(C)C)CC2C1]

To a solution of tert-butyl 8-((1-(tert-butoxycarbonyl)piperidin-4-yl)(methyl)amino)-2-chloro-6,6a,7,8,9,10-hexahydro-5H-pyrido[1',2':4,5]pyrazino[2,3-c]pyridazine-5-carboxylate (100 mg, 0.19 mmol) and 2-hydroxyphenylboronic acid (103 mg, 0.74 mmol) in 1,4-dioxane (8.00 mL) and water (0.80 mL) was added potassium carbonate (129 mg, 0.93 mmol) and Pd(dppf)$_2$Cl$_2$ (15.2 mg, 0.02 mmol) at 25° C. The mixture was stirred at 100° C. for 18 h. The volatiles were removed and the residue was purified by silica gel chromatography column (DCM:MeOH=80:1 DCM:MeOH=30:1) to give the desired product (50 mg, 0.08 mmol, 45.1% yield) as a light yellow solid. LCMS m/z calcd for $C_{32}H_{47}N_6O_5$ [M+H]$^+$: 595.4; Found: 595.4.

Step 14: 2-(8-(methyl(piperidin-4-yl)amino)-6,6a,7,8,9,10-hexahydro-5H-pyrido[1',2':4,5]pyrazino[2,3-c]pyridazin-2-yl)phenol To a stirred solution of tert-butyl 8-((1-(tert-butoxycarbonyl)piperidin-4-yl)(methyl)amino)-2-(2-hydroxyphenyl)-6,6a,7,8,9,10-hexahydro-5H-pyrido[1',2':4,5]pyrazino[2,3-c]pyridazine-5-carboxylate (50 mg, 0.08 mmol) in DCM (3.00 mL) was added TFA (1.5 mL) at 25° C. After 1 h, the volatiles were removed under reduced pressure to give the crude 2-(8-(methyl(piperidin-4-yl)amino)-6,6a,7,8,9,10-hexahydro-5H-pyrido[1',2':4,5]pyrazino[2,3-c]pyridazin-2-yl)phenol (50 mg, 0.07 mmol, 80.7% yield). LCMS m/z calcd for $C_{22}H_{31}N_6O$ [M+H]$^+$: 395.3; Found: 395.3.

Intermediate 69. 2-((6aR,9S)-9-methyl-6,6a,7,8,9,10-hexahydro-5H-pyrazino[1',2':4,5]pyrazino[2,3-c]pyridazin-2-yl)phenol Int-69

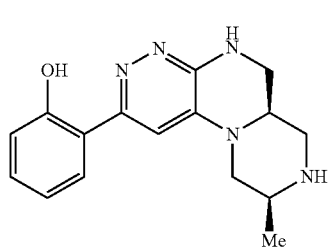

Step 1: methyl O-benzyl-N-(tert-butoxycarbonyl)-L-seryl-L-alaninate

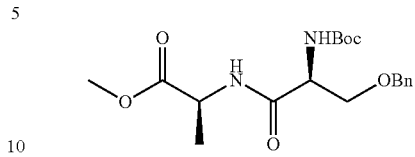

To a stirred suspension solution of O-benzyl-N-(tert-butoxycarbonyl)-L-serine (20.0 g, 67.7 mmol) and 1-hydroxybenzotriazole hydrate (11.0 g, 81.3 mmol) in CH$_2$Cl$_2$ (451 mL) was added DIPEA (14.2 mL, 81.3 mmol) at 0° C. The reaction mixture was added EDCI (15.6 g, 81.3 mmol) and stirred at 0° C. for 15 minutes. Then, the reaction mixture was added to a mixture of L-serine methyl ester hydrochloride (11.3 g, 81.3 mmol) in DIPEA (14.2 mL, 81.3 mmol) and DMF (30 mL) dropwise at 0° C. over 5 minutes. The reaction was warmed up to room temperature and stirred for 3 hours. The reaction was added water (500 mL), and extracted with DCM (300 mL×3). The organic phases were dried over Na$_2$SO$_4$, filtered and concentrated. The residue was purified by flash silica gel column chromatography (ethyl acetate and heptane, 0% to 100%) to give methyl O-benzyl-N-(tert-butoxycarbonyl)-L-seryl-L-alaninate (26.1 g, yield: 99%). LCMS calculated for $C_{19}H_{28}N_2O^6$ (M+H)$^+$: m/z=381.2; found: 381.0.

Step 2: methyl O-benzyl-L-seryl-L-alaninate

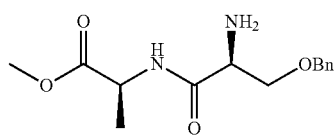 [SMILES: COC(=O)[C@H](C)NC(=O)[C@@H](N)COCc1ccccc1]

To a solution of methyl O-benzyl-N-(tert-butoxycarbonyl)-L-seryl-L-alaninate (26.1 g, 68.6 mmol) in DCM (260 mL) was added TFA (51.4 mL, 672.3 mmol) at room temperature. The reaction was stirred at room temperature for 3 hours. The reaction mixture was basified to between pH 7 and pH 8 via saturated aqueous NaHCO$_3$ solution, extracted with DCM (100 mL×3), and washed with brine (100 mL×1). The combined organic phases were dried over Na$_2$SO$_4$, filtered and concentrated. The residue was directly used for the next step without purification (16.9 g crude). LCMS calculated for $C_{14}H_{20}N_2O_4$ (M+H)$^+$: m/z=281.1; found: 281.0.

Step 3: (3S,6S)-3-((benzyloxy)methyl)-6-methylpiperazine-2,5-dione

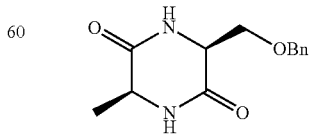

To a solution of methyl O-benzyl-L-seryl-L-alaninate (16.9 g, 60.3 mmol) in dioxane (169 mL) was stirred at 100°

C. for overnight. The reaction was cooled to room temperature (white solid was precipitated out). The white precipitate was filtered, collected, and washed with cold MTBE (100 mL) to give (3S,6S)-3-((benzyloxy)methyl)-6-methylpiperazine-2,5-dione (11 g, yield: 73%).

Step 4:
(2R,5S)-2-((benzyloxy)methyl)-5-methylpiperazine

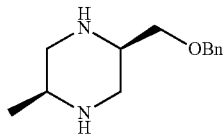 [SMILES: C[C@H]1CN[C@@H](COCc2ccccc2)CN1]

To a solution of (3S,6S)-3-((benzyloxy)methyl)-6-methylpiperazine-2,5-dione (9.0 g, 36.3 mmol) in THF (201 mL) was added borane dimethyl sulfide complex (27.5 mL, 290.0 mmol) under ice-water bath. The reaction was stirred at 60° C. for overnight. The reaction was cooled under ice-water bath, and slowly added MeOH (200 mL). The reaction mixture was warmed up to room temperature, added 1 N HCl aqueous solution to pH 3, and then stirred at 50° C. for 3 hours. The reaction mixture was basified to pH 12 via 1 N NaOH aqueous solution and extracted with $CHCl_3$ (200 mL×3). The combined organic phases were dried over $Na_2SO_4$, filtered and concentrated. The residue was directly used for the next step without purification (9.8 g crude). LCMS calculated for $C_{13}H_{20}N_2O$ (M+H)$^+$: m/z=221.2; found: 221.2.

Step 5: ((2R,5S)-5-methylpiperazin-2-yl)methanol

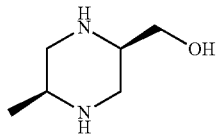

To a solution of (2R,5S)-2-((benzyloxy)methyl)-5-methylpiperazine (0.29 g, 1.3 mmol) in DCM (13 mL) was added 1 M $BCl_3$ in DCM solution (5.2 mL, 5.2 mmol) at 78° C. The reaction was slowly warmed up to room temperature and stirred for overnight. The reaction was cooled under ice-water bath, and slowly added MeOH (10 mL). The reaction mixture was concentrated to dryness. The residue was directly used for the next step without purification (0.23 g crude). LCMS calculated for $C_6H_{14}N_2O$ (M+H)$^+$: m/z=131.1; found: 131.0.

Step 6: di-tert-butyl (2R,5S)-2-(hydroxymethyl)-5-methylpiperazine-1,4-dicarboxylate

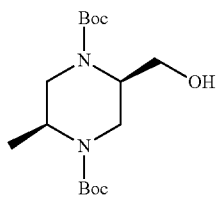 [SMILES: C[C@H]1CN(C(=O)OC(C)(C)C)[C@@H](CO)CN1C(=O)OC(C)(C)C]

To a solution of ((2R,5S)-5-methylpiperazin-2-yl)methanol (9.0 g, 69.1 mmol) in DCM (376 mL) was added TEA (120.0 mL, 864.0 mmol), and di-tert-butyl dicarbonate (45.3 g, 207.0 mmol) at 0° C. The reaction was stirred at room temperature for overnight, and then concentrated to dryness. The residue was directly used for the next step without purification (24.0 g crude). LCMS calculated for $C_{16}H_{30}N_2O_5$ (M+H)$^+$: m/z=331.2; found: 331.0.

Step 7: tert-butyl (2S,5R)-5-(hydroxymethyl)-2-methylpiperazine-1-carboxylate

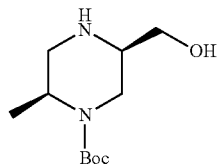 [SMILES: C[C@H]1CN[C@@H](CO)CN1C(=O)OC(C)(C)C]

To a solution of di-tert-butyl (2R,5S)-2-(hydroxymethyl)-5-methylpiperazine-1,4-dicarboxylate (14.0 g, 42.4 mmol) in EtOH (78.5 mL) was added a solution of NaOH (8.5 g, 211.9 mmol) in water (78.5 mL). The reaction mixture was stirred at 80° C. for overnight. The reaction was cooled to room temperature, added 1 N HCl aqueous solution to pH 9, and extracted with $CHCl_3$ (100 mL×3). The combined organic phases were dried over $Na_2SO_4$, filtered and concentrated. The residue was purified by flash silica gel column chromatography (DCM and MeOH with 0.1% TEA, 0% to 10%) to give tert-butyl (2S,5R)-5-(hydroxymethyl)-2-methylpiperazine-1-carboxylate (2.7 g, yield: 28%). LCMS calculated for $C_{11}H_{22}N_2O_3$ (M+H)$^+$: m/z=231.2; found: 231.0.

Step 8-12: di-tert-butyl (6aR,9S)-2-(2-hydroxyphenyl)-9-methyl-6a,7,9,10-tetrahydro-5H-pyrazino[1',2':4,5]pyrazino[2,3-c]pyridazine-5,8(6H)-dicarboxylate

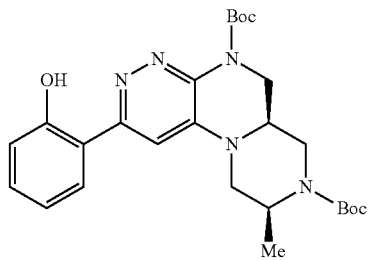 [SMILES: C[C@H]1CN2c3cc(-c4ccccc4O)nnc3N(C(=O)OC(C)(C)C)C[C@H]2CN1C(=O)OC(C)(C)C]

The title compound was prepared using procedure analogous to those described for Int-9, step 1 to step 5, using appropriate starting materials. LCMS calc. for $C_{26}H_{35}N_5O_5$ [M+H]$^+$: m/z=498.3; Found: 498.5.

Step 13: 2-(6aR,9S)-9-methyl-6,6a,7,8,9,10-hexahydro-5H-pyrazino[1',2':4,5]pyrazino[2,3-c]pyridazin-2-yl)phenol (Int-69)

2 M HCl in i-PrOAc (21 mL) was added to di-tert-butyl (6aR,9S)-2-(2-hydroxyphenyl)-9-methyl-6a,7,9,10-tetrahydro-5H-pyrazino[1',2':4,5]pyrazino[2,3-c]pyridazine-5,8

(6H)-dicarboxylate (1.07 g, 2.15 mmol). The reaction was stirred at ambient temperature overnight. The starting material was dissolved initially and precipitated out after 5 min. The solid was filtered off, washed with EtOAc and heptanes in small portions, dried under air-flow to give the desired product, 2-((6aR,9S)-9-methyl-6,6a,7,8,9,10-hexahydro-5H-pyrazino[1',2':4,5]pyrazino[2,3-c]pyridazin-2-yl)phenol (626 mg), as white solid. LCMS calc. for $C_{16}H_{20}N_5O$ [M+H]$^+$: m/z=298.2; Found: 298.0. $^1$H NMR (300 MHz, CDCl$_3$) δ 7.55 (d, J=9.0 Hz, 1H), 7.44 (t, J=6.0 Hz, 1H), 7.30 (s, 1H), 7.04 (t, J=6.0, 2H), 4.25 (dd, J=15.0, 3.0, 1H), 4.10-4.03 (m, 2H), 3.74 (dd, J=12.0, 6.0, 2H), 3.55-3.37 (m, 3H), 1.48 (d, J=6.0, 3H).

SYNTHESIS OF EXAMPLES

The Examples disclosed herein are embodiments of the invention.

Example 1a and 1b. (2S,4R)-4-hydroxy-1-((2S)-2-(2-(2-(2-hydroxyphenyl)-5,6,6a,7,9,10-hexahydro-8H-pyrazino[1',2':4,5]pyrazino[2,3-c]pyridazin-8-yl)acetamido)-3,3-dimethylbutanoyl)-N—((S)-1-(4-(4-methylthiazol-5-yl)phenyl)ethyl)pyrrolidine-2-carboxamide (Ex 1a and Ex 1b)

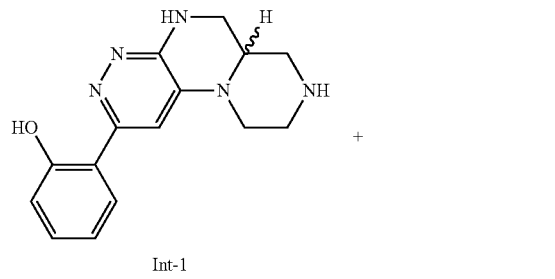

Int-1

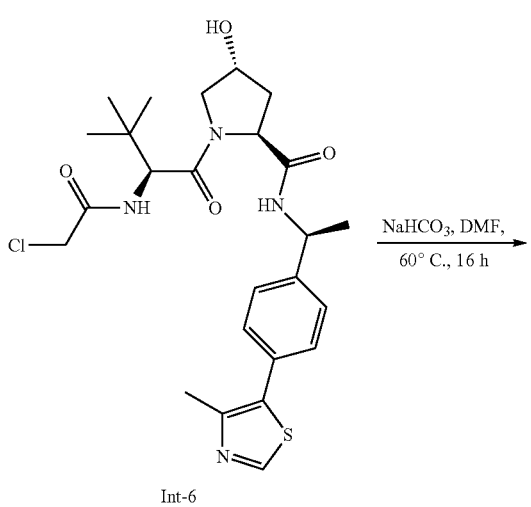

Int-6

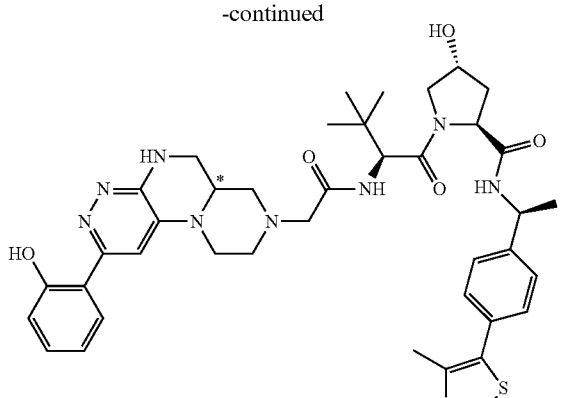

Ex 1a

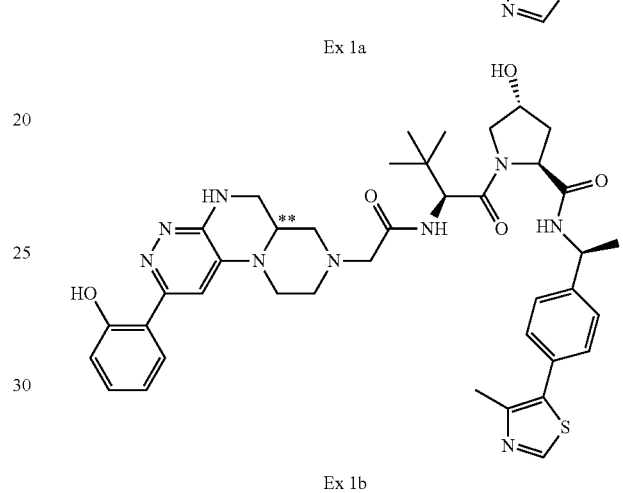

Ex 1b

To a solution of 2-(6,6a,7,8,9,10-hexahydro-5H-pyrazino[1',2':4,5]pyrazino[2,3-c]pyridazin-2-yl)phenol (Int-1) (30 mg, 0.11 mmol) in DMF (5 mL) was added (2S,4R)-1-((S)-2-(2-chloroacetamido)-3,3-dimethylbutanoyl)-4-hydroxy-N—((S)-1-(4-(4-methylthiazol-5-yl)phenyl)ethyl)pyrrolidine-2-carboxamide (Int-6) (55.2 mg, 0.11 mmol) and NaHCO$_3$ (26.7 mg, 0.32 mmol). The mixture was stirred at 60° C. for 18 h. The reaction mixture was concentrated under vacuum, the residue was purified by prep-HPLC, MeCN in H$_2$O (0.1% NH$_4$OH) from 5% to 95% to give (2S,4R)-4-hydroxy-1-((2S)-2-(2-(2-(2-hydroxyphenyl)-5,6,6a,7,9,10-hexahydro-8H-pyrazino[1',2':4,5]pyrazino[2,3-c]pyridazin-8-yl)acetamido)-3,3-dimethylbutanoyl)-N—((S)-1-(4-(4-methylthiazol-5-yl)phenyl)ethyl)pyrrolidine-2-carboxamide (Ex 1a) (12 mg, 0.015 mmol, 14% yield) as a white solid. LCMS calc'd for $C_{40}H_{49}N_9O_5S$: 767.36; Found: LCMS [m/z]: 769.0. $^1$H NMR (DMSO-d$_6$+D$_2$O, 400 MHz): δ 4.73 (s, 1H), 8.98 (s, 1H), 8.41 (s, 1H), 7.94-7.95 (m, 1H), 7.76-7.79 (m, 1H), 7.19-7.44 (m, 9H), 6.85-6.86 (m, 3H), 5.13 (s, 1H), 4.87-4.90 (m, 1H), 4.43-4.53 (m, 2H), 4.30 (s, 1H), 4.08-4.12 (m, 1H), 3.61 (s, 2H), 3.44-3.47 (m, 1H), 2.95-3.21 (m, 8H), 2.33-2.45 (m, 7H), 2.10 (br, 3H), 1.82 (br, 2H), 1.24-1.50 (m, 8H), 0.95 (s, 9H), 0.77 (br, 2H), and (2S,4R)-4-hydroxy-1-((2S)-2-(2-(2-(2-hydroxyphenyl)-5,6,6a,7,9,10-hexahydro-8H-pyrazino[1',2':4,5]pyrazino[2,3-c]pyridazin-8-yl)acetamido)-3,3-dimethylbutanoyl)-N—((S)-1-(4-(4-methylthiazol-5-yl)phenyl)ethyl)pyrrolidine-2-carboxamide (Ex 1b). LCMS calc'd for $C_{40}H_{49}N_9O_5S$: 767.36; Found: LCMS [m/z]: 769.0 $^1$H NMR (DMSO-d$_6$+D$_2$O, 400 MHz): δ 4.73 (s, 1H), 8.98 (s, 1H), 8.41 (s, 1H), 7.94-7.95 (m, 1H), 7.76-7.79 (m, 1H), 7.19-7.44 (m, 8H), 6.85-6.86 (m, 2H), 5.13 (s, 1H), 4.87-4.90 (m, 1H), 4.43-4.53 (m, 2H), 4.30 (s, 1H), 4.12-4.15 (m, 1H), 3.61 (s, 2H), 3.44-3.47 (m, 1H), 2.95-3.21 (m, 8H), 2.33-2.45 (m, 7H), 2.10 (br, 2H), 1.82 (br, 1H), 1.24-1.50 (m, 8H), 0.95 (s, 9H), 0.85 (br, 2H).

The examples in the table below were prepared according to the same method as example 1.

| Ex# | Name | MF | LCMS (M + H) | HNMR |
|---|---|---|---|---|
| Ex 2a | (2S,4R)-4-hydroxy-N-[[4-(5-methyl-1,3-thiazol-4-yl)phenyl]methyl]-1-[(2S)-2-[[2-[4-(2-hydroxyphenyl)-1,5,6,8,12-pentazatricyclo[8.4.0.0²,⁷]tetradeca-2,4,6-trien-12-yl]acetyl]amino]-3,3-dimethylbutanoyl]pyrrolidine-2-carboxamide (Diastereomer 1) | $C_{39}H_{47}N_9O_5S$ | 754.0 | $^1$H NMR(400 MH, MeOD): δ 8.85 (s, 1H), 7.69-7.70 (m, 1H), 7.34-7.46 (m, 6H), 7.18-7.22 (m, 1H), 7.12 (s, 1H), 6.83-6.89 (m, 2H), 4.79 (s, 1H), 4.49-4.60 (m, 4H), 4.29-4.37 (m, 1H), 3.79-3.93 (m, 3H), 3.40-3.63 (m, 3H), 3.21-3.25 (m, 3H), 3.04-3.14 (m, 4H), 2.43-2.48 (m, 3H), 2.39 (s, 3H), 2.05-2.24 (m, 4H), 1.10(s, 11H). |
| Ex 2b | (2S,4R)-4-hydroxy-N-[[4-(5-methyl-1,3-thiazol-4-yl)phenyl]methyl]-1-[(2S)-2-[[2-[4-(2-hydroxyphenyl)-1,5,6,8,12-pentazatricyclo[8.4.0.0²,⁷]tetradeca-2,4,6-trien-12-yl]acetyl]amino]-3,3-dimethylbutanoyl]pyrrolidine-2-carboxamide (Diastereomer 2) | $C_{39}H_{47}N_9O_5S$ | 754.0 | $^1$H NMR(400 MH, MeOD): δ 8.85 (s, 1H), 7.69-7.70 (m, 1H), 7.34-7.46 (m, 6H), 7.12-7.22 (m, 2H), 6.87-6.90 (m, 2H), 4.79 (s, 1H), 4.49-4.60 (m, 6H), 4.29-4.37 (m, 1H), 3.78-4.01 (m, 4H), 3.40-3.63 (m, 4H), 3.14-3.25 (m, 12H), 2.43-2.48 (m, 2H), 2.39 (s, 3H), 2.05-2.24 (m, 4H), 1.10(s, 13H). |
| Ex 6 | (2S,4R)-4-hydroxy-1-((2S)-2-(4-(2-(2-hydroxyphenyl)-5,6,6a,7,9,10-hexahydro-8H-pyrazino[1',2':4,5]pyrazino[2,3-c]pyridazin-8-yl)butanamido)-3,3-dimethylbutanoyl-N-((S)-1-(4-(4-methylthiazol-5-yl)phenyl)ethyl)pyrrolidine-2-carboxamide (Mixture of diastereomers) | $C_{42}H_{53}N_9O_5S$ | 796.3 | $^1$H NMR (400 MHz, MeOD) δ 9.59 (s, 1H), 7.58 (s, 1H), 7.50 (m, 5H), 7.35 (s, 1H), 7.05 (t, 2H), 5.34 (t, J = 10.8 Hz, 1H), 5.02 (m, J = 6.6 Hz, 2H), 4.56 (m, 1H), 4.51 (m, 1H), 4.42 (m, 1H), 4.07 (m, J = 25.5 Hz, 1H), 3.94 (m, 1H), 3.80 (s, 2H), 3.71 (m, 2H), 3.45 (m, 1H), 2.67 (d, J = 20.3 Hz, 2H), 2.56 (s, 3H), 2.21 (m, 2H), 2.11 (m, 2H), 2.03 (d, J = 5.7 Hz, 2H), 1.93 (m, 1H), 1.59 (d, J = 7.5 Hz, 1H), 1.52 (d, J = 5.3 Hz, 3H), 1.06 (d, J = 14.8 Hz, 9H). |
| Ex 7 | 2-(2-(2-hydroxyphenyl)-5,6,6a,7,9,10-hexahydro-8H-pyrazino[1',2':4,5]pyrazino[2,3-c]pyridazin-8-yl)ethyl ((R)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamate | $C_{41}H_{51}N_9O_6S$ | 798.2 | $^1$H NMR(DMSO-d$_6$, 400 MHz): δ 8.99 (s, 1H), 8.38-8.40 (m, 2H), 7.36-7.45 (m, 6H), 7.23 (s, 1H), 7.10 (s, 1H), 6.97-7.05 (m, 2H), 4.89-4.92 (m, 2H), 4.40-4.44 (m, 1H), 4.20-4.29 (m, 5H), 3.58-3.70 (m, 7H), 3.22-3.37 (m, 4H), 2.46 (s, 3H), 2.03-2.04 (m, 1H), 1.79 (s, 1H), 1.36-1.38 (m, 3H), 0.95 (s, 10H). |
| Ex 11 | (2S,4R)-4-hydroxy-1-((S)-2-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)acetamido)-3,3-dimethylbutanoyl)-N-((S)-1-(4-(4-methylthiazol-5-yl)phenyl)ethyl)pyrrolidine-2-carboxamide | $C_{45}H_{58}N_{10}O_5S$ | 851.3 | $^1$H NMR (CD$_3$OD, 400 MHz): δ 8.97 (s, 1H), 7.89-7.91 (m, 1H), 7.35-7.47 (m, 4H), 7.19-7.23 (m, 2H), 6.84-6.88 (m, 2H), 5.92-6.10 (m, 1H), 4.99-5.03 (m, 2H), 4.69 (s, 1H), 4.59-4.44 (m, 3H), 3.93-3.84 (m, 2H), 3.76-3.72 (m, 1H), 3.56-3.54 (m, 1H), 3.12-3.16 (m, 2H), 3.04-2.89 (m, 5H), 2.49-2.34 (m, 5H), 2.27-2.19 (m, 3H), 2.09-2.03 (m, 1H), 1.98-1.88 (m, 3H), 1.69-1.63 (m, 2H), 1.52-1.51 (m, 3H), 1.05 (s, 9H). |

Example 3. (2S,4R)-4-hydroxy-1-((2S)-2-(2-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)acetamido)-3,3-dimethylbutanoyl)-N—((S)-1-(4-(4-methylthiazol-5-yl)phenyl)ethyl)pyrrolidine-2-carboxamide, trihydrochloride (Ex 3)

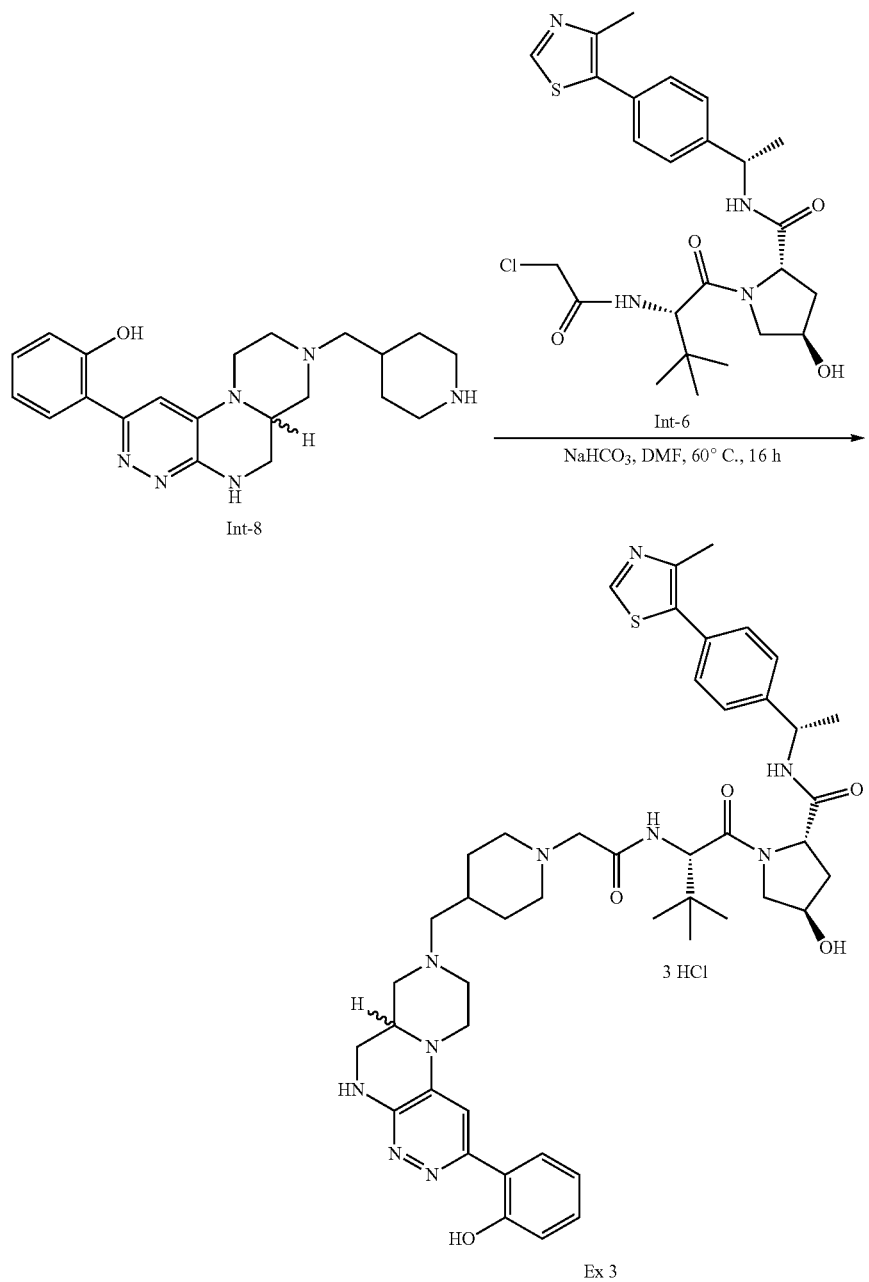 [SMILES: Oc1ccccc1-c1cc2c(nn1)NCC1CN(CC3CCNCC3)CCN21 ; Cc1ncsc1-c1ccc([C@H](C)NC(=O)[C@@H]2C[C@@H](O)CN2C(=O)[C@@H](NC(=O)CCl)C(C)(C)C)cc1 ; Cc1ncsc1-c1ccc([C@H](C)NC(=O)[C@@H]2C[C@@H](O)CN2C(=O)[C@@H](NC(=O)CN2CCC(CN3CCN4c5cc(-c6ccccc6O)nnc5NCC4C3)CC2)C(C)(C)C)cc1]

A mixture of 2-(6,6a,7,8,9,10-hexahydro-5H-pyrazino[1',2':4,5]pyrazino[2,3-c]pyridazin-2-yl)phenol (Int-8) (25 mg, 0.07 mmol) and (2S,4R)-1-((S)-2-(2-chloroacetamido)-3,3-dimethylbutanoyl)-4-hydroxy-N—((S)-1-(4-(4-methylthiazol-5-yl)phenyl)ethyl)pyrrolidine-2-carboxamide (Int-6) (37.7 mg, 0.07 mmol), NaHCO$_3$ (276 mg, 3.3 mmol) in DMF (3 mL) was stirred at 60° C. for 16 h. The reaction mixture was concentrated in vacuum to dryness and the residue was purified by prep-HPLC, eluted with CH$_3$CN in H$_2$O (0.1% HCl from 10% to 95%) to give (2S,4R)-4-hydroxy-1-((2S)-2-(2-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)acetamido)-3,3-dimethylbutanoyl)-N—((S)-1-(4-(4-methylthiazol-5-yl)phenyl)ethyl)pyrrolidine-2-carboxamide, trihydrochloride (Ex 3). (12.0 mg, 0.011 mmol, 16.4% yield) as a light yellow solid. LCMS calc'd for $C_{46}H_{60}N_{10}O_5S$: 864.3; Found: LCMS [m/z]=865.4. $^1$H NMR (400 MHz, CD$_3$OD-d$_4$) δ 9.01-9.03 (m, 1H), 8.47-7.49 (m, 1H), 7.50-7.59 (m, 5H), 7.41-7.45 (m, 1H), 7.36 (s, 1H), 7.03-7.07 (m, 2H), 4.97-5.05 (m, 2H), 4.45-4.66 (m, 4H), 4.26-4.29 (m, 1H), 3.60-4.14 (m, 10H), 3.45-3.52 (m, 3H), 3.01-3.31 (m, 4H), 2.64 (s, 3H), 2.36-2.44 (m, 1H), 2.16-2.35 (m, 2H), 1.90-2.01 (m, 1H), 1.72-1.79 (m, 2H), 1.51-1.63 (m, 3H), 1.01-1.07 (m, 9H).

The examples in the table below were prepared according to the same method as example 3 using appropriate starting materials.

| Ex# | Structure and Name | Calcd. (M + H)$^+$ m/z | Found (M + H)$^+$ m/z | HNMR |
|---|---|---|---|---|
| Ex 8 | 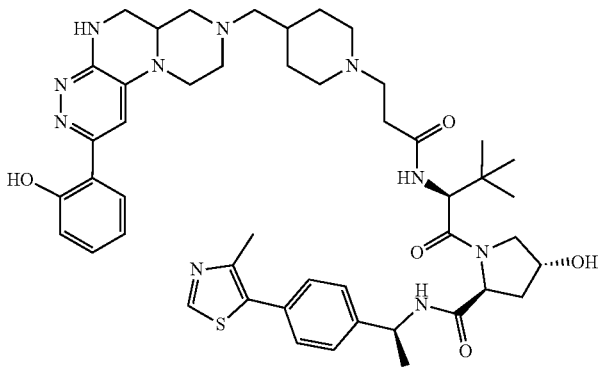 [SMILES: Cc1ncsc1-c1ccc([C@H](C)NC(=O)[C@@H]2C[C@@H](O)CN2C(=O)[C@@H](NC(=O)CCN2CCC(CN3CCN4c5cc(-c6ccccc6O)nnc5NCC4C3)CC2)C(C)(C)C)cc1]<br>(2S,4R)-4-hydroxy-1-((2S)-2-(3-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propanamido)-3,3-dimethylbutanoyl)-N-((S)-1-(4-(4-methylthiazol-5-yl)phenyl)ethyl)pyrrolidine-2-carboxamide | 879.5 | 879.5 | |
| Ex 65 | 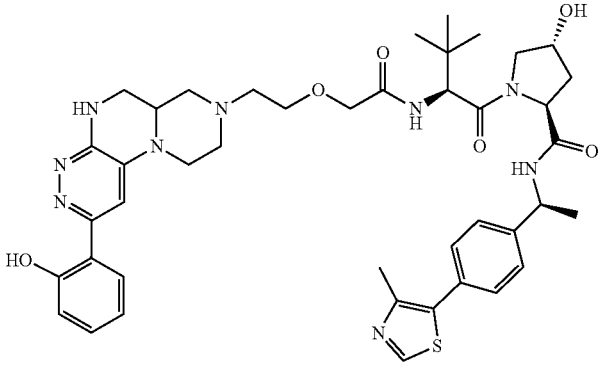 [SMILES: Cc1ncsc1-c1ccc([C@H](C)NC(=O)[C@@H]2C[C@@H](O)CN2C(=O)[C@@H](NC(=O)COCCN2CCN3c4cc(-c5ccccc5O)nnc4NCC3C2)C(C)(C)C)cc1]<br>(2S,4R)-4-hydroxy-1-((2S)-2-(2-(2-(2-(2-hydroxyphenyl)-5,6,6a,7,9,10-hexahydro-8H-pyrazino[1',2':4,5]pyrazino[2,3-c]pyridazin-8-yl)ethoxy)acetamido)-3,3-dimethylbutanoyl)-N-((S)-1-(4-(4-methylthiazol-5-yl)phenyl)ethyl)pyrrolidine-2-carboxamide | 812.4 | 812.1 | $^1$H NMR (400 MHz, CD$_3$OD) δ 8.85 (s, J = 3.4 Hz, 1H), 7.78 (m, J = 38.8 Hz, 1H), 7.45-7.32 (m, 4H), 7.25-7.12 (m, 2H), 6.89 (t, J = 7.2 Hz, 2H), 4.97 (m, J = 7.0 Hz, 1H), 4.71 (s, 1H), 4.55 (m, J = 8.1 Hz, 2H), 4.44 (s, 1H), 4.13-4.06 (dd, 1H), 4.03 (s, 1H), 3.94 (s, 1H), 3.84 (m, J = 11.0 Hz, 1H), 3.77 (m, J = 4.6 Hz, 3H), 3.63-3.51 (m, 2H), 3.08 (m, J = 23.7, 12.0 Hz, 2H), 2.79-2.70 (m, 2H), 2.45 (s, J = 1.1 Hz, 3H), 2.20 (m, J = 7.1 Hz, 1H), 2.00 (dt, J = 21.4, 12.6 Hz, 3H), 1.57 (d, J = 7.2 Hz, 1H), 1.48-1.39 (m, 3H), 1.05 (s, J = 2.0 Hz, 9H) |

| Ex# | Structure and Name | Calcd. (M + H)+ m/z | Found (M + H)+ m/z | HNMR |
|---|---|---|---|---|
| Ex 66 | 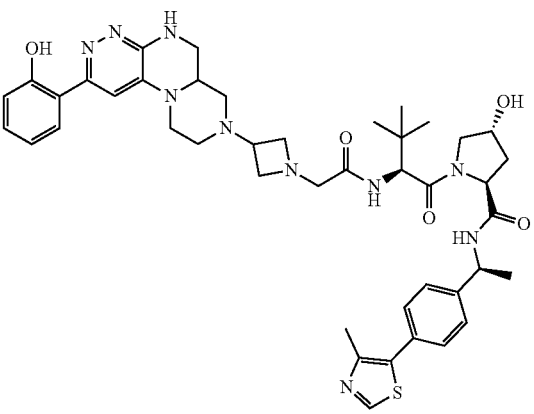 [SMILES: Cc1ncsc1-c1ccc([C@H](C)NC(=O)[C@@H]2C[C@@H](O)CN2C(=O)[C@@H](NC(=O)CN2CC(N3CCN4c5cc(-c6ccccc6O)nnc5NCC4C3)C2)C(C)(C)C)cc1]<br>(2S,4R)-4-hydroxy-1-((2S)-2-(2-(3-(2-(2-hydroxyphenyl)-5,6,6a,7,9,10-hexahydro-8H-pyrazino[1',2':4,5]pyrazino[2,3-c]pyridazin-8-yl)azetidin-1-yl)acetamido)-3,3-dimethylbutanoyl)-N-((S)-1-(4-(4-methylthiazol-5-yl)phenyl)ethyl)pyrrolidine-2-carboxamide | 823.4 | 823.5 | ¹HNMR (CD₃OD, 400 MHz): δ 9.66 (s, 1H), 8.44 (d, J = 8.4 Hz, 1H), 7.99 (s, 1H), 7.52 (m, J = 8.6 Hz, 2H), 7.48 (d, J = 7.9 Hz, 2H), 7.41 (m, J = 7.6 Hz, 1H), 7.19 (s, 1H), 7.03 (t, J = 8.3 Hz, 2H), 5.01 (d, J = 6.7 Hz, 1H), 4.63 (m, J = 5.3 Hz, 1H), 4.55 (t, J = 9.0 Hz, 1H), 4.44 (s, 1H), 4.29 (m, 2H), 4.23 (d, 2H), 3.86 (d, J = 11.7 Hz, 1H), 3.78 (s, 1H), 3.74 (d, J = 7.5 Hz, 1H), 3.72-3.68 (m, 1H), 3.67 (s, 1H), 3.64-3.58 (m, 1H), 3.00 (s, 1H), 2.86 (s, 1H), 2.57 (s, 3H), 2.42-2.34 (m, 1H), 2.21 (m, 2H), 2.02 (d, 1H), 1.93 (m, 1H), 1.62 (d, J = 6.9 Hz, 1H), 1.51 (d, J = 7.2 Hz, 3H), 1.06 (s, 9H). (Some protons were buried under solvent or water peak, not all protons were listed) |
| Ex 79 | 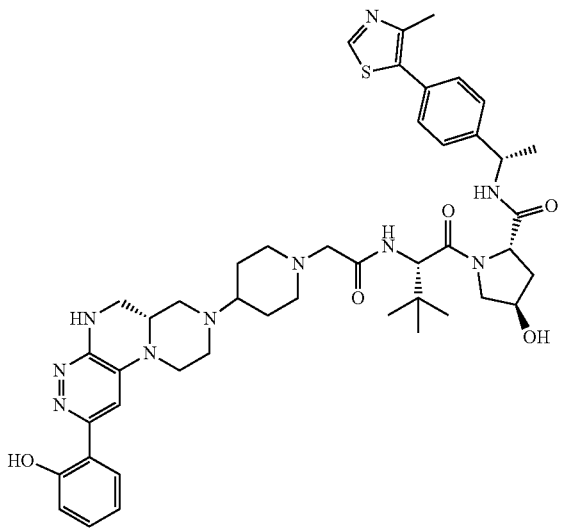 [SMILES: Cc1ncsc1-c1ccc([C@H](C)NC(=O)[C@@H]2C[C@@H](O)CN2C(=O)[C@@H](NC(=O)CN2CCC(N3CCN4c5cc(-c6ccccc6O)nnc5NC[C@@H]4C3)CC2)C(C)(C)C)cc1]<br>(2S,4R)-4-hydroxy-1-((S)-2-(2-(4-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)acetamido)-3,3-dimethylbutanoyl)-N-((S)-1-(4-(4-methylthiazol-5-yl)phenyl)ethyl)pyrrolidine-2-carboxamide | 851.4 | 851.4 | ¹H NMR(DMSO-d₆ + D₂O, 400 MHz): δ 8.97 (s, 1H), 7.89-7.92 (m, 1H), 7.43-7.45 (m, 2H), 7.30-7.38 (m, 2H), 7.16-7.23 (m, 2H), 6.85-6.90 (m, 2H), 4.86-4.91 (m, 1H), 4.38-4.51 (m, 2H), 4.24-4.29 (m, 1H), 3.99-4.04 (m, 1H), 3.19-3.24 (m, 2H), 3.03-3.17 (m, 3H), 2.87-2.95 (m, 4H), 2.46 (s, 3H), 2.22-2.37 (m, 3H), 2.06-2.21 (m, 3H), 1.71-1.84 (m, 4H), 1.46-1.48 (m, 2H), 1.38-1.42 (m, 3H), 1.17-1.23 (m, 2H), 0.97 (s, 9H). |

| Ex# | Structure and Name | Calcd. (M + H)+ m/z | Found (M + H)+ m/z | HNMR |
|---|---|---|---|---|
| Ex 80 | 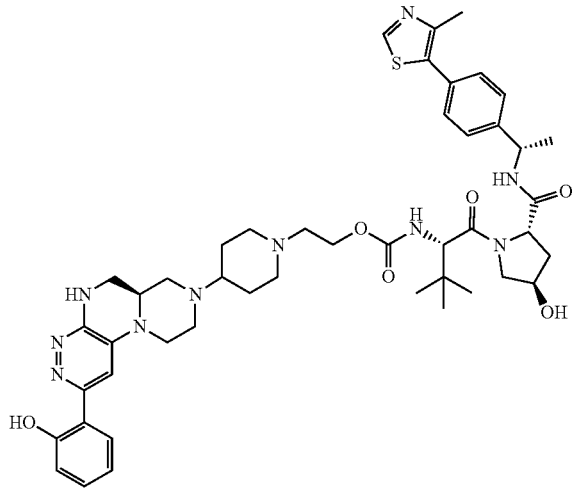 [SMILES: Cc1ncsc1-c1ccc([C@H](C)NC(=O)[C@@H]2C[C@@H](O)CN2C(=O)[C@@H](NC(=O)OCCN2CCC(N3CCN4c5cc(-c6ccccc6O)nnc5NC[C@H]4C3)CC2)C(C)(C)C)cc1]<br>2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl ((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamate | 881.4 | 881.3 | $^1$H NMR (CD$_3$OD, 400 MHz): δ 8.86 (s, 1H), 7.78-7.76 (m, 1H), 7.44-7.39 (m, 4H), 7.23-7.14 (m, 2H), 6.90-6.86 (m, 2H), 5.02-4.97 (m, 2H), 4.58-4.56 (m, 3H), 4.44 (s, 1H), 4.22-4.19 (m, 2H), 3.92-3.54 (m, 4H), 3.19-2.97 (m, 5H), 2.66-2.65 (m, 2H), 2.49-2.34 (m, 5H), 2.19-1.89 (m, 7H), 1.61-1.49 (m, 5H), 1.04 (s, 9H). |

Example 4. (2S,4R)-4-hydroxy-1-((2R)-2-(3-(2-(2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-N—((S)-1-(4-(4-methylthiazol-5-yl)phenyl)ethyl)pyrrolidine-2-carboxamide (Ex 4)

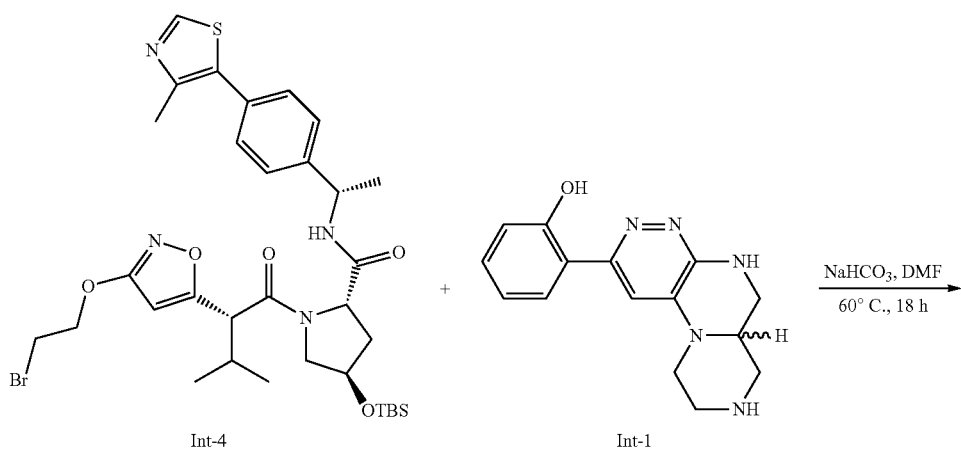

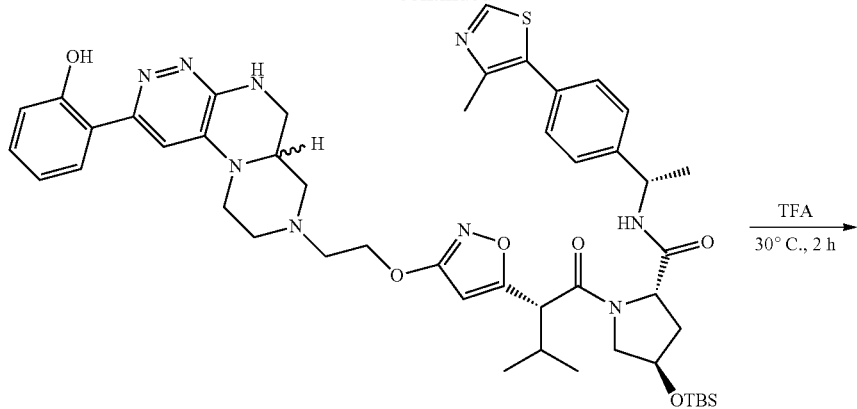

17

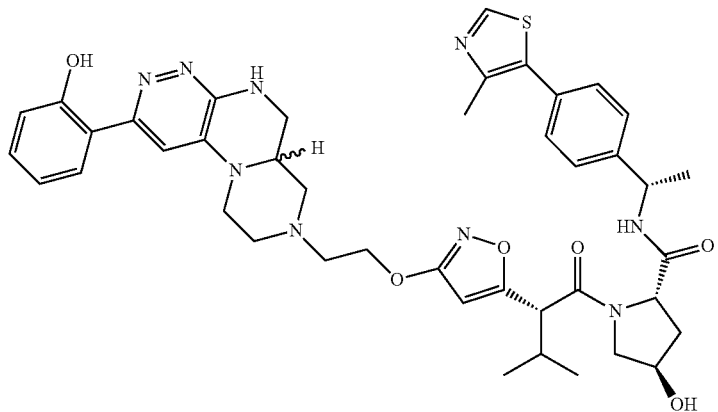

Ex 4

Step a. Synthesis of (2S,4R)-4-((tert-butyldimethyl-silyl)oxy)-1-((2R)-2-(3-(2-(2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-N—((S)-1-(4-(4-methylthiazol-5-yl)phenyl)ethyl)pyrrolidine-2-carboxamide (17)

To a solution of 2-(6,6a,7,8,9,10-hexahydro-5H-pyrazino[1',2':4,5]pyrazino[2,3-c]pyridazin-2-yl)phenol (Int-1) (22.0 mg, 0.06 mmol) and (2S,4R)-1-((R)-2-(3-(2-bromoethoxy)isoxazol-5-yl)-3-methylbutanoyl)-4-((tert-butyldimethylsilyl)oxy)-N—((S)-1-(4-(4-methylthiazol-5-yl)phenyl)ethyl)pyrrolidine-2-carboxamide (Int-4) (30 mg, 0.04 mmol) in DMF (3 mL) was added NaHCO$_3$ (36.0 mg, 0.4 mmol) at rt, the mixture was stirred at 60° C. for 16 h. The reaction was taken up in EtOAc (20 ml) and the organics were washed with water (20 mL×3) and brine (20 mL). The organics were then separated and dried (MgSO$_4$) before concentration in vacuum to dryness. The crude product was then purified by prep-HPLC (0.1% HCl, MeCN in water from 10%-90%) to give (2S,4R)-4-((tert-butyldimethylsilyl)oxy)-1-((2R)-2-(3-(2-(2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-N—((S)-1-(4-(4-methylthiazol-5-yl)phenyl)ethyl)pyrrolidine-2-carboxamide (17) (15 mg, 0.02 mmol, 31% yield) as a sticky colorless solid. LCMS calc'd for C$_{48}$H$_{63}$N$_9$O$_6$SSi: 921.4; Found: LCMS [M+H]: 922.5.

Step b. Synthesis of (2S,4R)-4-hydroxy-1-((2R)-2-(3-(2-(2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-N—((S)-1-(4-(4-methylthiazol-5-yl)phenyl)ethyl)pyrrolidine-2-carboxamide (Ex 4)

To a solution of (2S,4R)-4-((tert-butyldimethylsilyl)oxy)-1-((2R)-2-(3-(2-(2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-N—((S)-1-(4-(4-methylthiazol-5-yl)phenyl)ethyl)pyrrolidine-2-carboxamide (17) (15.0 mg, 0.02 mmol) in TFA (1.0 mL, 13 mmol). The solution was stirred at 50° C. for 2 h. The solution was concentrated, the residue was purified by prep-HPLC (eluted with H$_2$O:CH$_3$CN (0.1% NH$_4$OH) from 10%-90%) to give (2S,4R)-4-hydroxy-1-((2R)-2-(3-(2-(2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-N—((S)-1-(4-(4-methylthiazol-5-yl)phenyl)ethyl)pyrrolidine-2-carboxamide (Ex 4). (7.2 mg, 0.01 mmol, 52% yield) as a white solid. LCMS calc'd for C$_{42}$H$_{49}$N$_9$O$_6$S: 807.35; Found: LCMS [M+H]: 808.0. $^1$H NMR (400 MHz, MeOD): δ 8.87 (s, 1H), 7.76-7.78 (m, 1H), 7.36-7.45 (m, 4H), 7.15-7.23 (m, 2H), 6.87-6.90 (m, 2H), 5.97-6.03 (m, 1H), 5.00-5.04 (m, 1H), 4.37-4.51 (m, 4H), 3.48-3.95 (m, 5H), 2.86-3.29 (m, 5H), 2.48-2.51 (m, 3H), 1.90-2.45 (m, 5H), 1.49-1.65 (m, 3H), 1.01-1.10 (m, 3H), 0.80-0.90 (m, 3H).

Example 4a. (2S,4R)-4-hydroxy-1-((R)-2-(3-(2-((S)-2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-N—((S)-1-(4-(4-methylthiazol-5-yl)phenyl)ethyl)pyrrolidine-2-carboxamide 5H), 2.86-3.29 (m, 6H), 2.48-2.51 (m, 3H), 1.90-2.45 (m, 5H), 1.49-1.65 (m, 3H), 1.01-1.10 (m, 3H), 0.80-0.90 (m, 3H).

Example 4b. (2S,4R)-4-hydroxy-1-((R)-2-(3-(2-((R)-2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-N—((S)-1-(4-(4-methylthiazol-5-yl)phenyl)ethyl)pyrrolidine-2-carboxamide

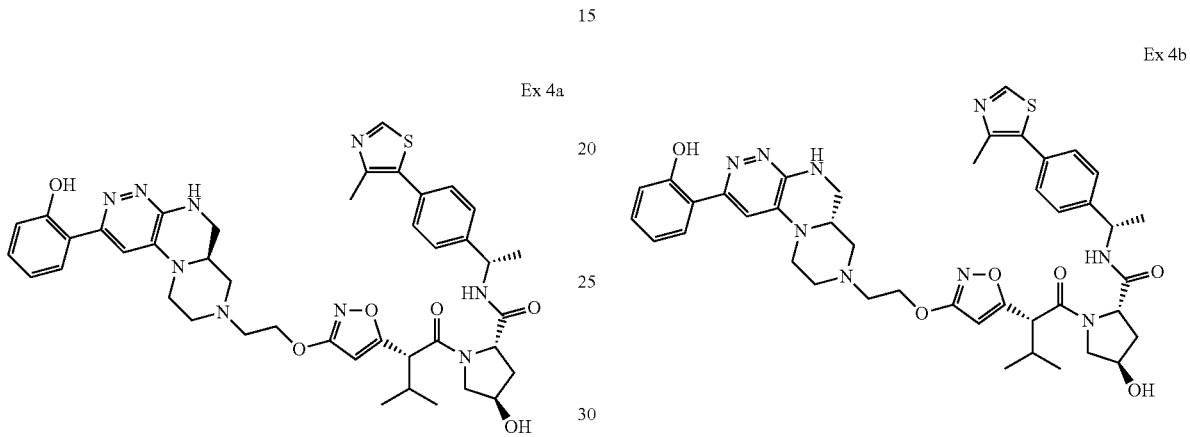

Ex 4a

Ex 4b

The title compound was prepared using procedure analogous to those described for example 4 with appropriate starting materials. LCMS m/z calcd for $C_{42}H_{50}N_9O_6S$ [M+H]$^+$: 808.4; Found: 808.1. $^1$H NMR (400 MHz, CD$_3$OD): δ 8.84 (s, 1H), 7.74-7.76 (m, 1H), 7.34-7.45 (m, 4H), 7.10-7.23 (m, 2H), 6.87-6.90 (m, 2H), 5.97-6.03 (m, 1H), 5.00-5.04 (m, 1H), 4.37-4.51 (m, 4H), 3.46-3.90 (m, The title compound was prepared using procedure analogous to those described for example 4 with appropriate starting materials. LCMS m/z calcd for $C_{42}H_{50}N_9O_6S$ [M+H]$^+$: 808.4; Found: 808.0.

Example 5. (2S,4R)-4-hydroxy-1-((2S)-2-(3-(2-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide (Ex 5)

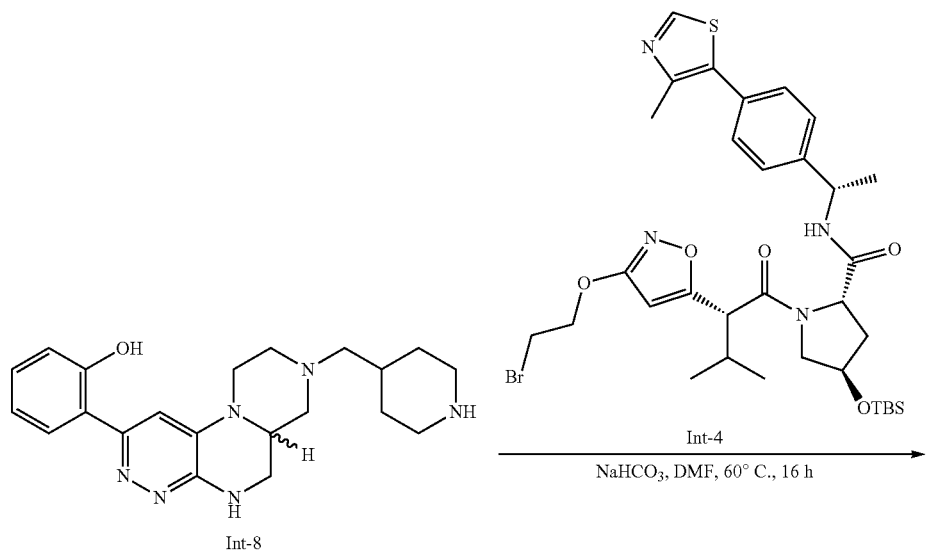

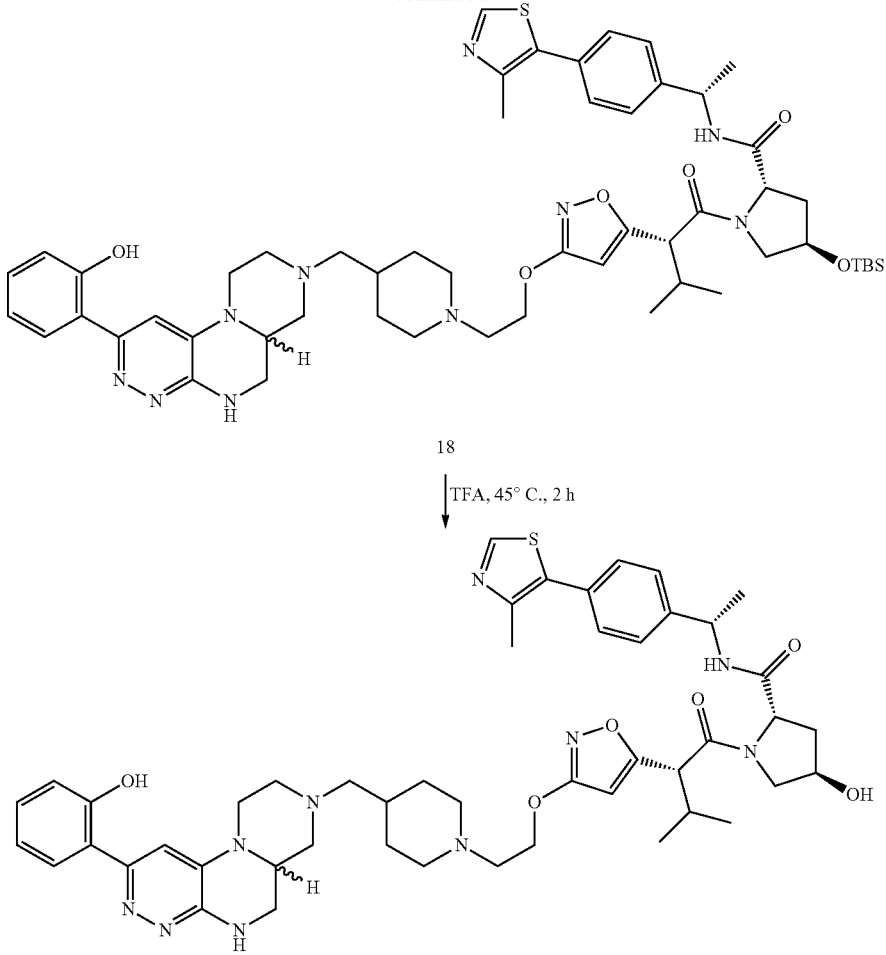

Step a. Synthesis of (2S,4R)-4-((tert-butyldimethyl-silyl)oxy)-1-((2R)-2-(3-(2-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide (18)

To a solution of (2S,4R)-1-((R)-2-(3-(2-bromoethoxy) isoxazol-5-yl)-3-methylbutanoyl)-4-((tert-butyldimethylsi-lyl)oxy)-N—((S)-1-(4-(4-methylthiazol-5-yl)phenyl)ethyl) pyrrolidine-2-carboxamide (Int-4) (55.8 mg, 0.08 mmol) and 2-(8-(piperidin-4-ylmethyl)-6,6a,7,8,9,10-hexahydro-5H-pyrazino[1',2':4,5]pyrazino[2,3-c]pyridazin-2-yl)phenol (Int-8) (25 mg, 0.07 mmol) in DMF (3 mL) were added NaHCO₃ (55.2 mg, 0.66 mmol) and sodium iodide (0.48 mg, 0.003 mmol) at rt, the mixture solution was stirred at 60° C. for 16 h. The residue was extracted with EtOAc (10 mL) and the organics were washed with water (30 mL×2) and saturated brine (30 ml). The organics were then separated and dried over MgSO₄ before concentration to dryness. The crude product was then purified by prep-TLC (PE:EtOAc=1:2) to give (2S,4R)-4-[tert-butyl(dimethyl)silyl]oxy-1-[(2R)-2-[3-[2-[4-[[4-(2-hydroxyphenyl)-1,5,6,8,12-pentazatricy-clo[8.4.0.02,7]tetradeca-2(7),3,5-trien-12-yl]methyl] piperidin-1-yl]ethoxy]-1,2-oxazol-5-yl]-3-methylbutanoyl]-N-[(1S)-1-[4-(4-methyl-1,3-thiazol-5-yl)phenyl]ethyl] pyrrolidine-2-carboxamide (18) (50 mg, 0.05 mmol, 75% yield) as a solid. LCMS calc'd for $C_{54}H_{74}N_{10}O_6SSi$: 1018.4; Found: LCMS [M+H]: 1019.6.

Step b. Synthesis of (2S,4R)-4-hydroxy-1-((2S)-2-(3-(2-(4-((2-(2-hydroxyphenyl)-5,6,6a,7,9,10-hexa-hydro-8H-pyrazino[1',2':4,5]pyrazino[2,3-c] pyridazin-8-yl)methyl)piperidin-1-yl)ethoxy) isoxazol-5-yl)-3-methylbutanoyl)-N—((S)-1-(4-(4-methylthiazol-5-yl)phenyl)ethyl)pyrrolidine-2-carboxamide (Ex 5)

A solution of (2S,4R)-4-[tert-butyl(dimethyl)silyl]oxy-1-[(2R)-2-[3-[2-[4-[[4-(2-hydroxyphenyl)-1,5,6,8,12-pentaza-tricyclo[8.4.0.02,7]tetradeca-2(7),3,5-trien-12-yl]methyl]pi-peridin-1-yl]ethoxy]-1,2-oxazol-5-yl]-3-methylbutanoyl]-N-[(1S)-1-[4-(4-methyl-1,3-thiazol-5-yl)phenyl]ethyl] pyrrolidine-2-carboxamide (18) (50 mg, 0.05 mmol) in trifluoroacetic acid (1.5 mL, 20 mmol) was stirred at 45° C. for 2 h. The mixture solution was concentrated, the residue was purified by prep-HPLC, eluted with CH₃CN in H₂O (0.1% HCl) from 10% to 95%) to give (2S,4R)-4-hydroxy-1-[(2R)-2-[3-[2-[4-[[4-(2-hydroxyphenyl)-1,5,6,8,12-pen-tazatricyclo[8.4.0.02,7]tetradeca-2(7),3,5-trien-12-yl] methyl]piperidin-1-yl]ethoxy]-1,2-oxazol-5-yl]-3- methylbutanoyl]-N-[(1S)-1-[4-(4-methyl-1,3-thiazol-5-yl)phenyl]ethyl]pyrrolidine-2-carboxamide; trihydrochloride (Ex. 6) (21 mg, 0.02 mmol, 38% yield) as a yellow solid. LCMS calc'd for $C_{48}H_{60}N_{10}O_6S$: 904.4; Found: LCMS [M+H]: 905.5. $^1$H NMR (400 MHz, MeOD): δ 10.00 (s, 1H), 7.36-7.58 (m, 7H), 7.02-7.06 (m, 2H), 6.06-6.11 (m, 1H), 5.02-5.05 (m, 1H), 4.23-4.64 (m, 6H), 3.62-3.96 (m, 11H), 3.31-3.50 (m, 2H), 3.18-3.29 (m, 4H), 2.56 (s, 3H), 1.72-2.45 (m, 8H), 1.49-1.65 (m, 3H), 1.01-1.10 (m, 3H), 0.80-0.90 (m, 3H). The examples in the table below were prepared according to the same method as example 5 using appropriate starting materials.

| Ex# | Structure and Name | Calcd. (M + H)+ m/z | Found (M + H)+ m/z | HNMR |
|---|---|---|---|---|
| Ex 9 | 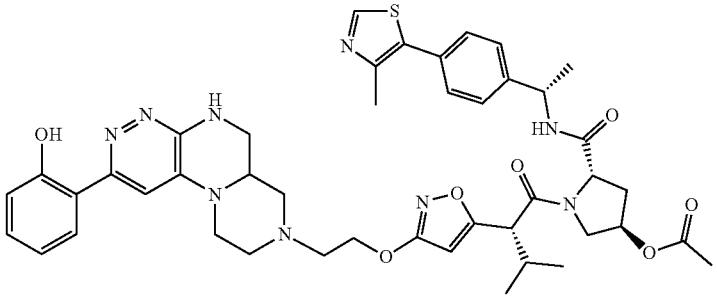 [SMILES: CC(=O)O[C@@H]1C[C@@H](C(=O)N[C@@H](C)c2ccc(-c3scnc3C)cc2)N(C(=O)[C@@H](c2cc(OCCN3CCN4c5cc(-c6ccccc6O)nnc5NCC4C3)no2)C(C)C)C1]<br>(3R,5S)-1-((2R)-2-(3-(2-(2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-5-(((S)-1-(4-(4-methylthiazol-5-yl)phenyl)ethyl)carbamoyl)pyrrolidin-3-yl acetate | 850.4 | 850.4 | $^1$HNMR (CD3OD, 400 MHz): δ 9.28-9.21 (m, 1H), 7.57-7.55 (m, 1H), 7.50-7.41 (m, 5H), 7.35-7.33 (m, 1H), 7.07-7.02 (m, 2H), 6.13-6.08 (m, 1H), 5.29-5.24 (m, 1H), 5.04-5.03 (m, 2H), 4.72-4.67 (m, 2H), 4.53-4.49 (m, 2H), 4.13-4.10 (m, 1H), 3.94-3.69 (m, 8H), 3.49-3.42 (m, 1H), 3.05-2.86 (m, 2H), 2.52-2.49 (m, 3H), 2.39-2.33 (m, 2H), 1.61-1.51 (m, 3H), 1.31-1.28 (m, 1H), 1.17-1.05 (m, 9H), 0.94-0.89 (m, 3H). |
| Ex 10 | 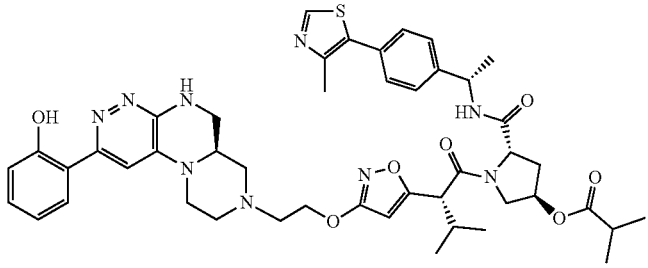 [SMILES: Cc1ncsc1-c1ccc([C@H](C)NC(=O)[C@@H]2C[C@@H](OC(=O)C(C)C)CN2C(=O)[C@@H](c2cc(OCCN3CCN4c5cc(-c6ccccc6O)nnc5NC[C@H]4C3)no2)C(C)C)cc1]<br>(3R,5S)-1-((R)-2-(3-(2-((S)-2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-5-(((S)-1-(4-(4-methylthiazol-5-yl)phenyl)ethyl)carbamoyl)pyrrolidin-3-yl isobutyrate | 878.4 | 878.5 | $^1$HNMR (CD3OD, 400 MHz): δ 9.28-9.21 (m, 1H), 7.57-7.55 (m, 1H), 7.50-7.41 (m, 5H), 7.35-7.33 (m, 1H), 7.07-7.02 (m, 2H), 6.13-6.08 (m, 1H), 5.29-5.24 (m, 1H), 5.04-5.03 (m, 2H), 4.72-4.67 (m, 3H), 4.53-4.49 (m, 2H), 4.13-4.10 (m, 1H), 3.94-3.69 (m, 8H), 3.49-3.42 (m, 1H), 3.05-2.86 (m, 2H), 2.52-2.49 (m, 3H), 2.39-2.33 (m, 2H), 1.61-1.51 (m, 3H), 1.31-1.28 (m, 1H), 1.17-1.05 (m, 9H), 0.94-0.89 (m, 3H). |

-continued

| Ex# | Structure and Name | Calcd. (M + H)+ m/z | Found (M + H)+ m/z | HNMR |
|---|---|---|---|---|
| Ex 12 | 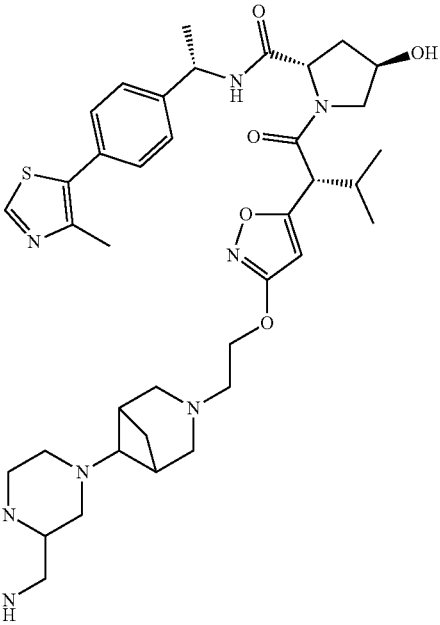<br>(2S,4R)-4-hydroxy-1-((2R)-2-(3-(2-(6-(2-(2-hydroxyphenyl)-5,6,6a,7,9,10-hexahydro-8H-pyrazino[1',2':4,5]pyrazino[2,3-c]pyridazin-8-yl)-3-azabicyclo[3.1.1]heptan-3-yl)ethoxy)isoxazol-5-yl)-3-methylbutanoyl)-N-((S)-1-(4-(4-methylthiazol-5-yl)phenyl)ethyl)pyrrolidine-2-carboxamide | 903.4 | 903.3 | 1HNMR(CD3OD-d4, 400 MHz) δ 8.84-8.80 (m, 1H), 7.79-7.75 (m, 1H), 7.47-7.45 (m, 4H), 7.42-7.37 (m, 2H), 6.94-6.95 (m, 2H), 5.97-5.95 (m, 1H), 5.03-5.00 (m, 2H), 4.51-4.50 (m, 4H), 4.49-4.35 (m, 3H), 3.69-3.67 (m, 1H), 3.53-3.51 (m, 3H), 3.49-3.45 (m, 1H), 3.08-3.05 (m, 6H), 2.99-2.88 (m, 2H), 2.47 (m, 6H), 2.45-2.41 (m, 1H), 2.15-2.11 (m, 2H), 1.94-1.90 (m, 2H), 1.72-1.70 (m, 2H), 1.49-1.47 (m, 3H), 1.09-1.06 (m, 3H), 0.92-0.83 (m, 3H). |
| Ex 13 | 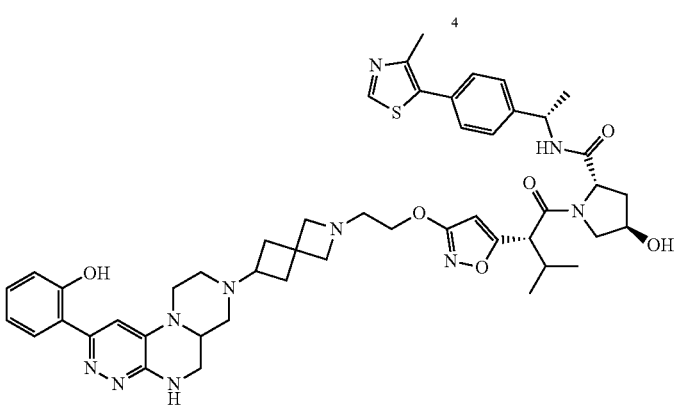 [SMILES: Cc1ncsc1-c1ccc([C@H](C)NC(=O)[C@@H]2C[C@@H](O)CN2C(=O)[C@@H](c2cc(OCCN3CC4(CC(N5CCN6c7cc(-c8ccccc8O)nnc7NCC6C5)C4)C3)no2)C(C)C)cc1]<br>(2S,4R)-4-hydroxy-1-((2R)-2-(3-(2-(6-(2-(2-hydroxyphenyl)-5,6,6a,7,9,10-hexahydro-8H-pyrazino[1',2':4,5]pyrazino[2,3-c]pyridazin-8-yl)-2-azaspiro[3.3]heptan-2-yl)ethoxy)isoxazol-5-yl)-3-methylbutanoyl)-N-((S)-1-(4-(4-methylthiazol-5-yl)phenyl)ethyl)pyrrolidine-2-carboxamide | 903.4 | 903.3 | 1H NMR (DMSO-d6, 400 MHz): δ 14.75 (s, 1H), 8.99 (s, 1H), 8.42-8.44 (m, 1H), 7.91-7.92 (m, 1H), 7.43-7.46 (m, 2H), 7.35-7.39 (m, 3H), 7.18-7.22 (m, 1H), 6.83-6.87 (m, 2H), 6.07 (s, 1H), 5.11-5.12 (m, 1H), 4.88-4.91 (m, 1H), 4.37 (s, 1H), 4.28 (s, 1H), 3.93-4.06 (m, 4H), 3.76-3.82 (m, 2H), 3.63-3.66 (m, 1H), 3.45-3.48 (m, 1H), 3.09-3.12 (m, 1H), 2.87-2.92 (m, 3H), 2.62-2.67 (m, 4H), 2.46 (s, 3H), 2.18-2.24 (m, 3H), 2.03-2.05 (m, 1H), 1.87-1.95 (m, 4H), 1.78-1.80 (m, 1H), 1.52-1.58 (m, 1H), 1.37-1.39 (m, 3H), 1.23 (s, 1H), 0.95-0.98 (m, 4H), 0.79-0.84 (m, 4H). |

| Ex# | Structure and Name | Calcd. (M + H)+ m/z | Found (M + H)+ m/z | HNMR |
|---|---|---|---|---|
| Ex 14 | 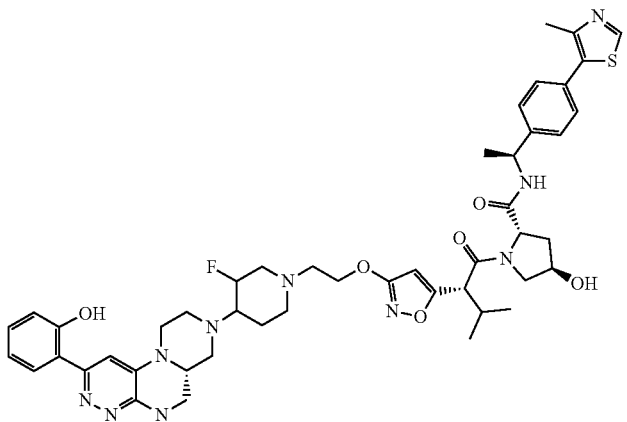<br>(2S,4R)-1-((2R)-2-(3-(2-(3-fluoro-4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 909.4 | 909.5 | $^1$HNMR (CD$_3$OD-d$_4$, 400 MHz): δ 9.82-9.70 (s, 1H), 7.60-7.40 (m, 7H), 7.10-7.02 (m, 2H), 6.10-6.07 (m, 1H), 5.79-5.75 (m, 1H), 5.06-4.95 (m, 2H), 4.62-4.52 (m, 2H), 4.49-4.44 (m, 2H), 4.24-4.23 (m, 1H), 3.99-3.3.63 (m, 11H), 3.45-3.42 (m, 2H), 3.40-3.38 (m, 3H), 2.98 (s, 1H), 2.57 (m, 3H), 2.47-2.45 (m, 2H), 2.32-2.31 (m, 3H), 1.95-1.93 (m, 1H), 1.51-1.25 (m, 3H), 1.06-1.04 (m, 3H), 0.94-0.89 (m, 3H). |
| Ex 15 | 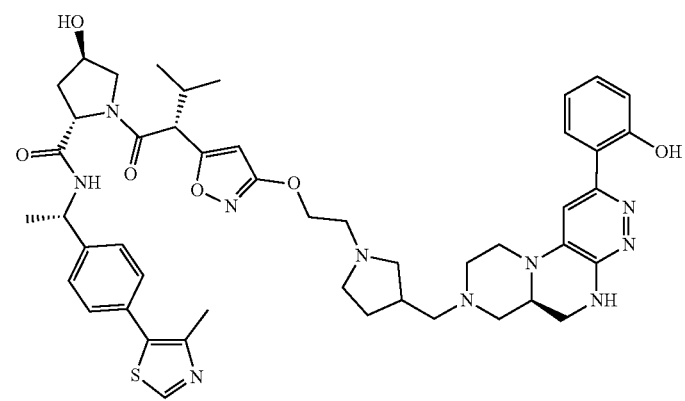 [SMILES: Cc1ncsc1-c1ccc([C@H](C)NC(=O)[C@@H]2C[C@@H](O)CN2C(=O)[C@@H](c2cc(OCCN3CCC(CN4CCN5c6cc(-c7ccccc7O)nnc6NC[C@H]5C4)C3)no2)C(C)C)cc1]<br>(2S,4R)-4-hydroxy-1-((2R)-2-(3-(2-(3-(((S)-2-(2-hydroxyphenyl)-5,6,6a,7,9,10-hexahydro-8H-pyrazino[1',2':4,5]pyrazino[2,3-c]pyridazin-8-yl)methyl)pyrrolidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 891.4 | 891.2 | $^1$H NMR(400 MHz, CD$_3$OD): δ 9.86 (s, 1H), 7.56-7.36 (m, 7H), 7.05-7.03 (m, 2H), 6.15 (m, 1H), 5.05-5.01 (m, 2H), 4.60 (m, 2H), 4.54-4.50 (m, 2H), 4.44 (m, 1H), 4.24 (m, 1H), 3.88-3.66 (m, 11H), 3.55-3.45 (m, 6H), 3.00-2.87 (m, 1H), 2.59 (s, 4H), 2.37-2.18 (m, 3H), 1.99-1.93 (m, 2H), 1.53-1.51 (m, 3H), 1.05-1.04 (m, 3H), 0.89-0.88 (m, 3H). |

| Ex# | Structure and Name | Calcd. (M + H)+ m/z | Found (M + H)+ m/z | HNMR |
|---|---|---|---|---|
| Ex 16 | 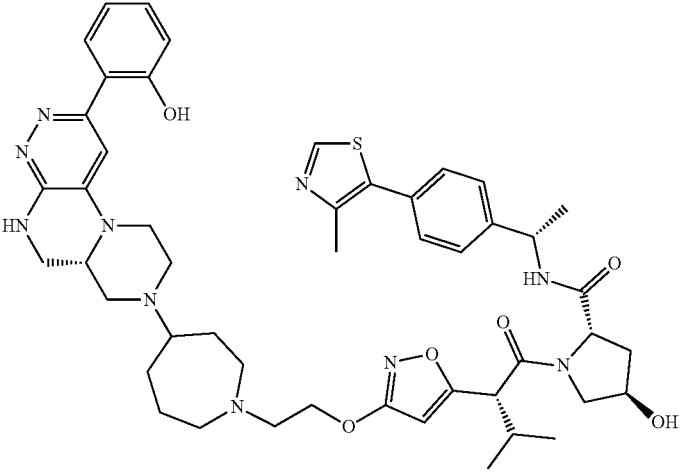 [SMILES: Cc1ncsc1-c1ccc([C@H](C)NC(=O)[C@@H]2C[C@@H](O)CN2C(=O)[C@@H](c2cc(OCCN3CCCC(N4CCN5c6cc(-c7ccccc7O)nnc6NC[C@H]5C4)CC3)no2)C(C)C)cc1]<br>(2S,4R)-4-hydroxy-1-((2R)-2-(3-(2-(4-((S)-2-(2-hydroxyphenyl)-5,6,6a,7,9,10-hexahydro-8H-pyrazino[1',2':4,5]pyrazino[2,3-c]pyridazin-8-yl)azepan-1-yl)ethoxy)isoxazol-5-yl)-3-methylbutanoyl)-N-((S)-1-(4-(4-methylthiazol-5-yl)phenyl)ethyl)pyrrolidine-2-carboxamide | 905.4 | 905.6 | $^1$HNMR (CD$_3$OD-d$_4$, 400 MHz): δ 9.45-9.40 (s, 1H), 7.60-7.40 (m, 7H), 7.10-7.02 (m, 2H), 6.64-6.58 (m, 1H), 5.45-5.44 (m, 1H), 5.06-4.95 (m, 1H), 4.70-4.64 (m, 2H), 4.53-4.44 (m, 3H), 4.19-4.18 (m, 1H), 3.85-3.60 (m, 12H), 3.48-3.43 (m, 3H), 2.70-2.69 (m, 1H), 2.57 (m, 3H), 2.49-2.45 (m, 3H), 2.32-2.31 (m, 3H), 2.00-1.94 (m, 3H), 1.51--1.25 (m, 3H), 1.06-1.04 (m, 3H), 0.94-0.89 (m, 3H). |
| Ex 17 | 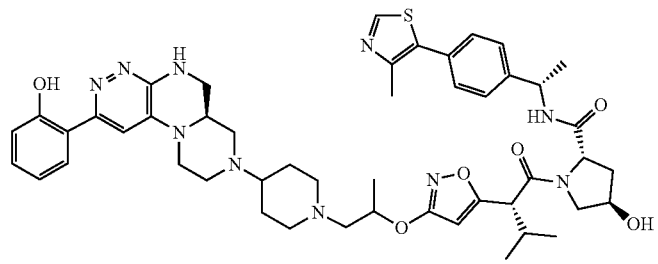 [SMILES: Cc1ncsc1-c1ccc([C@H](C)NC(=O)[C@@H]2C[C@@H](O)CN2C(=O)[C@@H](c2cc(OC(C)CN3CCC(N4CCN5c6cc(-c7ccccc7O)nnc6NC[C@H]5C4)CC3)no2)C(C)C)cc1]<br>(2S,4R)-4-hydroxy-1-((2R)-2-(3-((1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propan-2-yl)oxy)isoxazol-5-yl)-3-methylbutanoyl)-N-((S)-1-(4-(4-methylthiazol-5-yl)phenyl)ethyl)pyrrolidine-2-carboxamide | 905.4 | 905.2 | $^1$HNMR (CD$_3$OD-d$_4$, 400 MHz): δ 9.54 (s, 1H), 7.57-7.34 (m, 7H), 7.04-7.02 (m, 2H), 6.13-6.12 (m, 1H), 6.23-6.08 (m, 3H), 4.58-4.44 (m, 3H), 4.17 (s, 1H), 3.88-3.37 (m, 15H), 2.55 (s, 5H), 2.41-2.19 (m, 4H), 1.95-1.94 (m, 1H), 1.53-1.46 (m, 6H), 1.29-1.28 (m, 1H), 1.06-1.05 (m, 3H), 0.93-0.89 (m, 3H). |

-continued

| Ex# | Structure and Name | Calcd. (M + H)+ m/z | Found (M + H)+ m/z | HNMR |
|---|---|---|---|---|
| Ex 18 | (2S,4R)-4-hydroxy-1-((2R)-2-(3-(2-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)ethoxy)isoxazol-5-yl)-3-methylbutanoyl)-N-((S)-1-(4-(4-methylthiazol-5-yl)phenyl)ethyl)pyrrolidine-2-carboxamide (Diastereomer 1) | 877.4 | 877.3 | $^1$H NMR (400 MHz, CD$_3$OD) δ 9.82-9.79 (m, 1H), 7.57-7.31 (m, 7H), 7.06-7.02 (m, 2H), 6.14-6.09 (m, 1H), 5.05-5.01 (m, 1H), 4.83-4.81 (m, 2H), 4.63-4.44 (m, 5H), 4.21-4.10 (m, 3H), 3.85-3.41 (m, 12H), 3.12-2.97 (m, 1H), 2.62-2.59 (m, 5H), 2.40-2.20 (m, 2H), 1.93 (m, 1H), 1.61-1.51 (m, 3H), 1.07-1.04 (m, 3H), 0.92-0.88 (m, 3H) |
| Ex 19 | (2S,4R)-4-hydroxy-1-((2R)-2-(3-(2-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)ethoxy)isoxazol-5-yl)-3-methylbutanoyl)-N-((S)-1-(4-(4-methylthiazol-5-yl)phenyl)ethyl)pyrrolidine-2-carboxamide (Diastereomer 2) | 877.4 | 877.3 | $^1$H NMR (400 MHz, CD$_3$OD) δ 9.93-9.92 (m, 1H), 8.15-8.09 (m, 1H), 7.59-7.35 (m, 7H), 7.06-7.03 (m, 2H), 5.06-5.01 (m, 1H), 4.83-4.81 (m, 2H), 4.63-4.44 (m, 5H), 4.21-3.93 (m, 3H), 3.85-3.43 (m, 12H), 3.4-3.3 (m, 2H), 2.99-2.98 (m, 1H), 2.68-2.60 (m, 5H), 2.40-2.22 (m, 2H), 2.01-1.93 (m, 1H), 1.61-1.51 (m, 3H), 1.07-1.04 (m, 3H), 0.92-0.88 (m, 3H). |

| Ex# | Structure and Name | Calcd. (M + H)+ m/z | Found (M + H)+ m/z | HNMR |
|---|---|---|---|---|
| Ex 20 | 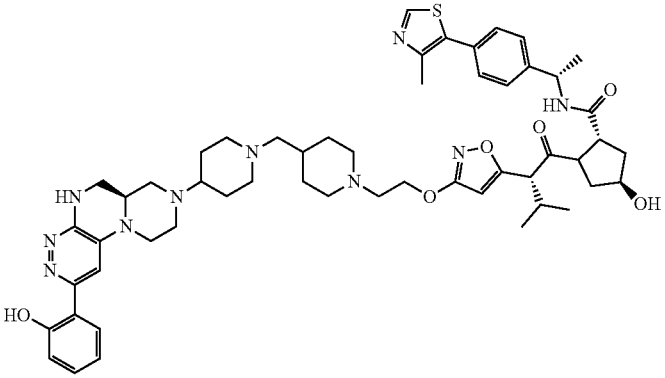 [SMILES: Cc1ncsc1-c1ccc([C@H](C)NC(=O)[C@@H]2C[C@@H](O)CC2C(=O)[C@@H](c2cc(OCCN3CCC(CN4CCC(N5CCN6c7cc(-c8ccccc8O)nnc7NC[C@H]6C5)CC4)CC3)no2)C(C)C)cc1]<br>(2S,4R)-4-hydroxy-1-((R)-2-(3-(2-(4-((4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)methyl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 988.5 | 988.4 | 1H NMR (400 MHz, DMSO-d6) δ 8.99-9.00 (m, 1H), 8.42-8.44 (m, 1H), 7.91-7.93 (m, 1H), 7.43-7.48 (m, 3H), 7.34-7.38 (m, 4H), 7.18-7.22 (m, 2H), 6.83-6.86 (m, 2H), 6.10 (s, 1H), 4.89-4.93 (m, 1H), 4.34-4.37 (m, 1H), 4.26-4.28 (m, 1H), 4.20-4.21 (m, 2H), 4.03-4.06 (m, 1H), 3.63-3.71 (m, 2H), 3.43-3.47 (m, 2H), 3.14-3.19 (m, 2H), 3.00-3.06 (m, 2H), 2.80-2.85 (m, 4H), 2.62-2.68 (m, 3H), 2.31-2.35 (m, 2H), 2.06-2.08 (m, 2H), 1.90-1.98 (m, 4H), 1.69-1.82 (m, 6H), 1.60-1.64 (m, 3H). 1.35-1.46 (m, 9H), 1.08-1.10 (m, 1H), 0.93-0.98 (m, 3H), 0.79-0.84 (m, 3H). |
| Ex 21 | 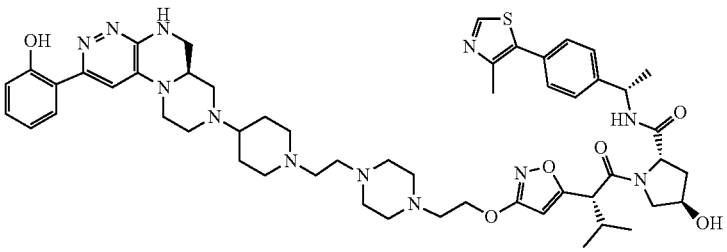 [SMILES: Cc1ncsc1-c1ccc([C@H](C)NC(=O)[C@@H]2C[C@@H](O)CN2C(=O)[C@@H](c2cc(OCCN3CCN(CCN4CCC(N5CCN6c7cc(-c8ccccc8O)nnc7NC[C@H]6C5)CC4)CC3)no2)C(C)C)cc1]<br>(2S,4R)-4-hydroxy-1-((R)-2-(3-(2-(4-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)piperazin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 1003.5 | 1003.8 | ¹H NMR (400 MHz, CD3OD) δ 9.80 (m, 1H), 7.59-7.35 (m, 7H), 7.04-7.02 (m, 2H), 8.11-8.10 (m, 1H), 5.04-5.02 (m, 2H), 4.75-4.42 (m, 8H), 4.19 (m, 1H), 3.96-3.38 (m, 20H), 2.98-2.87 (m, 3H), 2.58-2.55 (m, 5H), 2.39-1.92 (m, 6H), 1.61-1.48 (m, 3H), 1.28 (m, 3H), 1.06-1.02 (m, 3H), 0.89-0.85 (m, 3H). |

| Ex# | Structure and Name | Calcd. (M + H)+ m/z | Found (M + H)+ m/z | HNMR |
|---|---|---|---|---|
| Ex 22 | (2S,4R)-4-hydroxy-1-((R)-2-(3-(2-(4-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 1002.5 | 1002.7 | $^1$H NMR (400 MHz, CD$_3$OD) δ 9.88 (m, 1H), 7.56-7.36 (m, 7H), 7.05-7.03 (m, 2H), 8.12-8.10 (m, 1H), 5.05-5.02 (m, 1H), 4.62-4.44 (m, 5H), 4.19 (m, 1H), 3.82-3.48 (m, 18H), 3.13 (m, 4H), 2.60 (m, 5H), 2.35-1.83 (m, 12H), 1.81-1.58 (m, 4H), 1.06-1.04 (m, 3H), 0.89-0.88 (m, 3H). |
| Ex 23 | (2S,4R)-4-hydroxy-1-((2R)-2-(3-((1-(3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N-((S)-1-(4-(4-methylthiazol-5-yl)phenyl)ethyl)pyrrolidine-2-carboxamide (Synthesized from Int-25) | 919.5 | 919.7 | $^1$HNMR (CD$_3$OD-d$_4$, 400 MHz): δ 9.74 (s, 1H), 7.47-7.34 (m, 7H), 6.97-6.93 (m, 2H), 6.08-6.06 (m, 1H), 5.3-5.2 (m, 1H), 4.25-4.20 (m, 1H), 4.95-4.87 (m, 2H), 4.75-4.70 (m, 2H), 4.47-4.15 (m, 4H), 3.83-3.37 (m, 14H), 2.98-2.75 (m, 2H), 2.55 (s, 3H), 2.41-2.19 (m, 2H), 1.95-1.74 (m, 4H), 1.46-1.39 (m, 7H), 0.96-0.94 (m, 3H), 0.93-0.89 (m, 3H). |
| Ex 24 | (2S,4R)-4-hydroxy-1-((2R)-2-(3-((1-(3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N-((S)-1-(4-(4-methylthiazol-5-yl)phenyl)ethyl)pyrrolidine-2-carboxamide (Synthesized from Int-26) | 919.5 | 919.6 | $^1$HNMR (CD$_3$OD-d$_4$, 400 MHz): δ 9.74 (s, 1H), 7.47-7.34 (m, 7H), 6.97-6.93 (m, 2H), 6.08-6.06 (m, 1H), 5.2-5.1 (m, 1H), 4.25-4.20 (m, 1H), 4.95-4.87 (m, 2H), 4.75-4.70 (m, 2H), 4.47-4.15 (m, 4H), 3.83-3.37 (m, 14H), 2.98-2.75 (m, 2H), 2.55 (s, 3H), 2.41-2.19 (m, 2H), 1.95-1.74 (m, 4H), 1.46-1.39 (m, 7H), 0.96-0.94 (m, 3H), 0.93-0.89 (m, 3H). |

| Ex# | Structure and Name | Calcd. (M + H)+ m/z | Found (M + H)+ m/z | HNMR |
|---|---|---|---|---|
| Ex 25 | 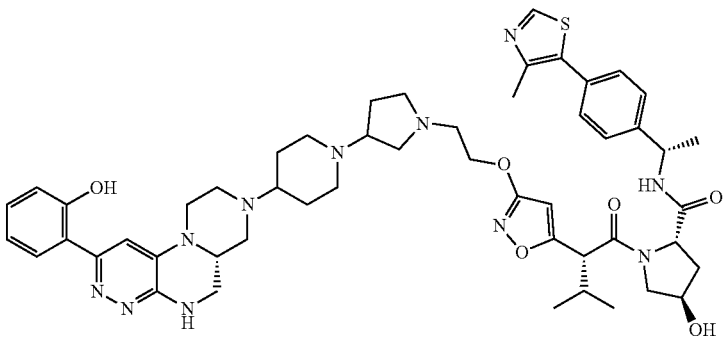 [SMILES: Cc1ncsc1-c1ccc([C@H](C)NC(=O)[C@@H]2C[C@@H](O)CN2C(=O)[C@@H](c2cc(OCCN3CCC(N4CCC(N5CCN6c7cc(-c8ccccc8O)nnc7NC[C@H]6C5)CC4)C3)no2)C(C)C)cc1]<br>(2S,4R)-4-hydroxy-1-((2R)-2-(3-(2-(3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl)ethoxy)isoxazol-5-yl)-3-methylbutanoyl)-N-((S)-1-(4-(4-methylthiazol-5-yl)phenyl)ethyl)pyrrolidine-2-carboxamide<br>(Synthesized from Int-29) | 960.5 | 960.4 | $^1$HNMR (CD$_3$OD-d$_4$, 400 MHz): δ 8.77-8.78 (m, 1H), 7.67-7.69 (m, 1H), 7.31-7.36 (m, 4H), 7.07-7.14 (m, 2H), 6.77-6.81 (m, 2H), 5.86-5.92 (m, 1H), 5.08-5.11 (m, 1H), 4.34-4.45 (m, 2H), 4.21-4.24 (m, 2H), 3.72-3.85 (m, 2H), 3.46-3.59 (m, 5H), 3.38-3.39 (m, 2H), 2.82-2.98 (m, 6H), 2.38 (s, 3H), 2.24-2.35 (m, 5H), 2.04-2.11 (m, 3H), 1.80-2.00 (m, 8H), 1.48-1.51 (m, 2H), 1.42-1.43 (m, 3H), 0.95-0.97 (m, 3H), 0.80-0.85 (m, 3H). |
| Ex 26 | 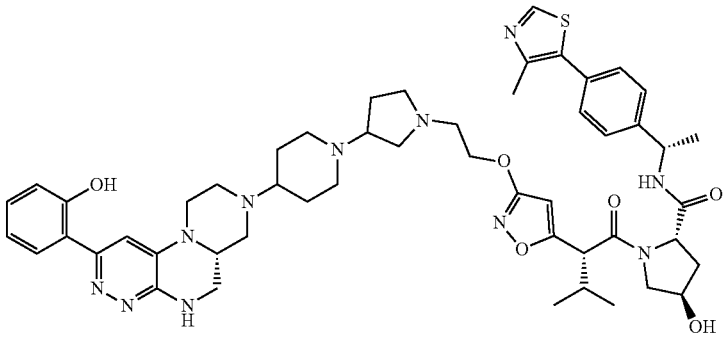 [SMILES: Cc1ncsc1-c1ccc([C@H](C)NC(=O)[C@@H]2C[C@@H](O)CN2C(=O)[C@@H](c2cc(OCCN3CCC(N4CCC(N5CCN6c7cc(-c8ccccc8O)nnc7NC[C@H]6C5)CC4)C3)no2)C(C)C)cc1]<br>(2S,4R)-4-hydroxy-1-((2R)-2-(3-(2-(3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl)ethoxy)isoxazol-5-yl)-3-methylbutanoyl)-N-((S)-1-(4-(4-methylthiazol-5-yl)phenyl)ethyl)pyrrolidine-2-carboxamide<br>(Synthesized from Int-30) | 960.5 | 960.4 | $^1$HNMR (CD$_3$OD-d$_4$, 400 MHz): δ 8.78 (s, 1H), 7.67-7.69 (m, 1H), 7.31-7.36 (m, 4H), 7.07-7.14 (m, 2 H), 6.77-6.81 (m, 2H), 5.86-5.92 (m, 1H), 5.08-5.11 (m, 1H), 4.34-4.45 (m, 2H), 4.21-4.24 (m, 2H), 3.72-3.85 (m, 2H), 3.46-3.59 (m, 5H), 3.38-3.39 (m, 2H), 2.82-2.98 (m, 6H), 2.38 (s, 3H), 2.24-2.35 (m, 5H), 2.04-2.11 (m, 3H), 1.80-2.00 (m, 8H), 1.48-1.51 (m, 2H), 1.42-1.43 (m, 3H), 0.95-0.97 (m, 3H), 0.80-0.85 (m, 3H). |

| Ex# | Structure and Name | Calcd. (M + H)+ m/z | Found (M + H)+ m/z | HNMR |
|---|---|---|---|---|
| Ex 38 | 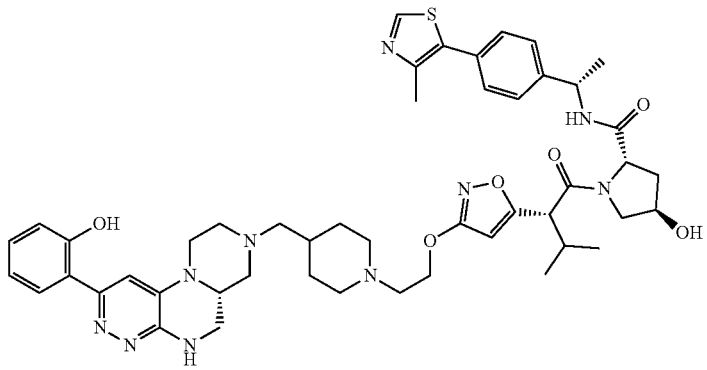 [SMILES: Cc1ncsc1-c1ccc([C@H](C)NC(=O)[C@@H]2C[C@@H](O)CN2C(=O)[C@@H](c2cc(OCCN3CCC(CN4CCN5c6cc(-c7ccccc7O)nnc6NC[C@H]5C4)CC3)no2)C(C)C)cc1]<br>(2S,4R)-4-hydroxy-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 905.4 | 905.5 | $^1$H NMR (400 MHz, CD$_3$OD): δ 9.87 (s, 1H), 7.13-7.76 (m, 7H), 6.86-6.89 (m, 2H), 5.95-6.01 (m, 1H), 5.01-5.03 (m, 1H), 4.33-4.50 (m, 4H), 3.31-3.82 (m, 6H), 3.00-3.25 (m, 5H), 2.80-2.83 (m, 2H), 2.48 (s, 3H), 2.14-2.28 (m, 8H), 1.81-1.96 (m, 4H), 1.52-1.59 (m, 2H), 1.27-1.31 (m, 2H), 1.01-1.10 (m, 3H), 0.80-0.90 (m, 3H). (Some protons were buried under solvent or water peak, not all protons were listed) |
| Ex 41 | 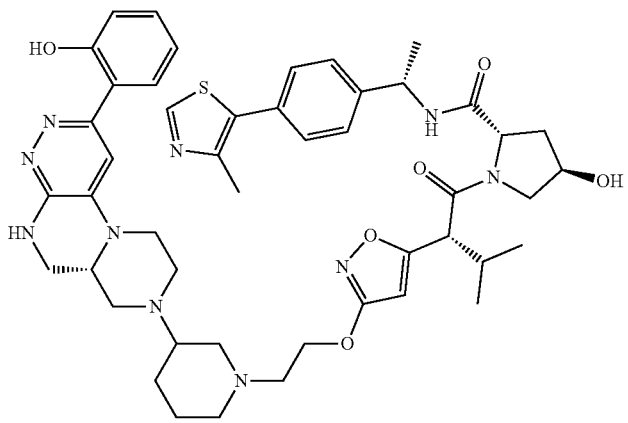 [SMILES: Cc1ncsc1-c1ccc([C@H](C)NC(=O)[C@@H]2C[C@@H](O)CN2C(=O)[C@@H](c2cc(OCCN3CCCC(N4CCN5c6cc(-c7ccccc7O)nnc6NC[C@H]5C4)C3)no2)C(C)C)cc1]<br>(2S,4R)-4-hydroxy-1-((2R)-2-(3-(2-(3-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide (diastereomer 1) | 891.4 | 891.6 | $^1$H NMR (DMSO-d$_6$, 400 MHz): δ8.97-9.03 (s, 1H), 8.38-8.48 (m, 1H), 8.09-8.20 (s, 1H), 7.35-7.50 (m, 6H), 7.13-7.20 (s, 1H), 6.94-7.11 (m, 2H), 6.13-6.21 (s, 1H), 5.72-5.79 (s, 1H), 4.86-4.95 (m, 1H), 4.53-4.61 (s, 2H), 4.25-4.40 (m, 3H), 4.12-4.23 (m, 2H), 3.97-4.08 (m, 4H), 3.66-3.73 (m, 4H), 3.04-3.18 (m, 4H), 2.88-2.96 (m, 2H), 2.44-2.47 (s,3H), 2.17-2.31 (m, 2H), 1.98-2.00 (m, 3H), 1.73-1.92 (m, 3H), 1.44-1.50 (m, 1H), 1.34-1.41 (m, 3H), 1.21-1.26 (s, 1H), 0.93-1.00 (m, 3H), 0.97-0.84 (m, 3H). |

| Ex# | Structure and Name | Calcd. (M + H)+ m/z | Found (M + H)+ m/z | HNMR |
|---|---|---|---|---|
| Ex 42 | (2S,4R)-4-hydroxy-1-((2R)-2-(3-(2-(3-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide (diastereomer 1) | 891.4 | 891.7 | |
| Ex 43 | (2S,4R)-4-hydroxy-1-((R)-2-(3-(2-((4-((S)-2-(2-hydroxyphenyl)-5,6,6a,7,9,10-hexahydro-8H-pyrazino[1',2':4,5]pyrazino[2,3-c]pyridazin-8-yl)cyclohexyl)(methyl)amino)ethoxy)isoxazol-5-yl)-3-methylbutanoyl)-N-((S)-1-(4-(4-methylthiazol-5-yl)phenyl)ethyl)pyrrolidine-2-carboxamide | 919.5 | 919.6 | $^1$H NMR (400 MHz, DMSO) δ 9.56 (s, 1H), 7.57-7.34 (m, 7H), 7.04-7.02 (m, 1H), 6.13 (s, 1H), 4.96-4.82 (m, 2 H), 4.64-4.61 (m, 3H), 4.52-4.48 (m, 4 H), 4.07-3.50 (m, 12 H), 3..03 (s, 3 H), 2.56 (s, 3H), 2.52-2.22 (m, 6 H), 2.14-1.80 (m, 5 H), 1.47-1.35 (m, 3H), 1.19-1.10 (m, 3H), 0.97 (d, J = 6.3 Hz, 3H), 0.81 (d, J = 6.7 Hz, 3H). |

-continued

| Ex# | Structure and Name | Calcd. (M + H)+ m/z | Found (M + H)+ m/z | HNMR |
|---|---|---|---|---|
| Ex 44 | (2S,4R)-4-hydroxy-1-((R)-2-(3-(2-(4-((S)-2-(2-hydroxyphenyl)-5,6,6a,7,9,10-hexahydro-8H-pyrazino[1',2':4,5]pyrazino[2,3-c]pyridazin-8-yl)-[1,4'-bipiperidin]-1-yl)ethoxy)isoxazol-5-yl)-3-methylbutanoyl)-N-((S)-1-(4-(4-methylthiazol-5-yl)phenyl)ethyl)pyrrolidine-2-carboxamide | 974.5 | 974.7 | $^1$H NMR (400 MHz, CD$_3$OD): δ 9.67 (s, 1H), 7.34-7.66 (m, 7H), 6.96-7.06 (m, 2H), 6.59-6.64 (m, 1H), 5.01-5.03 (m, 1H), 4.13-4.62 (m, 5H), 3.61-385 (m, 15H), 3.38-3.52 (m, 3 H), 2.48-2.56 (s, 6H), 2.14-2.48 (m, 6H), 1.81-1.96 (m, 1H), 1.52-1.59 (m, 3H), 1.01-1.10 (m, 3H), 0.80-0.90 (m, 3H). (Some protons were buried under solvent or water peak, not all protons were listed) |
| Ex 46 | (2S,4R)-4-hydroxy-N-((R)-2-hydroxy-1-(4-(4-methylthiazol-5-yl)phenyl)ethyl)-1-(2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)pyrrolidine-2-carboxamide | 921.4 | 921.6 | $^1$H NMR (400 MHz, CD$_3$OD): δ 9.64 (s, 1H), 7.26-7.46 (m, 7H), 6.92-6.97 (m, 2H), 6.02 (s, 1H), 5.39 (s, 2H), 4.80-4.95 (m, 2H), 4.46-4.75 (m, 4H), 3.25-3.77 (m, 19H), 3.10-3.15 (m, 2H), 2.48 (s, 3H), 1.49-2.48 (m, 8H), 0.92-1.00 (m, 3H), 0.80-0.90 (m, 3H). |

-continued

| Ex# | Structure and Name | Calcd. (M + H)+ m/z | Found (M + H)+ m/z | HNMR |
|---|---|---|---|---|
| Ex 47 | 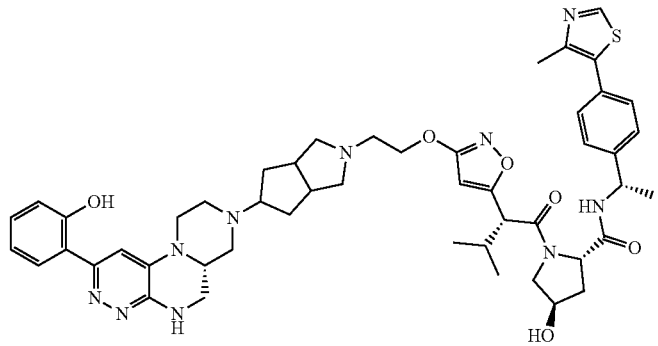 [SMILES: Cc1ncsc1-c1ccc([C@H](C)NC(=O)[C@@H]2C[C@@H](O)CN2C(=O)[C@@H](c2cc(OCCN3CC4CC(N5CCN6c7cc(-c8ccccc8O)nnc7NC[C@H]6C5)CC4C3)no2)C(C)C)cc1]<br>(2S,4R)-4-hydroxy-1-((2R)-2-(3-(2-(5-((S)-2-(2-hydroxyphenyl)-5,6,6a,7,9,10-hexahydro-8H-pyrazino[1',2':4,5]pyrazino[2,3-c]pyridazin-8-yl)hexahydrocyclopenta[c]pyrrol-2(1H)-yl)ethoxy)isoxazol-5-yl)-3-methylbutanoyl)-N-((S)-1-(4-(4-methylthiazol-5-yl)phenyl)ethyl)pyrrolidine-2-carboxamide | 917.4 | 917.5 | ¹H NMR (400 MHz, CD₃OD-d₄) δ 8.82-8.73 (m, 1H), 7.73-7.63 (m, 1H), 7.39-7.28 (m, 4H), 7.16-7.01 (m, 2H), 6.85-6.72 (m, 2H), 5.93-5.82 (m, 1H), 4.95-4.89 (m, 1H), 4.54-4.18 (m, 4H), 3.89-3.67 (m, 2H), 3.59-3.38 (m, 4H), 3.27-3.24 (s, 1H), 3.08-3.01 (m, 1H), 2.92-2.73 (m, 3H), 2.62-2.45 (m, 6H), 2.39-2.36 (m, 3H), 2.28-2.06 (m, 5H), 1.91-1.77 (m, 2H), 1.52-1.18 (m, 7H), 1.00-0.89 (m, 3H), 0.82-0.76 (m, 3H). |
| Ex 52 | 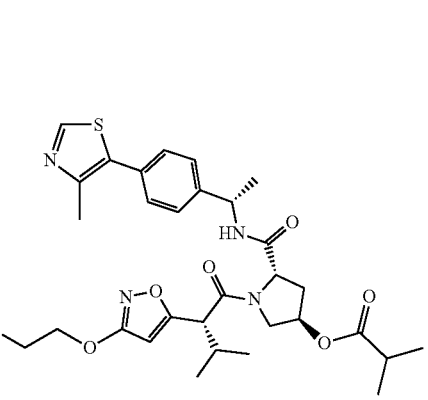<br>(3R,5S)-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-5-(((S)-1-(4-(4-methylthiazol-5-yl)phenyl)ethyl)carbamoyl)pyrrolidin-3-yl isobutyrate | 975.5 | 975.5 | ¹H NMR (400 MHz, CD₃OD) δ 9.60 (s, J = 28.1 Hz, 1H), 7.60-7.39 (m, 6H), 7.35 (s, 1H), 7.05 (t, J = 8.8 Hz, 2H), 6.09 (s, J = 14.9 Hz, 1H), 5.29 (s, 1H), 5.02 (dd, J = 14.0, 7.0 Hz, 1H), 4.62 (s, 2H), 4.55-4.46 (t, 2H), 4.24 (s, 1H), 3.99-3.90 (m, 2H), 3.86 (s, 2H), 3.83 (s, 1H), 3.78 (s, 1H), 3.73 (d, J = 9.9 Hz, 1H), 3.64 (s, 2H), 3.53-3.40 (m, 2H), 3.34 (s, 6H), 3.22 (s, 2H), 2.56 (s, J = 2.9 Hz, 3H), 2.49 (mm, J = 13.8, 6.7 Hz, 1H), 2.37 (dd, J = 13.8, 7.1 Hz, 2H), 2.25 (d, J = 17.2 Hz, 2H), 2.13-2.03 (m, 1H), 1.72 (d, J = 12.4 Hz, 2H), 1.61 (d, J = 7.0 Hz, 1H), 1.52 (d, J = 7.0 Hz, 2H), 1.11 (m, J = 22.3, 10.6, 5.0 Hz, 9H), 0.91 (dd, J = 12.0, 6.6 Hz, 3H). |

| Ex# | Structure and Name | Calcd. (M + H)+ m/z | Found (M + H)+ m/z | HNMR |
|---|---|---|---|---|
| Ex 54 | 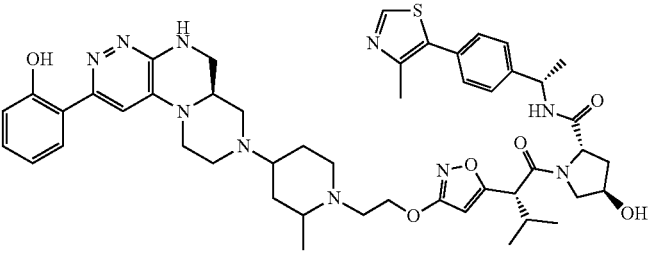 [SMILES: Cc1ncsc1-c1ccc([C@H](C)NC(=O)[C@@H]2C[C@@H](O)CN2C(=O)[C@@H](c2cc(OCCN3CCC(N4CCN5c6cc(-c7ccccc7O)nnc6NC[C@H]5C4)CC3C)no2)C(C)C)cc1]<br>(2S,4R)-4-hydroxy-1-((2R)-2-(3-(2-(4-((S)-2-(2-hydroxyphenyl)-5,6,6a,7,9,10-hexahydro-8H-pyrazino[1',2':4,5]pyrazino[2,3-c]pyridazin-8-yl)-2-methylpiperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 905.4 | 905.6 | ¹H NMR (400 MHz, CD₃OD) δ 9.59 (s, J = 21.8 Hz, 1H), 7.57 (d, J = 6.5 Hz, 1H), 7.54-7.40 (m, 5H), 7.35 (s, 1H), 7.05 (t, J = 8.5 Hz, 2H), 6.10 (s, J = 22.2 Hz, 1H), 5.03 (m, J = 13.9, 7.0 Hz, 2H), 4.65 (s, 2H), 4.51 (t, J = 7.9 Hz, 2H), 4.42 (s, J = 17.9 Hz, 1H), 4.18 (s, 1H), 3.92 (s, 4H), 3.80 (dd, J = 23.3, 11.9 Hz, 4H), 3.72 (d, J = 9.6 Hz, 2H), 3.63 (d, J = 10.5 Hz, 2H), 3.50 (m, J = 10.3 Hz, 3H), 2.56 (s, 5H), 2.38 (m, 2H), 2.26-2.11 (m, 2H), 1.96 (m, J = 23.8, 15.5 Hz, 1H), 1.65-1.45 (m, 6H), 1.06 (d, J = 6.3 Hz, 3H), 0.90 (t, J = 8.1 Hz, 3H). |
| Ex 55 | 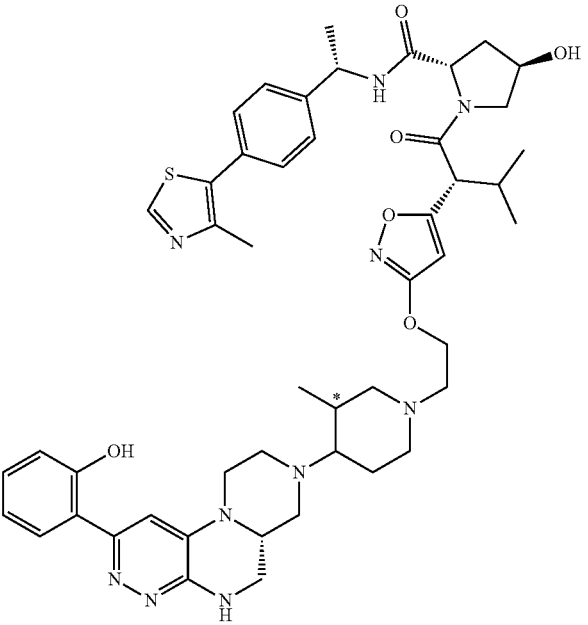 [SMILES: Cc1ncsc1-c1ccc([C@H](C)NC(=O)[C@@H]2C[C@@H](O)CN2C(=O)[C@@H](c2cc(OCCN3CCC(N4CCN5c6cc(-c7ccccc7O)nnc6NC[C@H]5C4)C(C)C3)no2)C(C)C)cc1]<br>(2S,4R)-4-hydroxy-1-((2R)-2-(3-(2-(4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide (diastereomer 1) | 905.4 | 905.5 | ¹H NMR (400 MHz, DMSO) δ 10.63 (s, 1H), 8.99 (s, 1H), 8.41 (d, J = 7.7 Hz, 1H), 8.19 (s, 1H), 7.51-7.30 (m, 7H), 7.20 (s, 1H), 7.07 (d, J = 8.3 Hz, 1H), 6.99 (t, J = 7.6 Hz, 1H), 6.09 (s, 1H), 4.95-4.84 (m, 1H), 4.75-4.49 (m, 2H), 4.35 (t, J = 7.9 Hz, 1H), 4.31-4.24 (m, 1H), 3.72-3.50 (m, 9H), 3.20-2.76 (m, 6H), 2.75-2.54 (m, 1H), 2.45 (s, 3H), 2.34-2.30 (m, 1H), 2.30-2.14 (m, 3H), 2.07-1.72 (m, 5H), 1.41 (dd, J = 37.3, 6.9 Hz, 3H), 1.26-1.04 (m, 3H), 0.99-0.93 (m, 3H), 0.82 (dd, J = 14.3, 6.6 Hz, 3H). |

| Ex# | Structure and Name | Calcd. (M + H)+ m/z | Found (M + H)+ m/z | HNMR |
|---|---|---|---|---|
| Ex 56 | (2S,4R)-4-hydroxy-1-((2R)-2-(3-(2-(4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide (diastereomer 2) | 905.4 | 905.6 | $^1$H NMR (400 MHz, DMSO) δ 10.40 (s, 1H), 8.99 (s, 1H), 8.45 (d, J = 8.3 Hz, 1H), 8.05 (s, 1H), 7.56-7.20 (m, 7H), 7.15 (s, 1H), 7.11-7.02 (m, 1H), 6.96 (t, J = 7.0 Hz, 1H), 6.10 (s, 1H), 4.96-4.82 (m, 1H), 4.63-4.49 (m, 2H), 4.36 (t, J = 8.0 Hz, 1H), 4.32-4.26 (m, 1H), 3.78-3.59 (m, 9H), 3.24-2.73 (m, 6H), 2.72-2.64 (m, 1H), 2.46 (s, 3H), 2.35-2.32 (m, 1H), 2.26-2.14 (m, 3H), 2.04-1.88 (m, 5H), 1.47-1.35 (m, 3H), 1.19-1.10 (m, 3H), 0.97 (d, J = 6.3 Hz, 3H), 0.81 (d, J = 6.7 Hz, 3H). |
| Ex 57 | (2S,4R)-4-hydroxy-1-((2R)-2-(3-((1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propan-2-yl)oxy)isoxazol-5-yl)-3-methylbutanoyl)-N-((S)-1-(4-(4-methylthiazol-5-yl)phenyl)ethyl)pyrrolidine-2-carboxamide | 905.4 | 905.5 | $^1$HNMR of (CD$_3$OD-d$_4$, 400 MHz): δ 9.54 (s, 1H), 7.57-7.34 (m, 7H), 7.04-7.02 (m, 2H), 6.13-6.12 (m, 1 H), 6.23-6.08 (m, 3H), 4.58-4.44 (m, 3 H), 4.17 (s, 1H), 3.88-3.37 (m, 15H), 2.55 (s, 5H), 2.41-2.19 (m, 4H), 1.95-1.94 (m, 1H), 1.53-1.46 (m, 6H), 1.29-1.28 (m, 1H), 1.06-1.05 (m, 3H), 0.93-0.89 (m, 3H). |

| Ex# | Structure and Name | Calcd. (M + H)+ m/z | Found (M + H)+ m/z | HNMR |
|---|---|---|---|---|
| Ex 58 | (2S,4R)-4-hydroxy-1-((2R)-2-(3-(2-(4-(1-((S)-2-(2-hydroxyphenyl)-5,6,6a,7,9,10-hexahydro-8H-pyrazino[1',2':4,5]pyrazino[2,3-c]pyridazin-8-yl)ethyl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide (diastereomer 1) | 919.5 | 919.7 | $^1$H NMR (400 MHz, CD$_3$OD) δ 8.78 (s, 1H), 7.57-7.48 (m, 1H), 7.39-7.27 (m, 5H), 7.23 (t, J = 7.7 Hz, 1H), 7.02 (s, 1H), 6.86 (d, J = 7.6 Hz, 2H), 5.97 (s, 1H), 5.13-5.07 (m, 1H), 4.96-4.92 (m, 1H), 4.55-4.45 (m, 3H), 4.40 (t, J = 8.3 Hz, 1H), 4.37-4.32 (m, 1H), 3.96-3.84 (m, 1H), 3.74 (dd, J = 10.7, 4.3 Hz, 1H), 3.62 (d, J = 9.7 Hz, 1H), 3.57-3.45 (m, 6H), 3.41-3.35 (m, 3H), 3.06-3.00 (m, 2H), 2.87-2.79 (m, 1H), 2.78-2.67 (m, 2H), 2.38 (s, 3H), 2.14-2.02 (m, 1H), 2.01-1.81 (m, 4H), 1.51 (d, J = 7.0 Hz, 1H), 1.42 (d, J = 7.1 Hz, 2H), 1.21-1.19 (m, 2H), 0.94 (dd, J = 16.6, 6.5 Hz, 6H), 0.80 (d, J = 6.7 Hz, 3H). |
| Ex 59 | (2S,4R)-4-hydroxy-1-((2R)-2-(3-(2-(4-(1-((S)-2-(2-hydroxyphenyl)-5,6,6a,7,9,10-hexahydro-8H-pyrazino[1',2':4,5]pyrazino[2,3-c]pyridazin-8-yl)ethyl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide (diastereomer 2) | 919.5 | 919.7 | $^1$H NMR (400 MHz, CD$_3$OD) δ 8.78 (s, 1H), 7.55-7.49 (m, 1H), 7.36-7.31 (m, 5H), 7.26-7.23 (m, 1H), 7.02 (s, 1H), 6.87 (d, J = 8.0 Hz, 2H), 6.00 (s, 1H), 5.12-5.08 (m, 1H), 4.95-4.93 (m, 1H), 4.54-4.44 (m, 3H), 4.40 (t, J = 8.1 Hz, 1H), 4.34-4.27 (m, 1H), 3.94-3.89 (m, 1H), 3.74 (dd, J = 10.8, 3.6 Hz, 1H), 3.62 (d, J = 9.8 Hz, 1H), 3.55-3.46 (m, 6H), 3.40-3.36 (m, 3H), 3.10-2.89 (m, 2H), 3.00-2.66 (m, 3H), 2.38 (s, 3H), 2.13-2.05 (m, 1H), 1.97-1.72 (m, 4H), 1.51 (d, J = 7.1 Hz, 1H), 1.42 (d, J = 7.0 Hz, 2H), 1.21-1.18 (m, 2H), 0.93 (dd, J = 14.9, 6.5 Hz, 6H), 0.80 (d, J = 6.7 Hz, 3H) |

| Ex# | Structure and Name | Calcd. (M + H)+ m/z | Found (M + H)+ m/z | HNMR |
|---|---|---|---|---|
| Ex 60 | 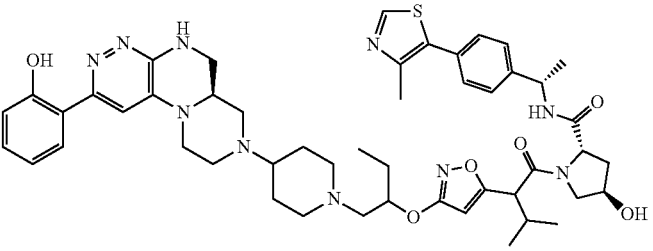 [SMILES: CCC(CN1CCC(N2CCN3c4cc(-c5ccccc5O)nnc4NC[C@H]3C2)CC1)Oc1cc(C(C(=O)N2C[C@H](O)C[C@H]2C(=O)N[C@@H](C)c2ccc(-c3scnc3C)cc2)C(C)C)on1]<br>(2S,4R)-4-hydroxy-1-(2-(3-((1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)butan-2-yl)oxy)isoxazol-5-yl)-3-methylbutanoyl)-N-((S)-1-(4-(4-methylthiazol-5-yl)phenyl)ethyl)pyrrolidine-2-carboxamide | 919.5 | 919.6 | $^1$H NMR (400 MHz, CD$_3$OD) δ 9.50 (s, 1H), 7.59-7.39 (m, 6H), 7.34 (s, 1H), 7.04 (t, J = 8.6 Hz, 2H), 6.13 (s, 1H), 5.14-4.97 (m, 2H), 4.61-4.38 (m, 3H), 4.21-4.07 (m, 1H), 3.91-3.60 (m, 11H), 3.55-3.38 (m, 4H), 2.57-2.49 (m, 4H), 2.45-2.29 (m, 3H), 2.25-2.14 (m, 2H), 2.01-1.79 (m, 3H), 1.61 (dd, J = 10.2, 7.2 Hz, 1H), 1.51 (t, J = 6.8 Hz, 3H), 1.39-1.24 (m, 1H), 1.06 (d, J = 6.4 Hz, 3H), 1.00 (dd, J = 11.5, 7.3 Hz, 3H), 0.90 (d, J = 6.7 Hz, 3H). |
| Ex 61 | 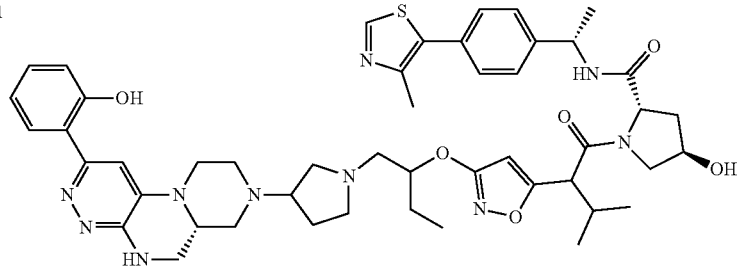<br>(2S,4R)-4-hydroxy-1-(2-(3-((1-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)butan-2-yl)oxy)isoxazol-5-yl)-3-methylbutanoyl)-N-((S)-1-(4-(4-methylthiazol-5-yl)phenyl)ethyl)pyrrolidine-2-carboxamide (mixture 1) | 905.4 | 905.4 | $^1$H NMR (400 MHz, CD$_3$OD) δ 9.60 (s, 1H), 7.56-7.40 (m, 6H), 7.30 (s, 1H), 7.04 (t, J = 7.6 Hz, 2H), 6.12 (s, 1H), 5.05-5.00 (m, 2H), 4.82-4.26 (m, 3H), 4.24-3.35 (m, 16H), 2.58-2.50 (m, 4H), 2.47-2.30 (m, 2H), 2.20 (dd, J = 14.9, 11.0 Hz, 1H), 1.98-1.79 (m, 3H), 1.62-1.54 (m, 1H), 1.53-1.43 (m, 3H), 1.29 (s, 1H), 1.07-0.96 (m, 6H), 0.93-0.83 (m, 3H). |
| Ex 62 | 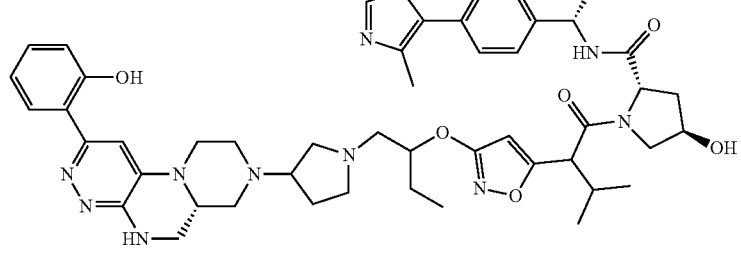<br>(2S,4R)-4-hydroxy-1-(2-(3-((1-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)butan-2-yl)oxy)isoxazol-5-yl)-3-methylbutanoyl)-N-((S)-1-(4-(4-methylthiazol-5-yl)phenyl)ethyl)pyrrolidine-2-carboxamide (mixture 2) | 905.4 | 905.4 | |

| Ex# | Structure and Name | Calcd. (M + H)+ m/z | Found (M + H)+ m/z | HNMR |
|---|---|---|---|---|
| Ex 63 | 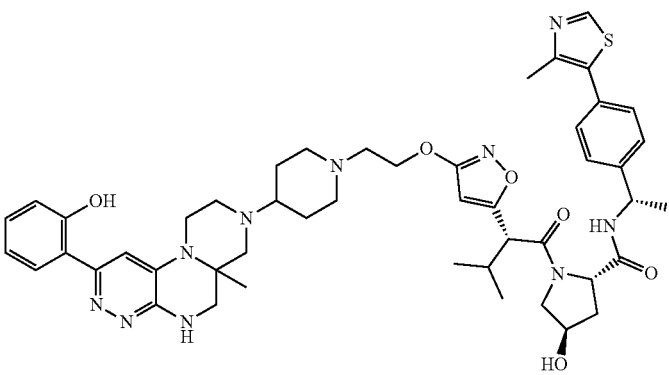 [SMILES: Cc1ncsc1-c1ccc([C@H](C)NC(=O)[C@@H]2C[C@@H](O)CN2C(=O)[C@@H](c2cc(OCCN3CCC(N4CCN5c6cc(-c7ccccc7O)nnc6NCC5(C)C4)CC3)no2)C(C)C)cc1]<br>(2S,4R)-4-hydroxy-1-((2R)-2-(3-(2-(4-(2-(2-hydroxyphenyl)-6a-methyl-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 905.4 | 905.4 | $^1$H NMR (400 MHz, CD$_3$OD): δ 10.02 (s, 1H), 7.59-7.43 (m, 6H), 7.30 (s, 1H), 7.07-7.2 (m, 2H), 6.12-6.07 (m, 1H), 5.06-4.90 (m, 1H), 4.64-4.36 (m, 5H), 3.93-3.44 (m, 15H), 2.61-2.60 (m, 5H), 2.48-2.34 (m, 4H), 1.95-1.93 (m, 1H), 1.71-1.70 (m, 3H), 1.52-1.49 (m, 3H), 1.07-1.05 (m, 3H), 0.91-0.85 (m, 3H). (Some protons were buried under solvent or water peak, not all protons were listed) |
| Ex 67 | 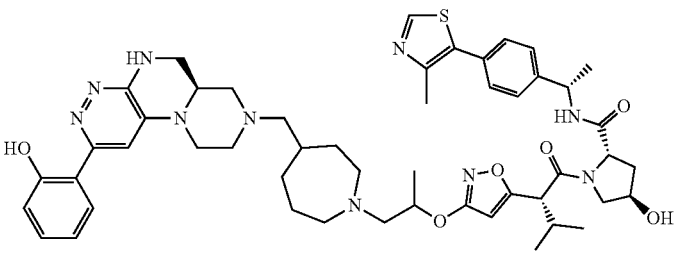 [SMILES: Cc1ncsc1-c1ccc([C@H](C)NC(=O)[C@@H]2C[C@@H](O)CN2C(=O)[C@@H](c2cc(OC(C)CN3CCCC(CN4CCN5c6cc(-c7ccccc7O)nnc6NC[C@H]5C4)CC3)no2)C(C)C)cc1]<br>(2S,4R)-4-hydroxy-1-((2R)-2-(3-((1-(4-(((S)-2-(2-hydroxyphenyl)-5,6,6a,7,9,10-hexahydro-8H-pyrazino[1',2':4,5]pyrazino[2,3-c]pyridazin-8-yl)methyl)azepan-1-yl)propan-2-yl)oxy)isoxazol-5-yl)-3-methylbutanoyl)-N-((S)-1-(4-(4-methylthiazol-5-yl)phenyl)ethyl)pyrrolidine-2-carboxamide (mixture 1) | 933.5 | 933.6 | $^1$HNMR (CD$_3$OD-d4, 400 MHz): δ 9.82-9.77 (s, 1H), 7.60-7.35 (m, 7H), 7.08-6.13 (m, 2H), 6.15-6.13 (m, 1 H), 5.22-5.03 (m, 3H), 4.55-4.27 (m, 3H), 3.90-3.36 (m, 15H), 3.27-3.19 (m, 3H), 2.59 (s, 3H), 2.42-1.94 (m, 9H), 1.55-1.53 (m, 1H), 1.48-1.45 (m, 6H) 1.08-1.07 (m, 3H), 0.95-0.91 (m, 3H). |

| Ex# | Structure and Name | Calcd. (M + H)⁺ m/z | Found (M + H)⁺ m/z | HNMR |
|---|---|---|---|---|
| Ex 68 | (2S,4R)-4-hydroxy-1-((2R)-2-(3-((1-(4-(((S)-2-(2-hydroxyphenyl)-5,6,6a,7,9,10-hexahydro-8H-pyrazino[1',2':4,5]pyrazino[2,3-c]pyridazin-8-yl)methyl)azepan-1-yl)propan-2-yl)oxy)isoxazol-5-yl)-3-methylbutanoyl)-N-((S)-1-(4-(4-methylthiazol-5-yl)phenyl)ethyl)pyrrolidine-2-carboxamide (mixture 2) | 933.5 | 933.5 | ¹HNMR (CD₃OD-d₄, 400 MHz): δ 9.87 (s, 1H), 7.59-7.36 (m, 7H), 7.05-7.03 (m, 2H), 6.15-6.13 (m, 1 H), 5.21-5.03 (m, 3H), 4.53-4.46 (m, 3H), 3.89-3.32 (m, 15H), 3.27-3.19 (m, 3H), 2.58 (s, 3H), 2.42-1.95 (m, 9H), 1.54-1.48 (m, 7H), 1.08-1.07 (m, 3H), 0.93-0.91 (m, 3H) |
| Ex 69 | (2S,4R)-4-hydroxy-1-((2R)-2-(3-(2-(4-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide (diastereomer 1) | 960.5 | 960.6 | ¹HNMR (CD₃OD-d₄, 400 MHz): δ 9.91 (s, 1H), 7.28-7.50 (m, 7H), 6.94-6.97 (m, 2H), 6.03 (s, 1H), 4.93-4.98 (m, 2H), 4.43-4.55 (m, 4H), 3.89-4.41 (m, 6H), 3.54-3.7 (m, 13H), 3.29-3.39 (m, 4H 2.52-2.60 (m, 5H), 2.10-2.4 (m, 6H), 1.83 (s, 1H), 1.42-1.52 (m, 3H), 0.95-0.97 (m, 3H), 0.78-0.83 (m, 3H) |
| Ex 70 | (2S,4R)-4-hydroxy-1-((2R)-2-(3-(2-(4-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide (diastereomer 2) | 960.5 | 960.6 | ¹H NMR (CD₃OD-d₄, 400 MHz): δ 9.83-9.85 (m, 1H), 7.26-7.48 (m, 7H), 6.93-6.97 (m, 2H), 6.03 (s, 1H), 4.92-4.96 (m, 2H), 4.40-4.55 (m, 4H), 3.79-4.34 (m, 6H), 3.53-3.77 (m, 13H), 3.22-3.39 (m, 4H), 2.44-2.51 (m, 6H), 2.11-2.23 (m, 5H), 1.86-1.92 (m, 1H), 1.42-1.52 (m, 3H), 0.95-0.97 (m, 3H), 0.79-0.83 (m, 3H). |

| Ex# | Structure and Name | Calcd. (M + H)+ m/z | Found (M + H)+ m/z | HNMR |
|---|---|---|---|---|
| Ex 71 | (2S,4R)-4-hydroxy-1-((2R)-2-(3-(2-(3-(2-(2-hydroxyphenyl)-6a-methyl-5,6,6a,7,9,10-hexahydro-8H-pyrazino[1',2':4,5]pyrazino[2,3-c]pyridazin-8-yl)pyrrolidin-1-yl)ethoxy)isoxazol-5-yl)-3-methylbutanoyl)-N-((S)-1-(4-(4-methylthiazol-5-yl)phenyl)ethyl)pyrrolidine-2-carboxamide (mixture 1) | 891.4 | 891.6 | $^1$H NMR (400 MHz, CD$_3$OD): δ 9.98 (s, 1H), 7.58-7.40 (m, 7H), 7.05-7.02 (m, 2H), 6.14 (m, 1H), 5.06-5.03 (m, 2H), 4.79-3.37 (m, 20H), 2.60-2.56 (m, 3H), 2.39-2.35 (m, 2H), 2.41-2.39 (m, 1H), 2.35-2.19 (m, 1H), 1.59-1.50 (m, 6H), 1.04-1.03 (m, 3H), 0.92-0.90 (m, 3H). (Some protons were buried under solvent or water peak, not all protons were listed) |
| Ex 72 | (2S,4R)-4-hydroxy-1-((2R)-2-(3-(2-(3-(2-(2-hydroxyphenyl)-6a-methyl-5,6,6a,7,9,10-hexahydro-8H-pyrazino[1',2':4,5]pyrazino[2,3-c]pyridazin-8-yl)pyrrolidin-1-yl)ethoxy)isoxazol-5-yl)-3-methylbutanoyl)-N-((S)-1-(4-(4-methylthiazol-5-yl)phenyl)ethyl)pyrrolidine-2-carboxamide (mixture 2) | 891.4 | 891.6 | $^1$H NMR (400 MHz, CD$_3$OD): δ 9.90 (s, 1H), 7.56-7.40 (m, 7H), 7.03-7.01 (m, 2H), 6.14 (m, 1H), 5.04-5.01 (m, 2H), 4.62-3.38 (m, 20H), 2.60-2.57 (m, 3H), 2.40-2.37 (m, 2H), 2.37-2.36 (m, 1H), 2.21-2.20 (m, 1H), 1.61-1.49 (m, 6H), 1.06-1.03 (m, 3H), 0.92-0.90 (m, 3H) (Some protons were buried under solvent or water peak, not all protons were listed) |
| Ex 76 | (2S,4R)-4-hydroxy-1-((R)-2-(3-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 891.4 | 891.4 | $^1$H NMR (400 MHz, DMSO-d$_6$ + D$_2$O): δ 8.97 (s, 1H), 7.89-7.91 (m, 1H), 7.35-7.47 (m, 4H), 7.19-7.23 (m, 2H), 6.84-6.88 (m, 2H), 5.92-6.10 (m, 1H), 4.87-4.92 (m, 1H), 4.34-4.38 (m, 1H), 4.21-4.28 (m, 3H), 3.99-4.02 (m, 1H), 3.63-3.72 (m, 2H), 3.43-3.47 (m, 2H), 3.12-3.16 (m, 2H), 3.02-3.05 (m, 2H), 2.93-2.96 (m, 2H), 2.81-2.86 (m, 1H), 2.64-2.66 (m, 2H), 2.45 (s, 3H), 2.18-2.32 (m, 3H), 1.89-2.02 (m, 4H), 1.73-1.81 (m, 3H), 1.41-1.46 (m, 3H), 1.37-1.40 (m, 3H), 0.94-0.97 (m, 3H), 0.78-0.83 (m, 3H). |

| Ex# | Structure and Name | Calcd. (M + H)+ m/z | Found (M + H)+ m/z | HNMR |
|---|---|---|---|---|
| Ex 77 | 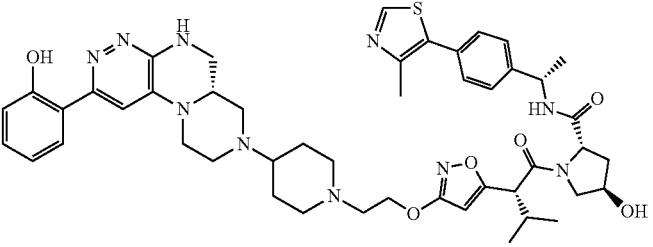 [SMILES: Cc1ncsc1-c1ccc([C@H](C)NC(=O)[C@@H]2C[C@@H](O)CN2C(=O)[C@@H](c2cc(OCCN3CCC(N4CCN5c6cc(-c7ccccc7O)nnc6NC[C@@H]5C4)CC3)no2)C(C)C)cc1]<br>(2S,4R)-4-hydroxy-1-((R)-2-(3-(2-(4-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 891.4 | 891.4 | ¹H NMR (DMSO-d₆ + D₂O, 400 MHz): δ 8.97 (s, 1H), 7.89-7.91 (m, 1H), 7.35-7.47 (m, 4H), 7.19-7.23 (m, 2H), 6.84-6.88 (m, 2H), 5.92-6.10 (m, 1H), 4.87-4.92 (m, 1H), 4.34-4.38 (m, 1H), 4.21-4.28 (m, 3H), 3.99-4.02 (m, 1H), 3.63-3.72 (m, 2H), 3.43-3.47 (m, 2H), 3.12-3.16 (m, 2H), 3.02-3.05 (m, 2H), 2.93-2.96 (m, 2H), 2.81-2.86 (m, 1H), 2.64-2.66 (m, 2H), 2.45 (s, 3H), 2.18-2.32 (m, 3H), 1.89-2.02 (m, 4H), 1.73-1.81 (m, 3H), 1.41-1.46 (m, 3H), 1.37-1.40 (m, 3H), 0.94-0.97 (m, 3H), 0.78-0.83 (m, 3H). |
| Ex 78 | 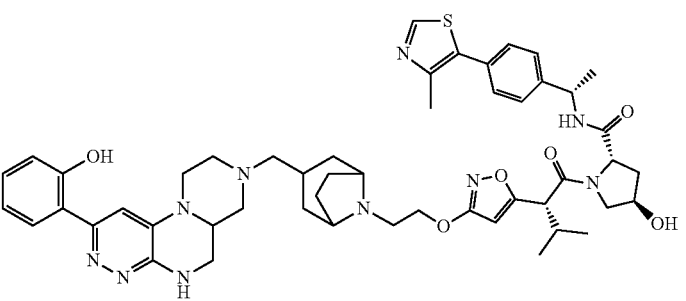 [SMILES: Cc1ncsc1-c1ccc([C@H](C)NC(=O)[C@@H]2C[C@@H](O)CN2C(=O)[C@@H](c2cc(OCCN3C4CCC3CC(CN3CCN5c6cc(-c7ccccc7O)nnc6NCC5C3)C4)no2)C(C)C)cc1]<br>(2S,4R)-4-hydroxy-1-((2R)-2-(3-(2-(3-((2-(2-hydroxyphenyl)-5,6,6a,7,9,10-hexahydro-8H-pyrazino[1',2':4,5]pyrazino[2,3-c]pyridazin-8-yl)methyl)-8-azabicyclo[3.2.1]octan-8-yl)ethoxy)isoxazol-5-yl)-3-methylbutanoyl)-N-((S)-1-(4-(4-methylthiazol-5-yl)phenyl)ethyl)pyrrolidine-2-carboxamide | 931.5 | 931.3 | ¹H NMR (400 MHz, CD₃OD-d4): δ 9.69-9.74 (m, 1H), 7.42-7.58 (m, 6H), 7.35 (s, 1H), 7.03-7.07 (m, 2H), 6.07-6.13 (m, 1H), 5.00-5.07 (m, 1H), 4.65-4.70 (m, 2H), 4.38-4.57 (s, 3H), 4.11-4.27 (m, 3H), 3.83-3.99 (m, 5H), 3.69-3.75 (m, 1H), 3.58-3.62 (m, 1H), 3.37-3.52 (m, 4H), 3.18-3.22 (m, 2H), 2.58 (s, 3H), 2.33-2.43 (m, 3H), 2.14-2.27 (m, 4H), 1.91-1.99 (m, 3H), 1.51-1.62 (m, 3H), 1.28-1.37 (t, 3H), 1.05-1.06 (d, J = 6.4 Hz, 3H), 1.05-1.06 (d, J = 6.4 Hz, 3H). |

-continued

| Ex# | Structure and Name | Calcd. (M + H)+ m/z | Found (M + H)+ m/z | HNMR |
|---|---|---|---|---|
| Ex 81 | 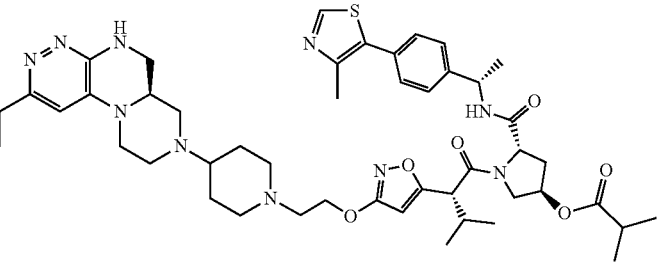<br>(3R,5S)-1-((R)-2-(3-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-5-(((S)-1-(4-(4-methylthiazol-5-yl)phenyl)ethyl)carbamoyl)pyrrolidin-3-yl isobutyrate | 961.5 | 961.4 | $^1$H NMR (DMSO-$d_6$ + $D_2O$, 400 MHz): δ 8.97 (s, 1H), 7.89-7.91 (m, 1H), 7.35-7.47 (m, 4H), 7.19-7.23 (m, 2H), 6.84-6.88 (m, 2H), 5.92-6.10 (m, 1H), 4.87-4.92 (m, 1H), 4.34-4.38 (m, 1H), 4.21-4.28 (m, 3H), 3.99-4.02 (m, 1H), 3.63-3.72 (m, 2H), 3.43-3.47 (m, 2H), 3.12-3.16 (m, 2H), 3.02-3.05 (m, 2H), 2.93-2.96 (m, 2H), 2.81-2.86 (m, 1H), 2.64-2.66 (m, 2H), 2.45 (s, 3H), 2.18-2.32 (m, 3H), 1.89-2.02 (m, 4H), 1.73-1.81 (m, 3H), 1.41-1.46 (m, 3H), 1.37-1.40 (m, 3H), 0.94-0.97 (m, 3H), 0.78-0.83 (m, 3H). |
| Ex 84 | 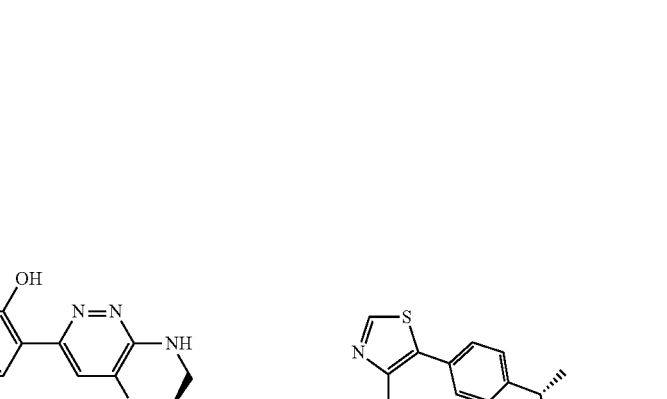<br>(2S,4R)-4-hydroxy-1-((2R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)azepan-1-yl)ethoxy)isoxazol-5-yl)-3-methylbutanoyl)-N-((S)-1-(4-(4-methylthiazol-5-yl)phenyl)ethyl)pyrrolidine-2-carboxamide | 919.5 | 919.4 | $^1$HNMR (CD$_3$OD-$d_4$, 400 MHz): δ 8.87 (s, 1H), 7.78-7.76 (m, 2H), 7.45-7.39 (m, 4H), 7.21-7.14 (m, 2H), 6.88-6.86 (m, 2H), 6.01 (s, 1H), 5.03-5.01 (m, 1H), 4.50-4.32 (m, 4H), 3.70-3.53 (m, 6H), 3.03-2.78 (m, 9H), 2.47-2.46 (m, 3H), 2.38-2.33 (m, 1H), 2.23-217 (m, 4H), 1.94-1.81 (m, 7H), 1.62-1.71 (m, 1H), 1.51-1.43 (m, 4H), 1.42-1.35 (m, 1H), 1.05-1.04 (m, 3H), 0.9-1.87 (m, 3H). |

| Ex# | Structure and Name | Calcd. (M + H)+ m/z | Found (M + H)+ m/z | HNMR |
|---|---|---|---|---|
| Ex 85 | (2S,4R)-4-hydroxy-1-((2R)-2-(3-(2-(3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide (diastereomer 1) | 905.4 | 905.3 | $^1$H NMR (400 MHz, CD$_3$OD-d4): δ 8.86-8.87 (m, 1H), 7.75-7.78 (m, 1H), 7.33-7.45 (m, 4H), 7.19-7.24 (m, 1H), 7.13-7.15 (m, 1H), 6.87-6.91 (m, 2H), 5.97-6.02 (m, 1H), 5.00-5.04 (m, 1H), 4.47-4.51 (m, 1H), 4.35-4.40 (m, 3H), 3.91-3.94 (m, 1H), 3.78-3.82 (m, 4H), 3.24-3.28 (m, 2H), 3.05-3.13 (m, 2H), 2.89-3.02 (m, 4H), 2.46-2.47 (m, 3H), 2.14-2.37 (m, 7H), 1.87-2.03 (m, 4H), 1.65-1.82 (m, 3H), 1.47-1.56 (m, 3H), 0.99-1.03 (m, 3H), 0.82-0.90 (m, 3H). |
| Ex 86 | (2S,4R)-4-hydroxy-1-((2R)-2-(3-(2-(3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide (diastereomer 2) | 905.4 | 905.3 | $^1$H NMR (400 MHz, CD$_3$OD-d$_4$): δ 8.85-8.87 (m, 1H), 7.76-7.79 (m, 1H), 7.33-7.45 (m, 4H), 7.21-7.23 (m, 1H), 7.12-7.15 (m, 1H), 6.86-6.90 (m, 2H), 5.96-6.02 (m, 1H), 4.97-5.04 (m, 1H), 4.47-4.51 (m, 1H), 4.32-4.41 (m, 3H), 3.88-3.91 (m, 1H), 3.79-3.82 (m, 1H), 3.44-3.66 (m, 4H), 3.17-3.27 (m, 2H), 2.98-3.07 (m, 4H), 2.82-2.86 (m, 2H), 2.46-2.47 (m, 3H), 2.09-2.40 (m, 7H), 1.90-1.97 (m, 2H), 1.63-1.79 (m, 5H), 1.49-1.56 (m, 3H), 0.99-1.03 (m, 3H), 0.85-0.89 (m, 3H). |

| Ex# | Structure and Name | Calcd. (M + H)+ m/z | Found (M + H)+ m/z | HNMR |
|---|---|---|---|---|
| Ex 87 | (2S,4R)-4-hydroxy-1-((2R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)-3,3-dimethylpiperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 933.5 | 933.5 | $^1$HNMR (CD$_3$OD-d$_4$, 400 MHz): δ 8.87 (s, 1H), 7.78-776 (m, 2H), 7.45-7.39 (m, 4H), 7.21-7.14 (m, 2H), 6.88-6.86 (m, 2H), 6.01 (s, 1H), 5.03-5.01 (m, 1H), 4.50-4.32 (m, 4H), 3.70-3.53 (m, 6H), 3.03-2.78 (m, 9H), 2.47-2.46 (m, 3H), 2.38-2.33 (m, 1H), 2.23-217 (m, 4H), 1.94-1.81 (m, 7H), 1.62-1.71 (m, 1H), 1.51-1.43 (m, 4H), 1.42-1.35 (m, 1H), 1.05-1.04 (m, 3H), 0.9-1.87 (m, 3H). |
| Ex 90 | (2S,4R)-4-hydroxy-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)-3,6-dihydropyridin-1(2H)-yl)ethoxy)isoxazol-5-yl)-3-methylbutanoyl)-N-((S)-1-(4-(4-methylthiazol-5-yl)phenyl)ethyl)pyrrolidine-2-carboxamide | 903.4 | 903.6 | $^1$H NMR (400 MHz, CD$_3$OD-d4): δ 8.85-8.87 (m, 1H), 7.74-7.77 (m, 1H), 7.37-7.45 (m, 4H), 7.20-7.24 (m, 1H), 7.13-7.15 (m, 1H), 6.87-6.91 (m, 2H), 5.97-6.03 (m, 1H), 5.66 (s, 1H), 4.99-5.05 (m, 1H), 4.48-4.53 (m, 1H), 4.38-4.44 (m, 3H), 3.91-3.94 (m, 2H), 3.60-3.69 (m, 2H), 3.47-3.52 (m, 1H), 3.10-3.27 (m, 4H), 2.93-3.07 (m, 7H), 2.75-2.83 (m, 2H), 2.46-2.47 (m, 3H), 2.21-2.40 (m, 3H), 2.13-2.21 (m, 2H), 1.92-2.03 (m, 1H), 1.75-1.81 (m, 1H), 1.51-1.60 (m, 3H), 1.04-1.06 (m, 3H), 0.86-0.89 (m, 3H). |

| Ex# | Structure and Name | Calcd. (M + H)+ m/z | Found (M + H)+ m/z | HNMR |
|---|---|---|---|---|
| Ex 93 | (2S,4R)-4-hydroxy-1-((2R)-2-(3-(2-(3-hydroxy-4-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 893.4 | 893.4 | $^1$HNMR (CD$_3$OD-d$_4$, 400 MHz): δ 8.77 (s, 1H), 7.66-7.64 (m, 1H), 7.35-7.29 (m, 4H), 7.13-7.03 (m, 2H), 6.81-6.78 (m, 2H), 5.92-5.86 (s, 1H), 4.94-4.90 (m, 1H), 4.41-4.11 (m, 5H), 3.73-3.44 (m, 5H), 3.02-2.83 (m, 5H), 2.75-2.68 (m, 4H), 2.44-2.22 (m, 8H), 2.13-2.07 (m, 1H), 1.88-1.85 (m, 2H), 1.50-1.40 (m, 3H), 0.95-0.94 (m, 3H), 0.82-0.78 (m, 3H). |
| Ex 94 | (2S,4R)-4-hydroxy-1-((2R)-2-(3-(2-(3-hydroxy-4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 907.4 | 907.6 | $^1$H NMR (400 MHz, CD$_3$OD) δ 9.30 (s, 1H), 7.56-7.40 (m, 6H), 7.31-7.21 (m, 1H), 7.04 (t, J = 9.1 Hz, 2H), 6.11 (s, 1H), 5.07-5.01 (m, 1H), 4.84-4.74 (m, 4H), 4.67-4.64 (m, 1H), 4.50 (t, J = 8.4 Hz, 1H), 4.46-4.42 (m, 1H), 4.15-3.94 (m, 1H), 3.87-3.81 (m, 1H), 3.76-3.61 (m, 7H), 3.52-3.46 (m, 1H), 3.27-3.19 (m, 2H), 3.15-3.11 (m, 1H), 2.52 (s, 3H), 2.52-2.51 (m, 1H), 2.42-2.15 (m, 3H), 2.10-1.77 (m, 2H), 1.60 (d, J = 6.5 Hz, 1H), 1.52 (d, J = 7.0 Hz, 3H), 1.40-1.10 (m, 2H), 1.05 (d, J = 6.7 Hz, 3H), 0.89 (d, J = 6.5 Hz, 3H). |

-continued

| Ex# | Structure and Name | Calcd. (M + H)+ m/z | Found (M + H)+ m/z | HNMR |
|---|---|---|---|---|
| Ex 95 | 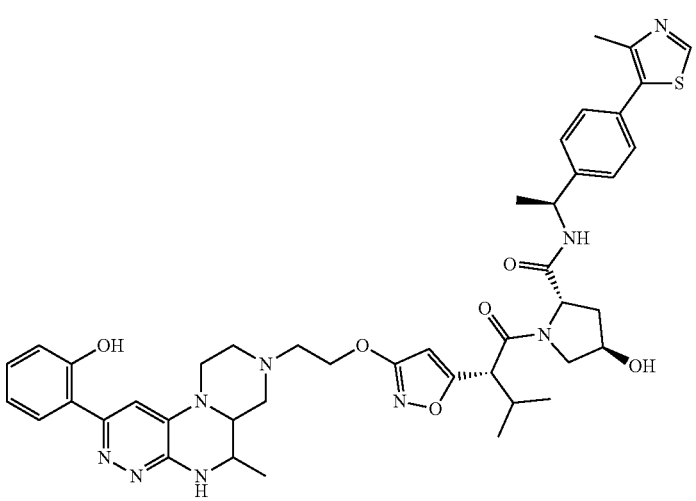 [SMILES: Cc1ncsc1-c1ccc([C@H](C)NC(=O)[C@@H]2C[C@@H](O)CN2C(=O)[C@@H](c2cc(OCCN3CCN4c5cc(-c6ccccc6O)nnc5NC(C)C4C3)no2)C(C)C)cc1]<br>(2S,4R)-4-hydroxy-1-((2R)-2-(3-(2-(2-(2-hydroxyphenyl)-6-methyl-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-N-((S)-1-(4-(4-methylthiazol-5-yl)phenyl)ethyl)pyrrolidine-2-carboxamide | 822.4 | 822.5 | $^1$H NMR (400 MHz, CD$_3$OD-d4): δ8.75-8.78 (m, 1H), 7.67-7.69 (m, 1H), 7.25-7.36 (m, 4H), 7.08-7.15 (m, 2H), 6.76-6.81 (m, 2H), 5.87-5.94 (m, 1H), 4.90-4.96 (m, 1H), 4.26-4.23 (m, 4H), 3.72-3.87 (m, 1H), 3.50-3.65 (m, 2H), 3.31-3.43 (m, 1H), 3.00-3.11 (m, 3H), 2.85-2.97 (m, 2H), 2.76-2.83 (m, 2H), 2.35-2.38 (m, 3H), 2.22-2.31 (m, 2H), 2.03-2.09 (m, 1H), 1.82-1.98 (m, 2H), 1.39-1.50 (m, 3H), 1.16-1.24 (m, 3H), 0.92-0.96 (m, 3H), 0.75-0.82 (m, 3H). |
| Ex 96 | 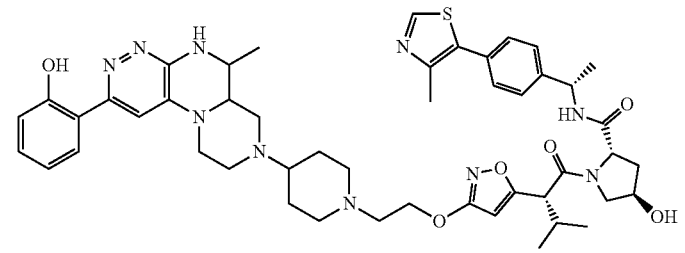 [SMILES: Cc1ncsc1-c1ccc([C@H](C)NC(=O)[C@@H]2C[C@@H](O)CN2C(=O)[C@@H](c2cc(OCCN3CCC(N4CCN5c6cc(-c7ccccc7O)nnc6NC(C)C5C4)CC3)no2)C(C)C)cc1]<br>(2S,4R)-4-hydroxy-1-((2R)-2-(3-(2-(4-(2-(2-hydroxyphenyl)-6-methyl-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 905.4 | 905.3 | $^1$H NMR (400 MHz, CD$_3$OD-d4): δ 8.85-8.87 (m, 1H), 7.77-7.79 (m, 1H), 7.38-7.46 (m, 4H), 7.15-7.23 (m, 2H), 6.89-6.90 (m, 2H), 5.95-6.02 (m, 1H), 5.00-5.06 (m, 1H), 4.49-4.53 (m, 1H), 4.42-4.45 (m, 1H), 4.33-4.35 (m, 2H), 3.94-3.97 (m, 1H), 3.81-3.85 (m, 1H), 3.60-3.72 (m, 2H), 3.41-3.49 (m, 1H), 3.09-3.25 (m, 4H), 2.90-3.06 (m, 2H), 2.80-2.93 (m, 2H), 2.48 (s, 3H), 2.33-2.43 (m, 3H), 2.07-2.20 (m, 4H), 1.89-1.98 (m, 3H), 1.58-1.66 (m, 2H), 1.51-1.54 (m, 3H), 1.24-1.31 (m, 3H), 1.04-1.06 (d, J = 6.4 Hz, 3H), 0.88-0.92 (m, 3H). |

| Ex# | Structure and Name | Calcd. (M + H)+ m/z | Found (M + H)+ m/z | HNMR |
|---|---|---|---|---|
| Ex 97 | 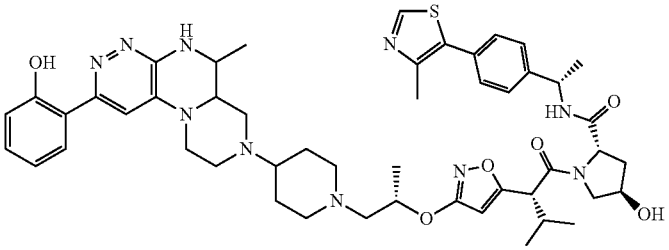 [SMILES: Cc1ncsc1-c1ccc([C@H](C)NC(=O)[C@@H]2C[C@@H](O)CN2C(=O)[C@@H](c2cc(O[C@@H](C)CN3CCC(N4CCN5c6cc(-c7ccccc7O)nnc6NC(C)C5C4)CC3)no2)C(C)C)cc1]<br>(2S,4R)-4-hydroxy-1-((2R)-2-(3-(((2S)-1-(4-(2-(2-hydroxyphenyl)-6-methyl-5,6,6a,7,9,10-hexahydro-8H-pyrazino[1',2':4,5]pyrazino[2,3-c]pyridazin-8-yl)piperidin-1-yl)propan-2-yl)oxy)isoxazol-5-yl)-3-methylbutanoyl)-N-((S)-1-(4-(4-methylthiazol-5-yl)phenyl)ethyl)pyrrolidine-2-carboxamide | 919.5 | 919.3 | ¹H NMR (400 MHz, CD₃OD-d4): δ 8.85-8.87 (m, 1H), 7.76-7.78 (m, 1H), 7.38-7.45 (m, 4H), 7.14-7.23 (m, 2H), 6.89-6.90 (m, 2H), 5.93-6.00 (m, 1H), 5.00-5.05 (m, 1H), 4.39-4.53 (m, 2H), 3.93-4.07 (m, 1H), 3.82-3.86 (m, 1H), 3.61-3.72 (m, 2H), 3.36-3.61 (m, 2H), 2.89-3.23 (m, 6H), 2.72-2.78 (m, 1H), 2.47-2.50 (m, 4H), 2.31-2.39 (m, 3H), 2.13-2.20 (m, 3H), 1.92-2.09 (m, 2H), 1.85-1.89 (m, 2H), 1.58-1.68 (m, 2H), 1.51-1.55 (m, 3H), 1.28-1.37 (m, 6H), 1.04-1.06 (m, 3H), 0.89-0.93 (m, 3H). |
| Ex 98 | 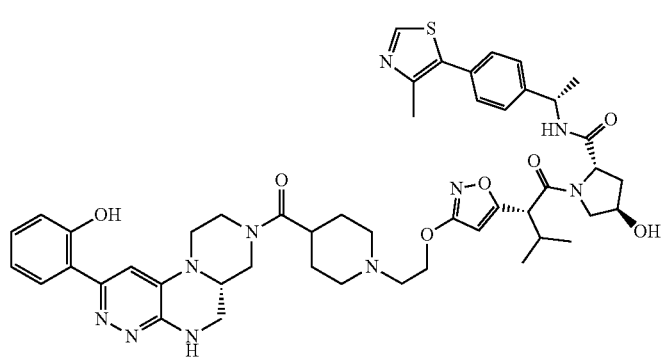 [SMILES: Cc1ncsc1-c1ccc([C@H](C)NC(=O)[C@@H]2C[C@@H](O)CN2C(=O)[C@@H](c2cc(OCCN3CCC(C(=O)N4CCN5c6cc(-c7ccccc7O)nnc6NC[C@H]5C4)CC3)no2)C(C)C)cc1]<br>(2S,4R)-4-hydroxy-1-((R)-2-(3-(2-(4-((S)-2-(2-hydroxyphenyl)-6,6a,7,8,9,10-hexahydro-5H-pyrazino[1',2':4,5]pyrazino[2,3-c]pyridazine-8-carbonyl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 919.4 | 919.4 | ¹H NMR (400 MHz, CD₃OD) δ 8.86-8.87 (m, 1H), 7.74-7.78 (m, 1H), 7.37-7.45 (m, 4H), 7.15-7.24 (m, 2H), 6.87-6.91 (m, 2H), 5.95-6.01 (m, 1H), 4.99-5.05 (m, 1H), 4.43-4.67 (m, 13H), 2.75-3.20 (m, 8H), 2.47 (s, 3H), 2.15-2.44 (m, 4H), 1.77-1.98 (m, 5H), 1.47-1.60 (m, 3H), 1.02-1.06 (m, 3H), 0.88-0.92 (m, 3H). |

| Ex# | Structure and Name | Calcd. (M + H)+ m/z | Found (M + H)+ m/z | HNMR |
|---|---|---|---|---|
| Ex 99 | 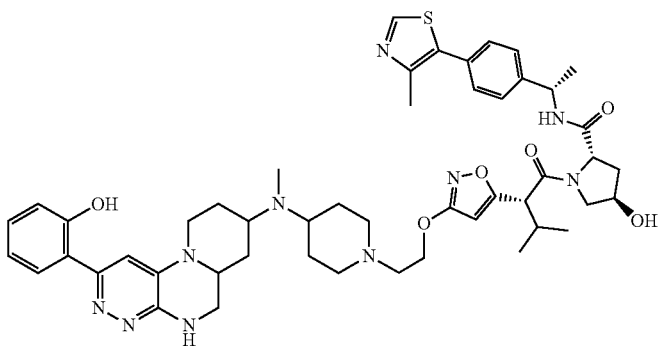 [SMILES: Cc1ncsc1-c1ccc([C@H](C)NC(=O)[C@@H]2C[C@@H](O)CN2C(=O)[C@@H](c2cc(OCCN3CCC(N(C)C4CCN5c6cc(-c7ccccc7O)nnc6NCC5C4)CC3)no2)C(C)C)cc1]<br>(2S,4R)-4-hydroxy-1-((2R)-2-(3-(2-(4-((2-(2-hydroxyphenyl)-6,6a,7,8,9,10-hexahydro-5H-pyrido[1',2':4,5]pyrazino[2,3-c]pyridazin-8-yl)(methyl)amino)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 919.5 | 919.6 | $^1$H NMR (400 MHz, CD$_3$OD-d$_4$): δ 8.86-8.87 (m, 1H), 7.76-7.78 (m, 1H), 7.37-7.45 (m, 4H), 7.15-7.23 (m, 2H), 6.86-6.90 (m, 2H), 5.95-6.01 (m, 1H), 4.99-5.05 (m, 1H), 4.49-4.53 (m, 1H), 4.43-4.44 (m, 1H), 4.31-4.34 (m, 2H), 4.14-4.17 (m, 1H), 3.81-3.85 (m, 1H), 3.54-3.68 (m, 3H), 3.46-3.49 (m, 1H), 3.34 (s, 1H), 3.06-3.13 (m, 2H), 2.86-2.99 (m, 2H), 2.77-2.82 (m, 2H), 2.64-2.69 (m, 1H), 2.47 (s, 3H), 2.31-2.40 (m, 1H), 2.28 (s, 3H), 2.15-2.22 (m, 3H), 1.92-2.04 (m, 3H), 1.80-1.85 (m, 2H), 1.64-1.72 (m, 3H), 1.58-1.60 (m, 1H), 1.51-1.53 (d, J = 7.2 Hz, 3H), 1.04-1.06 (m, J = 6.4 Hz, 3H), 0.88-0.89 (m, J = 6.8 Hz, 3H). |

Example 8. (2S,4R)-4-hydroxy-1-((2S)-2-(3-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propanamido)-3,3-dimethylbutanoyl)-N—((S)-1-(4-(4-methylthiazol-5-yl)phenyl)ethyl)pyrrolidine-2-carboxamide

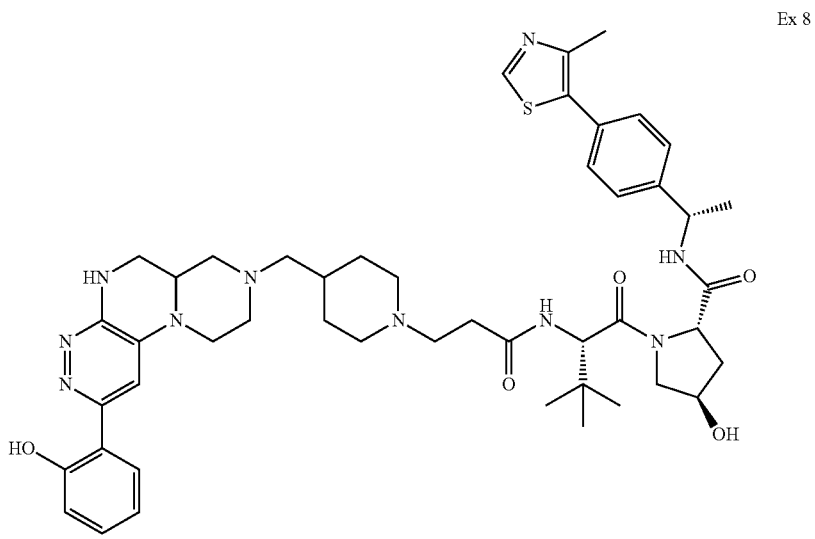 [SMILES: Cc1ncsc1-c1ccc([C@H](C)NC(=O)[C@@H]2C[C@@H](O)CN2C(=O)[C@@H](NC(=O)CCN2CCC(CN3CCN4c5cc(-c6ccccc6O)nnc5NCC4C3)CC2)C(C)(C)C)cc1]

Ex 8

Step 1: tert-butyl 3-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propanoate

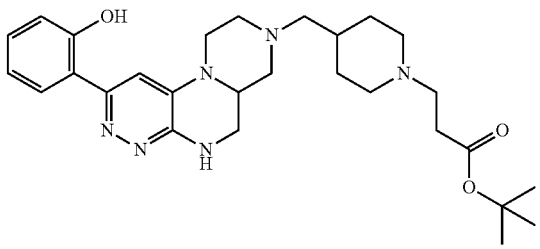 [SMILES: CC(C)(C)OC(=O)CCN1CCC(CN2CCN3c4cc(-c5ccccc5O)nnc4NCC3C2)CC1]

The title compound was prepared using procedure analogous to those described for Example 3, with tert-butyl 3-bromopropanoate replacing Int-6. LCMS m/z calcd for $C_{28}H_{41}N_6O_3$ [M+H]$^+$: 509.3; Found: 509.1.

Step 2: 3-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propanoic acid

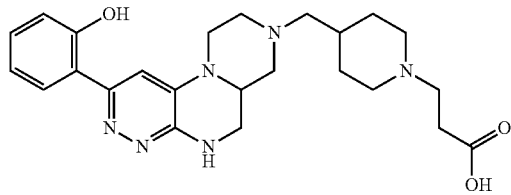 [SMILES: O=C(O)CCN1CCC(CN2CCN3c4cc(-c5ccccc5O)nnc4NCC3C2)CC1]

To a solution of tert-butyl 3-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propanoate (27.0 mg, 0.05 mmol) in DCM (3 mL) and TFA (0.5 mL, 6.53 mmol), the mixture solution was stirred at 25° C. for 1 h. The residue was diluted with EtOAc (10 mL) and the organic layer washed with water (2×10 mL) then saturated brine (1×10 mL). The organic layer was separated, dried over MgSO$_4$, and filtered. The filtration was concentrated to dryness under reduced pressure. The residue was purified by prep-TLC (PE:EA=1:2) to give 3-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propanoic acid (20 mg, 0.04 mmol, 83.3% yield) as a solid. LCMS m/z calcd for $C_{24}H_{33}N_6O_3$ [M+H]$^+$: 453.2; Found: 453.2.

Step 3: (2S,4R)-4-hydroxy-1-((2S)-2-(3-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propanamido)-3,3-dimethylbutanoyl)-N—((S)-1-(4-(4-methylthiazol-5-yl)phenyl)ethyl)pyrrolidine-2-carboxamide To a mixture of (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide (23.6 mg, 0.05 mmol), DIEA (0.02 mL, 0.13 mmol) and 3-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propanoic acid (20.0 mg, 0.04 mmol) in DMF (1 mL) was added HATU (33.6 mg, 0.09 mmol), the mixture was stirred at 25° C. for 16 h. The reaction mixture was concentrated to dryness and the residue was purified by prep-HPLC (eluting with CH$_3$CN in H$_2$O (0.1% NH$_3$·H$_2$O from 10% to 95%) to get (2S,4R)-4-hydroxy-1-((2S)-2-(3-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propanamido)-3,3-dimethylbutanoyl)-N—((S)-1-(4-(4-methylthiazol-5-yl)phenyl)ethyl)pyrrolidine-2-carboxamide (1.63 mg, 0.002 mmol, 3.8% yield) as a light yellow solid. LCMS m/z calcd for $C_{47}H_{63}N_{10}O_5S$ [M+H]$^+$: 879.5; Found: 879.6. $^1$H NMR (CD$_3$OD, 400 MHz): δ 8.97 (m, 1H), 7.76-7.74 (m, 1H), 7.45-7.41 (m, 4H), 7.28-7.20 (m, 2H), 6.85-6.82 (m, 2H), 4.97-5.05 (m, 2H), 4.45-4.66 (m, 4H), 3.89-3.87 (m, 2H), 3.76-3.73 (m, 1H), 3.61-3.52 (m, 1H), 3.01-2.95 (m, 6H), 2.67-5.63 (m, 2H), 2.47 (s, 3H), 2.44-2.41 (m, 2H), 2.30-2.28 (m, 2H), 2.22-2.20 (m, 2H), 2.07-1.92 (m, 3H), 1.78-1.73 (m, 3H), 1.1.70-1.67 (m, 1H), 1.51-1.49 (m, 3H), 1.01-0.98 (m, 9H).

Example 27. (2S,4R)-4-hydroxy-1-((R)-2-(3-((S)-1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)-1-oxopropan-2-yl)oxy)isoxazol-5-yl)-3-methylbutanoyl)-N—((S)-1-(4-(4-methylthiazol-5-yl)phenyl)ethyl)pyrrolidine-2-carboxamide Ex 27

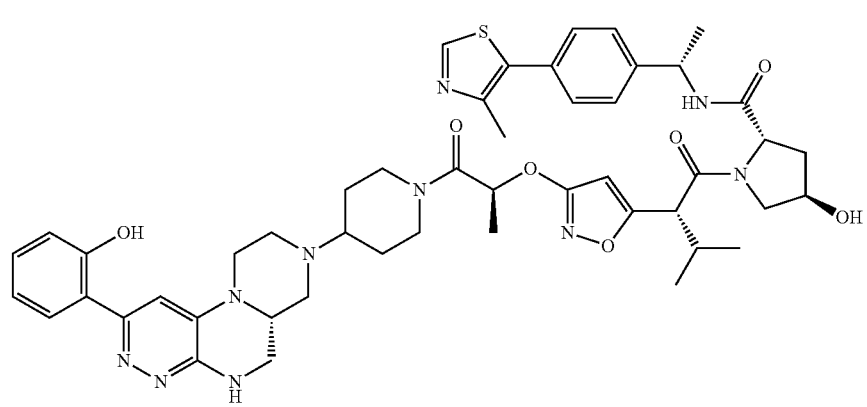

Step 1: (2S,4R)-4-((tert-butyldimethylsilyl)oxy)-1-((R)-2-(3-((S)-1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)-1-oxopropan-2-yl)oxy)isoxazol-5-yl)-3-methylbutanoyl)-N—((S)-1-(4-(4-methylthiazol-5-yl)phenyl)ethyl)pyrrolidine-2-carboxamide

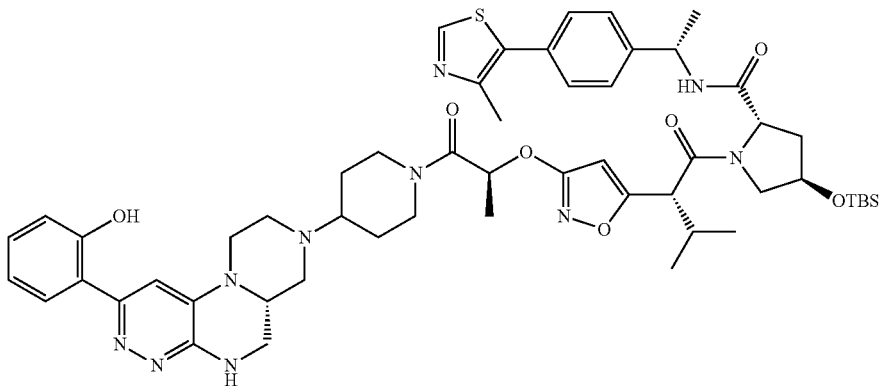 [SMILES: Cc1ncsc1-c1ccc([C@H](C)NC(=O)[C@@H]2C[C@@H](O[Si](C)(C)C(C)(C)C)CN2C(=O)[C@@H](c2cc(O[C@@H](C)C(=O)N3CCC(N4CCN5c6cc(-c7ccccc7O)nnc6NC[C@H]5C4)CC3)no2)C(C)C)cc1]

To a solution of Int-28 (30 mg, 0.04 mmol), (S)-2-(8-(piperidin-4-yl)-6,6a,7,8,9,10-hexahydro-5H-pyrazino[1',2':4,5]pyrazino[2,3-c]pyridazin-2-yl)phenol (13.4 mg, 0.04 mmol) and DIEA (0.02 mL, 0.11 mmol) in DMF (5 mL) was added HATU (41.6 mg, 0.11 mmol). The resulted mixture was stirred at 30° C. for 16 h. The volatiles were removed under reduced pressure and the residue was purified by prep-HPLC (eluting with CH$_3$CN in H$_2$O: (0.1% NH$_3$·H$_2$O) from 10% to 95%) to give (2S,4R)-4-((tert-butyldimethylsilyl)oxy)-1-((R)-2-(3-(((S)-1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)-1-oxopropan-2-yl)oxy)isoxazol-5-yl)-3-methylbutanoyl)-N—((S)-1-(4-(4-methylthiazol-5-yl)phenyl)ethyl)pyrrolidine-2-carboxamide (20 mg, 0.02 mmol, 42% yield) as a yellow solid. LCMS m/z calcd for C$_{54}$H$_{73}$N$_{10}$O$_7$SSi [M+H]$^+$: 1033.5; Found: 1033.4.

Step 2: (2S,4R)-4-hydroxy-1-(2-(3-(((S)-1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)-1-oxopropan-2-yl)oxy)isoxazol-5-yl)-3-methylbutanoyl)-N—((S)-1-(4-(4-methylthiazol-5-yl)phenyl)ethyl)pyrrolidine-2-carboxamide A solution of (2S,4R)-4-((tert-butyldimethylsilyl)oxy)-1-4R)-2-(3-(((S)-1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)-1-oxopropan-2-yl)oxy)isoxazol-5-yl)-3-methylbutanoyl)-N—((S)-1-(4-(4-methylthiazol-5-yl)phenyl)ethyl)pyrrolidine-2-carboxamide (20 mg, 0.02 mmol) in trifluoroacetic acid (0.5 mL) was stirred at 45° C. for 1 h. The volatiles were removed under reduced pressure and the residue was purified by prep-HPLC (eluting with CH$_3$CN in H$_2$O (0.1% NH$_3$·H$_2$O) from 10% to 95% to give (2S,4R)-4-((tert-butyldimethylsilyl)oxy)-1-4R)-2-(3-(((S)-1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)-1-oxopropan-2-yl)oxy)isoxazol-5-yl)-3-methylbutanoyl)-N—((S)-1-(4-(4-methylthiazol-5-yl)phenyl)ethyl)pyrrolidine-2-carboxamide (4.2 mg, 0.005 mmol, 23% yield) as a white solid. LCMS m/z calcd for C$_{48}$H$_{59}$N$_{10}$O$_7$S [M+H]$^+$: 919.4; Found: 919.4. $^1$H NMR (CD$_3$OD, 400 MHz): δ 8.82-8.87 (m, 1H), 7.74-7.77 (m, 1H), 7.35-7.44 (m, 4H), 7.10-7.24 (m, 2H), 6.87-6.89 (m, 2H), 6.05 (s, 1H), 5.46-5.48 (m, 1H), 4.50-4.63 (m, 5H), 3.53-4.09 (m, 8H), 3.08-3.27 (m, 4H), 2.93-2.96 (m, 1H), 2.66-2.72 (m, 2H), 2.37-2.47 (m, 5H), 1.87-2.20 (m, 6H), 1.47-1.59 (m, 5H), 1.05-1.06 (m, 3H), 0.85-0.91 (m, 3H).

The examples in the table below were prepared according to the same method as example 27 using appropriate starting materials.

| Ex# | Structure and Name | Calcd. (M + H)$^+$ m/z | Found (M + H)$^+$ m/z | HNMR |
|---|---|---|---|---|
| Ex 28 | (2S,4R)-4-hydroxy-1-(2-(3-(((2R)-1-(3-((S)-2-(2-hydroxyphenyl)-5,6,6a,7,9,10-hexahydro-8H- | 905.4 | 905.4 | $^1$HNMR (CD$_3$OD, 400 MHz): δ 9.58-9.55 (m, 1H), 7.57-7.35 (m, 8H), 7.06-7.02 (m, 2H), 6.08-6.04 (m, 1H), 5.29-5.18 (m, 1H), 4.56-4.50 (m, 2H), 4.41-4.38 (m, 1H), 4.25-4.13 (m, 2H), 4.00 (m, 2H), 3.87-3.73 (m, 6H), 3.68-3.59 (m, 2H), 3.50-3.38 (m, 4H), 2.99 (s, 1H), 2.86 (s, 1H), 2.55 (d, J = 5.6 Hz, 3H), 2.52-2.37 (m, 2H), 2.19 (m, 1H), 1.56 (m, 1H), 1.55-1.53 (m, 2H), 1.50-1.48 (m, 1H), 1.41-1.39 (m, 1H), 1.28 (m, 1H), 1.02 (t, J = 13.6 Hz, 3H), 0.88 (t, J = 14 Hz, 3H). |

| Ex# | Structure and Name | Calcd. (M + H)+ m/z | Found (M + H)+ m/z | HNMR |
|---|---|---|---|---|
| | pyrazino[1',2':4,5]pyrazino[2,3-c]pyridazin-8-yl)pyrrolidin-1-yl)-1-oxopropan-2-yl)oxy)isoxazol-5-yl)-3-methylbutanoyl)-N-((S)-1-(4-(4-methylthiazol-5-yl)phenyl)ethyl)pyrrolidine-2-carboxamide (synthesized from Int-19) | | | |
| Ex 29 | (2S,4R)-4-hydroxy-1-(2-(3-(((2R)-1-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)-1-oxopropan-2-yl)oxy)isoxazol-5-yl)-3-methylbutanoyl)-N-((S)-1-(4-(4-methylthiazol-5-yl)phenyl)ethyl)pyrrolidine-2-carboxamide (synthesized from Int-20) | 905.4 | 905.4 | ¹HNMR (CD₃OD, 400 MHz): δ 9.88-9.85 (m, 1H), 7.58-7.38 (m, 7H), 7.05-7.03 (m, 2H), 6.07-6.05 (m, 1H), 5.21-5.04 (m, 3H), 4.55-4.42 (m, 3H), 4.21-3.43 (m, 16H), 2.67-2.55 (m, 5H), 2.36-2.19 (m, 2H), 1.93-1.90 (m, 1H), 1.60-1.45 (m, 6H), 1.05-1.06 (m, 3H), 0.85-0.91 (m, 3H) |
| Ex 30 | (2S,4R)-4-hydroxy-1-((2R)-2-(3-(2-(4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)-2-oxoethoxy)isoxazol-5-yl)-3-methylbutanoyl)-N-((S)-1-(4-(4-methylthiazol-5-yl)phenyl)ethyl)pyrrolidine-2-carboxamide (Diastereomer 1) | 919.4 | 919.4 | ¹HNMR (CD₃OD-d₄, 400 MHz): δ 9.48 (s, 1H), 7.62-748 (m, 7H), 7.10-7.05 (m, 2H), 6.10-6.07 (m, 1H), 5.79-5.75 (m, 1H), 4.52-4.45 (m, 3H), 3.99-3.45 (m, 14H), 2.57 (m, 4H), 2.47-1.95 (m, 5H), 1.51-1.45(m, 3H), 1.92-0.90 (m, 12H) |
| Ex 31 | (2S,4R)-4-hydroxy-1-((2R)-2-(3-(2-(4-((S)-2-(2-hydroxyphenyl)-5,6,6a,7,9,10- | 919.4 | 919.4 | ¹HNMR (CD₃OD-d₄, 400 MHz): δ 9.45 (s, 1H), 7.60-7.40 (m, 7H), 7.10-7.02 (m, 2H), 6.10-6.07 (m, 1H), 5.06-4.95 (m, 3H), 4.62-4.45 (m, 2H), 3.99-3.42 (m, 11H), 3.08-2.70 (m, 5H), 2.57 (m, 3H), 2.47-2.31 (m, 3H), 1.95-1.93 (m, 2H), 1.51-1.42 (m, 3H), 1.06-1.04 (m, 3H), 0.94-0.89 (m, 3H). |

| Ex# | Structure and Name | Calcd. (M + H)+ m/z | Found (M + H)+ m/z | HNMR |
|---|---|---|---|---|
| | hexahydro-8H-pyrazino[1',2':4,5]pyrazino[2,3-c]pyridazin-8-yl)-3-methylpiperidin-1-yl)-2-oxoethoxy)isoxazol-5-yl)-3-methylbutanoyl)-N-((S)-1-(4-(4-methylthiazol-5-yl)phenyl)ethyl)pyrrolidine-2-carboxamide (Diastereomer 2) | | | |
| Ex 73 | (2S,4R)-4-hydroxy-1-((R)-2-(3-(((R)-1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)-1-oxopropan-2-yl)oxy)isoxazol-5-yl)-3-methylbutanoyl)-N-((S)-1-(4-(4-methylthiazol-5-yl)phenyl)ethyl)pyrrolidine-2-carboxamide | 919.4 | 919.4 | $^1$HNMR (CD$_3$OD, 400 MHz): δ 8.83-8.86 (m, 1H), 7.76-7.79 (m, 1H), 7.35-7.44 (m, 4H), 7.13-7.23 (m, 2H), 6.87-6.90 (m, 2H), 6.03-6.07 (m, 1H), 5.44-5.49(m, 1H), 4.95-5.03 (m, 1H), 4.43-4.57 (m, 3H), 3.52-3.96 (m, 7H), 2.94-3.26 (m, 5H), 2.66-2.74 (m, 2H), 2.34-2.48 (m, 5H), 1.89-2.20 (m, 6H), 1.46-1.54 (m, 7H), 1.04-1.06 (m, 3H), 0.84-0.93 (m, 3H). |

Example 32. (2S,4R)-4-hydroxy-1-(2-(3-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)isoxazol-5-yl)-3-methylbutanoyl)-N—((S)-1-(4-(4-methylthiazol-5-yl)phenyl)ethyl)pyrrolidine-2-carboxamide

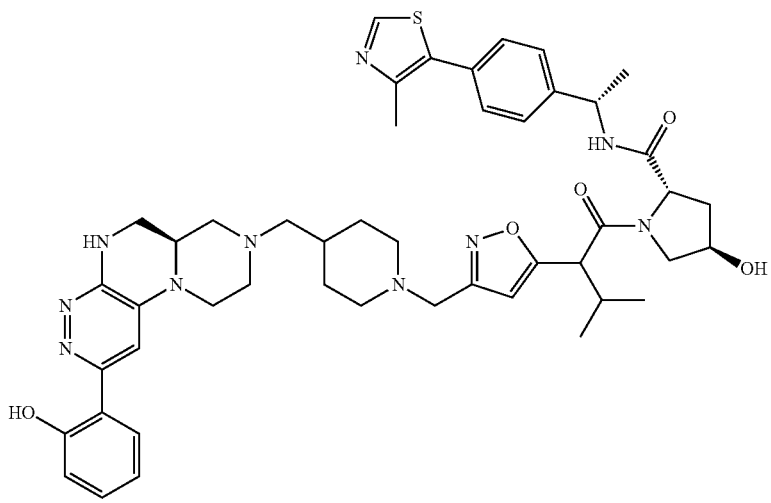

Ex 32

Step 1: (2S,4R)-4-((tert-butyldimethylsilyl)oxy)-1-(2-(3-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)isoxazol-5-yl)-3-methylbutanoyl)-N—((S)-1-(4-(4-methylthiazol-5-yl)phenyl)ethyl)pyrrolidine-2-carboxamide

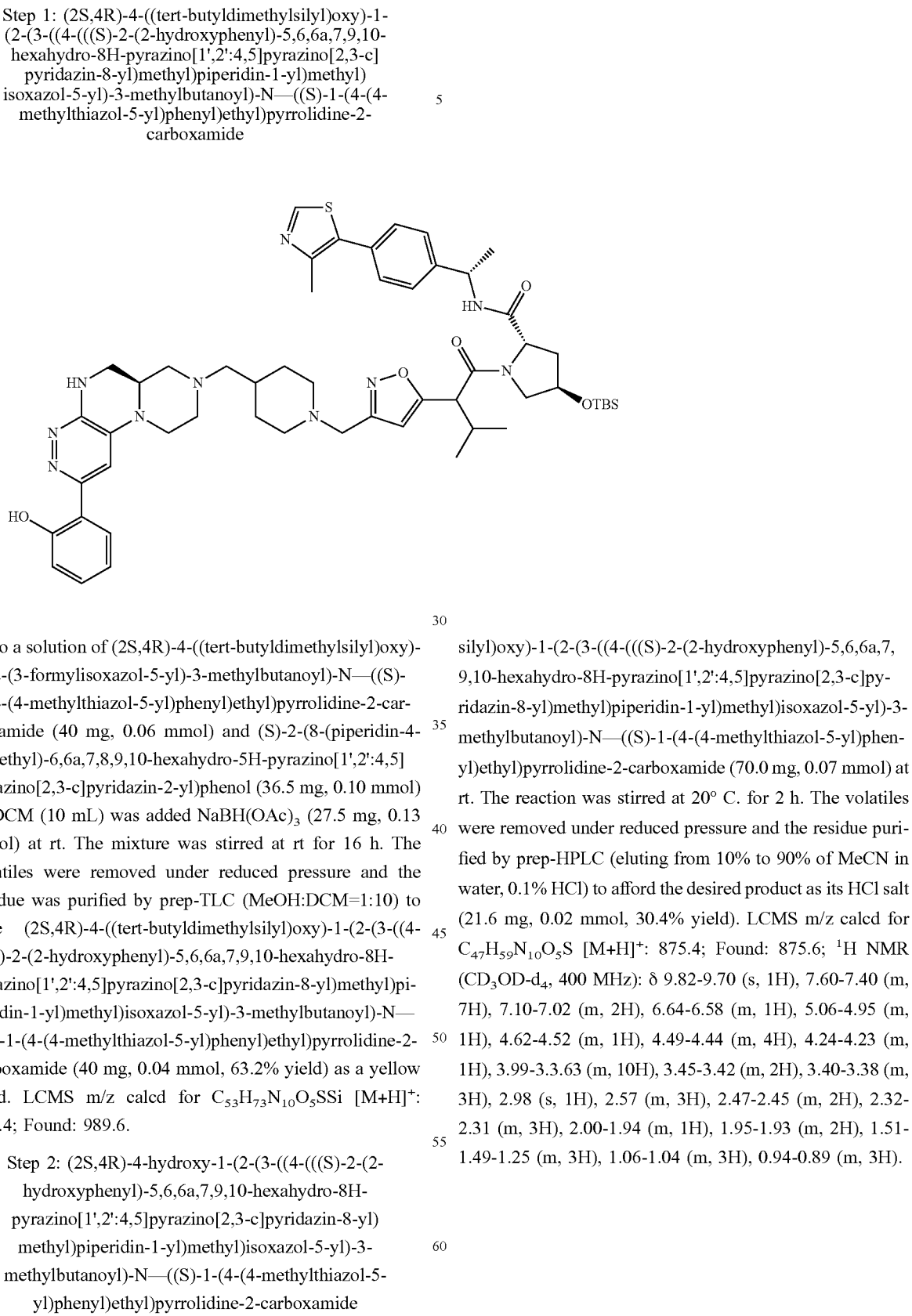

To a solution of (2S,4R)-4-((tert-butyldimethylsilyl)oxy)-1-(2-(3-formylisoxazol-5-yl)-3-methylbutanoyl)-N—((S)-1-(4-(4-methylthiazol-5-yl)phenyl)ethyl)pyrrolidine-2-carboxamide (40 mg, 0.06 mmol) and (S)-2-(8-(piperidin-4-ylmethyl)-6,6a,7,8,9,10-hexahydro-5H-pyrazino[1',2':4,5]pyrazino[2,3-c]pyridazin-2-yl)phenol (36.5 mg, 0.10 mmol) in DCM (10 mL) was added NaBH(OAc)₃ (27.5 mg, 0.13 mmol) at rt. The mixture was stirred at rt for 16 h. The volatiles were removed under reduced pressure and the residue was purified by prep-TLC (MeOH:DCM=1:10) to give (2S,4R)-4-((tert-butyldimethylsilyl)oxy)-1-(2-(3-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)isoxazol-5-yl)-3-methylbutanoyl)-N—((S)-1-(4-(4-methylthiazol-5-yl)phenyl)ethyl)pyrrolidine-2-carboxamide (40 mg, 0.04 mmol, 63.2% yield) as a yellow solid. LCMS m/z calcd for $C_{53}H_{73}N_{10}O_5SSi$ [M+H]⁺: 989.4; Found: 989.6.

Step 2: (2S,4R)-4-hydroxy-1-(2-(3-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)isoxazol-5-yl)-3-methylbutanoyl)-N—((S)-1-(4-(4-methylthiazol-5-yl)phenyl)ethyl)pyrrolidine-2-carboxamide To a solution of TBAF (1 M in THF, 0.21 mL, 0.21 mmol) in THF (5 mL) was added (2S,4R)-4-((tert-butyldimethylsilyl)oxy)-1-(2-(3-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)isoxazol-5-yl)-3-methylbutanoyl)-N—((S)-1-(4-(4-methylthiazol-5-yl)phenyl)ethyl)pyrrolidine-2-carboxamide (70.0 mg, 0.07 mmol) at rt. The reaction was stirred at 20° C. for 2 h. The volatiles were removed under reduced pressure and the residue purified by prep-HPLC (eluting from 10% to 90% of MeCN in water, 0.1% HCl) to afford the desired product as its HCl salt (21.6 mg, 0.02 mmol, 30.4% yield). LCMS m/z calcd for $C_{47}H_{59}N_{10}O_5S$ [M+H]⁺: 875.4; Found: 875.6; ¹H NMR (CD₃OD-d₄, 400 MHz): δ 9.82-9.70 (s, 1H), 7.60-7.40 (m, 7H), 7.10-7.02 (m, 2H), 6.64-6.58 (m, 1H), 5.06-4.95 (m, 1H), 4.62-4.52 (m, 1H), 4.49-4.44 (m, 4H), 4.24-4.23 (m, 1H), 3.99-3.3.63 (m, 10H), 3.45-3.42 (m, 2H), 3.40-3.38 (m, 3H), 2.98 (s, 1H), 2.57 (m, 3H), 2.47-2.45 (m, 2H), 2.32-2.31 (m, 3H), 2.00-1.94 (m, 1H), 1.95-1.93 (m, 2H), 1.51-1.49-1.25 (m, 3H), 1.06-1.04 (m, 3H), 0.94-0.89 (m, 3H).

The examples in the table below were prepared according to the same method as example 32 using appropriate starting materials.

| Ex# | Structure and Name | Calcd. (M + H)+ m/z | Found (M + H)+ m/z | HNMR |
|---|---|---|---|---|
| Ex 33 | 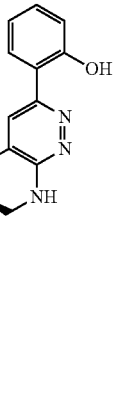<br>(2S,4R)-4-hydroxy-1-((R)-2-(3-(3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propyl)isoxazol-5-yl)-3-methylbutanoyl)-N-((S)-1-(4-(4-methylthiazol-5-yl)phenyl)ethyl)pyrrolidine-2-carboxamide | 889.5 | 889.5 | $^1$HNMR (CD$_3$OD-d$_4$, 400 MHz): δ 7.57-7.34 (m, 8H), 7.04-7.02 (m, 2H), 6.34 (m, 1H), 4.51-4.44 (m, 2H), 3.81-3.61 (m, 10H), 3.50-3.41 (m, 2H), 3.22-3.10 (m, 5H), 2.80-2.69 (m, 3H), 2.52 (m, 5H), 2.47-2.39 (m, 2H), 2.29-2.13 (m, 5H), 1.96-1.92 (m, 1H), 1.60-1.47(m, 3H), 1.28 (m, 1H), 1.06-1.05 (m, 3H), 0.87-0.85 (m, 3H) |
| Ex 39 | 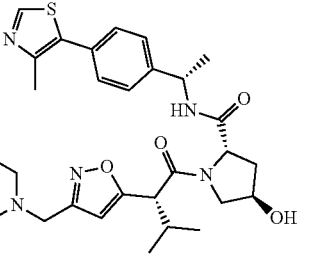<br>(2S,4R)-4-hydroxy-1-((R)-2-(3-((4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)methyl)isoxazol-5-yl)-3-methylbutanoyl)-N-((S)-1-(4-(4-methylthiazol-5-yl)phenyl)ethyl)pyrrolidine-2-carboxamide | 861.4 | 861.5 | $^1$HNMR (400 MHz, CD$_3$OD): δ 9.87 (s, 1H), 7.34-7.66 (m, 7H), 6.96-7.06 (m, 2H), 6.59-6.64 (m, 1H), 5.49(s, 1H), 5.01-5.03 (m, 1H), 4.33-4.60 (m, 4H), 3.31-4.02 (m, 13H), 2.56 (s, 5H), 2.14-2.48 (m, 4H), 1.81-1.96 (m, 1H), 1.52-1.59 (m, 3H), 1.01-1.10 (m, 3H), 0.80-0.90 (m, 3H). (Some protons were buried under solvent or water peak, not all protons were listed) |
| Ex 45 | 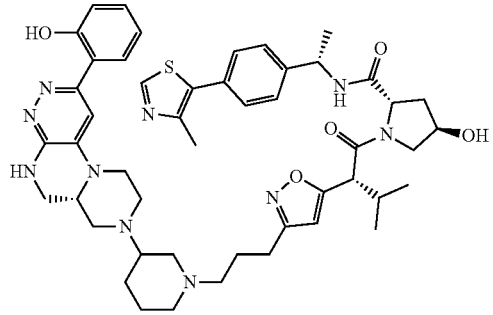 [SMILES: Cc1ncsc1-c1ccc([C@H](C)NC(=O)[C@@H]2C[C@@H](O)CN2C(=O)[C@@H](c2cc(CCCN3CCCC(N4CCN5c6cc(-c7ccccc7O)nnc6NC[C@H]5C4)C3)no2)C(C)C)cc1]<br>(2S,4R)-4-hydroxy-1-((2R)-2-(3-(3-(3-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propyl)isoxazol-5-yl)-3-methylbutanoyl)-N-((S)-1-(4-(4- | 889.5 | 889.6 | $^1$H NMR(400 MHz, CD$_3$OD): δ 8.89 (s, 1H), 7.68-7.70 (m, 1H), 7.25-7.39 (m, 4H), 6.95-7.20 (m, 2H), 6.75-6.80(m, 2H), 6.20(s, 1H), 4.85-4.93 (m, 1H), 4.25-4.45 (m, 2H), 3.38-3.85(m, 6H), 2.96-3.20(m, 3H), 2.75-2.90 (m, 2H), 2.14-2.62 (m, 10H), 2.01-2.10(m, 2H), 1.70-1.90(m, 7H), 1.52-1.59 (m, 4H), 1.01-1.10 (m, 3H), 0.80-0.90 (m, 3H). (Some protons were buried under solvent or water peak, not all protons were listed) |

-continued

| Ex# | Structure and Name | Calcd. (M + H)+ m/z | Found (M + H)+ m/z | HNMR |
|---|---|---|---|---|
| | methylthiazol-5-yl)phenyl)ethyl)pyrrolidine-2-carboxamide | | | |
| Ex 74 | (2S,4R)-4-hydroxy-1-((2R)-2-(3-(3-(2-(2-hydroxyphenyl)-5,6,6a,7,9,10-hexahydro-8H-pyrazino[1',2':4,5]pyrazino[2,3-c]pyridazin-8-yl)propyl)isoxazol-5-yl)-3-methylbutanoyl)-N-((S)-1-(4-(4-methylthiazol-5-yl)phenyl)ethyl)pyrrolidine-2-carboxamide | 806.4 | 806.3 | ¹HNMR (CD₃OD, 400 MHz): δ 8.87-8.81 (m, 1H), 7.78-7.73 (m, 1H), 7.46-7.33 (m, 4H), 7.22-7.13 (m, 2H), 6.90-6.83 (m, 2H), 6.31-6.26 (m, 1H), 5.04-4.94 (m, 2H), 4.59-4.41 (m, 2H), 3.91-3.47 (m, 6H), 3.25-3.07 (m, 3H), 2.75-2.70 (m, 2H), 2.48-2.38 (m, 6H), 2.24-2.18 (m, 2H), 1.96-1.86 (m, 4H), 1.52-1.46 (m, 3H), 1.07-1.05 (m, 3H), 0.90-0.81 (m, 3H). |
| Ex 88 | (2S,4R)-4-hydroxy-1-((2R)-2-(3-(3-(3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propyl)isoxazol-5-yl)-3-methylbutanoyl)-N-((S)-1-(4-(4-methylthiazol-5-yl)phenyl)ethyl)pyrrolidine-2-carboxamide (diastereomer 1) | 903.5 | 903.6 | ¹H NMR (400 MHz, CD3OD-d4): δ 8.86-8.87 (m, 1H), 7.75-7.78 (m, 1H), 7.33-7.45 (m, 4H), 7.19-7.23 (m, 1H), 7.12-7.15 (m, 1H), 6.86-6.90 (m, 2H), 6.23-6.28 (m, 1H), 4.98-5.06 (m, 3H), 4.46-4.51(m, 1H), 4.05-4.40 (m, 1H), 3.75-3.93 (m, 2H), 3.45-3.60 (m, 2H), 3.08-3.25 (m, 4H), 2.95-3.03 (m, 3H), 2.67-2.71 (m, 2H), 2.47-2.63 (m, 2H), 2.47 (s, 3H), 2.23-2.41 (m, 3H), 2.09-2.19 (m, 3H), 1.83-1.96 (m, 6H), 1.55-1.82 (m, 3H), 1.47-1.57 (m, 3H), 0.98-1.04 (m, 3H), 0.81-0.87 (m, 3H). |

| Ex# | Structure and Name | Calcd. (M + H)+ m/z | Found (M + H)+ m/z | HNMR |
|---|---|---|---|---|
| Ex 89 | (2S,4R)-4-hydroxy-1-((2R)-2-(3-(3-(3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propyl)isoxazol-5-yl)-3-methylbutanoyl)-N-((S)-1-(4-(4-methylthiazol-5-yl)phenyl)ethyl)pyrrolidine-2-carboxamide (diastereomer 2) | 903.5 | 903.7 | $^1$H NMR (400 MHz, CD$_3$OD-d$_4$): δ 8.85-8.87 (m, 1H), 7.76-7.78 (m, 1H), 7.33-7.44 (m, 4H), 7.19-7.23 (m, 1H), 7.11-7.15 (m, 1H), 6.86-6.90 (m, 2H), 6.23-6.28 (m, 1H), 4.98-5.04 (m, 3H), 4.46-4.50 (m, 1H), 4.05-4.40 (m, 1H), 3.75-3.85 (m, 3H), 3.48-3.60 (m, 2H), 3.20-3.25 (m, 1H), 2.96-3.13 (m, 6H), 2.66-2.70 (m, 2H), 2.44-2.47 (m, 4H), 2.13-2.32 (m, 5H), 1.82-2.03 (m, 5H), 1.73-1.83 (m, 5H), 1.48-1.57 (m, 3H), 0.97-1.05 (m, 3H), 0.83-0.87 (m, 3H). |
| Ex 91 | (2S,4R)-4-hydroxy-1-((R)-2-(3-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)isoxazol-5-yl)-3-methylbutanoyl)-N-((S)-1-(4-(4-methylthiazol-5-yl)phenyl)ethyl)pyrrolidine-2-carboxamide | 875.4 | 875.4 | $^1$HNMR (CD$_3$OD-d$_4$, 400 MHz): δ 9.74 (s, 1H), 7.47-7.34 (m, 7H), 6.97-6.93 (m, 2H), 6.08-6.06 (m, 1H), 4.25-4.20 (m, 1H), 4.95-4.87 (m, 2H), 4.75-4.70 (m, 2H), 4.47-4.15 (m, 4H), 3.83-3.37 (m, 14H), 2.98-2.75 (m, 2H), 2.55 (s, 3H), 2.41-2.19 (m, 2H), 1.95-1.74 (m, 4H), 1.46-1.39 (m, 6H), 0.96-0.94 (m, 3H), 0.93-0.89(m, 3H). |

Example 34. (2S,4R)-4-hydroxy-1-(2-(3-(2-((2-0S)-2-(2-hydroxyphenyl)-5,6,6a,7,9,10-hexahydro-8H-pyrazino[1',2':4,5]pyrazino[2,3-c]pyridazin-8-yl)ethyl)(methyl)amino)ethyl)isoxazol-5-yl)-3-methylbutanoyl)-N—((S)-1-(4-(4-methylthiazol-5-yl)phenyl)ethyl)pyrrolidine-2-carboxamide

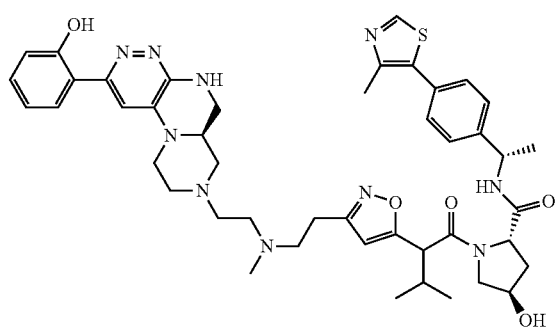

Ex 34

Step 1: (2S,4R)-4-hydroxy-1-(2-(3-(2-((2-((S)-2-(2-hydroxyphenyl)-5,6,6a,7,9,10-hexahydro-8H-pyrazino[1',2':4,5]pyrazino[2,3-c]pyridazin-8-yl)ethyl)amino)ethyl)isoxazol-5-yl)-3-methylbutanoyl)-N—((S)-1-(4-(4-methylthiazol-5-yl)phenyl)ethyl)pyrrolidine-2-carboxamide

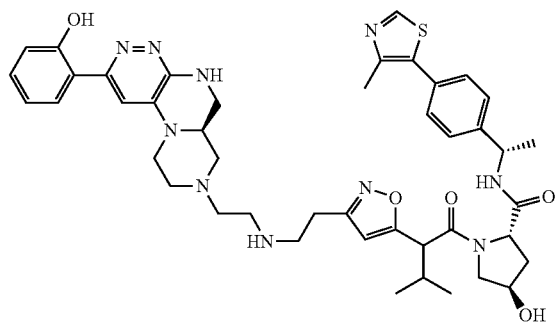 [SMILES: Cc1ncsc1-c1ccc([C@H](C)NC(=O)[C@@H]2C[C@@H](O)CN2C(=O)C(c2cc(CCNCCN3CCN4c5cc(-c6ccccc6O)nnc5NC[C@H]4C3)no2)C(C)C)cc1]

To a solution of (S)-2-(8-(2-aminoethyl)-6,6a,7,8,9,10-hexahydro-5H-pyrazino[1',2':4,5]pyrazino[2,3-c]pyridazin-2-yl)phenol (20 mg, 0.06 mmol) and (2S,4R)-4-((tert-butyldimethylsilyl)oxy)-1-(3-methyl-2-(3-(2-oxoethyl)isoxazol-5-yl)butanoyl)-N—((S)-1-(4-(4-methylthiazol-5-yl)phenyl)ethyl)pyrrolidine-2-carboxamide (58.7 mg, 0.09 mmol) in DCM (30 mL) was added NaBH(OAc)$_3$ (25.4 mg, 0.12 mmol) at rt. The mixture was stirred at rt for 16 h. The volatiles were removed under reduced pressure and the residue was purified by prep-TLC (MeOH:DCM=1:10). TBS group removal was achieved upon work-up and purification to give (2S,4R)-4-hydroxy-1-(2-(3-(2-((2-((S)-2-(2-hydroxyphenyl)-5,6,6a,7,9,10-hexahydro-8H-pyrazino[1',2':4,5]pyrazino[2,3-c]pyridazin-8-yl)ethyl)amino)ethyl)isoxazol-5-yl)-3-methylbutanoyl)-N—((S)-1-(4-(4-methylthiazol-5-yl)phenyl)ethyl)pyrrolidine-2-carboxamide (20 mg, 0.024 mmol, 39.1% yield) as a yellow solid). LCMS m/z calcd for $C_{44}H_{55}N_{10}O_5S$ [M+H]$^+$: 835.4; Found: 835.5.

Step 2: (2S,4R)-4-hydroxy-1-(2-(3-(2-((2-((S)-2-(2-hydroxyphenyl)-5,6,6a,7,9,10-hexahydro-8H-pyrazino[1',2':4,5]pyrazino[2,3-c]pyridazin-8-yl)ethyl)(methyl)amino)ethyl)isoxazol-5-yl)-3-methylbutanoyl)-N—((S)-1-(4-(4-methylthiazol-5-yl)phenyl)ethyl)pyrrolidine-2-carboxamide To a solution of (2S,4R)-4-hydroxy-1-(2-(3-(2-((2-((S)-2-(2-hydroxyphenyl)-5,6,6a,7,9,10-hexahydro-8H-pyrazino[1',2':4,5]pyrazino[2,3-c]pyridazin-8-yl)ethyl)amino)ethyl)isoxazol-5-yl)-3-methylbutanoyl)-N—((S)-1-(4-(4-methylthiazol-5-yl)phenyl)ethyl)pyrrolidine-2-carboxamide (10.0 mg, 0.01 mmol) in DCM (3 mL) was added sodium triacetoxyborohydride (7.6 mg, 0.04 mmol) and paraformaldehyde (0.36 mg, 0.01 mmol). The reaction was stirred at 30° C. for 16 h. Aqueous NaOH (5% w/w, 0.5 mL) was added and the resulted mixture was stirred at rt for another 30 min. The volatiles were removed and the residue was purified by prep-HPLC, eluted with MeCN in H$_2$O (0.1% TFA) from 10% to 90% to give the desired product as its TFA salt (2.7 mg, 0.002 mmol, 17.7% yield). LCMS m/z calcd for $C_{45}H_{57}N_{10}O_5S$ [M+H]$^+$: 849.4; Found: 849.5. $^1$H NMR (CD$_3$OD-d$_4$, 400 MHz): δ 8.79-8.77 (m, 1H), 7.46-7.23 (m, 7H), 6.95-6.90 (m, 2H), 6.30-6.27 (m, 1H), 4.94-4.91 (m, 2H), 4.47-4.25 (m, 1H), 4.02-3.99 (m, 1H), 3.80-3.34 (m, 11H), 3.17-3.15 (m, 1H), 2.93-2.90 (m, 3H), 2.79-2.73 (m, 2H), 2.59 (s, 1H), 2.37-2.33 (m, 5H), 2.07-2.03 (m, 2H), 1.85-1.78 (m, 1H), 1.48-1.20 (m, 5H), 0.96-0.93 (m, 3H), 0.79-0.72 (m, 3H).

The examples in the table below were prepared according to the same method as example 34 using appropriate starting materials.

| Ex# | Structure and Name | Calcd. (M + H)+ m/z | Found (M + H)+ m/z | HNMR |
|---|---|---|---|---|
| Ex 92 | 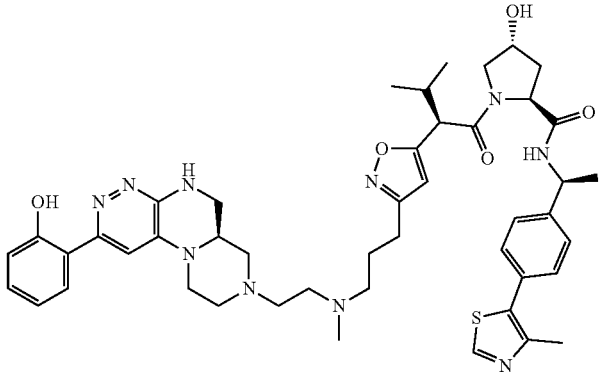 [SMILES: Cc1ncsc1-c1ccc([C@H](C)NC(=O)[C@@H]2C[C@@H](O)CN2C(=O)[C@@H](c2cc(CCCN(C)CCN3CCN4c5cc(-c6ccccc6O)nnc5NC[C@H]4C3)no2)C(C)C)cc1]<br>(2S,4R)-4-hydroxy-1-((R)-2-(3-(3-((2-((S)-2-(2-hydroxyphenyl)-5,6,6a,7,9,10-hexahydro-8H-pyrazino[1',2':4,5]pyrazino[2,3-c]pyridazin-8-yl)ethyl)(methyl)amino)propyl)isoxazol-5-yl)-3-methylbutanoyl)-N-((S)-1-(4-(4-methylthiazol-5-yl)phenyl)ethyl)pyrrolidine-2-carboxamide | 863.4 | 863.5 | $^1$HNMR (CD$_3$OD-d$_4$, 400 MHz): δ 9.47-9.40 (m, 1H), 7.59-7.42 (m, 7H), 7.09-7.02 (m, 2H), 6.38-6.35 (m, 1 H), 5.17-5.11 (m, 2H), 4.55-4.42 (m, 1 H), 4.31-3.98 (m, 1H), 3.85-3.44 (m, 11H), 3.27-3.26 (m, 1H), 3.02-3.01 (m, 3H), 2.93-2.85 (m, 3H), 2.71 (s, 3H), 2.56-2.52 (m, 3H), 2.45-2.42 (m, 1H), 2.25-2.18 (m, 2H), 1.96-1.92 (m, 1H), 1.62-1.35 (m, 5H), 1.07-1.04 (m, 3H), 0.91-0.86 (m, 3H). |

Example 35. (2S,4R)—N—((S)-1-(4-cyanophenyl)ethyl)-4-hydroxy-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)pyrrolidine-2-carboxamide To a mixture of (2S,4R)-4-hydroxy-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)pyrrolidine-2-carboxylic acid (17.2 mg, 0.02 mmol), Et$_3$N (6.1 mg, 0.07 mmol) and (S)-4-(1-aminoethyl)benzonitrile (4.3 mg, 0.03 mmol) in DMF (5 mL) was added HATU (11.1 mg, 0.03 mmol). The mixture was stirred at 25° C. for 2 h. Water (10 mL) was added, and the resulted mixture was extracted with ethyl acetate (5 mL×2). The combined organic phase was washed with brine (5 mL), dried with anhydrous Na$_2$SO$_4$, filtered, and the filtrate was concentrated in vacuo. The residue was further purified by prep-HPLC, eluting with CH$_3$CN in H$_2$O (0.1% NH$_3$·H$_2$O) from 10% to 95% to obtain (2S,4R)—N—((S)-1-(4-cyanophenyl)ethyl)-4-hydroxy-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)pyrrolidine-2-carboxamide (1.3 mg, 0.001 mmol, 5.8% yield). LCMS m/z calcd for C$_{45}$H$_{57}$N$_{10}$O$_6$[M+H]$^+$: 833.4; Found: 833.2; $^1$H NMR (400 MHz, CD$_3$OD): δ 7.78-7.76 (m, 1H), 7.69-7.67 (m, 2H), 7.49-7.46 (m, 2H), 7.21-7.19 (m, 1H), 7.14 (m, 1H), 6.90-6.86 (m, 2H), 6.00 (s, 1H), 5.02-4.94 (m, 2H), 4.58 (s, 1H), 4.49-4.41 (m, 1H), 4.36-4.33 (m, 2H), 3.67-3.47 (m, 4H), 3.19-3.01 (m, 6H), 2.82-2.81 (m, 2H), 2.35-2.33 (m, 1H), 2.29-2.27 (m, 2H), 2.21-2.12 (m, 4H), 1.90-1.80 (m, 4H), 1.49-1.47 (m, 3H), 1.34-1.28 (m, 4H), 1.04-1.02 (m, 3H), 0.90-0.87 (m, 3H).

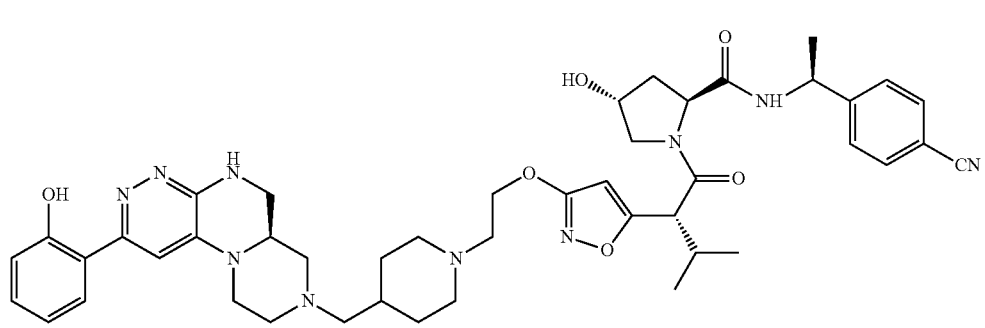

Ex 35

The examples in the table below were prepared according to the same method as example 35 using appropriate starting materials.

| Ex# | Structure and Name | Calcd. (M + H)+ m/z | Found (M + H)+ m/z | HNMR |
|---|---|---|---|---|
| Ex 36 | 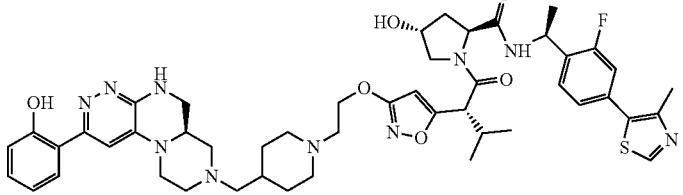<br>(2S,4R)-N-((S)-1-(2-fluoro-4-(4-methylthiazol-5-yl)phenyl)ethyl)-4-hydroxy-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)pyrrolidine-2-carboxamide | 923.4 | 923.6 | ¹HNMR (CD₃OD-d₄, 400 MHz): δ 9.51-9.48 (s, 1H), 7.60-7.40 (m, 6H), 7.05-7.02 (m, 2H), 6.10-6.04 (m, 1H), 5.29-5.25 (m, 2H), 4.71-4.24 (m, 6H), 3.96-3.62 (m, 10H), 3.59-3.36 (m, 3H), 3.23-3.22 (m, 2H), 2.93-2.69 (m, 2H), 2.57 (m, 3H), 2.49-2.31 (m, 4H), 2.00-1.70 (m, 3H), 1.51-1.25 (m, 3H), 1.06-1.04(m, 3H), (Some protons were buried under solvent or water peak, not all protons were listed) |
| Ex 37 | 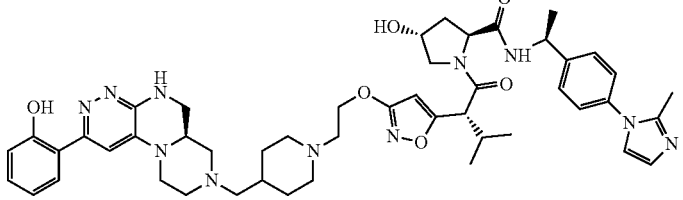<br>(2S,4R)-4-hydroxy-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N-((S)-1-(4-(2-methyl-1H-imidazol-1-yl)phenyl)ethyl)pyrrolidine-2-carboxamide | 888.5 | 888.6 | ¹HNMR (CD₃OD-d₄, 400 MHz): δ 7.60-7.32 (m, 9H), 7.08-7.04 (m, 2H), 6.13-6.09 (m, 1H), 5.12-5.03 (m, 2H), 4.71-4.41 (m, 6H), 4.19-4.18 (m, 1H), 3.87-3.62 (m, 10H), 3.50-3.43 (m, 2H), 3.27-3.25(m, 2H), 2.57 (s, 3H), 2.42-2.31 (m, 5H), 2.00-1.94 (m, 1H), 1.70-1.68(m, 2H), 1.51-1.25 (m, 3H), 1.06-1.04(m, 3H), 0.94-0.89(m, 3H). (Some protons were buried under solvent or water peak, not all protons were listed) |
| Ex 40 | 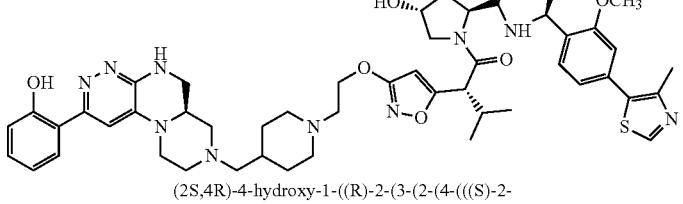<br>(2S,4R)-4-hydroxy-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N-((S)-1-(2-methoxy-4-(4-methylthiazol-5-yl)phenyl)ethyl)pyrrolidine-2-carboxamide | 935.4 | 935.6 | ¹H NMR(400 MHz, CD₃OD): δ 8.98 (s, 1H), 8.48-8.51(m, 1H), 7.50-7.51(m, 1H), 7.44-7.45(m, 1H), 7.40-7.41(m, 1H), 7.30-7.32(m, 1H), 7.01-7.18 (m, 4H), 6.01-6.09 (m, 1H), 5.39(s, 2H), 4.33-4.60 (m, 4H), 3.31-4.02 (m, 12H), 3.01-3.15(m, 2H), 2.56 (br, 2H), 2.48(s, 3H), 1.49-2.48 (m, 10H), 1.52-1.59 (m, 3H), 1.01-1.10 (m, 3H), 0.80-0.90 (m, 3H). (Some protons were buried under solvent or water peak, not all protons were listed) |

Example 48. (2S,4R)-4-hydroxy-1-((2R)-2-(3-(((2S)-1-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide (Synthesized from Int-20)

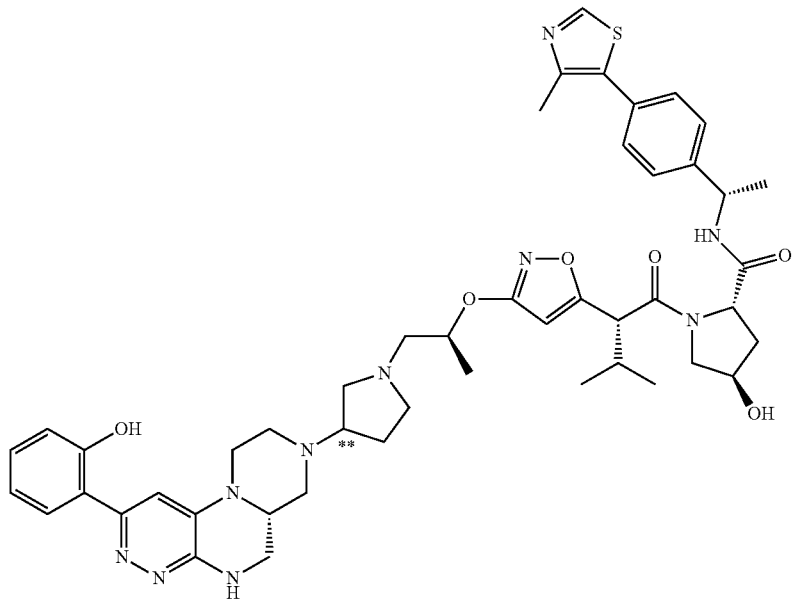 [SMILES: Cc1ncsc1-c1ccc([C@H](C)NC(=O)[C@@H]2C[C@@H](O)CN2C(=O)[C@@H](c2cc(O[C@@H](C)CN3CCC(N4CCN5c6cc(-c7ccccc7O)nnc6NC[C@H]5C4)C3)no2)C(C)C)cc1]

Step 1: (2S,4R)-4-((tert-butyldimethylsilyl)oxy)-1-((R)-2-(3-(((S)-1-hydroxypropan-2-yl)oxy)isoxazol-5-yl)-3-methylbutanoyl)-N—((S)-1-(4-(4-methylthiazol-5-yl)phenyl)ethyl)pyrrolidine-2-carboxamide

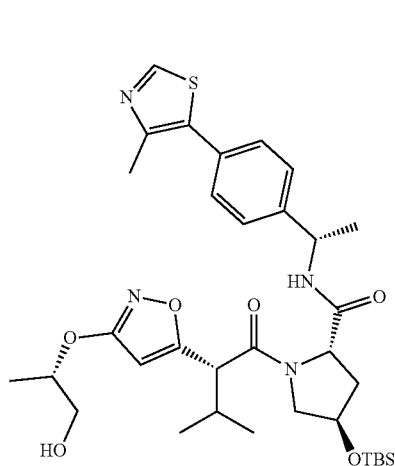 [SMILES: Cc1ncsc1-c1ccc([C@H](C)NC(=O)[C@@H]2C[C@@H](O[Si](C)(C)C(C)(C)C)CN2C(=O)[C@@H](c2cc(O[C@@H](C)CO)no2)C(C)C)cc1]

A solution of methyl (S)-2-((5-(((S)-1-((2S,4R)-4-((tert-butyldimethylsilyl)oxy)-2-(((S)-1-(4-(4-methylthiazol-5-yl)phenyl)ethyl)carbamoyl)pyrrolidin-1-yl)-3-methyl-1-oxobutan-2-yl)isoxazol-3-yl)oxy)propanoate (6.0 g, 8.6 mmol) in MeOH (75 mL) was added NaBH₄ (1.3 g, 4.8 mmol). The resulting mixture was stirred at rt for 3 h. The reaction was quenched with water (50 mL) and diluted with DCM (100 mL). The layers were separated, and the aqueous phase was extracted with DCM (1×100 mL). The combined organic layers were washed with brine (50 mL), dried over Na₂SO₄, filtered, and the filtrate was concentrated under reduced pressure to afford crude product as colorless oil, which was used directly in the next step. LCMS m/z calcd for $C_{34}H_{51}N_4O_6SSi$ [M+H]⁺: 671.3; Found: 671.2.

Step 2: (2S,4R)-4-((tert-butyldimethylsilyl)oxy)-1-((R)-3-methyl-2-(3-(((S)-1-oxopropan-2-yl)oxy)isoxazol-5-yl)butanoyl)-N—((S)-1-(4-(4-methylthiazol-5-yl)phenyl)ethyl)pyrrolidine-2-carboxamide

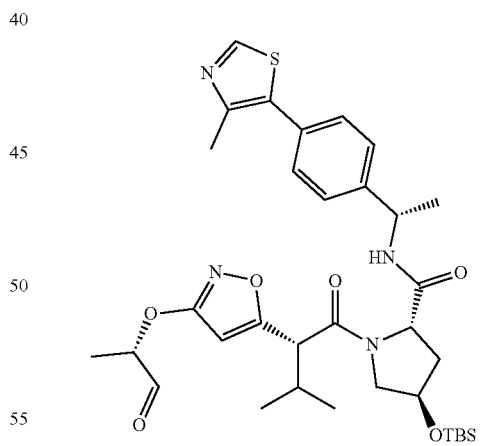

A solution of crude (2S,4R)-4-((tert-butyldimethylsilyl)oxy)-1-((R)-2-(3-(((S)-1-hydroxypropan-2-yl)oxy)isoxazol-5-yl)-3-methylbutanoyl)-N—((S)-1-(4-(4-methylthiazol-5-yl)phenyl)ethyl)pyrrolidine-2-carboxamide (2.6 g, 3.9 mmol) in ACN (30 mL) was added IBX (45 wt %, 2.7 g, 9.7 mmol). The resulting mixture was heated at 80° C. for 3 h. The reaction crude was cooled to rt and filtered under reduced pressure. The filter cake was washed by ACN (50 mL). The filtrate was concentrated in vacuum to give the crude product, which was purified by silica gel chromatography column, using EA/Heptane as eluents (20-80% EA in heptane) to afford the desired product (2.1 g, 72.9% yield over two steps) as a colorless oil. LCMS m/z calcd for $C_{34}H_{49}N_4O_6SSi$ [M+H]$^+$: 669.3; Found: 669.2.

Step 3: (2S,4R)-4-((tert-butyldimethylsilyl)oxy)-1-((2R)-2-(3-(((2S)-1-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide

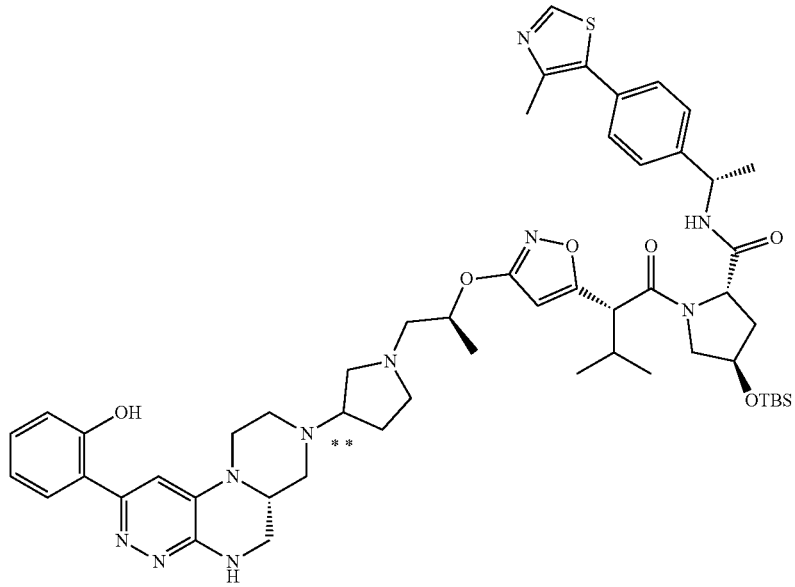 [SMILES: Cc1ncsc1-c1ccc([C@H](C)NC(=O)[C@@H]2C[C@@H](O[Si](C)(C)C(C)(C)C)CN2C(=O)[C@@H](c2cc(O[C@@H](C)CN3CCC(N4CCN5c6cc(-c7ccccc7O)nnc6NC[C@H]5C4)C3)no2)C(C)C)cc1]

A suspension of (2S,4R)-4-((tert-butyldimethylsilyl)oxy)-1-((R)-3-methyl-2-(3-(((S)-1-oxopropan-2-yl)oxy)isoxazol-5-yl)butanoyl)-N—((S)-1-(4-(4-methylthiazol-5-yl)phenyl)ethyl)pyrrolidine-2-carboxamide (2.1 g, 3.14 mmol) in DCM (20 mL) was added STAB (2000 mg, 9.4 mmol, 3.0 eq) and NaHCO$_3$ (1350 mg, 16 mmol, 5.0 eq). Then a solution of 2-((6aS)-8-(pyrrolidin-3-yl)-6,6a,7,8,9,10-hexahydro-5H-pyrazino[1',2':4,5]pyrazino[2,3-c]pyridazin-2-yl)phenol (Int-20, 1.7 g, 4.8 mmol) in DCM (20 mL) was added dropwise at rt. The resulting suspension was stirred at rt for 18 h. The reaction was quenched with water (50 mL). The organic layer was separated, washed with brine (50 mL), dried over Na$_2$SO$_4$, filtered, and the filtrate was concentrated in vacuo. The residue was purified by silica gel chromatography column using MeOH/DCM as eluents (0-10% MeOH in DCM) to afford the desired product (2.3 g, 72.9% yield) as a white solid. LCMS calc'd for $C_{53}H_{73}N_{10}O_6SSi$ [M+1-1]$^+$: 1005.5; Found: 1005.6.

Step 4: (2S,4R)-4-((tert-butyldimethylsilyl)oxy)-1-((R)-2-(3-(((S)-1-hydroxypropan-2-yl)oxy)isoxazol-5-yl)-3-methylbutanoyl)-N—((S)-1-(4-(4-methylthiazol-5-yl)phenyl)ethyl)pyrrolidine-2-carboxamide A mixture of (2S,4R)-4-((tert-butyldimethylsilyl)oxy)-1-((2R)-2-(3-(((2S)-1-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide (2.3 g, 2.29 mmol) in TFA (10.0 mL) was stirred at 25° C. for 1 h. The volatiles were removed under reduced pressure and the residue was purified by prep-HPLC (eluting 10% to 90% of MeCN in water, 0.1% HCl) to afford (2S,4R)-4-hydroxy-1-((2R)-2-(3-(((2S)-1-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide as its HCl salt (1282 mg, 55.6% yield) as a white solid. LCMS calc'd for $C_{47}H_{59}N_{10}O_6S$ [M+H]$^+$: 891.4; Found: 891.6; $^1$H NMR (CD$_3$OD-d$_4$, 400 MHz): δ 9.85 (s, 1H), 7.57-7.49 (m, 5H), 7.45-7.33 (m, 2H), 7.06-7.02 (m, 2H), 6.13 (s, 1H), 5.16 (m, 1H), 5.03-5.02 (m, 1H), 4.53-4.43 (m, 3H), 4.09 (m, 2H), 3.85-3.65 (m, 14H), 3.45-3.31 (m, 2H), 3.30-3.08 (m, 1H), 2.59 (m, 4H), 2.41-2.17 (m, 2H), 1.96-1.91 (m, 1H), 1.60-1.47 (m, 6H), 1.07-1.04 (m, 3H), 0.93-0.89 (m, 3H).

The examples in the table below were prepared according to the same method as example 48 using appropriate starting materials.

| Ex# | Structure and Name | Calcd. (M + H)+ m/z | Found (M + H)+ m/z | HNMR |
|---|---|---|---|---|
| Ex 49 | (2S,4R)-4-hydroxy-1-((2R)-2-(3-(((2S)-1-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N-((S)-1-(4-(4-methylthiazol-5-yl)phenyl)ethyl)pyrrolidine-2-carboxamide (synthesized from Int-19) | 891.4 | 891.6 | $^1$HNMR (CD$_3$OD-d$_4$, 400 MHz): δ 9.75 (s, 1H), 7.61-7.37 (m, 6H), 7.29(s, 1H), 7.07-6.97 (m, 2H), 6.19-6.13 (m, 1H), 5.19-5.04 (m, 3H), 4.56-4.46 (m, 2H), 4.12-3.44 (m, 16H), 3.26-2.20 (m, 9H), 2.00-1.90 (m, 1H), 1.56-1.46 (m, 6H), 1.10-1.06 (m, 3H), 0.93-0.91(m, 3H). |
| Ex 50 | (2S,4R)-4-hydroxy-1-((2R)-2-(3-(((2R)-1-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N-((S)-1-(4-(4-methylthiazol-5-yl)phenyl)ethyl)pyrrolidine-2-carboxamide (diastereomer 1) | 891.4 | 891.5 | |

| Ex# | Structure and Name | Calcd. (M + H)+ m/z | Found (M + H)+ m/z | HNMR |
|---|---|---|---|---|
| Ex 51 | (2S,4R)-4-hydroxy-1-((2R)-2-(3-(((2R)-1-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N-((S)-1-(4-(4-methylthiazol-5-yl)phenyl)ethyl)pyrrolidine-2-carboxamide (diastereomer 2) | 891.4 | 891.6 | |
| Ex 64 | (2S,4R)-4-hydroxy-1-((2R)-2-(3-(((2S)-1-(3-(2-(2-hydroxyphenyl)-6a-methyl-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N-((S)-1-(4-(4-methylthiazol-5-yl)phenyl)ethyl)pyrrolidine-2-carboxamide | 905.4 | 905.4 | ¹HNMR (CD₃OD-d₄, 400 MHz): δ 9.92 (s, 1H), 7.58-7.35 (m, 7H), 7.06-7.02 (m, 2H), 6.12 (s, 1H), 5.05-5.01 (m, 2H), 4.64-4.09 (m, 9H), 3.95-3.62 (m, 14H), 3.51-3.41 (m, 3H), 2.66-2.53 (m, 5H), 2.41-2.18 (m, 6H), 1.93 (s, 1H), 1.61-1.51 (m, 3H), 1.07-1.04 (m, 3H), 0.92-0.87(m, 3H) |
| Ex 100 | (2S,4R)-4-hydroxy-1-((R)-2-(3-(((S)-1-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N- | 919.5 | 919.5 | |

| Ex# | Structure and Name | Calcd. (M + H)+ m/z | Found (M + H)+ m/z | HNMR |
|---|---|---|---|---|
| | ((S)-1-(4-(4-methylthiazol-5-yl)phenyl)ethyl)pyrrolidine-2-carboxamide | | | |
| Ex 101 | 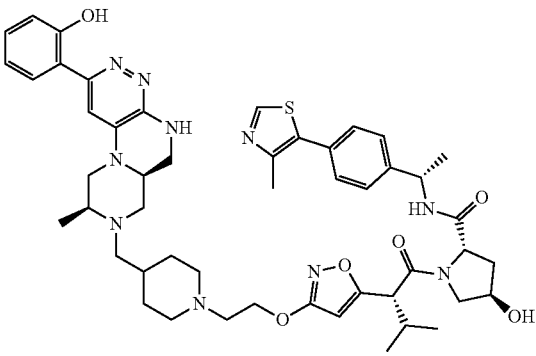 [SMILES: Cc1ncsc1-c1ccc([C@H](C)NC(=O)[C@@H]2C[C@@H](O)CN2C(=O)[C@@H](c2cc(OCCN3CCC(CN4C[C@@H]5CNc6nnc(-c7ccccc7O)cc6N5C[C@@H]4C)CC3)no2)C(C)C)cc1]<br>(2S,4R)-4-hydroxy-1-((R)-2-(3-(2-(4-((((6aS,9S)-2-(2-hydroxyphenyl)-9-methyl-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 919.5 | 919.4 | |
| Ex 102 | 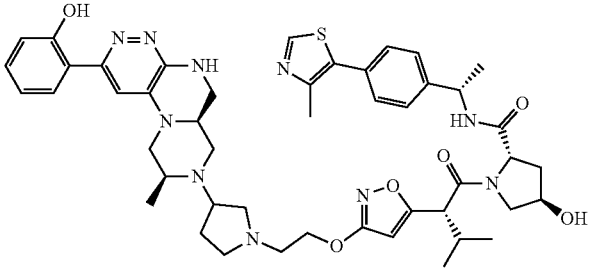 [SMILES: Cc1ncsc1-c1ccc([C@H](C)NC(=O)[C@@H]2C[C@@H](O)CN2C(=O)[C@@H](c2cc(OCCN3CCC(N4C[C@@H]5CNc6nnc(-c7ccccc7O)cc6N5C[C@@H]4C)C3)no2)C(C)C)cc1]<br>(2S,4R)-4-hydroxy-1-((2R)-2-(3-(2-(3-((6aS,9S)-2-(2-hydroxyphenyl)-9-methyl-5,6,6a,7,9,10-hexahydro-8H-pyrazino[1',2':4,5]pyrazino[2,3-c]pyridazin-8-yl)pyrrolidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 891.4 | 891.4 | |

Example 53. (5-(1-((2S,4R)-4-hydroxy-2-(((S)-1-(4-(4-methylthiazol-5-yl)phenyl)ethyl)carbamoyl)pyrrolidin-1-yl)-3-methyl-1-oxobutan-2-yl)isoxazol-3-yl)methyl 4-((S)-2-(2-hydroxyphenyl)-5,6,6a,7,9,10-hexahydro-8H-pyrazino[1',2':4,5]pyrazino[2,3-c]pyridazin-8-yl)piperidine-1-carboxylate

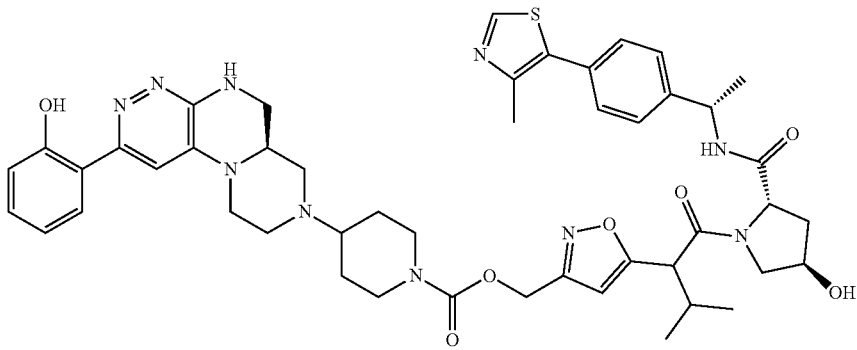 [SMILES: Cc1ncsc1-c1ccc([C@H](C)NC(=O)[C@@H]2C[C@@H](O)CN2C(=O)C(c2cc(COC(=O)N3CCC(N4CCN5c6cc(-c7ccccc7O)nnc6NC[C@H]5C4)CC3)no2)C(C)C)cc1]

Step 1: (5-(1-((2R,4R)-4-((tert-butyldimethylsilyl)oxy)-2-(((S)-1-(4-(4-methylthiazol-5-yl)phenyl)ethyl)carbamoyl)pyrrolidin-1-yl)-3-methyl-1-oxobutan-2-yl)isoxazol-3-yl)methyl 4-((S)-2-(2-hydroxyphenyl)-5,6,6a,7,9,10-hexahydro-8H-pyrazino[1',2':4,5]pyrazino[2,3-c]pyridazin-8-yl)piperidine-1-carboxylate

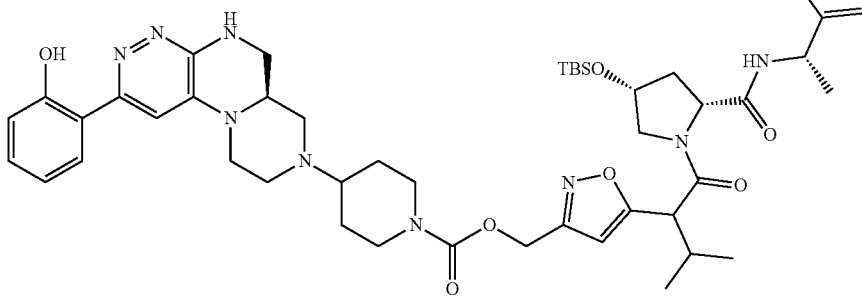

A solution of (2S,4R)-4-((tert-butyldimethylsilyl)oxy)-1-(2-(3-(hydroxymethyl)isoxazol-5-yl)-3-methylbutanoyl)-N—((S)-1-(4-(4-methylthiazol-5-yl)phenyl)ethyl)pyrrolidine-2-carboxamide (17 mg, 0.03 mmol) and CDI (4.4 mg, 0.03 mmol) in THF (2 mL) was stirred for 2 h at rt, then (S)-2-(8-(piperidin-4-yl)-6,6a,7,8,9,10-hexahydro-5H-pyrazino[1',2':4,5]pyrazino[2,3-c]pyridazin-2-yl)phenol (10 mg, 0.03 mmol) and DIPEA (0.02 mL, 0.14 mmol) were added sequentially. The resulted solution was stirred 80° C. for 16 h. The volatiles were removed under reduced pressure and the residue was purified on prep-TLC (MeOH:DCM=1:15) to give the desired product (22 mg, 0.021 mmol, 79.1% yield) as a colorless solid. LCMS calc'd for $C_{53}H_{71}N_{10}O_7SSi$ [M+H]$^+$: 1019.5; Found: 1019.3.

Step 2: (5-(1-((2S,4R)-4-hydroxy-2-(((S)-1-(4-(4-methylthiazol-5-yl)phenyl)ethyl)carbamoyl)pyrrolidin-1-yl)-3-methyl-1-oxobutan-2-yl)isoxazol-3-yl)methyl 4-((S)-2-(2-hydroxyphenyl)-5,6,6a,7,9,10-hexahydro-8H-pyrazino[1',2':4,5]pyrazino[2,3-c]pyridazin-8-yl)piperidine-1-carboxylate To a stirred solution of (5-(1-((2R,4R)-4-((tert-butyldimethylsilyl)oxy)-2-(((S)-1-(4-(4-methylthiazol-5-yl)phenyl)ethyl)carbamoyl)pyrrolidin-1-yl)-3-methyl-1-oxobutan-2-yl)isoxazol-3-yl)methyl 4-((S)-2-(2-hydroxyphenyl)-5,6,6a,7,9,10-hexahydro-8H-pyrazino[1',2':4,5]pyrazino[2,3-c]pyridazin-8-yl)piperidine-1-carboxylate (5.0 mg, 0.0049 mmol) in THF (0.50 mL) was added TBAF (1 M in THF, 0.5 mL, 0.50 mmol) at rt. After 5 h, The volatiles were removed under reduced pressure and the residue was dissolved in DCM (20 mL) and washed with water (10 mL×2) and brine (10 mL). The organic layer was separated, dried over $Na_2SO_4$, filtered, and concentrated. The crude was purified by prep-HPLC, eluting with MeCN in $H_2O$ (0.1% TFA) from 10% to 90% to give the desired product as its TFA salt (3.9 mg, 0.0034 mmol, 69.5% yield) as a white solid. LCMS calc'd for $C_{47}H_{57}N_{10}O_7S$ [M+H]+: 905.4; Found: 905.2; $^1$H NMR (400 MHz, $CD_3OD$) δ 8.93 (d, J=7.7 Hz, 1H), 7.56-7.28 (m, 7H), 7.04 (t, J=7.6 Hz, 2H), 6.40 (t, J=10.0 Hz, 1H), 5.25-4.98 (m, 2H), 4.61-4.22 (m, 6H), 4.11-3.35 (m, 13H), 3.19-2.80 (m, 3H), 2.48 (t, J=3.8 Hz, 3H), 2.44-2.08 (m, 5H), 2.10-1.65 (m, 4H), 1.54 (dt, J=14.4, 7.1 Hz, 3H), 1.07 (d, J=6.5 Hz, 3H), 0.88 (dd, J=10.2, 6.8 Hz, 3H).

Example 75. (2S,4R)-4-hydroxy-1-(2-(3-(((4-(2-(2-hydroxyphenyl)-5,6,6a,7,9,10-hexahydro-8H-pyrazino[1',2':4,5]pyrazino[2,3-c]pyridazin-8-yl)pyridin-2-yl)oxy)methyl)isoxazol-5-yl)-3-methylbutanoyl)-N—((S)-1-(4-(4-methylthiazol-5-yl)phenyl)ethyl)pyrrolidine-2-carboxamide

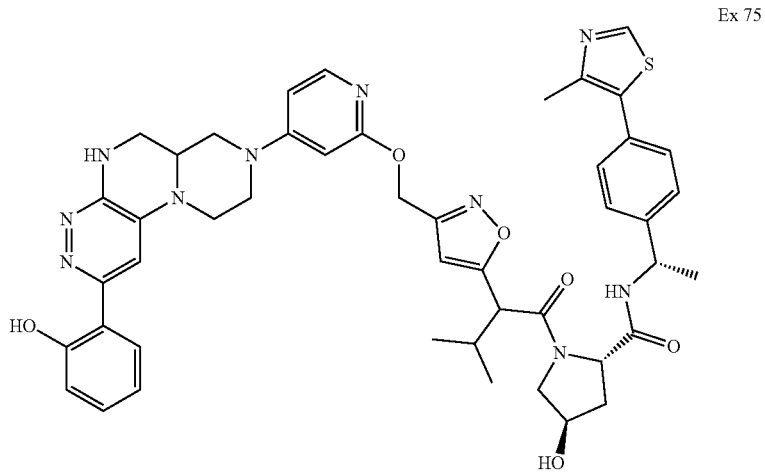 [SMILES: Cc1ncsc1-c1ccc([C@H](C)NC(=O)[C@@H]2C[C@@H](O)CN2C(=O)C(c2cc(COc3cc(N4CCN5c6cc(-c7ccccc7O)nnc6NCC5C4)ccn3)no2)C(C)C)cc1]

Ex 75

Step 1: (2S,4R)-4-((tert-butyldimethylsilyl)oxy)-1-(2-(3-(((4-fluoropyridin-2-yl)oxy)methyl)isoxazol-5-yl)-3-methylbutanoyl)-N—((S)-1-(4-(4-methylthiazol-5-yl)phenyl)ethyl)pyrrolidine-2-carboxamide

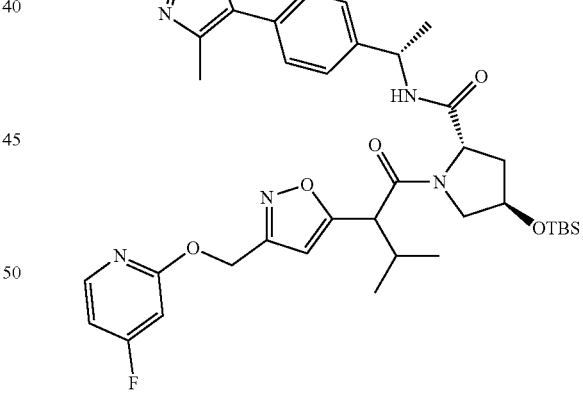

To a stirred mixture of 4-fluoropyridin-2-ol (28.9 mg, 0.26 mmol), (2S,4R)-4-[tert-butyl(dimethyl)silyl]oxy-1-[2-[3-(hydroxymethyl)-1,2-oxazol-5-yl]-3-methylbutanoyl]-N-[(1S)-1-[4-(4-methyl-1,3-thiazol-5-yl)phenyl]ethyl]pyrrolidine-2-carboxamide (80 mg, 0.13 mmol) and $Ph_3P$ (100 mg, 0.38 mmol) in THF (3 mL) was added DIAD (0.08 mL, 0.38 mmol) at rt. After 2 h, the volatiles were removed under reduced pressure. The residue was purified by prep-TLC (DCM:MeOH=50:1) to the desired product (75 mg, 0.10 mmol, 81% yield) as a white solid. LCMS calc'd for $C_{37}H_{49}FN_5O_5SSi$ [M+H]+: 722.3; Found: LCMS [M+H]: 722.5.

Step 2: (2S,4R)-4-((tert-butyldimethylsilyl)oxy)-1-(2-(3-(((4-(2-(2-hydroxyphenyl)-5,6,6a,7,9,10-hexahydro-8H-pyrazino[1',2':4,5]pyrazino[2,3-c]pyridazin-8-yl)pyridin-2-yl)oxy)methyl)isoxazol-5-yl)-3-methylbutanoyl)-N—((S)-1-(4-(4-methylthiazol-5-yl)phenyl)ethyl)pyrrolidine-2-carboxamide

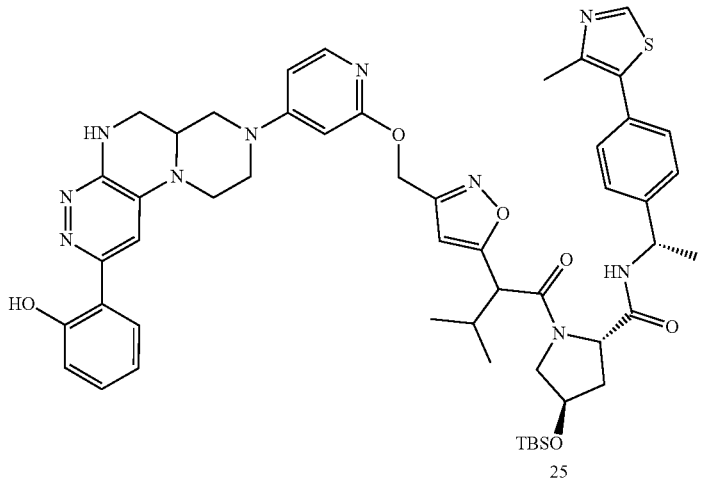

A mixture of 2-(6,6a,7,8,9,10-hexahydro-5H-pyrazino[1',2':4,5]pyrazino[2,3-c]pyridazin-2-yl)phenol; hydrochloride (37 mg, 0.12 mmol) and (2S,4R)-4-((tert-butyldimethylsilyl)oxy)-1-(2-(3-(((4-(4-fluoropyridin-2-yl)oxy)methyl)isoxazol-5-yl)-3-methylbutanoyl)-N—((S)-1-(4-(4-methylthiazol-5-yl)phenyl)ethyl)pyrrolidine-2-carboxamide (70 mg, 0.10 mmol), $K_2CO_3$ (0.05 mL, 0.29 mmol) in $CH_3CN$ (3 mL) was stirred at 90° C. for 16 h. The reaction was quenched with $H_2O$ (20 mL) and extracted with EA (20 mL×3). The organic layers were combined, dried over $Na_2SO_4$, filtered and concentrated in vacuo. The residue was purified by prep-TLC (DCM:MeOH=10:1) to give the desired product (30 mg, 0.03 mmol, 31.4% yield) as a colorless oil. LCMS calc'd for $C_{52}H_{65}N_{10}O_6SSi$ $[M+1-1]^+$: 985.4; Found: 985.6.

Step 3: (2S,4R)-4-hydroxy-1-(2-(3-(((4-(2-(2-hydroxyphenyl)-5,6,6a,7,9,10-hexahydro-8H-pyrazino[1',2':4,5]pyrazino[2,3-c]pyridazin-8-yl)pyridin-2-yl)oxy)methyl)isoxazol-5-yl)-3-methylbutanoyl)-N—((S)-1-(4-(4-methylthiazol-5-yl)phenyl)ethyl)pyrrolidine-2-carboxamide To a stirred solution of (2S,4R)-4-((tert-butyldimethylsilyl)oxy)-1-(2-(3-(((4-(2-(2-hydroxyphenyl)-5,6,6a,7,9,10-hexahydro-8H-pyrazino[1',2':4,5]pyrazino[2,3-c]pyridazin-8-yl)pyridin-2-yl)oxy)methyl)isoxazol-5-yl)-3-methylbutanoyl)-N—((S)-1-(4-(4-methylthiazol-5-yl)phenyl)ethyl)pyrrolidine-2-carboxamide (30 mg, 0.03 mmol) in DCM (2 mL) was added TFA (3.0 mL) at rt. After 1 h, the volatiles were removed and the residue was purified by prep-HPLC, eluted with $CH_3CN$ in $H_2O$ (0.1% HCl) from 5.0% to 95.0% to give (2S,4R)-4-hydroxy-1-(2-(3-(((4-(2-(2-hydroxyphenyl)-5,6,6a,7,9,10-hexahydro-8H-pyrazino[1',2':4,5]pyrazino[2,3-c]pyridazin-8-yl)pyridin-2-yl)oxy)methyl)isoxazol-5-yl)-3-methylbutanoyl)-N—((S)-1-(4-(4-methylthiazol-5-yl)phenyl)ethyl)pyrrolidine-2-carboxamide as its HCl salt (3.6 mg, 0.003 mmol, 12% yield) as a gray solid. LCMS calc'd for $C_{46}H_{51}N_{10}O_6S$ $[M+H]^+$: 871.4; Found: 871.3. H NMR (400 MHz, $CD_3OD$-$d_4$): δ 9.70-9.77 (m, 1H), 7.91-7.93 (m, 1H), 7.41-7.56 (m, 7H), 7.15 (s, 1H), 7.02-7.06 (m, 2H), 6.80-6.82 (m, 1H), 6.41-6.35 (m, 1H), 5.35 (s, 2H), 5.01-5.06 (m, 2H), 4.38-4.60 (m, 2H), 4.07-4.22 (m, 4H), 3.79-3.86 (m, 2H), 3.58-3.74 (m, 3H), 3.32-3.39 (m, 2H), 2.57-2.58 (m, 3H), 2.36-2.43 (m, 1H), 2.17-2.24 (m, 1H), 1.88-1.99 (m, 1H), 1.45-1.59 (m, 3H), 1.05-1.06 (m, 3H), 0.83-0.87 (m, 3H).

Example 82. (2S,4R)-4-hydroxy-1-((2S)-2-(1-(3-(2-(2-hydroxyphenyl)-5,6,6a,7,9,10-hexahydro-8H-pyrazino[1',2':4,5]pyrazino[2,3-c]pyridazin-8-yl)propyl)azetidine-3-carboxamido)-3,3-dimethylbutanoyl)-N—((S)-1-(4-(4-methylthiazol-5-yl)phenyl)ethyl)pyrrolidine-2-carboxamide Ex 82

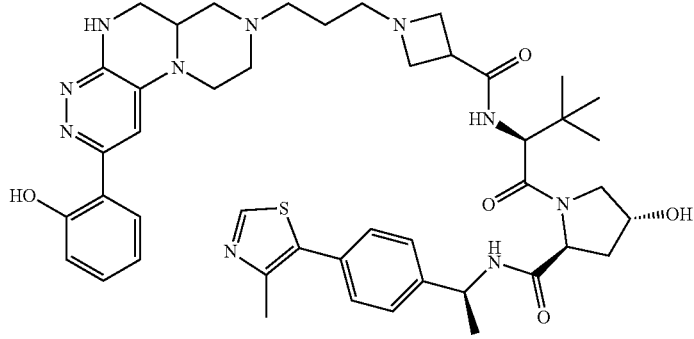

Step 1: tert-butyl 3-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamoyl)azetidine-1-carboxylate

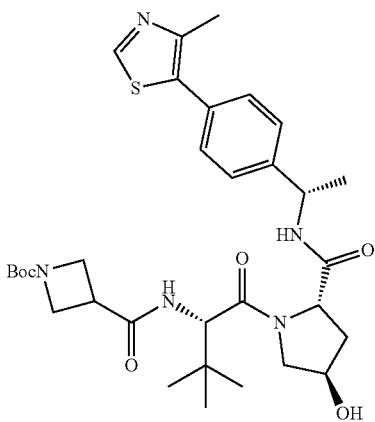 [SMILES: Cc1ncsc1-c1ccc([C@H](C)NC(=O)[C@@H]2C[C@@H](O)CN2C(=O)[C@@H](NC(=O)C2CN(C(=O)OC(C)(C)C)C2)C(C)(C)C)cc1]

To a stirred mixture of (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide (110 mg, 0.25 mmol), 1-[(2-methylpropan-2-yl)oxycarbonyl]azetidine-3-carboxylic acid (50 mg, 0.25 mmol) and DIEA (0.12 mL, 0.75 mmol) in DMF (10 mL) was added HATU (189 mg, 0.50 mmol) at rt. After 16 h, the reaction mixture was diluted with EtOAc (20 mL) and washed with water (2×20 mL) and saturated brine (20 mL). The organic layer was separated, dried over MgSO$_4$, filtered, and concentrated to dryness. The crude was then purified by prep-TLC (DCM:MeOH=15:1) to give the desired product (100 mg, 0.15 mmol, 64.1% yield) as an oil. LCMS calc'd for C$_{32}$H$_{47}$N$_5$O$_6$S [M+H]$^+$: 629.2; Found: 629.3.

Step 2: (2S,4R)-1-((S)-2-(azetidine-3-carboxamido)-3,3-dimethylbutanoyl)-4-hydroxy-N—((S)-1-(4-(4-methylthiazol-5-yl)phenyl)ethyl)pyrrolidine-2-carboxamide

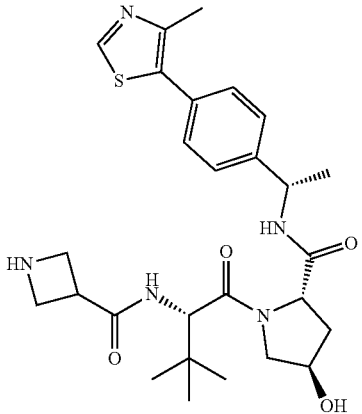 [SMILES: Cc1ncsc1-c1ccc([C@H](C)NC(=O)[C@@H]2C[C@@H](O)CN2C(=O)[C@@H](NC(=O)C2CNC2)C(C)(C)C)cc1]

To a stirred solution of tert-butyl 3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]azetidine-1-carboxylate (120 mg, 0.19 mmol) in DCM (2 mL) was added TFA (0.5 mL) at 25° C. After 1 h, the volatiles were removed to give the desired product (100 mg, 0.18 mmol, 94.7% yield) as an oil. LCMS calc'd for C$_{27}$H$_{38}$N$_5$O$_4$S [M+H]$^+$: 529.2; Found: 529.3.

Step 3: (2S,4R)-4-hydroxy-1-((2S)-2-(1-(3-(2-(2-hydroxyphenyl)-5,6,6a,7,9,10-hexahydro-8H-pyrazino[1',2':4,5]pyrazino[2,3-c]pyridazin-8-yl)propyl)azetidine-3-carboxamido)-3,3-dimethylbutanoyl)-N—((S)-1-(4-(4-methylthiazol-5-yl)phenyl)ethyl)pyrrolidine-2-carboxamide To a stirred solution of (2S,4R)-1-((S)-2-(azetidine-3-carboxamido)-3,3-dimethylbutanoyl)-4-hydroxy-N—((S)-1-(4-(4-methylthiazol-5-yl)phenyl)ethyl)pyrrolidine-2-carboxamide (55 mg, 0.10 mmol) in DCM (2 mL) was added 3-(2-(2-hydroxyphenyl)-5,6,6a,7,9,10-hexahydro-8H-pyrazino[1',2':4,5]pyrazino[2,3-c]pyridazin-8-yl)propanal (35.4 mg, 0.10 mmol) and sodium triacetoxyborohydride (132 mg, 0.63 mmol) at rt. After 16 h, the reaction mixture was concentrated to dryness and the residue was purified by prep-HPLC (0.1% NH$_4$OH) to give the desired product (5.6 mg, 0.006 mmol, 5.8% yield) as a white solid. LCMS calc'd for C$_{45}$H$_{59}$N$_{10}$O$_5$S [M+H]$^+$: 851.4; Found: 851.5. $^1$H NMR (CD$_3$OD, 400 MHz): δ 8.87-8.81 (m, 1H), 7.78-7.73 (m, 1H), 7.46-7.33 (m, 4H), 7.22-7.13 (m, 2H), 6.90-6.83 (m, 2H), 6.31-6.26 (m, 1H), 5.04-4.94 (m, 2H), 4.59-4.41 (m, 2H), 3.91-3.47 (m, 6H), 3.25-3.07 (m, 3H), 2.75-2.70 (m, 2H), 2.48-2.38 (m, 6H), 2.24-2.18 (m, 2H), 1.96-1.86 (m, 4H), 1.52-1.46 (m, 2H), 1.07-1.05 (m, 3H), 0.90-0.81 (m, 3H).

Example 83. (2S,4R)-4-hydroxy-1-((2R)-2-(3-((1-(3-((S)-2-(2-hydroxyphenyl)-5,6,6a,7,9,10-hexahydro-8H-pyrazino[1',2':4,5]pyrazino[2,3-c]pyridazin-8-yl)propyl)pyrrolidin-3-yl)oxy)isoxazol-5-yl)-3-methylbutanoyl)-N—((S)-1-(4-(4-methylthiazol-5-yl)phenyl)ethyl)pyrrolidine-2-carboxamide Ex 83

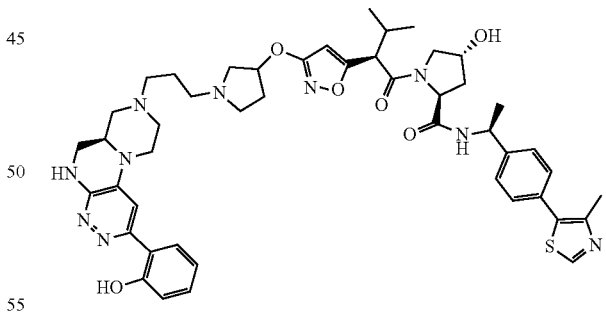

The title compound was prepared using procedure analogous to those described for Example 83, step 3 with appropriate starting materials. LCMS m/z calcd for C$_{47}$H$_{59}$N$_{10}$O$_6$S [M+H]$^+$: 891.4; Found: 891.4. $^1$H NMR (CD$_3$OD, 400 MHz): δ 8.87-8.81 (m, 1H), 7.78-7.73 (m, 1H), 7.46-7.33 (m, 4H), 7.22-7.13 (m, 2H), 6.90-6.83 (m, 2H), 6.31-6.26 (m, 1H), 5.04-4.94 (m, 2H), 4.59-4.41 (m, 2H), 3.91-3.47 (m, 6H), 3.25-3.07 (m, 3H), 2.75-2.70 (m, 2H), 2.48-2.38 (m, 6H), 2.24-2.18 (m, 2H), 1.96-1.86 (m, 4H), 1.52-1.46 (m, 2H), 1.07-1.05 (m, 3H), 0.90-0.81 (m, 3H)

Biological Assays
SMARCA2 Bromodomain Binary and Ternary Binding Assay

Recombinant bromodomain of SMARCA2 protein was purchased from Active Motif (Catalog #: 31449). VHL/ElonginB/ElonginC (VCB)N-terminal his$_6$-tagged VHL ("his$_6$" disclosed as SEQ ID NO: 4) (uniprot accession number P40337; M54-D213; MEAGRPRPVLRSVNSREP-SQVIFCNRSPRVVLPVWLNFDGEPQPYPTLPPGTGR-RIHSYR GHLWLFRDAGTHDGLLVNQTELFVPSLN- V-DGQPIFANITLPVYTLKERCLQVVRSLVKP ENYRRL-DIVRSLYEDLEDHPNVQKDLERLTQERIAHQRMGD (SEQ ID NO: 1)), Elongin B (Q15370; M1-K104; MDVF-LMIRRHKTTIFTDAKESSTVFELKRIVEGILKRPPD-EQRLYKDDQLLDDGKTLGEC GFTSQTARPQAPAT-VGLAFRADDTFEALCIEPFSSPP ELPDVMK (SEQ ID NO: 2)), Elongin C (Q15369; M17-C$_{112}$; MYVKLIS-SDGHEFIVKREHALTSGTIKAMLSGPGQFAENET-NEVNFREIPSHVLSKV CMYFTYKVRYTNSSTEIPEF-PIAPEIALELLMAANF LDC (SEQ ID NO: 3)) complex were co-expressed and the complex was purified by Ni-affinity, TEV protease was then used to remove his$_6$-tagged (SEQ ID NO: 4), and the complex was further purified by size-exclusion chromatography before use.

The inhibitory activity of compounds was evaluated in vitro using TR-FRET assay with white 384-well low volume microplate (PerkinElmer ProxiPlate Plus), in which the compound competes the same binding site with the ligand, and thus lead to dose-dependent TR-FRET signal reduction. The cooperativity of the compounds for ternary complex formation with E3 ligase was evaluated in the absence or presence of saturating concentrations of VCB. Testing compounds were dissolved in DMSO at 10 μM and tested in 9-dose IC$_{50}$. The assay mixture was prepared by mixing SMARCA2 (10 nM final), biotinylated probe (25 nM final), and assay buffer or VCB (5 μM) in 1× AlphaLISA Epigenetics Buffer (PerkinElmer AL008F) with 1 mM TCEP. The compounds in DMSO were added to each well in 3-fold serial dilution by dispenser (TECAN D300E) and incubate for 20 minutes at room temperature before addition of detection reagents, Lance Eu W1024 anti-6×His (0.6 nM final, PerkinElmer AD0110) and Streptavidin Surelight APC (6 nM final, PerkinElmer CR130-100). The plate was then sealed and further incubated at 4° C. overnight in dark, and then was read by Envision multimode plate reader (PerkinElmer, 2102-0010). The ratio of florescence signal at 665/620 was used in data analysis. Percentage inhibition was calculated by % inhibition=100×($F_{DMSO}$−F)/($F_{DMSO}$−$F_{PC}$), in which $F_{DMSO}$ is DMSO control, and $F_{PC}$ is positive control. IC$_{50}$ values were determined from dose response curve by fitting the percent inhibition against compound concentration using GraphPad Prism software.

SMARCA4 Bromodomain Binary and Ternary Binding Assay

Recombinant bromo domain of SMARCA4 protein, was purchased from Active Motif (31401). The inhibitory activity of compounds was evaluated in vitro using TR-FRET assay with white 384-well low volume microplate (PerkinElmer ProxiPlate Plus), in which the compound competes the same binding site with the ligand, and thus lead to dose-dependent TR-FRET signal reduction. The cooperativity of the compounds for ternary complex formation with E3 ligase was evaluated in the absence or presence of saturating concentrations of VCB. Testing compounds were dissolved in DMSO at 10 mM and tested in 9-point IC$_{50}$ mode. The assay mixture was prepared by mixing SMARCA4 (20 nM final), biotinylated probe (25 nM final), and assay buffer or VCB (5 μM) in 1× AlphaLISA Epigenetics Buffer (PerkinElmer AL008F) with 1 mM TCEP. The compounds of interest in DMSO were added to each well in 3-fold serial dilution by dispenser (TECAN D300E). and incubate for 20 minutes at room temperature before addition of detection reagents, Lance Eu W1024 anti-6×His (0.6 nM final, PerkinElmer AD0110) and Streptavidin Surelight APC (6 nM final, PerkinElmer CR130-100). The plate was then sealed and further incubated at 4° C. overnight in dark, and then was read by Envision multimode plate reader (PerkinElmer, 2102-0010). The ratio of florescence signal at 665/620 was used in data analysis. Percentage inhibition was calculated by % inhibition=100×($F_{DMSO}$−F)/($F_{DMSO}$−$F_{PC}$), in which $F_{DMSO}$ is DMSO control, and $F_{PC}$ is positive control. IC$_{50}$ values were determined from dose response curve by fitting the percent inhibition against compound concentration using GraphPad Prism software.

Cellular Assay Protocol-SMARCA
Cell Treatment and in Cell Western (ICW) for Detecting SMARCA Proteins Compound titration and cell culture: Compounds were dissolved in DMSO to make 10 mM stock and 3-fold series dilutions were further conducted keeping the highest concentration 10 μM. NCIH1693 and NCIH520 cells were maintained in PRMI 1640 medium (Corning Cellgro, Catalog #:10-040-CV) supplemented with 10% v/v FBS (GE Healthcare, Catalog #: SH30910.03) by splitting 1:3 twice a week.

To determine SMACRA2 and SMARCA4 protein degradation DC$_{50}$ values in NCIH1693 and NCIH520 cells by In Cell Western (ICW) analysis. Cells were trypsinized and 30 thousand cells/well were seeded into 384-well plates and were allowed to grow for 5 hours at 37° C. Eight-point, 3-fold serial dilutions of compounds from 10 mM stocks were added to the cells (using digital Dispenser D300-Tecan, keeping highest concentration 10 μM and normalizing with DMSO at the highest dispensed volume). Plates were incubated at 37° C. for overnight (maximum 18 hours). Cells incubated with DMSO was used as a vehicle control.

To perform In Cell Western, medium was removed from all the wells leaving cells attached to the surface. After removing the medium, cells were fixed within the plates with 40 μL of 4% formaldehyde by incubating at room temperature for 30 minutes, and then permeabilized with wash buffer (1×PBS with 0.1% Triton X-100) by washing the plate 5 times with 50 μL/well. Before labeling with primary antibodies, cells were blocked with 30 μL/well of blocking buffer (Licor Odyssey blocking buffer PBS #927-40000) for 30 minutes at room temperature. To measure SMARCA2 or SMARCA4 proteins, cells were labeled with 20 μL/well of anti SMARCA2 or SMACRA4 antibodies (Cell Signaling BRM #11966S 1:1000, Cell Signaling BRG #49360S 1:1000) diluted in Li-Cor Odyssey blocking buffer-PBS #927-40000, followed by overnight incubation at 4° C.

The next day, plates were washed 5×5 minutes with 50 μL/well of washing buffer to remove all the excess primary antibody and then 20 μL from a mixture of secondary antibody and fluorescent DNA specific dye (Goat anti rabbit 1:500 IRDye-800CW #92632211, and DRAQ5™ 1:2000-#ab108410) was added to each well. Plates were incubated for 1 hour at room temperature with gentle rocking. Cells were washed 5 times with 50 μL/well wash buffer, followed by one last wash with DI water, followed by 10 mins drying at 37° C. oven before scanning. Plates were scanned using Li-Cor Odyssey CLx imaging system to acquire integrated intensities at 700 nm and 800 nm. SMARCA signals were normalized to total cell count and then these normalized values were used to calculate the percent degradation relative to DMSO control and maximum inhibition. $DC_{50}$s were calculated by using the GraphPad Prism4 program based on sigmoidal dose response equation ([Inhibitor] vs. normalized response—Variable slope).

Cell Proliferation Assay to Determine $IC_{50}$ in NCIH1693 and NCIH1708 Cells.

One thousand NCIH1693 or NCIH1703 cells per well were seeded in 96 well plate and incubated at 37° C. for 5 hrs. A series of three-fold dilution of compounds from 10 mM stock concentration were added to the cells by using digital Dispenser D300-Tecan, keeping highest concentration 10 µM and normalizing with DMSO at the highest dispensed volume). Cells incubated with DMSO was used as a vehicle control. After compound treatment plates were incubated at 37° C. for 4 days and cell viability was measured by measuring ATP content from the cell lysate using ATPlite Luminescence assay system (PerkinElmer Cat. no #6016941). Percentage of viable cells, relative to DMSO vehicle control and maximum inhibition, was calculated and plotted in Graphpad Prism ([Inhibitor] vs. normalized response Variable slope) to determine cell proliferation $IC_{50}$ values on day 4.

SMARCA2 HiBiT Degradation Assay in HEK293T Cells

Compounds were prepared in a low dead volume plate at 3-fold serial dilution, and then transferred 25 nL/well into a 384 well plate (Corning: #356661) by Agilent Bravo liquid dispenser. SMARCA2-HiBiT monoclonal HEK293T cells were added at 5,000/well/25 uL into the compound containing 384 well plate. After 24 h incubation, 25 uL/well of Nano-Glo HiBiT Lytic detection buffer (Promega: N3050) was added to the wells and incubate for 10 min on a shaker, centrifuged for 5 min, and then RLU was detected on a microplate reader (Envision, PerkinElmer). The RLU ratio values are normalized to percent inhibition as follows: % inhibition=((HC−LC)−(compound−LC))/(HC−LC))*100, where HC=high control=mean signal of DMSO only; LC=low control=mean signal of 100% inhibition of RLU by 1 µM PRT1001728. An 11-point dose response curve for each compound will be generated using normalized % inhibition to determine IC50 values based on the equation: Y=Bottom+((Top−Bottom)/(1+((IC50/X)^Slope))), where Y is the % inhibition in the presence of X inhibitor concentration; Top=the top plateau of the curve; Bottom=the bottom plateau of the curve; Slope=Hill coefficient; DC50=concentration of compound with 50% degradation in relation to top/high control. DC50 values were determined by using XLfit Model 205.

TABLE 2

Biological data*
$IC_{50}$__SM2__T refers to ternary binding potency in SMARCA2 FRET assay;
$IC_{50}$__SM4__T refers to ternary binding potency in SMARCA4 FRET assay;
$DC_{50}/D_{max}$ %(SM2__H520) refers to SMARCA2 degradation potency/maximum SMARCA2 degradation within the concentrations tested in H520 cells;
$DC_{50}/D_{max}$ %(SM4__H520) refers to SMARCA4 degradation potency/maximum SMARCA4 degradation within the concentrations tested in H520 cells;
$DC_{50}/D_{max}$ % (SM2__H1693) refers to SMARCA2 degradation potency/maximum SMARCA2 degradation within the concentrations tested in H520 cells in H1693 cells;
$IC_{50}$(PRO__H1693) refers to antiproliferation potency in H1693 cells.

| Ex | $IC_{50}$ (SM 2__T) | $IC_{50}$__ (SM4__T) | $DC_{50}/D_{max}$ % (SM2__H520) | $DC_{50}/D_{max}$ % (SM4__H520) | $DC_{50}/D_{max}$ % (SM2__H1693) | $IC_{50}$ (PRO__H1693) |
|---|---|---|---|---|---|---|
| 1a | B |   | B/A | B/A |   | B |
| 1b | A | A | B/A | B/A | A/A | B |
| 2a | B | B | B/A | C/B | B/A | B |
| 2b | A | A | C/A | D/C | C/A | C |
| 3  | A |   | A/A | B/A |   |   |
| 4  | A |   | A/A | B/A |   | A |
| 5  | A |   | A/A | A/A |   |   |

*A = $IC_{50}$ or $DC_{50}$ < 0.1 µM; B = 0.1 µM =< $IC_{50}$ or $DC_{50}$ < 1 µM; C = 1 µM =< $IC_{50}$ or $DC_{50}$ < 10 µM; D = $IC_{50}$ or $DC_{50}$ >= 10 µM; or A = $D_{max}$ > 75%; B = 50% < $D_{max}$ <= 75%; C = $D_{max}$ <= 50%

SMARCA2 HiBiT and SMARCA4 HiBiT Degradation Assay (Cellular)

Preparation of SMARCA2/4-HiBiT Knock-in Cells

HiBiT peptide knock-in of SMARCA2 in LgBiT expressing HEK293T cells was performed by CRISPR-mediated tagging system as described Promega. The homozygous HiBiT knock-in on c-terminus SMARCA2 was confirmed by sanger sequence. SMARCA2-HiBiT knock-in Hela monoclonal cell (CS302366) and SMARCA4-HiBiT knock-in Hela monoclonal cell (CS3023226) were purchased from Promega. The heterozygous HiBiT-knock-in was confirmed by sanger sequence in both SMARCA2-HiBiT and SMARCA4-HiBiT monoclonal cells.

SMARCA2 HiBiT and SMARCA4 HiBiT Degradation Assay in HeLa Cells

Dispense 10 µL aliquot of prepared Hela-SMARCA2-HiBiT or Hela-SMARCA4-HiBiT cells (1:1 ratio of cells: Trypan Blue (#1450013, Bio-Rad)) onto cell counting slide (#145-0011, Bio-Rad) and obtain cell density and cell viability using cell counter (TC20, Bio-Rad). Remove appropriate volume of resuspended cells from culture flask to accommodate 2500 cells/well@20 µL/well. Transfer Hela-HiBiT cells to 50 ml conical (#430290, Corning). Spin down at 1000 rpm for 5 min using tabletop centrifuge (SPINCHRON 15, Beckman). Discard supernatant and resuspend cell pellet in modified EMEM (#30-2003, ATCC) cell culture media containing 10% FBS (F2422-500ML, Sigma), and 1× Penicillin/Streptomycin (200 g/1) (30-002-CI, Corning) to a cell density of 125,000 cells/ml. Dispense 20 μL of resuspended Hela-HiBit cells per well in 384-well TC treated plate (#12-565-343, Thermo Scientific) using standard cassette (#50950372, Thermo Scientific) on Multidrop Combi (#5840310, Thermo Scientific) inside laminar flow cabinet. Dispense test compounds onto plates using digital liquid dispenser (D300E, Tecan). Incubate plates in humidified tissue culture incubator @37° C. for 18 hours. Add 20 ul of prepared Nano-Glo® HiBiT Lytic detection buffer (N3050, Promega) to each well of 384-well plate using small tube cassette (#24073295, Thermo Scientific) on Multidrop Combi, incubate @RT for 30-60 min. Read plates on microplate reader (Envision 2105, PerkinElmer) using 384 well Ultra-Sensitive luminescence mode. Raw data files and compound information reports are swept into centralized data lake and deconvoluted using automated scripts designed by TetraScience, Inc. Data analysis, curve-fitting and reporting done in Dotmatics Informatics Suite using Screening Ultra module.

TABLE xx

HiBiT assay data*
$DC_{50}/D_{max}$ %(SM2-293T) refers to SMARCA2 degradation potency/maximum SMARCA2 degradation within the concentrations tested in 293T HiBiT assay;
$DC_{50}/D_{max}$ %(SM2-HeLa) refers to SMARCA2 degradation potency/maximum SMARCA2 degradation within the concentrations tested in HeLa HiBiT assay;
$DC_{50}/D_{max}$ %(SM4-HeLa) refers to SMARCA4 degradation potency/maximum SMARCA4 degradation within the concentrations tested in HeLa HiBiT assay;

| Ex | $DC_{50}/D_{max}$ % (SM2-293T) | $DC_{50}/D_{max}$ % (SM2-HeLa) | $DC_{50}/D_{max}$ % (SM4-HeLa) |
|---|---|---|---|
| 4a | | | |
| 4b | | | |
| 7 | B/A | | |
| 8 | B/A | | |
| 9 | A/A | | |
| 10 | A/A | | |
| 11 | A/A | | |
| 12 | B/A | | |
| 13 | A/A | | |
| 14 | A/A | | |
| 15 | A/A | | |
| 16 | A/A | | |
| 17 | A/A | | |
| 18 | A/A | | |
| 19 | A/A | | |
| 20 | A/A | | |
| 21 | A/A | | |
| 22 | A/A | | |
| 23 | A/A | | |
| 24 | A/A | | |
| 25 | | A/A | B/B |
| 26 | | A/A | B/B |
| 27 | | A/A | B/B |
| 28 | | A/A | B/C |
| 29 | | A/A | B/C |
| 30 | | A/A | A/A |
| 31 | A/A | | |
| 32 | A/A | | |
| 33 | A/A | | |
| 34 | | A/A | D/C |
| 35 | A/A | | |
| 36 | A/A | | |
| 37 | A/A | | |
| 38 | | A/A | A/A |
| 39 | A/A | | |
| 40 | A/A | | |
| 41 | | A/A | A/A |
| 42 | | A/A | A/A |
| 43 | | A/A | A/A |
| 44 | A/A | | |
| 45 | | A/A | A/B |
| 46 | | A/A | B/A |
| 47 | | A/A | A/A |
| 48 | | A/A | A/B |
| 49 | | A/A | A/A |
| 50 | | A/A | A/A |
| 51 | | A/A | A/A |
| 52 | A/A | | |
| 53 | A/A | | |
| 54 | | A/A | A/A |
| 55 | | A/A | A/A |
| 56 | A/A | | |
| 57 | | A/A | B/B |
| 58 | | A/A | A/A |
| 59 | | A/A | A/A |
| 60 | | A/A | A/B |
| 61 | | A/A | A/B |
| 62 | | A/A | A/A |
| 63 | | A/A | A/A |
| 64 | | A/A | A/A |
| 65 | B/A | | |
| 66 | B/A | | |
| 67 | A/A | | |
| 68 | | A/A | B/A |
| 69 | | A/A | A/A |
| 70 | | A/A | A/A |
| 71 | | A/A | A/A |
| 72 | | A/A | A/A |
| 73 | | A/A | B/B |
| 74 | A/A | | |
| 75 | B/A | | |
| 76 | | A/A | A/A |
| 77 | A/A | | |
| 78 | A/A | | |
| 79 | A/A | | |
| 80 | A/A | | |
| 81 | A/A | | |
| 82 | A/A | | |
| 83 | A/A | | |
| 84 | A/A | | |
| 85 | A/A | | |
| 86 | | A/A | A/A |
| 87 | A/A | | |
| 88 | A/A | | |
| 89 | A/A | | |
| 90 | | A/A | A/A |
| 91 | A/A | | |
| 92 | | A/A | D/C |
| 93 | | A/A | A/A |
| 94 | | A/A | A/A |
| 95 | | A/A | A/A |
| 96 | | A/A | A/A |
| 97 | | A/A | A/A |
| 98 | | A/A | A/A |
| 99 | | A/A | A/A |
| 100 | | A/A | A/A |
| 101 | | A/A | A/A |
| 102 | | A/A | A/A |

A = $IC_{50}$ or $DC_{50}$ <0.1 μM; B = 0.1 μM = <$IC_{50}$ or $DC_{50}$ <1 μM; C = 1 μM = <$IC_{50}$ or $DC_{50}$ <10 μM; D = $IC_{50}$ or $DC_{50}$ >=10 μM; or A = $D_{max}$ >75%; B = 50%< $D_{max}$ <=75%; C = $D_{max}$ <=50%

In some embodiments, the disclosure is directed to the following aspects:

Aspect 1. A compounds of Formula (I):

PTM-ULM     (I)

or a pharmaceutically acceptable salt or solvate thereof, wherein
PTM is a moiety of Formula IA:

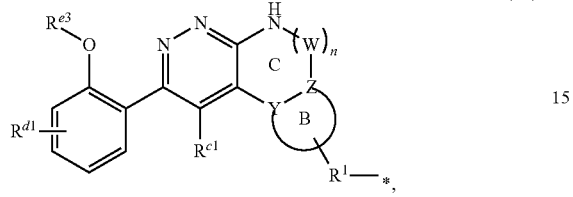

(IA)

wherein
$R^1$ is a covalent bond, or chemical moiety that links PTM and ULM;
* is a point of attachment to ULM;
n=0-3;
W is optionally substituted —$CH_2$—, —C(O)—, —S(O)—, or —S(O)$_2$—; wherein when n=2 or 3, only one W may be —C(O)—, —S(O)—, or —S(O)$_2$—;
$R^{c1}$ and $R^{d1}$ are independently H, D, Halo, $C_{1-3}$ alkyl, $C_{1-3}$ haloalkyl, or $C_{1-4}$ alkoxyl;
$R^{e3}$ is H, —C(O)$R^f$, or —P(O)(O$R^g$)$_2$; wherein $R^f$ and $R^g$ are independently H, $C_{1-4}$ alkyl, $C_{1-4}$ substituted alkyl, $C_{3-8}$ cyclcoalkyl, $C_{3-8}$ substituted cyclcoalkyl, $C_{3-8}$ heterocyclcoalkyl, or $C_{3-8}$ substituted heterocyclcoalkyl;
Z and Y are each independently N; C$R^h$ wherein $R^h$=H or absent; or, if $R^1$ is attached to Z, then Z is C and Y is N or C$R^h$ wherein $R^h$ is H; or if $R^1$ is attached to Y, then Y is C and Z is N or C$R^h$ wherein $R^h$ is H;
B is an optionally substituted 5-7 membered cycloalkyl ring, an optionally substituted 5-7 membered heteroaryl ring, or an optionally substituted 5-7 membered heterocyclic ring, wherein ring B is fused to ring C through Y and Z; and ULM is a small molecule E3 Ubiquitin Ligase binding moiety that binds a Von Hippel-Lindau E3 Ubiquitin Ligase.

Aspect 2. The compound according to aspect 1, wherein $R^1$ is a covalent bond.

Aspect 3. The compound according to aspect 1, wherein $R^1$ is a chemical moiety represented by the formula:

-(A)$_q$-, wherein:
q is an integer from 1 to 14;
each A is independently selected from the group consisting of C$R^{1a}R^{1b}$, O, S, SO, SO$_2$, N$R^{1c}$, SO$_2$N$R^{1c}$, SON$R^{1c}$, SO(=N$R^{1c}$), SO(=N$R^{1c}$)N$R^{1d}$, CON$R^{1c}$, N$R^{1c}$CON$R^{1d}$, N$R^{1c}$C(O)O, N$R^{1c}$SO$_2$N$R^{1d}$, CO, C$R^{1a}$=C$R^{1b}$, Si$R^{1a}R^{1b}$, P(O)$R^{1a}$, P(O)O$R^{1a}$, (C$R^{1a}R^{1b}$)$_{1-4}$, —(C$R^{1a}R^{1b}$)$_{1-4}$O(C$R^{1a}R^{1b}$)$_{1-4}$, —(C$R^{1a}R^{1b}$)$_{1-4}$S(C$R^{1a}R^{1b}$)$_{1-4}$, —(C$R^{1a}R^{1b}$)$_{1-4}$NR(C$R^{1a}R^{1b}$)$_{1-4}$,N$R^{1c}$C(=NCN)N$R^{1d}$N$R^{1c}$C(=NCN), N$R^{1c}$C(=NO$_2$)N$R^{1d}$, 3-11 membered cycloalkyl, optionally substituted with 0-6 $R^{1a}$ and/or $R^{1b}$ groups, 3-11 membered heterocyclyl optionally substituted with 0-6 $R^{1a}$ and/or $R^{1b}$ groups, aryl optionally substituted with 0-6 $R^{1a}$ and/or $R^{1b}$ groups, or heteroaryl optionally substituted with 0-6 $R^{1a}$ and/or $R^{1b}$ groups,
wherein $R^{1a}$, $R^{1b}$, $R^{1c}$, $R^{1d}$ and $R^{1e}$ are each independently, —H, D, -halo, —$C_1$-$C_8$alkyl, —O—$C_1$-$C_8$alkyl, —$C_1$-$C_6$haloalkyl, —S—$C_1$-$C_8$alkyl, —NH$C_1$-$C_8$alkyl, —N($C_1$-$C_8$alkyl)$_2$, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)($C_1$-$C_8$alkyl), —OH, —NH$_2$, —SH, —SO$_2C_1$-$C_8$alkyl, SO(NH)$C_1$-$C_8$alkyl, P(O)(O$C_1$-$C_8$alkyl)($C_1$-$C_8$alkyl), —P(O) (O$C_1$-$C_8$alkyl)$_2$, —CH=CH($C_1$-$C_8$alkyl), —C($C_1$-$C_8$alkyl)=CH($C_1$-$C_8$alkyl), —C($C_1$-$C_8$alkyl)=C($C_1$-$C_8$alkyl)$_2$, —Si(OH)$_3$, —Si($C_1$-$C_8$alkyl)$_3$, —Si (OH)($C_1$-$C_8$alkyl)$_2$, —C(O)$C_1$-$C_8$alkyl, —CO$_2$H, —CN, —CF$_3$, —CHF$_2$, —CH$_2$F, —NO$_2$, —SF$_5$, —SO$_2$NH$C_1$-$C_8$alkyl, —SO$_2$N($C_1$-$C_8$alkyl)$_2$, —SO (NH)NH$C_1$-$C_8$alkyl, —SO(NH)N($C_1$-$C_8$alkyl)$_2$, —SONH$C_1$-$C_8$alkyl, —SON($C_1$-$C_8$alkyl)$_2$, —CONH$C_1$-$C_8$alkyl, —CON($C_1$-$C_8$alkyl)$_2$, —N($C_1$-$C_8$alkyl)CONH($C_1$-$C_8$alkyl), —N($C_1$-$C_8$alkyl)CON($C_1$-$C_8$alkyl)$_2$, —NHCONH($C_1$-$C_8$alkyl), —NHCON($C_1$-$C_8$alkyl)$_2$, —NHCONH$_2$, —N($C_1$-$C_8$alkyl)SO$_2$NH($C_1$-$C_8$alkyl), —N($C_1$-$C_8$alkyl)SO$_2$N($C_1$-$C_8$alkyl)$_2$, —NHSO$_2$NH($C_1$-$C_8$alkyl), —NHSO$_2$N($C_1$-$C_8$alkyl)$_2$, or —NHSO$_2$NH$_2$; and where $R^{1a}$ or $R^{1b}$, each independently may be optionally linked to other groups to form cycloalkyl and/or heterocyclyl moiety, optionally substituted with 0-4 $R^{1e}$ groups.

Aspect 4. The compound according to aspect 3, wherein q=4 and $R^1$ is a chemical moiety represented by the formula: -$A_1$-$A_2$-$A_3$-$A_4$-, wherein each of $A_{1-4}$ is independently selected from the group consisting of O, S, SO, SO$_2$, N$R^{1c}$, SO$_2$N$R^{1c}$, SON$R^{1c}$, SO(=N$R^{1c}$), SO(=N$R^{1c}$)N$R^{1d}$, CON$R^{1c}$, N$R^{1c}$CON$R^{1d}$, N$R^{1c}$C(O)O, N$R^{1c}$SO$_2$N$R^{1d}$, CO, C$R^{1a}$=C$R^{1b}$, Si$R^{1a}R^{1b}$, P(O)$R^{1a}$, P(O)O$R^{1a}$, (C$R^{1a}R^{1b}$)$_{1-4}$, —(C$R^{1a}R^{1b}$)$_{1-4}$O(C$R^{1a}R^{1b}$)$_{1-4}$, —(C$R^{1a}R^{1b}$)$_{1-4}$S(C$R^{1a}R^{1b}$)$_{1-4}$, —(C$R^{1a}R^{1b}$)$_{1-4}$NR (C$R^{1a}R^{1b}$)$_{1-4}$, optionally substituted 3-11 membered cycloalkyl, 3-11 membered heterocyclyl, aryl, and heteroaryl;
wherein $R^{1a}$ and $R^{1b}$ are each independently selected from the group consisting of —H, D, -halo, —$C_1$-$C_8$alkyl, —O—$C_1$-$C_8$alkyl, —$C_1$-$C_6$haloalkyl, —S—$C_1$-$C_8$alkyl, —NH$C_1$-$C_8$alkyl, —N($C_1$-$C_8$alkyl)$_2$, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)($C_1$-$C_8$alkyl), —OH, —NH$_2$, —SH, —SO$_2C_1$-$C_8$alkyl, SO(NH)$C_1$-$C_8$alkyl, P(O) (O$C_1$-$C_8$alkyl)($C_1$-$C_8$alkyl), —P(O)(O$C_1$-$C_8$alkyl)$_2$, —CH=CH($C_1$-$C_8$alkyl), —C($C_1$-$C_8$alkyl)=CH($C_1$-$C_8$alkyl), —C($C_1$-$C_8$alkyl)=C($C_1$-$C_8$alkyl)$_2$, —Si (OH)$_3$, —Si($C_1$-$C_8$alkyl)$_3$, —Si(OH)($C_1$-$C_8$alkyl)$_2$, —C(O)$C_1$-$C_8$alkyl, —CO$_2$H, —CN, —NO$_2$, —SF$_5$, —SO$_2$NH$C_1$-$C_8$alkyl, —SO$_2$N($C_1$-$C_8$alkyl)$_2$, —SO (NH)NH$C_1$-$C_8$alkyl, —SO(NH)N($C_1$-$C_8$alkyl)$_2$, —SONH$C_1$-$C_8$alkyl, —SON($C_1$-$C_8$alkyl)$_2$, —CONH$C_1$-$C_8$alkyl, —CON($C_1$-$C_8$alkyl)$_2$, —N($C_1$-$C_8$alkyl)CONH($C_1$-$C_8$alkyl), —N($C_1$-$C_8$alkyl)CON ($C_1$-$C_8$alkyl)$_2$, —NHCONH($C_1$-$C_8$alkyl), —NHCON($C_1$-$C_8$alkyl)$_2$, —NHCONH$_2$, —N($C_1$-$C_8$alkyl)

SO$_2$NH(C$_1$-C$_8$alkyl), —N(C$_1$-C$_8$alkyl)SO$_2$N(C$_1$-C$_8$alkyl)$_2$, —NHSO$_2$NH(C$_1$-C$_8$alkyl), —NHSO$_2$N(C$_1$-C$_8$alkyl)$_2$, or —NHSO$_2$NH$_2$; and R$^{1c}$ and R$^{1d}$ are each independently selected from the group consisting of H, D, optionally substituted C$_{1-4}$ alkyl, C$_{3-8}$ cyclcoalkyl, C$_{3-8}$ heterocyclcoalkyl, aryl, or heteroaryl.

Aspect 5. The compound according to any one of aspects 1, or 3, wherein R$^1$ is a 3-11 membered cycloalkyl optionally substituted with 0-6 R$^{1a}$ and/or R$^{1b}$ groups, 3-11 membered heterocyclyl optionally substituted with 0-6 R$^{1a}$ and/or R$^{1b}$ groups, —(CR$^{1a}$R$^{1b}$)$_{1-5}$, —(CR$^{1a}$=CR$^{1b}$)—, —(CR$^{1a}$R$^{1b}$)$_{1-5}$-A- wherein A is O, S, or NR$^{1c}$, —(CR$^{1a}$R$^{1b}$)$_{1-5}$-A-(CR$^{1a}$R$^{1b}$)$_{1-5}$— wherein A is O, S, or NR$^{1c}$, —(CR$^{1a}$R$^{1b}$)$_{1-5}$-A-(CR$^{1a}$R$^{1b}$)$_{1-5}$-A- wherein A is O, S, or NR$^{1c}$, —(CR$^{1a}$R$^{1b}$)$_{1-5}$—(CR$^{1a}$=CR$^{1b}$)—(CR$^{1a}$R$^{1b}$)$_{1-5}$—, —(CR$^{1a}$R$^{1b}$)$_{1-5}$—CR$^{1a}$=CR$^{1b}$)—(CR$^{1a}$R$^{1b}$)$_{1-5}$-A- wherein A is O, S, or NR$^{1c}$, —(CR$^{1a}$R$^{1b}$)$_{1-5}$—(C≡C)—(CR$^{1a}$R$^{1b}$)$_{1-5}$—, —(CR$^{1a}$R$^{1b}$)$_{1-5}$—(C≡C)—(CR$^{1a}$R$^{1b}$)$_{1-5}$-A- wherein A is O, S, or NR$^{1c}$, —(C≡C)—(CR$^{1a}$R$^{1b}$)$_{1-5}$-A-(CR$^{1a}$R$^{1b}$)$_{1-5}$— wherein A is O, S, or NR$^{1c}$, —(C≡C)—(CR$^{1a}$R$^{1b}$)$_{1-5}$, —(CR$^{1a}$R$^{1b}$)$_{1-5}$-(3-11 membered cycloalkyl optionally substituted with 0-6 R$^{1a}$ and/or R$^{1b}$ groups)-, —(CR$^{1a}$R$^{1b}$)$_{1-5}$-(3-11 membered heterocyclyl optionally substituted with 0-6 R$^{1a}$ and/or R$^{1b}$ groups)-, -(3-11 membered cycloalkyl optionally substituted with 0-6 R$^{1a}$ and/or R$^{1b}$ groups)-(CR$^{1a}$R$^{1b}$)$_{1-5}$—, -(3-11 membered heterocyclyl optionally substituted with 0-6 R$^{1a}$ and/or R$^{1b}$ groups) —(CR$^{1a}$R$^{1b}$)$_{1-5}$—, —(CR$^{1a}$R$^{1b}$)$_{1-5}$ (3-11 membered cycloalkyl optionally substituted with 0-6 R$^{1a}$ and/or R$^{1b}$ groups)-A-, —(CR$^{1a}$R$^{1b}$)$_{1-5}$ (3-11 membered heterocyclyl optionally substituted with 0-6 R$^{1a}$ and/or R$^{1b}$ groups)-A-, —(CR$^{1a}$R$^{1b}$)$_{1-5}$-(3-11 membered cycloalkyl optionally substituted with 0-6 R$^{1a}$ and/or R$^{1b}$ groups)-(CR$^{1a}$R$^{1b}$)$_{1-5}$, —(CR$^{1a}$R$^{1b}$)$_{1-5}$-(3-11 membered cycloalkyl optionally substituted with 0-6 R$^{1a}$ and/or R$^{1b}$ groups)-A- wherein A is O, S, or NR$^{1c}$, —(CR$^{1a}$R$^{1b}$)$_{1-5}$-(3-11 membered cycloalkyl optionally substituted with 0-6 R$^{1a}$ and/or R$^{1b}$ groups)-(CR$^{1a}$R$^{1b}$)$_{1-5}$-A- wherein A is O, S, or NR$^{1c}$, —(CR$^{1a}$R$^{1b}$)$_{1-5}$-A-(3-11 membered cycloalkyl optionally substituted with 0-6 R$^{1a}$ and/or R$^{1b}$ groups)- wherein A is O, S, or NR$^{1c}$, —(CR$^{1a}$R$^{1b}$)$_{1-5}$-(3-11 membered heterocyclyl optionally substituted with 0-6 R$^{1a}$ and/or R$^{1b}$ groups)-(CR$^{1a}$R$^{1b}$)$_{1-5}$, —(CR$^{1a}$R$^{1b}$)$_{1-5}$-(3-11 membered heterocyclyl optionally substituted with 0-6 R$^{1a}$ and/or R$^{1b}$ groups)-(CR$^{1a}$R$^{1b}$)$_{1-5}$-A- wherein A is O, S, or NR$^{1c}$, —(CR$^{1a}$R$^{1b}$)$_{1-5}$-(3-11 membered heterocyclyl optionally substituted with 0-6 R$^{1a}$ and/or R$^{1b}$ groups)-A- wherein A is O, S, or NR$^{1c}$, —(CR$^{1a}$R$^{1b}$)$_{1-5}$-A-(3-11 membered heterocyclyl optionally substituted with 0-6 R$^{1a}$ and/or R$^{1b}$ groups)- wherein A is O, S, or NR$^{1c}$, —(CR$^{1a}$R$^{1b}$)$_{1-5}$-(3-11 membered cycloalkyl optionally substituted with 0-6 R$^{1a}$ and/or R$^{1b}$ groups)-(CR$^{1a}$R$^{1b}$)$_{1-5}$-A- wherein A is O, S, or NR$^{1c}$, —(CR$^{1a}$R$^{1b}$)$_{1-5}$-A-(3-11 membered cycloalkyl optionally substituted with 0-6 R$^{1a}$ and/or R$^{1b}$ groups)- wherein A is O, S, or NR$^{1c}$, —(CR$^{1a}$R$^{1b}$) A (3-11 membered cycloalkyl optionally substituted with 0-6 R$^{1a}$ and/or R$^{1b}$ groups)-(CR$^{1a}$R$^{1b}$)$_{1-5}$-A- wherein each A is independently O, S, or NR$^{1c}$, —(CR$^{1a}$R$^{1b}$)$_{1-5}$-A-(3-11 membered heterocyclyl optionally substituted with 0-6 R$^{1a}$ and/or R$^{1b}$ groups)-(CR$^{1a}$R$^{1b}$)$_{1-5}$-A- wherein each A is independently O, S, or NR$^{1c}$, —(CR$^{1a}$R$^{1b}$)$_{1-5}$-A-(CR$^{1a}$R$^{1b}$)$_{1-5}$-A- wherein A is O, S, or NR$^{1c}$, —(CR$^{1a}$R$^{1b}$)$_{1-5}$-A-(CR$^{1a}$R$^{1b}$)$_{1-5}$-A-(CR$^{1a}$R$^{1b}$)$_{1-5}$-A-(CR$^{1a}$R$^{1b}$)$_{1-5}$-A- wherein A is O, S, or NR$^{1c}$, —(CR$^{1a}$R$^{1b}$)$_{1-5}$-A-(CO) wherein A is O, S, or NR$^{1c}$, —(CR$^{1a}$R$^{1b}$)$_{1-5}$—(CR$^{1a}$=CR$^{1b}$)—(CR$^{1a}$R$^{1b}$)$_{1-5}$-A-(CO)— wherein A is O, S, or NR$^{1c}$, —(CR$^{1a}$R$^{1b}$)$_{1-5}$—(C≡C)—(CR$^{1a}$R$^{1b}$)$_{1-5}$-A-(CO)— wherein A is O, S, or NR$^{1c}$, —(CR$^{1a}$R$^{1b}$)$_{1-5}$-(3-11 membered cycloalkyl optionally substituted with 0-6 R$^{1a}$ and/or R$^{1b}$ groups)-(CR$^{1a}$R$^{1b}$)$_5$-A-(CO)— wherein A is O, S, or NR$^{1c}$, —(CR$^{1a}$R$^{1b}$)$_{1-5}$-A-(CO)-(3-11 membered cycloalkyl optionally substituted with 0-6 R$^{1a}$ and/or R$^{1b}$ groups)- wherein A is O, S, or NR$^{1c}$, —(CR$^{1a}$R$^{1b}$)$_{1-5}$-(3-11 membered heterocyclyl optionally substituted with 0-6 R$^{1a}$ and/or R$^{1b}$ groups)-(CR$^{1a}$R$^{1b}$)$_{1-5}$-A-(CO)— wherein A is O, S, or NR$^{1c}$, —(CR$^{1a}$R$^{1b}$)$_{1-5}$-A-(CO)-(3-11 membered heterocyclyl optionally substituted with 0-6 R$^{1a}$ and/or R$^{1b}$ groups)- wherein A is O, S, or NR$^{1c}$, —(CR$^{1a}$R$^{1b}$)$_{1-5}$-A-(3-11 membered cycloalkyl optionally substituted with 0-6 R$^{1a}$ and/or R$^{1b}$ groups)-A-(CO)— wherein each A is independently O, S, or NR$^{1c}$, -(3-11 membered cycloalkyl optionally substituted with 0-6 R$^{1a}$ and/or R$^{1b}$ groups)-CO—(CR$^{1a}$R$^{1b}$)$_{1-5}$-A- wherein A is O, S, or NR$^{1c}$, —(CR$^{1a}$R$^{1b}$)$_{1-5}$-(3-11 membered cycloalkyl optionally substituted with 0-6 R$^{1a}$ and/or R$^{1b}$ groups)-(CR$^{1a}$R$^{1b}$)$_{1-5}$-A-(CO)— wherein A is O, S, or NR$^{1c}$, —(CR$^{1a}$R$^{1b}$)$_{1-5}$-(3-11 membered heterocyclyl optionally substituted with 0-6 R$^{1a}$ and/or R$^{1b}$ groups)-(CR$^{1a}$R$^{1b}$)$_{1-5}$-A-(CO)— wherein A is O, S, or NR$^{1c}$, -(3-11 membered cycloalkyl optionally substituted with 0-6 R$^{1a}$ and/or R$^{1b}$ groups)-(CR$^{1a}$R$^{1b}$)$_{1-5}$—, or -(3-11 membered heterocyclyl optionally substituted with 0-6 R$^{1a}$ and/or R$^{1b}$ groups)-(CR$^{1a}$R$^{1b}$)$_{1-5}$—.

Aspect 6. The compound according to any one of aspects 1-5, wherein the compound of Formula IA is a compound of Formula IA-1:

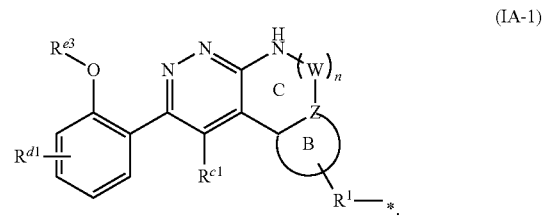

(IA-1)

Aspect 7. The compound according to any one of aspects 1-5, wherein the compound of Formula IA is a compound of Formula IA-2:

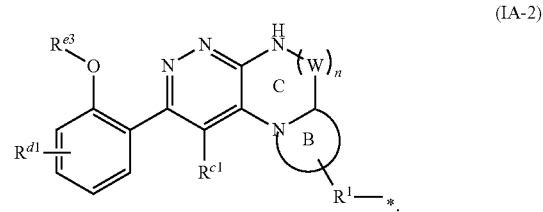

(IA-2)

Aspect 8. The compound according to any one of aspects 1-5 or 7, wherein the compound of Formula IA is a compound of Formula IA-3:

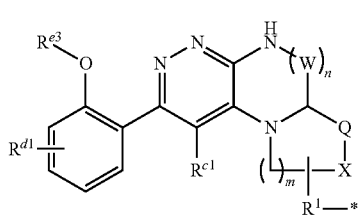

(IA-3)

wherein m=1 to 3;

X is optionally substituted —CH$_2$—, or NH; or, if R$^1$ is attached to X, then X is —CH— or N;

and Q is optionally substituted —CH$_2$—, optionally substituted —(CH$_2$)$_2$—, —C(O)—, optionally substituted —CH$_2$C(O)—, —S(O)—, —S(O)$_2$—, optionally substituted —CH$_2$S(O)$_2$—, or optionally substituted —CH$_2$S(O)—.

Aspect 9. The compound according to any one of aspects 1-5 or 7-8, wherein the compound of Formula IA is a compound of Formula IA-4:

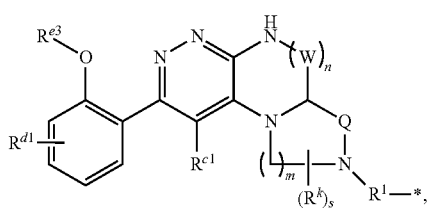

(IA-4)

wherein m=1 to 3; each R$^k$ is independently H, D, F, C$_{1-3}$ alkyl, C$_{1-3}$ haloalkyl, C$_{1-4}$ alkoxyl, substituted C$_{1-3}$ alkyl, substituted C$_{1-3}$ haloalkyl, or substituted C$_{1-4}$ alkoxyl; and s=0-7.

Aspect 10. The compound according to aspect 9, wherein the compound of Formula IA-4 is a compound of Formula IA-5:

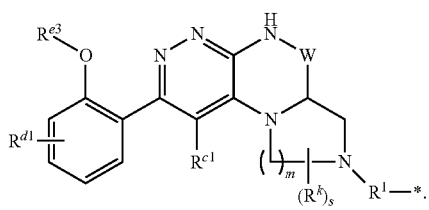

(IA-5)

Aspect 11. The compound according to any one of aspects 8-10, wherein m=2.

Aspect 12. The compound according to any one of aspects 8-11, wherein at least one W is optionally substituted —CH$_2$; and wherein when n=2 or 3, only one W may be —C(O)—, —S(O)—, or —S(O)$_2$—

Aspect 13. The compound according to any one of aspects 8-11, wherein at least one W is —C(O)—.

Aspect 14. The compound according to aspect 11, wherein the compound of Formula IA-5 is a compound of Formula IA-6:

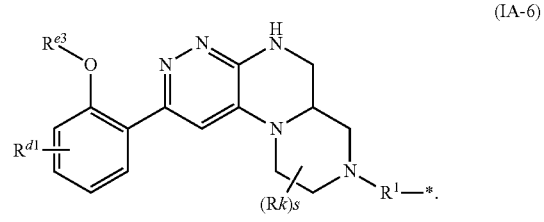

(IA-6)

Aspect 15. The compound according to any one of the preceding aspects, wherein R$^{e3}$ is H.

Aspect 16. The compound according to any one of the preceding aspects, wherein R$^{d1}$ is H.

Aspect 17. The compound according to any one of aspect 1-13, wherein R$^{c1}$ is H.

Aspect 18. The compound according to any one of the preceding aspects, wherein ULM is a moiety having the Formula ULM-I

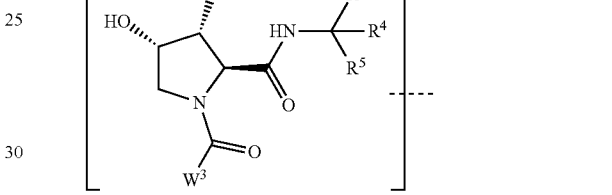

(ULM-I)

wherein the dashed line (----) indicates the position of attachment of ULM-I to R$^1$;

V is H or F;

R$^3$ is optionally substituted phenyl, optionally substituted napthyl, or an optionally substituted 5-10 membered heteroaryl;

one of R$^4$ or R$^5$ is H, D, haloalkyl, optionally substituted alkyl, optionally substituted cycloalkyl, optionally substituted heterocycloalkyl, —COR$^d$, CONR$^{e1}$R$^{e2}$;

the other of R$^4$ or R$^5$ is H or D;

or R$^4$ and R$^5$, together with the carbon atom to which they are both attached, form an optionally substituted 3-5 membered cycloalkyl, heterocyclyl;

W$^3$ is an optionally substituted aryl, optionally substituted heteroaryl, or

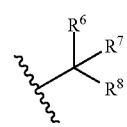

R$^6$ and R$^7$ are independently H, D, optionally substituted alkyl, optionally substituted cycloalkyl, or optionally substituted haloalkyl, or R$^6$, R$^7$, and the carbon atom to which they are attached form an optionally substituted cycloalkyl or optionally substituted heterocyclyl;

R$^8$ is an optionally substituted heterocyclyl, optionally substituted heteroaryl, optionally substituted aryl, CONR$^a$R$^b$, NR$^a$R$^b$,

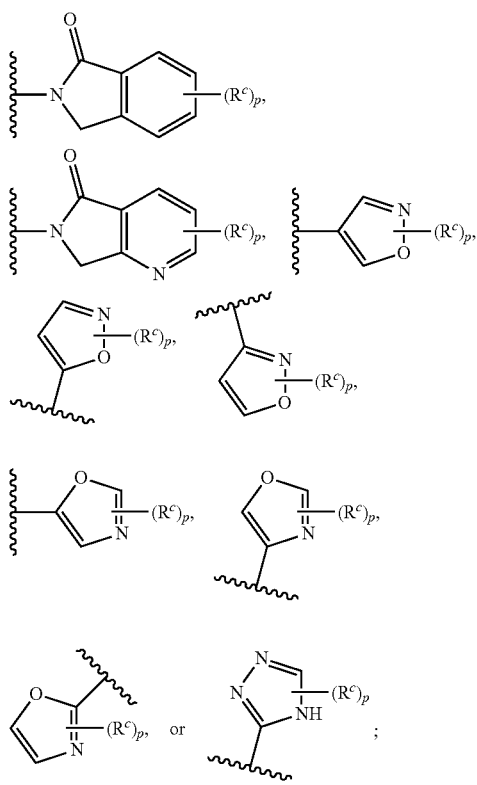

$R^a$ is selected from H or optionally substituted alkyl;

$R^b$ is selected from H, —C(O)—* wherein * is a point of attachment to $R^1$, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (cycloalkyl)carbonyl, optionally substituted (heterocyclyl) carbonyl, or optionally substituted aralkyl;

each $R^c$ is independently H, halo, optionally substituted alkoxy, cyano, optionally substituted alkyl, haloalkyl, or haloalkoxy;

each $R^d$ is independently selected from H, optionally substituted alkyl or $NR^{e1}R^{e2}$;

each $R^{e1}$ and $R^{e2}$ is independently H, D, optionally substituted alkyl, or $R^{e1}$ and $R^{e2}$ together with the nitrogen atom to which they are attached form a 4-7 membered heterocyclyl; and p is 0, 1, 2, 3, or 4.

Aspect 19. The compound according to aspect 18, wherein $R^8$ is optionally substituted heterocyclyl.

Aspect 20. The compound according to aspect 18, wherein $R^8$ is optionally substituted heteroaryl.

Aspect 21. The compound according to aspect 18, wherein $R^8$ is optionally substituted aryl.

Aspect 22. The compound according to aspect 18, wherein $R^8$ is $CONR^aR^b$.

Aspect 23. The compound according to aspect 18, wherein $R^8$ is $NR^aR^b$.

Aspect 24. The compound according to aspect 18, wherein $R^8$ is

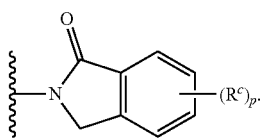

Aspect 25. The compound according to aspect 18, wherein $R^8$ is

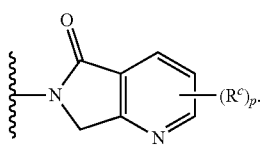

Aspect 26. The compound according to aspect 18, wherein $R^8$ is

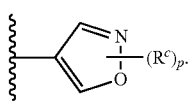

Aspect 27. The compound according to aspect 18, wherein $R^8$ is

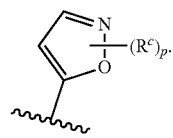

Aspect 28. The compound according to aspect 18, wherein $R^8$ is

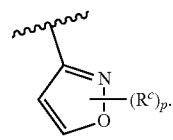

Aspect 29. The compound according to aspect 18, wherein $R^8$ is

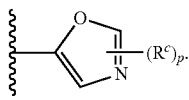

Aspect 30. The compound according to aspect 18, wherein $R^8$ is

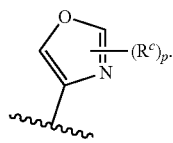

Aspect 31. The compound according to aspect 18, wherein R$^8$ is

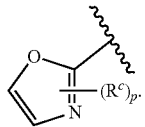

Aspect 32. The compound according to aspect 18, wherein R$^8$ is

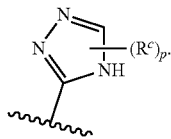

Aspect 33. The compound according to any one of aspects 18-32, wherein R$^3$ is optionally substituted phenyl having the formula:

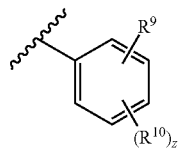

wherein

R$^9$ is H, D, halo, —CN, —OH, —NO$_2$, —NR$^{e1}$R$^{e2}$, —OR$^{e1}$, —CONR$^{e1}$R$^{e2}$, —NR$^{e1}$COR$^{e2}$, —SO$_2$NR$^{e1}$R$^{e2}$, —NR$^{e1}$SO$_2$R$_{e2}$, optionally substituted alkyl, optionally substituted alkoxyl, optionally substituted haloalkyl, optionally substituted haloalkoxy; optionally substituted aryl; optionally substituted heteroaryl; optionally substituted cycloalkyl; or optionally substituted heterocyclyl;

R$^{10}$ is H, D, halo, CN, optionally substituted alkyl, optionally substituted haloalkyl, hydroxy, —NH (optionally substituted alkyl), —N(optionally substituted alkyl)$_2$, optionally substituted alkoxy, or optionally substituted haloalkoxy; and z is 0, 1, 2, 3, or 4.

Aspect 34. The compound according to aspect 33, wherein R$^9$ is

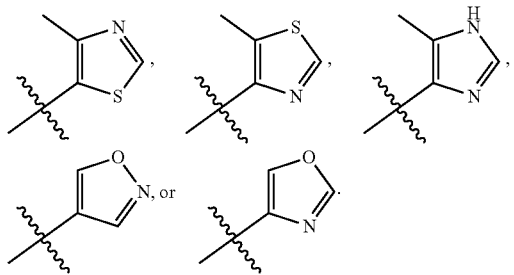

each optionally substituted.

Aspect 35. The compound according to aspect 34, wherein R$^9$ is

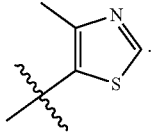 [SMILES: *c1scnc1C]

Aspect 36. The compound according to any one of aspects 33-35, wherein R$^{10}$ is H, D, hydroxy, halogen, —NH(C$_1$-C$_4$alkyl), or C$_1$-C$_6$alkoxy, and z is 0, 1, 2, 3, or 4.

Aspect 37. The compound according to any one of aspects 18-36, wherein W$^3$ is

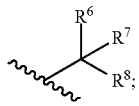

R$^6$ is H;
R$^7$ is H, or optionally substituted alkyl;
R$^8$ is

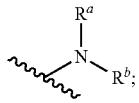

R$^a$ is H or optionally substituted alkyl;
R$^b$ is H, —C(O)—* wherein * is a point of attachment to R$^1$, optionally substituted alkyl, optionally substituted alkylcarbonyl, or optionally substituted (cycloalkyl)carbonyl.

Aspect 38. The compound according to aspect 37, wherein
R$^7$ is H, C$_1$-C$_6$alkyl, C$_1$-C$_6$alk-OH, C$_1$-C$_6$alk-NH$_2$, —C$_1$-C$_6$alk-CONH—*, or —C$_1$-C$_6$alk-NHCO—*;
R$^8$ is —NH—*, or —NHCOR$^{11}$;
* is a point of attachment of the ULM to R$^1$; and
R$^{11}$ is

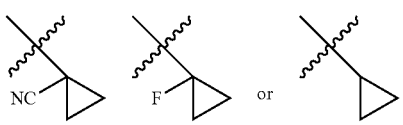

Aspect 39. The compound according to any one of aspects 18-36, wherein
W$^3$ is

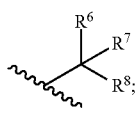

$R^6$ is H;
$R^7$ is H, or optionally substituted alkyl;
$R^8$ is

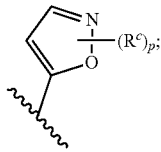

$R^c$ is H or optionally substituted alkyl; and p=1.

Aspect 40. The compound according to any one of aspects 18-39, wherein ULM-I is a compound of formula:

(ULM-IA)
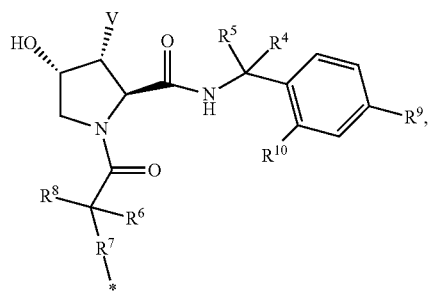

(ULM-IB)
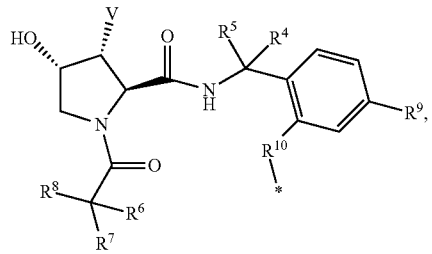

(ULM-IC)
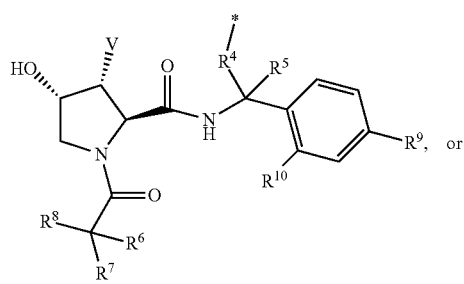

(ULM-ID)
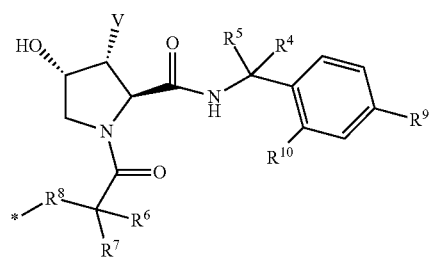

* is a point of attachment of the ULM to $R^1$.

Aspect 41. The compound of aspect 40, wherein $R^9$ is optionally substituted

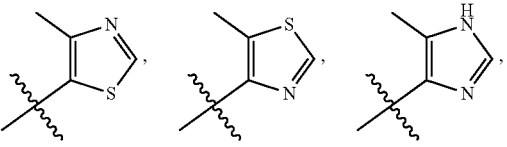

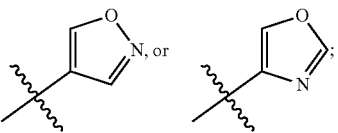

and $R^{10}$ is H, D, hydroxy, halogen, —NH($C_1$-$C_6$alkyl), or —O$C_1$-$C_6$alkyl.

Aspect 42. The compound according to aspect 40 or 41, wherein the compound of Formula I is a compound of Formula IA-7 or IA-8:

(IA-7)
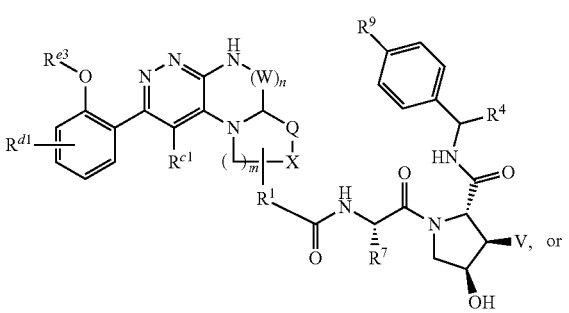

(IA-8)
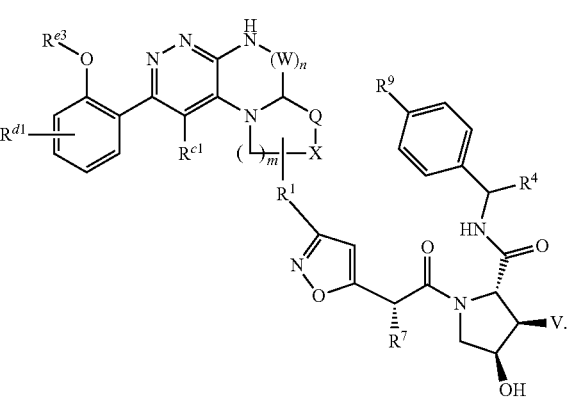

Aspect 43. The compound according to aspect 42, wherein the compound of Formula I is a compound of Formula IA-9 or IA-10:

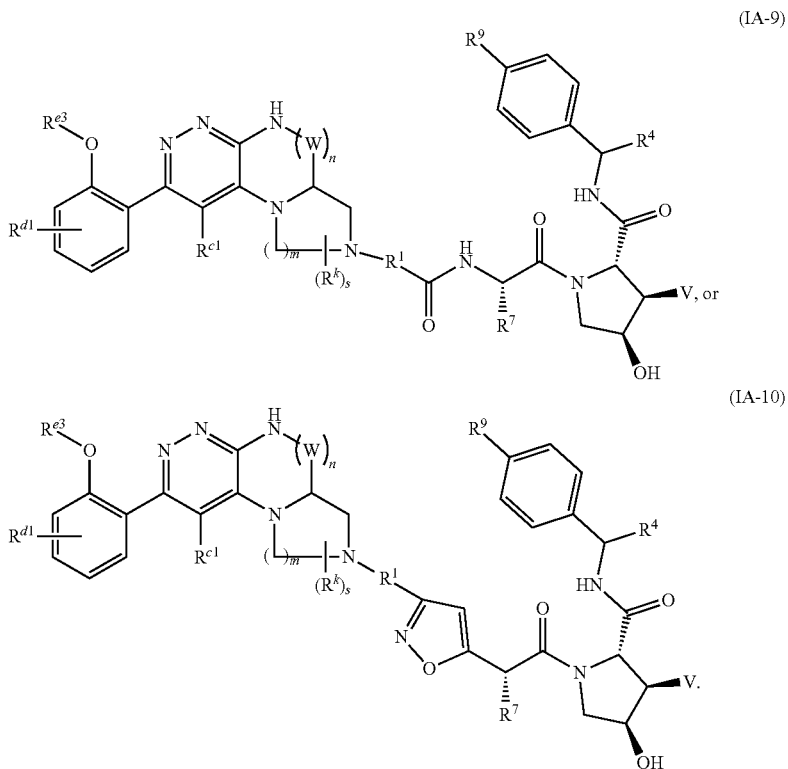

Aspect 44. The compound according to any one of aspects 1-43, wherein $R^1$ is —$CR^{1a}$=$CR^{1b}$—.

Aspect 45. The compound according to any one of aspects 1-43, wherein $R^1$ is —$(CR^{1a}R^{1b})_{1-5}$-.

Aspect 46. The compound according to any one of aspects 1-43, wherein $R^1$ is —$(CR^{1a}R^{1b})_{1-5}$-A- wherein A is O, S, or $NR^{1c}$.

Aspect 47. The compound according to any one of aspects 1-43, wherein $R^1$ is —$(CR^{1a}R^{1b})_{1-5}$-A-$(CR^{1a}R^{1b})_{1-5}$— wherein A is O, S, or $NR^{1c}$.

Aspect 48. The compound according to any one of aspects 1-43, wherein $R^1$ is —(C≡C)—$(CR^{1a}R^{1b})_{1-5}$-.

Aspect 49. The compound according to any one of aspects 1-43, wherein $R^1$ is —$(CR^{1a}R^{1b})_{1-5}$-(3-11 membered cycloalkyl optionally substituted with 0-6 $R^{1a}$ and/or $R^{1b}$ groups)-.

Aspect 50. The compound according to any one of aspects 1-43, wherein $R^1$ is —$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$.

Aspect 51. The compound according to any one of aspects 1-43, wherein $R^1$ is —$(CR^{1a}R^{1b})_{1-5}$-(3-11 membered heterocyclyl optionally substituted with 0-6 $R^{1a}$ and/or $R^{1b}$ groups)-$(CR^{1a}R^{1b})_{1-5}$.

Aspect 52. The compound according to any one of aspects 1-43, wherein $R^1$ is —$(CR^{1a}R^{1b})_{1-5}$-(3-11 membered heterocyclyl optionally substituted with 0-6 $R^{1a}$ and/or $R^{1b}$ groups)-.

Aspect 53. The compound according to any one of aspects 1-43, wherein $R^1$ is -(3-11 membered heterocyclyl optionally substituted with 0-6 $R^{1a}$ and/or $R^{1b}$ groups) —$(CR^{1a}R^{1b})_{1-5}$—.

Aspect 54. The compound according to any one of aspects 1-43, wherein $R^1$ is —$(CR^{1a}R^{1b})_{1-5}$-(3-11 membered cycloalkyl optionally substituted with 0-6 $R^{1a}$ and/or $R^{1b}$ groups)-$(CR^{1a}R^{1b})_{1-5}$-A- wherein A is O, S, or $NR^{1c}$.

Aspect 55. The compound according to any one of aspects 1-43, wherein $R^1$ is —$(CR^{1a}R^{1b})_{1-5}$-(3-11 membered heterocyclyl optionally substituted with 0-6 $R^{1a}$ and/or $R^{1b}$ groups)-$(CR^{1a}R^{1b})_{1-5}$-A- wherein A is O, S, or $NR^{1c}$.

Aspect 56. The compound according to any one of aspects 1-43, wherein $R^1$ is —$(CR^{1a}R^{1b})_{1-5}$-(3-11 membered heterocyclyl optionally substituted with 0-6 $R^{1a}$ and/or $R^{1b}$ groups)-A- wherein A is O, S, or $NR^{1c}$.

Aspect 57. The compound according to any one of aspects 1-43, wherein $R^1$ is —$(CR^{1a}R^{1b})_{1-5}$-A-(3-11 membered heterocyclyl optionally substituted with 0-6 $R^{1a}$ and/or $R^{1b}$ groups)- wherein A is O, S, or $NR^{1c}$.

Aspect 58. The compound according to any one of aspects 1-43, wherein $R^1$ is —$(CR^{1a}R^{1b})_{1-5}$-A-(3-11 membered cycloalkyl optionally substituted with 0-6 $R^{1a}$ and/or $R^{1b}$ groups)- wherein A is O, S, or $NR^{1c}$.

Aspect 59. The compound according to any one of aspects 1-43, wherein $R^1$ is —$(CR^{1a}R^{1b})_{1-5}$-A-$(CR^{1a}R^{1b})_{1-5}$-A- wherein A is O, S, or $NR^{1c}$.

Aspect 60. A pharmaceutical composition comprising a compound according to any one of aspects 1 to 59 and a pharmaceutically acceptable excipient.

Aspect 61. A method of treating cancer in a subject in need thereof comprising administering to the subject a compound of any one of aspects 1 to 59.

Aspect 62. The method of aspect 61, wherein the cancer is SMARCA4 deleted cancer.

Aspect 63. The method of either one of aspect 61 or 62, wherein the cancer is squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

What is claimed:
1. A compound of Formula IA-7 or IA-8:

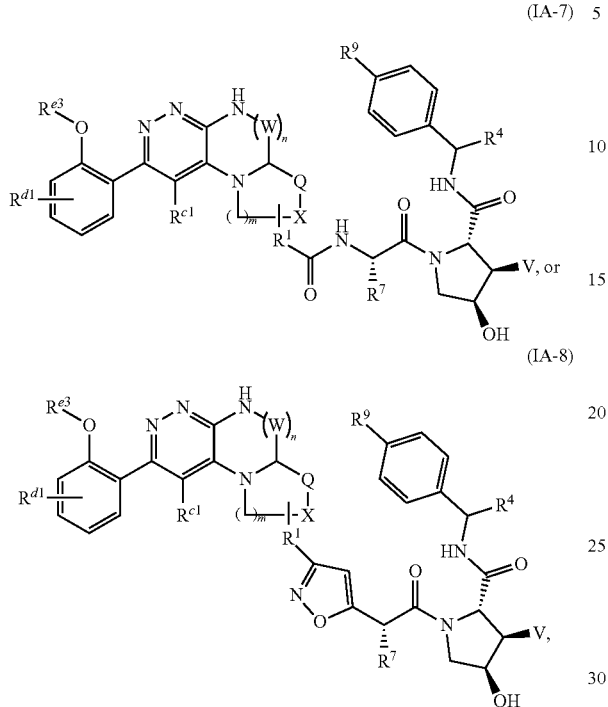

or a pharmaceutically acceptable salt thereof,
wherein:
$R^1$ is a chemical moiety represented by the formula:

-(A)$_q$-, wherein:
q is an integer from 1 to 14;
each A is independently selected from the group consisting of $CR^{1a}R^{1b}$, O, S, SO, $SO_2$, $NR^{1c}$, $SO_2NR^{1c}$, $SONR^{1c}$, $SO(=NR^{1c})$, $SO(=NR^{1c})NR^{1d}$, $CONR^{1c}$, $NR^{1c}CONR^{1d}$, $NR^{1c}C(O)O$, $NR^{1c}SO_2NR^{1d}$, CO, $CR^{1a}=CR^{1b}$, C≡C, $SiR^{1a}R^{1b}$, $P(O)R^{1a}$, $P(O)OR^{1a}$, $(CR^{1a}R^{1b})_{1-4}$, $(CR^{1a}R^{1b})_{1-4}O(CR^{1a}R^{1b})_{1-4}$, $(CR^{1a}R^{1b})_{1-4}S(CR^{1a}R^{1b})_{1-4}$, $(CR^{1a}R^{1b})_{1-4}NR(CR^{1a}R^{1b})_{1-4}$, $NR^{1c}C(=NCN)NR^{1d}NR^{1c}C(=NCN)$, $NR^{1c}C(=NCO_2)NR^{1d}$, 3-11 membered cycloalkyl, optionally substituted with 0-6 $R^{1a}$ and/or $R^{1b}$ groups, 3-11 membered heterocyclyl optionally substituted with 0-6 $R^{1a}$ and/or $R^{1b}$ groups, aryl optionally substituted with 0-6 $R^{1a}$ and/or $R^{1b}$ groups, or heteroaryl optionally substituted with 0-6 $R^{1a}$ and/or $R^{1b}$ groups, wherein $R^{1a}$, $R^{1b}$, $R^{1c}$, $R^{1d}$ and $R^{1e}$ are each independently, —H, D, -halo, —$C_1$-$C_8$alkyl, —O—$C_1$-$C_8$alkyl, —$C_1$-$C_6$haloalkyl, —S—$C_1$-$C_8$alkyl, —NH$C_1$-$C_8$alkyl, —N($C_1$-$C_8$alkyl)2, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)($C_1$-$C_8$alkyl), —OH, —NH$_2$, —SH, —SO$_2C_1$-$C_8$alkyl, SO(NH)$C_1$-$C_8$alkyl, P(O)(O$C_1$-$C_8$alkyl)($C_1$-$C_8$alkyl), —P(O)(O$C_1$-$C_8$alkyl)$_2$, —C≡C—$C_1$-$C_8$alkyl, —C≡CH, —CH=CH($C_1$-$C_8$alkyl), —C($C_1$-$C_8$alkyl)=CH($C_1$-$C_8$alkyl), —C($C_1$-$C_8$alkyl)=C($C_1$-$C_8$alkyl)$_2$, —Si(OH)$_3$, —Si($C_1$-$C_8$alkyl)$_3$, —Si(OH)($C_1$-$C_8$alkyl)$_2$, —C(O)$C_1$-$C_8$alkyl, —CO$_2$H, —CN, —CF$_3$, —CHF$_2$, —CH$_2$F, —NO$_2$, —SF$_5$, —SO$_2$NH$C_1$-$C_8$alkyl, —SO$_2$N($C_1$-$C_8$alkyl)$_2$, —SO(NH)NH$C_1$-$C_8$alkyl, —SO(NH)N($C_1$-$C_8$alkyl)$_2$, —SONH$C_1$-$C_8$alkyl, —SON($C_1$-$C_8$alkyl)$_2$, —CONH$C_1$-$C_8$alkyl, —CON($C_1$-$C_8$alkyl)$_2$, —N($C_1$-$C_8$alkyl)CONH($C_1$-$C_8$alkyl), —N($C_1$-$C_8$alkyl)CON($C_1$-$C_8$alkyl)$_2$, —NHCONH($C_1$-$C_8$alkyl), —NHCON($C_1$-$C_8$alkyl)$_2$, —NHCONH$_2$, —N($C_1$-$C_8$alkyl)SO$_2$NH($C_1$-$C_8$alkyl), —N($C_1$-$C_8$alkyl)SO$_2$N($C_1$-$C_8$alkyl)$_2$, —NHSO$_2$NH($C_1$-$C_8$alkyl), —NHSO$_2$N($C_1$-$C_8$alkyl)$_2$, or —NHSO$_2$NH$_2$; and where $R^{1a}$ or $R^{1b}$, each independently may be optionally linked to other groups to form cycloalkyl and/or heterocyclyl moiety, optionally substituted with 0-4 $R^{1e}$ groups;

m=1 to 3;

n=0 to 3;

W is —CH$_2$—, —C(O)—, —S(O)—, or —S(O)$_2$—; wherein when n=2 or 3, only one W may be —C(O)—, —S(O)—, or —S(O)$_2$—;

$R^{c1}$ and $R^{d1}$ are independently H, D, Halo, $C_{1-3}$ alkyl, $C_{1-3}$ haloalkyl, or $C_{1-4}$ alkoxyl;

$R^{e3}$ is H, —C(O)$R^f$, or —P(O)(OR$^g$)$_2$; wherein $R^f$ and $R^g$ are independently H, $C_{1-4}$ alkyl, $C_{3-8}$ cyclcoalkyl, or $C_{3-8}$ heterocyclcoalkyl;

X is —CH$_2$—, or NH; or, if $R^1$ is attached to X, then X is —CH— or N; and Q is —CH$_2$—, —(CH$_2$)$_2$—, —C(O)—, —CH$_2$C(O)—, —S(O)—, —S(O)$_2$—, —CH$_2$S(O)$_2$—, or —CH$_2$S(O)—;

$R^9$ is —CN or

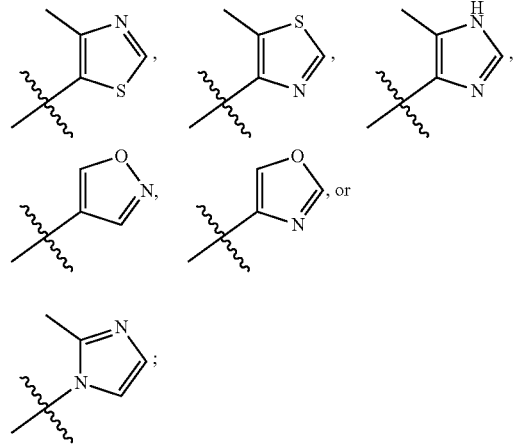

V is H or F;

$R^4$ is H, D, haloalkyl, alkyl, cycloalkyl, heterocycloalkyl, —COR$^d$, or —CONR$^{e1}$R$^{e2}$;

$R^7$ is H, D, alkyl, cycloalkyl, or haloalkyl, $R^d$ is H, or alkyl;

each $R^{e1}$ and $R^{e2}$ is independently H, D, alkyl,
or $R^{e1}$ and $R^{e2}$ together with the nitrogen atom to which they are attached form a 4-7 membered heterocyclyl.

2. A compound, where said compound is a compound of Formula IA-9a or IA-10a:

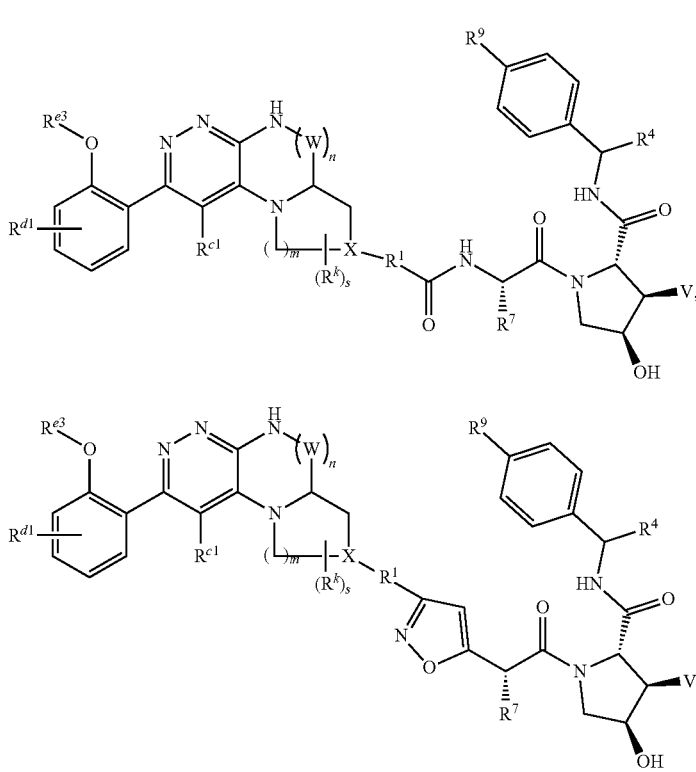

(IA-9a)

(IA-10a)

or a pharmaceutically acceptable salt thereof,
wherein X is N or CH;
$R^1$ is a chemical moiety represented by the formula:

$-(A)_q-$, wherein:
q is an integer from 1 to 14;
each A is independently selected from the group consisting of $CR^{1a}R^{1b}$, O, S, SO, $SO_2$, $NR^{1c}$, $SO_2NR^{1c}$, $SONR^{1c}$, $SO(=NR^{1c})$, $SO(=NR^{1c})NR^{1d}$, $CONR^{1c}$, $NR^{1c}CONR^{1d}$, $NR^{1c}C(O)O$, $NR^{1c}SO_2NR^{1d}$, CO, $CR^{1a}=CR^{1b}$, C≡C, $SiR^{1a}R^{1b}$, $P(O)R^{1a}$, $P(O)OR^{1a}$, $(CR^{1a}R^{1b})_{1-4}$, $(CR^{1a}R^{1b})_{1-4}O(CR^{1a}R^{1b})_{1-4}$, $(CR^{1a}R^{1b})_{1-4}S(CR^{1a}R^{1b})_{1-4}$, $(CR^{1a}R^{1b})_{1-4}NR(CR^{1a}R^{1b})_{1-4}$, $NR^{1c}C(=NCN)NR^{1d}NR^{1c}C(=NCN)$, $NR^{1c}C(=NCO_2)NR^{1d}$, 3-11 membered cycloalkyl, optionally substituted with 0-6 $R^{1a}$ and/or $R^{1b}$ groups, 3-11 membered heterocyclyl optionally substituted with 0-6 $R^{1a}$ and/or $R^{1b}$ groups, aryl optionally substituted with 0-6 $R^{1a}$ and/or $R^{1b}$ groups, or heteroaryl optionally substituted with 0-6 $R^{1a}$ and/or $R^{1b}$ groups,
wherein $R^{1a}$, $R^{1b}$, $R^{1c}$, $R^{1d}$ and $R^{1e}$ are each independently, —H, D, -halo, —$C_1$-$C_8$alkyl, —N($C_1$-$C_8$alkyl)2, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)₂, N-(3-11 membered cycloalkyl)($C_1$-$C_8$alkyl), —OH, —$NH_2$, —SH, —$SO_2C_1$-$C_8$alkyl, $SO(NH)C_1$-$C_8$alkyl, $P(O)(OC_1$-$C_8$alkyl)($C_1$-$C_8$alkyl), —$P(O)(OC_1$-$C_8$alkyl)₂, —C≡C—$C_1$-$C_8$alkyl, —C≡CH, —CH=CH($C_1$-$C_8$alkyl), —C($C_1$-$C_8$alkyl)=CH ($C_1$-$C_8$alkyl), —C($C_1$-$C_8$alkyl)=C($C_1$-$C_8$alkyl)₂, —Si(OH)₃, —Si($C_1$-$C_8$alkyl)₃, —Si(OH)($C_1$-$C_8$alkyl)₂, —C(O)$C_1$-$C_8$alkyl, —$CO_2$H, —CN, —$CF_3$, —$CHF_2$, —$NO_2$, —$SF_5$, —$SO_2NHC_1$-$C_8$alkyl, —$SO_2N(C_1$-$C_8$alkyl)₂, —SO(NH)NHC_1$-$C_8$alkyl, —SO(NH)N($C_1$-$C_8$alkyl)₂, —SONHC_1$-$C_8$alkyl, —SON($C_1$-$C_8$alkyl)₂, —CONHC_1$-$C_8$alkyl, —CON($C_1$-$C_8$alkyl)₂, —N($C_1$-$C_8$alkyl)CONH($C_1$-$C_8$alkyl), —N($C_1$-$C_8$alkyl)CON($C_1$-$C_8$alkyl)₂, —NHCONH($C_1$-$C_8$ alkyl), —NHCON($C_1$-$C_8$ alkyl)₂, —$NHCONH_2$, —N($C_1$-$C_8$alkyl)$SO_2$NH($C_1$-$C_8$alkyl), —N($C_1$-$C_8$alkyl)$SO_2$N($C_1$-$C_8$alkyl)₂, —$NHSO_2$NH($C_1$-$C_8$alkyl), —$NHSO_2$N($C_1$-$C_8$alkyl)₂, or —$NHSO_2NH_2$; and where $R^{1a}$ or $R^{1b}$, each independently may be optionally linked to other groups to form cycloalkyl and/or heterocyclyl moiety, optionally substituted with 0-4 $R^{1e}$ groups;

n=0-3;

m=1 to 3;

$R^k$ is $C_{1-3}$ alkyl, and s=0 or 1;

W is —$CH_2$—, —C(O)—, —S(O)—, or —$S(O)_2$—; wherein when n=2 or 3, only one W may be —C(O)—, —S(O)—, or —$S(O)_2$—;

$R^{c1}$ and $R^{d1}$ are independently H, D, Halo, $C_{1-3}$ alkyl, $C_{1-3}$ haloalkyl, or $C_{1-4}$ alkoxyl;

$R^{e3}$ is H, —C(O)$R^f$, or —$P(O)(OR^g)_2$; wherein $R^f$ and $R^g$ are independently H, $C_{1-4}$ alkyl, $C_{3-8}$ cyclcoalkyl, or $C_{3-8}$ heterocyclcoalkyl;

$R^9$ is —CN or

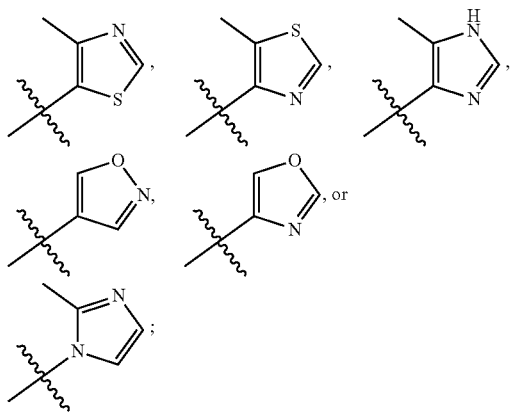

V is H or F;
$R^4$ is H, D, haloalkyl, alkyl, cycloalkyl, heterocycloalkyl, —$COR^d$, or —$CONR^{e1}R^{e2}$;
$R^7$ is H, D, alkyl, cycloalkyl, or haloalkyl,
$R^d$ is H, or alkyl;
each $R^{e1}$ and $R^{e2}$ is independently H, D, alkyl,
or $R^{e1}$ and $R^{e2}$ together with the nitrogen atom to which they are attached form a 4-7 membered heterocycyl.

3. The compound according to claim 2, wherein the compound is a compound of formula IA-11 or IA-12:

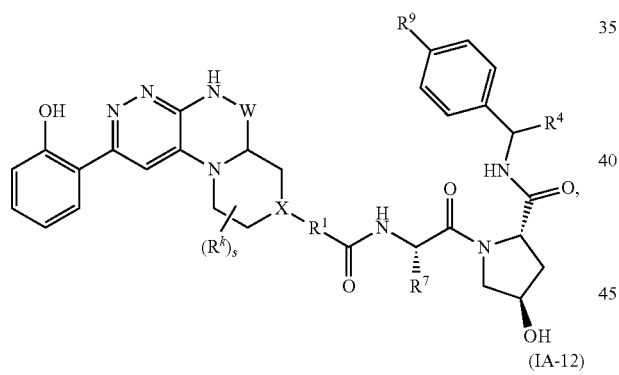

wherein W is —$CH_2$— or —$CH(CH_3)$—;
X is N or CH;
each $R^k$ is independently $C_{1-3}$ alkyl, and s=0 or 1;
$R^1$ is:
  a covalent bond;
  3-11 membered cycloalkyl optionally substituted with 0-6 $R^{1a}$ and/or $R^{1b}$ groups;
  3-11 membered heterocyclyl optionally substituted with 0-6 $R^{1a}$ and/or $R^{1b}$ groups;
  —$(CR^{1a}R^{1b})_{1-5}$;
  —$(CR^{1a}=CR^{1b})$—;
  —$(CR^{1a}R^{1b})_{1-5}$-A- wherein A is O, S, or $NR^{1c}$;
  —$(CR^{1a}R^{1b})_{1-5}$-A-$(CR^{1a}R^{1b})_{1-5}$— wherein A is O, S, or $NR^{1c}$;
  —$(CR^{1a}R^{1b})_{1-5}$-A-$(CR^{1a}R^{1b})_{1-5}$-A- wherein A is O, S, or $NR^{1c}$;
  —$(CR^{1a}R^{1b})_{1-5}$—$(CR^{1a}=CR^{1b})$—$(CR^{1a}R^{1b})_{1-5}$—;
  —$(CR^{1a}R^{1b})_{1-5}$—$(CR^{1a}=CR^{1b})$—$(CR^{1a}R^{1b})_{1-5}$-A- wherein A is O, S, or $NR^{1c}$;
  —$(CR^{1a}R^{1b})_{1-5}$—(C≡C)—$(CR^{1a}R^{1b})_{1-5}$—;
  —$(CR^{1a}R^{1b})_{1-5}$—(C≡C)—$(CR^{1a}R^{1b})_{1-5}$-A- wherein A is O, S, or $NR^{1c}$;
  —(C≡C)—$(CR^{1a}R^{1b})_{1-5}$-A-$(CR^{1a}R^{1b})_{1-5}$— wherein A is O, S, or $NR^{1c}$;
  —(C≡C)—$(CR^{1a}R^{1b})_{1-5}$;
  —$(CR^{1a}R^{1b})_{1-5}$-(3-11 membered cycloalkyl optionally substituted with 0-6 $R^{1a}$ and/or $R^{1b}$ groups)-;
  —$(CR^{1a}R^{1b})_{1-5}$-(3-11 membered heterocyclyl optionally substituted with 0-6 $R^{1a}$ and/or $R^{1b}$ groups)-;
  -(3-11 membered cycloalkyl optionally substituted with 0-6 $R^{1a}$ and/or $R^{1b}$ groups)-$(CR^{1a}R^{1b})_{1-5}$;
  -(3-11 membered cycloalkyl optionally substituted with 0-6 $R^{1a}$ and/or $R^{1b}$ groups)-$(CR^{1a}R^{1b})_{1-5}$-A- wherein A is O, S, or $NR^{1c}$;
  -(3-11 membered heterocyclyl optionally substituted with 0-6 $R^{1a}$ and/or $R^{1b}$ groups)-$(CR^{1a}R^{1b})_{1-5}$-A- wherein A is O, S, or $NR^{1c}$;
  -(3-11 membered heterocyclyl optionally substituted with 0-6 $R^{1a}$ and/or $R^{1b}$ groups)-$(CR^{1a}R^{1b})_{1-5}$—;
  —$(CR^{1a}R^{1b})_{1-5}$ (3-11 membered cycloalkyl optionally substituted with 0-6 $R^{1a}$ and/or $R^{1b}$ groups)-A- wherein A is O, S, or $NR^{1c}$;
  —$(CR^{1a}R^{1b})_{1-5}$ (3-11 membered heterocyclyl optionally substituted with 0-6 $R^{1a}$ and/or $R^{1b}$ groups)-A- wherein A is O, S, or $NR^{1c}$;
  —$(CR^{1a}R^{1b})_{1-5}$ (3-11 membered cycloalkyl optionally substituted with 0-6 $R^{1a}$ and/or $R^{1b}$ groups)-$(CR^{1a}R^{1b})_{1-5}$;
  —$(CR^{1a}R^{1b})_{1-5}$-(3-11 membered cycloalkyl optionally substituted with 0-6 $R^{1a}$ and/or $R^{1b}$ groups)-A- wherein A is O, S, or $NR^{1c}$;
  —$(CR^{1a}R^{1b})_{1-5}$-A-(3-11 membered cycloalkyl optionally substituted with 0-6 $R^{1a}$ and/or $R^{1b}$ groups)- wherein A is O, S, or $NR^{1c}$;
  —$(CR^{1a}R^{1b})_{1-5}$ (3-11 membered heterocyclyl optionally substituted with 0-6 $R^{1a}$ and/or $R^{1b}$ groups)-$(CR^{1a}R^{1b})_{1-5}$;
  —$(CR^{1a}R^{1b})_{1-5}$ (3-11 membered heterocyclyl optionally substituted with 0-6 $R^{1a}$ and/or $R^{1b}$ groups)-$(CR^{1a}R^{1b})_{1-5}$-A- wherein A is O, S, or $NR^{1c}$;
  —$(CR^{1a}R^{1b})_{1-5}$ (3-11 membered heterocyclyl optionally substituted with 0-6 $R^{1a}$ and/or $R^{1b}$ groups)-A- wherein A is O, S, or $NR^{1c}$;
  —$(CR^{1a}R^{1b})_{1-5}$-A-(3-11 membered heterocyclyl optionally substituted with 0-6 $R^{1a}$ and/or $R^{1b}$ groups)- wherein A is O, S, or $NR^{1c}$;

—(CR$^{1a}$R$^{1b}$)$_{1-5}$ (3-11 membered cycloalkyl optionally substituted with 0-6 R$^{1a}$ and/or R$^{1b}$ groups)-(CR$^{1a}$R$^{1b}$)$_{1-5}$-A- wherein A is O, S, or NR$^{1c}$;

—(CR$^{1a}$R$^{1b}$)$_{1-5}$-A-(3-11 membered cycloalkyl optionally substituted with 0-6 R$^{1a}$ and/or R$^{1b}$ groups)- wherein A is O, S, or NR$^{1c}$;

—(CR$^{1a}$R$^{1b}$)$_{1-5}$-A-(3-11 membered cycloalkyl optionally substituted with 0-6 R$^{1a}$ and/or R$^{1b}$ groups)-(CR$^{1a}$R$^{1b}$)$_{1-5}$-A- wherein each A is independently O, S, or NR$^{1c}$;

—(CR$^{1a}$R$^{1b}$)$_{1-5}$-A-(3-11 membered heterocyclyl optionally substituted with 0-6 R$^{1a}$ and/or R$^{1b}$ groups)-(CR$^{1a}$R$^{1b}$)$_{1-5}$-A- wherein each A is independently O, S, or NR$^{1c}$;

—(CR$^{1a}$R$^{1b}$)$_{1-5}$-A-(CR$^{1a}$R$^{1b}$)$_{1-5}$-A- wherein A is O, S, or NR$^{1c}$;

—(CR$^{1a}$R$^{1b}$)$_{1-5}$-A-(CR$^{1a}$R$^{1b}$)$_{1-5}$-A-(CR$^{1a}$R$^{1b}$)$_{1-5}$-A-(CR$^{1a}$R$^{1b}$)$_{1-5}$-A- wherein each A is independently O, S, or NR$^{1c}$;

—(CR$^{1a}$R$^{1b}$)$_{1-5}$-A-(CO) wherein A is O, S, or NR$^{1c}$;

—(CR$^{1a}$R$^{1b}$)$_{1-5}$—(CR$^{1a}$=CR$^{1b}$)—(CR$^{1a}$R$^{1b}$)$_{1-5}$-A-(CO)— wherein A is O, S, or NR$^{1c}$;

—(CR$^{1a}$R$^{1b}$)$_{1-5}$—(C≡C)—(CR$^{1a}$R$^{1b}$)$_{1-5}$-A-(CO)— wherein A is O, S, or NR$^{1c}$;

—(CR$^{1a}$R$^{1b}$)$_{1-5}$-(3-11 membered cycloalkyl optionally substituted with 0-6 R$^{1a}$ and/or R$^{1b}$ groups)-(CR$^{1a}$R$^{1b}$)$_{1-5}$-A-(CO)— wherein A is O, S, or NR$^{1c}$;

—(CR$^{1a}$R$^{1b}$)$_{1-5}$-A-(CO)-(3-11 membered cycloalkyl optionally substituted with 0-6 R$^{1a}$ and/or R$^{1b}$ groups)- wherein A is O, S, or NR$^{1c}$;

—(CR$^{1a}$R$^{1b}$)$_{1-5}$-(3-11 membered heterocyclyl optionally substituted with 0-6 R$^{1a}$ and/or R$^{1b}$ groups)-(CR$^{1a}$R$^{1b}$)$_{1-5}$-A-(CO)— wherein A is O, S, or NR$^{1c}$;

—(CR$^{1a}$R$^{1b}$)$_{1-5}$-A-(CO)-(3-11 membered heterocyclyl optionally substituted with 0-6 R$^{1a}$ and/or R$^{1b}$ groups)- wherein A is O, S, or NR$^{1c}$;

—(CR$^{1a}$R$^{1b}$)$_{1-5}$-A-(3-11 membered cycloalkyl optionally substituted with 0-6 R$^{1a}$ and/or R$^{1b}$ groups)-A-(CO)— wherein each A is independently O, S, or NR$^{1c}$;

-(3-11 membered cycloalkyl optionally substituted with 0-6 R$^{1a}$ and/or R$^{1b}$ groups)-CO—(CR$^{1a}$R$^{1b}$)$_{1-5}$-A- wherein A is O, S, or NR$^{1c}$;

—(CR$^{1a}$R$^{1b}$)$_{1-5}$-(3-11 membered cycloalkyl optionally substituted with 0-6 R$^{1a}$ and/or R$^{1b}$ groups)-(CR$^{1a}$R$^{1b}$)$_{1-5}$-A-(CO)— wherein A is O, S, or NR$^{1c}$;

—(CR$^{1a}$R$^{1b}$)$_{1-5}$-(3-11 membered heterocyclyl optionally substituted with 0-6 R$^{1a}$ and/or R$^{1b}$ groups)-(CR$^{1a}$R$^{1b}$)$_{1-5}$-A-(CO)— wherein A is O, S, or NR$^{1c}$;

-(3-11 membered cycloalkyl optionally substituted with 0-6 R$^{1a}$ and/or R$^{1b}$ groups)-(CR$^{1a}$R$^{1b}$)$_{1-5}$—;

-(3-11 membered heterocyclyl optionally substituted with 0-6 R$^{1a}$ and/or R$^{1b}$ groups)-(CR$^{1a}$R$^{1b}$)$_{1-5}$—;

-A-(3-11 membered heterocyclyl optionally substituted with 0-6 R$^{1a}$ and/or R$^{1b}$ groups)-(CR$^{1a}$R$^{1b}$)$_{1-5}$-A- wherein each A is independently O, S, or NR$^{1c}$;

-(3-11 membered heterocyclyl optionally substituted with 0-6 R$^{1a}$ and/or R$^{1b}$ groups)-(CR$^{1a}$R$^{1b}$)$_{1-5}$-(3-11 membered heterocyclyl optionally substituted with 0-6 R$^{1a}$ and/or R$^{1b}$ groups)-(CR$^{1a}$R$^{1b}$)$_{1-5}$-A- wherein A is O, S, or NR$^{1c}$;

-(3-11 membered heterocyclyl optionally substituted with 0-6 R$^{1a}$ and/or R$^{1b}$ groups)-(3-11 membered heterocyclyl optionally substituted with 0-6 R$^{1a}$ and/or R$^{1b}$ groups)-(CR$^{1a}$R$^{1b}$)$_{1-5}$-A- wherein A is O, S, or NR$^{1c}$;

-(3-11 membered heterocyclyl optionally substituted with 0-6 R$^{1a}$ and/or R$^{1b}$ groups)-A-(CR$^{1a}$R$^{1b}$)$_{1-5}$-A- wherein each A is independently O, S, or NR$^{1c}$;

-(3-11 membered heterocyclyl optionally substituted with 0-6 R$^{1a}$ and/or R$^{1b}$ groups)-(CO)-A-(CR$^{1a}$R$^{1b}$)$_{1-5}$— wherein A is O, S, or NR$^{1c}$;

-(heteroaryl optionally substituted with 0-4 R$^{1a}$ and/or R$^{1b}$ groups)-A-(CR$^{1a}$R$^{1b}$)$_{1-5}$— wherein A is O, S, or NR$^{1c}$;

-(3-11 membered cycloalkyl optionally substituted with 0-6 R$^{1a}$ and/or R$^{1b}$ groups)-(CO)—(CR$^{1a}$R$^{1b}$)$_{1-5}$-A- wherein A is O, S, or NR$^{1c}$;

-(3-11 membered cycloalkyl optionally substituted with 0-6 R$^{1a}$ and/or R$^{1b}$ groups)-(CO)-A-(CR$^{1a}$R$^{1b}$)$_{1-5}$— wherein A is O, S, or NR$^{1c}$; or —(CO)-(3-11 membered cycloalkyl optionally substituted with 0-6 R$^{1a}$ and/or R$^{1b}$ groups)-(CR$^{1a}$R$^{1b}$)$_{1-5}$-A- wherein A is O, S, or NR$^{1c}$;

R$^4$ is H, —CH$_3$, or —CH$_2$OH;

R$^7$ is —C(CH$_3$)$_3$ or —CH(CH$_3$)$_2$; and

R$^9$ is —CN,

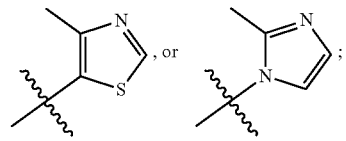

R$^{1a}$, R$^{1b}$, R$^{1c}$, and R$^{1e}$ are each independently, —H, D, -halo, —C$_1$-C$_8$alkyl, —C$_1$-C$_6$haloalkyl, —O—C$_1$-C$_8$alkyl, —S—C$_1$-C$_8$alkyl, —NHC$_1$-C$_8$alkyl, —N(C$_1$-C$_8$alkyl)2, 3-11 membered cycloalkyl, aryl, heteroaryl, 3-11 membered heterocyclyl, —O-(3-11 membered cycloalkyl), —S-(3-11 membered cycloalkyl), NH-(3-11 membered cycloalkyl), N(3-11 membered cycloalkyl)$_2$, N-(3-11 membered cycloalkyl)(C$_1$-C$_8$alkyl), —OH, —NH$_2$, —SH, —SO$_2$C$_1$-C$_8$alkyl, SO(NH)C$_1$-C$_8$alkyl, P(O)(OC$_1$-C$_8$alkyl)(C$_1$-C$_8$alkyl), —P(O)(OC$_1$-C$_8$alkyl)$_2$, —C≡C—C$_1$-C$_8$alkyl, —C≡CH, —CH=CH(C$_1$-C$_8$alkyl), —C(C$_1$-C$_8$alkyl)=CH(C$_1$-C$_8$alkyl), —C(C$_1$-C$_8$alkyl)=C(C$_1$-C$_8$alkyl)$_2$, —Si(OH)$_3$, —Si(C$_1$-C$_8$alkyl)$_3$, —Si(OH)(C$_1$-C$_8$alkyl)$_2$, —C(O)C$_1$-C$_8$alkyl, —CO$_2$H, —CN, —CF$_3$, —CHF$_2$, —CH$_2$F, —NO$_2$, —SF$_5$, —SO$_2$NHC$_1$-C$_8$alkyl, —SO$_2$N(C$_1$-C$_8$alkyl)$_2$, —SO(NH)NHC$_1$-C$_8$alkyl, —SO(NH)N(C$_1$-C$_8$alkyl)$_2$, —SONHC$_1$-C$_8$alkyl, —SON(C$_1$-C$_8$alkyl)$_2$, —CONHC$_1$-C$_8$alkyl, —CON(C$_1$-C$_8$alkyl)$_2$, —N(C$_1$-C$_8$alkyl)CONH(C$_1$-C$_8$alkyl), —N(C$_1$-C$_8$alkyl)CON(C$_1$-C$_8$alkyl)$_2$, —NHCONH(C$_1$-C$_8$alkyl), —NHCON(C$_1$-C$_8$alkyl)$_2$, —NHCONH$_2$, —N(C$_1$-C$_8$alkyl)SO$_2$NH(C$_1$-C$_8$alkyl), —N(C$_1$-C$_8$alkyl)SO$_2$N(C$_1$-C$_8$alkyl)$_2$, —NHSO$_2$NH(C$_1$-C$_8$alkyl), —NHSO$_2$N(C$_1$-C$_8$alkyl)$_2$, or —NHSO$_2$NH$_2$; or where R$^{1a}$ or R$^{1b}$, each independently may be optionally linked to other groups to form cycloalkyl and/or a heterocyclyl moiety, optionally substituted with 0-4 R$^{1e}$ groups.

4. The compound according to claim 3, wherein W is —CH$_2$—.

5. The compound according to claim 3, wherein R$^4$ is —CH$_3$.

6. The compound according to claim 3, wherein R⁹ is

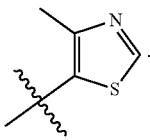 [SMILES: *c1scnc1C]

7. The compound according to claim 3, wherein R¹ is:
—(CR$^{1a}$R$^{1b}$)$_{1-5}$;
—(CR$^{1a}$R$^{1b}$)$_{1-5}$-A- wherein A is O, S, or NR$^{1c}$;
—(CR$^{1a}$R$^{1b}$)$_{1-5}$-A-(CR$^{1a}$R$^{1b}$)$_{1-5}$ wherein A is O, S, or NR$^{1c}$;
-(3-11 membered heterocyclyl optionally substituted with 0-6 R$^{1a}$ and/or R$^{1b}$ groups)-(CO)—(CR$^{1a}$R$^{1b}$)$_{1-5}$-A- wherein A is O, S, or NR$^{1c}$;
-(3-11 membered heterocyclyl optionally substituted with 0-6 R$^{1a}$ and/or R$^{1b}$ groups)-(CO)-A-(CR$^{1a}$R$^{1b}$)$_{1-5}$— wherein A is O, S, or NR$^{1c}$;
—(CR$^{1a}$R$^{1b}$)$_{1-5}$-(3-11 membered cycloalkyl optionally substituted with 0-6 R$^{1a}$ and/or R$^{1b}$ groups)-A- wherein A is O, S, or NR$^{1c}$;
—(CR$^{1a}$R$^{1b}$)$_{1-5}$-(3-11 membered heterocyclyl optionally substituted with 0-6 R$^{1a}$ and/or R$^{1b}$ groups)-(CR$^{1a}$R$^{1b}$)$_{1-5}$;
—(CR$^{1a}$R$^{1b}$)$_{1-5}$-(3-11 membered heterocyclyl optionally substituted with 0-6 R$^{1a}$ and/or R$^{1b}$ groups)-(CR$^{1a}$R$^{1b}$)$_{1-5}$-A- wherein A is O, S, or NR$^{1c}$;
-A-(3-11 membered heterocyclyl optionally substituted with 0-6 R$^{1a}$ and/or R$^{1b}$ groups)-(CR$^{1a}$R$^{1b}$)$_{1-5}$-A- wherein each A is independently O, S, or NR$^{1c}$;
-(3-11 membered heterocyclyl optionally substituted with 0-6 R$^{1a}$ and/or R$^{1b}$ groups)-(CR$^{1a}$R$^{1b}$)$_{1-5}$-(3-11 membered heterocyclyl optionally substituted with 0-6 R$^{1a}$ and/or R$^{1b}$ groups)-(CR$^{1a}$R$^{1b}$)$_{1-5}$-A- wherein A is O, S, or NR$^{1c}$;
-(3-11 membered heterocyclyl optionally substituted with 0-6 R$^{1a}$ and/or R$^{1b}$ groups)-(3-11 membered heterocyclyl optionally substituted with 0-6 R$^{1a}$ and/or R$^{1b}$ groups)-(CR$^{1a}$R$^{1b}$)$_{1-5}$-A- wherein A is O, S, or NR$^{1c}$;
-(3-11 membered heterocyclyl optionally substituted with 0-6 R$^{1a}$ and/or R$^{1b}$ groups)-A-(CR$^{1a}$R$^{1b}$)$_{1-5}$-A- wherein each A is independently O, S, or NR$^{1c}$;
-(3-11 membered heterocyclyl optionally substituted with 0-6 R$^{1a}$ and/or R$^{1b}$ groups)-(CR$^{1a}$R$^{1b}$)$_{1-5}$-A- wherein A is O, S, or NR$^{1c}$;
-(3-11 membered heterocyclyl optionally substituted with 0-6 R$^{1a}$ and/or R$^{1b}$ groups)-A-(CR$^{1a}$R$^{1b}$)$_{1-5}$-A- wherein each A is independently O, S, or NR$^{1c}$;
-(heterocyclyl optionally substituted with 0-4 R$^{1a}$ and/or R$^{1b}$ groups)-A-(CR$^{1a}$R$^{1b}$)$_{1-5}$— wherein A is O, S, or NR$^{1c}$;
-(3-11 membered cycloalkyl optionally substituted with 0-6 R$^{1a}$ and/or R$^{1b}$ groups)-(CO)—(CR$^{1a}$R$^{1b}$)$_{1-5}$-A- wherein A is O, S, or NR$^{1c}$;
-(3-11 membered cycloalkyl optionally substituted with 0-6 R$^{1a}$ and/or R$^{1b}$ groups)-(CO)-A-(CR$^{1a}$R$^{1b}$)$_{1-5}$— wherein A is O, S, or NR$^{1c}$; or
—(CO)-(3-11 membered cycloalkyl optionally substituted with 0-6 R$^{1a}$ and/or R$^{1b}$ groups)-(CR$^{1a}$R$^{1b}$)$_{1-5}$-A- wherein A is O, S, or NR$^{1c}$.

8. The compound according to claim 3, wherein each R$^{1a}$, each R$^{1b}$, and each R$^{1c}$ is independently H or C$_1$-C$_6$alkyl.

9. The compound according to claim 3, wherein the compound is a compound of formula IA-13a, IA-13b, IA-14a or IA-14b:

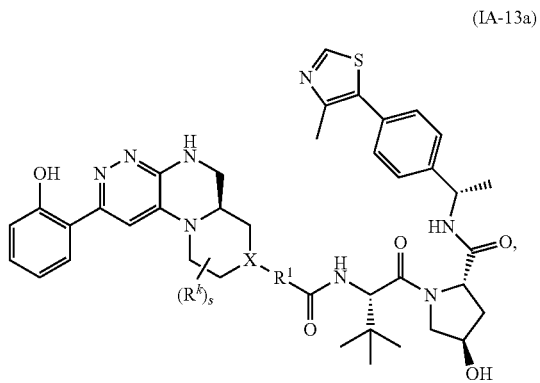

(IA-13a)

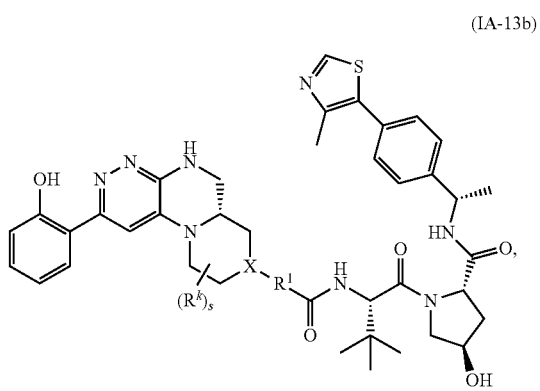

(IA-13b)

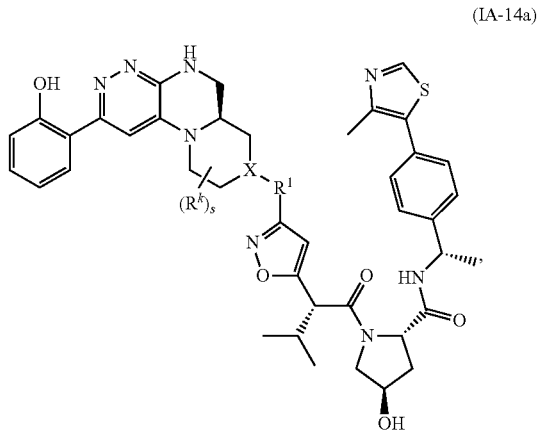

(IA-14a)

-continued (IA-14b)

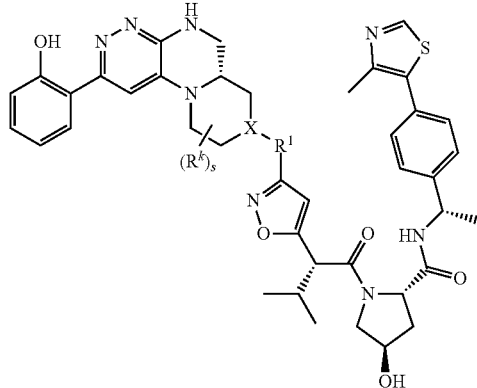

wherein X is N or CH.

10. The compound according to claim 9, wherein $R^1$ is -(3-11 membered heterocyclyl)-$(CR^{1a}R^{1b})_{1-3}$—O—, wherein each $R^{1a}$ is H and each $R^{1b}$ is independently H, or —$C_1$-$C_8$alkyl.

11. The compound according to claim 9, wherein $R^1$ is -(3-11 membered heterocyclyl)-(CO)—$(CR^{1a}R^{1b})_{1-3}$—O— wherein each $R^{1a}$ is H and each $R^{1b}$ is independently H, or —$C_1$-$C_8$alkyl.

12. The compound according to claim 9, wherein the compound is a compound of formula IA-15a, IA-15b, IA-16a, or IA-16b:

(IA-15a)

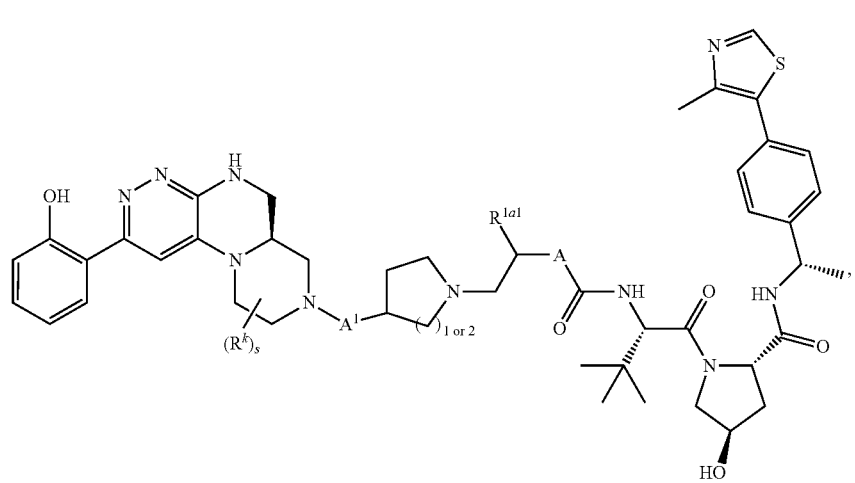

(IA-15b)

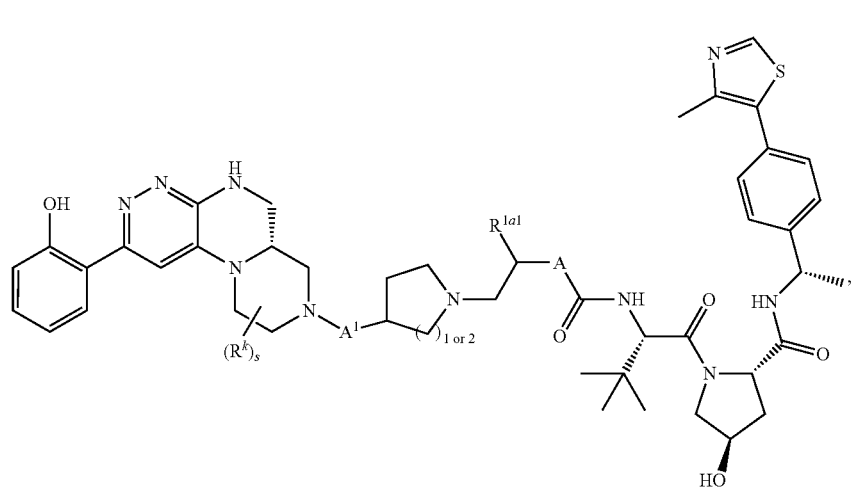

(IA-16a)

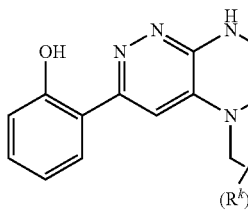 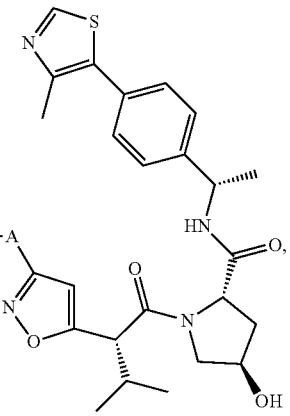

(IA-16b)

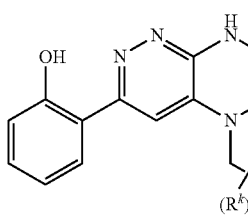 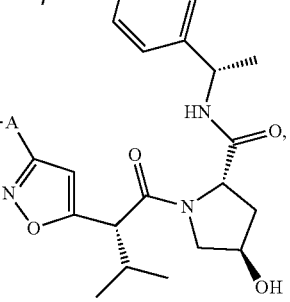

wherein A is O, S, or NR$^{1c}$,
R$^{1a1}$ is H or —C$_1$-C$_8$alkyl;
R$^{1c}$ is —H, or —C$_1$-C$_8$alkyl;
A$^1$ is a covalent bond or —(CR$^{1a}$R$^{1b}$)$_{1-3}$.

13. The compound according to claim 12, wherein A is O and R$^{1a1}$ is —C$_1$-C$_8$alkyl.

14. The compound according to claim 12, wherein A$^1$ is a covalent bond.

15. The compound according to claim 12, wherein A is O.

16. A pharmaceutical composition comprising a compound according to claim 2 and a pharmaceutically acceptable excipient.

17. A compound according to claim 1, or a pharmaceutically acceptable salt thereof, wherein the compound is:
(2S,4R)-4-hydroxy-1-((S)-2-(2-((R)-2-(2-hydroxyphenyl)-5,6,6a,7,9,10-hexahydro-8H-pyrazino[1',2':4,5]pyrazino[2,3-c]pyridazin-8-yl)acetamido)-3,3-dimethylbutanoyl)-N—((S)-1-(4-(4-methylthiazol-5-yl)phenyl)ethyl)pyrrolidine-2-carboxamide;
(2S,4R)-4-hydroxy-1-((S)-2-(2-((S)-2-(2-hydroxyphenyl)-5,6,6a,7,9,10-hexahydro-8H-pyrazino[1',2':4,5]pyrazino[2,3-c]pyridazin-8-yl)acetamido)-3,3-dimethylbutanoyl)-N—((S)-1-(4-(4-methylthiazol-5-yl)phenyl)ethyl)pyrrolidine-2-carboxamide;
(2S,4R)-4-hydroxy-1-((S)-2-(2-((S)-2-(2-hydroxyphenyl)-5,6,6a,7,9,10-hexahydro-8H-pyrazino[1',2':4,5]pyrazino[2,3-c]pyridazin-8-yl)acetamido)-3,3-dimethylbutanoyl)-N-(4-(5-methylthiazol-4-yl)benzyl)pyrrolidine-2-carboxamide;
(2S,4R)-4-hydroxy-1-((S)-2-(2-((R)-2-(2-hydroxyphenyl)-5,6,6a,7,9,10-hexahydro-8H-pyrazino[1',2':4,5]pyrazino[2,3-c]pyridazin-8-yl)acetamido)-3,3-dimethylbutanoyl)-N-(4-(5-methylthiazol-4-yl)benzyl)pyrrolidine-2-carboxamide;
(2S,4R)-4-hydroxy-1-((S)-2-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)-4-methylpiperidin-1-yl)acetamido)-3,3-dimethylbutanoyl)-N—((S)-1-(4-(4-methylthiazol-5-yl)phenyl)ethyl)pyrrolidine-2-carboxamide;
(2S,4R)-4-hydroxy-1-((S)-2-(2-(4-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)acetamido)-3,3-dimethylbutanoyl)-N—((S)-1-(4-(4-methylthiazol-5-yl)phenyl)ethyl)pyrrolidine-2-carboxamide;
(2S,4R)-4-hydroxy-1-((R)-2-(3-(2-((S)-2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-N—((S)-1-(4-(4-methylthiazol-5-yl)phenyl)ethyl)pyrrolidine-2-carboxamide;
(2S,4R)-4-hydroxy-1-((R)-2-(3-(2-((R)-2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-N—((S)-1-(4-(4-methylthiazol-5-yl)phenyl)ethyl)pyrrolidine-2-carboxamide;
(2S,4R)-4-hydroxy-1-((S)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((S)-2-(3-(2-(4-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((S)-2-(4-((R)-2-(2-hydroxyphenyl)-5,6,6a,7,9,10-hexahydro-8H-pyrazino[1',2':4,5]pyrazino[2,3-c]pyridazin-8-yl)butanamido)-3,3-dimethylbutanoyl)-N—((S)-1-(4-(4-methylthiazol-5-yl)phenyl)ethyl)pyrrolidine-2-carboxamide;

(2S,4R)-4-hydroxy-1-((S)-2-(4-((S)-2-(2-hydroxyphenyl)-5,6,6a,7,9,10-hexahydro-8H-pyrazino[1',2':4,5]pyrazino[2,3-c]pyridazin-8-yl)butanamido)-3,3-dimethylbutanoyl)-N—((S)-1-(4-(4-methylthiazol-5-yl)phenyl)ethyl)pyrrolidine-2-carboxamide;

2-((S)-2-(2-hydroxyphenyl)-5,6,6a,7,9,10-hexahydro-8H-pyrazino[1',2':4,5]pyrazino[2,3-c]pyridazin-8-yl)ethyl ((R)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamate;

2-((R)-2-(2-hydroxyphenyl)-5,6,6a,7,9,10-hexahydro-8H-pyrazino[1',2':4,5]pyrazino[2,3-c]pyridazin-8-yl)ethyl ((R)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamate;

(2S,4R)-4-hydroxy-1-((S)-2-(3-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propanamido)-3,3-dimethylbutanoyl)-N—((S)-1-(4-(4-methylthiazol-5-yl)phenyl)ethyl)pyrrolidine-2-carboxamide;

(2S,4R)-4-hydroxy-1-((S)-2-(3-(4-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propanamido)-3,3-dimethylbutanoyl)-N—((S)-1-(4-(4-methylthiazol-5-yl)phenyl)ethyl)pyrrolidine-2-carboxamide;

(3R,5S)-1-((R)-2-(3-(2-((S)-2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-5-(((S)-1-(4-(4-methylthiazol-5-yl)phenyl)ethyl)carbamoyl)pyrrolidin-3-yl acetate;

(3R,5S)-1-((R)-2-(3-(2-((R)-2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-5-(((S)-1-(4-(4-methylthiazol-5-yl)phenyl)ethyl)carbamoyl)pyrrolidin-3-yl acetate;

(3R,5S)-1-((R)-2-(3-(2-((S)-2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-5-(((S)-1-(4-(4-methylthiazol-5-yl)phenyl)ethyl)carbamoyl)pyrrolidin-3-yl isobutyrate;

(3R,5S)-1-((R)-2-(3-(2-((R)-2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-5-(((S)-1-(4-(4-methylthiazol-5-yl)phenyl)ethyl)carbamoyl)pyrrolidin-3-yl isobutyrate;

(2S,4R)-4-hydroxy-1-((S)-2-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)acetamido)-3,3-dimethylbutanoyl)-N—((S)-1-(4-(4-methylthiazol-5-yl)phenyl)ethyl)pyrrolidine-2-carboxamide;

(2S,4R)-4-hydroxy-1-((S)-2-(2-(4-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)acetamido)-3,3-dimethylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(6-((S)-2-(2-hydroxyphenyl)-5,6,6a,7,9,10-hexahydro-8H-pyrazino[1',2':4,5]pyrazino[2,3-c]pyridazin-8-yl)-3-azabicyclo[3.1.1]heptan-3-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(6-((R)-2-(2-hydroxyphenyl)-5,6,6a,7,9,10-hexahydro-8H-pyrazino[1',2':4,5]pyrazino[2,3-c]pyridazin-8-yl)-3-azabicyclo[3.1.1]heptan-3-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(6-((S)-2-(2-hydroxyphenyl)-5,6,6a,7,9,10-hexahydro-8H-pyrazino[1',2':4,5]pyrazino[2,3-c]pyridazin-8-yl)-2-azaspiro[3.3]heptan-2-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(6-((R)-2-(2-hydroxyphenyl)-5,6,6a,7,9,10-hexahydro-8H-pyrazino[1',2':4,5]pyrazino[2,3-c]pyridazin-8-yl)-2-azaspiro[3.3]heptan-2-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((R)-1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-(4-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((S)-3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((R)-3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((S)-3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1- yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((R)-3-((R)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-((S)-3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-((S)-3-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-((R)-3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-((R)-3-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((R)-1-((S)-3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((R)-1-((S)-3-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((R)-1-((R)-3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((R)-1-((R)-3-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((S)-3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((R)-3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((R)-3-(4-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((S)-3-(4-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((S)-3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((S)-3-(4-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((R)-3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((R)-3-(4-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3S,4R)-4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)-2-oxoethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3S,4S)-4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)-2-oxoethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3R,4R)-4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)-2-oxoethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3R,4S)-4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)-2-oxoethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((3S,4R)-4-((R)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)-2-oxoethoxy)isoxazol-5-yl)-3- methylbutanoyl)-N—((S)-1-(4-(4-methylthiazol-5-yl)
phenyl)ethyl)pyrrolidine-2-carboxamide;
(2S,4R)-4-hydroxy-1-((R)-2-(3-(2-((3R,4R)-4-((R)-2-(2-
hydroxyphenyl)-5,6,6a,7,9,10-hexahydro-8H-pyrazino
[1',2':4,5]pyrazino[2,3-c]pyridazin-8-yl)-3-methylpip-
eridin-1-yl)-2-oxoethoxy)isoxazol-5-yl)-3-
methylbutanoyl)-N—((S)-1-(4-(4-methylthiazol-5-yl)
phenyl)ethyl)pyrrolidine-2-carboxamide;
(2S,4R)-4-hydroxy-1-((R)-2-(3-(2-((3R,4S)-4-((R)-2-(2-
hydroxyphenyl)-5,6,6a,7,9,10-hexahydro-8H-pyrazino
[1',2':4,5]pyrazino[2,3-c]pyridazin-8-yl)-3-methylpip-
eridin-1-yl)-2-oxoethoxy)isoxazol-5-yl)-3-
methylbutanoyl)-N—((S)-1-(4-(4-methylthiazol-5-yl)
phenyl)ethyl)pyrrolidine-2-carboxamide;
(2S,4R)-4-hydroxy-1-((R)-2-(3-(2-((3 S,4S)-4-((R)-2-(2-
hydroxyphenyl)-5,6,6a,7,9,10-hexahydro-8H-pyrazino
[1',2':4,5]pyrazino[2,3-c]pyridazin-8-yl)-3-methylpip-
eridin-1-yl)-2-oxoethoxy)isoxazol-5-yl)-3-
methylbutanoyl)-N—((S)-1-(4-(4-methylthiazol-5-yl)
phenyl)ethyl)pyrrolidine-2-carboxamide;
(2S,4R)-4-hydroxy-1-((R)-2-(3-(2-((S)-3-((S)-2-(2-hy-
droxyphenyl)-5,6,6a,7,9,10-hexahydro-8H-pyrazino
[1',2':4,5]pyrazino[2,3-c]pyridazin-8-yl)piperidin-1-yl)
ethoxy)isoxazol-5-yl)-3-methylbutanoyl)-N—((S)-1-
(4-(4-methylthiazol-5-yl)phenyl)ethyl)pyrrolidine-2-
carboxamide;
(2S,4R)-4-hydroxy-1-((R)-2-(3-(2-((R)-3-((S)-2-(2-hy-
droxyphenyl)-5,6,6a,7,9,10-hexahydro-8H-pyrazino
[1',2':4,5]pyrazino[2,3-c]pyridazin-8-yl)piperidin-1-yl)
ethoxy)isoxazol-5-yl)-3-methylbutanoyl)-N—((S)-1-
(4-(4-methylthiazol-5-yl)phenyl)ethyl)pyrrolidine-2-
carboxamide;
(2S,4R)-4-hydroxy-1-((R)-2-(3-(2-((R)-3-((R)-2-(2-hy-
droxyphenyl)-5,6,6a,7,9,10-hexahydro-8H-pyrazino
[1',2':4,5]pyrazino[2,3-c]pyridazin-8-yl)piperidin-1-yl)
ethoxy)isoxazol-5-yl)-3-methylbutanoyl)-N—((S)-1-
(4-(4-methylthiazol-5-yl)phenyl)ethyl)pyrrolidine-2-
carboxamide;
(2S,4R)-4-hydroxy-1-((R)-2-(3-(2-((S)-3-((R)-2-(2-hy-
droxyphenyl)-5,6,6a,7,9,10-hexahydro-8H-pyrazino
[1',2':4,5]pyrazino[2,3-c]pyridazin-8-yl)piperidin-1-yl)
ethoxy)isoxazol-5-yl)-3-methylbutanoyl)-N—((S)-1-
(4-(4-methylthiazol-5-yl)phenyl)ethyl)pyrrolidine-2-
carboxamide;
(2S,4R)-4-hydroxy-1-((R)-2-(3-(((S)-1-((R)-3-((S)-2-(2-
hydroxyphenyl)-5,6,6a,7,9,10-hexahydro-8H-pyrazino
[1',2':4,5]pyrazino[2,3-c]pyridazin-8-yl)pyrrolidin-1-
yl)propan-2-yl)oxy)isoxazol-5-yl)-3-methylbutanoyl)-
N—((S)-1-(4-(4-methylthiazol-5-yl)phenyl)ethyl)
pyrrolidine-2-carboxamide;
(2S,4R)-4-hydroxy-1-((R)-2-(3-(((S)-1-((S)-3-((S)-2-(2-
hydroxyphenyl)-5,6,6a,7,9,10-hexahydro-8H-pyrazino
[1',2':4,5]pyrazino[2,3-c]pyridazin-8-yl)pyrrolidin-1-
yl)propan-2-yl)oxy)isoxazol-5-yl)-3-methylbutanoyl)-
N—((S)-1-(4-(4-methylthiazol-5-yl)phenyl)ethyl)
pyrrolidine-2-carboxamide;
(2S,4R)-4-hydroxy-1-((R)-2-(3-(((S)-1-((S)-3-((R)-2-(2-
hydroxyphenyl)-5,6,6a,7,9,10-hexahydro-8H-pyrazino
[1',2':4,5]pyrazino[2,3-c]pyridazin-8-yl)pyrrolidin-1-
yl)propan-2-yl)oxy)isoxazol-5-yl)-3-methylbutanoyl)-
N—((S)-1-(4-(4-methylthiazol-5-yl)phenyl)ethyl)
pyrrolidine-2-carboxamide;
(2S,4R)-4-hydroxy-1-((R)-2-(3-(((S)-1-((R)-3-((R)-2-(2-
hydroxyphenyl)-5,6,6a,7,9,10-hexahydro-8H-pyrazino
[1',2':4,5]pyrazino[2,3-c]pyridazin-8-yl)pyrrolidin-1-
yl)propan-2-yl)oxy)isoxazol-5-yl)-3-methylbutanoyl)-
N—((S)-1-(4-(4-methylthiazol-5-yl)phenyl)ethyl)
pyrrolidine-2-carboxamide;
(2S,4R)-4-hydroxy-1-((R)-2-(3-(((R)-1-((R)-3-((S)-2-(2-
hydroxyphenyl)-5,6,6a,7,9,10-hexahydro-8H-pyrazino
[1',2':4,5]pyrazino[2,3-c]pyridazin-8-yl)pyrrolidin-1-
yl)propan-2-yl)oxy)isoxazol-5-yl)-3-methylbutanoyl)-
N—((S)-1-(4-(4-methylthiazol-5-yl)phenyl)ethyl)
pyrrolidine-2-carboxamide;
(2S,4R)-4-hydroxy-1-((R)-2-(3-(((R)-1-((S)-3-((S)-2-(2-
hydroxyphenyl)-5,6,6a,7,9,10-hexahydro-8H-pyrazino
[1',2':4,5]pyrazino[2,3-c]pyridazin-8-yl)pyrrolidin-1-
yl)propan-2-yl)oxy)isoxazol-5-yl)-3-methylbutanoyl)-
N—((S)-1-(4-(4-methylthiazol-5-yl)phenyl)ethyl)
pyrrolidine-2-carboxamide;
(2S,4R)-4-hydroxy-1-((R)-2-(3-(((R)-1-((S)-3-((R)-2-(2-
hydroxyphenyl)-5,6,6a,7,9,10-hexahydro-8H-pyrazino
[1',2':4,5]pyrazino[2,3-c]pyridazin-8-yl)pyrrolidin-1-
yl)propan-2-yl)oxy)isoxazol-5-yl)-3-methylbutanoyl)-
N—((S)-1-(4-(4-methylthiazol-5-yl)phenyl)ethyl)
pyrrolidine-2-carboxamide;
(2S,4R)-4-hydroxy-1-((R)-2-(3-(((R)-1-((R)-3-((R)-2-(2-
hydroxyphenyl)-5,6,6a,7,9,10-hexahydro-8H-pyrazino
[1',2':4,5]pyrazino[2,3-c]pyridazin-8-yl)pyrrolidin-1-
yl)propan-2-yl)oxy)isoxazol-5-yl)-3-methylbutanoyl)-
N—((S)-1-(4-(4-methylthiazol-5-yl)phenyl)ethyl)
pyrrolidine-2-carboxamide;
(2S,4R)-4-hydroxy-1-((R)-2-(3-(2-((2R,4R)-4-((S)-2-(2-
hydroxyphenyl)-5,6,6a,7,9,10-hexahydro-8H-pyrazino
[1',2':4,5]pyrazino[2,3-c]pyridazin-8-yl)-2-methylpip-
eridin-1-yl)ethoxy)isoxazol-5-yl)-3-methylbutanoyl)-
N—((S)-1-(4-(4-methylthiazol-5-yl)phenyl)ethyl)
pyrrolidine-2-carboxamide;
(2S,4R)-4-hydroxy-1-((R)-2-(3-(2-((2S,4R)-4-((S)-2-(2-
hydroxyphenyl)-5,6,6a,7,9,10-hexahydro-8H-pyrazino
[1',2':4,5]pyrazino[2,3-c]pyridazin-8-yl)-2-methylpip-
eridin-1-yl)ethoxy)isoxazol-5-yl)-3-methylbutanoyl)-
N—((S)-1-(4-(4-methylthiazol-5-yl)phenyl)ethyl)
pyrrolidine-2-carboxamide;
(2S,4R)-4-hydroxy-1-((R)-2-(3-(2-((2R,4S)-4-((S)-2-(2-
hydroxyphenyl)-5,6,6a,7,9,10-hexahydro-8H-pyrazino
[1',2':4,5]pyrazino[2,3-c]pyridazin-8-yl)-2-methylpip-
eridin-1-yl)ethoxy)isoxazol-5-yl)-3-methylbutanoyl)-
N—((S)-1-(4-(4-methylthiazol-5-yl)phenyl)ethyl)
pyrrolidine-2-carboxamide;
(2S,4R)-4-hydroxy-1-((R)-2-(3-(2-((2S,4S)-4-((S)-2-(2-
hydroxyphenyl)-5,6,6a,7,9,10-hexahydro-8H-pyrazino
[1',2':4,5]pyrazino[2,3-c]pyridazin-8-yl)-2-methylpip-
eridin-1-yl)ethoxy)isoxazol-5-yl)-3-methylbutanoyl)-
N—((S)-1-(4-(4-methylthiazol-5-yl)phenyl)ethyl)
pyrrolidine-2-carboxamide;
(2S,4R)-4-hydroxy-1-((R)-2-(3-(2-((2R,4R)-4-((R)-2-(2-
hydroxyphenyl)-5,6,6a,7,9,10-hexahydro-8H-pyrazino
[1',2':4,5]pyrazino[2,3-c]pyridazin-8-yl)-2-methylpip-
eridin-1-yl)ethoxy)isoxazol-5-yl)-3-methylbutanoyl)-
N—((S)-1-(4-(4-methylthiazol-5-yl)phenyl)ethyl)
pyrrolidine-2-carboxamide;
(2S,4R)-4-hydroxy-1-((R)-2-(3-(2-((2S,4R)-4-((R)-2-(2-
hydroxyphenyl)-5,6,6a,7,9,10-hexahydro-8H-pyrazino
[1',2':4,5]pyrazino[2,3-c]pyridazin-8-yl)-2-methylpip-
eridin-1-yl)ethoxy)isoxazol-5-yl)-3-methylbutanoyl)-
N—((S)-1-(4-(4-methylthiazol-5-yl)phenyl)ethyl)
pyrrolidine-2-carboxamide;
(2S,4R)-4-hydroxy-1-((R)-2-(3-(2-((2R,4S)-4-((R)-2-(2-
hydroxyphenyl)-5,6,6a,7,9,10-hexahydro-8H-pyrazino
[1',2':4,5]pyrazino[2,3-c]pyridazin-8-yl)-2-methylpip-
eridin-1-yl)ethoxy)isoxazol-5-yl)-3-methylbutanoyl)-

N—((S)-1-(4-(4-methylthiazol-5-yl)phenyl)ethyl) pyrrolidine-2-carboxamide;

(2S,4R)-4-hydroxy-1-((R)-2-(3-(2-((2S,4S)-4-((R)-2-(2-hydroxyphenyl)-5,6,6a,7,9,10-hexahydro-8H-pyrazino[1',2':4,5]pyrazino[2,3-c]pyridazin-8-yl)-2-methylpiperidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(2-((3R,4S)-4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(2-((3S,4R)-4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(2-((3R,4R)-4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(2-((3S,4S)-4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(2-((3R,4S)-4-((R)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(2-((3S,4R)-4-((R)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(2-((3R,4R)-4-((R)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(2-((3S,4S)-4-((R)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(2-(4-((S)-1-((S)-2-(2-hydroxyphenyl)-5,6,6a,7,9,10-hexahydro-8H-pyrazino[1',2':4,5]pyrazino[2,3-c]pyridazin-8-yl)ethyl)piperidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(2-(4-((R)-1-((S)-2-(2-hydroxyphenyl)-5,6,6a,7,9,10-hexahydro-8H-pyrazino[1',2':4,5]pyrazino[2,3-c]pyridazin-8-yl)ethyl)piperidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(2-(4-((S)-1-((R)-2-(2-hydroxyphenyl)-5,6,6a,7,9,10-hexahydro-8H-pyrazino[1',2':4,5]pyrazino[2,3-c]pyridazin-8-yl)ethyl)piperidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(2-(4-((R)-1-((R)-2-(2-hydroxyphenyl)-5,6,6a,7,9,10-hexahydro-8H-pyrazino[1',2':4,5]pyrazino[2,3-c]pyridazin-8-yl)ethyl)piperidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(2-(4-((R)-3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-((S)-3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-((S)-3-((R)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-((R)-3-((R)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((S)-3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(2-((R)-3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(2-((R)-3-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(2-((S)-3-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(3-((S)-3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propyl)isoxazol-5-yl)-3-methylbutanoyl)-N—

((S)-1-(4-(4-methylthiazol-5-yl)phenyl)ethyl) pyrrolidine-2-carboxamide;

(2S,4R)-4-hydroxy-1-((R)-2-(3-(3-((R)-3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propyl)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((R)-2-(3-(3-((R)-3-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propyl)isoxazol-5-yl)-3-methylbutanoyl)-N—((S)-1-(4-(4-methylthiazol-5-yl)phenyl)ethyl) pyrrolidine-2-carboxamide; or (2S,4R)-4-hydroxy-1-((R)-2-(3-(3-((S)-3-(((R)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propyl)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((2S)-2-(2-(2-(2-hydroxyphenyl)-5,6,6a,7,9,10-hexahydro-8H-pyrazino[1',2':4,5]pyrazino[2,3-c]pyridazin-8-yl)acetamido)-3,3-dimethylbutanoyl)-N—((S)-1-(4-(4-methylthiazol-5-yl)phenyl)ethyl)pyrrolidine-2-carboxamide;

(2S,4R)-4-hydroxy-N-[[4-(5-methyl-1,3-thiazol-4-yl)phenyl]methyl]-1-[(2S)-2-[[2-[4-(2-hydroxyphenyl)-1,5,6,8,12-pentazatricyclo[8.4.0.02,7]tetradeca-2,4,6-trien-12-yl]acetyl]amino]-3,3-dimethylbutanoyl]pyrrolidine-2-carboxamide;

(2S,4R)-4-hydroxy-1-((2S)-2-(2-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)acetamido)-3,3-dimethylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-N—((S)-1-(4-(4-methyl-1λ³, 3λ²-thiazol-5-yl)phenyl)ethyl)pyrrolidine-2-carboxamide;

(2S,4R)-4-hydroxy-1-((2S)-2-(3-(2-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2S)-2-(4-(2-(2-hydroxyphenyl)-5,6,6a,7,9,10-hexahydro-8H-pyrazino[1',2':4,5]pyrazino[2,3-c]pyridazin-8-yl)butanamido)-3,3-dimethylbutanoyl)-N—((S)-1-(4-(4-methylthiazol-5-yl)phenyl)ethyl)pyrrolidine-2-carboxamide;

2-(2-(2-hydroxyphenyl)-5,6,6a,7,9,10-hexahydro-8H-pyrazino[1',2':4,5]pyrazino[2,3-c]pyridazin-8-yl)ethyl ((R)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamate;

(2S,4R)-4-hydroxy-1-((2S)-2-(3-(4-((2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propanamido)-3,3-dimethylbutanoyl)-N—((S)-1-(4-(4-methylthiazol-5-yl)phenyl)ethyl)pyrrolidine-2-carboxamide;

(2S,4R)-4-hydroxy-1-((2S)-2-(2-(2-(2-(2-hydroxyphenyl)-5,6,6a,7,9,10-hexahydro-8H-pyrazino[1',2':4,5]pyrazino[2,3-c]pyridazin-8-yl)ethoxy)acetamido)-3,3-dimethylbutanoyl)-N—((S)-1-(4-(4-methylthiazol-5-yl)phenyl)ethyl)pyrrolidine-2-carboxamide;

(2S,4R)-4-hydroxy-1-((2S)-2-(2-(3-(2-(2-hydroxyphenyl)-5,6,6a,7,9,10-hexahydro-8H-pyrazino[1',2':4,5]pyrazino[2,3-c]pyridazin-8-yl)azetidin-1-yl)acetamido)-3,3-dimethylbutanoyl)-N—((S)-1-(4-(4-methylthiazol-5-yl)phenyl)ethyl)pyrrolidine-2-carboxamide;

2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl ((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamate;

(2S,4R)-4-hydroxy-1-((2R)-2-(3-(2-(2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-N—((S)-1-(4-(4-methylthiazol-5-yl)phenyl)ethyl)pyrrolidine-2-carb oxamide;

(3R,5S)-1-((2R)-2-(3-(2-(2-(2-hydroxyphenyl)-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-5-(((S)-1-(4-(4-methylthiazol-5-yl)phenyl)ethyl)carbamoyl)pyrrolidin-3-yl acetate;

(2S,4R)-4-hydroxy-1-((2R)-2-(3-(2-(6-(2-(2-hydroxyphenyl)-5,6,6a,7,9,10-hexahydro-8H-pyrazino[1',2':4,5]pyrazino[2,3-c]pyridazin-8-yl)-3-azabicyclo [3.1.1] heptan-3-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((2R)-2-(3-(2-(6-(2-(2-hydroxyphenyl)-5,6,6a,7,9,10-hexahydro-8H-pyrazino[1',2':4,5]pyrazino[2,3-c]pyridazin-8-yl)-2-azaspiro[3.3]heptan-2-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-1-((2R)-2-(3-(2-(3-fluoro-4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-4-hydroxy-N—((S)-1-(4-(4-methylthiazol-5-yl)phenyl)ethyl) pyrrolidine-2-carboxamide;

(2S,4R)-4-hydroxy-1-((2R)-2-(3-(2-(3-(((S)-2-(2-hydroxyphenyl)-5,6,6a,7,9,10-hexahydro-8H-pyrazino[1',2':4,5]pyrazino[2,3-c]pyridazin-8-yl)methyl)pyrrolidin-1-yl)ethoxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((2R)-2-(3-(2-(4-((S)-2-(2-hydroxyphenyl)-5,6,6a,7,9,10-hexahydro-8H-pyrazino[1',2':4,5]pyrazino[2,3-c]pyridazin-8-yl)azepan-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-((1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propan-2-yl)oxy)isoxazol-5-yl)-3-methylbutanoyl)-N—((S)-1-(4-(4-methylthiazol-5-yl)phenyl)ethyl) pyrrolidine-2-carboxamide;

(2S,4R)-4-hydroxy-1-((2R)-2-(3-(2-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-((4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)methyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)piperazin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-((1-(3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(3-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-((4-((S)-2-(2-hydroxyphenyl)-5,6,6a,7,9,10-hexahydro-8H-pyrazino[1',2':4,5]pyrazino[2,3-c]pyridazin-8-yl)cyclohexyl)(methyl)amino)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-((S)-2-(2-hydroxyphenyl)-5,6,6a,7,9,10-hexahydro-8H-pyrazino[1',2':4,5]pyrazino[2,3-c]pyridazin-8-yl)-[1,4'-bipiperidin]-1'-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-N—((R)-2-hydroxy-1-(4-(4-methylthiazol-5-yl)phenyl)ethyl)-1-(2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)pyrrolidine-2-carboxamide;

(2S,4R)-4-hydroxy-1-((2R)-2-(3-(2-(5-((S)-2-(2-hydroxyphenyl)-5,6,6a,7,9,10-hexahydro-8H-pyrazino[1',2':4,5]pyrazino[2,3-c]pyridazin-8-yl)hexahydrocyclopenta[c]pyrrol-2(1H)-yl)ethoxy)isoxazol-5-yl)-3-methylbutanoyl)-N—((S)-1-(4-(4-methylthiazol-5-yl)phenyl)ethyl)pyrrolidine-2-carboxamide;

(3R,5 S)-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-5-(((S)-1-(4-(4-methylthiazol-5-yl)phenyl)ethyl)carbamoyl)pyrrolidin-3-yl isobutyrate;

(2S,4R)-4-hydroxy-1-((2R)-2-(3-(2-(4-((S)-2-(2-hydroxyphenyl)-5,6,6a,7,9,10-hexahydro-8H-pyrazino[1',2':4,5]pyrazino[2,3-c]pyridazin-8-yl)-2-methylpiperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(4-(1-((S)-2-(2-hydroxyphenyl)-5,6,6a,7,9,10-hexahydro-8H-pyrazino[1',2':4,5]pyrazino[2,3-c]pyridazin-8-yl)ethyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-(2-(3-((1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)butan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-(2-(3-((1-3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)butan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(4-(2-(2-hydroxyphenyl)-6a-methyl-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-((1-(4-(((S)-2-(2-hydroxyphenyl)-5,6,6a,7,9,10-hexahydro-8H-pyrazino[1',2':4,5]pyrazino[2,3-c]pyridazin-8-yl)methyl)azepan-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(4-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(3-(2-(2-hydroxyphenyl)-6a-methyl-5,6,6a,7,9,10-hexahydro-8H-pyrazino[1',2':4,5]pyrazino[2,3-c]pyridazin-8-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-((R)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(3-((2-(2-hydroxyphenyl)-5,6,6a,7,9,10-hexahydro-8H-pyrazino[1',2':4,5]pyrazino[2,3-c]pyridazin-8-yl)methyl)-8-azabicyclo[3.2.1]octan-8-yl)ethoxy)isoxazol-5-yl)-3-methylbutanoyl)-N—((S)-1-(4-(4-methylthiazol-5-yl)phenyl)ethyl)pyrrolidine-2-carboxamide;

(3R,5S)-1-((R)-2-(3-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-5-(((S)-1-(4-(4-methylthiazol-5-yl)phenyl)ethyl)carbamoyl)pyrrolidin-3-yl isobutyrate;

(2S,4R)-4-hydroxy-1-((2R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)azepan-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)-3,3-dimethylpiperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)-3,6-dihydropyridin-1(2H)-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(3-hydroxy-4-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(3-hydroxy-4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(2-(2-(2-hydroxyphenyl)-6-methyl-5,6,6a,7,9,10-hexahydro-8H-pyrazino[1',2':4,5]pyrazino[2,3-c]pyridazin-8-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(4-(2-(2-hydroxyphenyl)-6-methyl-5,6,6a,7,9,10-hexahydro-8H-pyrazino[1',2':4,5]pyrazino[2,3-c]pyridazin-8-yl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(((2S)-1-(4-(2-(2-hydroxyphenyl)-6-methyl-5,6,6a,7,9,10-hexahydro-8H-pyrazino[1',2':4,5]pyrazino[2,3-c]pyridazin-8-yl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-((S)-2-(2-hydroxyphenyl)-6,6a,7,8,9,10-hexahydro-5H-pyrazino[1',2':4,5]pyrazino[2,3-c]pyridazine-8-carbonyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(4-((2-(2-hydroxyphenyl)-6,6a,7,8,9,10-hexahydro-5H-pyrido[1,2:4,5]pyrazino[2,3-c]pyridazin-8-yl)(methyl)amino)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)-1-oxopropan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-(2-(3-(((2R)-1-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)-1-oxopropan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(4-((S)-2-(2-hydroxyphenyl)-5,6,6a,7,9,10-hexahydro-8H-pyrazino[1',2':4,5]pyrazino[2,3-c]pyridazin-8-yl)-3-methylpiperidin-1-yl)-2-oxoethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((R)-1-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)-1-oxopropan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-(2-(3-((4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)methyl)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(3-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propyl)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-((4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)methyl)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(3-(3-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)propyl)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(3-(2-(2-hydroxyphenyl)-5,6,6a,7,9,10-hexahydro-8H-pyrazino[1',2':4,5]pyrazino[2,3-c]pyridazin-8-yl)propyl)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(3-(3-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propyl)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-((S)-2-(2-hydroxyphenyl)-5,6,6a,7,9,10-hexahydro-8H-pyrazino[1',2':4,5]pyrazino[2,3-c]pyridazin-8-yl)piperidin-1-yl)ethyl)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-(2-(3-(2-((2-((S)-2-(2-hydroxyphenyl)-5,6,6a,7,9,10-hexahydro-8H-pyrazino[1',2':4,5]pyrazino[2,3-c]pyridazin-8-yl)ethyl)(methyl)amino)ethyl)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(3-((2-((S)-2-(2-hydroxyphenyl)-5,6,6a,7,9,10-hexahydro-8H-pyrazino[1',2':4,5]pyrazino[2,3-c]pyridazin-8-yl)ethyl)(methyl)amino)propyl)isoxazol-5-yl)-3-methylbutanoyl)-N—((S)-1-(4-(4-methylthiazol-5-yl)phenyl)ethyl)pyrrolidine-2-carboxamide;

(2S,4R)—N—((S)-1-(4-cyanophenyl)ethyl)-4-hydroxy-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)pyrrolidine-2-carboxamide;

(2S,4R)—N—((S)-1-(2-fluoro-4-(4-methylthiazol-5-yl)phenyl)ethyl)-4-hydroxy-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)pyrrolidine-2-carboxamide;

(2S,4R)-4-hydroxy-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(2-methyl-1H-imidazol-1-yl)phenyl)ethyl)pyrrolidine-2-carboxamide;

(2S,4R)-4-hydroxy-1-((R)-2-(3-(2-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(2-methoxy-4-(4-methylthiazol-5-yl)phenyl)ethyl)pyrrolidine-2-carboxamide;

(2S,4R)-4-hydroxy-1-((2R)-2-(3-(((2S)-1-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(((2R)-1-(3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(((2S)-1-(3-(2-(2-hydroxyphenyl)-6a-methyl-5,6,6a,7,9,10-hexahydro-8H-pyrazino [1',2':4,5]pyrazino[2,3-c]pyridazin-8-yl)pyrrolidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(((S)-1-(4-(((S)-2-(2-hydroxyphenyl)-5,6,6a,7,9,10-hexahydro-8H-pyrazino[1',2':4,5]pyrazino[2,3-c]pyridazin-8-yl)methyl)piperidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((R)-2-(3-(2-(4-(((6aS,9 S)-2-(2-hydroxyphenyl)-9-methyl-5,6,6a,7,9,10-hexahydro-8H-pyrazino[1',2':4,5]pyrazino[2,3-c]pyridazin-8-yl)methyl)piperidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2R)-2-(3-(2-(3-((6aS,9S)-2-(2-hydroxyphenyl)-9-methyl-5,6,6a,7,9,10-hexahydro-8H-pyrazino[1',2':4,5]pyrazino[2,3-c]pyridazin-8-yl)pyrrolidin-1-yl)ethoxy)isoxazol-5-yl)-3-methylbutanoyl)-N—((S)-1-(4-(4-methylthiazol-5-yl)phenyl)ethyl)pyrrolidine-2-carboxamide;

(5-(1-((2S,4R)-4-hydroxy-2-(((S)-1-(4-(4-methylthiazol-5-yl)phenyl)ethyl)carbamoyl)pyrrolidin-1-yl)-3-methyl-1-oxobutan-2-yl)isoxazol-3-yl)methyl 4-((S)-2-(2-hydroxyphenyl)-5,6,6a,7,9,10-hexahydro-8H-pyrazino[1',2':4,5]pyrazino[2,3-c]pyridazin-8-yl)piperidine-1-carboxylate;

(2S,4R)-4-hydroxy-1-(2-(3-(((4-(2-(2-hydroxyphenyl)-5,6,6a,7,9,10-hexahydro-8H-pyrazino[1',2':4,5]pyrazino[2,3-c]pyridazin-8-yl)pyridin-2-yl)oxy)methyl)isoxazol-5-yl)-3-methylbutanoyl)-N—((S)-1-(4-(4-methylthiazol-5-yl)phenyl)ethyl)pyrrolidine-2-carboxamide;

(2S,4R)-4-hydroxy-1-((2S)-2-(1-(3-(2-(2-hydroxyphenyl)-5,6,6a,7,9,10-hexahydro-8H-pyrazino[1',2':4,5]pyrazino[2,3-c]pyridazin-8-yl)propyl)azetidine-3-carboxamido)-3,3-dimethylbutanoyl)-N—((S)-1-(4-(4-methylthiazol-5-yl)phenyl)ethyl)pyrrolidine-2-carboxamide; or (2S,4R)-4-hydroxy-1-((2R)-2-(3-((1-(3-((S)-2-(2-hydroxyphenyl)-5,6,6a,7,9,10-hexahydro-8H-pyrazino[1',2':4,5]pyrazino[2,3-c]pyridazin-8-yl)propyl)pyrrolidin-3-yl)oxy)isoxazol-5-yl)-3-methylbutanoyl)-N—((S)-1-(4-(4-methylthiazol-5-yl)phenyl)ethyl)pyrrolidine-2-carboxamide.

18. A compound of claim 17, or a pharmaceutically acceptable salt thereof, wherein the compound is (2S,4R)-4-hydroxy-1-((R)-2-(3-(((S)-1-((R)-3-((S)-2-(2-hydroxyphenyl)-5,6,6a,7,9,10-hexahydro-8H-pyrazino[1',2':4,5]pyrazino[2,3-c]pyridazin-8-yl)pyrrolidin-1-yl)propan-2-yl)oxy)isoxazol-5-yl)-3-methylbutanoyl)-N—((S)-1-(4-(4-methylthiazol-5-yl)phenyl)ethyl)pyrrolidine-2-carboxamide.

\* \* \* \* \*